US012378229B2

(12) United States Patent
Abbott et al.

(10) Patent No.: US 12,378,229 B2
(45) Date of Patent: Aug. 5, 2025

(54) GPR84 ANTAGONISTS AND USES THEREOF

(71) Applicant: Liminal BioSciences Limited, Cambridge (GB)

(72) Inventors: Shaun Abbott, Pointe Claire (CA); Mylène De Léséleuc, Montreal (CA); Julien Martel, Laval (CA); Elyse Bourque, L'Étang-du-Nord (CA); Jeremy Green, Waltham, MA (US); Alexandre Larivée, Montreal (CA); Jean-Benoît Giguère, Montreal (CA); Elodie Landagaray, Montreal (CA); Claudio Sturino, L'ile-Bizard (CA)

(73) Assignee: Liminal BioSciences Limited, Cambridge (GB)

( * ) Notice: Subject to any disclaimer, the term of this patent is extended or adjusted under 35 U.S.C. 154(b) by 0 days.

(21) Appl. No.: 17/649,744

(22) Filed: Feb. 2, 2022

(65) Prior Publication Data

US 2023/0091528 A1    Mar. 23, 2023

Related U.S. Application Data

(60) Provisional application No. 63/144,701, filed on Feb. 2, 2021.

(51) Int. Cl.
| | |
|---|---|
| *C07D 405/12* | (2006.01) |
| *C07D 213/69* | (2006.01) |
| *C07D 319/12* | (2006.01) |
| *C07D 401/12* | (2006.01) |
| *C07D 401/14* | (2006.01) |
| *C07D 403/06* | (2006.01) |
| *C07D 405/06* | (2006.01) |
| *C07D 405/14* | (2006.01) |
| *C07D 407/12* | (2006.01) |
| *C07D 409/14* | (2006.01) |
| *C07D 413/06* | (2006.01) |
| *C07D 413/12* | (2006.01) |
| *C07D 413/14* | (2006.01) |
| *C07D 417/12* | (2006.01) |
| *C07D 471/04* | (2006.01) |
| *C07D 491/052* | (2006.01) |
| *C07D 498/04* | (2006.01) |

(52) U.S. Cl.
CPC ......... *C07D 405/12* (2013.01); *C07D 213/69* (2013.01); *C07D 319/12* (2013.01); *C07D 401/12* (2013.01); *C07D 401/14* (2013.01); *C07D 403/06* (2013.01); *C07D 405/06* (2013.01); *C07D 405/14* (2013.01); *C07D 407/12* (2013.01); *C07D 409/14* (2013.01); *C07D 413/06* (2013.01); *C07D 413/12* (2013.01); *C07D 413/14* (2013.01); *C07D 417/12* (2013.01); *C07D 471/04* (2013.01); *C07D 491/052* (2013.01); *C07D 498/04* (2013.01)

(58) Field of Classification Search
CPC .................................................. C07D 405/12
See application file for complete search history.

(56) References Cited

U.S. PATENT DOCUMENTS

| | | | |
|---|---|---|---|
| 5,112,839 A | 5/1992 | Gericke et al. | |
| 5,234,923 A | 8/1993 | Poss et al. | |
| 5,294,722 A | 3/1994 | Kim | |
| 5,356,911 A | 10/1994 | Muller-Gliemann et al. | |
| 5,374,615 A | 12/1994 | Poss | |
| 5,378,720 A | 1/1995 | Hlasta et al. | |
| 5,407,948 A | 4/1995 | Fey et al. | |
| 5,466,701 A | 11/1995 | Hlasta et al. | |
| 5,470,975 A | 11/1995 | Atwal | |
| 5,510,362 A | 4/1996 | Matassa et al. | |
| 5,512,576 A | 4/1996 | Desai et al. | |
| 5,599,823 A | 2/1997 | M uller-Gliemann et al. | |
| 5,607,957 A | 3/1997 | Castro Pineiro et al. | |
| 5,869,428 A | 2/1999 | Morishima et al. | |
| 5,935,984 A * | 8/1999 | Goldmann ........... | C07D 233/90 514/400 |
| 6,265,350 B1 | 7/2001 | Schnatterer et al. | |
| 6,642,390 B2 | 11/2003 | Kolb et al. | |
| 6,670,307 B2 | 12/2003 | Schnatterer et al. | |
| 6,949,571 B2 | 9/2005 | Nagato et al. | |
| 7,067,540 B2 | 6/2006 | Devadas et al. | |
| 7,105,548 B2 | 9/2006 | Cosford et al. | |
| 7,183,287 B2 | 2/2007 | Durley | |
| 7,253,190 B2 | 8/2007 | Cosford et al. | |
| 7,268,151 B2 | 9/2007 | Cosford et al. | |
| 7,319,108 B2 | 1/2008 | Schwink et al. | |

(Continued)

FOREIGN PATENT DOCUMENTS

| | | |
|---|---|---|
| CA | 2020370 A1 | 1/1991 |
| CA | 2809478 A1 | 9/2014 |

(Continued)

OTHER PUBLICATIONS

Pillaiyar "6-(Ar)Alkylamino-Substituted Uracil Derivatives: Lipid Mimetics with Potent Activity at the Orphan G Protein-Coupled Receptor 84 (GPR84)" ACS Omega 2018, 3, 3365-3383.*
Pozharskii et al. Heterocycles in Life and Society Wiley, 1997, pp. 1-6.*
Pitt "Heteroaromatic Rings of the Future" J. Med. Chem. 2009, 52, 2952-2963.*
Carnelley, "Action of heat on the mixed vapours of benzene and toluene. Two new methylene-diphenylenes." Journal of the Chemical Society, Transactions, 1880, 37, 701-720.*

(Continued)

*Primary Examiner* — David K O'Dell
(74) *Attorney, Agent, or Firm* — Dechert LLP

(57) ABSTRACT

The present invention provides compounds, compositions thereof, and methods of using the same for the inhibition of GPR84, and the treatment of GPR84-mediated disorders.

29 Claims, No Drawings

(56) References Cited

U.S. PATENT DOCUMENTS

| | | |
|---|---|---|
| 7,332,508 B2 | 2/2008 | Sorensen et al. |
| 7,348,334 B2 | 3/2008 | Iqbal et al. |
| 7,371,767 B2 | 5/2008 | Cosford et al. |
| 7,563,811 B2 | 7/2009 | Nagato et al. |
| 7,569,592 B2 | 8/2009 | Cosford et al. |
| 7,629,363 B2 | 12/2009 | Devadas et al. |
| 7,728,017 B2 | 6/2010 | Lauffer et al. |
| 7,759,367 B2 | 7/2010 | Smith |
| 7,795,271 B2 | 9/2010 | Durley |
| 7,799,924 B2 | 9/2010 | Sorensen et al. |
| 7,879,896 B2 | 2/2011 | Allegretti et al. |
| 7,932,390 B2 | 4/2011 | Chen et al. |
| 7,939,549 B2 | 5/2011 | Nagato et al. |
| 7,973,060 B2 | 7/2011 | Kim et al. |
| 7,989,441 B2 | 8/2011 | Chen et al. |
| 7,989,478 B2 | 8/2011 | Tomigahara et al. |
| 7,998,987 B2 | 8/2011 | Lauffer et al. |
| 8,013,005 B2 | 9/2011 | Allegretti et al. |
| 8,017,635 B2 | 9/2011 | Lyga et al. |
| 8,084,471 B2 | 12/2011 | Hamilton et al. |
| 8,158,659 B2 | 4/2012 | Allegretti et al. |
| 8,236,846 B2 | 8/2012 | Allegretti et al. |
| 8,242,150 B2 | 8/2012 | Fischer et al. |
| 8,299,101 B2 | 10/2012 | Cid-N nez et al. |
| 8,299,104 B2 | 10/2012 | Schwink et al. |
| 8,344,013 B2 | 1/2013 | Allegretti et al. |
| 8,349,875 B2 | 1/2013 | Allegretti et al. |
| 8,399,493 B2 | 3/2013 | Bolea et al. |
| 8,518,975 B2 | 8/2013 | Aslanian et al. |
| 8,569,351 B2 | 10/2013 | Allegretti et al. |
| 8,623,879 B2 | 1/2014 | Giovannini et al. |
| 8,623,901 B2 | 1/2014 | Giovannini et al. |
| 8,664,220 B2 | 3/2014 | Clark et al. |
| 8,664,254 B2 | 3/2014 | Choi et al. |
| 8,778,983 B2 | 7/2014 | Clark et al. |
| 8,841,323 B2 | 9/2014 | Imogai et al. |
| 8,895,755 B2 | 11/2014 | Allegretti et al. |
| 8,906,939 B2 | 12/2014 | Cid-Nunez et al. |
| 8,927,543 B2 | 1/2015 | Labeguere et al. |
| 9,012,485 B2 | 4/2015 | Choi et al. |
| 9,034,900 B2 | 5/2015 | Bennett et al. |
| 9,067,891 B2 | 6/2015 | Cid-Nunez et al. |
| 9,096,603 B2 | 8/2015 | Giovannini et al. |
| 9,102,679 B2 | 8/2015 | Giovannini et al. |
| 9,114,138 B2 | 8/2015 | Cid-Nunez et al. |
| 9,115,114 B2 | 8/2015 | Bennett et al. |
| 9,132,122 B2 | 9/2015 | Cid-Nunez et al. |
| 9,139,565 B2 | 9/2015 | Oyelere et al. |
| 9,150,514 B2 | 10/2015 | Allegretti et al. |
| 9,181,233 B2 | 11/2015 | Heiser et al. |
| 9,187,437 B2 | 11/2015 | Das et al. |
| 9,255,095 B2 | 2/2016 | Labeguere et al. |
| 9,266,834 B2 | 2/2016 | Imogai et al. |
| 9,271,978 B2 | 3/2016 | Liu et al. |
| 9,272,990 B2 | 3/2016 | Seiders et al. |
| 9,273,008 B2 | 3/2016 | Choi et al. |
| 9,359,379 B2 | 6/2016 | Buckman et al. |
| 9,533,967 B2 | 1/2017 | Short et al. |
| 9,540,322 B2 | 1/2017 | Jorgensen et al. |
| 9,547,197 B2 | 1/2017 | Lim |
| 9,598,367 B2 | 3/2017 | Liu et al. |
| 9,598,372 B2 | 3/2017 | Boloor |
| 9,643,922 B2 | 5/2017 | Jorgensen et al. |
| 9,675,593 B2 | 6/2017 | Buckman et al. |
| 9,861,637 B2 | 1/2018 | Liu et al. |
| 9,963,440 B2 | 5/2018 | Short et al. |
| 10,000,456 B2 | 6/2018 | Clark et al. |
| 10,023,592 B2 | 7/2018 | Boloor |
| 10,047,083 B2 | 8/2018 | Labeguere et al. |
| 10,125,102 B2 | 11/2018 | Kotian et al. |
| 10,130,625 B2 | 11/2018 | Sintim et al. |
| 10,202,343 B2 | 2/2019 | Jorgensen et al. |
| 10,329,260 B2 | 6/2019 | Kotian et al. |
| 10,336,724 B2 | 7/2019 | Tsai et al. |
| 10,376,497 B2 | 8/2019 | Buckman et al. |
| 10,428,082 B2 | 10/2019 | Janganati et al. |
| 10,508,127 B2 | 12/2019 | Rosch et al. |
| 10,562,915 B2 | 2/2020 | Boloor |
| 10,568,879 B2 | 2/2020 | Menet et al. |
| 10,633,345 B2 | 4/2020 | Kotian et al. |
| 10,653,674 B2 | 5/2020 | Short et al. |
| 10,689,346 B2 | 6/2020 | Kotian et al. |
| 10,898,474 B2 | 1/2021 | Buckman et al. |
| 2004/0259917 A1 | 12/2004 | Cosford et al. |
| 2005/0176775 A1 | 8/2005 | Devadas et al. |
| 2007/0060608 A1 | 3/2007 | Vanderslice et al. |
| 2007/0088033 A1 | 4/2007 | Devadas et al. |
| 2007/0167621 A1 | 7/2007 | Durley |
| 2007/0299065 A1 | 12/2007 | Mederski et al. |
| 2008/0280949 A1 | 11/2008 | Albert et al. |
| 2009/0137557 A1 | 5/2009 | Ku et al. |
| 2009/0170847 A1 | 7/2009 | Lee et al. |
| 2009/0270350 A1 | 10/2009 | Devadas et al. |
| 2010/0249092 A1 | 9/2010 | Singh et al. |
| 2010/0298384 A1 | 11/2010 | Takhi et al. |
| 2011/0045101 A1 | 2/2011 | Selby et al. |
| 2011/0281845 A1 | 11/2011 | Chen et al. |
| 2011/0313001 A1 | 12/2011 | Fischer et al. |
| 2012/0028931 A1 | 2/2012 | Leonardi et al. |
| 2013/0109652 A1 | 5/2013 | Imogai et al. |
| 2013/0253019 A1 | 9/2013 | Hutchinson et al. |
| 2013/0281503 A1 | 10/2013 | Melander et al. |
| 2014/0073634 A1 | 3/2014 | Jones et al. |
| 2016/0122333 A1 | 5/2016 | Short et al. |
| 2016/0256440 A1 | 9/2016 | Short et al. |
| 2017/0114323 A1 | 4/2017 | Theunissen et al. |
| 2018/0237424 A1 | 8/2018 | Legeai-Mallet et al. |
| 2019/0209548 A1 | 7/2019 | Sintim et al. |
| 2019/0209656 A1 | 7/2019 | Petry et al. |
| 2019/0270706 A1 | 9/2019 | Jorgensen et al. |
| 2019/0321343 A1 | 10/2019 | Buckman et al. |
| 2020/0038391 A1 | 2/2020 | Cid-Nunez et al. |
| 2020/0039943 A1 | 2/2020 | Veiseh et al. |
| 2020/0148703 A1 | 5/2020 | Boloor |
| 2020/0206196 A1 | 7/2020 | Stewart et al. |
| 2020/0247762 A1 | 8/2020 | McCormick et al. |
| 2020/0255413 A1 | 8/2020 | Teng et al. |
| 2020/0270231 A1 | 8/2020 | Aliper et al. |
| 2020/0270234 A1 | 8/2020 | Aliper et al. |
| 2020/0331874 A1 | 10/2020 | Shapiro et al. |
| 2020/0331894 A1 | 10/2020 | Tsai et al. |

FOREIGN PATENT DOCUMENTS

| | | |
|---|---|---|
| CN | 104513213 A | 4/2015 |
| CN | 104844533 A | 8/2015 |
| CN | 104876912 A | 9/2015 |
| CN | 106316975 A | 1/2017 |
| CN | 104876912 B | 7/2017 |
| CN | 109369623 A | 2/2019 |
| CN | 109456250 A | 3/2019 |
| CN | 104844533 B | 4/2019 |
| CN | 110396089 A | 11/2019 |
| CN | 109369623 B | 4/2020 |
| EP | 0407342 A2 | 1/1991 |
| EP | 0488532 A1 | 6/1992 |
| EP | 3372590 A1 | 9/2018 |
| EP | 3403649 A1 | 11/2018 |
| GB | 2263639 A | 8/1993 |
| KR | 1020150136294 A | 12/2015 |
| KR | 101666759 B1 | 10/2016 |
| WO | WO-199318029 A1 | 9/1993 |
| WO | WO-199320066 A1 | 10/1993 |
| WO | WO-1996016952 A1 | 6/1996 |
| WO | WO-1999052893 A1 | 10/1999 |
| WO | WO-1999065901 A1 | 12/1999 |
| WO | WO-2001096308 A1 | 12/2001 |
| WO | WO-2002081454 A1 | 10/2002 |
| WO | WO-2003029210 A2 | 4/2003 |
| WO | WO-2003047577 A2 | 6/2003 |
| WO | WO-2003051315 A2 | 6/2003 |
| WO | WO-2003051833 A2 | 6/2003 |
| WO | WO-2003053922 A2 | 7/2003 |
| WO | WO-2003059904 A1 | 7/2003 |

(56) References Cited

FOREIGN PATENT DOCUMENTS

| | | |
|---|---|---|
| WO | WO-2003068230 A1 | 8/2003 |
| WO | WO-2003090699 A1 | 11/2003 |
| WO | WO-2004030637 A2 | 4/2004 |
| WO | WO-2004044046 A2 | 5/2004 |
| WO | WO-2004054973 A2 | 7/2004 |
| WO | WO-2004087677 A2 | 10/2004 |
| WO | WO-2004089306 A2 | 10/2004 |
| WO | WO-2005018557 A2 | 3/2005 |
| WO | WO-2005028439 A1 | 3/2005 |
| WO | WO-2005070925 A1 | 8/2005 |
| WO | WO-2006030032 A1 | 3/2006 |
| WO | WO-2006058597 A1 | 6/2006 |
| WO | WO-2006130403 A1 | 12/2006 |
| WO | WO-2006133147 A2 | 12/2006 |
| WO | WO-2007006591 A2 | 1/2007 |
| WO | WO-2007018469 A1 | 2/2007 |
| WO | WO-2007043835 A1 | 4/2007 |
| WO | WO-2007062370 A2 | 5/2007 |
| WO | WO-2007064797 A2 | 6/2007 |
| WO | WO-2007083978 A1 | 7/2007 |
| WO | WO-2007091176 A1 | 8/2007 |
| WO | WO-2007104783 A2 | 9/2007 |
| WO | WO-2007132948 A1 | 11/2007 |
| WO | WO-2007136125 A1 | 11/2007 |
| WO | WO-2007143597 A2 | 12/2007 |
| WO | WO-2008000697 A1 | 1/2008 |
| WO | WO-2008025886 A1 | 3/2008 |
| WO | WO-2008030408 A2 | 3/2008 |
| WO | WO-2008064317 A1 | 5/2008 |
| WO | WO-2008064318 A2 | 5/2008 |
| WO | WO-2008107479 A1 | 9/2008 |
| WO | WO-2008107480 A1 | 9/2008 |
| WO | WO-2008107481 A1 | 9/2008 |
| WO | WO-2008133896 A2 | 11/2008 |
| WO | WO-2008143649 A2 | 11/2008 |
| WO | WO-2008156580 A1 | 12/2008 |
| WO | WO-2009016498 A1 | 2/2009 |
| WO | WO-2009032277 A1 | 3/2009 |
| WO | WO-2009033704 A1 | 3/2009 |
| WO | WO-2009087949 A1 | 7/2009 |
| WO | WO-2009089482 A1 * | 7/2009 ............... A61P 1/16 |
| WO | WO-2009121919 A1 | 10/2009 |
| WO | WO-2009137538 A2 | 11/2009 |
| WO | WO-2009137651 A2 | 11/2009 |
| WO | WO-2010021693 A2 | 2/2010 |
| WO | WO-2010077582 A1 | 7/2010 |
| WO | WO-2010112437 A1 | 10/2010 |
| WO | WO-2010131145 A1 | 11/2010 |
| WO | WO-2010131146 A1 | 11/2010 |
| WO | WO-2010131147 A1 | 11/2010 |
| WO | WO-2011029633 A1 | 3/2011 |
| WO | WO-2011041461 A2 | 4/2011 |
| WO | WO-2011041462 A2 | 4/2011 |
| WO | WO-2011057112 A1 | 5/2011 |
| WO | WO-2011107530 A2 | 9/2011 |
| WO | WO-2011126903 A2 | 10/2011 |
| WO | WO-2011140202 A2 | 11/2011 |
| WO | WO-2011159632 A1 | 12/2011 |
| WO | WO-2011159634 A1 | 12/2011 |
| WO | WO-2011159635 A1 | 12/2011 |
| WO | WO-2012011707 A2 | 1/2012 |
| WO | WO-2012040532 A1 | 3/2012 |
| WO | WO-2012041158 A1 | 4/2012 |
| WO | WO-2012050868 A1 | 4/2012 |
| WO | WO-2012058531 A2 | 5/2012 |
| WO | WO-2012078593 A2 | 6/2012 |
| WO | WO-2012164085 A1 | 12/2012 |
| WO | WO-2013078320 A1 | 5/2013 |
| WO | WO-2013092791 A1 | 6/2013 |
| WO | WO-2014031928 A2 | 2/2014 |
| WO | WO-2014048065 A1 | 4/2014 |
| WO | WO-2014055548 A1 | 4/2014 |
| WO | WO-2014095798 A1 | 6/2014 |
| WO | WO-2014096965 A2 | 6/2014 |
| WO | WO-2014113485 A1 | 7/2014 |
| WO | WO-2014179144 A1 | 11/2014 |
| WO | WO-2015058160 A1 | 4/2015 |
| WO | WO-2015134998 A1 | 9/2015 |
| WO | WO-2015162216 A1 | 10/2015 |
| WO | WO-2015196072 A2 | 12/2015 |
| WO | WO-2015197550 A1 | 12/2015 |
| WO | WO-2016014674 A1 | 1/2016 |
| WO | WO-2016058704 A1 | 4/2016 |
| WO | WO-2016139227 A1 | 9/2016 |
| WO | WO-2016169911 A1 | 10/2016 |
| WO | WO-2017040459 A1 | 3/2017 |
| WO | WO-2017069601 A1 | 4/2017 |
| WO | WO-2017132528 A1 | 8/2017 |
| WO | WO-2017207754 A1 | 12/2017 |
| WO | WO-2018067615 A1 | 4/2018 |
| WO | WO-2018195439 A2 | 10/2018 |
| WO | WO-2018208985 A2 | 11/2018 |
| WO | WO-2018210822 A1 | 11/2018 |
| WO | WO-2018227228 A1 | 12/2018 |
| WO | WO-2019060693 A1 | 3/2019 |
| WO | WO-2019076329 A1 | 4/2019 |
| WO | WO-2019096944 A1 | 5/2019 |
| WO | WO-2019165158 A1 | 8/2019 |
| WO | WO-202003313 A1 | 1/2020 |
| WO | WO-2020006724 A1 | 1/2020 |
| WO | WO-2020008013 A1 | 1/2020 |
| WO | WO-2020011811 A1 | 1/2020 |
| WO | WO-2020011812 A1 | 1/2020 |
| WO | WO-2020011816 A1 | 1/2020 |
| WO | WO-2020013646 A1 | 1/2020 |
| WO | WO-2020020851 A1 | 1/2020 |
| WO | WO-2020023846 A1 | 1/2020 |
| WO | WO-2020033413 A2 | 2/2020 |
| WO | WO-2020055164 A1 * | 3/2020 ......... A61K 31/4365 |
| WO | WO-2020033413 A3 | 5/2020 |
| WO | WO-2020118194 A1 | 6/2020 |
| WO | WO-2020131597 A1 | 6/2020 |
| WO | WO-2020170202 A1 | 8/2020 |
| WO | WO-2020170203 A1 | 8/2020 |
| WO | WO-2021123394 A1 * | 6/2021 ............. A61P 25/00 |
| WO | WO-2022167457 A1 | 8/2022 |

OTHER PUBLICATIONS

STN-Chemical database registry RN 2094309-66-5 entry for 1N-[2-(cyclopropylamino)-4-fluorophenyl]-4-hydroxy-6-methyl-2-oxo-(2H)-Pyridineacetamide, Entered STN ED: May 2, 2017.*

"http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Apr. 1, 2015.*

"http://web.archive.org/web/20070406205858/http://www.aurorafinechemicals.com/english/order.html" dated Apr. 6, 2007, accessed Feb. 19, 2015.*

STN-Chemical Database Registry for 3-cyano-N-[3-[(cyclopropylamino)carbonyl]phenyl]-4,6-dimethyl-2-oxo-1(2H)-Pyridineacetamide, RN 1029772-20-0 entered into STN: Jun. 22, 2008.*

Jenkins "Discovery and Characterization of Novel Antagonists of the Proinflammatory Orphan Receptor GPR84." ACS Pharmacology & Translational Science, 2021, 4(5), 1598-1613.*

Luscombe "20 Years an Orphan: Is GPR84 a Plausible Medium-Chain Fatty Acid-Sensing Receptor?" DNA and Cell Biology vol. 39, No. 11, 2020 pp. 1926-1937.*

Chen "Modulation of the G-Protein-Coupled Receptor 84 (GPR84) by Agonists and Antagonists" J. Med. Chem. 2020, 63, 15399-15409.*

Marsango "Therapeutic validation of an orphan G protein-coupled receptor: The case of GPR84" Br J Pharmacol. 2022;179:3529-3541.*

Desrivot "Effect of GLPG1205, a GPR84 Modulator, on CYP2C9, CYP2C19, and CYP1A2 Enzymes: In Vitro and Phase 1 Studies" Clinical Pharmacology in Drug Development 2021, 10(9) 1007-1017.*

Torkildsen "Disease-modifying treatments for multiple sclerosis—a review of approved medications" European Journal of Neurology 2015, 23 (Suppl. 1):18-27.*

(56) References Cited

OTHER PUBLICATIONS

Alavi "The role of orphan G protein-coupled receptors in the pathophysiology of multiple sclerosis: A review" Life Sciences 224 (2019) 33-40.*
Bae, Cancer Targeted Drug Delivery, Springer: New York, 2013, p. v.*
Hayat, M.A. Autophagy Cancer, Other Pathologies, Inflammation, Immunity, Infection, and Aging vol. 5 Academic Press: Sand Diego, 2015, p. xxi.*
Carlo C. Maley and Mel Greaves Frontiers in Cancer Research Springer: 2016, pp. 18-19.*
Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Ledford "US cancer institute overhauls cell lines" Nature Feb. 25, 2016 vol. 530 p. 391.*
Johnson, et. al. "Relationships between drug activity in NCI preclinical in vitro and in vivo models and early clinical trials." British Journal of Cancer 2001, 84, 1424-1431.*
Bendele "Animal models of rheumatoid arthritis" J Musculoskel Neuron Interact 2001; 1(4):377-385.*
University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.*
Tomohiro Chiba "Emerging Therapeutic Strategies in Alzheimer's Disease" Intech 2013, 181-225.*
Le Bars, et. al. "Animal Models of Nociception" Pharmacological Reviews 2001, 53, 597-652, at p. 634.*
Costigan "Neuropathic Pain: A Maladaptive Response of the Nervous System to Damage" Annu. Rev. Neurosci. 2009. 32:1-32.*
Elborn "Cystic fibrosis" The Lancet, Published online Apr. 29, 2016 Online "http://dx.doi.org/10.1016/S0140-6736(16)00576-6" 1-13.*
Schober "New Advances in the Treatment of Metastatic Pancreatic Cancer" Digestion 2015;92:175-184.*
Zhao "Vaccine adjuvants: mechanisms and platforms" Signal Transduction and Targeted Therapy (2023) 8:283.*
Al Mahmud, Z. et al., "Three classes of ligands each bind to distinct sites on the orphan G protein-coupled receptor GPR84," *Scientific Reports*, pp. 1-15 (2017).
Ando, M. et al., "Discovery of novel phenethylpyridone derivatives as potent melanin-concentrating hormone 1 receptor antagonists," Bioorganic & Medicinal Chemistry Letters vol. 19, pp. 5186-5190 (2009).
Chen, L. et al., "Modulation of the G-Protein-Coupled Receptor 84 (GPR84) by Agonists and Antagonists," *J. Med. Chem.*, pp. 1-11.
Cosin-Roger, J. et al., "Metabolite Sensing CPCRs: Promising Therapeutic Targets for Cancer Treatment," *Cells*, vol. 9, pp. 1-33 (2020).
Dietrich, P.A., et .al., "GPR84 sustains aberrant ß-catenin signaling in leukemic stem cells for maintenance of MLL leukemogenesis," *Blood*, vol. 124, No. 22, pp. 3284-3294 (2013).
Fredriksson, R. et. al., "The G-Protein-Coupled Receptors in the Human Genome Form Five Main Families. Phylogenetic Analysis, Paralogon Groups, and Fingerprints," *Mol. Pharmacol.*, vol. 63, No. 6, pp. 1256-1272 (2003).
Gamo, K. et. al., "G-Protein-Coupled Receptor Screen Reveals a Role for Chemokine Receptor CCR5 in Suppressing Microglial Neurotoxicity," *The Journal of Neuroscience*, 28(46), pp. 11980-11988 (2008).
International Search Report and Written Opinion for International Application No. PCT/EP2022/052400, dated Jul. 27, 2022.
International Search Report and Written Opinion for International Application No. PCT/EP2022/052419, dated Jul. 11, 2022.

Labeguere, F. et al., "Discovery of 9-Cyclopropylethynyl-2-((S-1-[1,4]dioxan-2-ylmethoxy)-6,7-dihydropyrimido[6,1-a]isoquinolin-4-one (GLPG1205), a Unique GPR84 Negative Allosteric Modulator Undergoing Evaluation in a Phase II Clinical Trial," *J. Med. Chem.*, vol. 63, pp. 13526-13545 (2020).
Mancini, S.J. et al., "On-target and off-target effects of novel orthosteric and allosteric activators of GPR84," *Scientific Reports*, vol. 9, pp. 1-15 (2019).
Nanthakumar, C.B. et. al., "Dissecting fibrosis: therapeutic insights from the small-molecule toolbox," *Nature Reviews*, vol. 14, pp. 693-720 (2015).
News & Analysis, BioBusiness Briefs, Target Watch, "GPR84: an immune response dial," vol. 19, p. 374 (2020).
Partial International Search Report for International Application PCT/EP/2022/052400 dated May 10, 2022.
Partial International Search Report for International Application PCT/EP/2022/052419 dated May 20, 2022.
Raghu G. and Selman, M. "Nintedanib and Pirfenidone, New Antifibrotic Treatments Indicated for Idiopathic Pulmonary Fibrosis Offer Hopes and Raises Questions," *Am. J. Resp. and Crit. Care Med.*, vol. 191, No. 3, pp. 252-254 (2015).
Reddy, N. et. al., "Dual catalysis by Cu(i): facile single step click and intramolecular C—O bond formation leading to triazole tethered dihydrobenzodioxines/benzoxazines/benzoxathiines/benzodioxepines," *Organic & Biomolecular Chemistry*, vol. 11, No. 42, pp. 7350-7360 (2013).
Thanigaimalai, P. et. al., ("6-(Ar)Alkylamino-Substituted Uracil Derivatives: Lipid Mimetics with Potent Activity at the Orphan G Protein-Coupled Receptor 84 (GPR84)," *ACS Omega*, vol. 3, No. 3, pp. 3365-3383 (2018).
Vincetti, P. et. al., "Discovery of Multitarget Antivirals Acting on Both the Dengue Virus NS5-NS3 Interaction and the Host Src/Fyn Kinases," *J. Med. Chem.*, vol. 58, pp. 4964-4975 (2015).
Wacker, D. et al., "How ligands illuminate GPCR molecular pharmacology," *Cell*, pp. 1-29, (2017).
Yu, J. et. al., "Synthesis and antitumor activity of novel 2,3-diethanethio-2,3,5-trideoxy-5-triazolo nucleoside anlogues," *European J. Med. Chem.*, Elsevier, Amsterdam, NL, vol. 45, No. 7, pp. 3219-3222 (2010).
Bouchard C., et al. in "G protein-coupled receptor 84, a microglia-associated protein expressed in neuroinflammatory conditions." Glia. 2007; 55(8):790-800.
Gagnon, L., et al. in "A Newly Discovered Antifibrotic Pathway Regulated by Two Fatty Acid Receptors: GPR40 and GPR84." American J. of Path., 2018, 188(5); 1132-1148.
Labéguère F., et al. in "Discovery of 9-Cyclopropylethynyl-2-((S)-1-[1,4]dioxan-2-ylmethoxy)-6,7-dihydropyrimido[6,1-a]isoquinolin-4-one (GLPG1205), a Unique GPR84 Negative Allosteric Modulator Undergoing Evaluation in a Phase II Clinical Trial." J Med Chem. 2020; 63(22):13526-13545.
Luscombe V. B., et al. in DNA Cell Biol. Nov. 2020;39(11):1926-1937, describes GPR84, its role as an inflammation-induced receptor highly expressed on immune cells, its subsequent physiological activity, and exemplary medical conditions where patients would benefit from receiving a GPR84 antagonist (See, e.g., Tables 1 and 2 in Luscombe VB, et al.).
Nguyen Q. T., et al. in "PBI-4050 reduces pulmonary hypertension, lung fibrosis, and right ventricular dysfunction in heart failure." Cardiovasc Res. 2020; 116(1):171-182.
Nicol, L. S., et al. in "The role of G-protein receptor 84 in experimental neuropathic pain." J. Neurosci. 2015; 35(23):8959-69.
Puengel, T., et al. in "The Medium-Chain Fatty Acid Receptor GPR84 Mediates Myeloid Cell Infiltration Promoting Steatohepatitis and Fibrosis." J Clin Med. 2020; 9(4):1140.
Recio C., et al. in "Activation of the Immune-Metabolic Receptor GPR84 Enhances Inflammation and Phagocytosis in Macrophages." Front Immunol. 2018; 9:1419.
Simard, J. C., et al. in "Fatty acid mimetic PBI-4547 restores metabolic homeostasis via GPR84 in mice with non-alcoholic fatty liver disease." Sci Rep. 2020; 10, 12778.

(56) References Cited

OTHER PUBLICATIONS

Wei L., et al. in "Agonists for G-protein-coupled receptor 84 (GPR84) alter cellular morphology and motility but do not induce pro-inflammatory responses in microglia." J Neuroinflammation. 2017; 14(1):198.

Yin, C. et al. in "Regulatory role of Gpr84 in the switch of alveolar macrophages from CD11blo to CD11bhi status during lung injury process." Mucosal Immun. 2020; 13(6): 892-907.

Kalisiak, J. et al., "Efficient Synthesis of 2-Substituted-1,2,3-triazoles," Org. Lett., 10(15):3171-3174 (2008).

STN Registry Database, Registry No. 876592-08-4 for "4-Phenyl-1H-1,2,3-triazole-1-methano,l" entered on Mar. 13, 2006, 3 pages.

STN Registry Database, Registry No. 1043552-81-3 for "4-[4-(1,1-Dimethylethyl)phenyl]-1H-1,2,3-triazole-1-methanol," entered on Aug. 25, 2008, 3 pages.

Doohyun, L. et al., "Efficient Syntheses of 1,2,3-Triazoloamide Derivatives Using Solid- and Solution-Phase Synthetic Approaches," Molecules, vol. 20, No. 11, (2015) pp. 19984-20013.

Mohammadi, L. et al., "Synthesis of nanomagnetic supported thiourea-copper(I) catalyst and its application the syntheses of triazoles and benzamides," Applied Organometallic Chemistry, Longman Group UK, Ltd, Hobohoken, USA, vol. 32, No. 1 (2017).

Paolo, V. et al., "Discovery of Multitarget Antivirals Acting on Both the Dengue Virus NS5-NS3 Interaction and the Host Src/Fyn Kinases," Journal of Medicinal Chemistry, vol. 58, No. 12 (2015) pp. 4964-4975.

\* cited by examiner

GPR84 ANTAGONISTS AND USES THEREOF

CROSS REFERENCE TO RELATED APPLICATIONS

This application claims the benefit of and priority to U.S. Provisional Patent Application Ser. No. 63/144,701, filed Feb. 2, 2021; the contents of which are hereby incorporated by reference.

TECHNICAL FIELD OF THE INVENTION

The present invention relates to compounds and methods useful for antagonizing G-protein coupled receptor 84 (GPR84). The invention also provides pharmaceutically acceptable compositions comprising compounds of the present invention and methods of using said compositions in the treatment of various disorders.

BACKGROUND OF THE INVENTION

The G-protein coupled receptor 84 (GPR84), also known as EX33, GPCR4, and G protein-coupled receptor 84, is a medium chain fatty acid receptor mainly expressed in immune cells and upregulated under inflammatory conditions.

GPR84 was isolated and characterized from human B cells (Wittenberger et al. 2001. *J. Mol. Biol.* 307, 799-813.) as the result of an expressed sequence tag data mining strategy, and also using a degenerate primer reverse transcriptase-polymerase chain reaction (RT-PCR) approach aimed to identify novel chemokine receptors expressed in neutrophils (Yousefi S et al. 2001. *J. Leukoc. Biol.* 69, 1045-1052.).

GPR84 remained an orphan GPCR until the identification of medium-chain Free Fatty Acids (FFAs) with carbon chain lengths of 9-14 as ligands for this receptor (Wang J et al. 2006. *J. Biol. Chem.* 281, 34457-34464.). GPR84 was described to be activated by capric acid (C10:0), undecanoic acid (C11:0) and lauric acid (C12:0) with potencies of 5 µM, 9 µM and 11 µM, respectively. Three small molecules were also described to have some GPR84 agonist activity: 3,3'-diindolylmethane (DIM) (Wang et al. 2006), embelin (Hakak Y et al. 2007. WO2007027661 (A2).) and 6-n-octylaminouracil (6-OAU) (Suzuki M et al. 2013. *J. Biol. Chem.* 288, 10684-10691.).

GPR84 has been shown to be expressed in immune cells at least but not limited to polymorphonuclear leukocytes (PMN), neutrophils, monocytes, T cells and B cells. (Hakak et al. 2007; Venkataraman C, Kuo F. 2005. *Immunol. Lett.* 101, 144-153; Wang et al. 2006; Yousefi et al. 2001). Higher levels of GPR84 were measured in neutrophils and eosinophils than in T-cells and B-cells. GPR84 expression was demonstrated in tissues that may play a role in the propagation of the inflammatory response such as lung, spleen, bone marrow.

For example, in a recent review, du Bois reported the current status of therapies for lung interstitial diseases, such as idiopathic pulmonary fibrosis (IPF). There are almost 300 distinct injurious or inflammatory causes of interstitial lung disease that can result in diffuse lung scarring, and the initial stages of the IPF pathology are very likely to involve inflammation (du Bois R M. 2010. *Nat. Rev. Drug Discov.* 9, 129-140.), and combination therapies involving anti-inflammatory treatment could be advantageously used.

The expression of GPR84 was highly up-regulated in monocytes/macrophages upon LPS stimulation (Wang et al. 2006).

GPR84 knock-out (KO) mice are viable and indistinguishable from wild-type littermate controls (Venkataraman & Kuo 2005). The proliferation of T and B cells in response to various mitogens is reported to be normal in GPR84-deficient mice (Venkataraman & Kuo 2005). T helper 2 (Th2) differentiated T cells from GPR84 KO mice secreted higher levels of IL4, IL5, IL13, the 3 major $Th_2$ cytokines, compared to wild-type littermate controls. In contrast, the production of the Th1 cytokine, INFγ, was similar in Th1 differentiated T cells from GPR84 KO mice and wild-type littermate (Venkataraman & Kuo 2005).

In addition, capric acid, undecanoic acid and lauric acid dose dependently increased the secretion of interleukin-12 p40 subunit (IL-12 p40) from RAW264.7 murine macrophage-like cells stimulated with LPS. The pro-inflammatory cytokine IL-12 plays a pivotal role in promoting cell-mediated immunity to eradicate pathogens by inducing and maintaining T helper 1 (Th1) responses and inhibiting T helper 2 (Th2) responses. Medium-chain FFAs, through their direct actions on GPR84, may affect Th1/Th2 balance.

Berry et al. identified a whole-blood 393-gene transcriptional signature for active tuberculosis (TB) (Berry M P R et al. 2010. *Nature* 466, 973-977.). GPR84 was part of this whole-blood 393-gene transcriptional signature for active TB indicating a potential role for GPR84 in infectious diseases.

GPR84 expression was also described in microglia, the primary immune effector cells of the central nervous system (CNS) of myeloid-monocytic origin (Bouchard C et al. 2007. *Glia* 55, 790-800.). As observed in peripheral immune cells, GPR84 expression in microglia was highly inducible under inflammatory conditions such as TNFα and IL1 treatment but also notably endotoxemia and experimental autoimmune encephalomyelitis (EAE), suggesting a role in neuro-inflammatory processes. Those results suggest that GPR84 would be up-regulated in CNS not only during endotoxemia and multiple sclerosis, but also in all neurological conditions in which TNFα or IL-1β pro-inflammatory cytokines are produced, including brain injury, infection, Alzheimer's disease (AD), Parkinson's disease (PD).

GPR84 expression was also observed in adipocytes and shown to be enhanced by inflammatory stimuli (Nagasaki H et al. 2012. *FEBS Lett.* 586, 368-372.). The results suggest that the expression of GPR84 is triggered by TNFα from infiltrating macrophages and exacerbates the vicious cycle between adiposity and diabetes/obesity, and therefore the inhibition of GPR84 activity might be beneficial for the treatment of endocrine and/or metabolic diseases.

GPR84 expression is also upregulated in microglia surrounding the neurons, after nerve injury. (Gamo et al, 2008. *J. Neurosi.* 28(46), 11980-11988.). Furthermore, in GPR84 knock-out mice, hypersensitivity to mechanical stimuli were significantly reduced or completely absent in mouse models of inflammatory and neuropathic pain (Nicol L S C et al. 2015. *J. Neurosci.* 35, 8959-8969.). Molecules which block the activation of GPR84 may therefore have the potential to deliver broad-spectrum analgesia.

GPR84 expression is increased in human leukemic stem cells (LSC) from acute myeloid leukemia (AML) patients compared to hematopoietic stem cells from healthy donors.

GPR84 simultaneously augments β-catenin signaling and an oncogenic transcription program essential for establishment of MLL leukemia (Dietrich et al, 2014. *Blood* 124(22), 3284-3294). Suppression of GPR84 significantly inhibited cell growth in pre-LSCs, reduced LSC frequency and impaired reconstitution of stem cell-derived MLL leukemia, which represents a particularly aggressive and drug-resistant subtype of AML. Targeting the oncogenic GPR84/β-catenin signaling axis may represent a novel therapeutic strategy for AML and possibly other leukemias.

GPR84 expression is increased by 49.9 times in M1 type macrophages isolated from aortic atherosclerotic lesions of LDLR-/- mice fed a western diet (Kadl A et al. 2010. *Circ. Res.* 107, 737-746.). Therefore, molecules targeting GPR84 may have a potential benefit in treatment of atherosclerosis.

In experimental esophagitis, GPR84 is upregulated in the esophageal tissue, mainly in the epithelial cells, and is significantly decreased in rats treated with either omeprazole (proton pump inhibitor) or STW5, an herbal preparation shown to ameliorate esophagitis without affecting refluxate pH (Abdel-Aziz H et al. 2015. *Mol. Med.* 21, 1011-1024.). This finding is supported by Western blot and immunohistochemistry in rat tissue and HET-1A cells, a human esophageal squamous cell line. GPR84 was also found to be significantly upregulated in esophageal biopsies from patients with grade B reflux esophagitis. Molecules that block the GPR84 receptor activity may therefore represent a new therapeutic paradigm for the treatment of esophagitis.

Therefore, the identification and development of novel compounds, processes for their preparation and their use in the preparation of a medicament would be highly desirable for patients suffering from inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions.

Additionally, the identification and development of novel compounds for use in the preparation of a medicament for the prophylaxis and/or treatment of one or more fibrotic diseases, and more particularly NASH and/or IPF remains highly desirable.

SUMMARY OF THE INVENTION

It has now been found that compounds of this invention, and pharmaceutically acceptable compositions thereof, are effective as antagonists of GPR84. In certain embodiments, the invention provides for compounds of the formulae presented herein.

Compounds of the present invention, and pharmaceutically acceptable compositions thereof, are useful for treating a variety of diseases, disorders or conditions, associated with GPR84. Such diseases, disorders, or conditions include those described herein.

Compounds provided by this invention are also useful for the study of GPR84 in biological and pathological phenomena; the study of fibrotic processes occurring in bodily tissues; and the comparative evaluation of new GPR84 inhibitors or other regulators of neutrophil and macrophage chemotaxis in vitro or in vivo.

DETAILED DESCRIPTION OF CERTAIN EMBODIMENTS

1. General Description of Certain Embodiments of the Invention

In certain aspects, the present invention provides a compound of formula I:

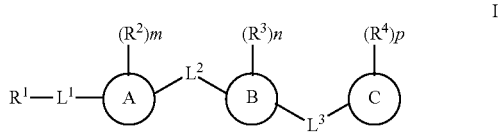

or a pharmaceutically acceptable salt thereof, wherein each of Ring A, Ring B, Ring C, $L^1$, $L^2$, $L^3$, $R^1$, $R^2$, $R^3$, $R^4$, m, n, and p, is as defined below and described in embodiments herein, both singly and in combination.

In some embodiments, the present invention provides a pharmaceutical composition comprising a compound of formula I and a pharmaceutically acceptable carrier, adjuvant, or diluent.

In some embodiments, the present invention provides a method of treating a GPR84-mediated disease, disorder, or condition comprising administering to a patient in need thereof, a compound of formula I, or a pharmaceutically acceptable salt thereof.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

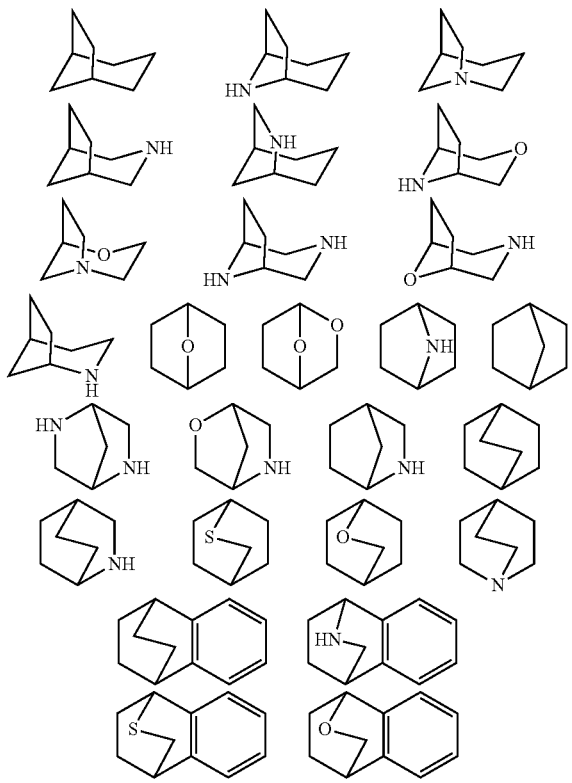

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $—(CH_2)_n—$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R°$; $-(CH_2)_{0-4}OR°$; $-O(CH_2)_{0-4}R°$, $-O-(CH_2)_{0-4}C(O)OR°$; $-(CH_2)_{0-4}CH(OR°)_2$; $-(CH_2)_{0-4}SR°$; $-(CH_2)_{0-4}Ph$, which may be substituted with $R°$; $-(CH_2)_{0-4}O(CH_2)_{0-1}Ph$ which may be substituted with $R°$; $-CH=CHPh$, which may be substituted with $R°$; $-(CH_2)_{0-4}O(CH_2)_{0-1}$-pyridyl which may be substituted with $R°$; $-NO_2$; $-CN$; $-N_3$; $-(CH_2)_{0-4}N(R°)_2$; $-(CH_2)_{0-4}N(R°)C(O)R°$; $-N(R°)C(S)R°$; $-(CH_2)_{0-4}N(R°)C(O)NR°_2$; $-N(R°)C(S)NR°_2$; $-(CH_2)_{0-4}N(R°)C(O)OR°$; $-N(R°)N(R°)C(O)R°$; $-N(R°)N(R°)C(O)NR°_2$; $-N(R°)N(R°)C(O)OR°$; $-N(R°)C(NR°)N(R°)_2$; $-(CH_2)_{0-4}C(O)R°$; $-C(S)R°$; $-(CH_2)_{0-4}C(O)OR°$; $-(CH_2)_{0-4}C(O)SR°$; $-(CH_2)_{0-4}C(O)OSiR°_3$; $-(CH_2)_{0-4}OC(O)R°$; $-OC(O)(CH_2)_{0-4}SR°$; $-SC(S)SR°$; $-(CH_2)_{0-4}SC(O)R°$; $-(CH_2)_{0-4}C(O)NR°_2$; $-C(S)NR°_2$; $-C(S)SR°$; $-SC(S)SR°$, $-(CH_2)_{0-4}OC(O)NR°_2$; $-C(O)N(OR°)R°$; $-C(O)C(O)R°$; $-C(O)CH_2C(O)R°$; $-C(NOR°)R°$; $-(CH_2)_{0-4}SSR°$; $-(CH_2)_{0-4}S(O)_2R°$; $-(CH_2)_{0-4}S(O)_2OR°$; $-(CH_2)_{0-4}OS(O)_2R°$; $-S(O)_2NR°_2$; $-(CH_2)_{0-4}S(O)R°$; $-N(R°)S(O)_2NR°_2$; $-N(R°)S(O)_2R°$; $-N(OR°)R°$; $-C(NH)NR°_2$; $-P(O)_2R°$; $-P(O)R°_2$; $-OP(O)R°_2$; $-OP(O)(OR°)_2$; $-SiR°_3$; $-(C_{1-4}$ straight or branched alkylene)O$-N(R°)_2$; or $-(C_{1-4}$ straight or branched alkylene)C(O)O$-N(R°)_2$, wherein each $R°$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

In certain embodiments, a suitable monovalent substituents on a substitutable carbon atom of an "optionally substituted" group are independently halogen; $-(CH_2)_{0-4}R°$; $-(CH_2)_{0-4}OR°$; $-O(CH_2)_{0-4}R°$, $-O-(CH_2)_{0-4}C(O)OR°$; $-(CH_2)_{0-4}CH(OR°)_2$; $-(CH_2)_{0-4}SR°$; $-(CH_2)_{0-4}Ph$, which may be substituted with $R°$; $-(CH_2)_{0-4}O(CH_2)_{0-1}Ph$ which may be substituted with $R°$; $-CH=CHPh$, which may be substituted with $R°$; $-(CH_2)_{0-4}O(CH_2)_{0-1}$-pyridyl which may be substituted with $R°$; $-NO_2$; $-CN$; $-N_3$; $-(CH_2)_{0-4}N(R°)_2$; $-(CH_2)_{0-4}N(R°)C(O)R°$; $-N(R°)C(S)R°$; $-(CH_2)_{0-4}N(R°)C(O)NR°_2$; $-N(R°)C(S)NR°_2$; $-(CH_2)_{0-4}N(R°)C(O)OR°$; $-N(R°)N(R°)C(O)R°$; $-N(R°)N(R°)C(O)NR°_2$; $-N(R°)N(R°)C(O)OR°$; $-N(R°)C(NR°)N(R°)_2$; $-(CH_2)_{0-4}C(O)R°$; $-C(S)R°$; $-(CH_2)_{0-4}C(O)OR°$; $-(CH_2)_{0-4}C(O)SR°$; $-(CH_2)_{0-4}C(O)OSiR°_3$; $-(CH_2)_{0-4}OC(O)R°$; $-OC(O)(CH_2)_{0-4}SR°$; $-SC(S)SR°$; $-(CH_2)_{0-4}SC(O)R°$; $-(CH_2)_{0-4}C(O)NR°_2$; $-C(S)NR°_2$; $-C(S)SR°$; $-SC(S)SR°$, $-(CH_2)_{0-4}OC(O)NR°_2$; $-C(O)N(OR°)R°$; $-C(O)C(O)R°$; $-C(O)CH_2C(O)R°$; $-C(NOR°)R°$; $-(CH_2)_{0-4}SSR°$; $-(CH_2)_{0-4}S(O)_2R°$; $-(CH_2)_{0-45}(O)_2OR°$; $-(CH_2)_{0-4}OS(O)_2R°$; $-S(O)_2NR°_2$; $-(CH_2)_{0-4}S(O)R°$; $-N(R°)S(O)_2NR°_2$; $-N(R°)S(O)_2R°$; $-N(OR°)R°$; $-C(NH)NR°_2$; $-P(O)_2R°$; $-P(O)R°_2$; $-OP(O)R°_2$; $-OP(O)(OR°)_2$; $-SiR°_3$; $-(C_{1-4}$ straight or branched alkylene)O$-N(R°)_2$; or $-(C_{1-4}$ straight or branched alkylene)C(O)O$-N(R°)_2$, wherein each $R°$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 3-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR°$_3$, —OSiR°$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R, —S(O)$_2$NR$^\dagger{}_2$, —C(S)NR$^\dagger{}_2$, —C(NH)NR$^\dagger{}_2$, or —N(R$^\dagger$)$^{S(O)}{}_2$R; wherein each R is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

In certain embodiments, $R^1$ of a provided compound comprises one or more deuterium atoms. In certain embodiments, $R^2$ of a provided compound comprises one or more deuterium atoms. In certain embodiments, $R^3$ of a provided compound comprises one or more deuterium atoms. In certain embodiments, $R^4$ of a provided compound comprises one or more deuterium atoms. In certain embodiments, $R^5$ of a provided compound comprises one or more deuterium atoms. In certain embodiments, $L^1$ of a provided compound comprises one or more deuterium atoms. In certain embodiments, $L^2$ of a provided compound comprises one or more deuterium atoms. In certain embodiments, $L^3$ of a provided compound comprises one or more deuterium atoms. In certain embodiments, Ring A of a provided compound comprises one or more deuterium atoms. In certain embodiments, Ring B of a provided compound comprises one or more deuterium atoms. In certain embodiments, Ring C of a provided compound comprises one or more deuterium atoms. In certain embodiments, R of a provided compound may be substituted with one or more deuterium atoms. In certain embodiments, $R^z$ of a provided compound may be substituted with one or more deuterium atoms.

The structures as drawn represent relative configurations, unless labeled as absolute configurations. The invention contemplates individual enantiomers and racemic mixtures.

As used herein, a "GPR84 antagonist" or a "GPR84 inhibitor" is a molecule that reduces, inhibits, or otherwise diminishes one or more of the biological activities of GPR84 (e.g. Gαi signaling, increased immune cell migration, and secretion of proinflammatory cytokines). Antagonism using the GPR84 antagonist does not necessarily indicate a total elimination of the GPR84 activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of GPR84 compared to an appropriate control. In some embodiments, the GPR84 antagonist reduces, inhibits, or otherwise diminishes the activity of GPR84. The presently disclosed compounds bind directly to GPR84 and inhibit its activity.

By "specific antagonist" is intended an agent that reduces, inhibits, or otherwise diminishes the activity of a defined target greater than that of an unrelated target. For example, a GPR84 specific antagonist reduces at least one biological activity of GPR84 by an amount that is statistically greater than the inhibitory effect of the antagonist on any other protein (e.g., other GPCRs). In some embodiments, the $IC_{50}$ of the antagonist for the target is about 90%, 80%, 70%, 60%, 50%, 40%, 30%, 20%, 10%, 5%, 1%, 0.1%, 0.01%, 0.001% or less of the $IC_{50}$ of the antagonist for a non-target. The presently disclosed compounds may or may not be a specific GPR84 antagonist. A specific GPR84 antagonist reduces the biological activity of GPR84 by an amount that is statistically greater than the inhibitory effect of the antagonist on any other protein (e.g., other GPCRs). In certain embodiments, the GPR84 antagonist specifically inhibits the activity of GPR84. In some of these embodiments, the $IC_{50}$ of the GPR84 antagonist for GPR84 is about 90%, 80%, 70%, 60%, 50%, 40%, 30%, 20%, 10%, 0.1%, 0.01%, 0.001%, or less of the $IC_{50}$ of the GPR84 antagonist for a closely related GPCR (e.g., a free fatty acid receptor (FFAR) such as GPR40 (FFAR1), GPR41 (FFAR3), GPR43 (FFAR2), or GPR120 (FFAR4)) or other type of GPCR (e.g., a Class A GPCR).

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., *Angew. Chem. Int. Ed.* 2002, 41, 2596-99 and Sun et al., *Bioconjugate Chem.*, 2006, 17, 52-57. In some embodiments, such moieties may be attached via a strained alkyne. Methods of using strained alkynes to enable rapid Cu-free click chemistry are known in the art and include those described by Jewett et al., *J Am. Chem. Soc.* 2010, 132(11), 3688-3690.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$ $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethyl-rhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

A compound of the present invention may be tethered to an E3 ligase binding moiety. It will be appreciated that such compounds are useful as degraders (see, for example, Kostic and Jones, *Trends Pharmacol. Sci.*, 2020, 41(5), 305-31; Ottis and Crews, *ACS Chem. Biol.* 2017, 12(4), 892-898.). One of ordinary skill in the art will recognize that an E3 ligase binding moiety may be attached to a provided compound via a suitable substituent as defined above. Such degraders have been found to be useful for the targeted degradation of G-protein coupled receptors (Li et al. *Acta Pharm. Sin. B.* 2020, 10(9), 1669-1679.).

As used herein, the term "E3 ligase binding moiety" is used interchangeably with the term "E3 ligase binder" and relates to any moiety capable of binding to and/or recruiting an E3 ligase (e.g., cIAP1, MDM2, cereblon, VHL, APC/C) for targeted degradation.

A compound of the present invention may be tethered to a lysosome targeting moiety. It will be appreciated that such compounds are useful as degraders (see, for example, Banik et al. 2020. *Nature* 584, 291-297.). One of ordinary skill in the art will recognize that a lysosome targeting moiety may be attached to a provided compound via a suitable substituent as defined above. Such degraders have been found to be useful for the targeted degradation of secreted and membrane proteins (Banik et al. 2020).

As used herein, the term "lysosome targeting moiety" is used interchangeably with the term "lysosome binding moiety" and relates to any moiety capable of binding to and/or recruiting a cell surface lysosome targeting receptor (e.g., cation-independent mannose-6-phosphate receptor, CI-M6PR) for targeted degradation.

The terms "measurable affinity" and "measurably inhibit," as used herein, means a measurable change in a GPR84 activity between a sample comprising a compound of the present invention, or composition thereof, and a GPR84 GPCR, and an equivalent sample comprising a GPR84 GPCR, in the absence of said compound, or composition thereof.

3. Description of Exemplary Embodiments

As described above, in certain embodiments, the present invention provides a compound of formula I:

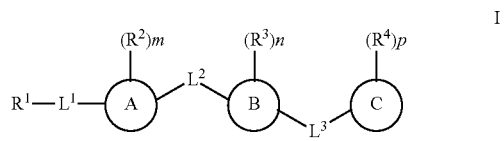

or an N-oxide, or a pharmaceutically acceptable salt thereof, wherein:

Ring A is phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; an 8-10 membered partially aromatic or heteroaromatic bicyclic heterocyclic ring having 1-4 heteroatoms independently selected from nitrogen, oxygen, and sulfur; or a 4-8 membered saturated or partially unsaturated monocyclic heterocyclic ring having 1-2 heteroatoms independently selected from nitrogen, oxygen, and sulfur;

Ring B is a 6-membered monocyclic partially unsaturated heterocyclyl or heteroaryl ring having 1-4 heteroatoms independently selected from nitrogen, oxygen, and sulfur; an 8-10 membered partially aromatic or heteroaromatic bicyclic heterocyclic ring having 1-4 heteroatoms independently selected from nitrogen, oxygen, and sulfur; or phenyl;

Ring C is a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; phenyl; a 3-7 membered saturated or partially unsaturated monocyclic carbocyclic ring; an 8-10 membered bicyclic heteroaromatic ring (having 1-5 heteroatoms independently selected from nitrogen, oxygen, and sulfur); or an 8-10 membered partially aromatic or heteroaromatic bicyclic heterocyclic ring having 1-4 heteroatoms independently selected from nitrogen, oxygen, and sulfur;

$R^1$ is selected from (i) a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 4-8 membered saturated or partially unsaturated monocyclic heterocyclic ring having 1-2 heteroatoms independently selected from nitrogen, oxygen, and sulfur; phenyl; or a $C_{1-6}$ aliphatic; each of which is substituted with q instances of $R^5$; and (ii) hydrogen, —CN, or —OR;

each instance of $R^2$, $R^4$, and $R^5$ is independently hydrogen, deuterium, $R^z$, halogen, —CN, —NO$_2$, —OR, —SR, —NR$_2$, —S(O)$_2$R, —S(O)$_2$NR$_2$, —S(O)R, —S(O)NR$_2$, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —Si(OR)R$_2$, —SiR$_3$, —P(O)(R)NR$_2$, —P(O)(R)OR or —P(O)R$_2$; or two $R^2$ groups are optionally taken together to form =O; two $R^4$ groups are optionally taken together to form =O; two $R^5$ groups are optionally taken together to form =O;

two R² groups are optionally taken together with their intervening atoms to form a 5-8 membered saturated, partially unsaturated, or aryl fused ring having 0-3 heteroatoms independently selected from nitrogen, oxygen and sulfur;

two R⁴ groups are optionally taken together with their intervening atoms to form an optionally substituted 5-8 membered saturated, partially unsaturated, or aryl fused ring having 0-3 heteroatoms independently selected from nitrogen, oxygen and sulfur; or two R⁵ groups are optionally taken together with their intervening atoms to form a 5-8 membered saturated, partially unsaturated, or aryl fused ring having 0-3 heteroatoms independently selected from nitrogen, oxygen and sulfur; or two R⁵ groups are optionally taken together with their intervening atoms to form a 3-7 membered saturated or partially unsaturated monocyclic carbocyclic ring;

each $R^z$ is independently selected from an optionally substituted group selected from $C_{1-6}$ aliphatic; phenyl; a 3-7 membered saturated or partially unsaturated monocyclic carbocyclic ring; a 4-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur;

each instance of R³ is independently selected from:
  (a) hydrogen, deuterium, halogen, —OR, —SR, —NR₂, —S(O)₂R, —S(O)₂NR₂, —S(O)R, —S(O)NR₂, —CF₂R, —CF₃, —CR₂(OR), —CR₂(NR₂), —C(O)R, —C(O)OR, —C(O)NR₂, —C(O)N(R)OR, —OC(O)R, —OC(O)NR₂, —C(S)NR₂, —N(R)C(O)OR, —N(R)C(O)R, —N(R)C(O)NR₂, —N(R)C(NR)NR₂, —N(R)NR₂, —N(R)S(O)₂NR₂, —N(R)S(O)₂R, —N=S(O)R₂, —S(NR)(O)R, —N(R)S(O)R, —N(R)CN; or
  (b) an optionally substituted group selected from $C_{1-6}$ aliphatic; phenyl; a 3-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur; or
  two R³ groups are optionally taken together to form =O or =S; or
  two R³ groups are optionally taken together with their intervening atoms to form a 5-8 membered saturated, partially unsaturated, or aryl fused ring having 0-3 heteroatoms independently selected from nitrogen, oxygen and sulfur;

L¹ is one of the following:
  (a) a $C_{1-5}$ bivalent straight or branched saturated or unsaturated hydrocarbon chain wherein 1-2 methylene units of the chain are independently and optionally replaced with —O—, —C(O)—, —C(S)—, —C(R)₂—, —CH(R)—, —CH(OR)—, —C(F)₂—, —N(R)—, —S—, —S(O)—, or —S(O)₂—; or
  (b) a covalent bond;

L² and L³ are independently one of the following:
  (a) a $C_{1-3}$ bivalent straight or branched saturated or unsaturated hydrocarbon chain wherein 1-2 methylene units of the chain are independently and optionally replaced with —O—, —C(O)—, —C(S)—, —C(R)₂—, —CH(R)—, —CH(OR)—, —C(F)₂—, —N(R)—, —S—, —S(O)—, or —S(O)₂—; or
  (b) a covalent bond;

each R is independently hydrogen, or an optionally substituted group selected from $C_{1-6}$ aliphatic; phenyl; an 8-10 membered bicyclic aryl ring, a 3-7 membered saturated or partially unsaturated monocyclic carbocyclic ring; a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; and an 8-10 membered bicyclic heteroaryl ring having 1-5 heteroatoms independently selected from nitrogen, oxygen, and sulfur; and/or two R groups on the same nitrogen are optionally taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur; and/or two R groups on vicinal carbons are taken together with the vicinal carbons to form an optionally substituted 3-7 membered monocyclic saturated or partially unsaturated carbocyclic ring or heterocyclic ring, wherein the heterocyclic ring has, in addition to the vicinal carbons, 0-3 heteroatoms independently selected from nitrogen, oxygen, and sulfur;

m is 0, 1, 2, 3, or 4;

n is 0, 1, 2, 3, or 4;

p is 0, 1, 2, 3, or 4; and q is 0, 1, 2, 3, or 4.

As defined generally above, Ring A is phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; an 8-10 membered partially aromatic or heteroaromatic bicyclic heterocyclic ring having 1-4 heteroatoms independently selected from nitrogen, oxygen, and sulfur; or a 4-8 membered saturated or partially unsaturated monocyclic heterocyclic ring having 1-2 heteroatoms independently selected from nitrogen, oxygen, and sulfur.

In some embodiments, Ring A is phenyl. In some embodiments, Ring A is a 3-7 membered saturated or partially unsaturated monocyclic carbocyclic ring. In some embodiments, Ring A is a 5-6 membered monocyclic heteroaryl ring having 1-4 heteroatoms independently selected from nitrogen, oxygen, and sulfur. In some embodiments, Ring A is an 8-10 membered partially aromatic or heteroaromatic bicyclic heterocyclic ring having 1-4 heteroatoms independently selected from nitrogen, oxygen, and sulfur. In some embodiments, Ring A is a 4-8 membered saturated or partially unsaturated monocyclic heterocyclic ring having 1-2 heteroatoms independently selected from nitrogen, oxygen, and sulfur.

In some embodiments, two R² groups are taken together to form =O and Ring A is a pyridone ring. In some embodiments, Ring A is piperazine ring. In some embodiments, Ring A is a pyridine ring.

In some embodiments, Ring A is

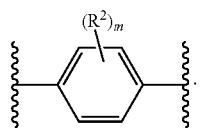

In some embodiments, Ring A is

In some embodiments, Ring A is

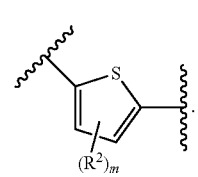

In some embodiments, Ring A is

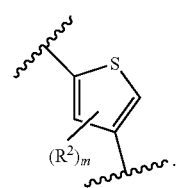

In some embodiments, Ring A is

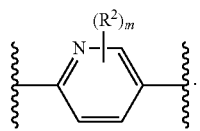

In some embodiments, Ring A is

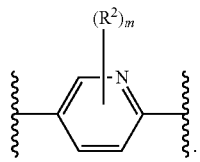

In some embodiments, Ring A is

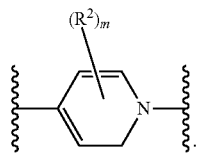

In some embodiments, Ring A is

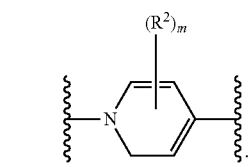

In some embodiments, Ring A is

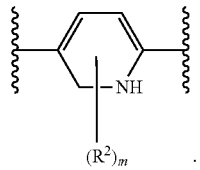

In some embodiments, Ring A is

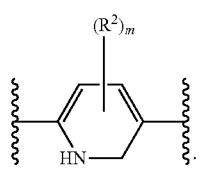

In some embodiments, Ring A is

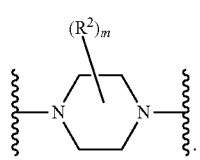

In some embodiments, Ring A is

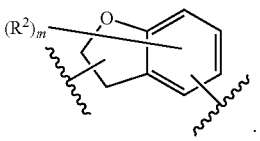

In some embodiments, the ⌇ on the left side of Ring A is connected to $L^1$ and the ⌇ on the right side of Ring A is connected to $L^2$. In some embodiments, the ⌇ on the right side of Ring A is connected to $L^1$ and the ⌇ on the left side of Ring A is connected to $L^2$.

In some embodiments, two R² groups are taken together to form =O and Ring A is

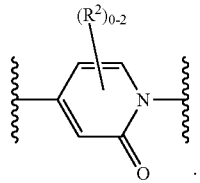

In some embodiments, two R² groups are taken together to form =O and Ring A is

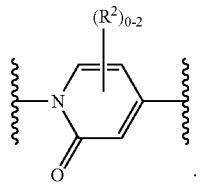

In some embodiments, two R² groups are taken together to form =O and Ring A is

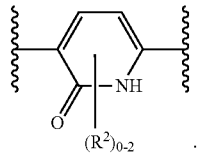

In some embodiments, two R² groups are taken together to form =O and Ring A is

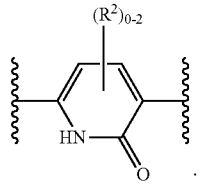

In some embodiments, two R² groups are taken together to form an optionally substituted aryl ring and Ring A with said optionally substituted aryl ring fused thereto is

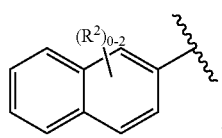

In some embodiments, two R² groups are taken together to form an optionally substituted aryl ring and Ring A with said optionally substituted aryl ring fused thereto is

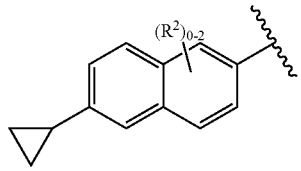

In some embodiments, ⌇ is attached to L². In some embodiments, two R² groups are taken together to form =O and Ring A is

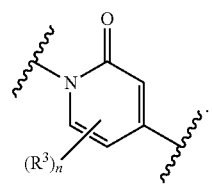

In some embodiments, two R² groups are taken together to form =O and Ring A is

In some embodiments, Ring A is selected from those depicted in Table 1, below.

As defined generally above, Ring B is a 6-membered monocyclic partially unsaturated heterocyclyl or heteroaryl ring having 1-4 heteroatoms independently selected from nitrogen, oxygen, and sulfur; an 8-10 membered partially aromatic or heteroaromatic bicyclic heterocyclic ring having 1-4 heteroatoms independently selected from nitrogen, oxygen, and sulfur; or phenyl.

In some embodiments, Ring B is a 6-membered monocyclic partially unsaturated heterocyclyl or heteroaryl ring having 1-4 heteroatoms independently selected from nitrogen, oxygen, and sulfur.

In some embodiments, Ring B is an 8-10 membered partially aromatic or heteroaromatic bicyclic heterocyclic ring having 1-4 heteroatoms independently selected from nitrogen, oxygen, and sulfur.

In some embodiments, Ring B is phenyl.

In some embodiments, Ring B is

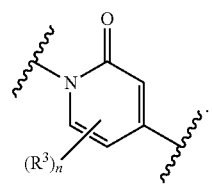

In some embodiments, Ring B is
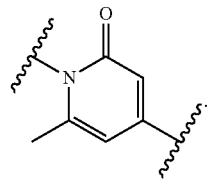
In some embodiments, Ring B is
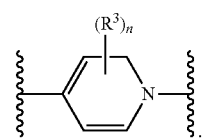
In some embodiments, Ring B is
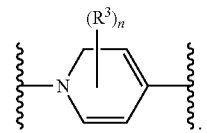
In some embodiments, Ring B is
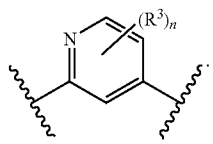
In some embodiments, Ring B is
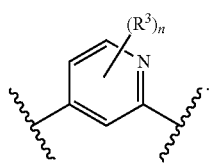
In some embodiments, Ring B is
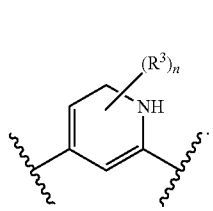
In some embodiments, Ring B is
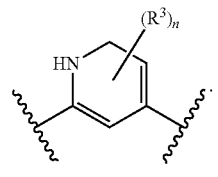
In some embodiments, Ring B is
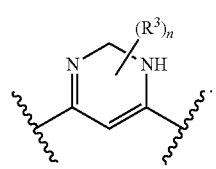
In some embodiments, Ring B is
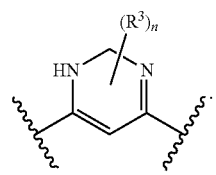
In some embodiments, Ring B is
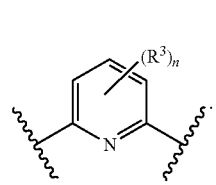
In some embodiments, Ring B is
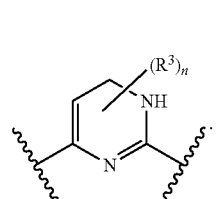
In some embodiments, Ring B is
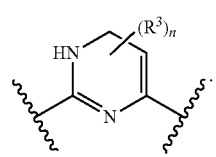

In some embodiments, Ring B is
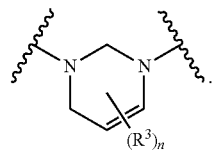
In some embodiments, Ring B is
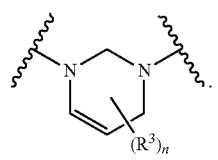
In some embodiments, Ring B is
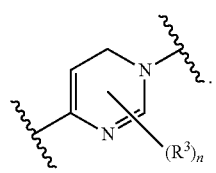
In some embodiments, Ring B is

In some embodiments, Ring B is
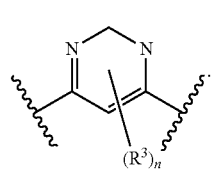
In some embodiments, Ring B is
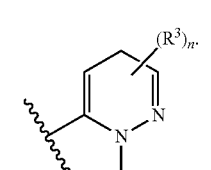
In some embodiments, Ring B is
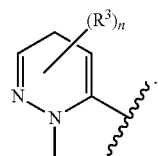
In some embodiments, Ring B is
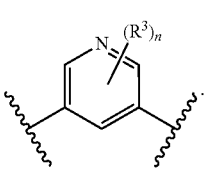
In some embodiments, Ring B is
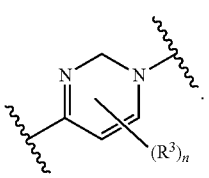
In some embodiments, Ring B is
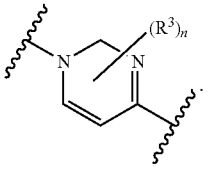
In some embodiments, Ring B is
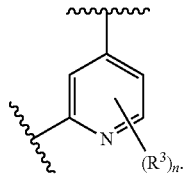
In some embodiments, Ring B is
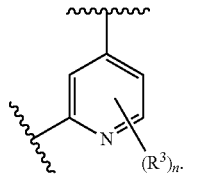

In some embodiments, Ring B is
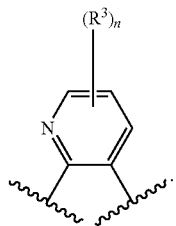
In some embodiments, Ring B is
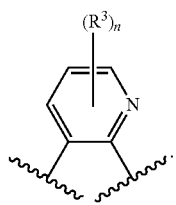
In some embodiments, Ring B is
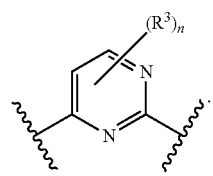
In some embodiments, Ring B is
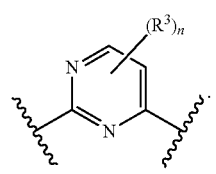
In some embodiments, Ring B is
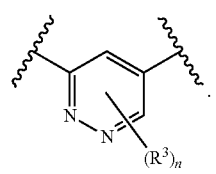
In some embodiments, Ring B is
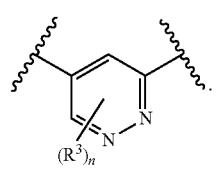
In some embodiments, Ring B is
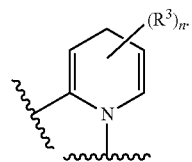
In some embodiments, Ring B is
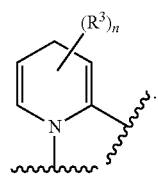
In some embodiments, Ring B is
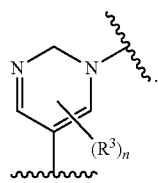
In some embodiments, Ring B is
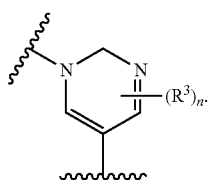
In some embodiments, Ring B is
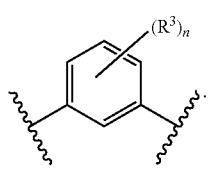
In some embodiments, Ring B is
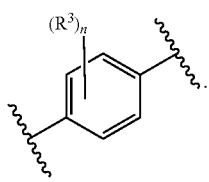

In some embodiments, Ring B is

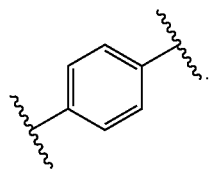 [SMILES: *c1ccc(*)cc1]

In some embodiments, Ring B is

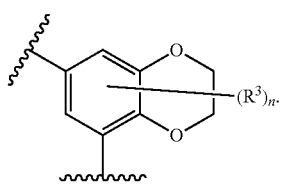

In some embodiments, Ring B is

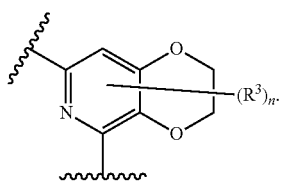

In some embodiments, Ring B is

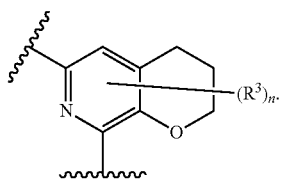

In some embodiments, Ring B is

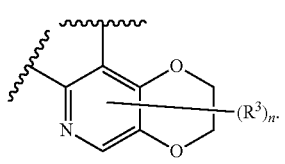

In some embodiments, Ring B is

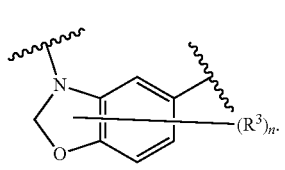

In some embodiments, two $R^3$ groups are taken together to form $=O$ and Ring B is

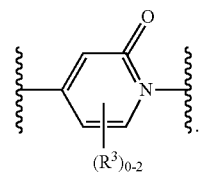

In some embodiments, two $R^3$ groups are taken together to form $=O$ and Ring B is

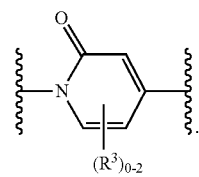

In some embodiments, two $R^3$ groups are taken together to form $=O$ and Ring B is

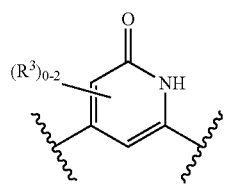

In some embodiments, two $R^3$ groups are taken together to form $=O$ and Ring B is

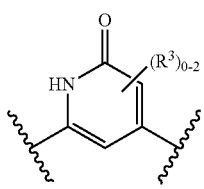

In some embodiments, two $R^3$ groups are taken together to form $=O$ and Ring B is

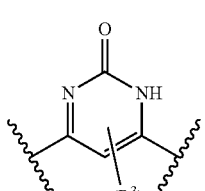

In some embodiments, two R³ groups are taken together to form =O and Ring B is

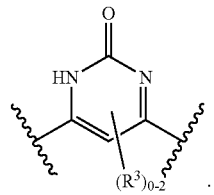

In some embodiments, two R³ groups are taken together to form =O and Ring B is

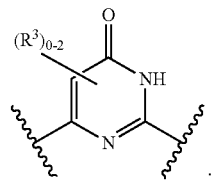

In some embodiments, two R³ groups are taken together to form =O and Ring B is

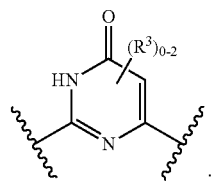

In some embodiments, two R³ groups are taken together to form =O and Ring B is

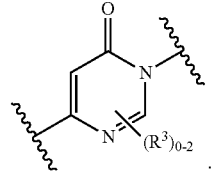

In some embodiments, two R³ groups are taken together to form =O and Ring B is

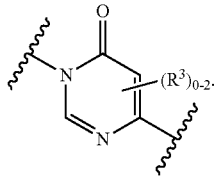

In some embodiments, two R³ groups are taken together to form =O and Ring B is

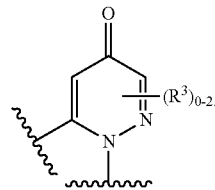

In some embodiments, two R³ groups are taken together to form =O and Ring B is

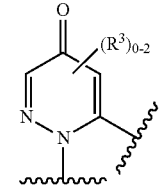

In some embodiments, two R³ groups are taken together to form =O and Ring B is

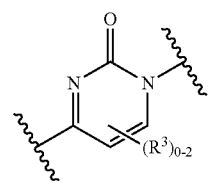

In some embodiments, two R³ groups are taken together to form =O and Ring B is

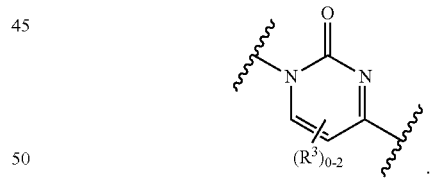

In some embodiments, two R³ groups are taken together to form =O and Ring B is

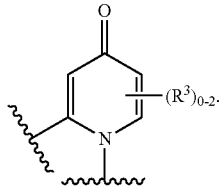

In some embodiments, two R³ groups are taken together to form =O and Ring B is

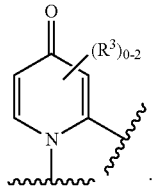

In some embodiments, two R³ groups are taken together to form =O and Ring B is

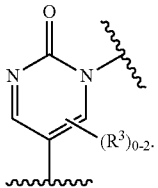

In some embodiments, two R³ groups are taken together to form =O and Ring B is

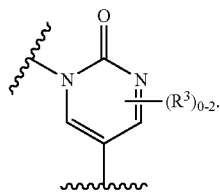

In some embodiments, two R³ groups are taken together to form =O and Ring B is

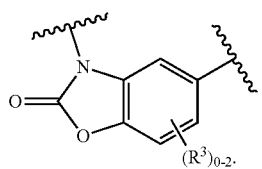

In some embodiments, two sets of R³ groups are taken together to each form =O and Ring B is

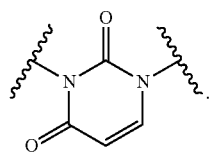 [SMILES: *n1ccc(=O)n(*)c1=O]

In some embodiments, two sets of R³ groups are taken together to each form =O and Ring B is

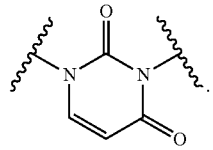 [SMILES: *n1ccc(=O)n(*)c1=O]

In some embodiments, the ⌇ on the left side of Ring B is connected to L² and the ⌇ on the right side of Ring B is connected to L³. In some embodiments, the ⌇ on the right side of Ring B is connected to L² and the ⌇ on the left side of Ring B is connected to L³.

In some embodiments, Ring B is selected from those depicted in Table 1, below.

As defined generally above, Ring C is a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; phenyl; a 3-7 membered saturated or partially unsaturated monocyclic carbocyclic ring; an 8-10 membered bicyclic heteroaromatic ring (having 1-5 heteroatoms independently selected from nitrogen, oxygen, and sulfur); or an 8-10 membered partially aromatic or heteroaromatic bicyclic heterocyclic ring having 1-4 heteroatoms independently selected from nitrogen, oxygen, and sulfur.

In some embodiments, Ring C is a 4-8 membered saturated or partially unsaturated monocyclic heterocyclic ring having 1-2 heteroatoms independently selected from nitrogen, oxygen, and sulfur. In some embodiments, Ring C is a 5-6 membered monocyclic heteroaryl ring having 1-4 heteroatoms independently selected from nitrogen, oxygen, and sulfur. In some embodiments, Ring C is phenyl. In some embodiments, Ring C is a 3-7 membered saturated or partially unsaturated monocyclic carbocyclic ring. In some embodiments, Ring C is an 8-10 membered bicyclic heteroaromatic ring (having 1-5 heteroatoms independently selected from nitrogen, oxygen, and sulfur). In some embodiments, Ring C is an 8-10 membered partially aromatic or heteroaromatic bicyclic heterocyclic ring having 1-4 heteroatoms independently selected from nitrogen, oxygen, and sulfur.

In some embodiments, Ring C is

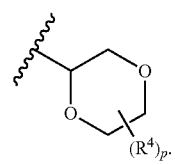

In some embodiments, Ring C is

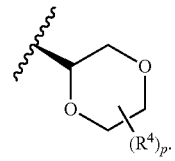

In some embodiments, Ring C is
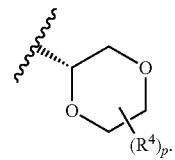
In some embodiments, Ring C is
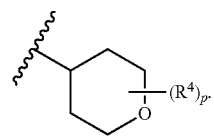
In some embodiments, Ring C is
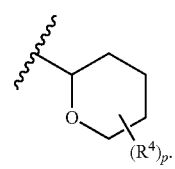
In some embodiments, Ring C is
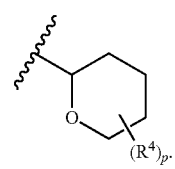
In some embodiments, Ring C is
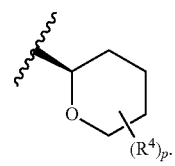
In some embodiments, Ring C is
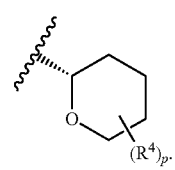
In some embodiments, Ring C is
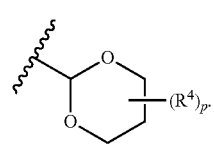
In some embodiments, Ring C is
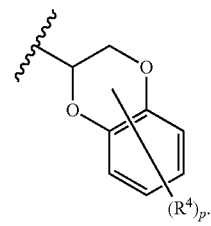
In some embodiments, Ring C is
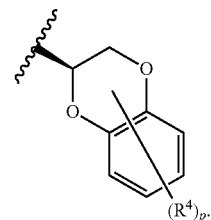
In some embodiments, Ring C is
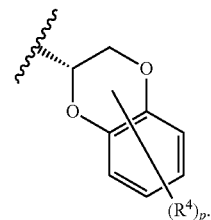
In some embodiments, Ring C is
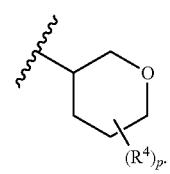
In some embodiments, Ring C is
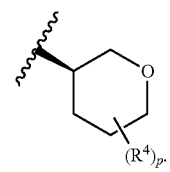

In some embodiments, Ring C is

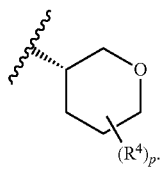

In some embodiments, Ring C is

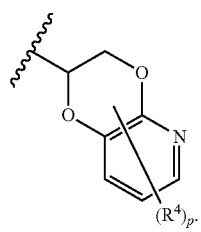

In some embodiments, Ring C is

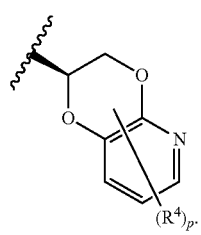

In some embodiments, Ring C is

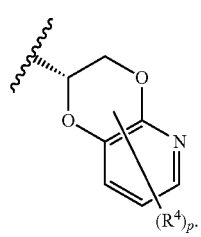

In some embodiments, Ring C is

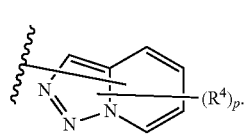

In some embodiments, Ring C is

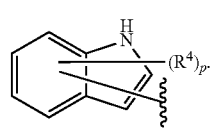

In some embodiments, Ring C is

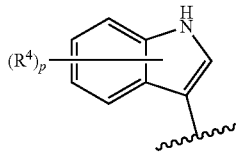

In some embodiments, Ring C is

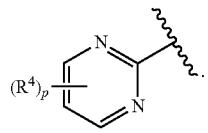

In some embodiments, Ring C is

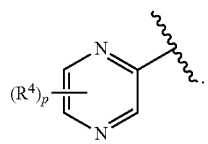

In some embodiments, Ring C is

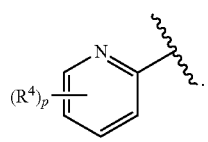

In some embodiments, Ring C is

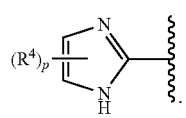

In some embodiments, Ring C is

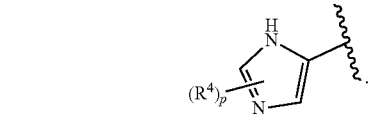

In some embodiments, Ring C is

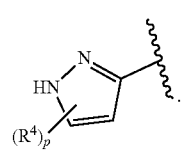

In some embodiments, Ring C is

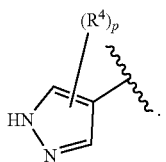

In some embodiments, Ring C is

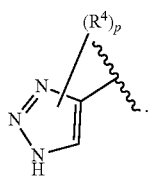

In some embodiments Ring C is

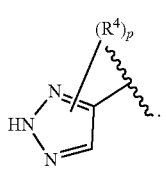

In some embodiments, Ring C is

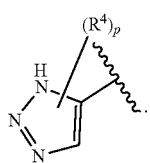

In some embodiments, Ring C is

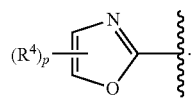

In some embodiments, Ring C is

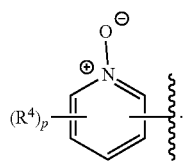

In some embodiments, Ring C is

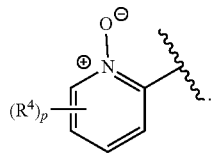

In some embodiments, Ring C is

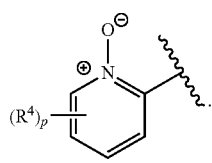

In some embodiments, Ring C is

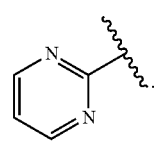 [SMILES: *c1ncccn1]

In some embodiments, Ring C is

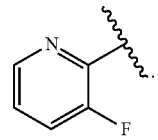 [SMILES: *c1ncccc1F]

In some embodiments, Ring C is

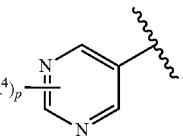

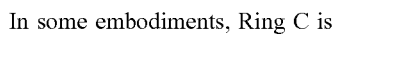

In some embodiments, Ring C is

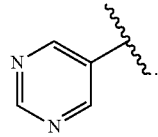

In some embodiments, Ring C is

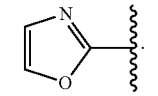

In some embodiments, Ring C is

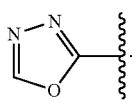

In some embodiments, Ring C is

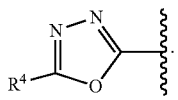

In some embodiments, Ring C is

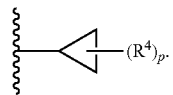

In some embodiments, Ring C is

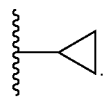

In some embodiments, Ring C is selected from those depicted in Table 1, below.

As defined generally above, $R^1$ is selected from (i) a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 4-8 membered saturated or partially unsaturated monocyclic heterocyclic ring having 1-2 heteroatoms independently selected from nitrogen, oxygen, and sulfur; phenyl; or a $C_{1-6}$ aliphatic; each of which is substituted with q instances of $R^5$; and (ii) hydrogen, —CN, or —OR.

In some embodiments, $R^1$ is a 3-7 membered saturated or partially unsaturated monocyclic carbocyclic ring which is substituted with q instances of $R^5$. In some embodiments, $R^1$ is a 5-6 membered monocyclic heteroaryl ring having 1-4 heteroatoms independently selected from nitrogen, oxygen, and sulfur which is substituted with q instances of $R^5$. In some embodiments, $R^1$ is a 4-8 membered saturated or partially unsaturated monocyclic heterocyclic ring having 1-2 heteroatoms independently selected from nitrogen, oxygen, and sulfur which is substituted with q instances of $R^5$. In some embodiments, $R^1$ is phenyl which is substituted with q instances of $R^5$. In some embodiments, $R^1$ is a $C_{1-6}$ aliphatic group substituted with q instances of $R^5$.

In some embodiments, $R^1$ is hydrogen. In some embodiments, $R^1$ is —CN. In some embodiments, $R^1$ is —OR.

In some embodiments, $R^1$ is methyl. In some embodiments, $R^1$ is

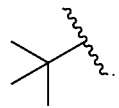

In some embodiments, $R^1$ is

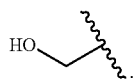

In some embodiments, $R^1$ is

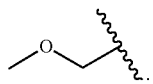 [SMILES: *COC]

In some embodiments, $R^1$ is

In some embodiments, $R^1$ is

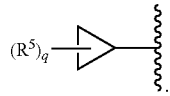

In some embodiments, $R^1$ is

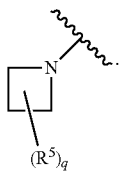

In some embodiments, $R^1$ is

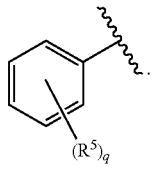

In some embodiments, R¹ is

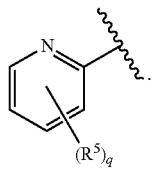

In some embodiments, R¹ is

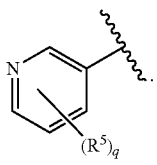

In some embodiments, R¹ is

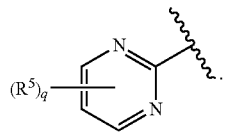

In some embodiments, R¹ is

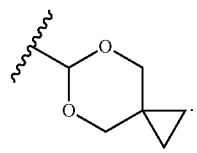 [SMILES: *C1OCC2(CC2)CO1]

In some embodiments, R¹ is —OMe. In some embodiments, R¹ is cyano.

In some embodiments, R¹ is selected from those depicted in Table 1, below.

As defined generally above, each instance of R², R⁴, and R⁵ is independently hydrogen, deuterium, R$^z$, halogen, —CN, —NO₂, —OR, —SR, —NR₂, —S(O)₂R, —S(O)₂NR₂, —S(O)R, —S(O)NR₂, —CF₂R, —CF₃, —CR₂(OR), —CR₂(NR₂), —C(O)R, —C(O)OR, —C(O)NR₂, —C(O)N(R)OR, —OC(O)R, —OC(O)NR₂, —C(S)NR₂, —N(R)C(O)OR, —N(R)C(O)R, —N(R)C(O)NR₂, —N(R)C(NR)NR₂, —N(R)NR₂, —N(R)S(O)₂NR₂, —N(R)S(O)₂R, —N=S(O)R₂, —S(NR)(O)R, —N(R)S(O)R, —N(R)CN, —Si(OR)R₂, —SiR₃, —P(O)(R)NR₂, —P(O)(R)OR or —P(O)R₂.

In some embodiments, R² is hydrogen, deuterium, R$^z$, halogen, —CN, —NO₂, —OR, —SR, —NR₂, —S(O)₂R, —S(O)₂NR₂, —S(O)R, —S(O)NR₂, —CF₂R, —CF₃, —CR₂(OR), —CR₂(NR₂), —C(O)R, —C(O)OR, —C(O)NR₂, —C(O)N(R)OR, —OC(O)R, —OC(O)NR₂, —C(S)NR₂, —N(R)C(O)OR, —N(R)C(O)R, —N(R)C(O)NR₂, —N(R)C(NR)NR₂, —N(R)NR₂, —N(R)S(O)₂NR₂, —N(R)S(O)₂R, —N=S(O)R₂, —S(NR)(O)R, —N(R)S(O)R, —N(R)CN, —Si(OR)R₂, —SiR₃, —P(O)(R)NR₂, —P(O)(R)OR or —P(O)R₂.

In some embodiments, R² is methyl. In some embodiments, R² is fluoro. In some embodiments, R² is bromo.

In some embodiments, R² is selected from those depicted in Table 1, below.

In some embodiments, R⁴ is hydrogen, deuterium, R$^z$, halogen, —CN, —NO₂, —OR, —SR, —NR₂, —S(O)₂R, —S(O)₂NR₂, —S(O)R, —S(O)NR₂, —CF₂R, —CF₃, —CR₂(OR), —CR₂(NR₂), —C(O)R, —C(O)OR, —C(O)NR₂, —C(O)N(R)OR, —OC(O)R, —OC(O)NR₂, —C(S)NR₂, —N(R)C(O)OR, —N(R)C(O)R, —N(R)C(O)NR₂, —N(R)C(NR)NR₂, —N(R)NR₂, —N(R)S(O)₂NR₂, —N(R)S(O)₂R, —N=S(O)R₂, —S(NR)(O)R, —N(R)S(O)R, —N(R)CN, —Si(OR)R₂, —SiR₃, —P(O)(R)NR₂, —P(O)(R)OR or —P(O)R₂.

In some embodiments, R⁴ is hydrogen.

In some embodiments, R⁴ is selected from those depicted in Table 1, below.

In some embodiments, R⁵ is hydrogen, deuterium, R$^z$, halogen, —CN, —NO₂, —OR, —SR, —NR₂, —S(O)₂R, —S(O)₂NR₂, —S(O)R, —S(O)NR₂, —CF₂R, —CF₃, —CR₂(OR), —CR₂(NR₂), —C(O)R, —C(O)OR, —C(O)NR₂, —C(O)N(R)OR, —OC(O)R, —OC(O)NR₂, —C(S)NR₂, —N(R)C(O)OR, —N(R)C(O)R, —N(R)C(O)NR₂, —N(R)C(NR)NR₂, —N(R)NR₂, —N(R)S(O)₂NR₂, —N(R)S(O)₂R, —N=S(O)R₂, —S(NR)(O)R, —N(R)S(O)R, —N(R)CN, —Si(OR)R₂, —SiR₃, —P(O)(R)NR₂, —P(O)(R)OR or —P(O)R₂.

In some embodiments, R⁵ is methyl. In some embodiments, R⁵ is fluoro, In some embodiments, R⁵ is

In some embodiments, R⁵ is

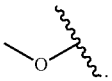

In some embodiments, R⁵ is selected from those depicted in Table 1, below.

As defined generally above, two R² groups are optionally taken together to form =O.

In some embodiments, two R² groups are taken together to form =O.

As defined generally above, two R⁴ groups are optionally taken together to form =O.

In some embodiments, two R⁴ groups are taken together to form =O.

As defined generally above, two R⁵ groups are optionally taken together to form =O.

In some embodiments, two R⁵ groups are taken together to form =O.

As defined generally above, two R² groups are optionally taken together with their intervening atoms to form a 5-8 membered saturated, partially unsaturated, or aryl fused ring having 0-3 heteroatoms independently selected from nitrogen, oxygen and sulfur.

In some embodiments, two R² groups are taken together with their intervening atoms to form a 5-8 membered saturated, partially unsaturated, or aryl fused ring having 0-3 heteroatoms independently selected from nitrogen, oxygen and sulfur.

As defined generally above, two R⁴ groups are optionally taken together with their intervening atoms to form a 5-8 membered saturated, partially unsaturated, or aryl fused ring having 0-3 heteroatoms independently selected from nitrogen, oxygen and sulfur.

In some embodiments, two R⁴ groups are taken together with their intervening atoms to form a 5-8 membered saturated, partially unsaturated, or aryl fused ring having 0-3 heteroatoms independently selected from nitrogen, oxygen and sulfur.

As defined generally above, two R⁵ groups are optionally taken together with their intervening atoms to form a 5-8 membered saturated, partially unsaturated, or aryl fused ring having 0-3 heteroatoms independently selected from nitrogen, oxygen and sulfur.

In some embodiments, two R⁵ groups are taken together with their intervening atoms to form a 5-8 membered saturated, partially unsaturated, or aryl fused ring having 0-3 heteroatoms independently selected from nitrogen, oxygen and sulfur.

As defined generally above, each $R^z$ is independently selected from an optionally substituted group selected from $C_{1-6}$ aliphatic; phenyl; a 4-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur.

In some embodiments, $R^z$ is an optionally substituted group selected from $C_{1-6}$ aliphatic; phenyl; a 4-7 membered saturated or partially unsaturated heterocyclic ring having 1-2 heteroatoms independently selected from nitrogen, oxygen, and sulfur; or a 5-6 membered heteroaryl ring having 1-4 heteroatoms independently selected from nitrogen, oxygen, and sulfur.

In some embodiments, $R^z$ is selected from those depicted in Table 1, below.

As defined generally above, R³ is independently selected from: (a) hydrogen, deuterium, halogen, —OR, —SR, —NR₂, —S(O)₂R, —S(O)₂NR₂, —S(O)R, —S(O)NR₂, —CF₂R, —CF₃, —CR₂(OR), —CR₂(NR₂), —C(O)R, —C(O)OR, —C(O)NR₂, —C(O)N(R)OR, —OC(O)R, —OC(O)NR₂, —C(S)NR₂, —N(R)C(O)OR, —N(R)C(O)R, —N(R)C(O)NR₂, —N(R)C(NR)NR₂, —N(R)NR₂, —N(R)S(O)₂NR₂, —N(R)S(O)₂R, —N=S(O)R₂, —S(NR)(O)R, —N(R)S(O)R, —N(R)CN; or (b) an optionally substituted group selected from $C_{1-6}$ aliphatic; phenyl; a 3-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur; or two R³ groups are optionally taken together to form =O; or two R³ groups are optionally taken together with their intervening atoms to form a 5-8 membered saturated, partially unsaturated, or aryl fused ring having 0-3 heteroatoms independently selected from nitrogen, oxygen and sulfur.

In some embodiments, R³ is hydrogen, deuterium, halogen, —OR, —SR, —NR₂, —S(O)₂R, —S(O)₂NR₂, —S(O)R, —S(O)NR₂, —CF₂R, —CF₃, —CR₂(OR), —CR₂(NR₂), —C(O)R, —C(O)OR, —C(O)NR₂, —C(O)N(R)OR, —OC(O)R, —OC(O)NR₂, —C(S)NR₂, —N(R)C(O)OR, —N(R)C(O)R, —N(R)C(O)NR₂, —N(R)NR₂, —N(R)S(O)₂NR₂, —N(R)S(O)₂R, —S(NR)(O)R, —N(R)S(O)R, or —N(R)CN.

In some embodiments, R³ is an optionally substituted group selected from $C_{1-6}$ aliphatic; phenyl; a 3-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur.

In some embodiments, R³ is methyl. In some embodiments, R³ is ethyl. In some embodiments, R³ is chloro. In some embodiments, R³ is

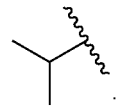 [SMILES: *C(C)C]

In some embodiments, R³ is

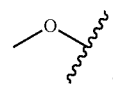

In some embodiments, R³ is

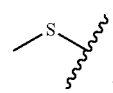

In some embodiments, R³ is —CF₃. In some embodiments, R³ is

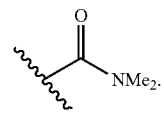

In some embodiments, R³ is

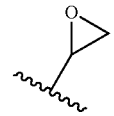

In some embodiments, R³ is

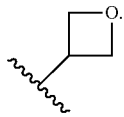

In some embodiments, two R³ groups are taken together to form =O or =S. In some embodiments, two R³ groups are taken together to form =O. In some embodiments, two R³ groups are taken together to form =S.

In some embodiments, two R³ groups are taken together with their intervening atoms to form a 5-8 membered saturated, partially unsaturated, or aryl fused ring having 0-3 heteroatoms independently selected from nitrogen, oxygen and sulfur.

In some embodiments, two $R^3$ groups are taken together with their intervening atoms to form

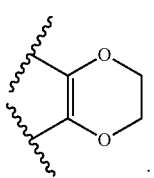

In some embodiments, two $R^3$ groups are taken together with their intervening atoms to form

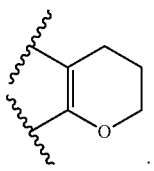

In some embodiments, $R^3$ is selected from those depicted in Table 1, below.

As defined generally above, $L^1$ is one of the following: (a) a $C_{1-5}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CH(OR)—, —C(F)$_2$—, —N(R)—, —S—, —S(O)—, or —S(O)$_2$—; or (b) a covalent bond.

In some embodiments, $L^1$ is a $C_{1-5}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CH(OR)—, —C(F)$_2$—, —N(R)—, —S—, —S(O)—, or —S(O)$_2$—.

In some embodiments, $L^1$ is a covalent bond.

In some embodiments, $L^1$ is

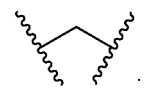 [SMILES: *C*]

In some embodiments, $L^1$ is

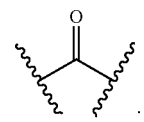 [SMILES: *C(*)=O]

In some embodiments, $L^1$ is

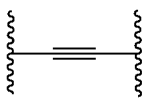

In some embodiments, $L^1$ is

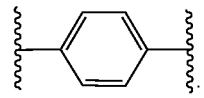

In some embodiments, $L^1$ is

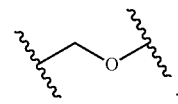 [SMILES: *CO*]

In some embodiments, $L^1$ is

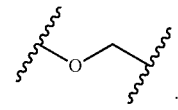

In some embodiments, $L^1$ is

In some embodiments, $L^1$ is

In some embodiments, $L^1$ is

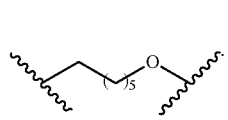

In some embodiments, $L^1$ is

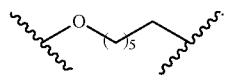

In some embodiments, $L^1$ is

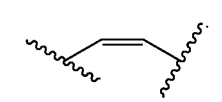

In some embodiments, L¹ is
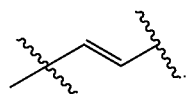 [SMILES: */C=C/*]
In some embodiments, L¹ is
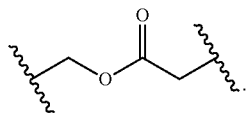 [SMILES: *COC(=O)C*]
In some embodiments, L¹ is
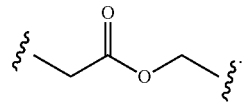
some embodiments, L¹ is
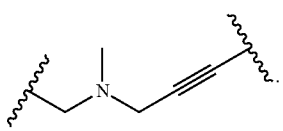 [SMILES: *C#CCN(C)C*]
In some embodiments, L¹ is
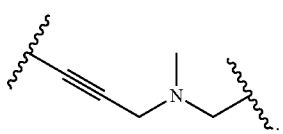 [SMILES: *C#CCN(C)C*]
In some embodiments, L¹ is
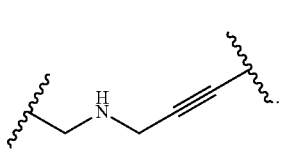 [SMILES: *C#CCNC*]
In some embodiments, L¹ is
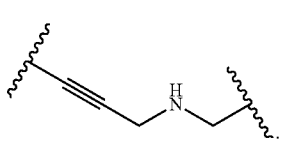
In some embodiments, L¹ is
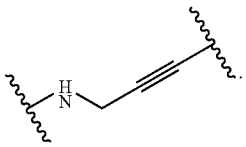 [SMILES: *C#CCN*]
In some embodiments, L¹ is
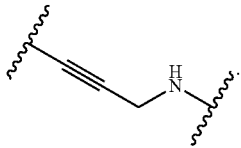 [SMILES: *C#CCN*]
In some embodiments, L¹ is
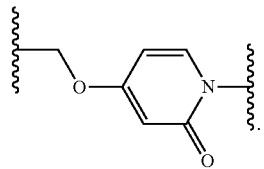
In some embodiments, L¹ is
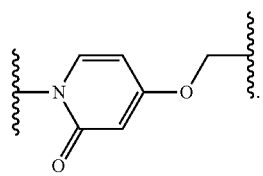 [SMILES: *COc1ccn(*)c(=O)c1]
In some embodiments, L¹ is
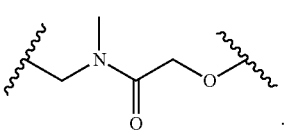 [SMILES: *CN(C)C(=O)CO*]
In some embodiments, L¹ is
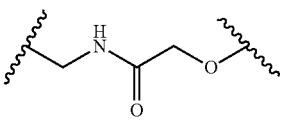
In some embodiments, L¹ is
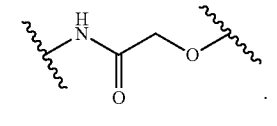 [SMILES: *NC(=O)CO*]

In some embodiments, the ⸲ on the left side of $L^1$ is connected to $R^1$ and the ⸲ on the right side of $L^1$ is connected to Ring A. In some embodiments, the ⸲ on the right side of $L^1$ is connected to $R^1$ and the ⸲ on the left side of $L^1$ is connected to Ring A.

In some embodiments, $L^1$ is selected from those depicted in Table 1, below.

As defined generally above, $L^2$ and $L^3$ are independently one of the following: (a) a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CH(OR)—, —C(F)$_2$—, —N(R)—, —S—, —S(O)—, or —S(O)$_2$—; or (b) a covalent bond.

In some embodiments, $L^2$ is a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CH(OR)—, —C(F)$_2$—, —N(R)—, —S—, —S(O)—, or —S(O)$_2$—.

In some embodiments, $L^2$ is a covalent bond.

In some embodiments, $L^2$ is

In some embodiments, $L^2$ is

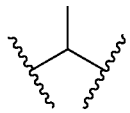

In some embodiments, $L^2$ is


In some embodiments, $L^2$ is

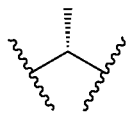

In some embodiments, $L^2$ is

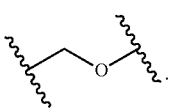

In some embodiments, $L^2$ is

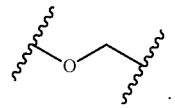

In some embodiments, $L^2$ is

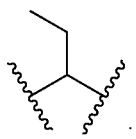 [SMILES: *C(*)CC]

In some embodiments $L^2$ is

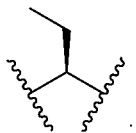

In some embodiments, $L^2$ is

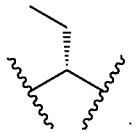

In some embodiments, $L^2$ is

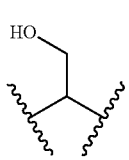

In some embodiments, $L^2$ is

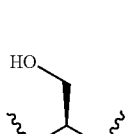

In some embodiments, $L^2$ is

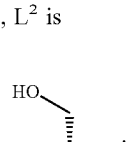

In some embodiments, $L^2$ is

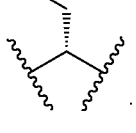

In some embodiments $L^2$ is

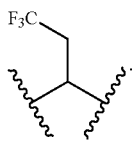

in some embodiments, $L^2$ is

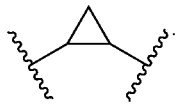

In some embodiments, $L^2$ is selected from those depicted in Table 1, below.

In some embodiments, $L^3$ is a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CH(OR)—, —C(F)$_2$—, —N(R)—, —S—, —S(O)—, or —S(O)$_2$—.

In some embodiments, $L^3$ is a covalent bond.

In some embodiments, $L^3$ is

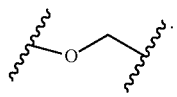

In some embodiments, $L^3$ is

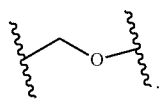

In some embodiments, $L^3$ is

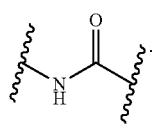 [SMILES: *NC(*)=O]

In some embodiments, $L^3$ is

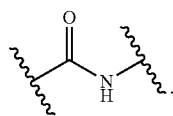 [SMILES: *NC(*)=O]

In some embodiments, $L^3$ is

In some embodiments, $L^3$ is

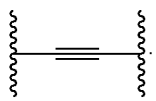

In some embodiments, the ⸾ on the left side of $L^3$ is connected to Ring B and the ⸾ on the right side of $L^3$ is connected to Ring C. In some embodiments, the ⸾ on the right side of $L^3$ is connected to Ring B and the ⸾ on the left side of $L^3$ is connected to Ring C.

In some embodiments, $L^3$ is selected from those depicted in Table 1, below.

As defined generally above, each R is independently hydrogen, or an optionally substituted group selected from $C_{1-6}$ aliphatic; phenyl; an 8-10 membered bicyclic aryl ring, a 3-7 membered saturated or partially unsaturated monocyclic carbocyclic ring; a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; and an 8-10 membered bicyclic heteroaryl ring having 1-5 heteroatoms independently selected from nitrogen, oxygen, and sulfur; and/or two R groups on the same nitrogen are optionally taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur; and/or two R groups on vicinal carbons are optionally taken together with the vicinal carbons to form an optionally substituted 3-7 membered monocyclic saturated or partially unsaturated carbocyclic ring or heterocyclic ring, wherein the heterocyclic ring has, in addition to the vicinal carbons, 0-3 heteroatoms independently selected from nitrogen, oxygen, and sulfur.

In some embodiments, R is hydrogen.

In some embodiments, R is an optionally substituted group selected from $C_{1-6}$ aliphatic; phenyl; an 8-10 membered bicyclic aryl ring, a 3-7 membered saturated or partially unsaturated monocyclic carbocyclic ring; a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; and an 8-10 membered bicyclic heteroaryl ring having 1-5 heteroatoms independently selected from nitrogen, oxygen, and sulfur.

In some embodiments, two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur.

In some embodiments, two R groups on vicinal carbons are optionally taken together with the vicinal carbons to form an optionally substituted 3-7 membered monocyclic saturated or partially unsaturated carbocyclic ring or heterocyclic ring, wherein the heterocyclic ring has, in addition to the vicinal carbons, 0-3 heteroatoms independently selected from nitrogen, oxygen, and sulfur.

In some embodiments, R is selected from those depicted in Table 1, below.

As defined generally above, m is 0, 1, 2, 3, or 4.

In some embodiments, m is 0. In some embodiments, m is 1. In some embodiments, m is 2. In some embodiments, m is 3. In some embodiments, m is 4.

In some embodiments, m is selected from those depicted in Table 1, below.

As defined generally above, n is 0, 1, 2, 3, or 4.

In some embodiments, n is 0. In some embodiments, n is 1. In some embodiments, n is 2. In some embodiments, n is 3. In some embodiments, n is 4.

In some embodiments, n is selected from those depicted in Table 1, below.

As defined generally above, p is 0, 1, 2, 3, or 4.

In some embodiments, p is 0. In some embodiments, p is 1. In some embodiments, p is 2. In some embodiments, p is 3. In some embodiments, p is 4.

In some embodiments, p is selected from those depicted in Table 1, below.

As defined generally above, q is 0, 1, 2, 3, or 4.

In some embodiments, q is 0. In some embodiments, q is 1. In some embodiments, q is 2. In some embodiments, q is 3. In some embodiments, q is 4.

In some embodiments, q is selected from those depicted in Table 1, below.

In some embodiments, the compound of formula I is not

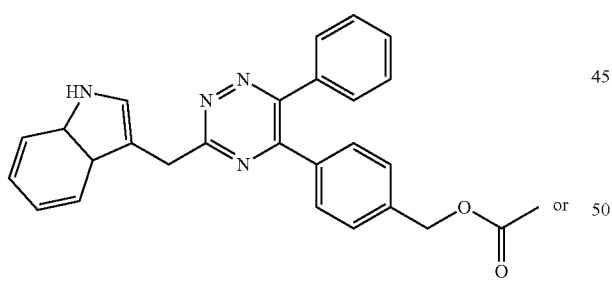

or

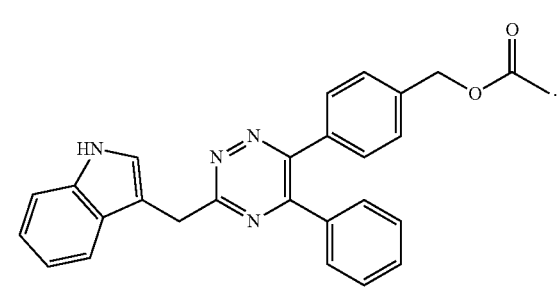 [SMILES: CC(=O)OCc1ccc(-c2nnc(Cc3c[nH]c4ccccc34)nc2-c2ccccc2)cc1]

In some embodiments, the compound of formula I is not

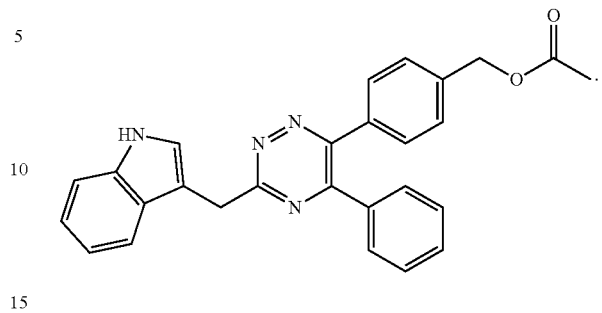

In some embodiments, the present invention provides a compound of formula I, wherein $L^3$ is —OCH$_2$—, Ring B is pyridone, two $R^3$ groups are taken together to form =O, and Ring C is oxetanyl, to provide a compound of formula I-a-1, I-a-2, or I-a-3:

I-a-1

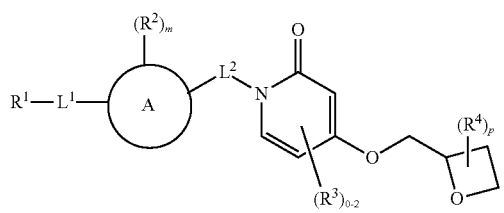

I-a-2

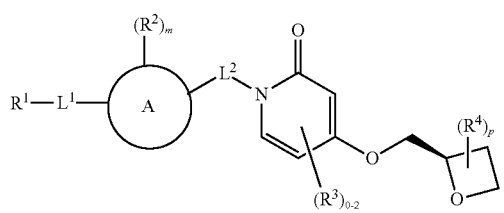

I-a-3

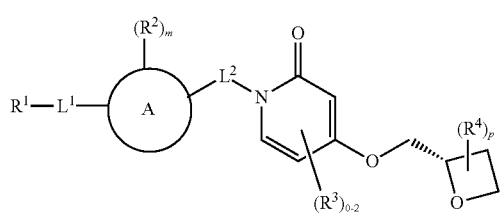

or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I, wherein $L^3$ is —OCH$_2$—, Ring B is pyridone, two $R^3$ groups are taken together to form =O, and Ring C is furanyl, to provide a compound of formula I-b-1, I-b-2, or I-b-3:

I-b-1

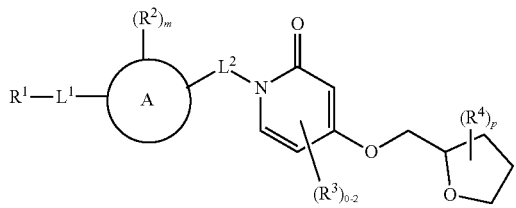

I-b-2

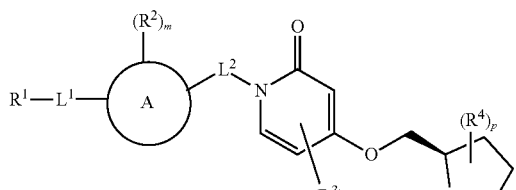

I-b-3

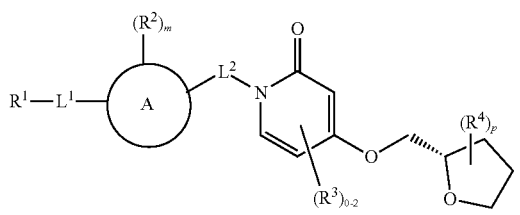

or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I, wherein $L^3$ is —$OCH_2$—, Ring B is pyridone, two $R^3$ groups are taken together to form =O, and Ring C is tetrahydropyranyl, to provide a compound of formula I-c-1, I-c-2, or I-c-3:

I-c-1

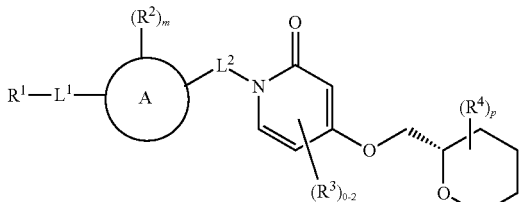

I-c-2

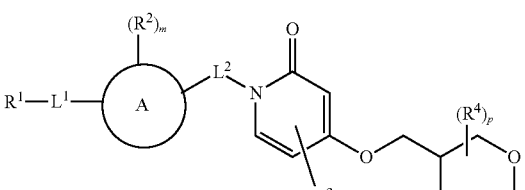

I-c-3

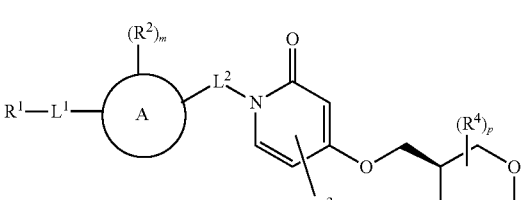

or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I, wherein $L^3$ is —$OCH_2$—, Ring B is pyridone, two $R^3$ groups are taken together to form =O, and Ring C is 1,4-dioxanyl, to provide a compound of formula I-d-1, I-d-2, or I-d-3:

I-d-1

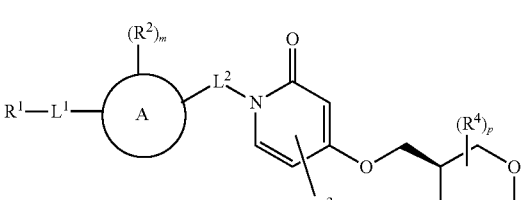

I-d-2

I-d-3 or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I, wherein Ring A is phenyl, thiophenyl, or pyridyl; Ring B is pyridone; and two $R^3$ groups are taken together to form =O; to provide a compound of formula I-e-1, I-e-2, or I-e-3:

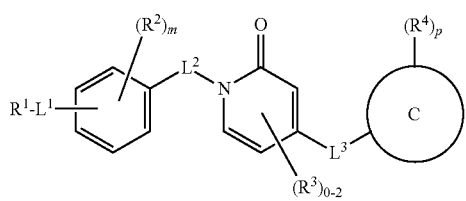
I-e-1

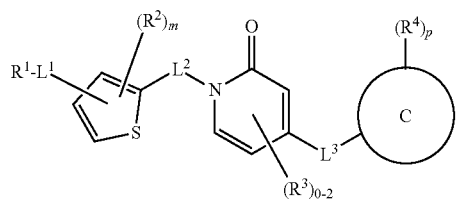
I-e-2

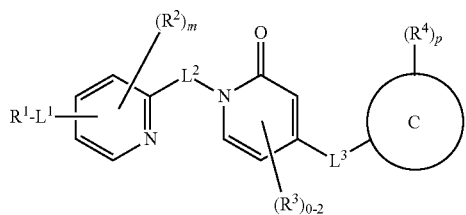
I-e-3 or a pharmaceutically acceptable salt thereof, wherein each of Ring C, $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I, wherein $L^1$ is

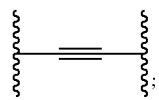

Ring A is phenyl, thiophenyl, or pyridyl; Ring B is pyridone; and two $R^3$ groups are taken together to form =O; to provide a compound of formula I-f-1, I-f-2, or I-f-3:

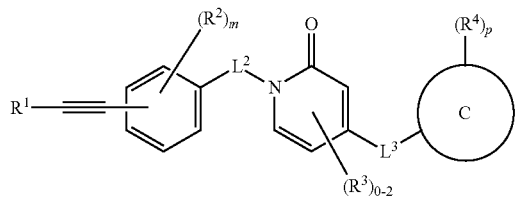
I-f-1

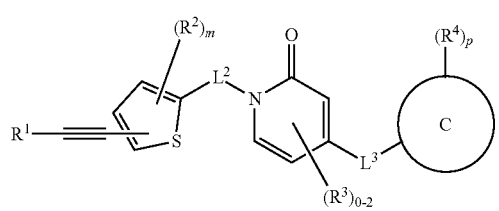
I-f-2

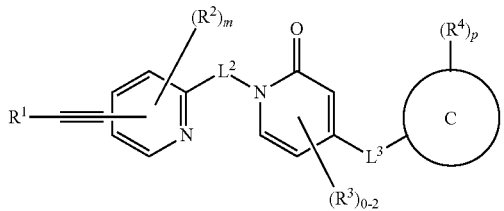
I-f-3 or a pharmaceutically acceptable salt thereof, wherein each of Ring C, $L^2$, $L^3$, $R^1$, $R^2$, $R^3$, $R^4$, m, and p is as defined above and described in embodiments herein, both singly and in combination.

In some embodiments, the present invention provides a compound of formula I, wherein Ring A is phenyl, thiophenyl, or pyridyl; Ring B is pyridone; two $R^3$ groups are taken together to form =O; and Ring C is oxetanyl; to provide a compound of formula I-g-1, I-g-2, or I-g-3:

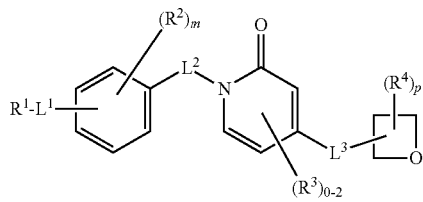
I-g-1

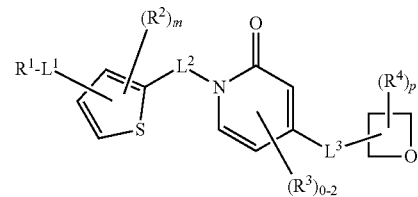
I-g-2

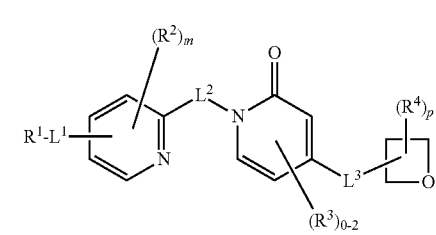
I-g-3 or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I, wherein Ring A is phenyl, thiophenyl, or pyridyl; Ring B is pyridone; two $R^3$ groups are taken together to form =O; and Ring C is furanyl, to provide a compound of formula I-h-1, I-h-2, or I-h-3:

I-h-1

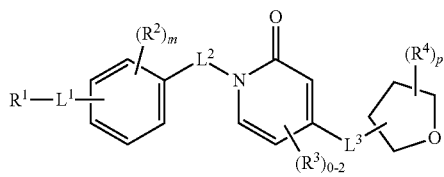

I-h-2

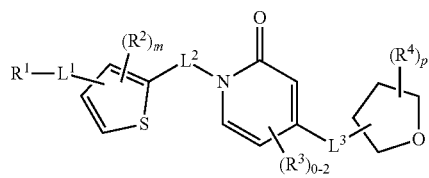

I-h-3

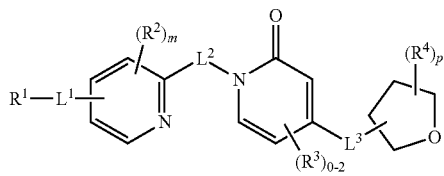

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I, wherein Ring A is phenyl, thiophenyl, or pyridyl; Ring B is pyridone; two $R^3$ groups are taken together to form =O; and Ring C is tetrahydropyranyl; to provide a compound of formula I-i-1, I-i-2, or I-i-3:

I-i-1

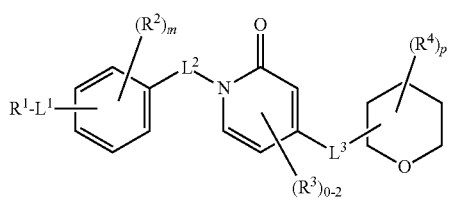

I-i-2

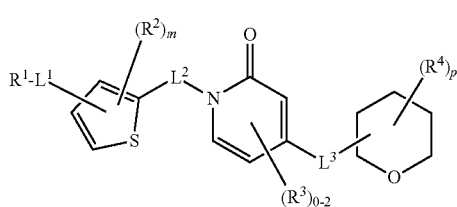

I-i-3

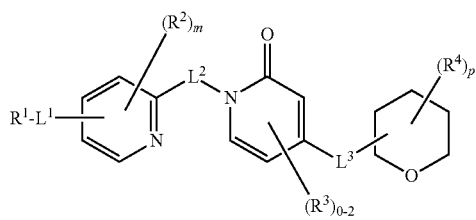

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I, wherein Ring A is phenyl, thiophenyl, or pyridyl; Ring B is pyridone; two $R^3$ groups are taken together to form =O; and Ring C is 1,4-dioxanyl; to provide a compound of formula I-j-1, I-j-2, or I-j-3:

I-j-1

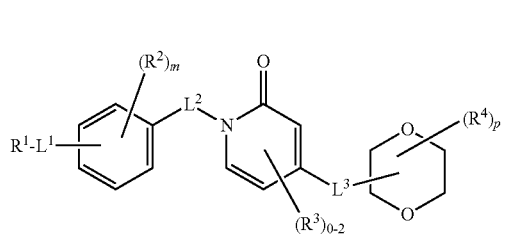

I-j-2

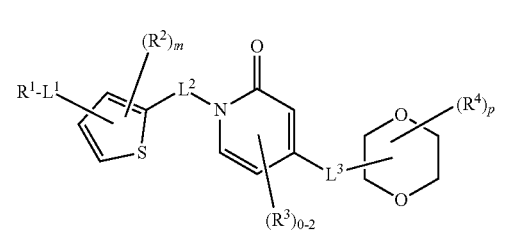

I-j-3

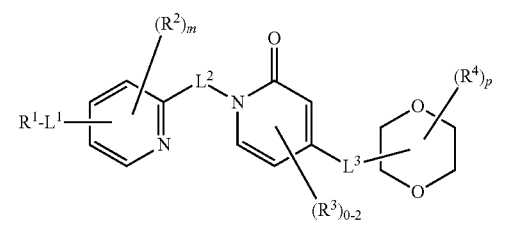

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I, wherein $L^3$ is —OCH$_2$—, Ring B is pyrimidone, two $R^3$ groups are taken together to form =O, and Ring C is oxetanyl, to provide a compound of formula II-a-1, II-a-2, or II-a-3:

II-a-1

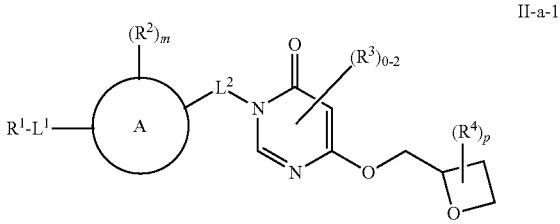

-continued

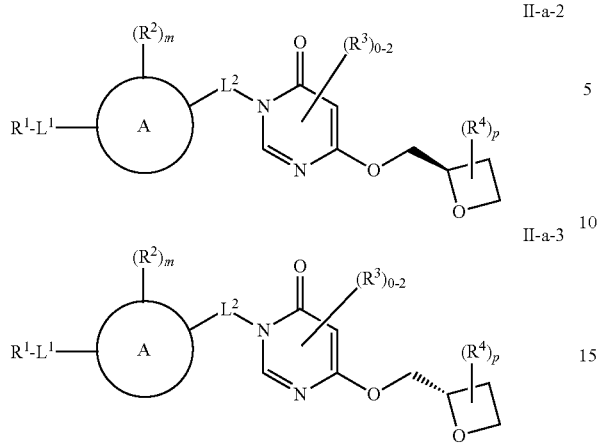

II-a-2

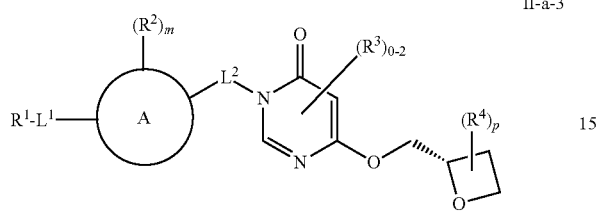

II-a-3 or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I, wherein $L^3$ is —$OCH_2$—, Ring B is pyrimidone, two $R^3$ groups are taken together to form =O, and Ring C is furanyl, to provide a compound of formula II-b-1, II-b-2, or II-b-3:

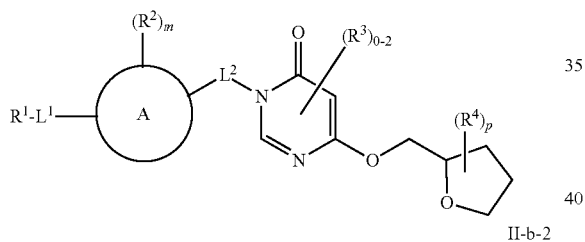

II-b-1

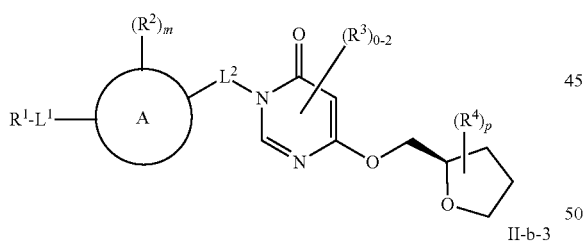

II-b-2

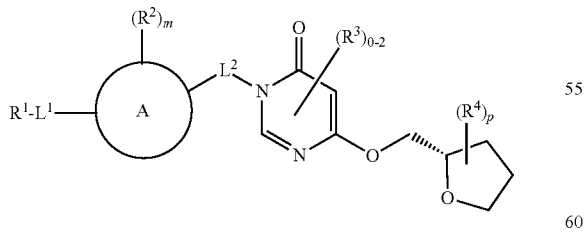

II-b-3 or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I, wherein $L^3$ is —$OCH_2$—, Ring B is pyrimidone, two $R^3$ groups are taken together to form =O, and Ring C is tetrahydropyranyl, to provide a compound of formula II-c-1, II-c-2, or II-c-3:

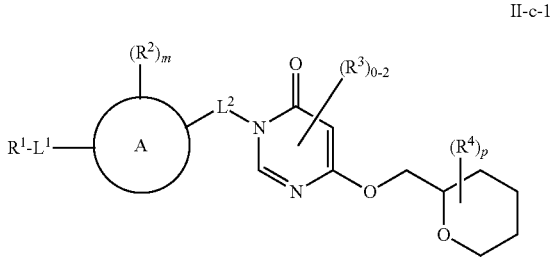

II-c-1

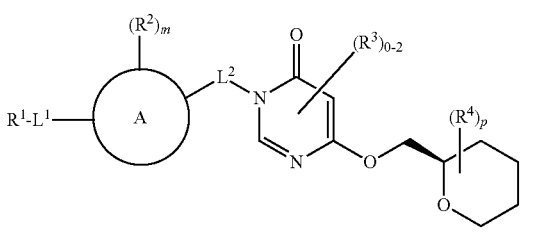

II-c-2

II-c-3

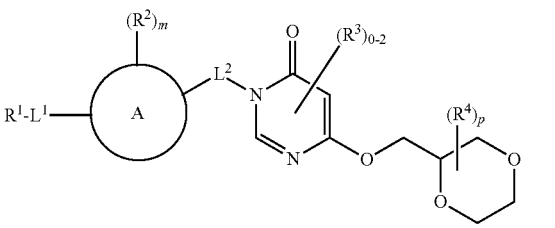

or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I, wherein $L^3$ is —$OCH_2$—, Ring B is pyrimidone, two $R^3$ groups are taken together to form =O, and Ring C is 1,4-dioxanyl, to provide a compound of formula II-d-1, II-d-2, or II-d-3:

II-d-1

-continued

II-d-2
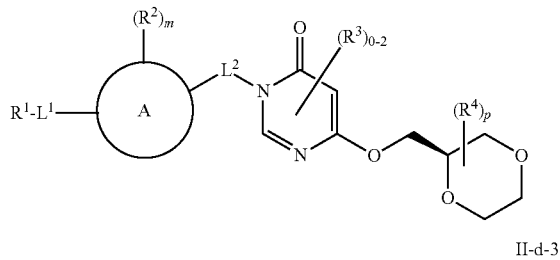

II-d-3
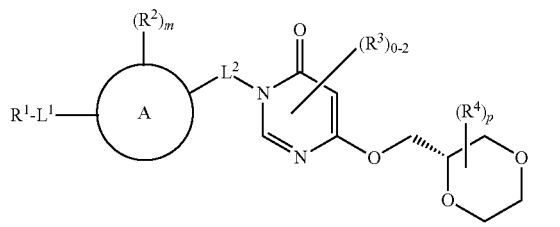

or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I, wherein Ring A is phenyl, thiophenyl, or pyridyl; Ring B is pyrimidone; and two $R^3$ groups are taken together to form =O; to provide a compound of formula II-e-1, II-e-2, or II-e-3:

II-e-1
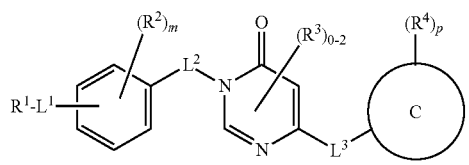

II-e-2
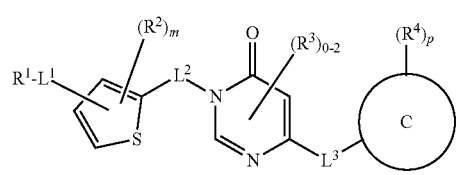

II-e-3
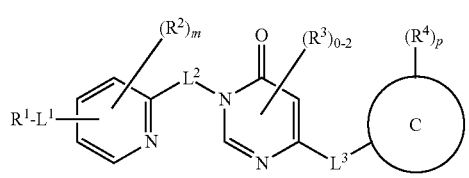

or a pharmaceutically acceptable salt thereof, wherein each of Ring C, $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I, wherein $L^1$ is

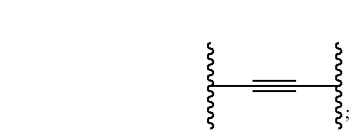

Ring A is phenyl, thiophenyl, or pyridyl; Ring B is pyrimidone; and two $R^3$ groups are taken together to form =O; to provide a compound of formula II-f-1, II-f-2, or II-f-3:

II-f-1
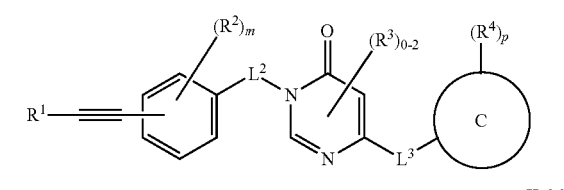

II-f-2
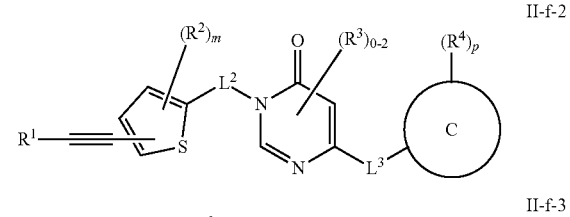

II-f-3
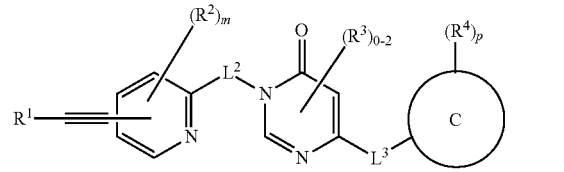

or a pharmaceutically acceptable salt thereof, wherein each of Ring C, $L^2$, $L^3$, $R^1$, $R^2$, $R^3$, $R^4$, m, and p is as defined above and described in embodiments herein, both singly and in combination.

In some embodiments, the present invention provides a compound of formula I, wherein Ring A is phenyl, thiophenyl, or pyridyl; Ring B is pyrimidone; two $R^3$ groups are taken together to form =O; and Ring C is oxetanyl; to provide a compound of formula II-g-1, II-g-2, or II-g-3:

II-g-1
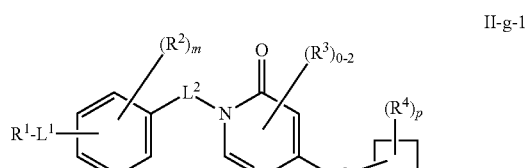

II-g-2
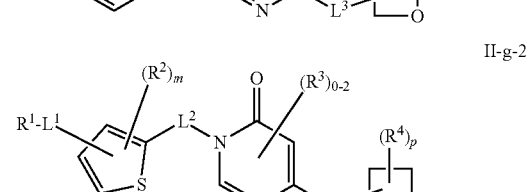

II-g-3

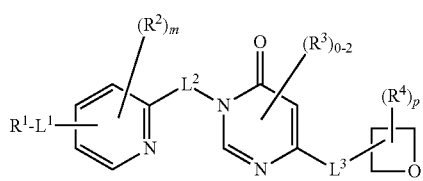

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I, wherein Ring A is phenyl, thiophenyl, or pyridyl; Ring B is pyrimidone; two $R^3$ groups are taken together to form =O; and Ring C is furanyl, to provide a compound of formula II-h-1, II-h-2, or II-h-3:

II-h-1

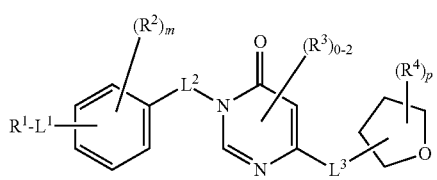

II-h-2

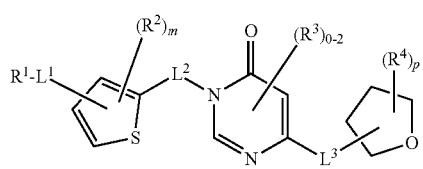

II-h-3

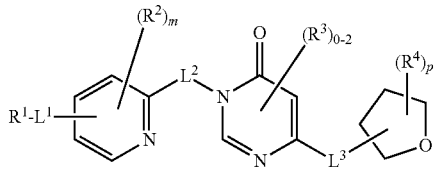

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I, wherein Ring A is phenyl, thiophenyl, or pyridyl; Ring B is pyrimidone; two $R^3$ groups are taken together to form =O; and Ring C is tetrahydropyranyl; to provide a compound of formula II-II-1, II-II-2, or II-II-3:

II-II-1

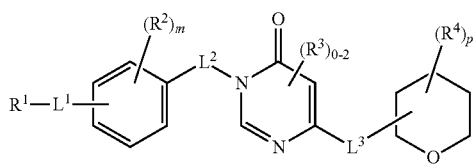

II-II-2

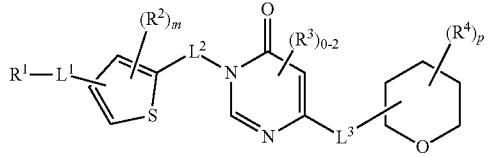

II-II-3

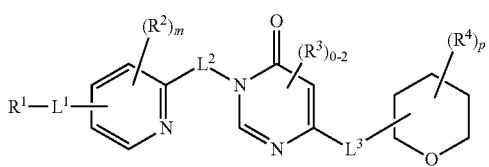

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I, wherein Ring A is phenyl, thiophenyl, or pyridyl; Ring B is pyrimidone; two $R^3$ groups are taken together to form =O; and Ring C is 1,4-dioxanyl; to provide a compound of formula II-j-1, II-j-2, or II-j-3:

II-j-1

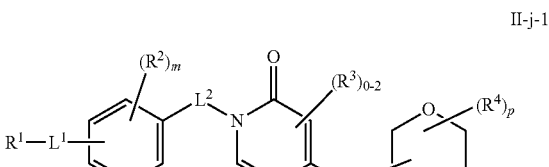

II-j-2

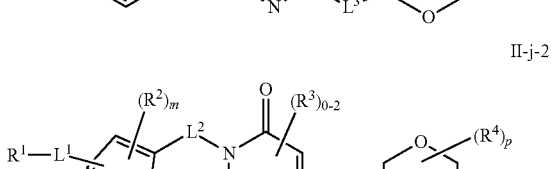

II-j-3

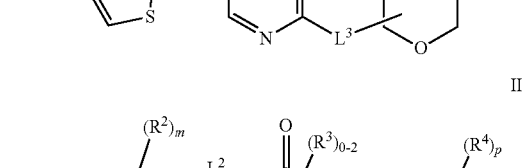

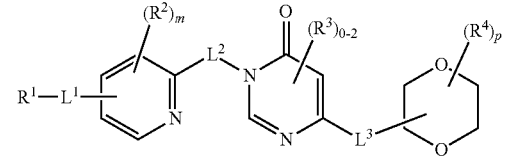

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I, wherein Ring A is phenyl; Ring B is pyrimidinone or pyrimidinethione; two $R^3$ groups are taken together to form =O or =S; an additional $R^3$ group and an $R^2$ group together form

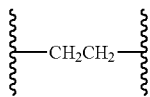

wherein the left ⸨ and right ⸨ represent points of attachment to Ring A and Ring B, respectively; and Ring C is as defined above; to provide a compound of formula III-a-1 or III-a-2:

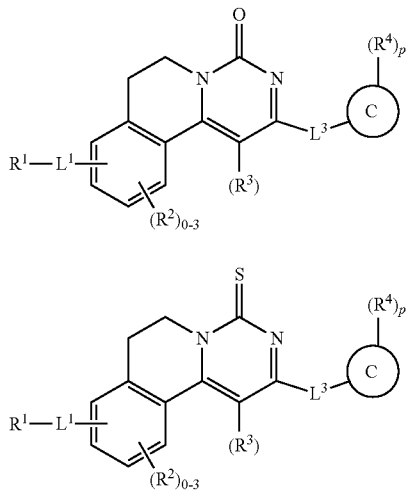

or a pharmaceutically acceptable salt thereof, wherein each of $L^1$, $L^3$, $R^1$, $R^2$, $R^3$, $R^4$, p, and Ring C is as defined above and described in embodiments herein, both singly and in combination.

In some embodiments, the present invention provides a compound of formula I, wherein Ring A is phenyl; Ring B is pyridinone or pyridinethione; two $R^3$ groups are taken together to form =O or =S; an additional $R^3$ group and an $R^2$ group together form

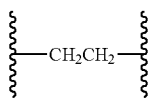

wherein the left ⸨ and right ⸨ represent points of attachment to Ring A and Ring B, respectively; and Ring C is as defined above; to provide a compound of formula III-b-1 or III-b-2:

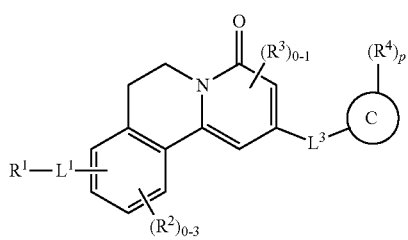

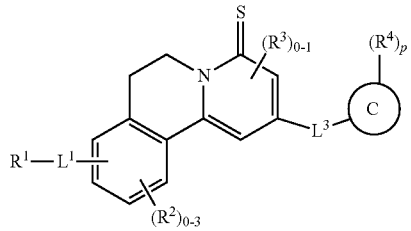

or a pharmaceutically acceptable salt thereof, wherein each of $L^1$, $L^3$, $R^1$, $R^2$, $R^3$, $R^4$, p, and Ring C is as defined above and described in embodiments herein, both singly and in combination.

In some embodiments, the present invention provides a compound of formula I, wherein Ring A is phenyl; Ring B is pyridinone or pyridinethione; two $R^3$ groups are taken together to form =O or =S; an additional $R^3$ group and an $R^2$ group together form

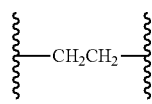

wherein the left ⸨ and right ⸨ represent points of attachment to Ring A and Ring B, respectively; and Ring C is as defined above; to provide a compound of formula III-c-1 or III-c-2:

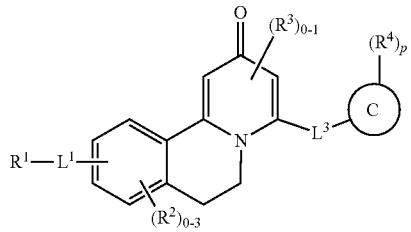

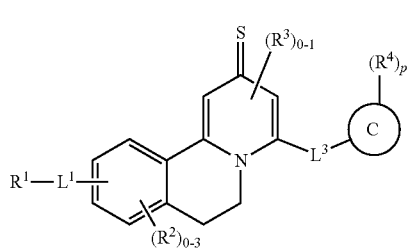

or a pharmaceutically acceptable salt thereof, wherein each of $L^1$, $L^3$, $R^1$, $R^2$, $R^3$, $R^4$, p, and Ring C is as defined above and described in embodiments herein, both singly and in combination.

In some embodiments, the present invention provides a compound of formula I, wherein Ring A is phenyl; Ring B is pyrimidinone or pyrimidinethione; two $R^3$ groups are taken together to form =O or =S; an additional $R^3$ group and an $R^2$ group together form

11

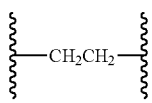

wherein the left ⸹ and right ⸹ represent points of attachment to Ring A and Ring B, respectively; and Ring C is as defined above to provide a compound of formula III-d-1 or III-d-2:

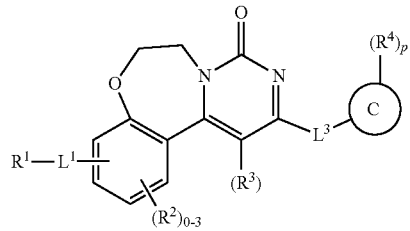

III-d-1

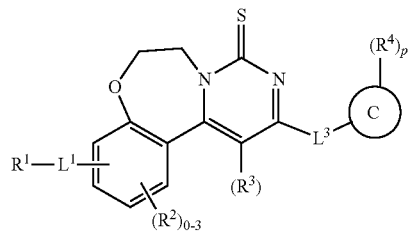

III-d-2 or a pharmaceutically acceptable salt thereof, wherein each of $L^1$, $L^3$, $R^1$, $R^2$, $R^3$, $R^4$, m, p, and Ring C is as defined above and described in embodiments herein, both singly and in combination.

In some embodiments, the present invention provides a compound of formula I, wherein Ring A is phenyl; Ring B is pyridinone; two $R^3$ groups are taken together to form =O; and Ring C is as defined above; to provide a compound of formula III-e-1:

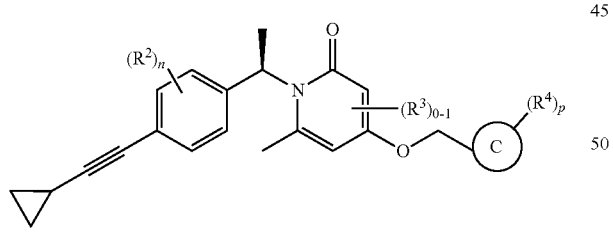

III-e-1 or a pharmaceutically acceptable salt thereof, wherein each of $R^2$, $R^3$, $R^4$, n, p, and Ring C is as defined above and described in embodiments herein, both singly and in combination. In some embodiments, Ring C and it $R^4$ substituent (s) is

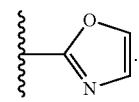

In some embodiments, Ring C and it $R^4$ substituent(s) is

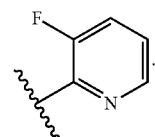 [SMILES: *c1ncccc1F]

In some embodiments, Ring C and it $R^4$ substituent(s) is

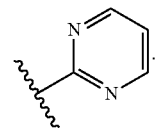 [SMILES: *c1ncccn1]

In some embodiments, Ring C and it $R^4$ substituent(s) is

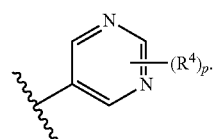

In some embodiments, Ring C and it $R^4$ substituent(s) is

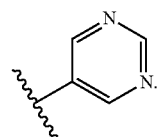 [SMILES: *c1cncnc1]

In some embodiments, the present invention provides a compound of formula I, wherein Ring A is pyridinone wherein two $R^2$ groups are taken together to form =O and one $R^2$ group is methyl; Ring B is phenyl; and Ring C is cyclopropyl; to provide a compound of formula III-f-1:

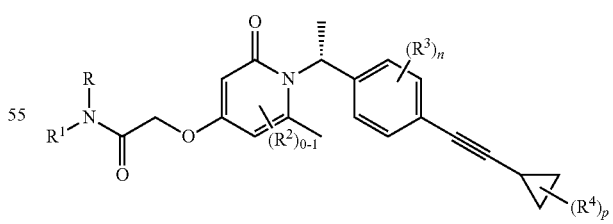

III-f-1 or a pharmaceutically acceptable salt thereof, wherein each of R, $R^1$, $R^2$, $R^3$, $R^4$, n, and p is as defined above and described in embodiments herein, both singly and in combination.

In certain embodiments, the present invention provides a compound of formula I-1*:

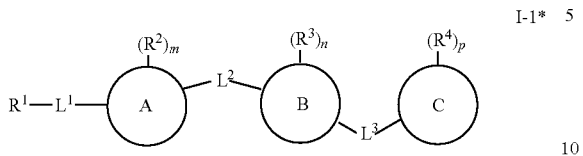

or an N-oxide, or a pharmaceutically acceptable salt thereof, wherein:

Ring A is phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; or a 4-8 membered saturated or partially unsaturated monocyclic heterocyclic ring having 1-2 heteroatoms independently selected from nitrogen, oxygen, and sulfur;

Ring B is a 6-membered monocyclic partially unsaturated heterocyclyl or heteroaryl ring having 1-4 heteroatoms independently selected from nitrogen, oxygen, and sulfur; an 8-10 membered partially aromatic or heteroaromatic bicyclic heterocyclic ring having 1-4 heteroatoms independently selected from nitrogen, oxygen, and sulfur; or phenyl;

Ring C is a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; phenyl; a 3-7 membered saturated or partially unsaturated monocyclic carbocyclic ring; or an 8-10 membered partially aromatic or heteroaromatic bicyclic heterocyclic ring having 1-4 heteroatoms independently selected from nitrogen, oxygen, and sulfur;

$R^1$ is selected from (i) a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 4-8 membered saturated or partially unsaturated monocyclic heterocyclic ring having 1-2 heteroatoms independently selected from nitrogen, oxygen, and sulfur; phenyl; or a $C_{1-6}$ aliphatic; each of which is substituted with q instances of $R^5$; and (ii) hydrogen, —CN, or —OR;

each instance of $R^2$, $R^4$, and $R^5$ is independently hydrogen, deuterium, $R^z$, halogen, —CN, —NO$_2$, —OR, —SR, —NR$_2$, —S(O)$_2$R, —S(O)$_2$NR$_2$, —S(O)R, —S(O)NR$_2$, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —Si(OR)R$_2$, —SiR$_3$, —P(O)(R)NR$_2$, —P(O)(R)OR or —P(O)R$_2$; or two $R^2$ groups are optionally taken together to form =O;

two $R^4$ groups are optionally taken together to form =O;

two $R^5$ groups are optionally taken together to form =O;

two $R^2$ groups are optionally taken together with their intervening atoms to form a 5-8 membered saturated, partially unsaturated, or aryl fused ring having 0-3 heteroatoms independently selected from nitrogen, oxygen and sulfur;

two $R^4$ groups are optionally taken together with their intervening atoms to form a 5-8 membered saturated, partially unsaturated, or aryl fused ring having 0-3 heteroatoms independently selected from nitrogen, oxygen and sulfur; or two $R^5$ groups are optionally taken together with their intervening atoms to form a 5-8 membered saturated, partially unsaturated, or aryl fused ring having 0-3 heteroatoms independently selected from nitrogen, oxygen and sulfur;

each $R^z$ is independently selected from an optionally substituted group selected from $C_{1-6}$ aliphatic; phenyl; a 4-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur;

each instance of $R^3$ is independently selected from:
(a) hydrogen, deuterium, halogen, —OR, —SR, —NR$_2$, —S(O)$_2$R, —S(O)$_2$NR$_2$, —S(O)R, —S(O)NR$_2$, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN; or
(b) an optionally substituted selected from $C_{1-6}$ aliphatic; phenyl; a 3-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur; or two $R^3$ groups are optionally taken together to form =O; or two $R^3$ groups are optionally taken together with their intervening atoms to form a 5-8 membered saturated, partially unsaturated, or aryl fused ring having 0-3 heteroatoms independently selected from nitrogen, oxygen and sulfur;

$L^1$ is one of the following:
(a) a $C_{1-5}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CH(OR)—, —C(F)$_2$—, —N(R)—, —S—, —S(O)—, or —S(O)$_2$—; or
(b) a covalent bond;

$L^2$ and $L^3$ are independently one of the following:
(a) a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CH(OR)—, —C(F)$_2$—, —N(R)—, —S—, —S(O)—, or —S(O)$_2$—; or
(b) a covalent bond;

each R is independently hydrogen, or an optionally substituted group selected from $C_{1-6}$ aliphatic; phenyl; an 8-10 membered bicyclic aryl ring, a 3-7 membered saturated or partially unsaturated monocyclic carbocyclic ring; a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; and an 8-10 membered bicyclic heteroaryl ring having 1-5 heteroatoms independently selected from nitrogen, oxygen, and sulfur; or two R groups on the same nitrogen are optionally taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur;

m is 0, 1, 2, 3, or 4;

n is 0, 1, 2, 3, or 4;

p is 0, 1, 2, 3, or 4; and q is 0, 1, 2, 3, or 4.

Compounds may be more specifically defined by reference to certain variables associated with Formula I-1*. For example, in some embodiments, Ring A is phenyl. In some embodiments, Ring A is a 3-7 membered saturated or partially unsaturated monocyclic carbocyclic ring. In some embodiments, Ring A is a 5-6 membered monocyclic heteroaryl ring having 1-4 heteroatoms independently selected from nitrogen, oxygen, and sulfur. In some embodiments, Ring A is a 4-8 membered saturated or partially unsaturated monocyclic heterocyclic ring having 1-2 heteroatoms independently selected from nitrogen, oxygen, and sulfur.

In some embodiments, two $R^2$ groups are taken together to form =O and Ring A is a pyridone ring. In some embodiments, Ring A is piperazine ring. In some embodiments, Ring A is a pyridine ring.

In some embodiments, Ring A is

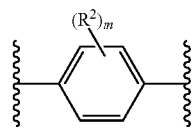

In some embodiments, Ring A is

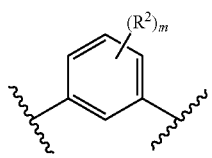

In some embodiments, Ring A is

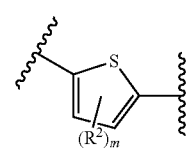

In some embodiments, Ring A is

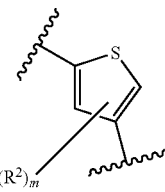

In some embodiments, Ring A is

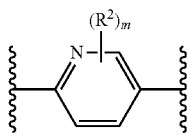

In some embodiments, Ring A is

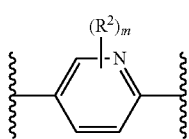

In some embodiments, Ring A is

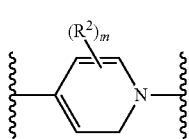

In some embodiments, Ring A is

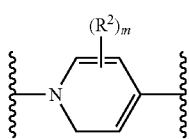

In some embodiments, Ring A is

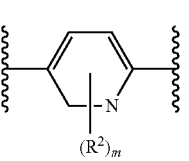

In some embodiments, Ring A is

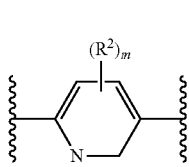

In some embodiments, Ring A is

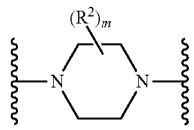

In some embodiments, two R² groups are taken together to form =O and Ring A is

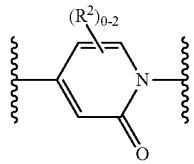

In some embodiments, two R² groups are taken together to form =O and Ring A is

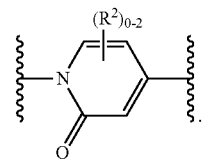

In some embodiments, two R² groups are taken together to form =O and Ring A is

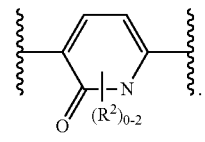

In some embodiments, two R² groups are taken together to form =O and Ring A is

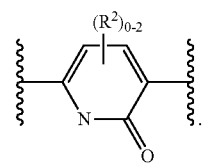

In some embodiments, Ring A is selected from those depicted in Table 1, below.

In some embodiments, Ring B is a 6-membered monocyclic partially unsaturated heterocyclyl or heteroaryl ring having 1-4 heteroatoms independently selected from nitrogen, oxygen, and sulfur. In some embodiments, Ring B is an 8-10 membered partially aromatic or heteroaromatic bicyclic heterocyclic ring having 1-4 heteroatoms independently selected from nitrogen, oxygen, and sulfur. In some embodiments, Ring B is phenyl.

In some embodiments, Ring B is

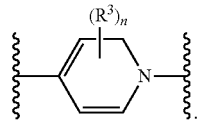

In some embodiments, Ring B is

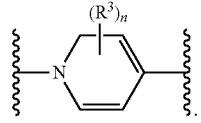

In some embodiments, Ring B is

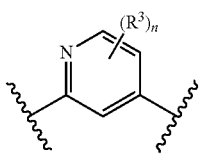

In some embodiments, Ring B is

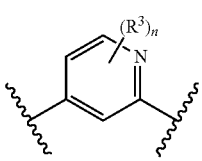

In some embodiments, Ring B is

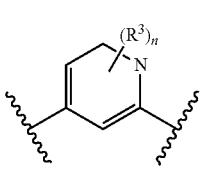

In some embodiments, Ring B is

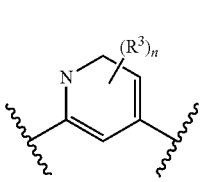

In some embodiments, Ring B is

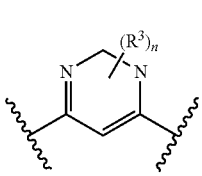

In some embodiments, Ring B is
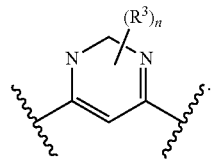
In some embodiments, Ring B is
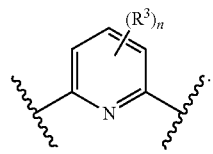
In some embodiments,
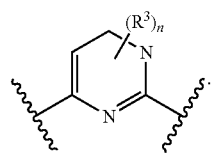
In some embodiments, Ring B is
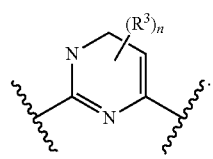
In some embodiments, Ring B is
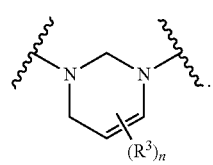
In some embodiments, Ring B is
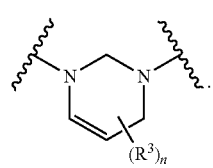
In some embodiments, Ring B is
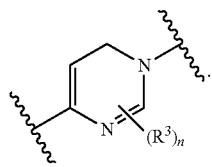
In some embodiments, Ring B is
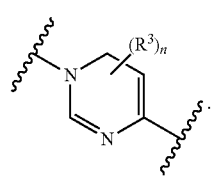
In some embodiments, Ring B is
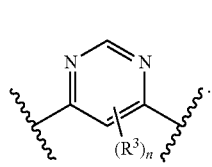
In some embodiments, Ring B is
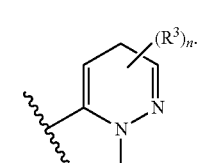
In some embodiments, Ring B is
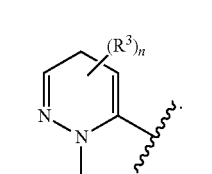
In some embodiments, Ring B is
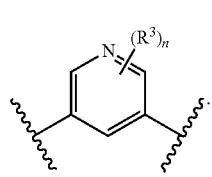

In some embodiments, Ring B is
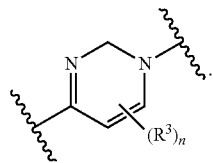
In some embodiments, Ring B is
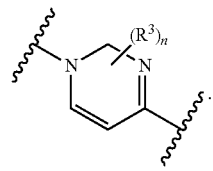
In some embodiments, Ring B is
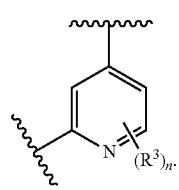
In some embodiments, Ring B is
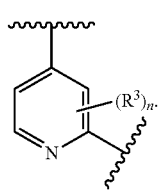
In some embodiments, Ring B is
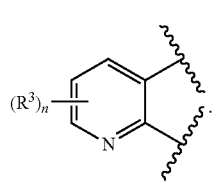
In some embodiments, Ring B is
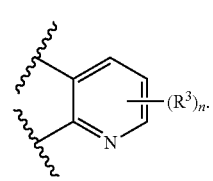
In some embodiments, Ring B is
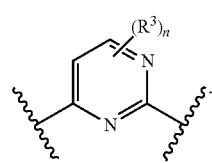
In some embodiments, Ring B is
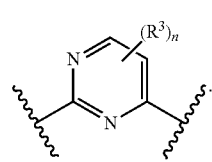
In some embodiments, Ring B is
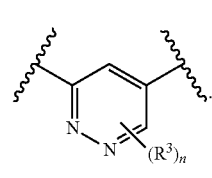
In some embodiments, Ring B is
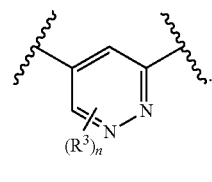
In some embodiments, Ring B is
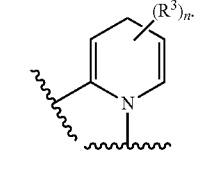
In some embodiments, Ring B is
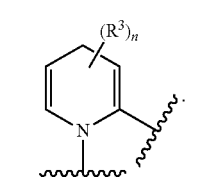

In some embodiments, Ring B is

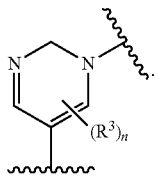

In some embodiments, Ring B is

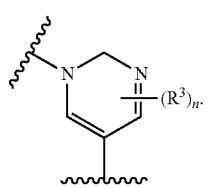

In some embodiments, Ring B is

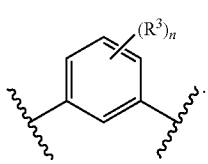

In some embodiments, Ring B is

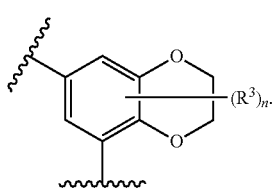

In some embodiments, Ring B is

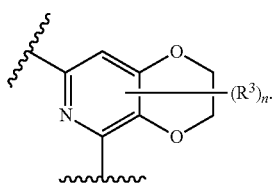

In some embodiments, Ring B is

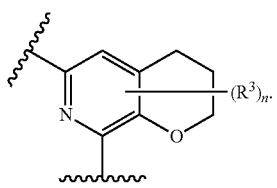

In some embodiments, Ring B is

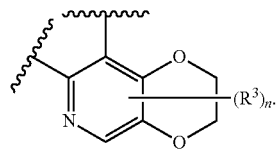

In some embodiments, Ring B is

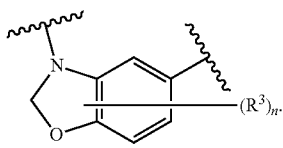

In some embodiments, two $R^3$ groups are taken together to form =O and Ring B is

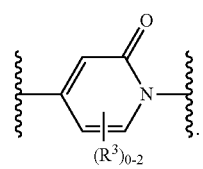

In some embodiments, two $R^3$ groups are taken together to form =O and Ring B is

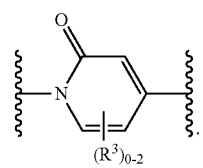

In some embodiments, two $R^3$ groups are taken together to form =O and Ring B is

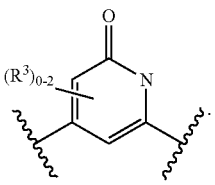

In some embodiments, two $R^3$ groups are taken together to form =O and Ring B is

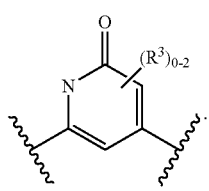

In some embodiments, two R³ groups are taken together to form =O and Ring B is

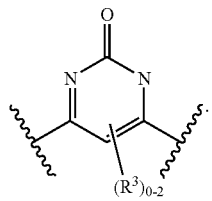

In some embodiments, two R³ groups are taken together to form =O and Ring B is

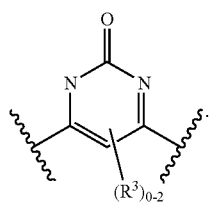

In some embodiments, two R³ groups are taken together to form =O and Ring B is

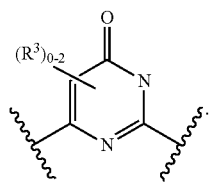

In some embodiments, two R³ groups are taken together to form =O and Ring B is

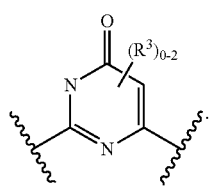

In some embodiments, two R³ groups are taken together to form =O and Ring B is

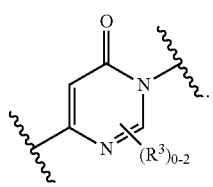

In some embodiments, two R³ groups are taken together to form =O and Ring B is

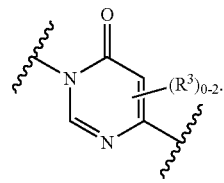

In some embodiments, two R³ groups are taken together to form =O and Ring B is

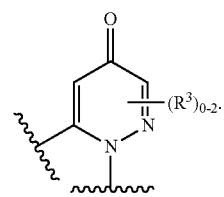

In some embodiments, two R³ groups are taken together to form =O and Ring B is

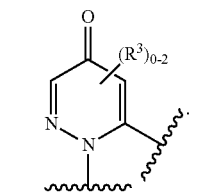

In some embodiments, two R³ groups are taken together to form =O and Ring B is

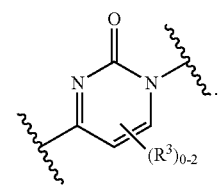

In some embodiments, two R³ groups are taken together to form =O and Ring B is

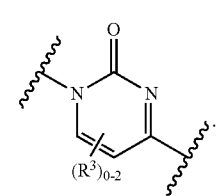

In some embodiments, two R³ groups are taken together to form =O and Ring B is

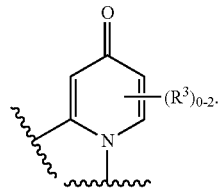

In some embodiments, two R³ groups are taken together to form =O and Ring B is

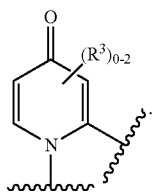

In some embodiments, two R³ groups are taken together to form =O and Ring B is

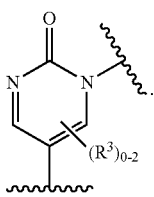

In some embodiments, two R³ groups are taken together to form =O and Ring B is

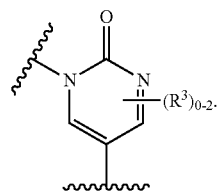

In some embodiments, two R³ groups are taken together to form =O and Ring B is

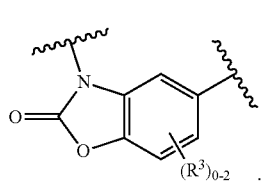

In some embodiments, two sets of R³ groups are taken together to each form =O and Ring B is

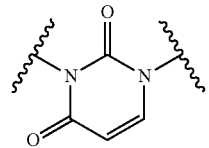

In some embodiments, two sets of R³ groups are taken together to each form =O and Ring B is

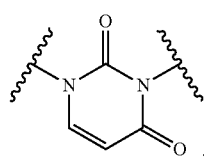 [SMILES: *n1ccc(=O)n(*)c1=O]

In some embodiments, Ring B is selected from those depicted in Table 1, below.

In some embodiments, Ring C is a 4-8 membered saturated or partially unsaturated monocyclic heterocyclic ring having 1-2 heteroatoms independently selected from nitrogen, oxygen, and sulfur. In some embodiments, Ring C is a 5-6 membered monocyclic heteroaryl ring having 1-4 heteroatoms independently selected from nitrogen, oxygen, and sulfur. In some embodiments, Ring C is phenyl. In some embodiments, Ring C is a 3-7 membered saturated or partially unsaturated monocyclic carbocyclic ring. In some embodiments, Ring C is an 8-10 membered partially aromatic or heteroaromatic bicyclic heterocyclic ring having 1-4 heteroatoms independently selected from nitrogen, oxygen, and sulfur.

In some embodiments, Ring C is

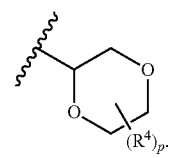

In some embodiments, Ring C is

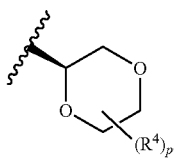

In some embodiments, Ring C is

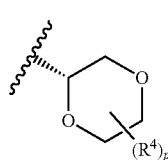

In some embodiments, Ring C is
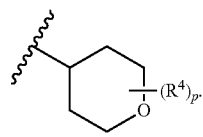
In some embodiments, Ring C is
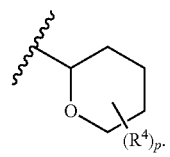
In some embodiments, Ring C is
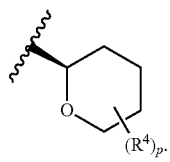
In some embodiments, Ring C is
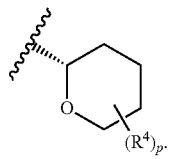
In some embodiments, Ring C is
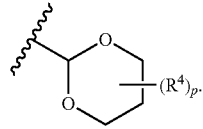
In some embodiments, Ring C is
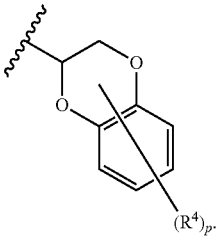
In some embodiments, Ring C is
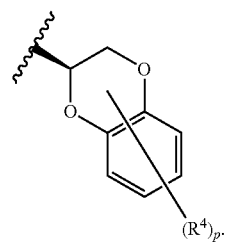
In some embodiments, Ring C is
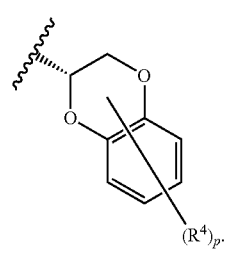
In some embodiments, Ring C is
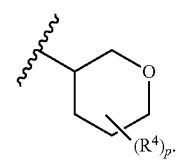
In some embodiments, Ring C is
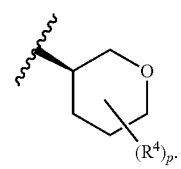
In some embodiments, Ring C is
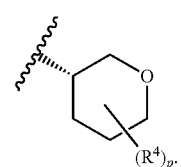

In some embodiments, Ring C is

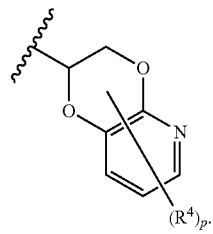

In some embodiments, Ring C is

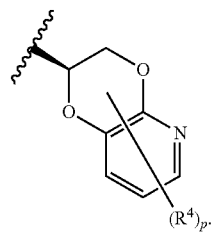

In some embodiments, Ring C is

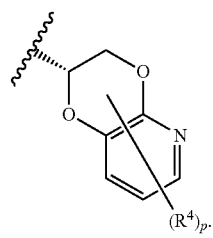

In some embodiments, Ring C is selected from those depicted in Table 1, below.

In some embodiments, $R^1$ is a 3-7 membered saturated or partially unsaturated monocyclic carbocyclic ring which is substituted with q instances of $R^5$. In some embodiments, $R^1$ is a 5-6 membered monocyclic heteroaryl ring having 1-4 heteroatoms independently selected from nitrogen, oxygen, and sulfur which is substituted with q instances of $R^5$. In some embodiments, $R^1$ is a 4-8 membered saturated or partially unsaturated monocyclic heterocyclic ring having 1-2 heteroatoms independently selected from nitrogen, oxygen, and sulfur which is substituted with q instances of $R^5$. In some embodiments, $R^1$ is phenyl which is substituted with q instances of $R^5$. In some embodiments, $R^1$ is a $C_{1-6}$ aliphatic group substituted with q instances of $R^5$.

In some embodiments, $R^1$ is hydrogen. In some embodiments, $R^1$ is —CN. In some embodiments, $R^1$ is —OR. In some embodiments, $R^1$ is methyl. In some embodiments, $R^1$ is

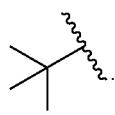

In some embodiments, $R^1$ is

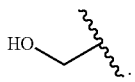

In some embodiments, $R^1$ is

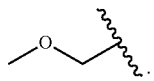

In some embodiments, $R^1$ is

In some embodiments, $R^1$ is

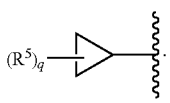

In some embodiments, $R^1$ is

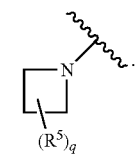

In some embodiments, $R^1$ is

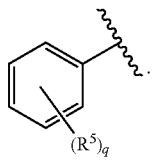

In some embodiments, $R^1$ is

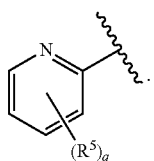

In some embodiments, $R^1$ is

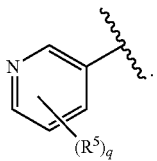

In some embodiments, $R^1$ is —OMe. In some embodiments, $R^1$ is cyano. In some embodiments, $R^1$ is selected from those depicted in Table 1, below.

In some embodiments, $R^2$ is hydrogen, deuterium, $R^z$, halogen, —CN, —NO$_2$, —OR, —SR, —NR$_2$, —S(O)$_2$R, —S(O)$_2$NR$_2$, —S(O)R, —S(O)NR$_2$, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —Si(OR)R$_2$, —SiR$_3$, —P(O)(R)NR$_2$, —P(O)(R)OR or —P(O)R$_2$. In some embodiments, $R^2$ is methyl. In some embodiments, $R^2$ is fluoro. In some embodiments, $R^2$ is bromo. In some embodiments, $R^2$ is selected from those depicted in Table 1, below.

In some embodiments, $R^4$ is hydrogen, deuterium, $R^z$, halogen, —CN, —NO$_2$, —OR, —SR, —NR$_2$, —S(O)$_2$R, —S(O)$_2$NR$_2$, —S(O)R, —S(O)NR$_2$, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —Si(OR)R$_2$, —SiR$_3$, —P(O)(R)NR$_2$, —P(O)(R)OR or —P(O)R$_2$. In some embodiments, $R^4$ is hydrogen. In some embodiments, $R^4$ is selected from those depicted in Table 1, below.

In some embodiments, $R^5$ is hydrogen, deuterium, $R^z$, halogen, —CN, —NO$_2$, —OR, —SR, —NR$_2$, —S(O)$_2$R, —S(O)$_2$NR$_2$, —S(O)R, —S(O)NR$_2$, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —Si(OR)R$_2$, —SiR$_3$, —P(O)(R)NR$_2$, —P(O)(R)OR or —P(O)R$_2$.

In some embodiments, $R^5$ is methyl. In some embodiments, $R^5$ is fluoro, In some embodiments, $R^5$ is

In some embodiments, $R^5$ is

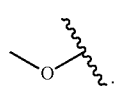

In some embodiments, $R^5$ is selected from those depicted in Table 1, below.

As defined generally above, two $R^2$ groups are optionally taken together to form =O.
In some embodiments, two $R^2$ groups are taken together to form =O.
As defined generally above, two $R^4$ groups are optionally taken together to form =O.
In some embodiments, two $R^4$ groups are taken together to form =O.
As defined generally above, two $R^5$ groups are optionally taken together to form =O.
In some embodiments, two $R^5$ groups are taken together to form =O.
As defined generally above, two $R^2$ groups are optionally taken together with their intervening atoms to form a 5-8 membered saturated, partially unsaturated, or aryl fused ring having 0-3 heteroatoms independently selected from nitrogen, oxygen and sulfur.
In some embodiments, two $R^2$ groups are taken together with their intervening atoms to form a 5-8 membered saturated, partially unsaturated, or aryl fused ring having 0-3 heteroatoms independently selected from nitrogen, oxygen and sulfur.
As defined generally above, two $R^4$ groups are optionally taken together with their intervening atoms to form a 5-8 membered saturated, partially unsaturated, or aryl fused ring having 0-3 heteroatoms independently selected from nitrogen, oxygen and sulfur.
In some embodiments, two $R^4$ groups are taken together with their intervening atoms to form a 5-8 membered saturated, partially unsaturated, or aryl fused ring having 0-3 heteroatoms independently selected from nitrogen, oxygen and sulfur.
In some embodiments, two $R^5$ groups are taken together with their intervening atoms to form a 5-8 membered saturated, partially unsaturated, or aryl fused ring having 0-3 heteroatoms independently selected from nitrogen, oxygen and sulfur.
In some embodiments, $R^z$ is an optionally substituted group selected from $C_{1-6}$ aliphatic; phenyl; a 4-7 membered saturated or partially unsaturated heterocyclic ring having 1-2 heteroatoms independently selected from nitrogen, oxygen, and sulfur; or a 5-6 membered heteroaryl ring having 1-4 heteroatoms independently selected from nitrogen, oxygen, and sulfur. In some embodiments, $R^z$ is selected from those depicted in Table 1, below.

In some embodiments, $R^3$ is hydrogen, deuterium, halogen, —OR, —SR, —NR$_2$, —S(O)$_2$R, —S(O)$_2$NR$_2$, —S(O)R, —S(O)NR$_2$, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN. In some embodiments, $R^3$ is an optionally substituted selected from $C_{1-6}$ aliphatic; phenyl; a 3-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur. In some embodiments, $R^3$ is methyl. In some embodiments, $R^3$ is ethyl. In some embodiments, $R^3$ is chloro. In some embodiments, $R^3$ is

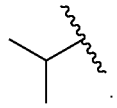

In some embodiments, R³ is

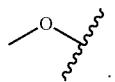

In some embodiments, R³ is

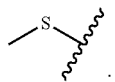

In some embodiments, R³ is —CF₃. In some embodiments, R³ is

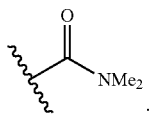

In some embodiments, R³ is

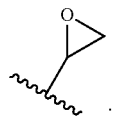

In some embodiments, R³ is

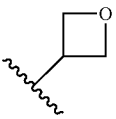

In some embodiments, two R³ groups are taken together to form =O. In some embodiments, two R³ groups are taken together with their intervening atoms to form a 5-8 membered saturated, partially unsaturated, or aryl fused ring having 0-3 heteroatoms independently selected from nitrogen, oxygen and sulfur.

In some embodiments, two R³ groups are taken together with their intervening atoms to form

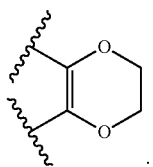 [SMILES: *C1=C(*)OCCO1]

In some embodiments, two R³ groups are taken together with their intervening atoms to form

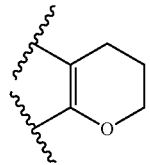

In some embodiments, R³ is selected from those depicted in Table 1, below.

In some embodiments, $L^1$ is a $C_{1-5}$ bivalent straight or branched saturated or unsaturated hydrocarbon chain wherein 1-2 methylene units of the chain are independently and optionally replaced with —O—, —C(O)—, —C(S)—, —C(R)₂—, —CH(R)—, —CH(OR)—, —C(F)₂—, —N(R)—, —S—, —S(O)—, or —S(O)₂—. In some embodiments, $L^1$ is a covalent bond. In some embodiments, $L^1$ is

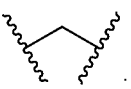

In some embodiments, $L^1$ is

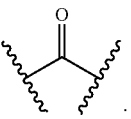 [SMILES: *C(*)=O]

In some embodiments, $L^1$ is

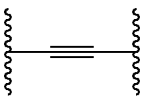

In some embodiments, $L^1$ is

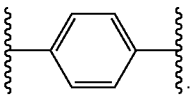

In some embodiments, $L^1$ is

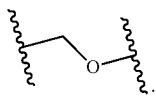

In some embodiments, $L^1$ is

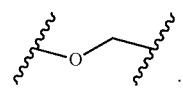

In some embodiments, $L^1$ is

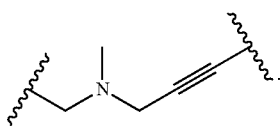

In some embodiments, $L^1$ is

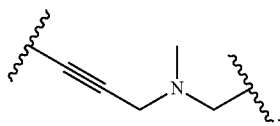 [SMILES: *C#CCN(C)C*]

In some embodiments, $L^1$ is

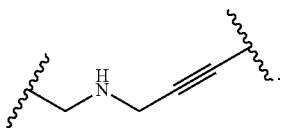 [SMILES: *C#CCNC*]

In some embodiments, $L^1$ is

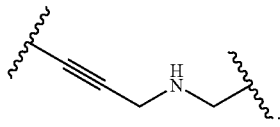 [SMILES: *C#CCNC*]

In some embodiments, $L^1$ is

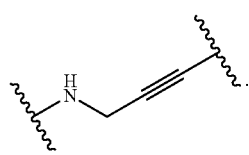 [SMILES: *C#CCN*]

In some embodiments, $L^1$ is

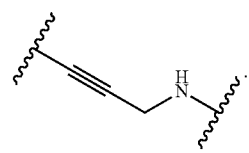 [SMILES: *C#CCN*]

In some embodiments, $L^1$ is

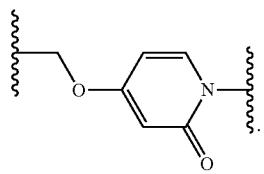

In some embodiments, $L^1$ is

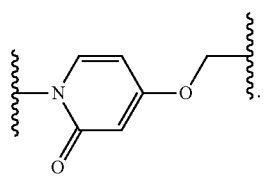 [SMILES: *COc1ccn(*)c(=O)c1]

In some embodiments, $L^1$ is selected from those depicted in Table 1, below.

In some embodiments, $L^2$ is a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —CH(OR)—, —C(F)$_2$—, —N(R)—S—, —S(O)—, or —S(O)$_2$—. In some embodiments, $L^2$ is a covalent bond. In some embodiments, $L^2$ is

In some embodiments, $L^2$ is

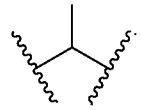 [SMILES: *C(*)C]

In some embodiments, $L^2$ is

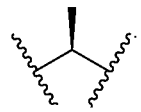

In some embodiments, $L^2$ is

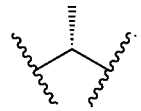

In some embodiments, L² is

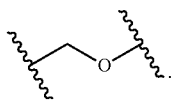 [SMILES: *CO*]

In some embodiments, L² is

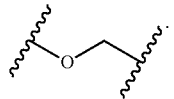 [SMILES: *CO*]

In some embodiments, L² is

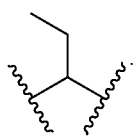 [SMILES: *C(*)CC]

In some embodiments, L² is

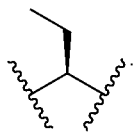

In some embodiments, L² is

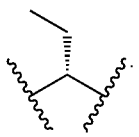

In some embodiments, L² is

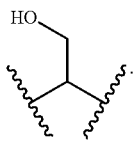

In some embodiments, L² is

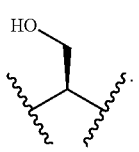

In some embodiments, L² is

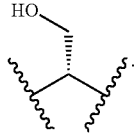

In some embodiments, L² is selected from those depicted in Table 1, below.

In some embodiments, L³ is a $C_{1-3}$ bivalent straight or branched saturated or unsaturated hydrocarbon chain wherein 1-2 methylene units of the chain are independently and optionally replaced with —O—, —C(O)—, —C(S)—, —C(R)₂—, —CH(R)—, —CH(OR)—, —C(F)₂—, —N(R)—S—, —S(O)—, or —S(O)₂—. In some embodiments, L³ is a covalent bond. In some embodiments, L³ is

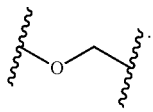 [SMILES: *CO*]

In some embodiments, L³ is

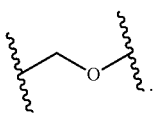

In some embodiments, L³ is

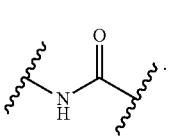 [SMILES: *NC(*)=O]

In some embodiments, L³ is

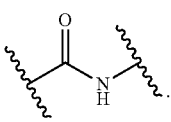 [SMILES: *NC(*)=O]

In some embodiments, L³ is

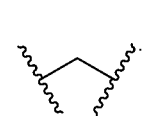

In some embodiments, L³ is selected from those depicted in Table 1, below.

In some embodiments, R is hydrogen. In some embodiments, R is an optionally substituted group selected from $C_{1-6}$ aliphatic; phenyl; an 8-10 membered bicyclic aryl ring, a 3-7 membered saturated or partially unsaturated monocyclic carbocyclic ring; a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; and an 8-10 membered bicyclic heteroaryl ring having 1-5 heteroatoms independently selected from nitrogen, oxygen, and sulfur. In some embodiments, two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur. In some embodiments, R is selected from those depicted in Table 1, below.

In some embodiments, m is 0. In some embodiments, m is 1. In some embodiments, m is 2. In some embodiments, m is 3. In some embodiments, m is 4. In some embodiments, is selected from those depicted in Table 1, below. In some embodiments, n is 0. In some embodiments, n is 1. In some embodiments, n is 2. In some embodiments, n is 3. In some embodiments, n is 4. In some embodiments, n is selected from those depicted in Table 1, below. In some embodiments, p is 0. In some embodiments, p is 1. In some embodiments, p is 2. In some embodiments, p is 3. In some embodiments, p is 4. In some embodiments, p is selected from those depicted in Table 1, below. In some embodiments, q is 0. In some embodiments, q is 1. In some embodiments, q is 2. In some embodiments, q is 3. In some embodiments, q is 4. In some embodiments, q is selected from those depicted in Table 1, below.

In some embodiments, the present invention provides a compound of formula I-1*, wherein $L^3$ is —OCH$_2$—, Ring B is pyridone, two $R^3$ groups are taken together to form =O, and Ring C is oxetanyl, to provide a compound of formula I-a-1*, I-a-2*, or I-a-3*:

I-a-1*

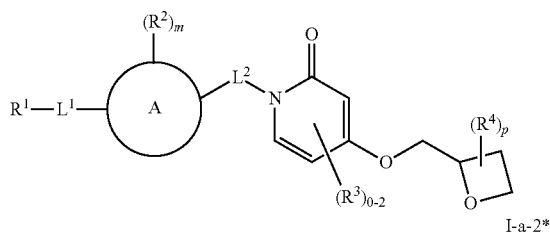

I-a-2*

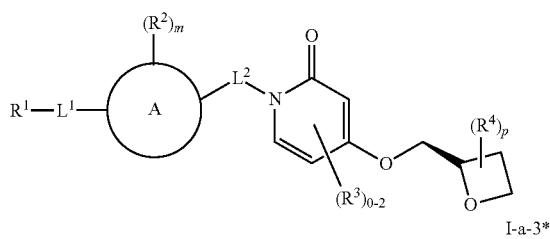

I-a-3*

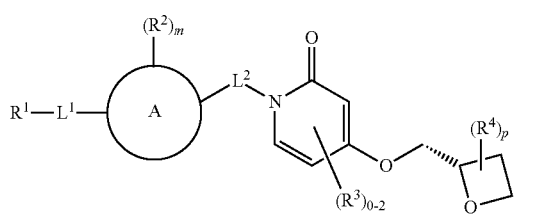

or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I-1*, wherein $L^3$ is —OCH$_2$—, Ring B is pyridone, two $R^3$ groups are taken together to form =O, and Ring C is furanyl, to provide a compound of formula I-b-1*, I-b-2*, or I-b-3*:

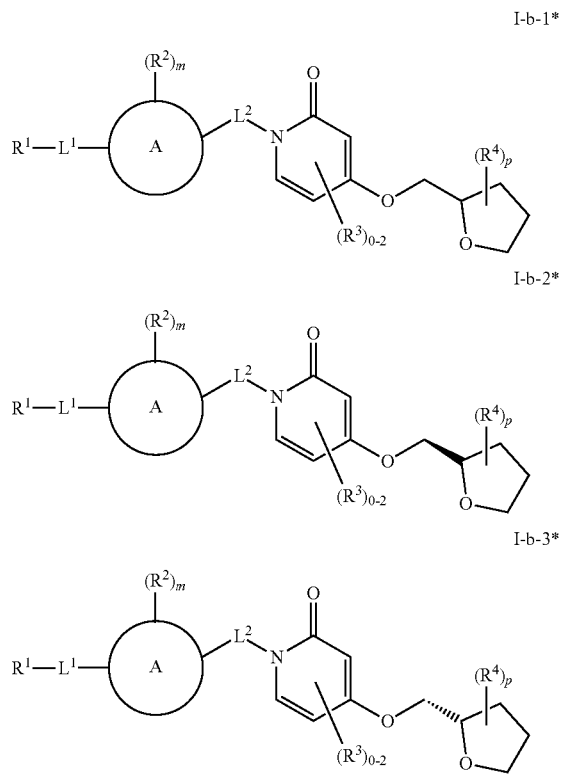

or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I-1*, wherein $L^3$ is —OCH$_2$—, Ring B is pyridone, two $R^3$ groups are taken together to form =O, and Ring C is tetrahydropyranyl, to provide a compound of formula I-c-1*, I-c-2*, or I-c-3*:

I-c-1*

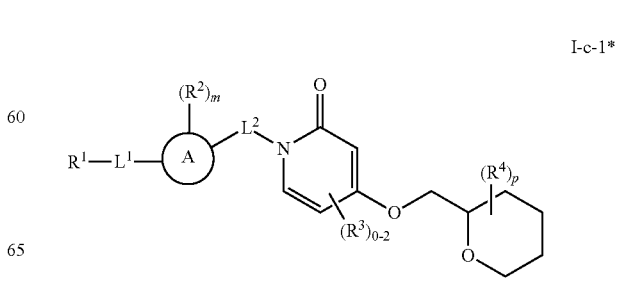

-continued

I-c-2*

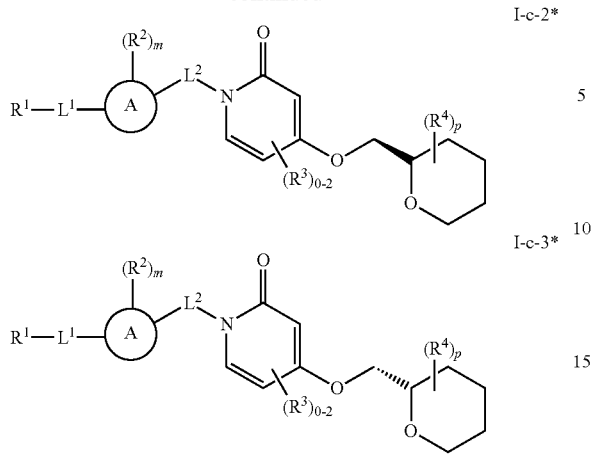

I-c-3* or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I-1*, wherein $L^3$ is —$OCH_2$—, Ring B is pyridone, two $R^3$ groups are taken together to form =O, and Ring C is 1,4-dioxanyl, to provide a compound of formula I-d-1*, I-d-2*, or I-d-3*:

I-d-1*

I-d-2*

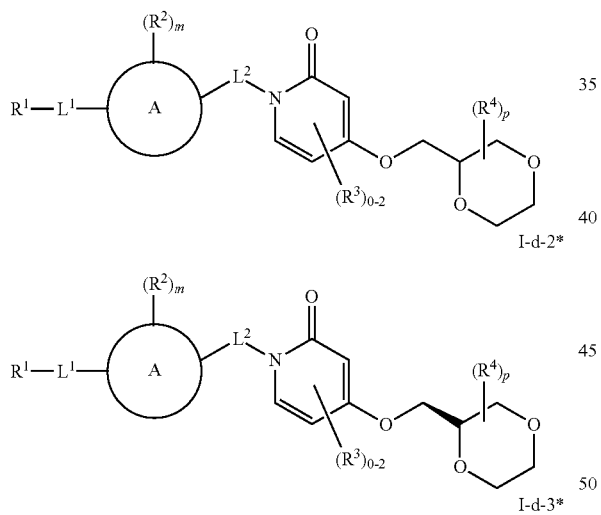

I-d-3* or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I-1*, wherein Ring A is phenyl, thiophenyl, or pyridyl; Ring B is pyridone; and two $R^3$ groups are taken together to form =O; to provide a compound of formula I-e-1*, I-e-2*, or I-e-3*:

I-e-1*

I-e-2*

I-e-3*

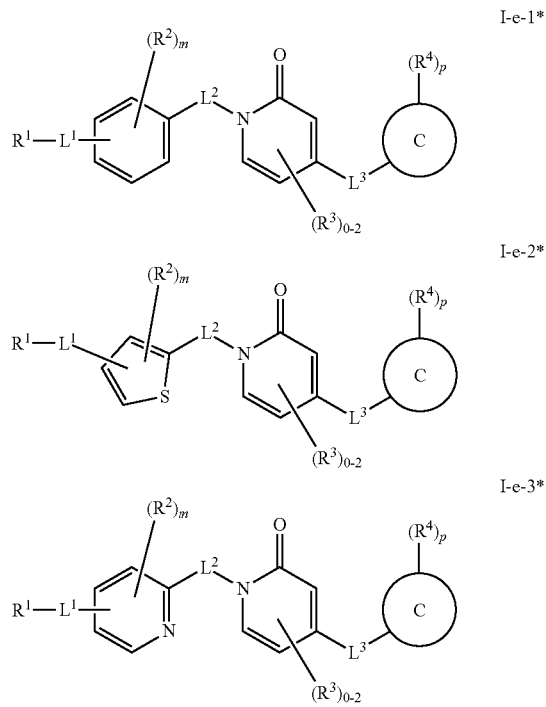

or a pharmaceutically acceptable salt thereof, wherein each of Ring C, $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I-1*, wherein $L^1$ is

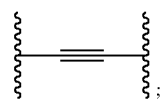

Ring A is phenyl, thiophenyl, or pyridyl; Ring B is pyridone; and two $R^3$ groups are taken together to form =O; to provide a compound of formula I-f-1*, I-f-2*, or I-f-3*:

I-f-1*

I-f-2*

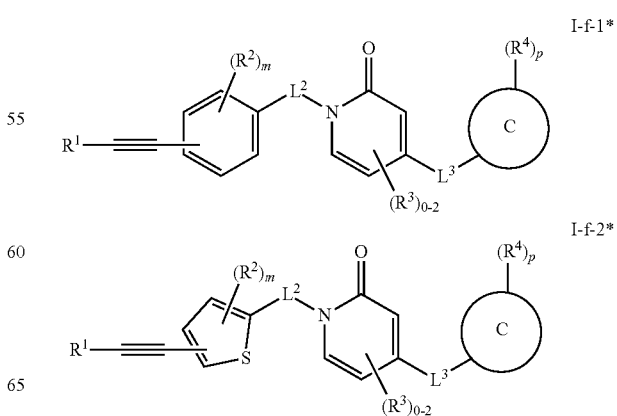

I-f-3*

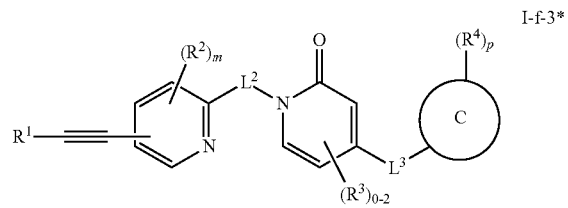

or a pharmaceutically acceptable salt thereof, wherein each of Ring C, $L^2$, $L^3$, $R^1$, $R^2$, $R^3$, $R^4$, m, and p is as defined above and described in embodiments herein, both singly and in combination.

In some embodiments, the present invention provides a compound of formula I-1*, wherein Ring A is phenyl, thiophenyl, or pyridyl; Ring B is pyridone; two $R^3$ groups are taken together to form =O; and Ring C is oxetanyl; to provide a compound of formula I-g-1*, I-g-2*, or I-g-3*:

I-g-1*

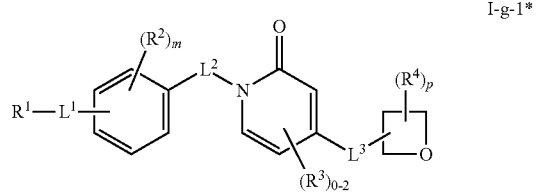

I-g-2*

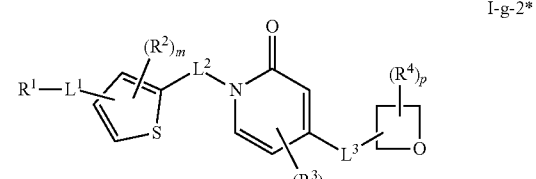

I-g-3*

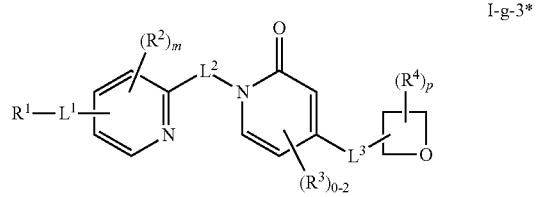

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I-1*, wherein Ring A is phenyl, thiophenyl, or pyridyl; Ring B is pyridone; two $R^3$ groups are taken together to form =O; and Ring C is furanyl, to provide a compound of formula I-h-1*, I-h-2*, or I-h-3*:

I-h-1*

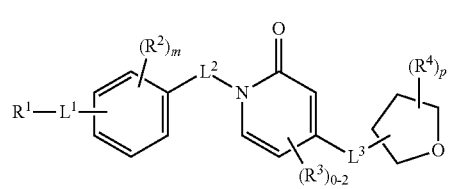

I-h-2*

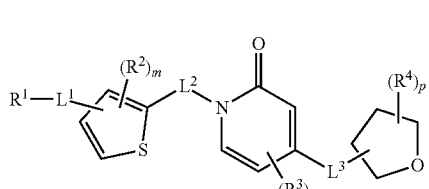

I-h-3*

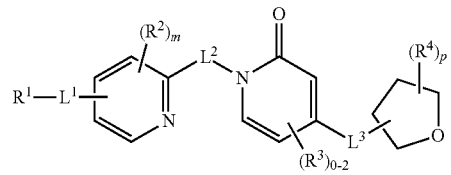

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I-1*, wherein Ring A is phenyl, thiophenyl, or pyridyl; Ring B is pyridone; two $R^3$ groups are taken together to form =O; and Ring C is tetrahydropyranyl; to provide a compound of formula I-i-1*, I-i-2*, or I-i-3*:

I-i-1*

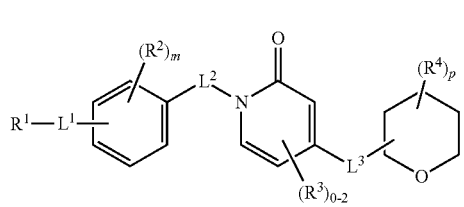

I-i-2*

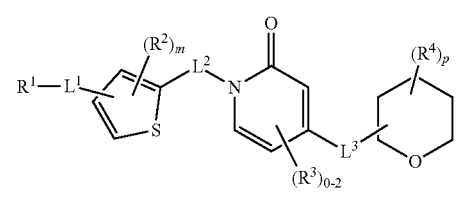

I-i-3*

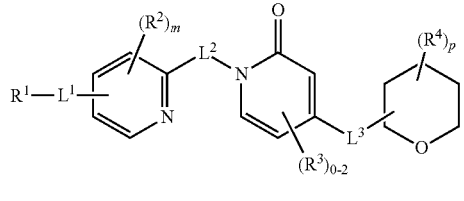

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I-1*, wherein Ring A is phenyl, thiophenyl, or pyridyl; Ring B is pyridone; two $R^3$ groups are taken together to form =O; and Ring C is 1,4-dioxanyl; to provide a compound of formula I-j-1*, I-j-2*, or I-j-3*:

I-j-1*

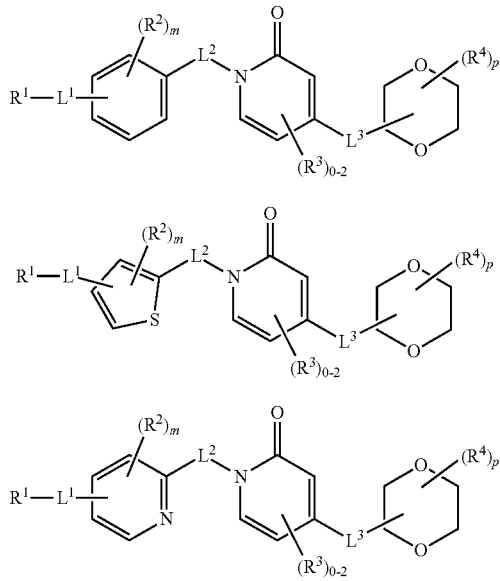

I-j-2*

I-j-3* or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I-1*, wherein $L^3$ is —$OCH_2$—, Ring B is pyrimidone, two $R^3$ groups are taken together to form =O, and Ring C is oxetanyl, to provide a compound of formula II-a-1*, II-a-2*, or II-a-3*:

II-a-1*

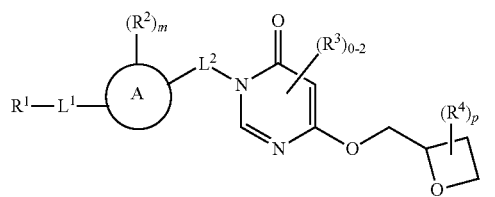

II-a-2*

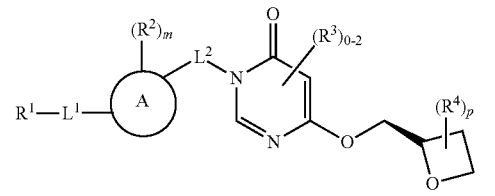

II-a-3*

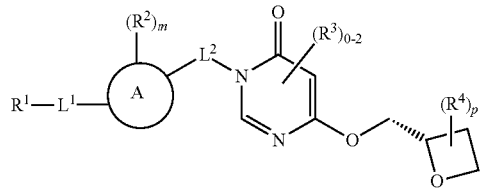

or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I-1*, wherein $L^3$ is —$OCH_2$—, Ring B is pyrimidone, two $R^3$ groups are taken together to form =O, and Ring C is furanyl, to provide a compound of formula II-b-1*, II-b-2*, or II-b-3*:

II-b-1*

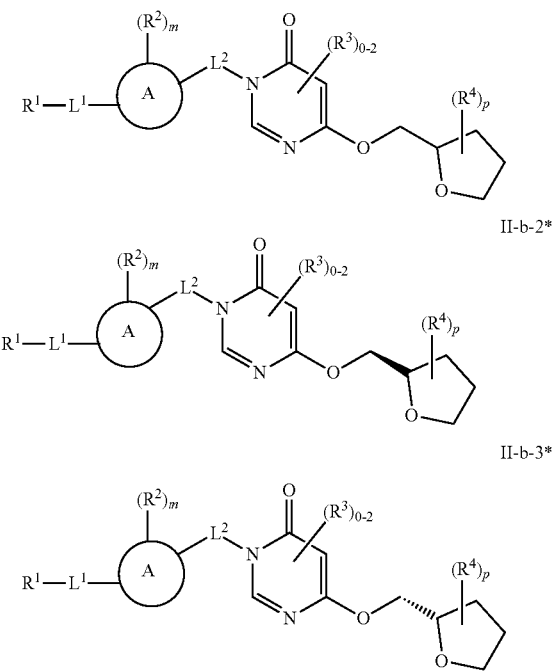

II-b-2*

II-b-3* or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I-1*, wherein $L^3$ is —$OCH_2$—, Ring B is pyrimidone, two $R^3$ groups are taken together to form =O, and Ring C is tetrahydropyranyl, to provide a compound of formula II-c-1*, II-c-2*, or II-c-3*:

II-c-1*

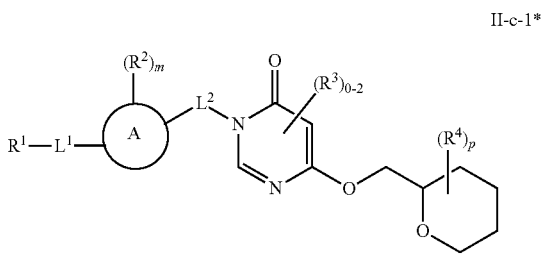

II-c-2*

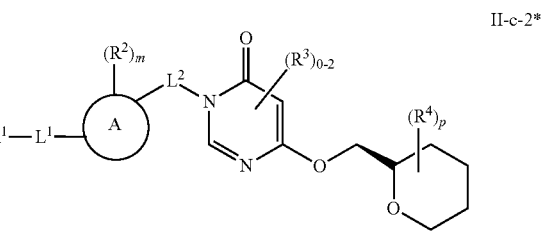

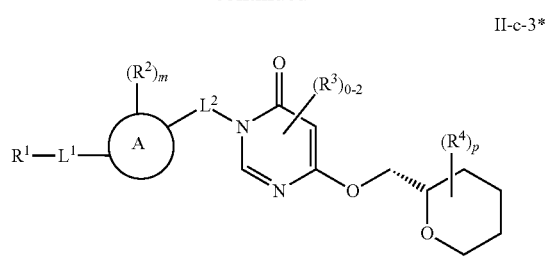

II-c-3* or a pharmaceutically acceptable salt thereof, wherein each of Ring A, $L^1$, $L^2$, $R^1$, $R^2$, $R^3$, $R^4$, m and p is as defined above and described in embodiments herein, both singly and in combination.

In some embodiments, the present invention provides a compound of formula I-1*, wherein $L^3$ is —$OCH_2$—, Ring B is pyrimidone, two $R^3$ groups are taken together to form =O, and Ring C is 1,4-dioxanyl, to provide a compound of formula II-d-1*, II-d-2*, or II-d-3*:

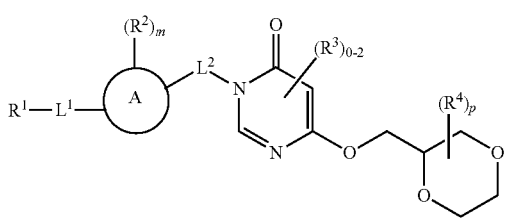

II-d-1*

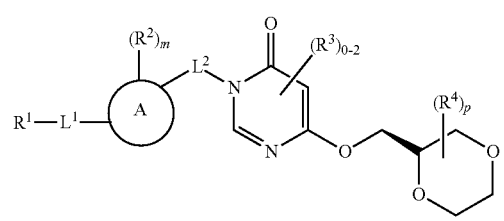

II-d-2*

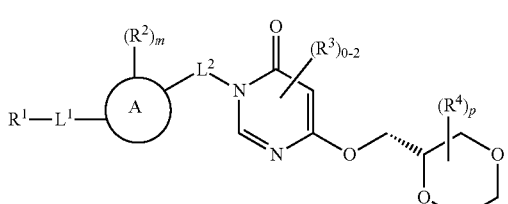

II-d-3* or a pharmaceutically acceptable salt thereof, wherein each of Ring A, $L^1$, $L^2$, $R^1$, $R^2$, $R^3$, $R^4$, m, and p is as defined above and described in embodiments herein, both singly and in combination.

In some embodiments, the present invention provides a compound of formula I-1*, wherein Ring A is phenyl, thiophenyl, or pyridyl; Ring B is pyrimidone; and two $R^3$ groups are taken together to form =O; to provide a compound of formula II-e-1*, II-e-2*, or II-e-3*:

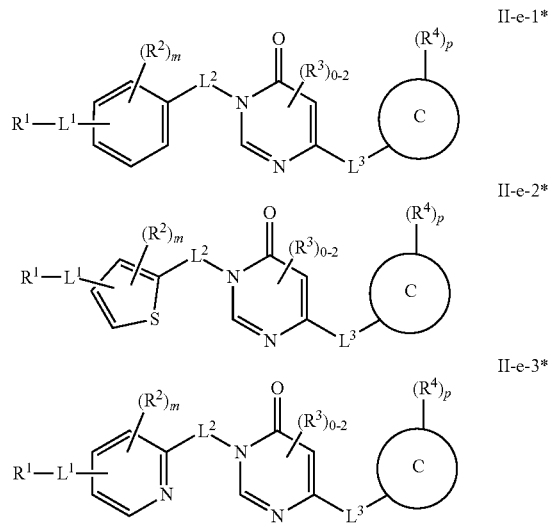

or a pharmaceutically acceptable salt thereof, wherein each of Ring C, $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I-1*, wherein $L^1$ is Ring A is phenyl, thiophenyl, or pyridyl; Ring B is pyrimidone; and two $R^3$ groups are taken together to form =O; to provide a compound of formula II-f-1*, II-f-2*, or II-f-3*:

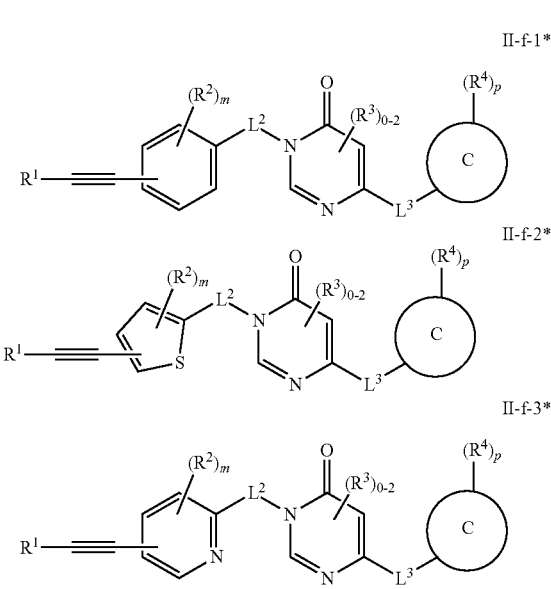

or a pharmaceutically acceptable salt thereof, wherein each of Ring C, $L^2$, $L^3$, $R^1$, $R^2$, $R^3$, $R^4$, m, and p is as defined above and described in embodiments herein, both singly and in combination.

In some embodiments, the present invention provides a compound of formula I-1*, wherein Ring A is phenyl, thiophenyl, or pyridyl; Ring B is pyrimidone; two R³ groups are taken together to form =O; and Ring C is oxetanyl; to provide a compound of formula II-g-1*, II-g-2*, or II-g-3*:

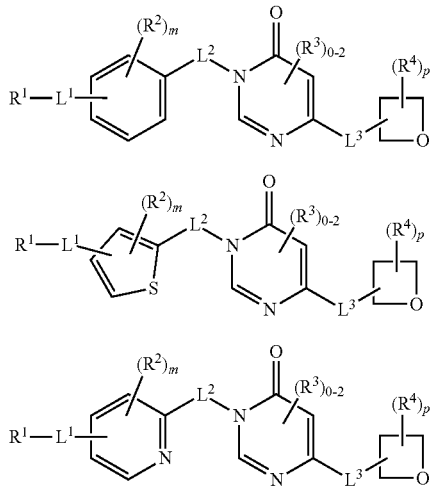

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I-1*, wherein Ring A is phenyl, thiophenyl, or pyridyl; Ring B is pyrimidone; two R³ groups are taken together to form =O; and Ring C is furanyl, to provide a compound of formula II-h-1*, II-h-2*, or II-h-3*:

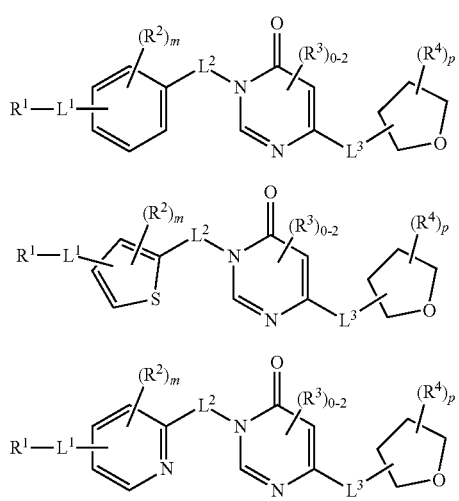

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I-1*, wherein Ring A is phenyl, thiophenyl, or pyridyl; Ring B is pyrimidone; two R³ groups are taken together to form =O; and Ring C is tetrahydropyranyl; to provide a compound of formula II-II-1*, II-II-2*, or II-II-3*:

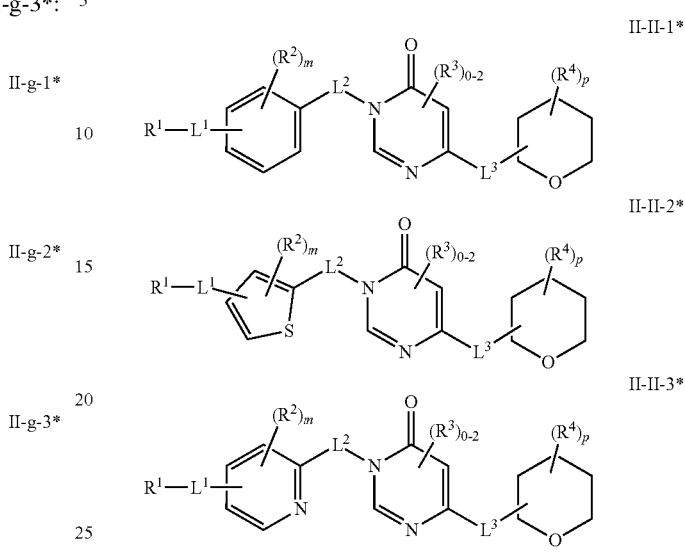

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

In some embodiments, the present invention provides a compound of formula I-1*, wherein Ring A is phenyl, thiophenyl, or pyridyl; Ring B is pyrimidone; two R³ groups are taken together to form =O; and Ring C is 1,4-dioxanyl; to provide a compound of formula II-j-1*, II-j-2*, or II-j-3*:

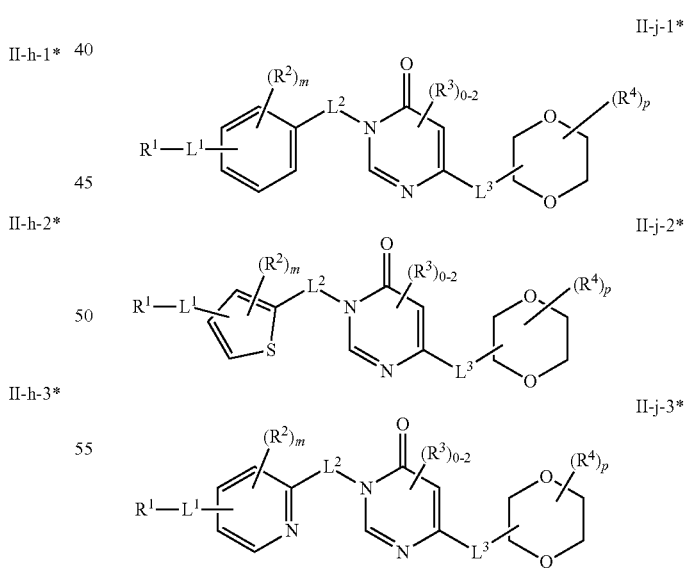

or a pharmaceutically acceptable salt thereof, wherein each of $L^1$, $L^2$, $L^3$, $R^1$, $R^2$, $R^3$, $R^4$, m, and p is as defined above and described in embodiments herein, both singly and in combination.

Exemplary compounds of the invention are set forth in Table 1, below.

TABLE 1
Selected Compounds
| Compound No. | Structure |
|---|---|
| I-1 | 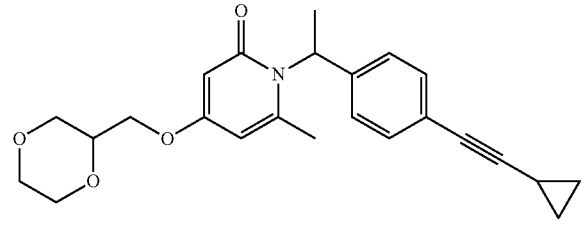 |
| I-2 | 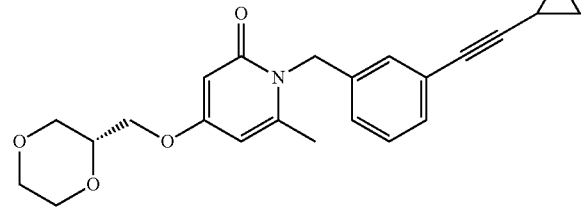 |
| I-3 | 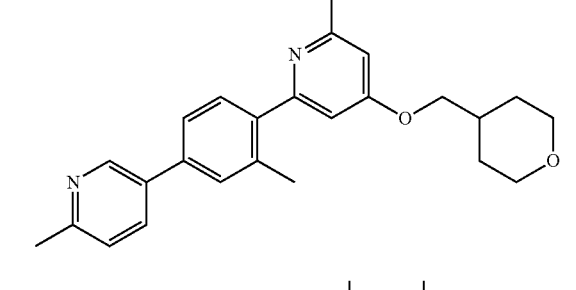 |
| I-4 | 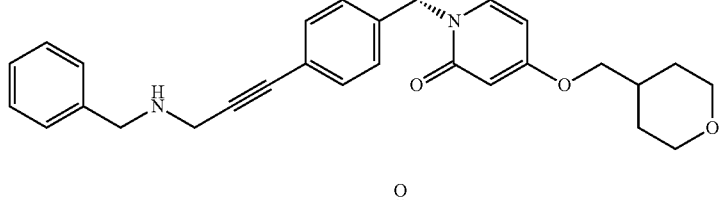 |
| I-5 | 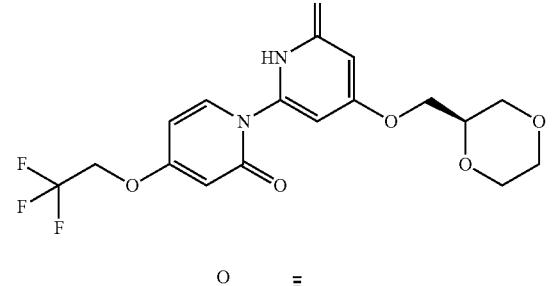 |
| I-6 | 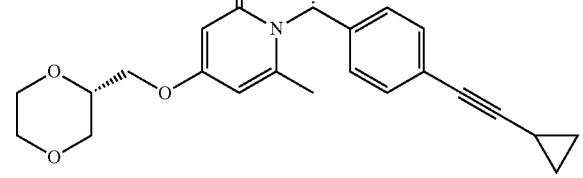 |

TABLE 1-continued
Selected Compounds
| Compound No. | Structure |
|---|---|
| I-7 | 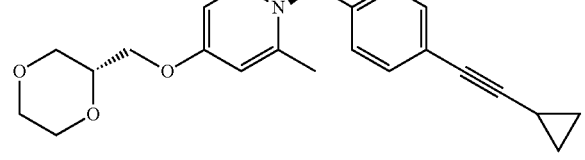 |
| I-8 | 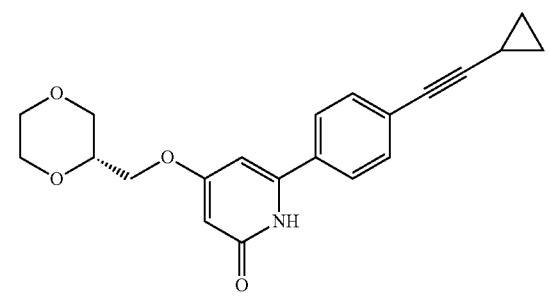 [SMILES: O=c1cc(OC[C@H]2COCCO2)cc(-c2ccc(C#CC3CC3)cc2)[nH]1] |
| I-9 | 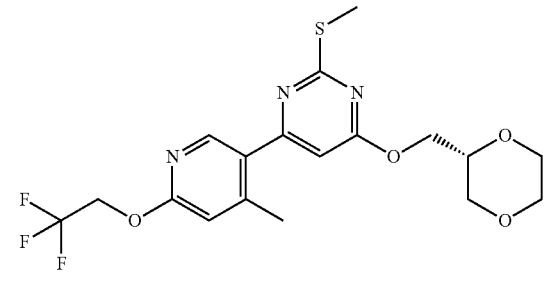 [SMILES: CSc1nc(OC[C@H]2COCCO2)cc(-c2cnc(OCC(F)(F)F)cc2C)n1] |
| I-10 | 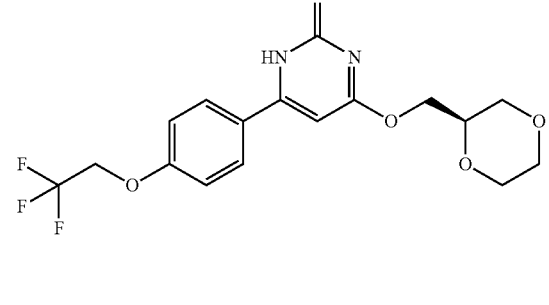 |
| I-11 | 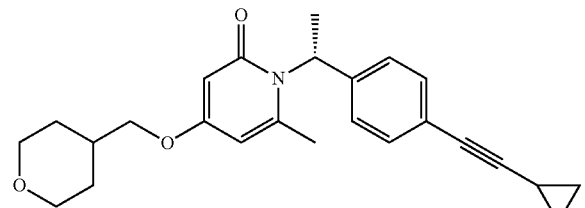 |

TABLE 1-continued
Selected Compounds
| Compound No. | Structure |
|---|---|
| I-12 | 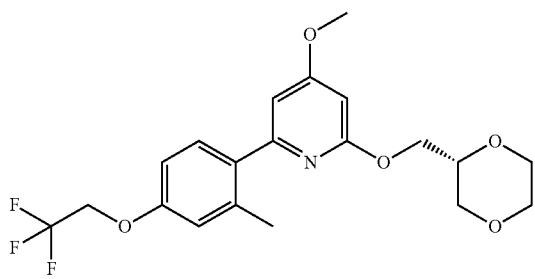 [SMILES: COc1cc(OC[C@H]2COCCO2)nc(-c2ccc(OCC(F)(F)F)cc2C)c1] |
| I-13 | 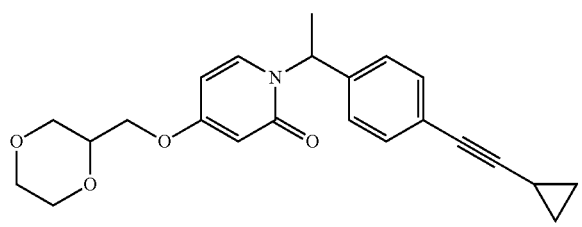 [SMILES: CC(c1ccc(C#CC2CC2)cc1)n1ccc(OCC2COCCO2)cc1=O] |
| I-14 | 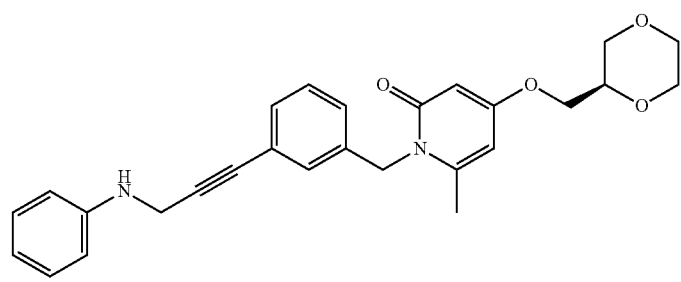 [SMILES: Cc1cc(OC[C@H]2COCCO2)cc(=O)n1Cc1cccc(C#CCNc2ccccc2)c1] |
| I-15 | 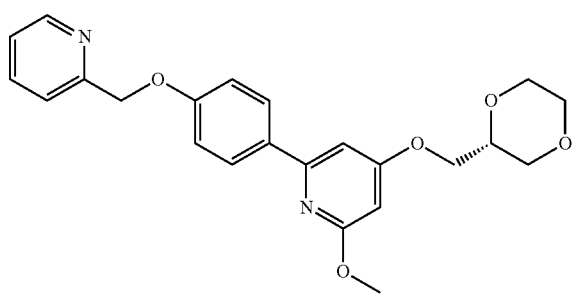 [SMILES: COc1cc(OC[C@H]2COCCO2)cc(-c2ccc(OCc3ccccn3)cc2)n1] |
| I-16 | 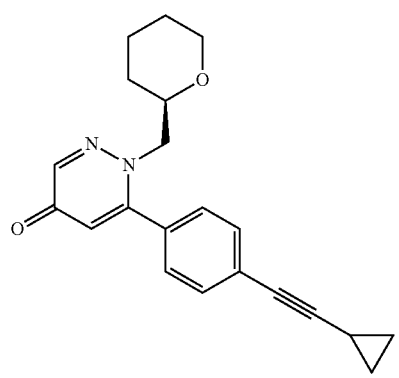 [SMILES: O=c1cnn(C[C@H]2CCCCO2)c(-c2ccc(C#CC3CC3)cc2)c1] |

TABLE 1-continued

Selected Compounds

| Compound No. | Structure |
|---|---|
| I-17 | 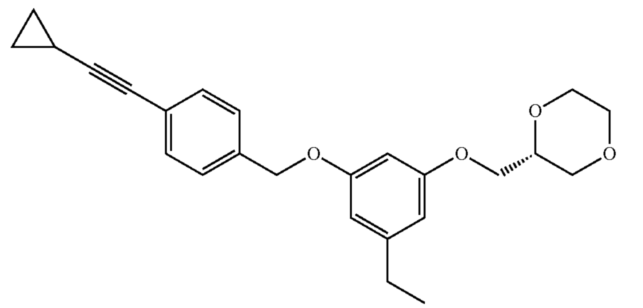 |
| I-18 | 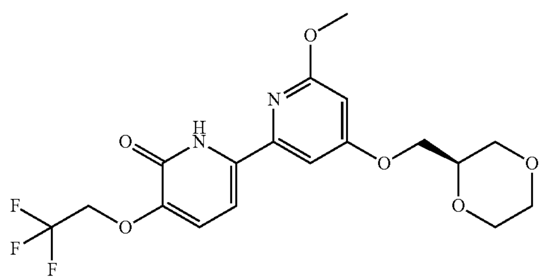 [SMILES: COc1cc(OC[C@H]2COCCO2)cc(-c2ccc(OCC(F)(F)F)c(=O)[nH]2)n1] |
| I-19 | 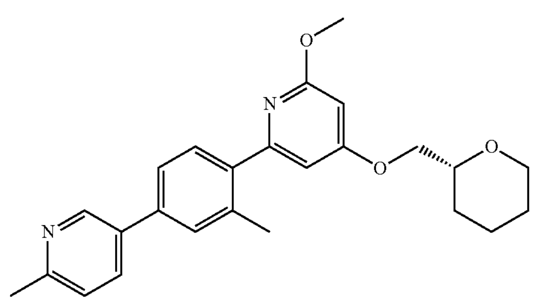 [SMILES: COc1cc(OC[C@H]2CCCCO2)cc(-c2ccc(-c3ccc(C)nc3)cc2C)n1] |
| I-20 | 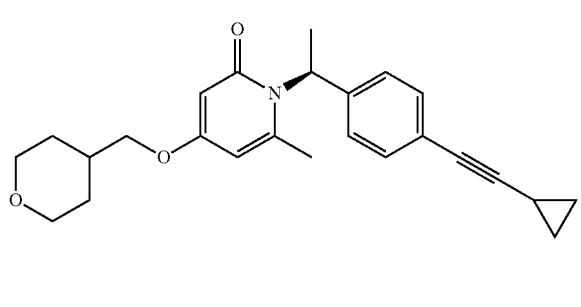 [SMILES: Cc1cc(OCC2CCOCC2)cc(=O)n1[C@@H](C)c1ccc(C#CC2CC2)cc1] |

TABLE 1-continued

Selected Compounds

| Compound No. | Structure |
|---|---|
| I-21 | 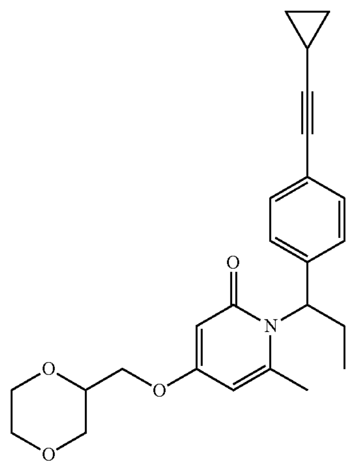 [SMILES: CCC(c1ccc(C#CC2CC2)cc1)n1c(C)cc(OCC2COCCO2)cc1=O] |
| I-22 | 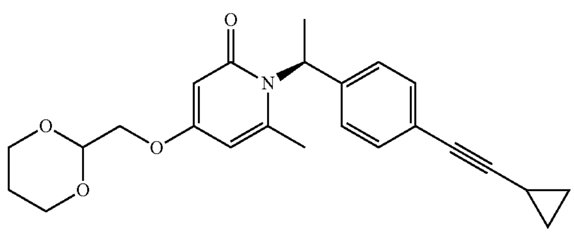 |
| I-23 | 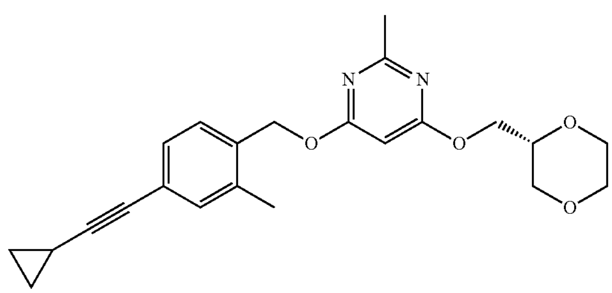 [SMILES: Cc1nc(OCc2ccc(C#CC3CC3)cc2C)cc(OC[C@H]2COCCO2)n1] |
| I-24 | 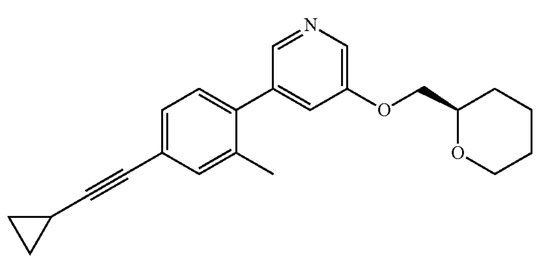 [SMILES: Cc1cc(C#CC2CC2)ccc1-c1cncc(OC[C@H]2CCCCO2)c1] |
| I-25 | 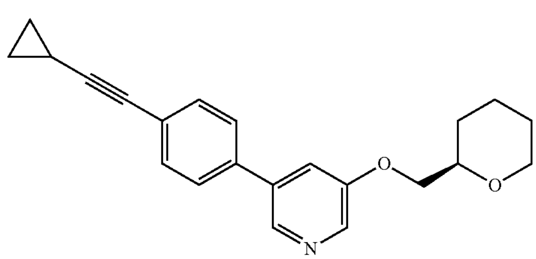 |

121 122
TABLE 1-continued
Selected Compounds
| Compound No. | Structure |
|---|---|
| I-26 | 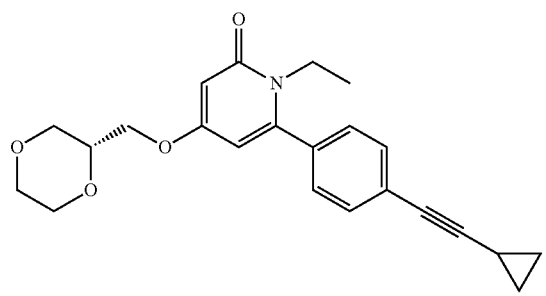 [SMILES: CCn1c(-c2ccc(C#CC3CC3)cc2)cc(OC[C@H]2COCCO2)cc1=O] |
| I-27 | 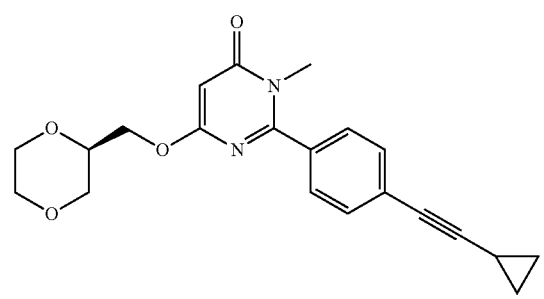 [SMILES: Cn1c(-c2ccc(C#CC3CC3)cc2)nc(OC[C@H]2COCCO2)cc1=O] |
| I-28 | 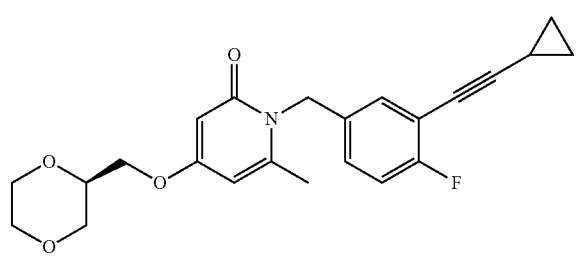 [SMILES: Cc1cc(OC[C@H]2COCCO2)cc(=O)n1Cc1ccc(F)c(C#CC2CC2)c1] |
| I-29 | 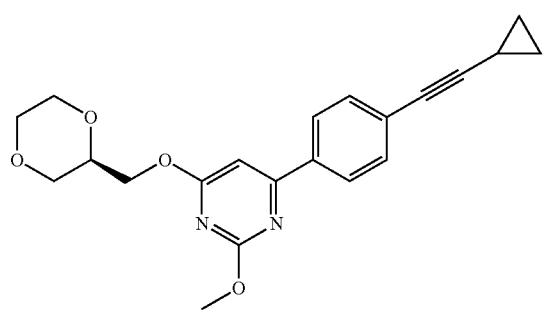 [SMILES: COc1nc(OC[C@H]2COCCO2)cc(-c2ccc(C#CC3CC3)cc2)n1] |
| I-30 | 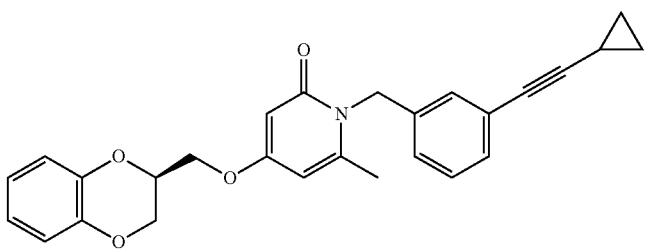 [SMILES: Cc1cc(OC[C@H]2COc3ccccc3O2)cc(=O)n1Cc1cccc(C#CC2CC2)c1] |

TABLE 1-continued

Selected Compounds

| Compound No. | Structure |
|---|---|
| I-31 | 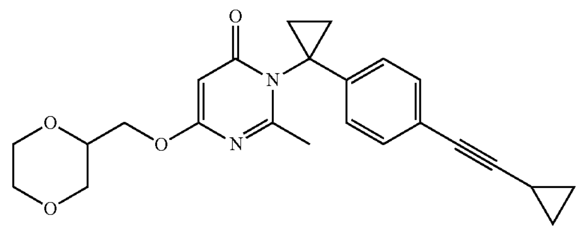 [SMILES: Cc1nc(OCC2COCCO2)cc(=O)n1C1(c2ccc(C#CC3CC3)cc2)CC1] |
| I-32 | 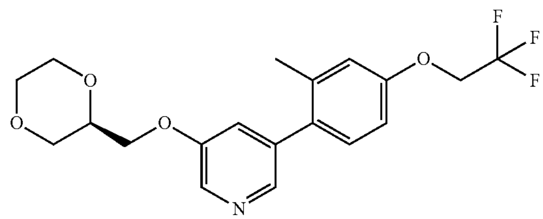 [SMILES: Cc1cc(OCC(F)(F)F)ccc1-c1cncc(OC[C@H]2COCCO2)c1] |
| I-33 | 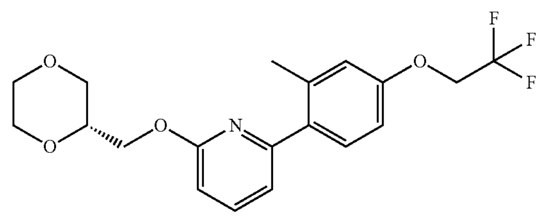 [SMILES: Cc1cc(OCC(F)(F)F)ccc1-c1cccc(OC[C@H]2COCCO2)n1] |
| I-34 | 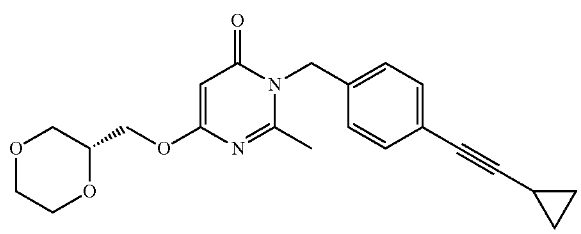 |
| I-35 | 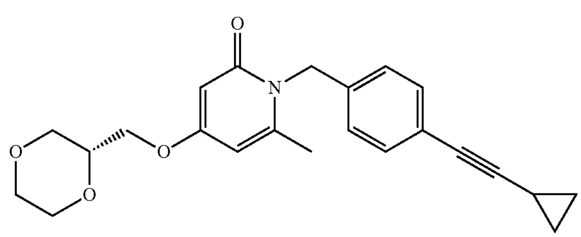 [SMILES: Cc1cc(OC[C@H]2COCCO2)cc(=O)n1Cc1ccc(C#CC2CC2)cc1] |
| I-36 | 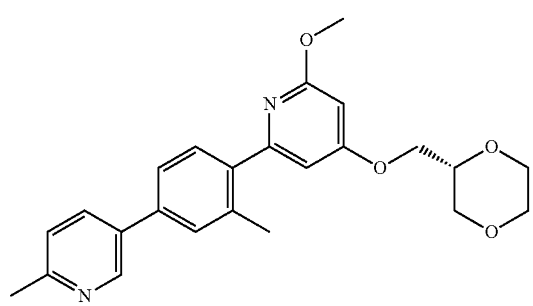 [SMILES: COc1cc(OC[C@H]2COCCO2)cc(-c2ccc(-c3ccc(C)nc3)cc2C)n1] |

TABLE 1-continued
Selected Compounds
| Compound No. | Structure |
|---|---|
| I-37 | 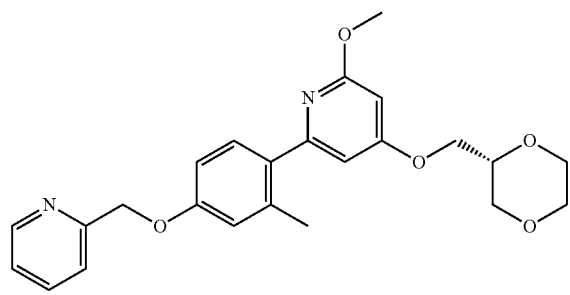 [SMILES: COc1cc(OC[C@H]2COCCO2)cc(-c2ccc(OCc3ccccn3)cc2C)n1] |
| I-38 | 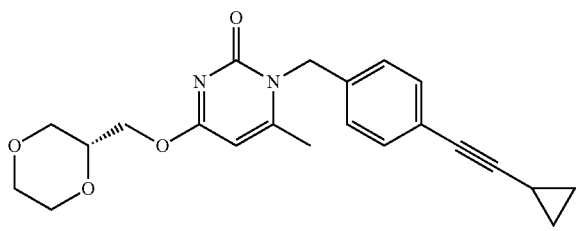 |
| I-39 | 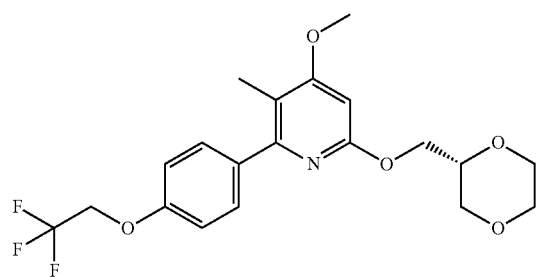 [SMILES: COc1cc(OC[C@H]2COCCO2)nc(-c2ccc(OCC(F)(F)F)cc2)c1C] |
| I-40 | 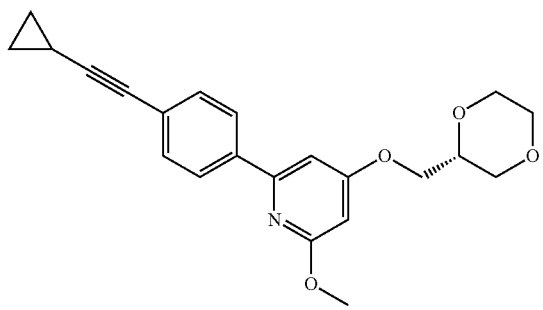 [SMILES: COc1cc(OC[C@H]2COCCO2)cc(-c2ccc(C#CC3CC3)cc2)n1] |
| I-41 | 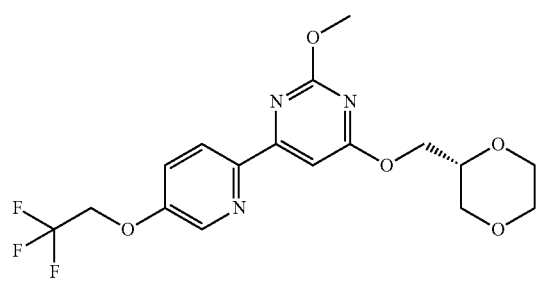 [SMILES: COc1nc(OC[C@H]2COCCO2)cc(-c2ccc(OCC(F)(F)F)cn2)n1] |

TABLE 1-continued
Selected Compounds
| Compound No. | Structure |
|---|---|
| I-42 | 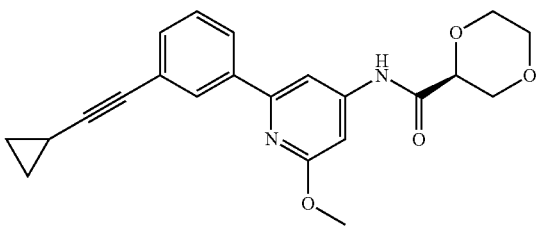 [SMILES: COc1cc(NC(=O)[C@@H]2COCCO2)cc(-c2cccc(C#CC3CC3)c2)n1] |
| I-43 | 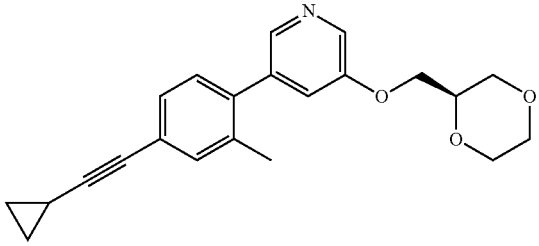 [SMILES: Cc1cc(C#CC2CC2)ccc1-c1cncc(OC[C@H]2COCCO2)c1] |
| I-44 | 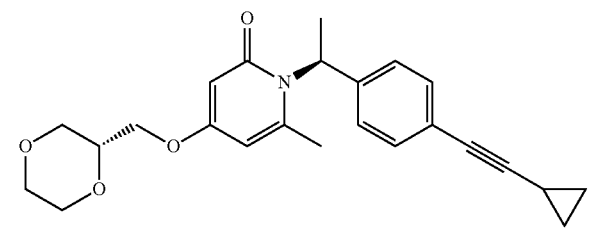 [SMILES: Cc1cc(OC[C@H]2COCCO2)cc(=O)n1[C@@H](C)c1ccc(C#CC2CC2)cc1] |
| I-45 | 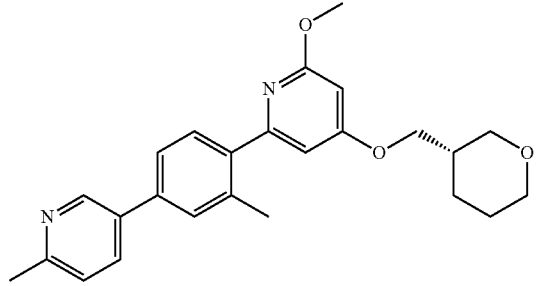 [SMILES: COc1cc(OC[C@H]2CCCOC2)cc(-c2ccc(-c3ccc(C)nc3)cc2C)n1] |
| I-46 | 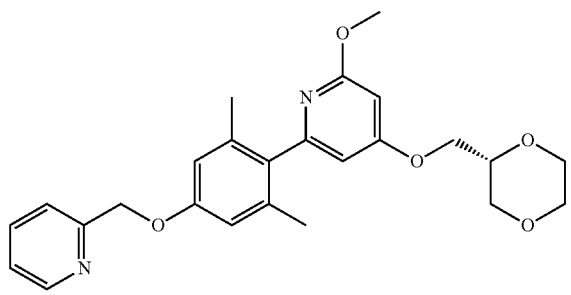 [SMILES: COc1cc(OC[C@H]2COCCO2)cc(-c2c(C)cc(OCc3ccccn3)cc2C)n1] |

TABLE 1-continued

Selected Compounds

| Compound No. | Structure |
|---|---|
| I-47 | 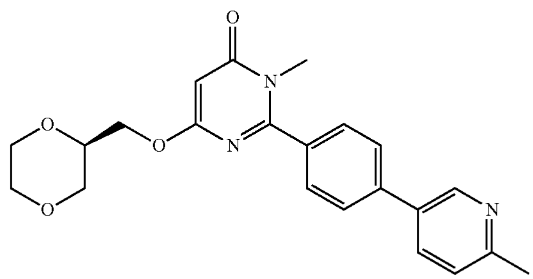 [SMILES: Cc1ccc(-c2ccc(-c3nc(OC[C@H]4COCCO4)cc(=O)n3C)cc2)cn1] |
| I-48 | 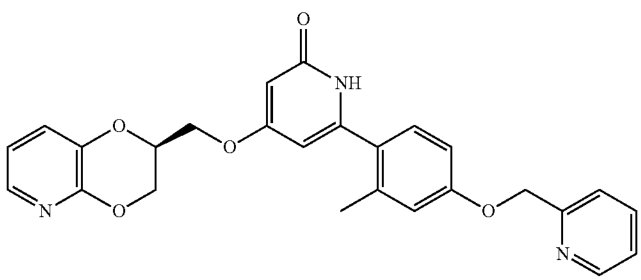 [SMILES: Cc1cc(OCc2ccccn2)ccc1-c1cc(OC[C@H]2COc3ncccc3O2)cc(=O)[nH]1] |
| I-49 | 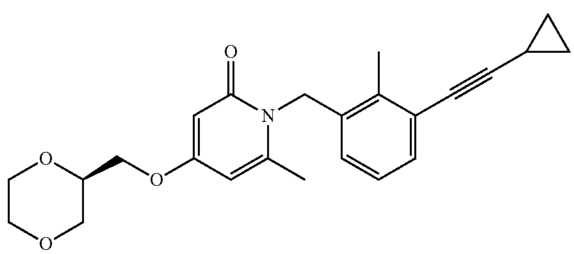 [SMILES: Cc1c(C#CC2CC2)cccc1Cn1c(C)cc(OC[C@H]2COCCO2)cc1=O] |
| I-50 | 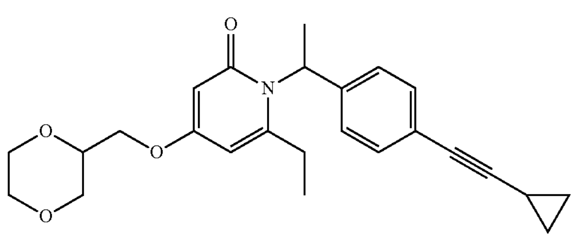 [SMILES: CCc1cc(OCC2COCCO2)cc(=O)n1C(C)c1ccc(C#CC2CC2)cc1] |
| I-51 | 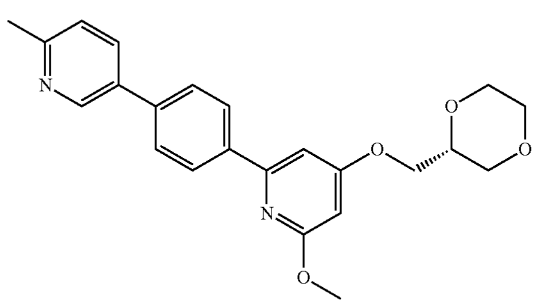 [SMILES: COc1cc(OC[C@H]2COCCO2)cc(-c2ccc(-c3ccc(C)nc3)cc2)n1] |

TABLE 1-continued
Selected Compounds
| Compound No. | Structure |
|---|---|
| I-52 | 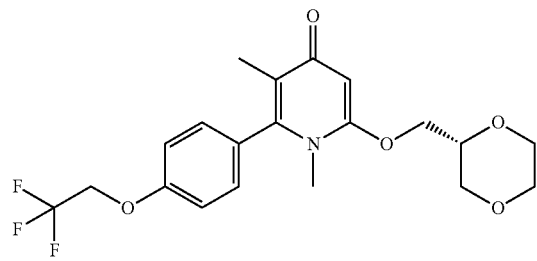 [SMILES: Cc1c(-c2ccc(OCC(F)(F)F)cc2)n(C)c(OC[C@H]2COCCO2)cc1=O] |
| I-53 | 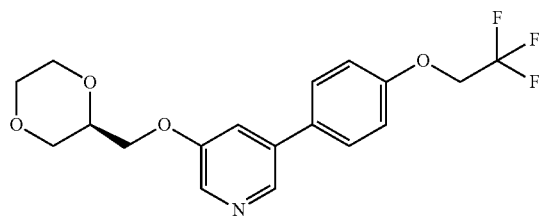 [SMILES: FC(F)(F)COc1ccc(-c2cncc(OC[C@H]3COCCO3)c2)cc1] |
| I-54 | 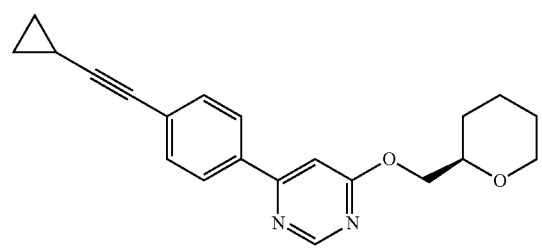 [SMILES: C(#CC1CC1)c1ccc(-c2cc(OC[C@H]3CCCCO3)ncn2)cc1] |
| I-55 | 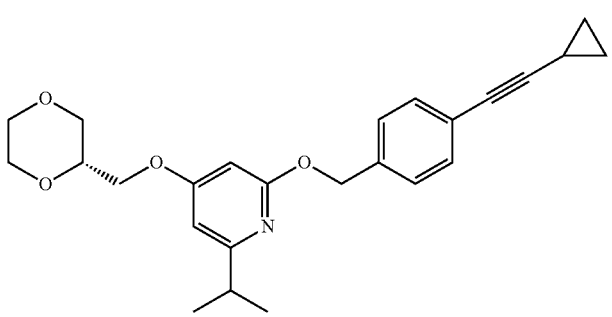 [SMILES: CC(C)c1cc(OC[C@H]2COCCO2)cc(OCc2ccc(C#CC3CC3)cc2)n1] |
| I-56 | 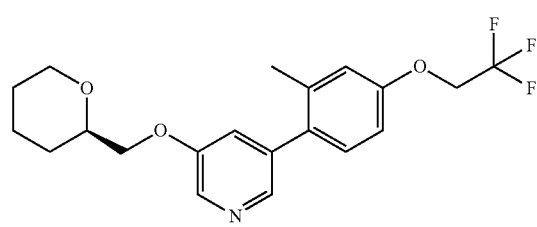 [SMILES: Cc1cc(OCC(F)(F)F)ccc1-c1cncc(OC[C@H]2CCCCO2)c1] |

TABLE 1-continued
Selected Compounds
| Compound No. | Structure |
|---|---|
| I-57 | 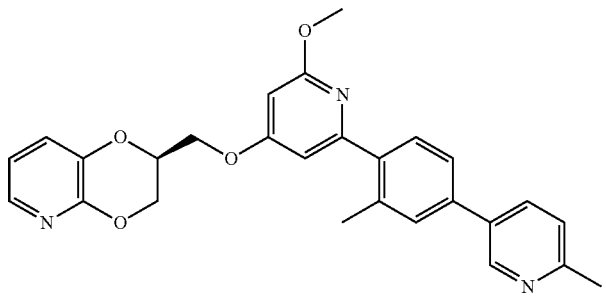 [SMILES: COc1cc(OC[C@H]2COc3ncccc3O2)cc(-c2ccc(-c3ccc(C)nc3)cc2C)n1] |
| I-58 | 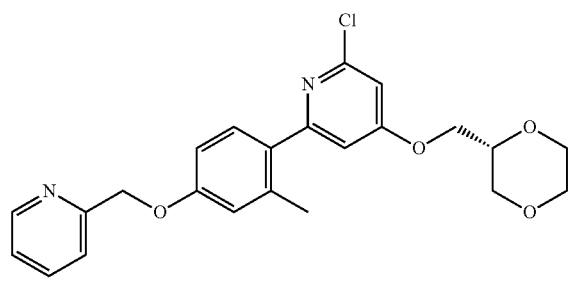 [SMILES: Cc1cc(OCc2ccccn2)ccc1-c1cc(OC[C@H]2COCCO2)cc(Cl)n1] |
| I-59 | 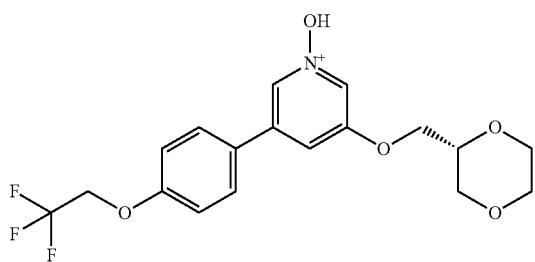 [SMILES: O[n+]1cc(OC[C@H]2COCCO2)cc(-c2ccc(OCC(F)(F)F)cc2)c1] |
| I-60 | 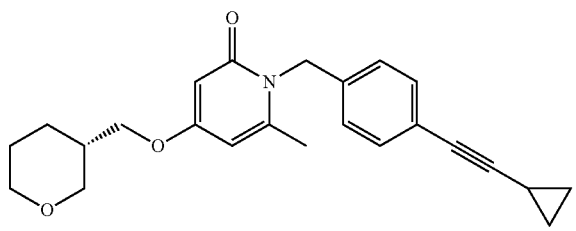 |
| I-61 | 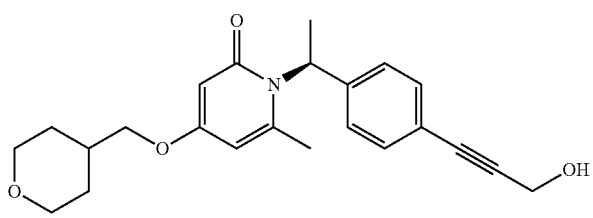 [SMILES: Cc1cc(OCC2CCOCC2)cc(=O)n1[C@@H](C)c1ccc(C#CCO)cc1] |

TABLE 1-continued

Selected Compounds

| Compound No. | Structure |
|---|---|
| I-62 | 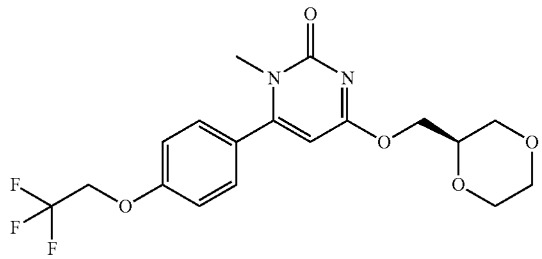 [SMILES: Cn1c(-c2ccc(OCC(F)(F)F)cc2)cc(OC[C@H]2COCCO2)nc1=O] |
| I-63 | 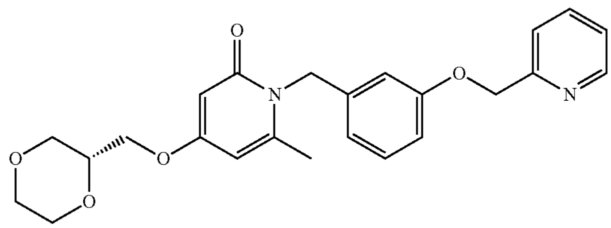 [SMILES: Cc1cc(OC[C@H]2COCCO2)cc(=O)n1Cc1cccc(OCc2ccccn2)c1] |
| I-64 | 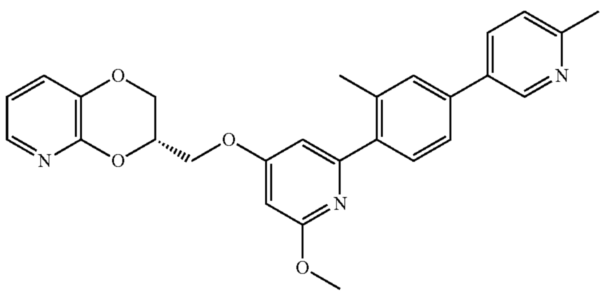 [SMILES: COc1cc(OC[C@H]2COc3cccnc3O2)cc(-c2ccc(-c3ccc(C)nc3)cc2C)n1] |
| I-65 | 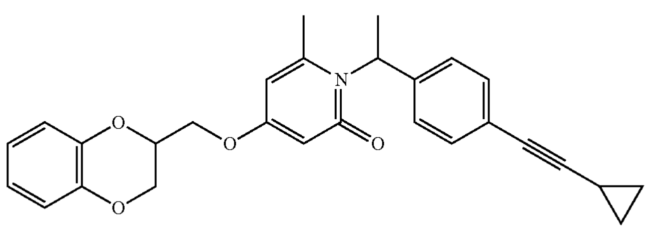 |
| I-66 | 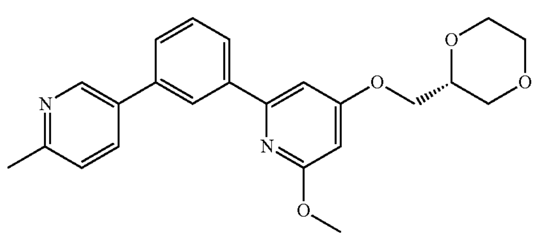 [SMILES: COc1cc(OC[C@H]2COCCO2)cc(-c2cccc(-c3ccc(C)nc3)c2)n1] |
| I-67 | 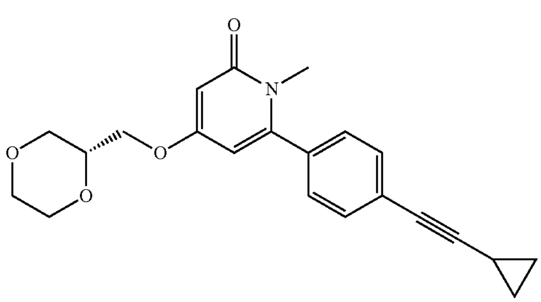 [SMILES: Cn1c(-c2ccc(C#CC3CC3)cc2)cc(OC[C@H]2COCCO2)cc1=O] |

TABLE 1-continued
Selected Compounds
| Compound No. | Structure |
|---|---|
| I-68 | 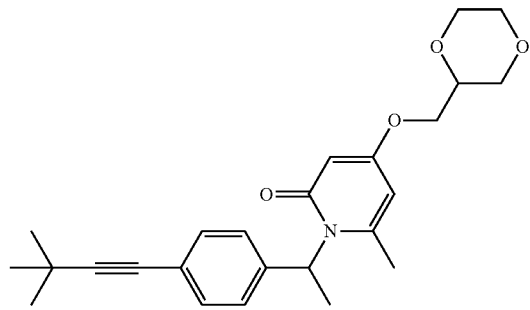 [SMILES: Cc1cc(OCC2COCCO2)cc(=O)n1C(C)c1ccc(C#CC(C)(C)C)cc1] |
| I-69 | 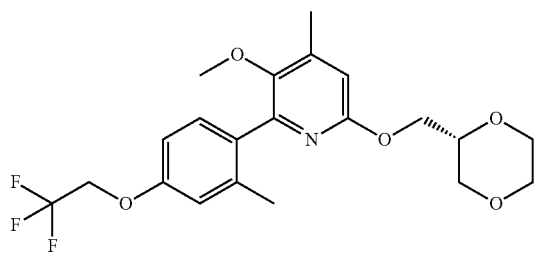 [SMILES: COc1c(C)cc(OC[C@H]2COCCO2)nc1-c1ccc(OCC(F)(F)F)cc1C] |
| I-70 | 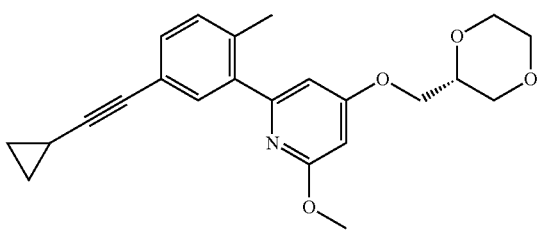 [SMILES: COc1cc(OC[C@H]2COCCO2)cc(-c2cc(C#CC3CC3)ccc2C)n1] |
| I-71 | 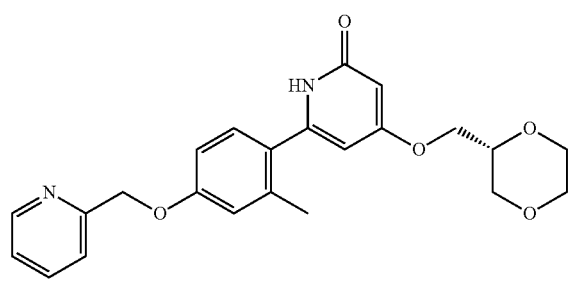 [SMILES: Cc1cc(OCc2ccccn2)ccc1-c1cc(OC[C@H]2COCCO2)cc(=O)[nH]1] |
| I-72 | 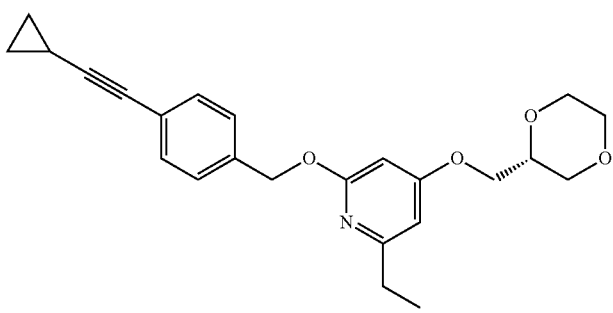 |

TABLE 1-continued
Selected Compounds
| Compound No. | Structure |
|---|---|
| I-73 | 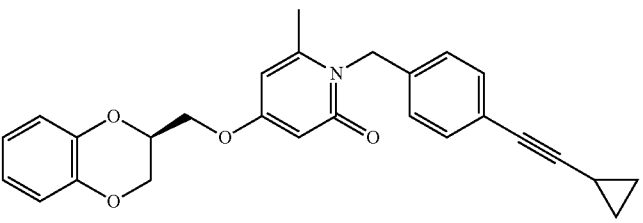 |
| I-74 | 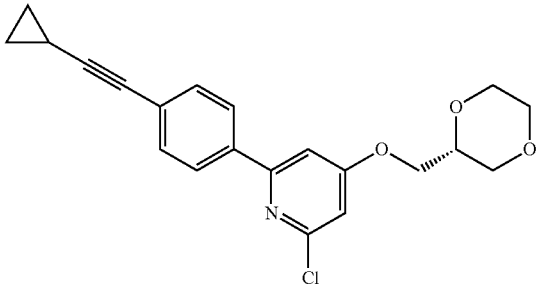 [SMILES: Clc1cc(OC[C@H]2COCCO2)cc(-c2ccc(C#CC3CC3)cc2)n1] |
| I-75 | 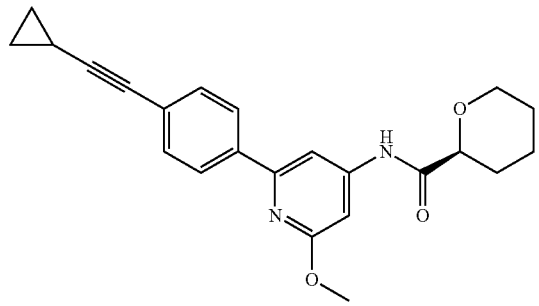 [SMILES: COc1cc(NC(=O)[C@@H]2CCCCO2)cc(-c2ccc(C#CC3CC3)cc2)n1] |
| I-76 | 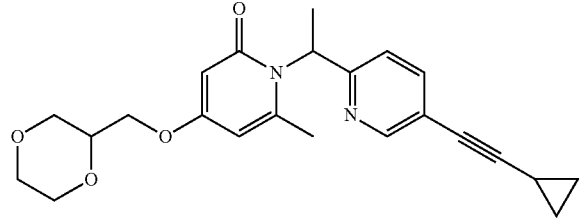 [SMILES: Cc1cc(OCC2COCCO2)cc(=O)n1C(C)c1ccc(C#CC2CC2)cn1] |
| I-77 | 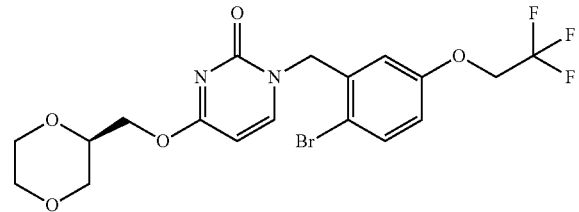 [SMILES: O=c1nc(OC[C@H]2COCCO2)ccn1Cc1cc(OCC(F)(F)F)ccc1Br] |
| I-78 | 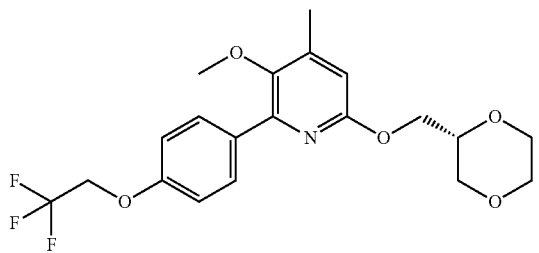 [SMILES: COc1c(C)cc(OC[C@H]2COCCO2)nc1-c1ccc(OCC(F)(F)F)cc1] |

TABLE 1-continued
Selected Compounds
| Compound No. | Structure |
|---|---|
| I-79 | 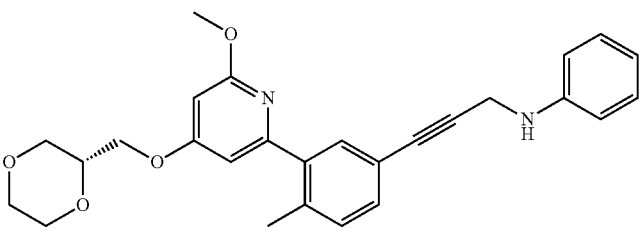 [SMILES: COc1cc(OC[C@H]2COCCO2)cc(-c2cc(C#CCNc3ccccc3)ccc2C)n1] |
| I-80 | 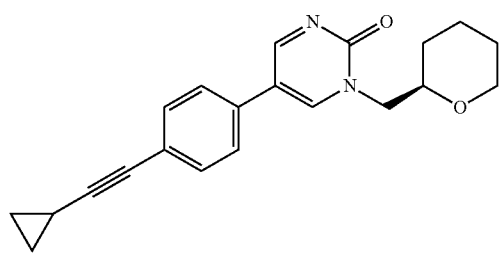 [SMILES: O=c1ncc(-c2ccc(C#CC3CC3)cc2)cn1C[C@H]1CCCCO1] |
| I-81 | 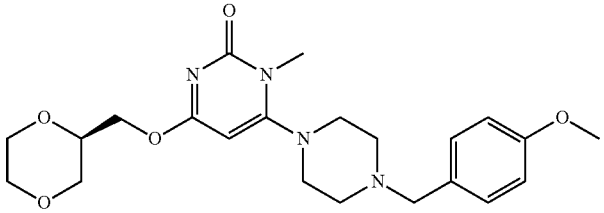 [SMILES: COc1ccc(CN2CCN(c3cc(OC[C@H]4COCCO4)nc(=O)n3C)CC2)cc1] |
| I-82 | 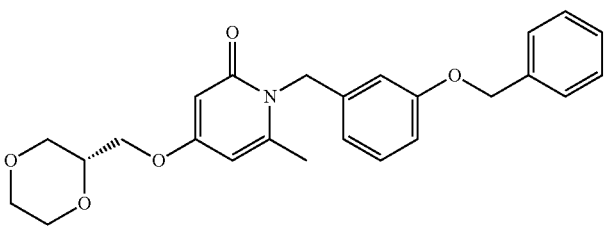 [SMILES: Cc1cc(OC[C@H]2COCCO2)cc(=O)n1Cc1cccc(OCc2ccccc2)c1] |
| I-83 | 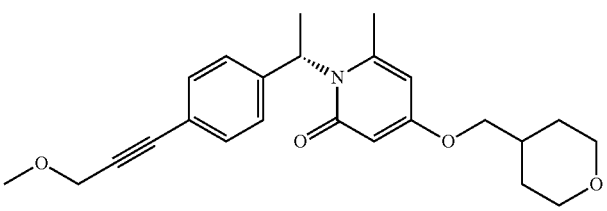 [SMILES: COCC#Cc1ccc([C@H](C)n2c(C)cc(OCC3CCOCC3)cc2=O)cc1] |
| I-84 | 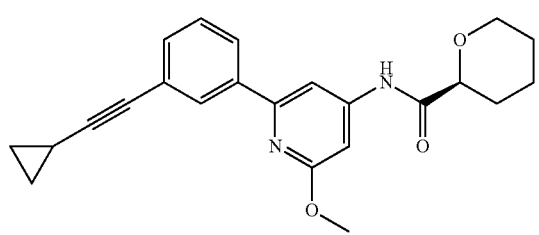 [SMILES: COc1cc(NC(=O)[C@@H]2CCCCO2)cc(-c2cccc(C#CC3CC3)c2)n1] |

TABLE 1-continued
Selected Compounds
| Compound No. | Structure |
|---|---|
| I-85 | 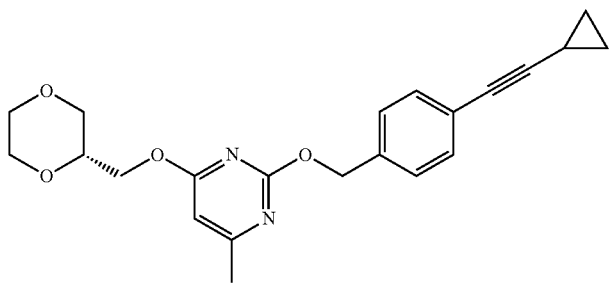 [SMILES: Cc1cc(OC[C@H]2COCCO2)nc(OCc2ccc(C#CC3CC3)cc2)n1] |
| I-86 | 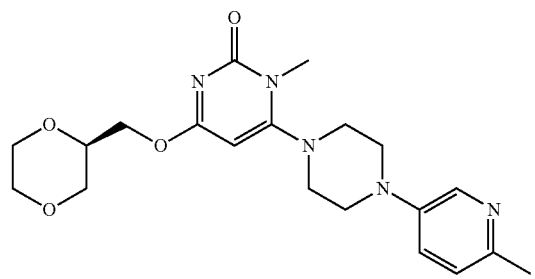 [SMILES: Cc1ccc(N2CCN(c3cc(OC[C@H]4COCCO4)nc(=O)n3C)CC2)cn1] |
| I-87 | 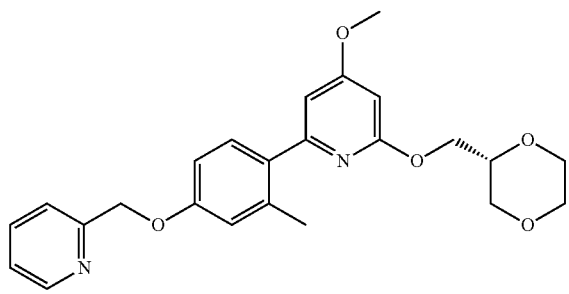 [SMILES: COc1cc(OC[C@H]2COCCO2)nc(-c2ccc(OCc3ccccn3)cc2C)c1] |
| I-88 | 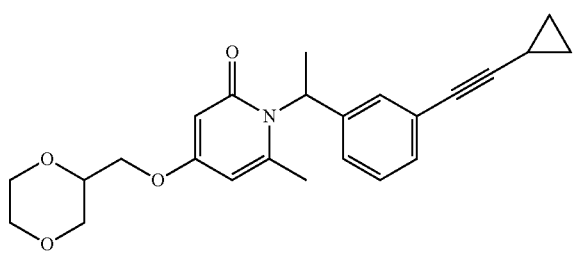 [SMILES: Cc1cc(OCC2COCCO2)cc(=O)n1C(C)c1cccc(C#CC2CC2)c1] |
| I-89 | 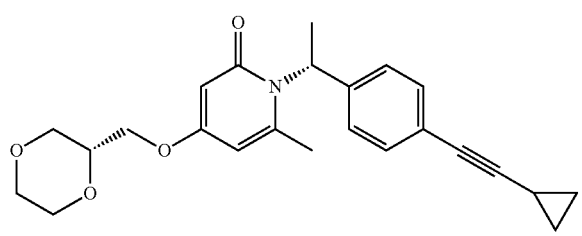 [SMILES: Cc1cc(OC[C@H]2COCCO2)cc(=O)n1[C@H](C)c1ccc(C#CC2CC2)cc1] |

TABLE 1-continued
Selected Compounds
| Compound No. | Structure |
|---|---|
| I-90 | 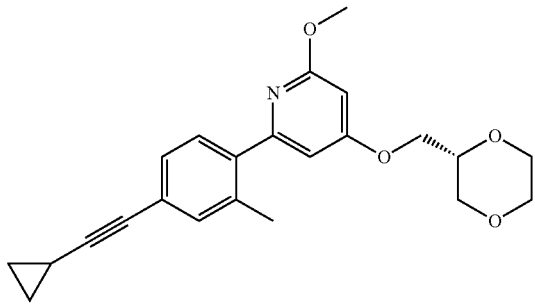 [SMILES: COc1cc(OC[C@H]2COCCO2)cc(-c2ccc(C#CC3CC3)cc2C)n1] |
| I-91 | 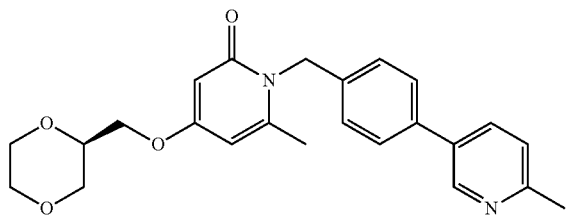 [SMILES: Cc1ccc(-c2ccc(Cn3c(C)cc(OC[C@H]4COCCO4)cc3=O)cc2)cn1] |
| I-92 | 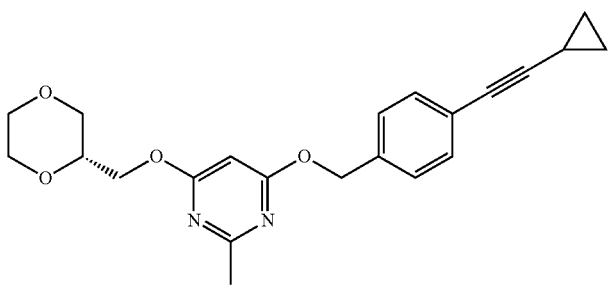 [SMILES: Cc1nc(OCc2ccc(C#CC3CC3)cc2)cc(OC[C@H]2COCCO2)n1] |
| I-93 | 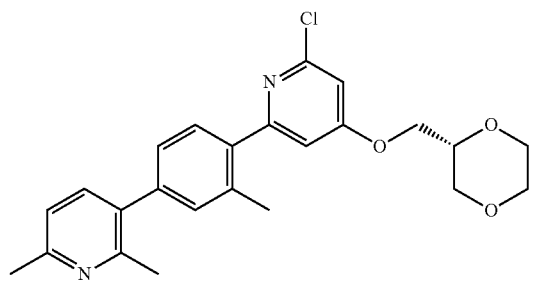 [SMILES: Cc1ccc(-c2ccc(-c3cc(OC[C@H]4COCCO4)cc(Cl)n3)c(C)c2)c(C)n1] |
| I-94 | 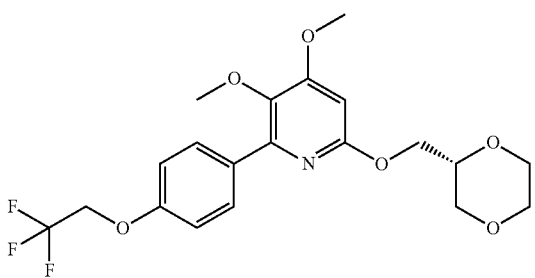 [SMILES: COc1cc(OC[C@H]2COCCO2)nc(-c2ccc(OCC(F)(F)F)cc2)c1OC] |

TABLE 1-continued
Selected Compounds
| Compound No. | Structure |
|---|---|
| I-95 | 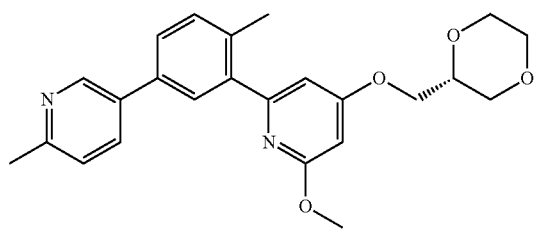 [SMILES: COc1cc(OC[C@H]2COCCO2)cc(-c2cc(-c3ccc(C)nc3)ccc2C)n1] |
| I-96 | 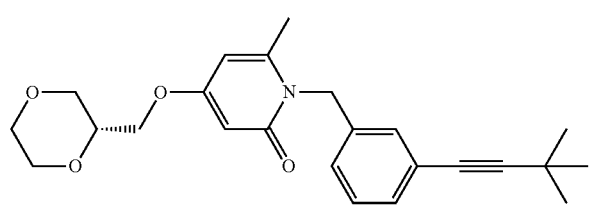 [SMILES: Cc1cc(OC[C@H]2COCCO2)cc(=O)n1Cc1cccc(C#CC(C)(C)C)c1] |
| I-97 | 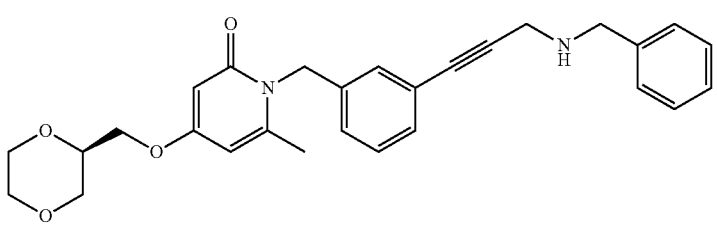 [SMILES: Cc1cc(OC[C@H]2COCCO2)cc(=O)n1Cc1cccc(C#CCNCc2ccccc2)c1] |
| I-98 | 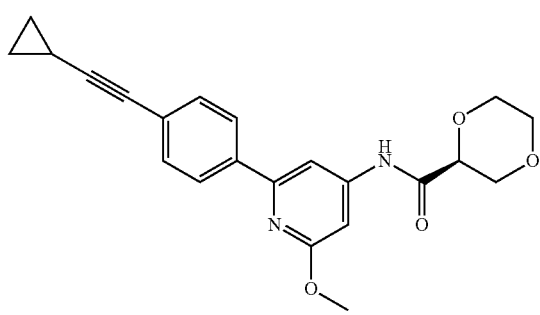 [SMILES: COc1cc(NC(=O)[C@@H]2COCCO2)cc(-c2ccc(C#CC3CC3)cc2)n1] |
| I-99 | 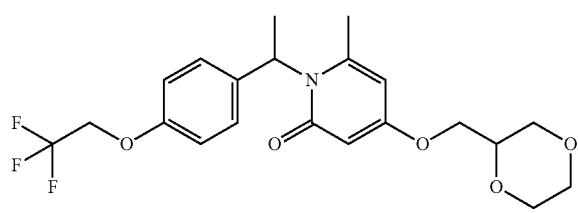 [SMILES: Cc1cc(OCC2COCCO2)cc(=O)n1C(C)c1ccc(OCC(F)(F)F)cc1] |
| I-100 | 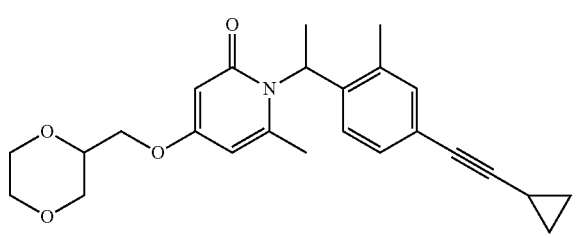 [SMILES: Cc1cc(C#CC2CC2)ccc1C(C)n1c(C)cc(OCC2COCCO2)cc1=O] |

TABLE 1-continued
Selected Compounds
| Compound No. | Structure |
|---|---|
| I-101 | 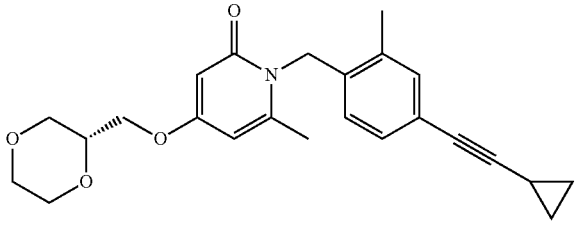 [SMILES: Cc1cc(C#CC2CC2)ccc1Cn1c(C)cc(OC[C@H]2COCCO2)cc1=O] |
| I-102 | 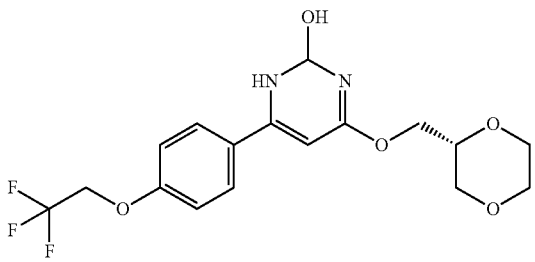 [SMILES: OC1N=C(OC[C@H]2COCCO2)C=C(c2ccc(OCC(F)(F)F)cc2)N1] |
| I-103 | 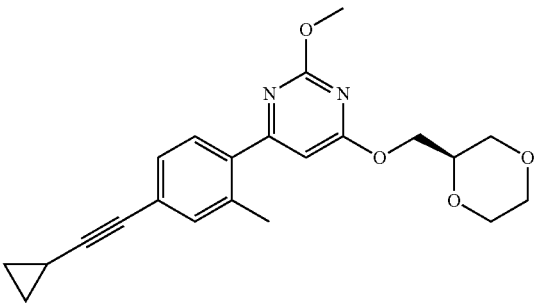 [SMILES: COc1nc(OC[C@H]2COCCO2)cc(-c2ccc(C#CC3CC3)cc2C)n1] |
| I-104 | 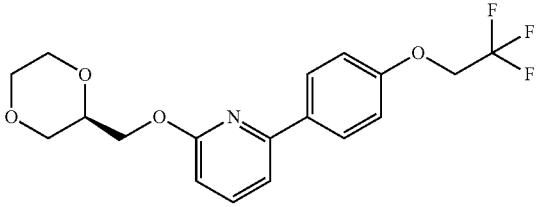 [SMILES: FC(F)(F)COc1ccc(-c2cccc(OC[C@H]3COCCO3)n2)cc1] |
| I-105 | 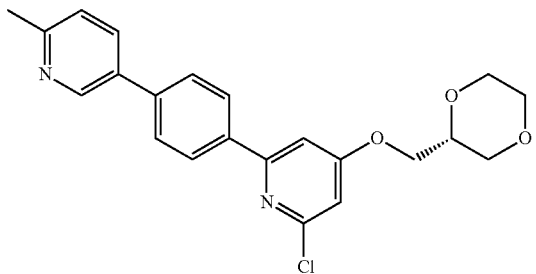 [SMILES: Cc1ccc(-c2ccc(-c3cc(OC[C@H]4COCCO4)cc(Cl)n3)cc2)cn1] |
| I-106 | 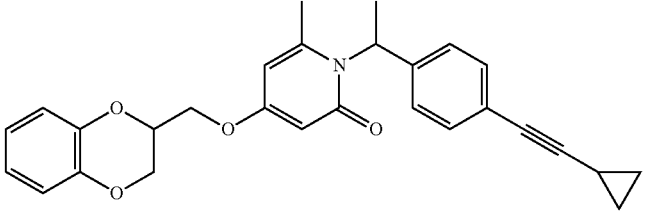 [SMILES: Cc1cc(OCC2COc3ccccc3O2)cc(=O)n1C(C)c1ccc(C#CC2CC2)cc1] |

TABLE 1-continued
Selected Compounds
| Compound No. | Structure |
|---|---|
| I-107 | 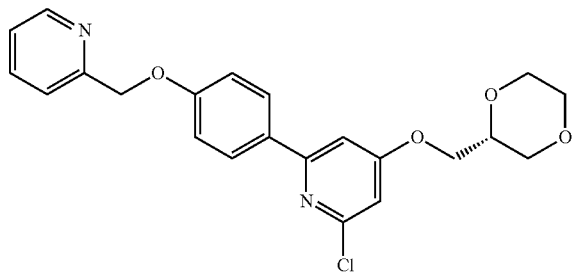 [SMILES: Clc1cc(OC[C@H]2COCCO2)cc(-c2ccc(OCc3ccccn3)cc2)n1] |
| I-108 | 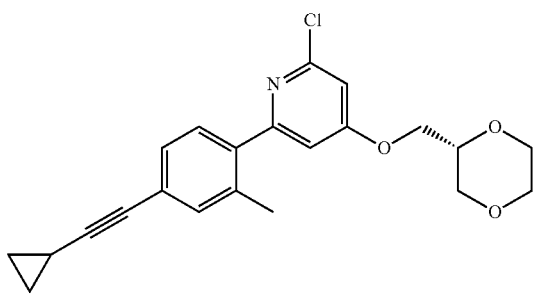 [SMILES: Cc1cc(C#CC2CC2)ccc1-c1cc(OC[C@H]2COCCO2)cc(Cl)n1] |
| I-109 | 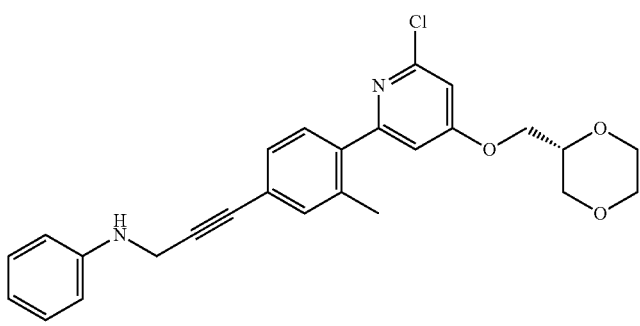 [SMILES: Cc1cc(C#CCNc2ccccc2)ccc1-c1cc(OC[C@H]2COCCO2)cc(Cl)n1] |
| I-110 | 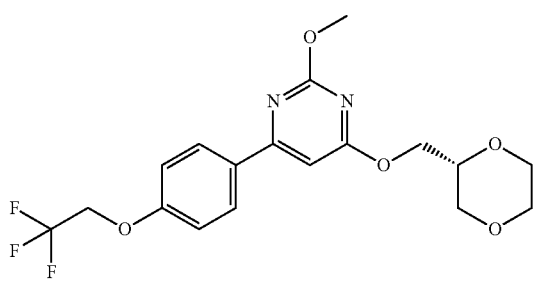 [SMILES: COc1nc(OC[C@H]2COCCO2)cc(-c2ccc(OCC(F)(F)F)cc2)n1] |
| I-111 | 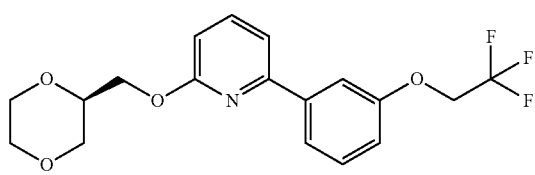 [SMILES: FC(F)(F)COc1cccc(-c2cccc(OC[C@H]3COCCO3)n2)c1] |

TABLE 1-continued
Selected Compounds
| Compound No. | Structure |
|---|---|
| I-112 | 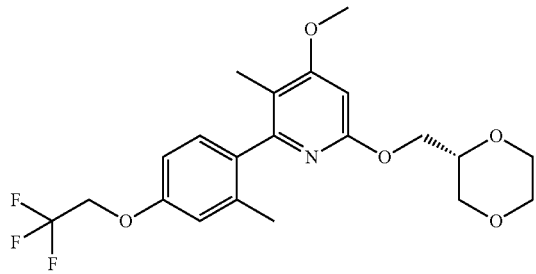 [SMILES: COc1cc(OC[C@H]2COCCO2)nc(-c2ccc(OCC(F)(F)F)cc2C)c1C] |
| I-113 | 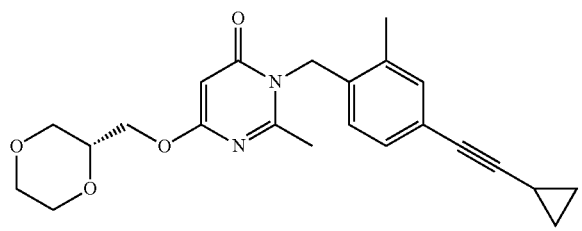 [SMILES: Cc1cc(C#CC2CC2)ccc1Cn1c(C)nc(OC[C@H]2COCCO2)cc1=O] |
| I-114 | 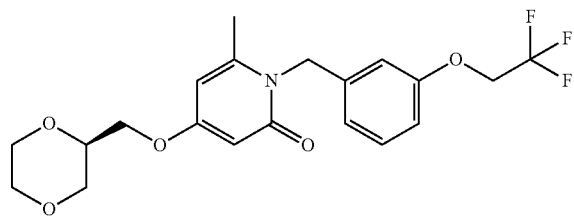 [SMILES: Cc1cc(OC[C@H]2COCCO2)cc(=O)n1Cc1cccc(OCC(F)(F)F)c1] |
| I-115 | 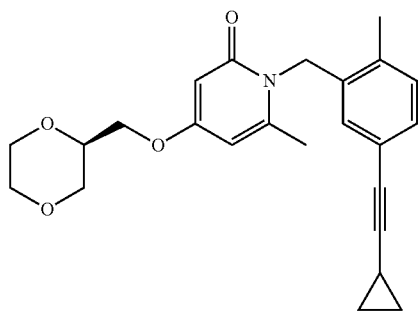 [SMILES: Cc1ccc(C#CC2CC2)cc1Cn1c(C)cc(OC[C@H]2COCCO2)cc1=O] |
| I-116 | 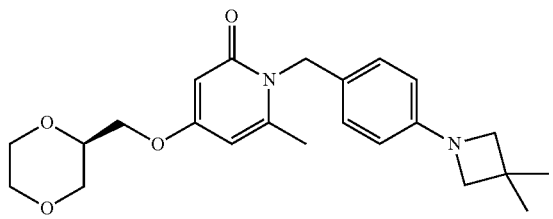 [SMILES: Cc1cc(OC[C@H]2COCCO2)cc(=O)n1Cc1ccc(N2CC(C)(C)C2)cc1] |
| I-117 | 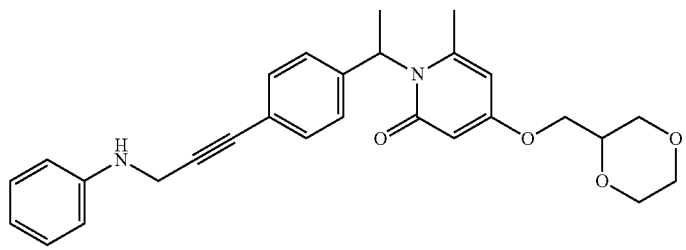 [SMILES: Cc1cc(OCC2COCCO2)cc(=O)n1C(C)c1ccc(C#CCNc2ccccc2)cc1] |

155
TABLE 1-continued
Selected Compounds
| Compound No. | Structure |
|---|---|
| I-118 | 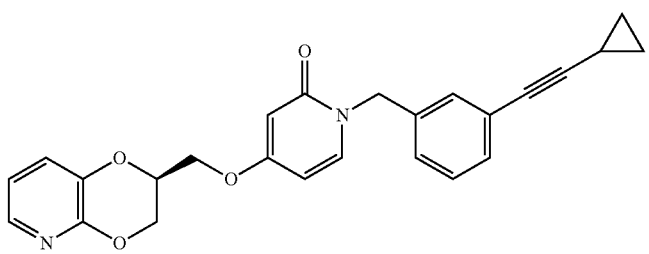 [SMILES: O=c1cc(OC[C@H]2COc3ncccc3O2)ccn1Cc1cccc(C#CC2CC2)c1] |
| I-119 | 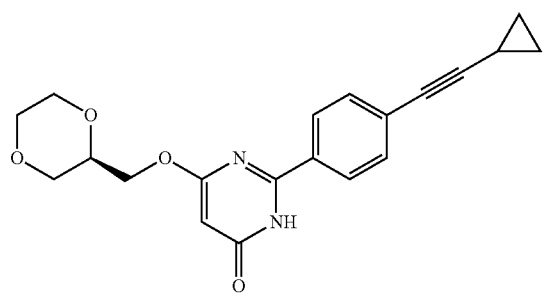 [SMILES: O=c1cc(OC[C@H]2COCCO2)nc(-c2ccc(C#CC3CC3)cc2)[nH]1] |
| I-120 | 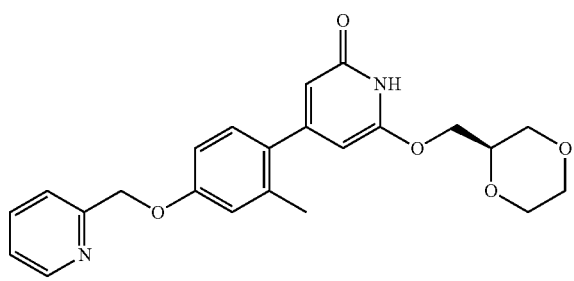 [SMILES: Cc1cc(OCc2ccccn2)ccc1-c1cc(OC[C@H]2COCCO2)[nH]c(=O)c1] |
| I-121 | 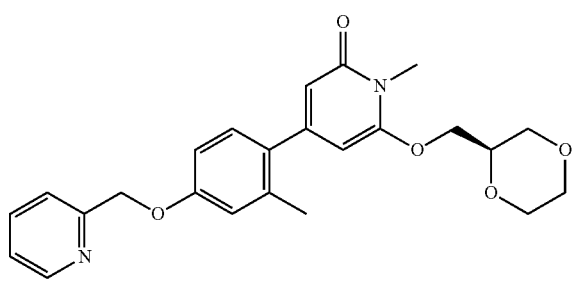 [SMILES: Cc1cc(OCc2ccccn2)ccc1-c1cc(OC[C@H]2COCCO2)n(C)c(=O)c1] |
| I-122 | 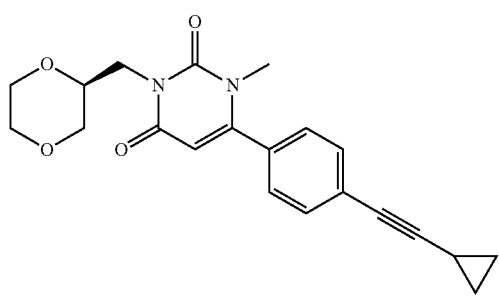 [SMILES: Cn1c(-c2ccc(C#CC3CC3)cc2)cc(=O)n(C[C@H]2COCCO2)c1=O] |

TABLE 1-continued

Selected Compounds

| Compound No. | Structure |
|---|---|
| I-123 | 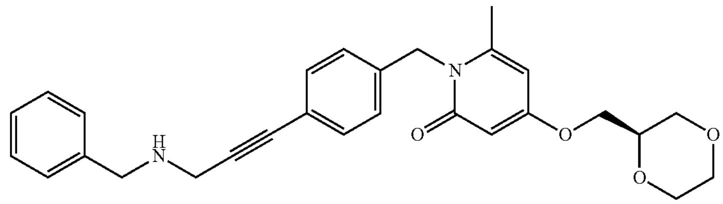 [SMILES: Cc1cc(OC[C@H]2COCCO2)cc(=O)n1Cc1ccc(C#CCNCc2ccccc2)cc1] |
| I-124 | 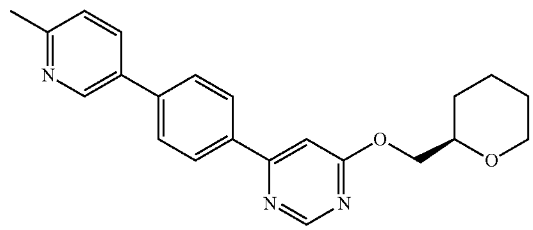 [SMILES: Cc1ccc(-c2ccc(-c3cc(OC[C@H]4CCCCO4)ncn3)cc2)cn1] |
| I-125 | 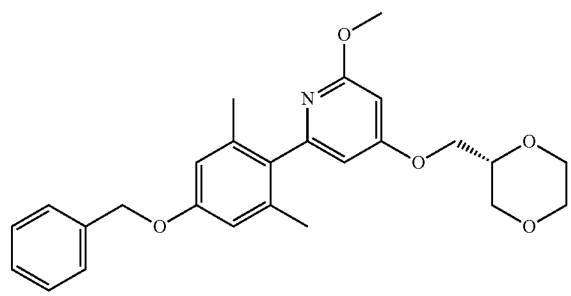 [SMILES: COc1cc(OC[C@H]2COCCO2)cc(-c2c(C)cc(OCc3ccccc3)cc2C)n1] |
| I-126 | 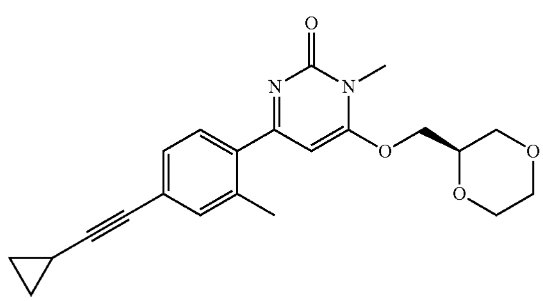 [SMILES: Cc1cc(C#CC2CC2)ccc1-c1cc(OC[C@H]2COCCO2)n(C)c(=O)n1] |
| I-127 | 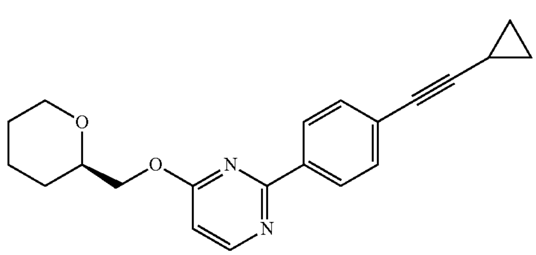 [SMILES: C(#CC1CC1)c1ccc(-c2nccc(OC[C@H]3CCCCO3)n2)cc1] |
| I-128 | 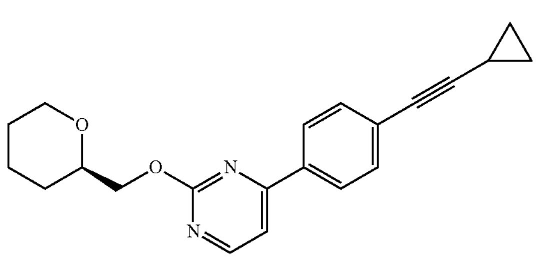 [SMILES: C(#CC1CC1)c1ccc(-c2ccnc(OC[C@H]3CCCCO3)n2)cc1] |

TABLE 1-continued
Selected Compounds
| Compound No. | Structure |
|---|---|
| I-129 | 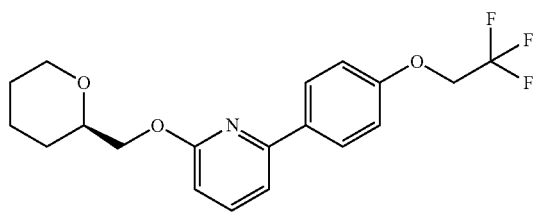 [SMILES: FC(F)(F)COc1ccc(-c2cccc(OC[C@H]3CCCCO3)n2)cc1] |
| I-130 | 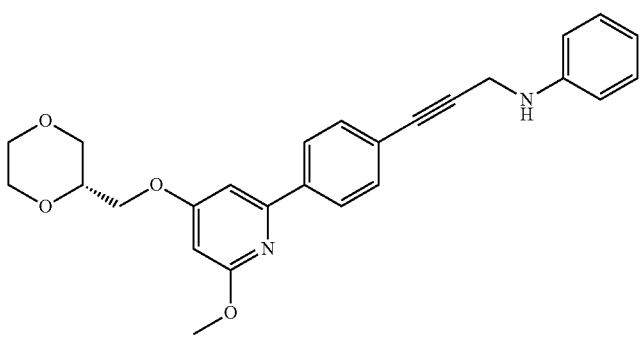 [SMILES: COc1cc(OC[C@H]2COCCO2)cc(-c2ccc(C#CCNc3ccccc3)cc2)n1] |
| I-131 | 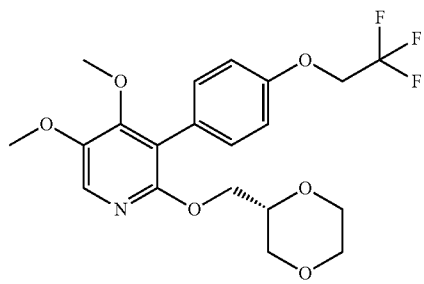 [SMILES: COc1cnc(OC[C@H]2COCCO2)c(-c2ccc(OCC(F)(F)F)cc2)c1OC] |
| I-132 | 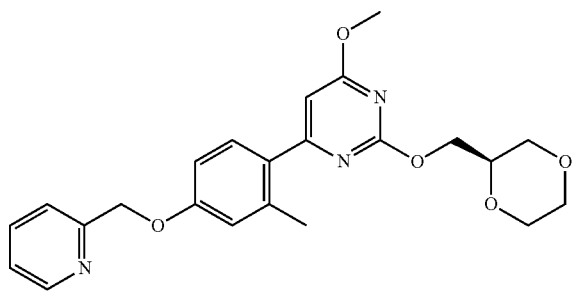 [SMILES: COc1cc(-c2ccc(OCc3ccccn3)cc2C)nc(OC[C@H]2COCCO2)n1] |
| I-133 | 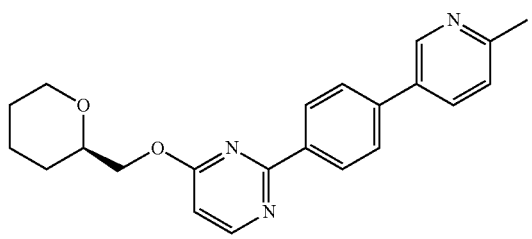 [SMILES: Cc1ccc(-c2ccc(-c3nccc(OC[C@H]4CCCCO4)n3)cc2)cn1] |

TABLE 1-continued
Selected Compounds
| Compound No. | Structure |
|---|---|
| I-134 | 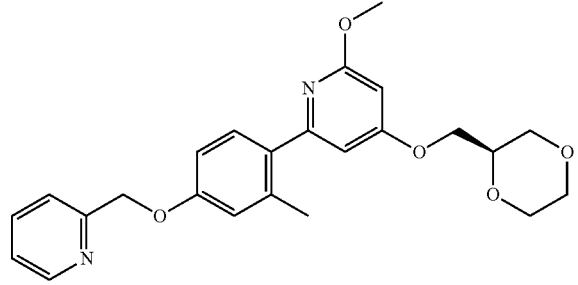 [SMILES: COc1cc(OC[C@H]2COCCO2)cc(-c2ccc(OCc3ccccn3)cc2C)n1] |
| I-135 | 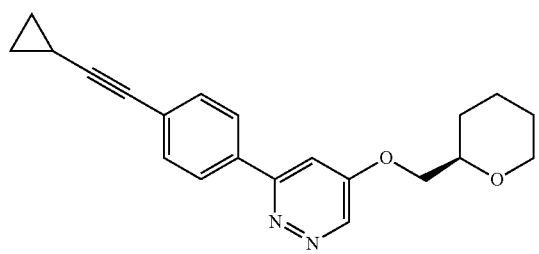 |
| I-136 | 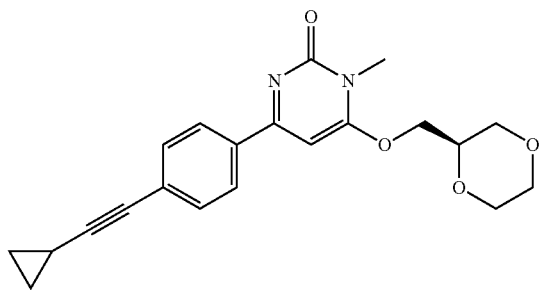 [SMILES: Cn1c(OC[C@H]2COCCO2)cc(-c2ccc(C#CC3CC3)cc2)nc1=O] |
| I-137 | 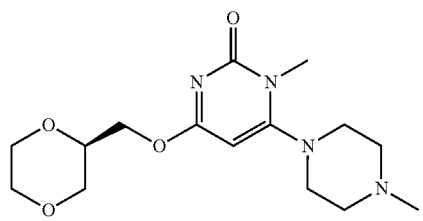 [SMILES: CN1CCN(c2cc(OC[C@H]3COCCO3)nc(=O)n2C)CC1] |
| I-138 | 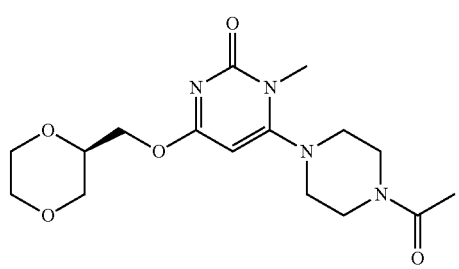 [SMILES: CC(=O)N1CCN(c2cc(OC[C@H]3COCCO3)nc(=O)n2C)CC1] |

TABLE 1-continued
Selected Compounds
| Compound No. | Structure |
|---|---|
| I-139 | 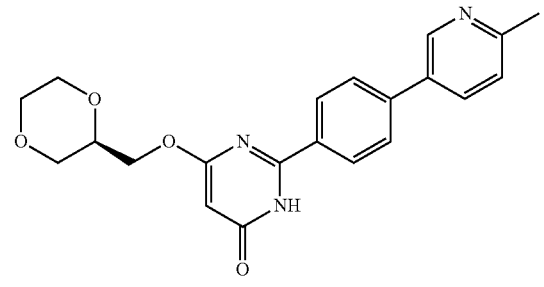 [SMILES: Cc1ccc(-c2ccc(-c3nc(OC[C@H]4COCCO4)cc(=O)[nH]3)cc2)cn1] |
| I-140 | 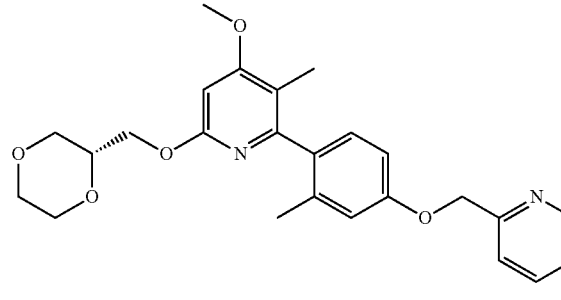 |
| I-141 | 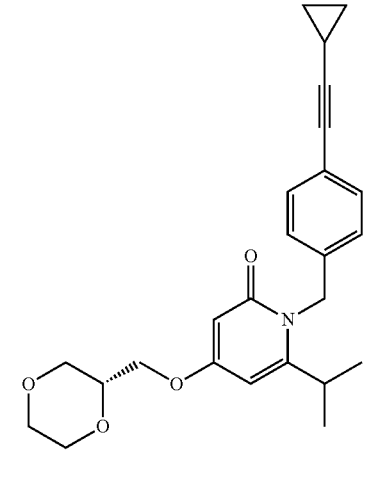 [SMILES: CC(C)c1cc(OC[C@H]2COCCO2)cc(=O)n1Cc1ccc(C#CC2CC2)cc1] |
| I-142 | 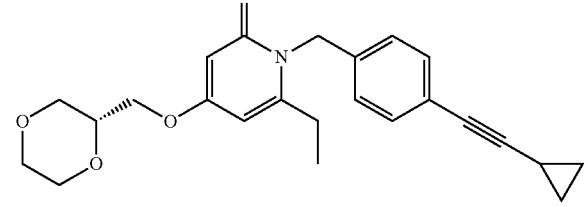 |

TABLE 1-continued
Selected Compounds
| Compound No. | Structure |
|---|---|
| I-143 | 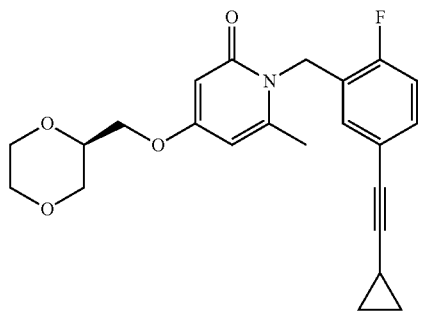 [SMILES: Cc1cc(OC[C@H]2COCCO2)cc(=O)n1Cc1cc(C#CC2CC2)ccc1F] |
| I-144 | 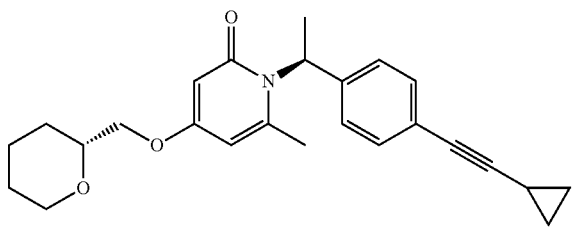 |
| I-145 | 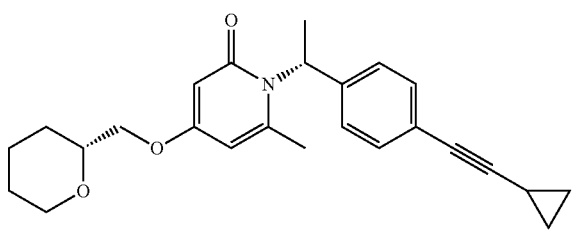 [SMILES: Cc1cc(OC[C@H]2CCCCO2)cc(=O)n1[C@H](C)c1ccc(C#CC2CC2)cc1] |
| I-146 | 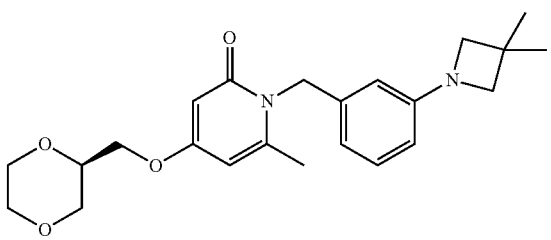 [SMILES: Cc1cc(OC[C@H]2COCCO2)cc(=O)n1Cc1cccc(N2CC(C)(C)C2)c1] |
| I-147 | 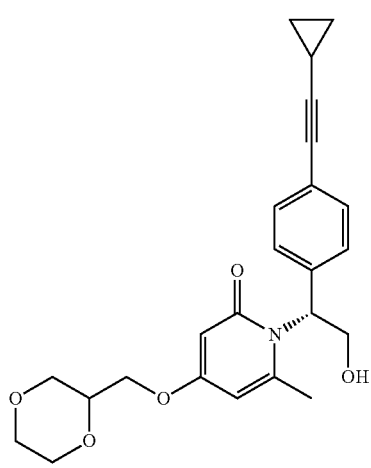 [SMILES: Cc1cc(OCC2COCCO2)cc(=O)n1[C@@H](CO)c1ccc(C#CC2CC2)cc1] |

TABLE 1-continued
Selected Compounds
| Compound No. | Structure |
|---|---|
| I-148 | 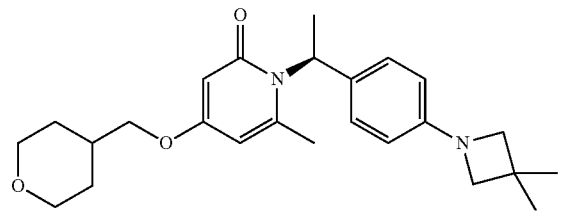 [SMILES: Cc1cc(OCC2CCOCC2)cc(=O)n1[C@@H](C)c1ccc(N2CC(C)(C)C2)cc1] |
| I-149 | 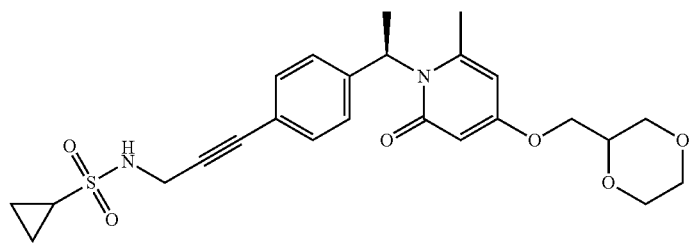 [SMILES: Cc1cc(OCC2COCCO2)cc(=O)n1[C@H](C)c1ccc(C#CCNS(=O)(=O)C2CC2)cc1] |
| I-150 | 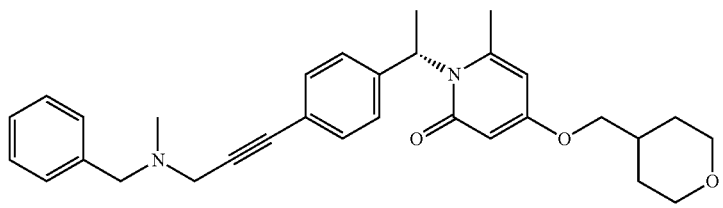 [SMILES: Cc1cc(OCC2CCOCC2)cc(=O)n1[C@@H](C)c1ccc(C#CCN(C)Cc2ccccc2)cc1] |
| I-151 | 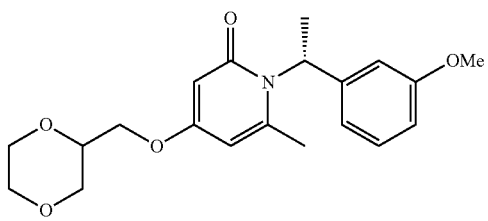 |
| I-152 | 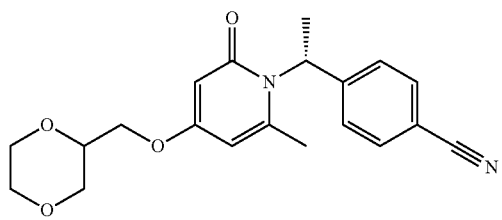 [SMILES: Cc1cc(OCC2COCCO2)cc(=O)n1[C@H](C)c1ccc(C#N)cc1] |
| I-153 | 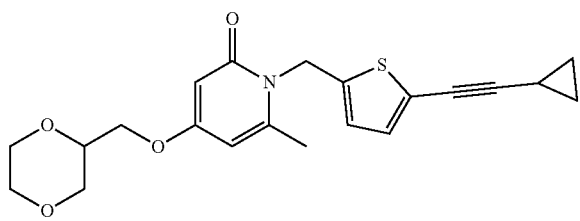 |

TABLE 1-continued
Selected Compounds
| Compound No. | Structure |
|---|---|
| I-154 | 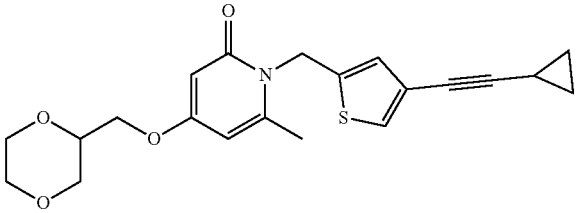 [SMILES: Cc1cc(OCC2COCCO2)cc(=O)n1Cc1cc(C#CC2CC2)cs1] |
| I-155 | 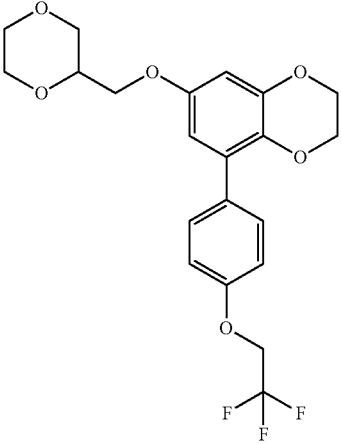 |
| I-156 | 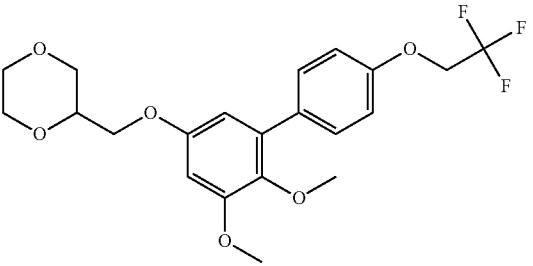 [SMILES: COc1cc(OCC2COCCO2)cc(-c2ccc(OCC(F)(F)F)cc2)c1OC] |
| I-157 | 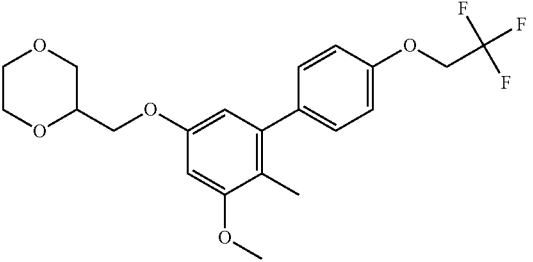 [SMILES: COc1cc(OCC2COCCO2)cc(-c2ccc(OCC(F)(F)F)cc2)c1C] |

TABLE 1-continued
Selected Compounds
| Compound No. | Structure |
|---|---|
| I-158 | 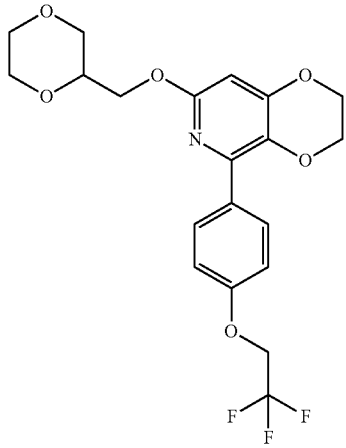 [SMILES: FC(F)(F)COc1ccc(-c2nc(OCC3COCCO3)cc3c2OCCO3)cc1] |
| I-159 | 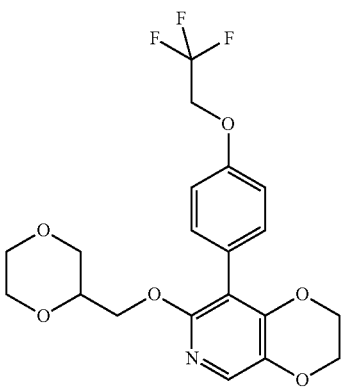 [SMILES: FC(F)(F)COc1ccc(-c2c(OCC3COCCO3)ncc3c2OCCO3)cc1] |
| I-160 | 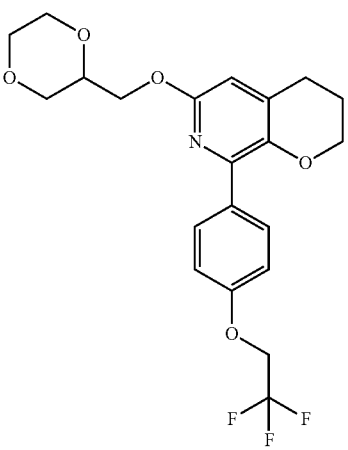 [SMILES: FC(F)(F)COc1ccc(-c2nc(OCC3COCCO3)cc3c2OCCC3)cc1] |
| I-161 | 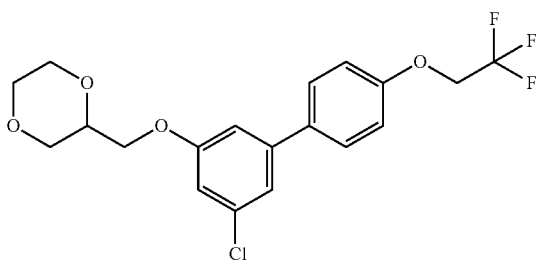 [SMILES: FC(F)(F)COc1ccc(-c2cc(Cl)cc(OCC3COCCO3)c2)cc1] |

TABLE 1-continued
Selected Compounds
| Compound No. | Structure |
|---|---|
| I-162 | 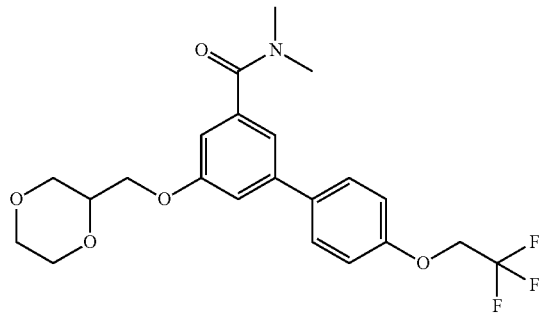 [SMILES: CN(C)C(=O)c1cc(OCC2COCCO2)cc(-c2ccc(OCC(F)(F)F)cc2)c1] |
| I-163 | 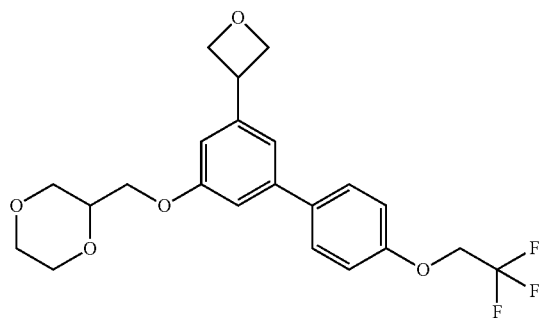 [SMILES: FC(F)(F)COc1ccc(-c2cc(OCC3COCCO3)cc(C3COC3)c2)cc1] |
| I-164 | 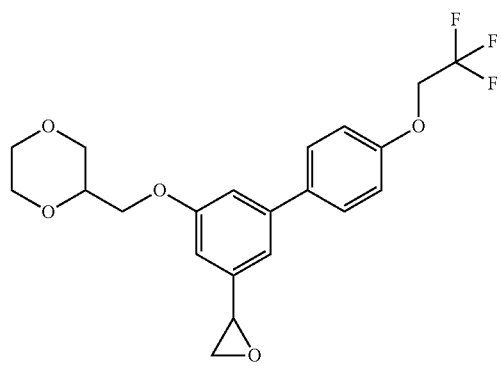 [SMILES: FC(F)(F)COc1ccc(-c2cc(OCC3COCCO3)cc(C3CO3)c2)cc1] |
| I-165 | 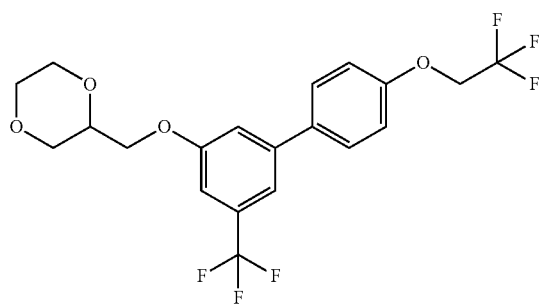 [SMILES: FC(F)(F)COc1ccc(-c2cc(OCC3COCCO3)cc(C(F)(F)F)c2)cc1] |

TABLE 1-continued
Selected Compounds
| Compound No. | Structure |
|---|---|
| I-166 | 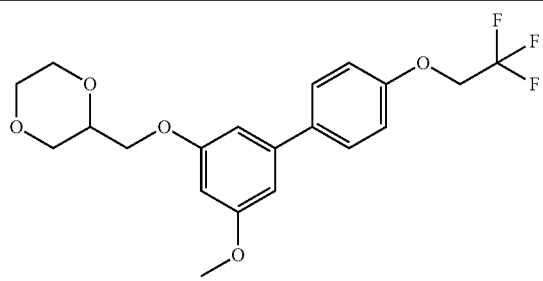 |
| I-167 | 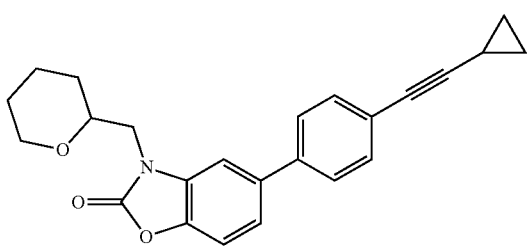 [SMILES: O=c1oc2ccc(-c3ccc(C#CC4CC4)cc3)cc2n1CC1CCCCO1] |
| I-168 | 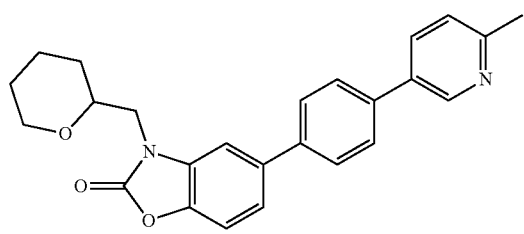 [SMILES: Cc1ccc(-c2ccc(-c3ccc4oc(=O)n(CC5CCCCO5)c4c3)cc2)cn1] |
| I-169 | 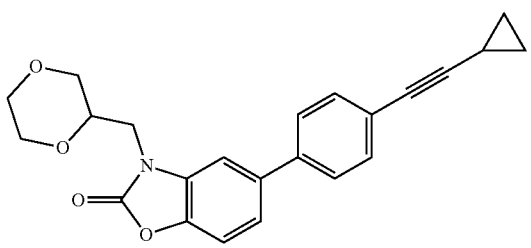 [SMILES: O=c1oc2ccc(-c3ccc(C#CC4CC4)cc3)cc2n1CC1COCCO1] |
| I-174 | 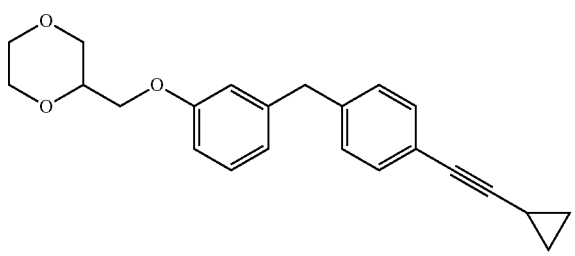 [SMILES: C(#CC1CC1)c1ccc(Cc2cccc(OCC3COCCO3)c2)cc1] |
| I-176 | 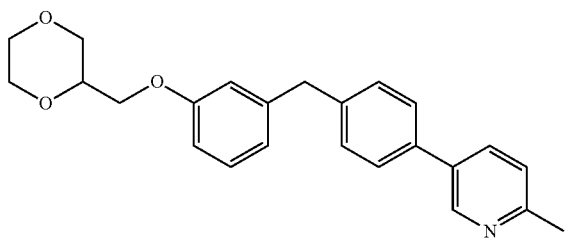 [SMILES: Cc1ccc(-c2ccc(Cc3cccc(OCC4COCCO4)c3)cc2)cn1] |

TABLE 1-continued
Selected Compounds
| Compound No. | Structure |
|---|---|
| I-177 | 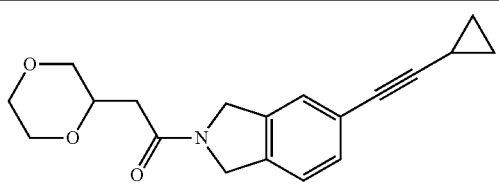 |
| I-180 | 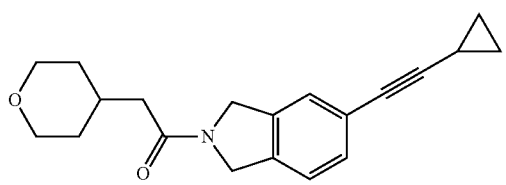 [SMILES: O=C(CC1CCOCC1)N1Cc2ccc(C#CC3CC3)cc2C1] |
| I-181 | 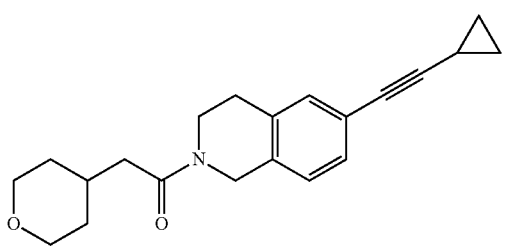 [SMILES: O=C(CC1CCOCC1)N1CCc2cc(C#CC3CC3)ccc2C1] |
| I-183 | 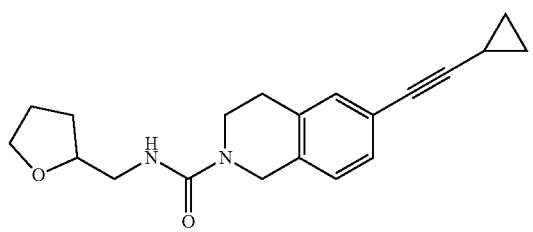 [SMILES: O=C(NCC1CCCO1)N1CCc2cc(C#CC3CC3)ccc2C1] |
| I-184 | 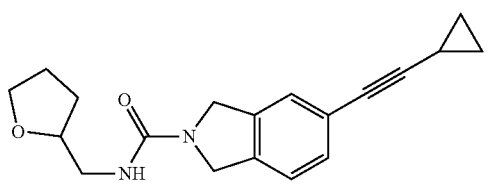 [SMILES: O=C(NCC1CCCO1)N1Cc2ccc(C#CC3CC3)cc2C1] |
| I-186 | 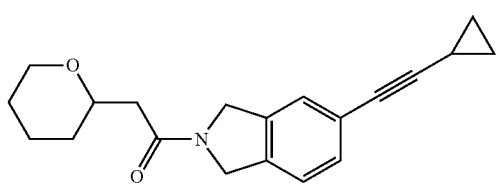 [SMILES: O=C(CC1CCCCO1)N1Cc2ccc(C#CC3CC3)cc2C1] |
| I-187 | 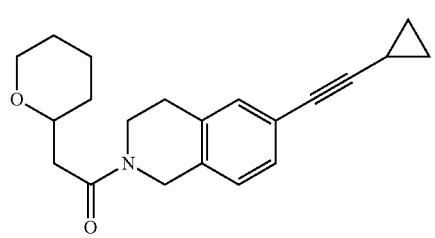 [SMILES: O=C(CC1CCCCO1)N1CCc2cc(C#CC3CC3)ccc2C1] |

TABLE 1-continued
Selected Compounds
| Compound No. | Structure |
|---|---|
| I-197 | 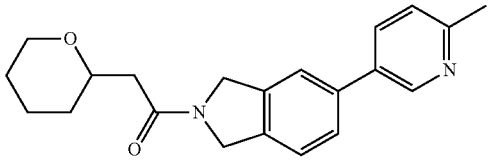 [SMILES: Cc1ccc(-c2ccc3c(c2)CN(C(=O)CC2CCCCO2)C3)cn1] |
| I-203 | 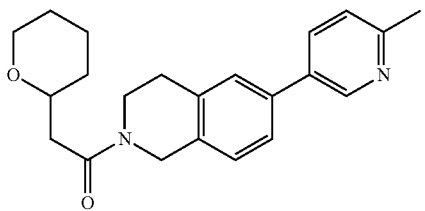 [SMILES: Cc1ccc(-c2ccc3c(c2)CCN(C(=O)CC2CCCCO2)C3)cn1] |
| I-206 | 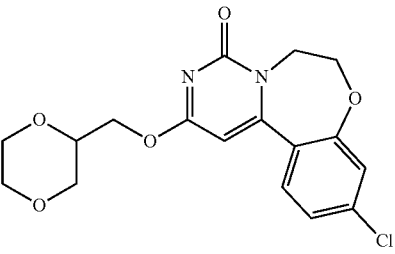 [SMILES: O=c1nc(OCC2COCCO2)cc2n1CCOc1cc(Cl)ccc1-2] |
| I-210 | 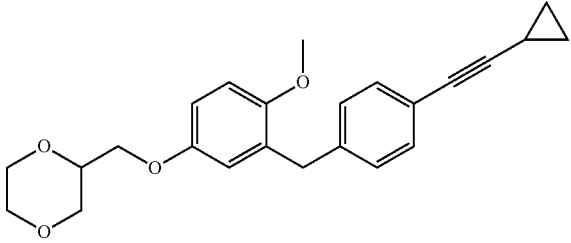 [SMILES: COc1ccc(OCC2COCCO2)cc1Cc1ccc(C#CC2CC2)cc1] |
| I-211 | 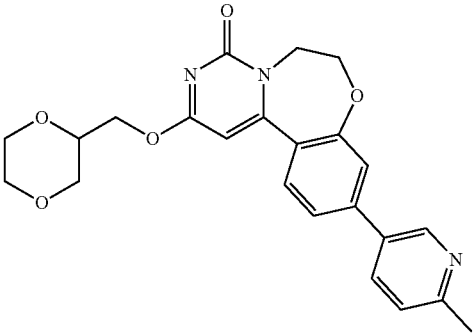 [SMILES: Cc1ccc(-c2ccc3c(c2)OCCn2c-3cc(OCC3COCCO3)nc2=O)cn1] |

TABLE 1-continued
Selected Compounds
| Compound No. | Structure |
|---|---|
| I-214 | 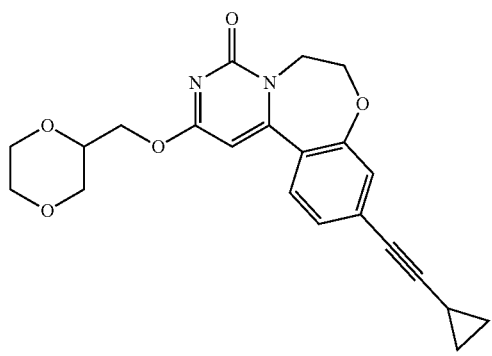 [SMILES: O=c1nc(OCC2COCCO2)cc2n1CCOc1cc(C#CC3CC3)ccc1-2] |
| I-215 | 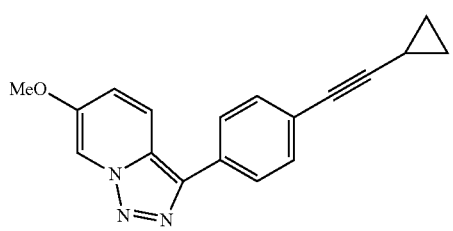 [SMILES: COc1ccc2c(-c3ccc(C#CC4CC4)cc3)nnn2c1] |
| I-216 | 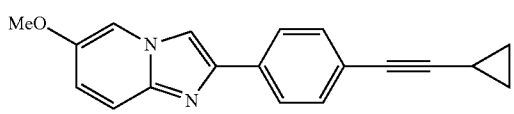 [SMILES: COc1ccc2nc(-c3ccc(C#CC4CC4)cc3)cn2c1] |
| I-217 | 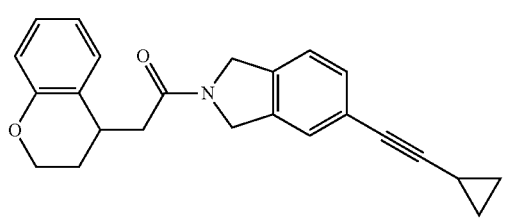 [SMILES: O=C(CC1CCOc2ccccc21)N1Cc2ccc(C#CC3CC3)cc2C1] |
| I-218 | 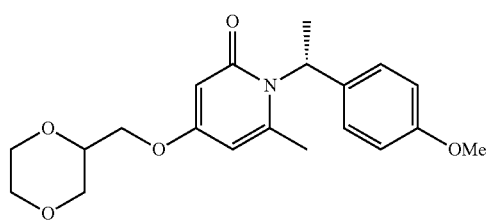 [SMILES: COc1ccc([C@@H](C)n2c(C)cc(OCC3COCCO3)cc2=O)cc1] |
| I-219 | 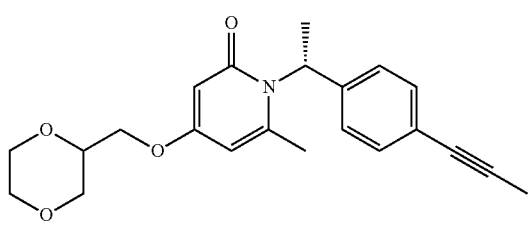 [SMILES: CC#Cc1ccc([C@@H](C)n2c(C)cc(OCC3COCCO3)cc2=O)cc1] |

TABLE 1-continued

Selected Compounds

| Compound No. | Structure |
|---|---|
| I-220 | 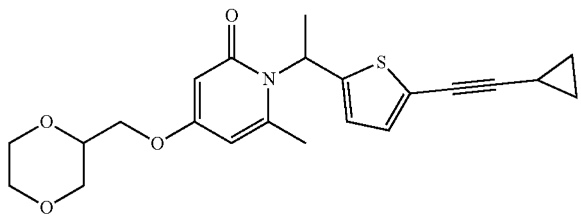 [SMILES: Cc1cc(OCC2COCCO2)cc(=O)n1C(C)c1ccc(C#CC2CC2)s1] |
| I-221 | 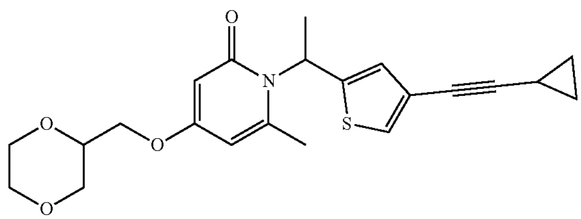 |
| I-222 | 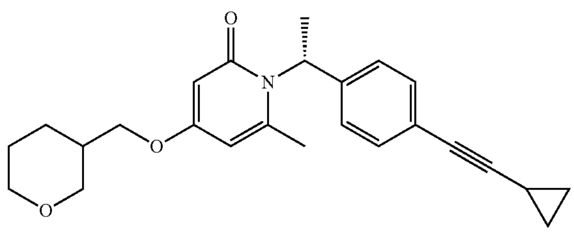 [SMILES: Cc1cc(OCC2CCCOC2)cc(=O)n1[C@H](C)c1ccc(C#CC2CC2)cc1] |
| I-223 | 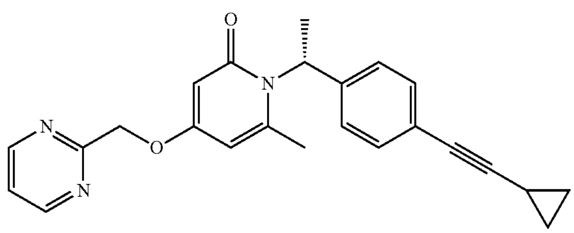 [SMILES: Cc1cc(OCc2ncccn2)cc(=O)n1[C@H](C)c1ccc(C#CC2CC2)cc1] |
| I-224 | 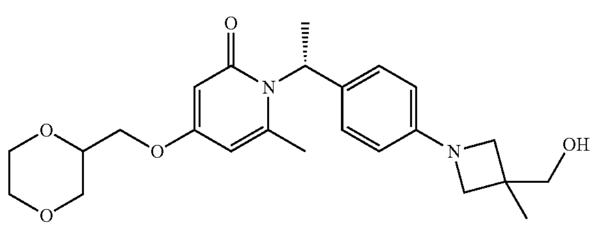 [SMILES: Cc1cc(OCC2COCCO2)cc(=O)n1[C@H](C)c1ccc(N2CC(C)(CO)C2)cc1] |
| I-225 | 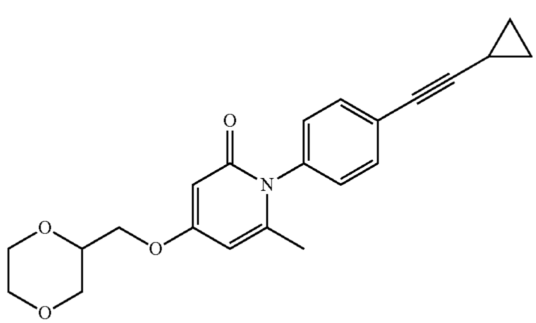 [SMILES: Cc1cc(OCC2COCCO2)cc(=O)n1-c1ccc(C#CC2CC2)cc1] |

TABLE 1-continued
Selected Compounds
| Compound No. | Structure |
|---|---|
| I-226 | 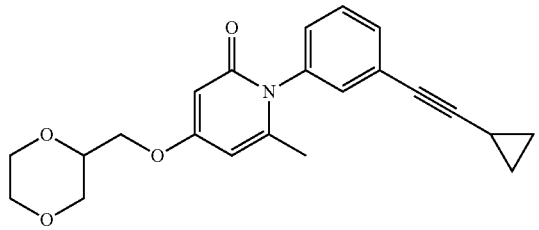 [SMILES: Cc1cc(OCC2COCCO2)cc(=O)n1-c1cccc(C#CC2CC2)c1] |
| I-227 | 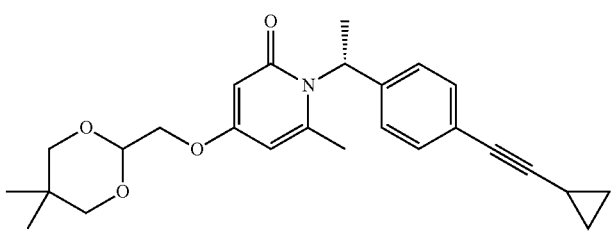 [SMILES: Cc1cc(OCC2OCC(C)(C)CO2)cc(=O)n1[C@H](C)c1ccc(C#CC2CC2)cc1] |
| I-228 | 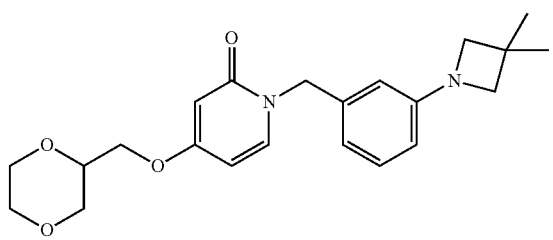 [SMILES: CC1(C)CN(c2cccc(Cn3ccc(OCC4COCCO4)cc3=O)c2)C1] |
| I-229 | 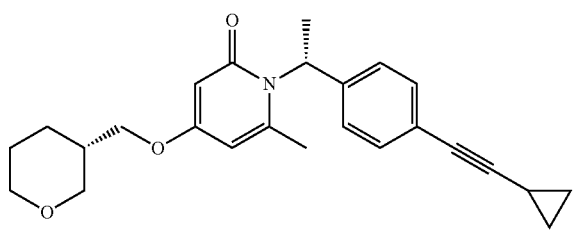 [SMILES: Cc1cc(OC[C@H]2CCCOC2)cc(=O)n1[C@H](C)c1ccc(C#CC2CC2)cc1] |
| I-230 | 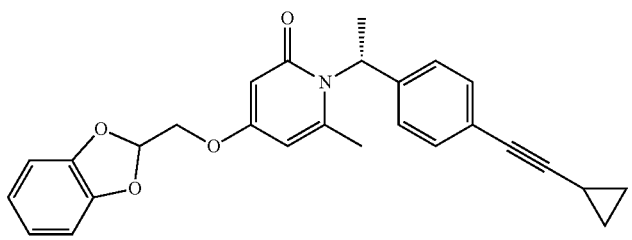 [SMILES: Cc1cc(OCC2Oc3ccccc3O2)cc(=O)n1[C@H](C)c1ccc(C#CC2CC2)cc1] |
| I-231 | 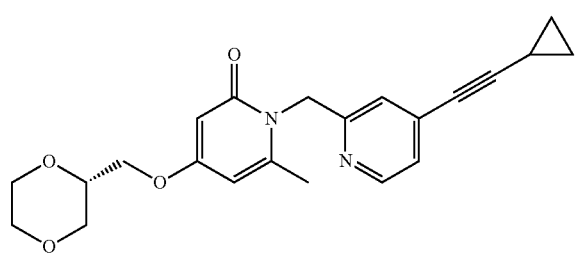 [SMILES: Cc1cc(OC[C@@H]2COCCO2)cc(=O)n1Cc1cc(C#CC2CC2)ccn1] |

TABLE 1-continued

Selected Compounds

| Compound No. | Structure |
|---|---|
| I-232 | 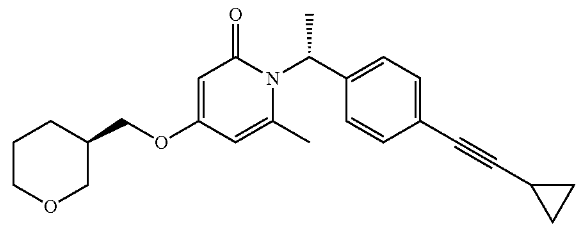 [SMILES: Cc1cc(OC[C@@H]2CCCOC2)cc(=O)n1[C@H](C)c1ccc(C#CC2CC2)cc1] |
| I-233 | 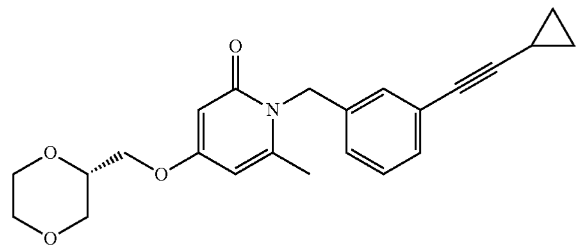 |
| I-234 | 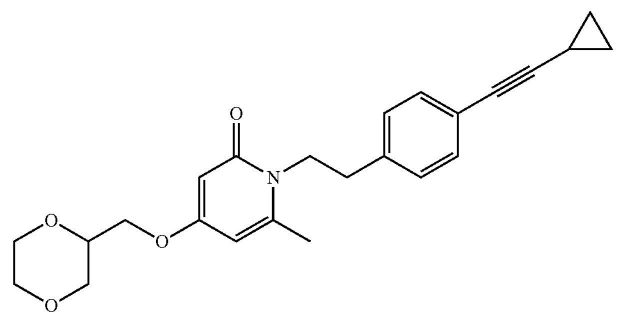 [SMILES: Cc1cc(OCC2COCCO2)cc(=O)n1CCc1ccc(C#CC2CC2)cc1] |
| I-235 | 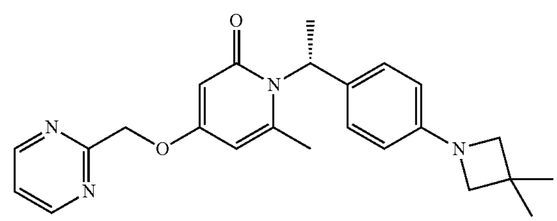 [SMILES: Cc1cc(OCc2ncccn2)cc(=O)n1[C@H](C)c1ccc(N2CC(C)(C)C2)cc1] |
| I-236 | 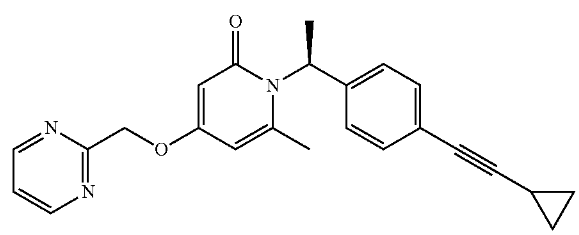 [SMILES: Cc1cc(OCc2ncccn2)cc(=O)n1[C@@H](C)c1ccc(C#CC2CC2)cc1] |
| I-237 | 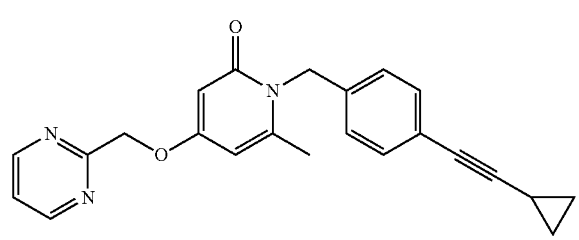 [SMILES: Cc1cc(OCc2ncccn2)cc(=O)n1Cc1ccc(C#CC2CC2)cc1] |

TABLE 1-continued

Selected Compounds

| Compound No. | Structure |
|---|---|
| I-238 | 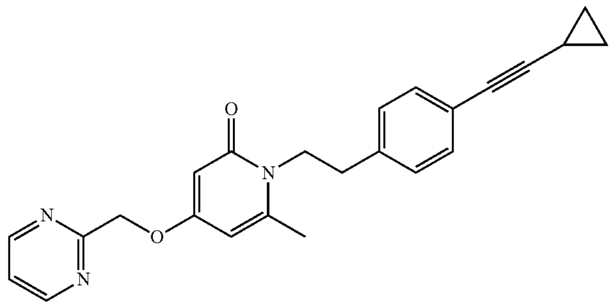 [SMILES: Cc1cc(OCc2ncccn2)cc(=O)n1CCc1ccc(C#CC2CC2)cc1] |
| I-239 | 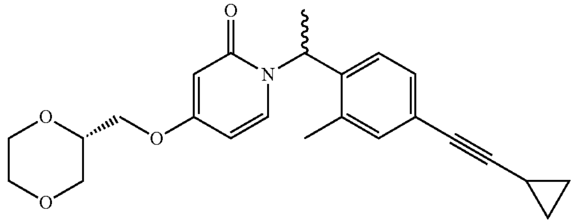 [SMILES: Cc1cc(C#CC2CC2)ccc1C(C)n1ccc(OC[C@@H]2COCCO2)cc1=O] |
| I-240 | 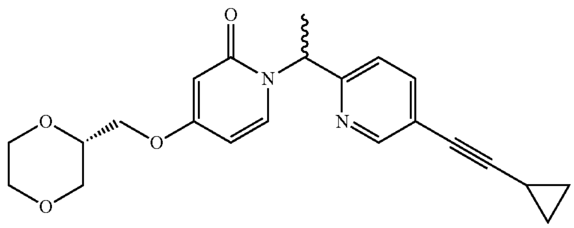 [SMILES: CC(c1ccc(C#CC2CC2)cn1)n1ccc(OC[C@@H]2COCCO2)cc1=O] |
| I-241 | 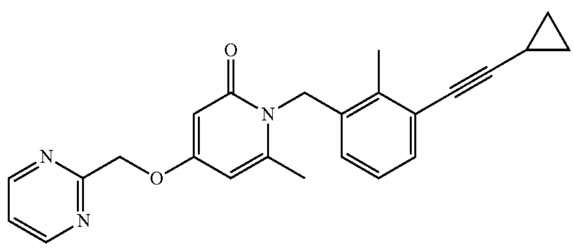 [SMILES: Cc1c(C#CC2CC2)cccc1Cn1c(C)cc(OCc2ncccn2)cc1=O] |
| I-242 | 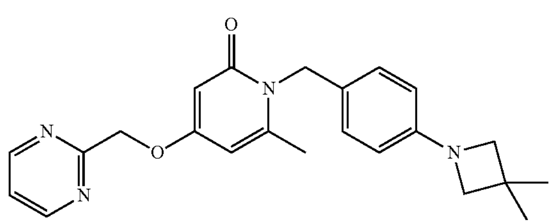 [SMILES: Cc1cc(OCc2ncccn2)cc(=O)n1Cc1ccc(N2CC(C)(C)C2)cc1] |
| I-243 | 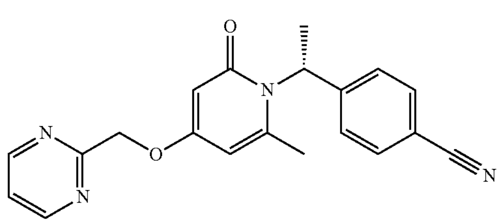 [SMILES: Cc1cc(OCc2ncccn2)cc(=O)n1[C@H](C)c1ccc(C#N)cc1] |

TABLE 1-continued
Selected Compounds
| Compound No. | Structure |
|---|---|
| I-244 | 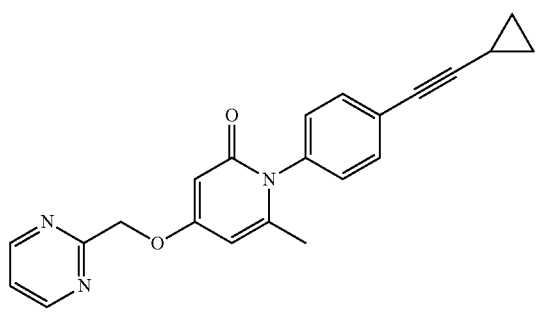 [SMILES: Cc1cc(OCc2ncccn2)cc(=O)n1-c1ccc(C#CC2CC2)cc1] |
| I-245 | 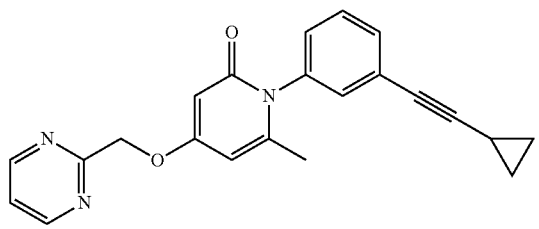 [SMILES: Cc1cc(OCc2ncccn2)cc(=O)n1-c1cccc(C#CC2CC2)c1] |
| I-246 | 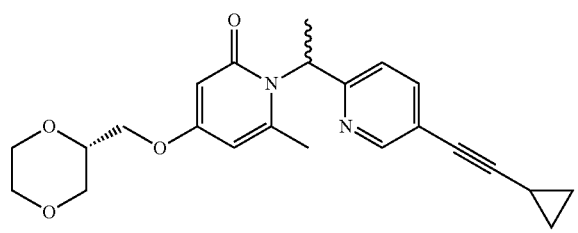 [SMILES: Cc1cc(OC[C@@H]2COCCO2)cc(=O)n1C(C)c1ccc(C#CC2CC2)cn1] |
| I-247 | 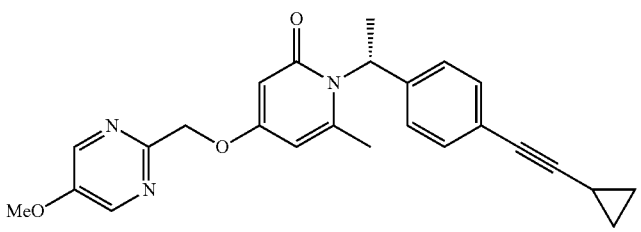 [SMILES: COc1cnc(COc2cc(C)n([C@H](C)c3ccc(C#CC4CC4)cc3)c(=O)c2)nc1] |
| I-248 | 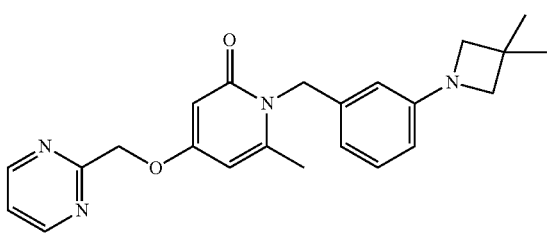 [SMILES: Cc1cc(OCc2ncccn2)cc(=O)n1Cc1cccc(N2CC(C)(C)C2)c1] |
| I-249 | 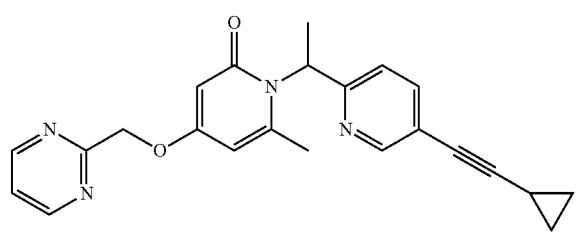 [SMILES: Cc1cc(OCc2ncccn2)cc(=O)n1C(C)c1ccc(C#CC2CC2)cn1] |

TABLE 1-continued

Selected Compounds

| Compound No. | Structure |
|---|---|
| I-250 | 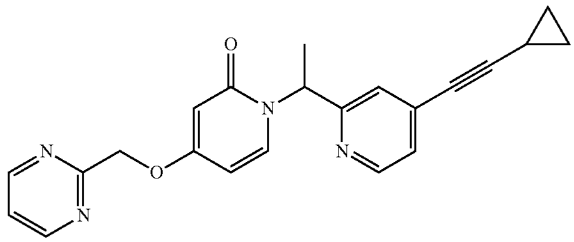 [SMILES: CC(c1cc(C#CC2CC2)ccn1)n1ccc(OCc2ncccn2)cc1=O] |
| I-251 | 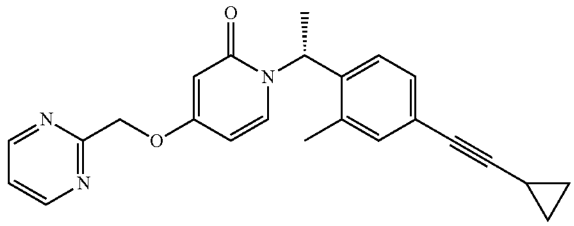 [SMILES: Cc1cc(C#CC2CC2)ccc1[C@@H](C)n1ccc(OCc2ncccn2)cc1=O] |
| I-252 | 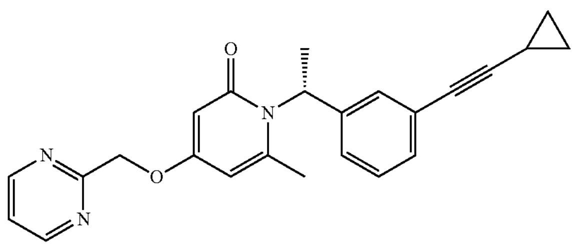 [SMILES: Cc1cc(OCc2ncccn2)cc(=O)n1[C@H](C)c1cccc(C#CC2CC2)c1] |
| I-253 | 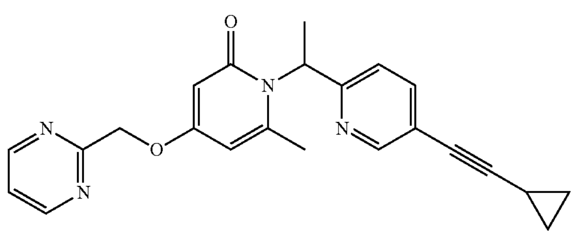 [SMILES: Cc1cc(OCc2ncccn2)cc(=O)n1C(C)c1ccc(C#CC2CC2)cn1] |
| I-254 | 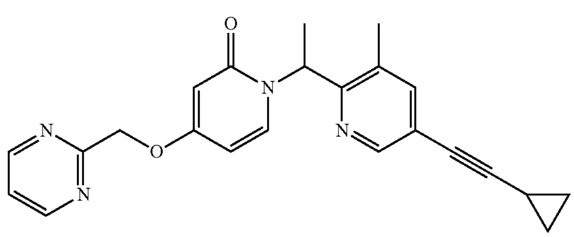 |
| I-255 | 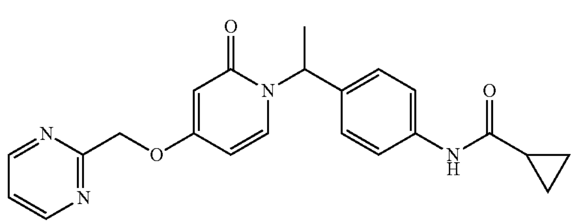 [SMILES: CC(c1ccc(NC(=O)C2CC2)cc1)n1ccc(OCc2ncccn2)cc1=O] |

TABLE 1-continued
Selected Compounds
| Compound No. | Structure |
|---|---|
| I-256 | 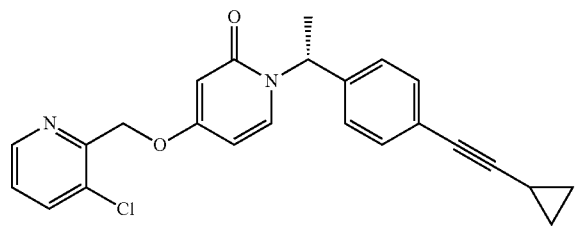 [SMILES: C[C@H](c1ccc(C#CC2CC2)cc1)n1ccc(OCc2ncccc2Cl)cc1=O] |
| I-257 | 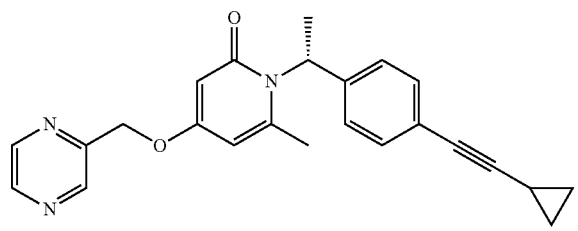 |
| I-258 | 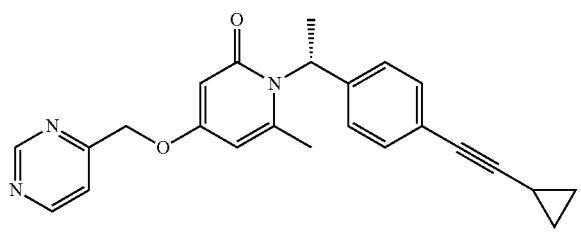 |
| I-259 | 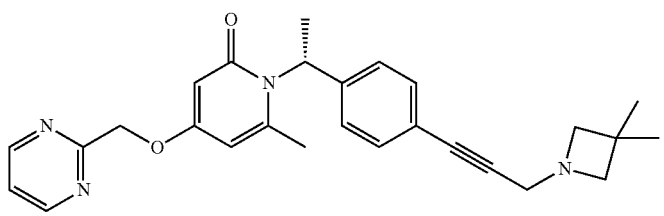 [SMILES: Cc1cc(OCc2ncccn2)cc(=O)n1[C@H](C)c1ccc(C#CCN2CC(C)(C)C2)cc1] |
| I-260 | 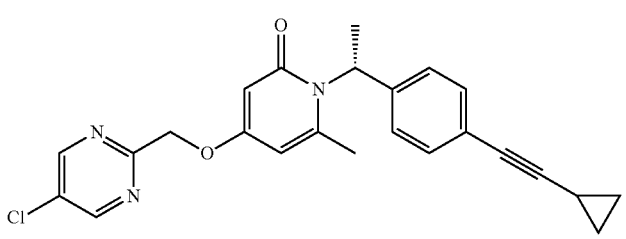 [SMILES: Cc1cc(OCc2ncc(Cl)cn2)cc(=O)n1[C@H](C)c1ccc(C#CC2CC2)cc1] |
| I-261 | 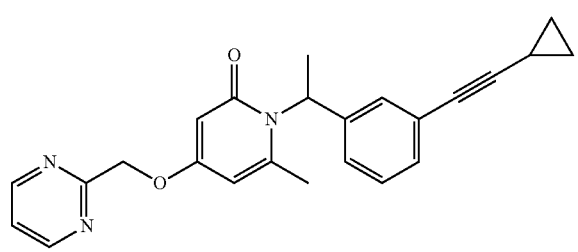 [SMILES: Cc1cc(OCc2ncccn2)cc(=O)n1C(C)c1cccc(C#CC2CC2)c1] |

TABLE 1-continued

Selected Compounds

| Compound No. | Structure |
|---|---|
| I-262 | 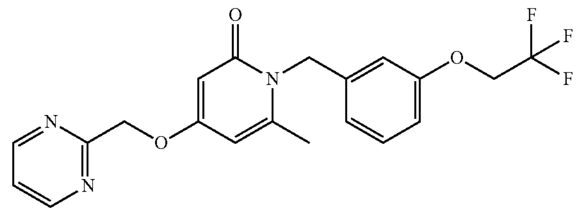 [SMILES: Cc1cc(OCc2ncccn2)cc(=O)n1Cc1cccc(OCC(F)(F)F)c1] |
| I-263 | 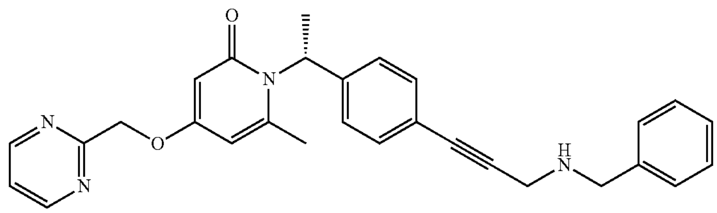 [SMILES: Cc1cc(OCc2ncccn2)cc(=O)n1[C@H](C)c1ccc(C#CCNCc2ccccc2)cc1] |
| I-264 | 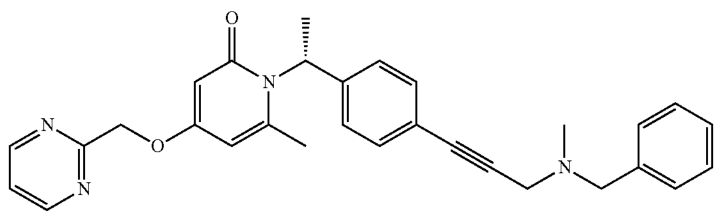 [SMILES: Cc1cc(OCc2ncccn2)cc(=O)n1[C@H](C)c1ccc(C#CCN(C)Cc2ccccc2)cc1] |
| I-265 | 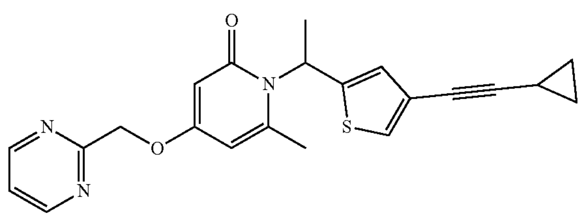 [SMILES: Cc1cc(OCc2ncccn2)cc(=O)n1C(C)c1cc(C#CC2CC2)cs1] |
| I-266 | 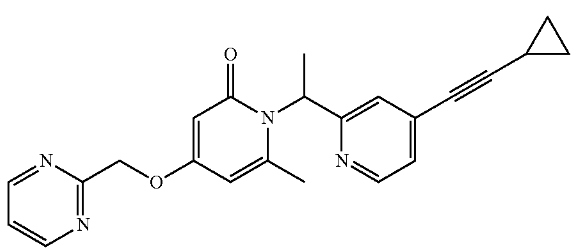 [SMILES: Cc1cc(OCc2ncccn2)cc(=O)n1C(C)c1cc(C#CC2CC2)ccn1] |
| I-267 | 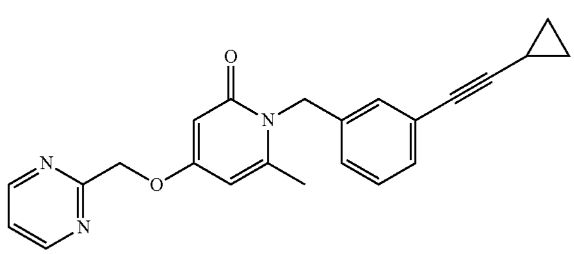 [SMILES: Cc1cc(OCc2ncccn2)cc(=O)n1Cc1cccc(C#CC2CC2)c1] |

TABLE 1-continued

Selected Compounds

| Compound No. | Structure |
|---|---|
| I-268 | 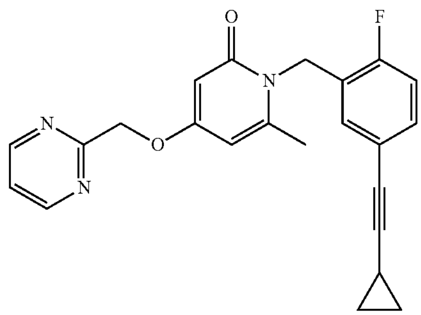 [SMILES: Cc1cc(OCc2ncccn2)cc(=O)n1Cc1cc(C#CC2CC2)ccc1F] |
| I-269 | 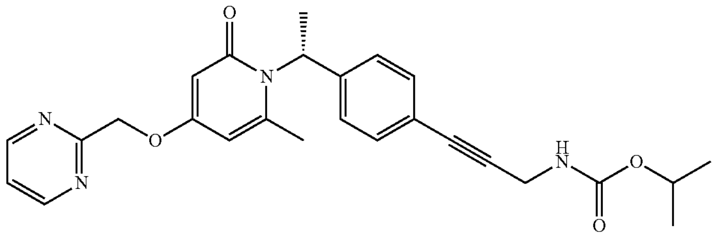 [SMILES: Cc1cc(OCc2ncccn2)cc(=O)n1[C@H](C)c1ccc(C#CCNC(=O)OC(C)C)cc1] |
| I-270 | 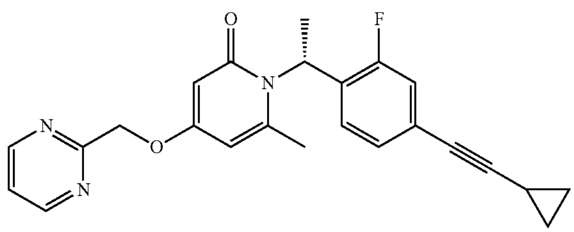 [SMILES: Cc1cc(OCc2ncccn2)cc(=O)n1[C@H](C)c1ccc(C#CC2CC2)cc1F] |
| I-271 | 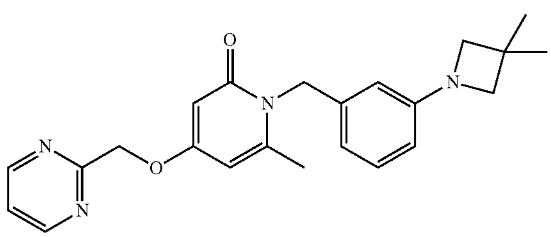 [SMILES: Cc1cc(OCc2ncccn2)cc(=O)n1Cc1cccc(N2CC(C)(C)C2)c1] |
| I-272 | 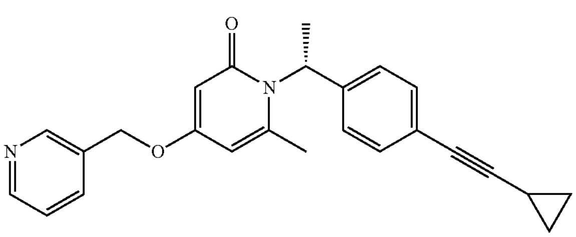 |
| I-273 | 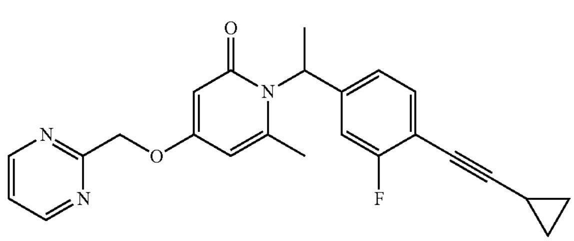 [SMILES: Cc1cc(OCc2ncccn2)cc(=O)n1C(C)c1ccc(C#CC2CC2)c(F)c1] |

TABLE 1-continued
Selected Compounds
| Compound No. | Structure |
|---|---|
| I-274 | 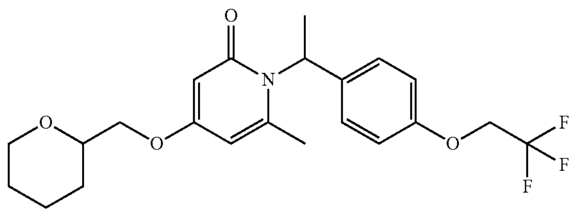 [SMILES: Cc1cc(OCC2CCCCO2)cc(=O)n1C(C)c1ccc(OCC(F)(F)F)cc1] |
| I-275 | 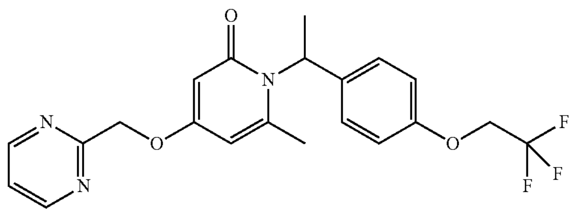 [SMILES: Cc1cc(OCc2ncccn2)cc(=O)n1C(C)c1ccc(OCC(F)(F)F)cc1] |
| I-276 | \ Enantiomer I |
| I-277 | 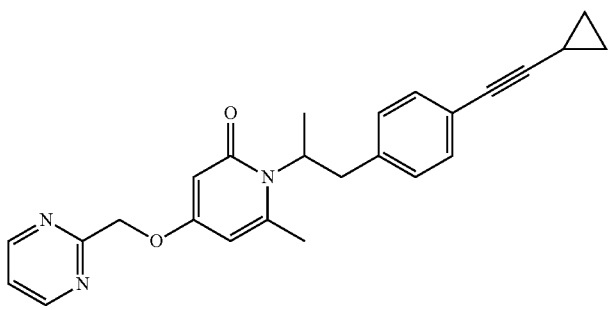\ Enantiomer II |
| I-278 | 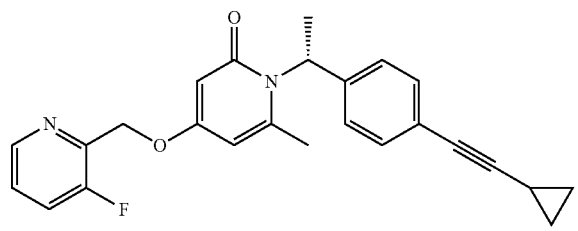 |

TABLE 1-continued

Selected Compounds

| Compound No. | Structure |
|---|---|
| I-279 | 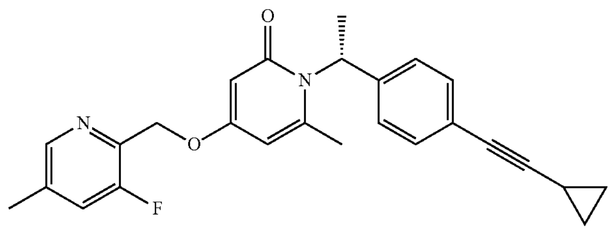 [SMILES: Cc1cnc(COc2cc(C)n([C@H](C)c3ccc(C#CC4CC4)cc3)c(=O)c2)c(F)c1] |
| I-280 | 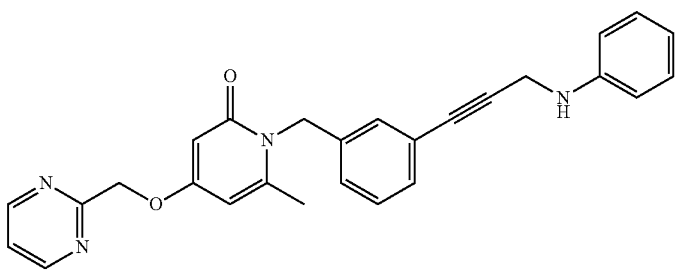 [SMILES: Cc1cc(OCc2ncccn2)cc(=O)n1Cc1cccc(C#CCNc2ccccc2)c1] |
| I-281 | Enantiomer I |
| I-282 | Enantiomer II |
| I-283 | 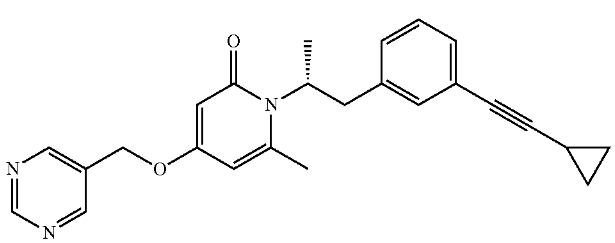 [SMILES: Cc1cc(OCc2cncnc2)cc(=O)n1[C@H](C)Cc1cccc(C#CC2CC2)c1] |
| I-284 | 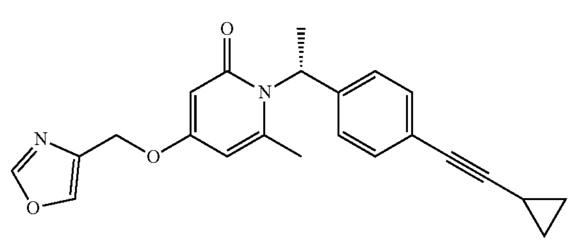 |

TABLE 1-continued

Selected Compounds

| Compound No. | Structure |
|---|---|
| I-285 | 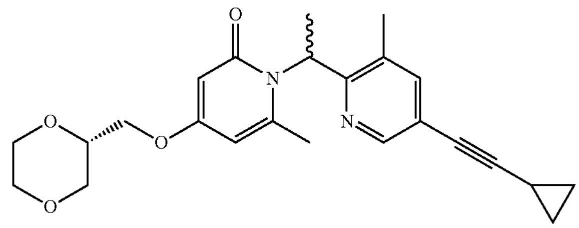 [SMILES: Cc1cc(C#CC2CC2)cnc1C(C)n1c(C)cc(OC[C@@H]2COCCO2)cc1=O] |
| I-286 | 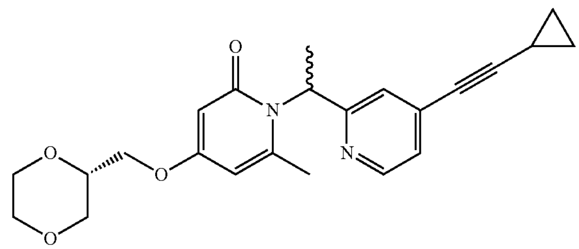 [SMILES: Cc1cc(OC[C@@H]2COCCO2)cc(=O)n1C(C)c1cc(C#CC2CC2)ccn1] |
| I-287 | 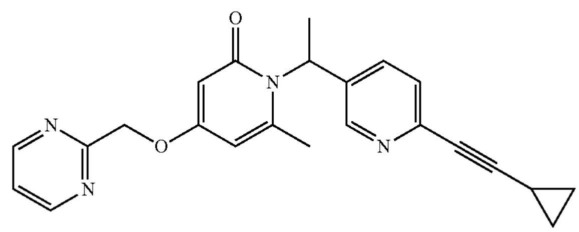 [SMILES: Cc1cc(OCc2ncccn2)cc(=O)n1C(C)c1ccc(C#CC2CC2)nc1] |
| I-288 | 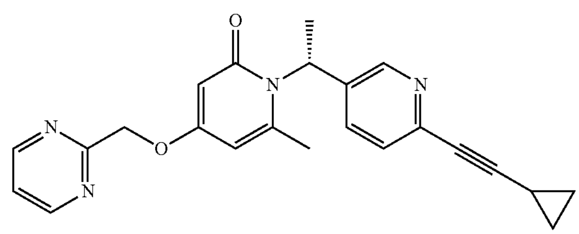 [SMILES: Cc1cc(OCc2ncccn2)cc(=O)n1[C@H](C)c1ccc(C#CC2CC2)nc1] |
| I-289 | 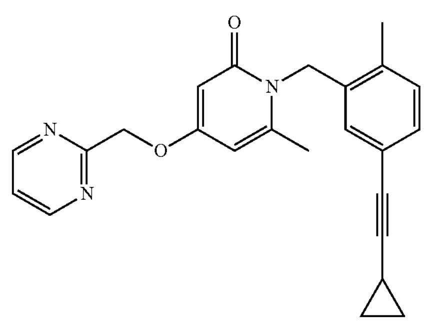 [SMILES: Cc1ccc(C#CC2CC2)cc1Cn1c(C)cc(OCc2ncccn2)cc1=O] |
| I-290 | 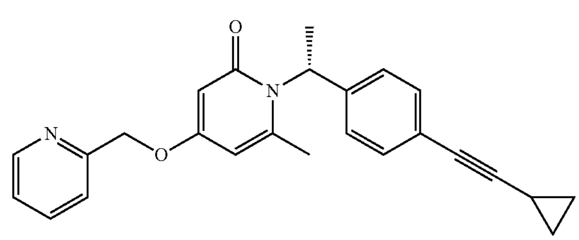 [SMILES: Cc1cc(OCc2ccccn2)cc(=O)n1[C@H](C)c1ccc(C#CC2CC2)cc1] |

TABLE 1-continued
Selected Compounds
| Compound No. | Structure |
|---|---|
| I-291 | 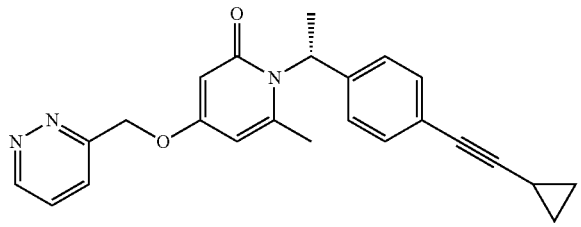 |
| I-292 | 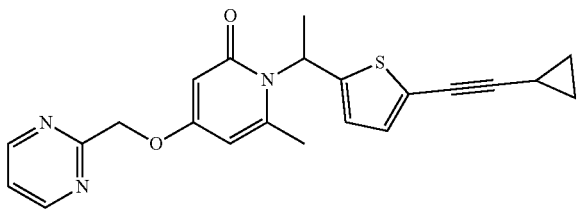 [SMILES: Cc1cc(OCc2ncccn2)cc(=O)n1C(C)c1ccc(C#CC2CC2)s1] |
| I-293 | 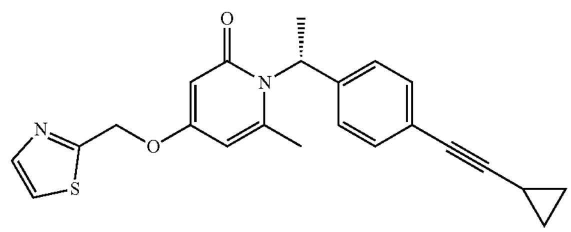 |
| I-294 | 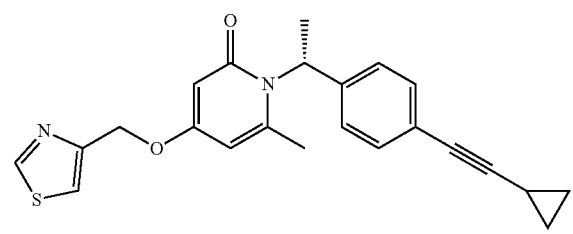 |
| I-295 | 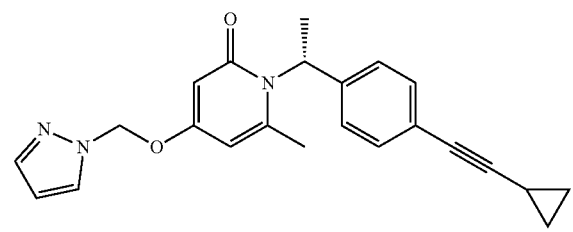 |
| I-296 | 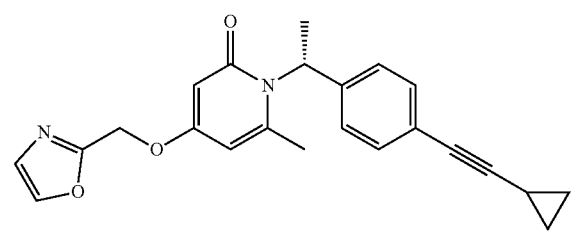 [SMILES: Cc1cc(OCc2nccs2)cc(=O)n1[C@H](C)c1ccc(C#CC2CC2)cc1] |

TABLE 1-continued
Selected Compounds
| Compound No. | Structure |
|---|---|
| I-297 | 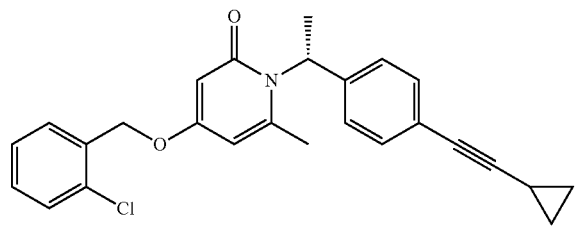 |
| I-298 | 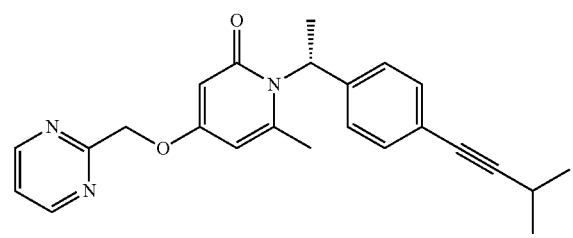 [SMILES: Cc1cc(OCc2ncccn2)cc(=O)n1[C@H](C)c1ccc(C#CC(C)C)cc1] |
| I-299 | 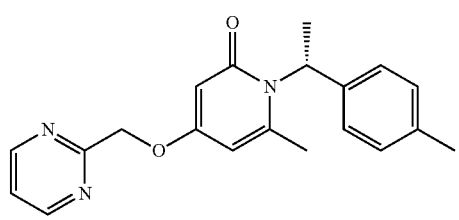 [SMILES: Cc1ccc([C@@H](C)n2c(C)cc(OCc3ncccn3)cc2=O)cc1] |
| I-300 | 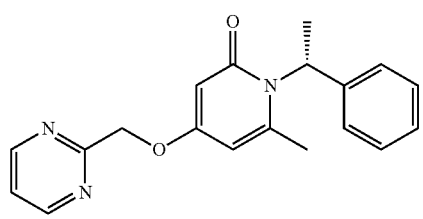 [SMILES: Cc1cc(OCc2ncccn2)cc(=O)n1[C@H](C)c1ccccc1] |
| I-301 | 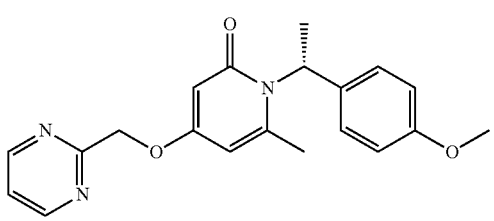 |
| I-302 | 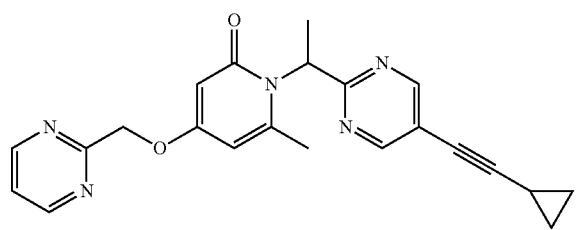 [SMILES: Cc1cc(OCc2ncccn2)cc(=O)n1C(C)c1ncc(C#CC2CC2)cn1] |

TABLE 1-continued

Selected Compounds

| Compound No. | Structure |
|---|---|
| I-303 | 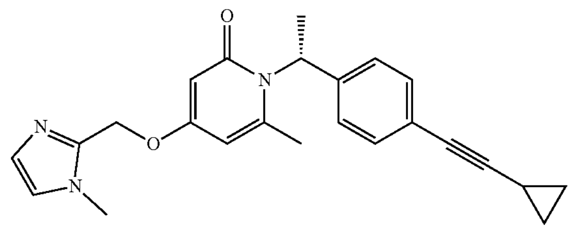 |
| I-304 | 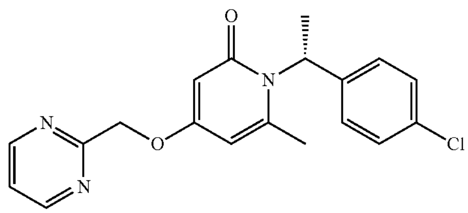 [SMILES: Cc1cc(OCc2ncccn2)cc(=O)n1[C@H](C)c1ccc(Cl)cc1] |
| I-305 | 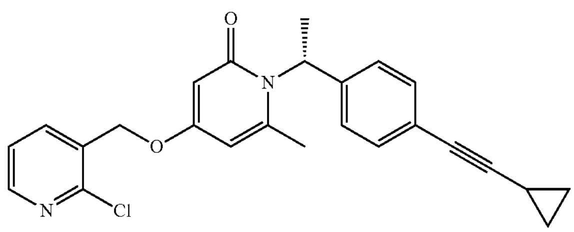 [SMILES: Cc1cc(OCc2cccnc2Cl)cc(=O)n1[C@H](C)c1ccc(C#CC2CC2)cc1] |
| I-306 | 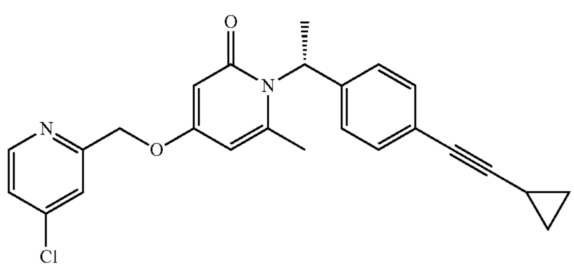 [SMILES: Cc1cc(OCc2cc(Cl)ccn2)cc(=O)n1[C@H](C)c1ccc(C#CC2CC2)cc1] |
| I-307 | 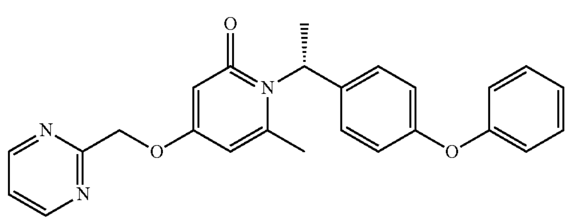 |
| I-308 | 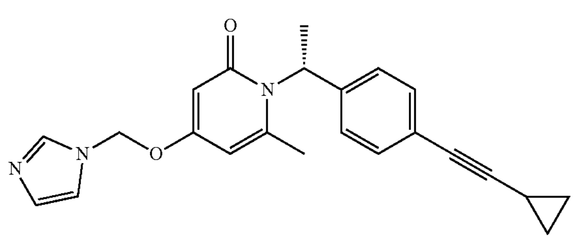 [SMILES: Cc1cc(OCn2ccnc2)cc(=O)n1[C@H](C)c1ccc(C#CC2CC2)cc1] |

TABLE 1-continued
Selected Compounds
| Compound No. | Structure |
|---|---|
| I-309 | 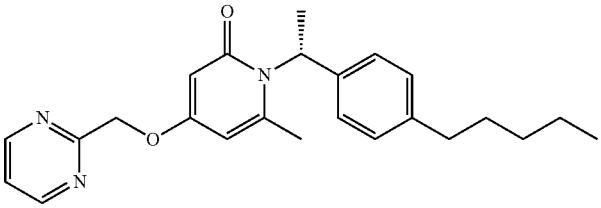 [SMILES: CCCCCc1ccc([C@@H](C)n2c(C)cc(OCc3ncccn3)cc2=O)cc1] |
| I-310 | 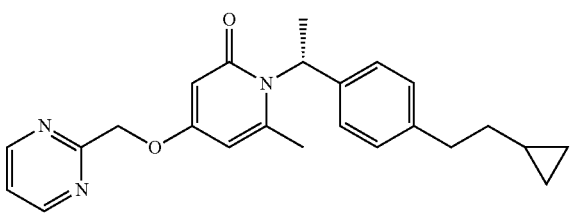 [SMILES: Cc1cc(OCc2ncccn2)cc(=O)n1[C@H](C)c1ccc(CCC2CC2)cc1] |
| I-311 | 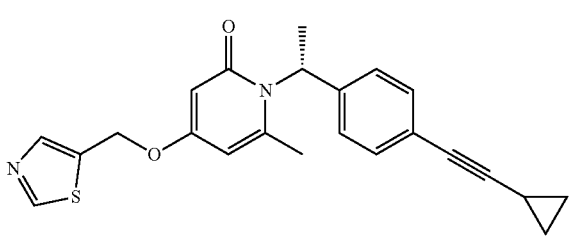 [SMILES: Cc1cc(OCc2cncs2)cc(=O)n1[C@H](C)c1ccc(C#CC2CC2)cc1] |
| I-312 | 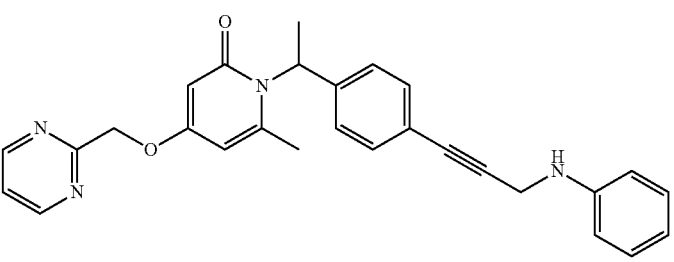 [SMILES: Cc1cc(OCc2ncccn2)cc(=O)n1C(C)c1ccc(C#CCNc2ccccc2)cc1] |
| I-313 | 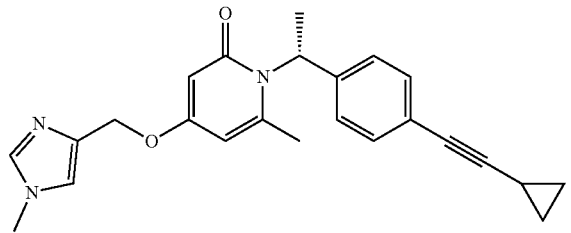 [SMILES: Cc1cc(OCc2cn(C)cn2)cc(=O)n1[C@H](C)c1ccc(C#CC2CC2)cc1] |
| I-314 | 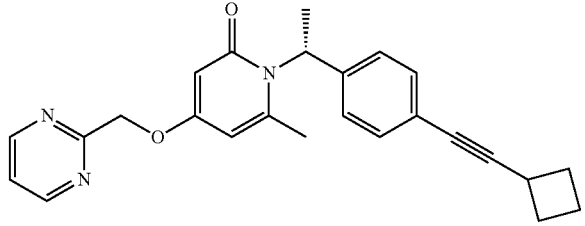 [SMILES: Cc1cc(OCc2ncccn2)cc(=O)n1[C@H](C)c1ccc(C#CC2CCC2)cc1] |

TABLE 1-continued
Selected Compounds
| Compound No. | Structure |
|---|---|
| I-315 | 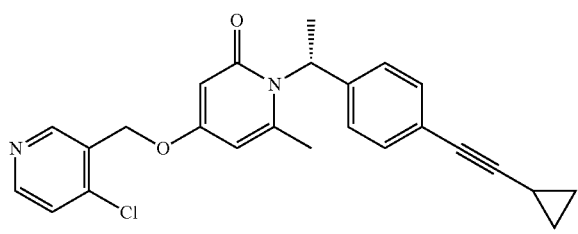 [SMILES: Cc1cc(OCc2cnccc2Cl)cc(=O)n1[C@H](C)c1ccc(C#CC2CC2)cc1] |
| I-316 | 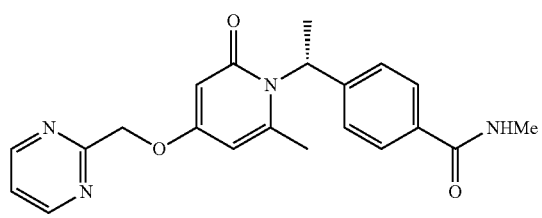 [SMILES: CNC(=O)c1ccc([C@@H](C)n2c(C)cc(OCc3ncccn3)cc2=O)cc1] |
| I-317 | 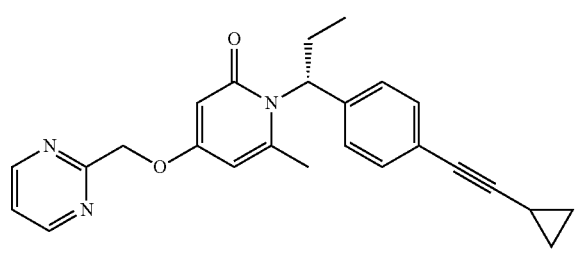 [SMILES: CC[C@H](c1ccc(C#CC2CC2)cc1)n1c(C)cc(OCc2ncccn2)cc1=O] |
| I-318 | 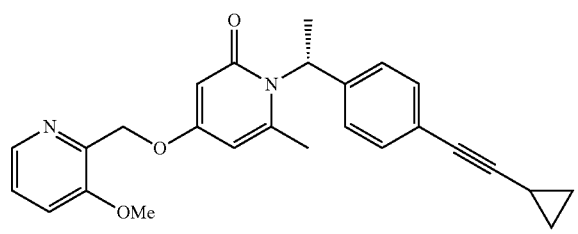 [SMILES: COc1cccnc1COc1cc(C)n([C@H](C)c2ccc(C#CC3CC3)cc2)c(=O)c1] |
| I-319 | 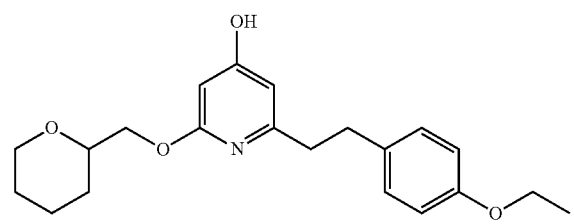 [SMILES: CCOc1ccc(CCc2cc(O)cc(OCC3CCCCO3)n2)cc1] |
| I-320 | 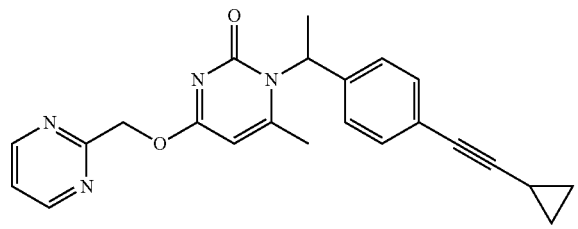 |

TABLE 1-continued
Selected Compounds
| Compound No. | Structure |
|---|---|
| I-321 | 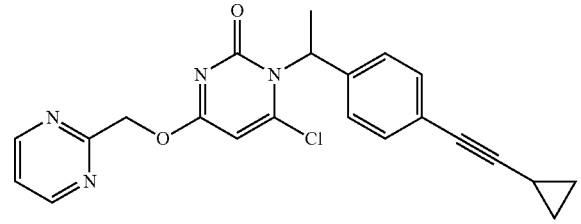 [SMILES: CC(c1ccc(C#CC2CC2)cc1)n1c(Cl)cc(OCc2ncccn2)nc1=O] |
| I-322 | 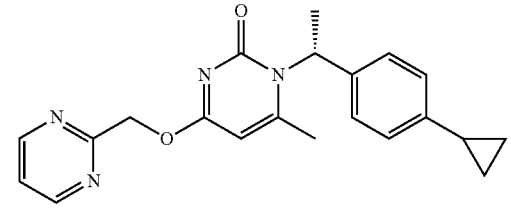 [SMILES: Cc1cc(OCc2ncccn2)nc(=O)n1[C@H](C)c1ccc(C2CC2)cc1] |
| I-323 | 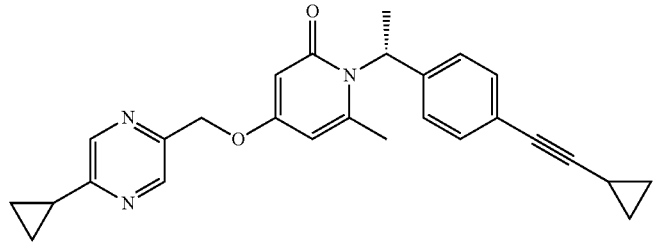 [SMILES: Cc1cc(OCc2cnc(C3CC3)cn2)cc(=O)n1[C@H](C)c1ccc(C#CC2CC2)cc1] |
| I-324 | 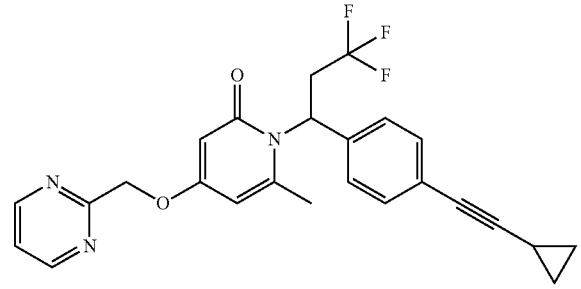 [SMILES: Cc1cc(OCc2ncccn2)cc(=O)n1C(CC(F)(F)F)c1ccc(C#CC2CC2)cc1] |
| I-325 | 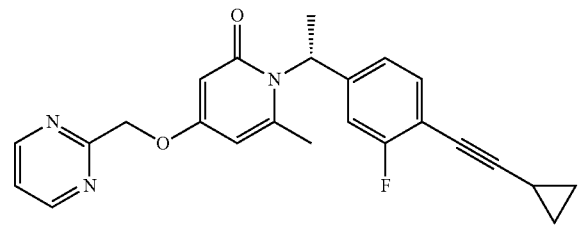 |
| I-326 | 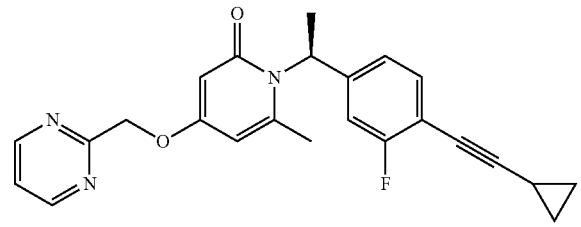 [SMILES: Cc1cc(OCc2ncccn2)cc(=O)n1[C@@H](C)c1ccc(C#CC2CC2)c(F)c1] |

TABLE 1-continued

Selected Compounds

| Compound No. | Structure |
|---|---|
| I-327 | 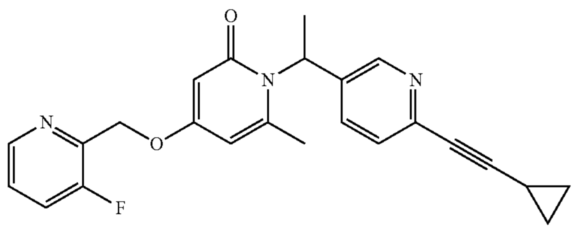 [SMILES: Cc1cc(OCc2ncccc2F)cc(=O)n1C(C)c1ccc(C#CC2CC2)nc1] |
| I-328 | 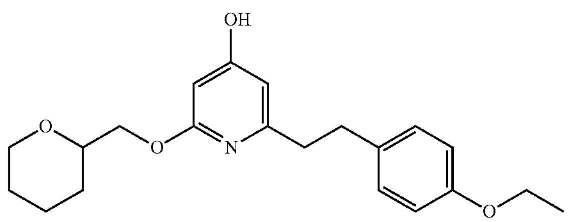 [SMILES: CCOc1ccc(CCc2cc(O)cc(OCC3CCCCO3)n2)cc1] |
| I-329 | 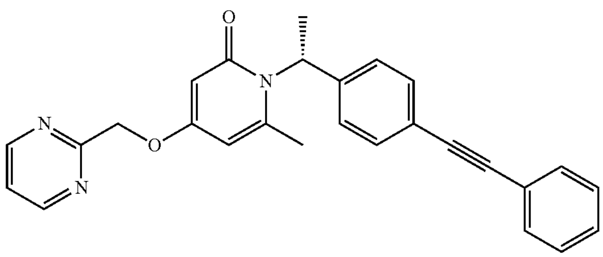 [SMILES: Cc1cc(OCc2ncccn2)cc(=O)n1[C@H](C)c1ccc(C#Cc2ccccc2)cc1] |
| I-340 | 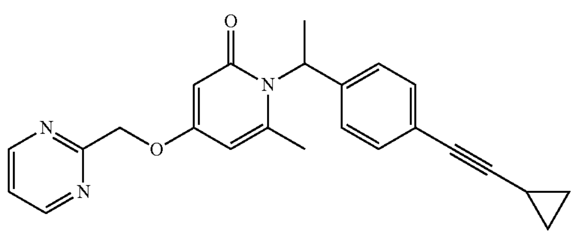 |
| I-341 | 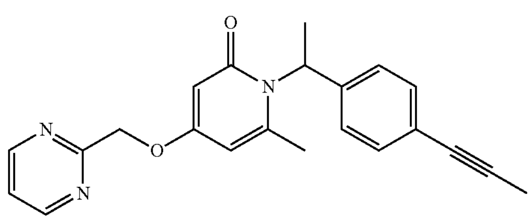 [SMILES: CC#Cc1ccc(C(C)n2c(C)cc(OCc3ncccn3)cc2=O)cc1] |
| I-342 | 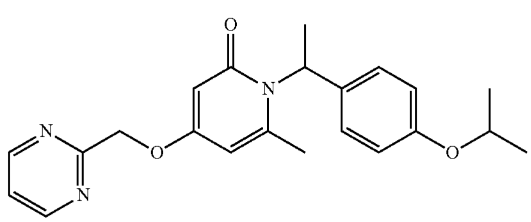 [SMILES: Cc1cc(OCc2ncccn2)cc(=O)n1C(C)c1ccc(OC(C)C)cc1] |

TABLE 1-continued
Selected Compounds
| Compound No. | Structure |
|---|---|
| I-343 | 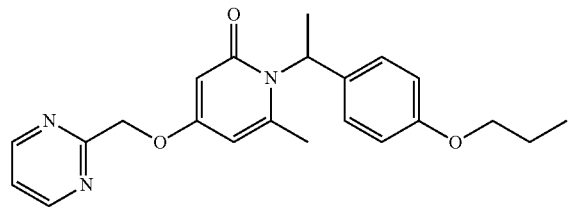 [SMILES: CCCOc1ccc(C(C)n2c(C)cc(OCc3ncccn3)cc2=O)cc1] |
| I-344 | 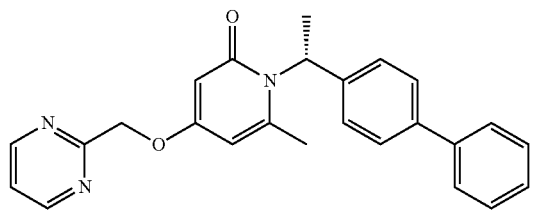 [SMILES: Cc1cc(OCc2ncccn2)cc(=O)n1[C@H](C)c1ccc(-c2ccccc2)cc1] |
| I-345 | 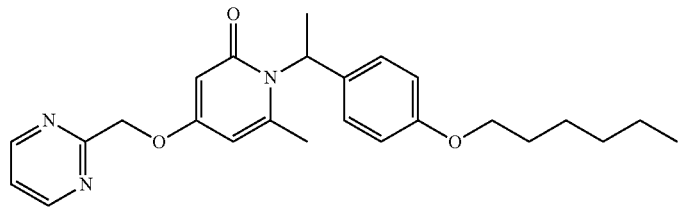 [SMILES: CCCCCCOc1ccc(C(C)n2c(C)cc(OCc3ncccn3)cc2=O)cc1] |
| I-346 | 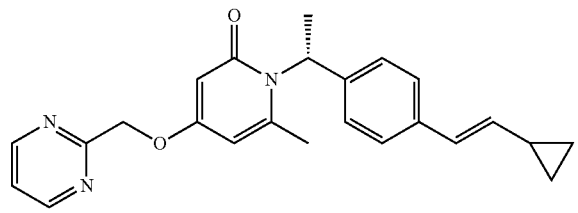 [SMILES: Cc1cc(OCc2ncccn2)cc(=O)n1[C@H](C)c1ccc(/C=C/C2CC2)cc1] |
| I-346 | 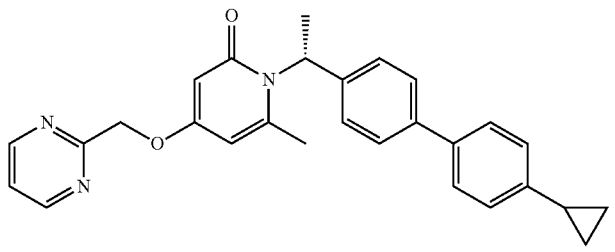 [SMILES: Cc1cc(OCc2ncccn2)cc(=O)n1[C@H](C)c1ccc(-c2ccc(C3CC3)cc2)cc1] |
| I-347 | 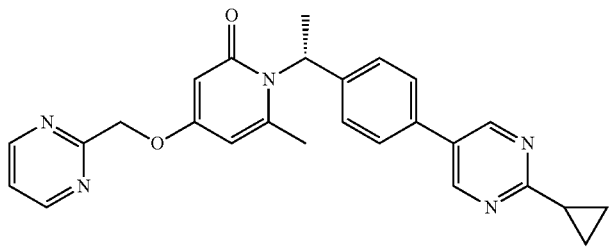 [SMILES: Cc1cc(OCc2ncccn2)cc(=O)n1[C@H](C)c1ccc(-c2cnc(C3CC3)nc2)cc1] |

TABLE 1-continued
Selected Compounds
| Compound No. | Structure |
|---|---|
| I-348 | 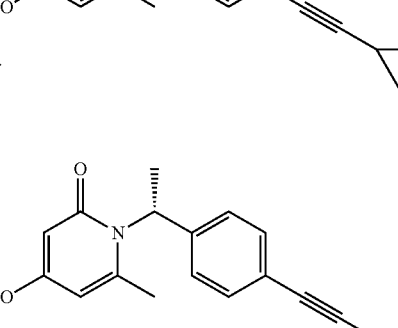 |
| I-349 | 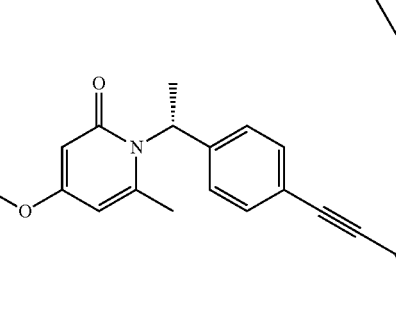 |
| I-350 | 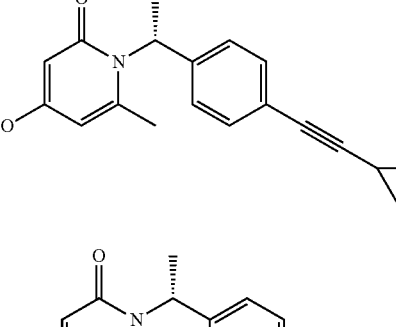 |
| I-351 | 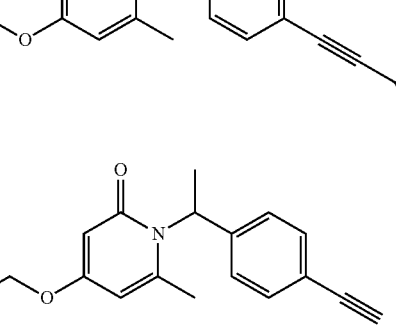 |
| I-352 | 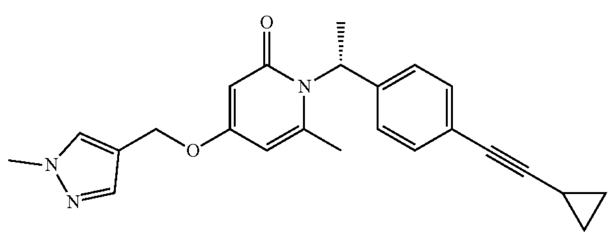 [SMILES: Cc1cc(OCc2cnn(C)c2)cc(=O)n1[C@H](C)c1ccc(C#CC2CC2)cc1] |
| I-353 | 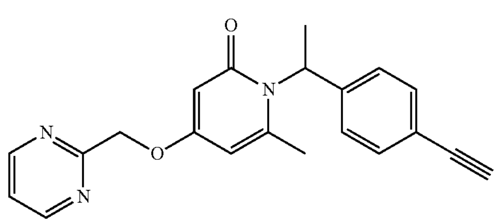 [SMILES: C#Cc1ccc(C(C)n2c(C)cc(OCc3ncccn3)cc2=O)cc1] |

TABLE 1-continued
Selected Compounds
| Compound No. | Structure |
|---|---|
| I-354 | 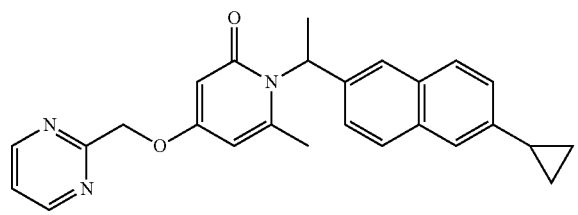 [SMILES: Cc1cc(OCc2ncccn2)cc(=O)n1C(C)c1ccc2cc(C3CC3)ccc2c1] |
| I-355 | 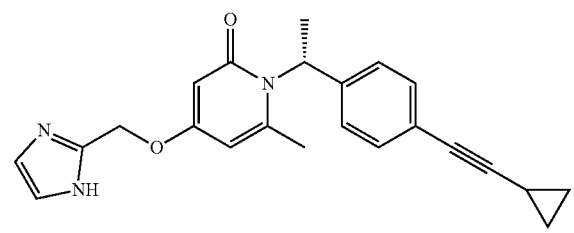 |
| I-356 | 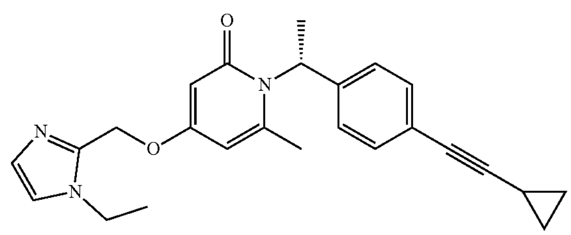 [SMILES: CCn1ccnc1COc1cc(C)n([C@H](C)c2ccc(C#CC3CC3)cc2)c(=O)c1] |
| I-357 | 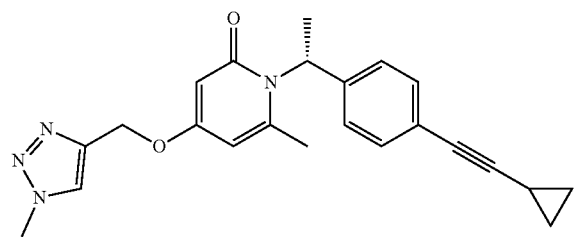 [SMILES: Cc1cc(OCc2cn(C)nn2)cc(=O)n1[C@H](C)c1ccc(C#CC2CC2)cc1] |
| I-358 | 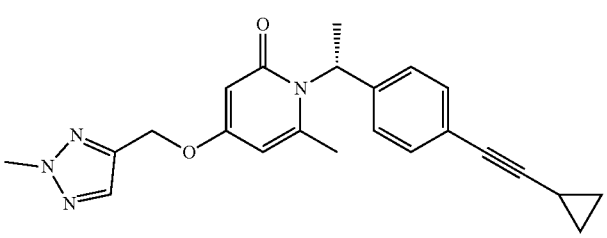 |
| I-359 | 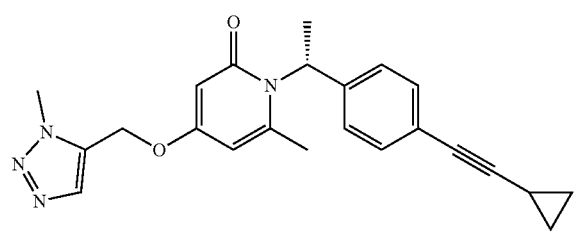 |

TABLE 1-continued

Selected Compounds

| Compound No. | Structure |
|---|---|
| I-360 | 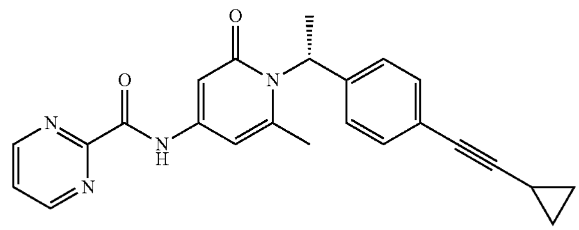 [SMILES: Cc1cc(NC(=O)c2ncccn2)cc(=O)n1[C@H](C)c1ccc(C#CC2CC2)cc1] |
| I-361 | 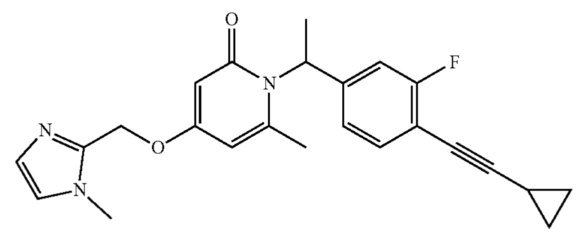 [SMILES: Cc1cc(OCc2nccn2C)cc(=O)n1C(C)c1ccc(C#CC2CC2)c(F)c1] |
| I-362 | 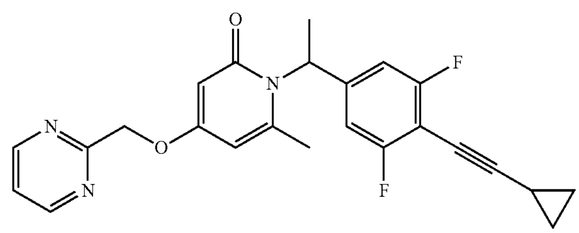 [SMILES: Cc1cc(OCc2ncccn2)cc(=O)n1C(C)c1cc(F)c(C#CC2CC2)c(F)c1] |
| I-363 | 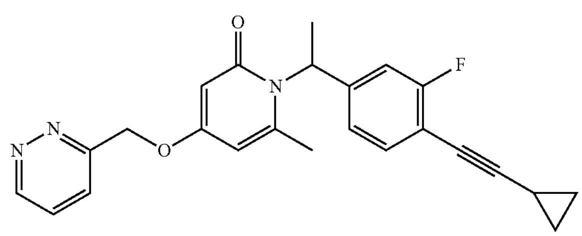 |
| I-364 | 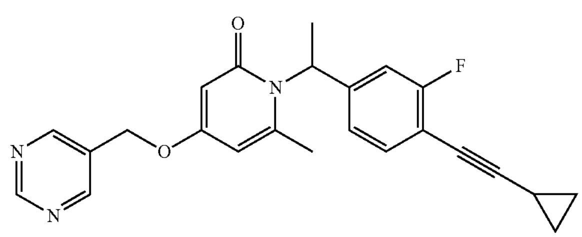 |
| I-365 | 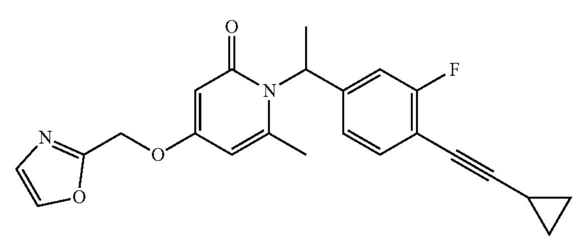 [SMILES: Cc1cc(OCc2ncco2)cc(=O)n1C(C)c1ccc(C#CC2CC2)c(F)c1] |

TABLE 1-continued

Selected Compounds

| Compound No. | Structure |
|---|---|
| I-366 | 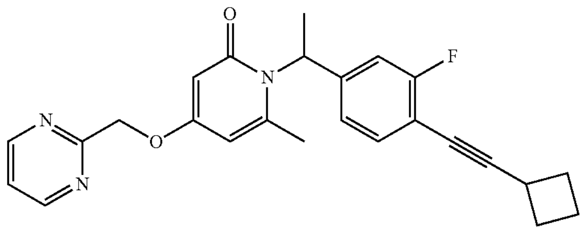 [SMILES: Cc1cc(OCc2ncccn2)cc(=O)n1C(C)c1ccc(C#CC2CCC2)c(F)c1] |
| I-367 | 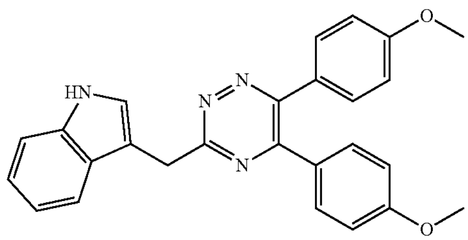 [SMILES: COc1ccc(-c2nnc(Cc3c[nH]c4ccccc34)nc2-c2ccc(OC)cc2)cc1] |
| I-368 | 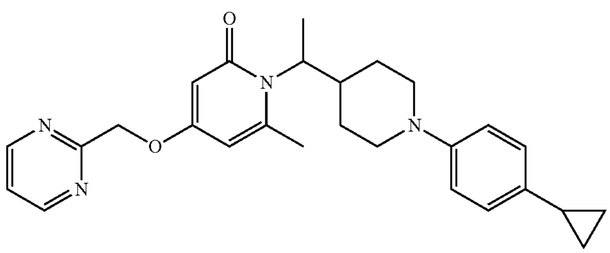 [SMILES: Cc1cc(OCc2ncccn2)cc(=O)n1C(C)C1CCN(c2ccc(C3CC3)cc2)CC1] |
| I-369 | 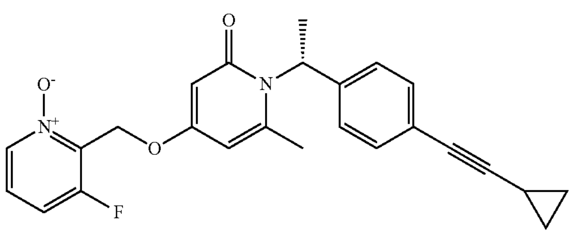 [SMILES: Cc1cc(OCc2c(F)ccc[n+]2[O-])cc(=O)n1[C@H](C)c1ccc(C#CC2CC2)cc1] |
| I-372 | 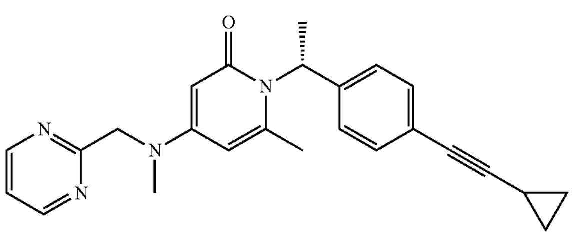 [SMILES: Cc1cc(N(C)Cc2ncccn2)cc(=O)n1[C@H](C)c1ccc(C#CC2CC2)cc1] |
| I-373 | 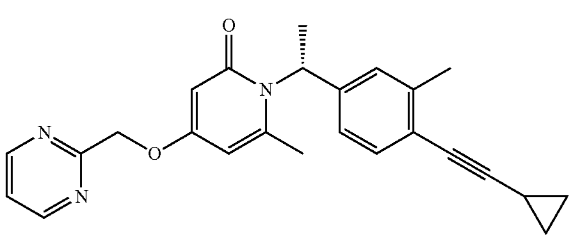 [SMILES: Cc1cc([C@@H](C)n2c(C)cc(OCc3ncccn3)cc2=O)ccc1C#CC1CC1] |

TABLE 1-continued

Selected Compounds

| Compound No. | Structure |
|---|---|
| I-374 | 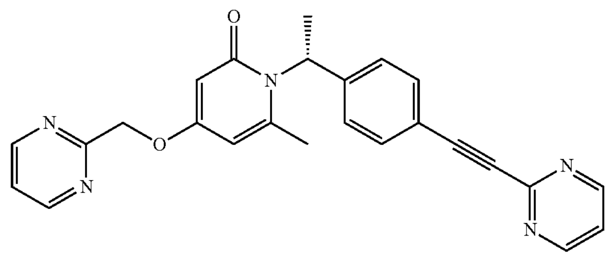 |
| I-375 | 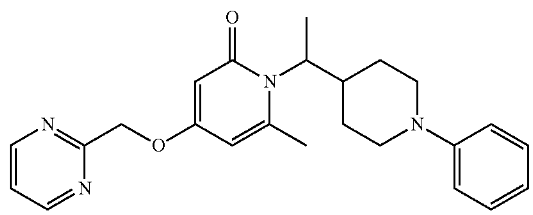 [SMILES: Cc1cc(OCc2ncccn2)cc(=O)n1C(C)C1CCN(c2ccccc2)CC1] |
| I-376 | 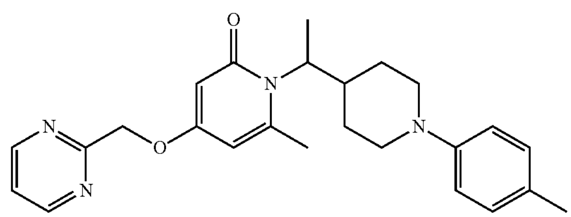 [SMILES: Cc1ccc(N2CCC(C(C)n3c(C)cc(OCc4ncccn4)cc3=O)CC2)cc1] |
| I-377 | 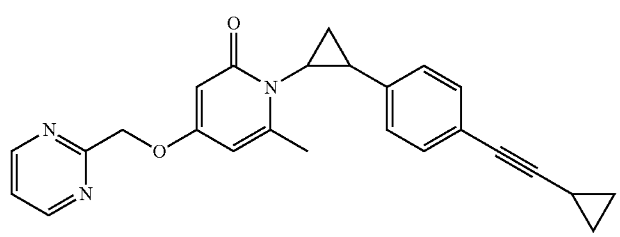 [SMILES: Cc1cc(OCc2ncccn2)cc(=O)n1C1CC1c1ccc(C#CC2CC2)cc1] |
| I-378 | 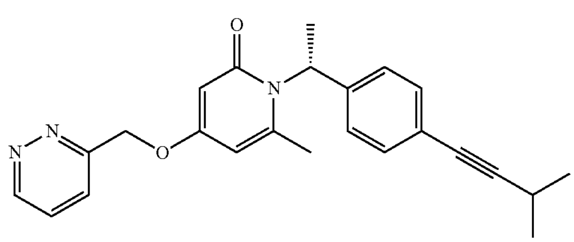 [SMILES: Cc1cc(OCc2cccnn2)cc(=O)n1[C@H](C)c1ccc(C#CC(C)C)cc1] |
| I-379 | 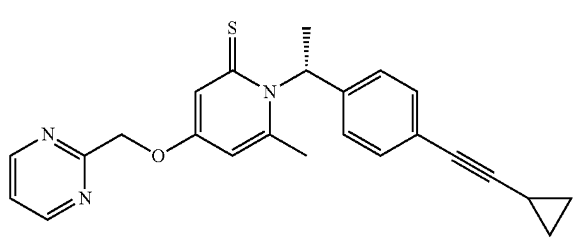 [SMILES: Cc1cc(OCc2ncccn2)cc(=S)n1[C@H](C)c1ccc(C#CC2CC2)cc1] |

TABLE 1-continued

Selected Compounds

| Compound No. | Structure |
|---|---|
| I-380 | 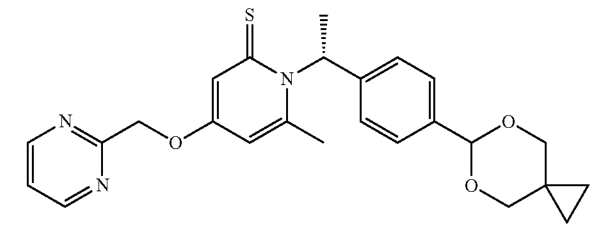 [SMILES: Cc1cc(OCc2ncccn2)cc(=S)n1[C@H](C)c1ccc(C2OCC3(CC3)CO2)cc1] |
| I-381 | 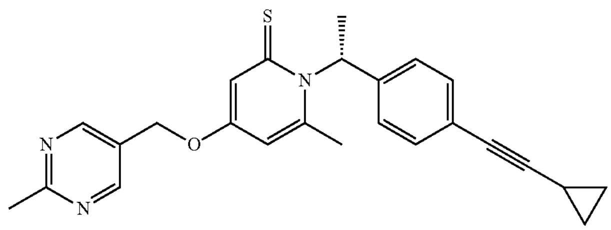 [SMILES: Cc1ncc(COc2cc(C)n([C@H](C)c3ccc(C#CC4CC4)cc3)c(=S)c2)cn1] |
| I-382 | 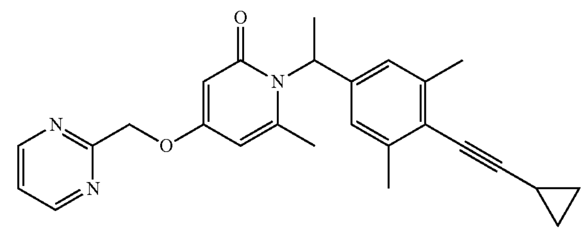 [SMILES: Cc1cc(C(C)n2c(C)cc(OCc3ncccn3)cc2=O)cc(C)c1C#CC1CC1] |
| I-383 | 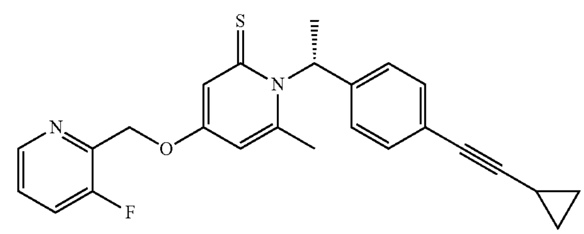 [SMILES: Cc1cc(OCc2ncccc2F)cc(=S)n1[C@H](C)c1ccc(C#CC2CC2)cc1] |
| I-384 | 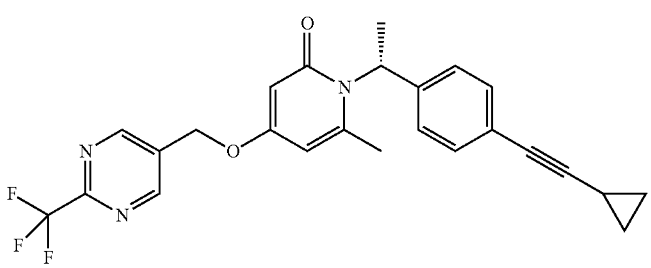 [SMILES: Cc1cc(OCc2cnc(C(F)(F)F)nc2)cc(=O)n1[C@H](C)c1ccc(C#CC2CC2)cc1] |
| I-385 | 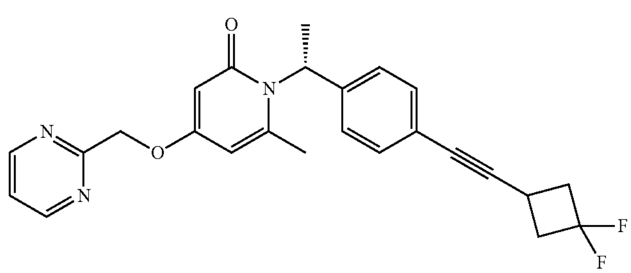 [SMILES: Cc1cc(OCc2ncccn2)cc(=O)n1[C@H](C)c1ccc(C#CC2CC(F)(F)C2)cc1] |

TABLE 1-continued

Selected Compounds

| Compound No. | Structure |
|---|---|
| I-386 | 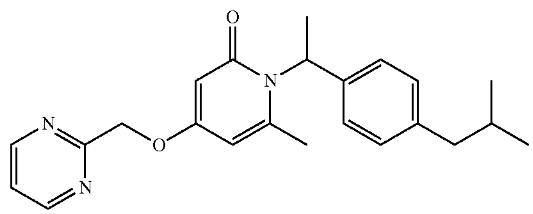 [SMILES: Cc1cc(OCc2ncccn2)cc(=O)n1C(C)c1ccc(CC(C)C)cc1] |
| I-387 | 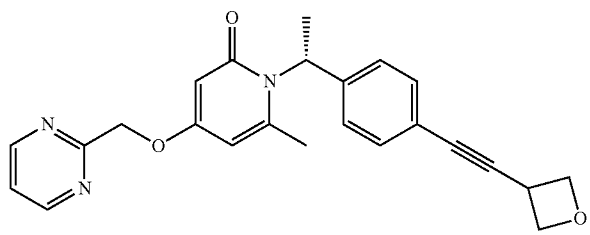 [SMILES: Cc1cc(OCc2ncccn2)cc(=O)n1[C@H](C)c1ccc(C#CC2COC2)cc1] |
| I-388 | 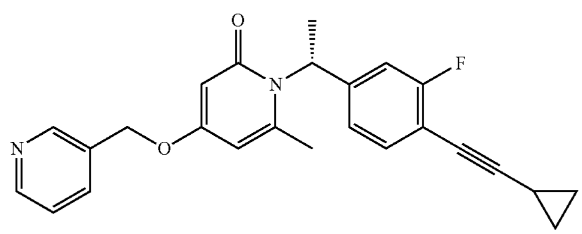 |
| I-389 | 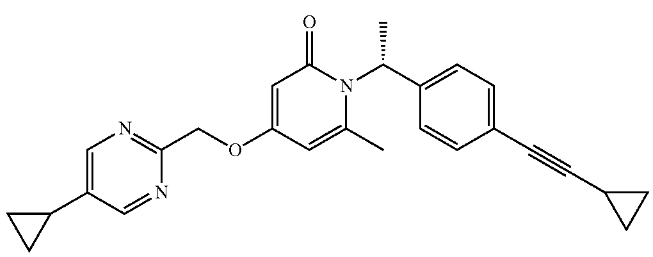 [SMILES: Cc1cc(OCc2ncc(C3CC3)cn2)cc(=O)n1[C@H](C)c1ccc(C#CC2CC2)cc1] |
| I-390 | 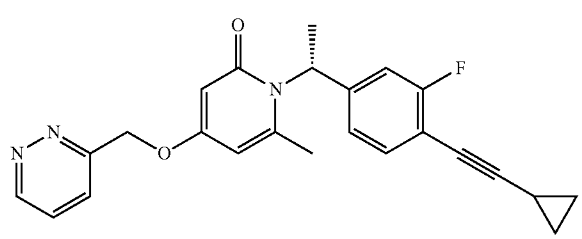 |
| I-391 | 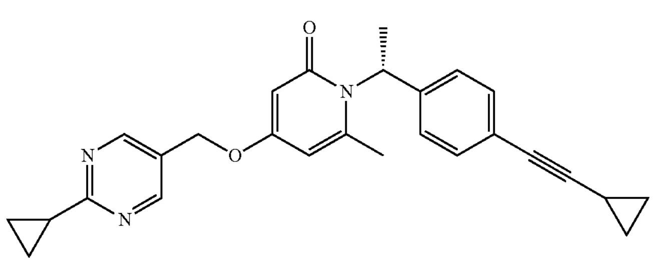 [SMILES: Cc1cc(OCc2cnc(C3CC3)nc2)cc(=O)n1[C@H](C)c1ccc(C#CC2CC2)cc1] |

TABLE 1-continued

Selected Compounds

| Compound No. | Structure |
|---|---|
| I-392 | 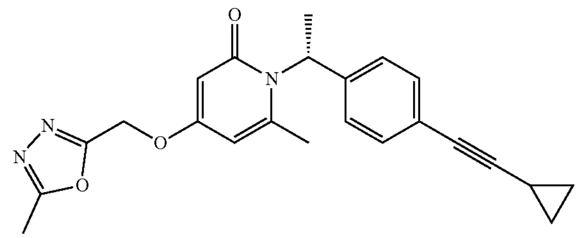 [SMILES: Cc1nnc(COc2cc(C)n([C@H](C)c3ccc(C#CC4CC4)cc3)c(=O)c2)o1] |
| I-393 | 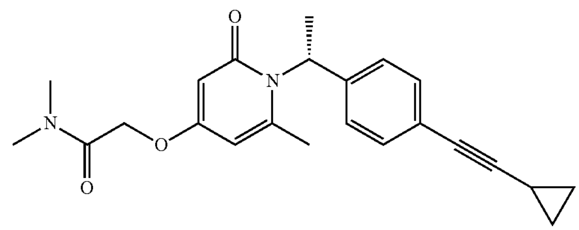 [SMILES: Cc1cc(OCC(=O)N(C)C)cc(=O)n1[C@H](C)c1ccc(C#CC2CC2)cc1] |
| I-394 | 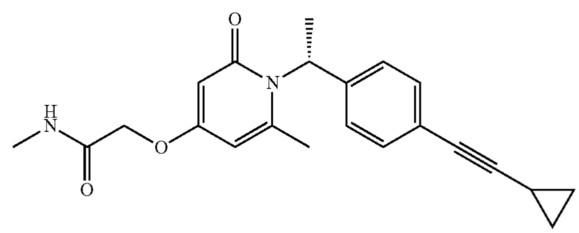 [SMILES: CNC(=O)COc1cc(C)n([C@H](C)c2ccc(C#CC3CC3)cc2)c(=O)c1] |
| I-395 | 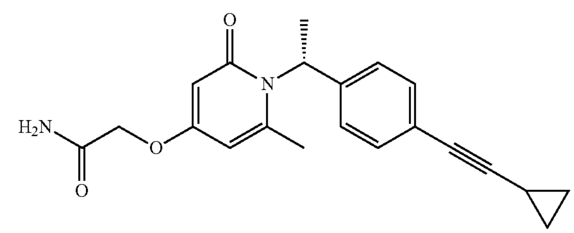 [SMILES: Cc1cc(OCC(N)=O)cc(=O)n1[C@H](C)c1ccc(C#CC2CC2)cc1] |
| I-396 | 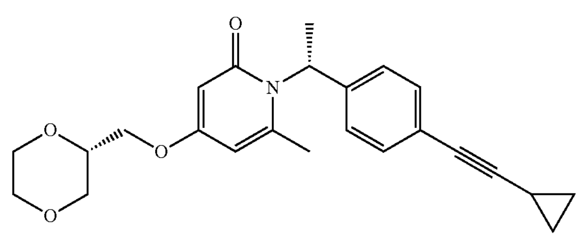 [SMILES: Cc1cc(OC[C@@H]2COCCO2)cc(=O)n1[C@H](C)c1ccc(C#CC2CC2)cc1] |

In some embodiments, the present invention provides a compound set forth in Table 1, above, or a pharmaceutically acceptable salt thereof. In some embodiments, the present invention provides a compound set forth in Table 1, above. In some embodiments, the present invention provides a pharmaceutical composition comprising a compound set forth in Table 1 above, or a pharmaceutically acceptable salt thereof, together with a pharmaceutically acceptable carrier, excipient, or diluent.

In some embodiments, the present invention provides a compound of formula I as defined above, or a pharmaceutically acceptable salt thereof, or a pharmaceutical composition comprising a compound of formula I as defined above, or a pharmaceutically acceptable salt thereof, and a pharmaceutically acceptable carrier, adjuvant, or vehicle for use as a medicament.

In chemical structures in Table 1, above, and the Examples, below, stereogenic centers are described according to the Enhanced Stereo Representation format (MDL/Biovia, e.g. using labels "or1", "or2", "abs", "and1").

In some embodiments, the invention also provides compounds of formula I described herein or pharmaceutical compositions described herein for use in a method for inhibiting GPR84 as described herein, in a method for modulating an immune response in a subject in need thereof as described herein and/or in a method for treating a GPR84-dependent disorder as described herein.

In some embodiments, the invention also provides compounds of formula I described herein or pharmaceutical compositions described herein for use in a method for inhibiting GPR84 as described herein.

In some embodiments, the invention also provides compounds of formula I described herein or pharmaceutical compositions described herein for use in a method for modulating an immune response in a subject in need thereof as described herein.

In some embodiments, the invention also provides compounds of formula I described herein or pharmaceutical compositions described herein for use in a method for treating a GPR84-dependent disorder as described herein.

In some embodiments, the invention also provides the use of a compound of formula I described herein or a pharmaceutical composition described herein for the manufacture of a medicament for inhibiting GPR84, a medicament for modulating an immune response in a subject in need thereof and/or a medicament for treating a GPR84-dependent disorder.

In some embodiments, the invention also provides the use of a compound of formula I described herein or a pharmaceutical composition described herein for the manufacture of a medicament for inhibiting GPR84.

In some embodiments, the invention also provides the use of a compound of formula I described herein or a pharmaceutical composition described herein for the manufacture of a medicament for modulating an immune response in a subject in need thereof.

In some embodiments, the invention also provides the use of a compound of formula I described herein, or a pharmaceutical composition described herein for the manufacture of a medicament treating a GPR84-dependent disorder.

In some embodiments, the invention also provides the use of compounds of formula I described herein or pharmaceutical compositions described herein in a method for inhibiting GPR84 as described herein, in a method for modulating an immune response in a subject in need thereof as described herein and/or in a method for treating a GPR84-dependent disorder as described herein.

In some embodiments, the invention also provides the use of compounds of formula I described herein, or pharmaceutical compositions described herein in a method for inhibiting GPR84 as described herein.

In some embodiments, the invention also provides the use of compounds of formula I described herein, or pharmaceutical compositions described herein in a method for modulating an immune response in a subject in need thereof as described herein.

In some embodiments, the invention also provides the use of compounds of formula I described herein, or pharmaceutical compositions described herein in a method for treating a GPR84-dependent disorder as described herein.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit GPR84, or a mutant thereof, in a biological sample or in a patient. In certain embodiments, the amount of compound in compositions of this invention is such that is effective to measurably inhibit GPR84, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of GPR84, or a mutant thereof.

The subject matter disclosed herein includes prodrugs, metabolites, derivatives, and pharmaceutically acceptable salts of compounds of the invention. Metabolites include compounds produced by a process comprising contacting a compound of the invention with a mammal for a period of time sufficient to yield a metabolic product thereof. If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A compound of the invention can be in the form of a "prodrug," which includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included. In aspects, the compounds of the invention are prodrugs of any of the formulae herein.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The compounds and compositions described herein are generally useful for the inhibition of signaling activity of one or more GPCRs. In some embodiments the GPCR inhibited by the compounds and methods of the invention is GPR84.

The presently disclosed compounds find use in inhibiting the activity of GPR84. GPR84 is a Gi-coupled G-protein-coupled receptor (GPCR) that is expressed on the surface of immune cells. GPR84 modulates the innate immune response in conditions such as fibrotic disorders.

Multiple studies have indicated GPR84 may be a potential target for the treatment of obesity and/or metabolic dysfunction.

GPR84 gene expression in human differentiated adipocytes in culture is highly upregulated by the major pro-inflammatory cytokines TNF-alpha and IL-1beta (Muredda et al. 2017. *Arch. Physiol. Biochem.* 124(2), 97-108). These data confirm activation of pro-inflammatory GPR84 signaling in the context of inflammation in fat cells, first described by Nagasaki in 2012 (Nagasaki et al, 2012, FEBS Letters, 586, 368-372).

IL-33, a member of the IL-1beta superfamily, in an autocrine manner, strongly upregulates GPR84 mRNA expression in human differentiated adipocytes, which correlates with enhanced production of pro-inflammatory cytokines and chemokines such as IL-1beta, CCL2, IL6, CXCL2 and CSF3 (Zaibi et al. 2018. *Cytokine*, 110, 189-193). This suggests GPR84 activation by pro-inflammatory stimuli in fat cells leads to further pro-inflammatory cytokine release and identifies the presence of a putative autocrine positive feedback loop.

GPR84 expression in liver is upregulated in patients with NASH and correlates with disease severity. GPR84 is upregulated in activated human and mouse macrophages and neutrophils. GPR84 mediated myeloid cell infiltration promoting steatohepatitis and fibrosis. Pharmacological inhibition of GPR84 significantly reduced macrophage accumulation, inflammation and fibrosis in NASH models, similarly to selonsertib (ASK1 inhibitor). These findings suggest GPR84 promotes myeloid cell infiltration in liver injury and is a valid therapeutic target for steatohepatitis and fibrosis in NAFLD/NASH (Puengel et al. 2020. *J. Clin. Med.* 9(4), 1140).

GPR84 deletion in mice was associated with decreased NAFLD-induced liver injury. Treatment with PBI-4547 (putative GPR84 antagonist) reduced NAFLD induced injury in liver, adipose tissue and promoted fatty acid oxidation (Simard et al. 2020. *Sci. Rep.* 10(1), 12778).

Mice with global deletion of Gpr84 [Gpr84 knockout (KO)] exhibit a mild impairment in glucose tolerance when fed a MCFA-enriched diet. The study demonstrated the regulation of mitochondrial metabolism in murine skeletal muscle by the medium-chain fatty acid receptor GPR84, an important player in glycemic control (Montgomery M K, et al. 2019. *FASEB J.* 33(11), 12264-12276).

Nutrient-sensing receptors located on enteroendocrine (EEC) cells modulate appetite via detection of luminal contents. Peiris et al. assessed the effects of obesity and gastric bypass-induced weight loss on expression of nutrient-sensing G-protein coupled receptors (GPCRs) and found that GPR84 expression was increased in obese mice. Further, obesity-induced overexpression of GPR84 further increased after Roux-en-Y gastric bypass surgery (RYGB). Several nutrient-sensing receptors including GPR84 induced activation of colonic EEC. Profound adaptive changes to the expression of these receptors occur in response to diet and weight loss induced by RYGB or calorie restriction. (Peiris M, et al. 2018. *Nutrients.* 10(10), 1529)

Du Toit et al. studied the effect of GPR84 deletion on obesity and diabetes development in mice fed long chain fatty acid (LCFA) or medium chain fatty acid rich (MCFA) diets and found no effect on body weight or glucose tolerance in mice fed either a high MCFA or LCFA diet. GPR84 may influence lipid metabolism, as GPR84 KO mice had smaller livers and increased myocar-dial triglyceride accumulation when fed LCFA diets, and increased liver triglyceride accumulation in responses to increased dietary MCFAs. (Du Toit et al. 2018 *Eur. J. Nutr.* 57(5), 1737-1746)

A review by Hara et al. indicated that GPR84 and other free fatty acid receptors (FFARs) primarily involved in energy metabolism are considered as key therapeutic targets in the pathology of obesity and type 2 diabetes. (Hara et al. 2014. *Biochim. Biophys. Acta.* 1841(9), 1292-300)

Nagasaki et al. conducted studies in mice that showed a high-fat diet up-regulated GPR84 expression in fat pads. These results suggest that GPR84 emerges in adipocytes in response to TNFα from infiltrating macrophages and exacerbates the vicious cycle between adiposity and diabesity. (Nagasaki H. et al. 2012. *FEBS Lett.* 586(4), 368-72)

Fibrosis is a process that can be triggered by chronic tissue damage because of toxic substances, viral infection, inflammation, or mechanical stress (Nanthakumar et al., 2015. *Nature Reviews Drug Discovery* 14, 693-720); and may be defined as the abnormal or excessive production and accumulation of extracellular matrix (ECM).

In particular, fibrosis is a key driver of progressive organ dysfunction in many inflammatory and metabolic diseases, including idiopathic pulmonary fibrosis (IPF), advanced liver disease (e.g. non-alcoholic steatohepatitis (NASH)) and advanced kidney disease. These conditions remain poorly treated despite advances in the understanding of the disease mechanism and, more recently, an increase in the number of clinical trials reflecting the need to identify new treatments, particularly in IPF (Nanthakumar et al., 2015).

Non-alcoholic fatty liver disease (NAFLD) is initially characterized by pure steatosis with progression to non-alcoholic steatohepatitis (NASH), mainly caused by excess energy intake and physical inactivity apart from genetic defects, and closely associated with obesity, insulin resistance, and other related metabolic complications. (Neuschwander-Tetri B A and Caldwell S H, 2003, *Hepatology* 37, 1202-1219). If untreated, NASH leads to lethal liver failure.

The mechanisms that promote the progression from NAFLD to NASH and end-stage liver diseases are complex and may be triggered by an acute inflammatory insult and oxidative stress. (Day and James 1998, *Hepatology* 27, 1463-1466).

GPR84 (also known as EX33) has been isolated and characterized from human B cells (Wittenberger et al. 2001, *J Mol. Biol.* 307, 799-813) and also using a degenerate primer reverse transcriptase-polymerase chain reaction (RT-PCR) approach (Yousefi et al., 2001). It remained an orphan GPCR until the identification of medium-chain Free Fatty Acids (FFAs) with carbon chain lengths of 9-14 as ligands for this receptor (Wang et al., 2006).

GPR84 is activated by medium-chain FFAs, such as capric acid (Cl 0:0), undecanoic acid (Cl 1:0) and lauric acid (12:0) which amplify lipopolysaccharide stimulated production of pro-inflammatory cytokines/chemokines (TNFα, IL-6, IL-8, CCL2 and others), and is highly expressed in neutrophils and monocytes (macrophages) (Miyamoto et al. 2016, *Int. J. Mol. Sci.* 17(4) 450).

In contrast, GPR84-ligand mediated chemotaxis of neutrophils and monocytes/macrophages is inhibited by GPR84 antagonists (Suzuki M et al. 2013. *J. Biol. Chem.* 288, 10684-10691.).

Although the recruitment of monocytes/macrophages to livers may appear to occur concomitantly with fibrogenesis in patients with chronic liver diseases (Marra et al 1998. *Am. J. Pathol.* 152, 423-430; Zimmermann et al. 2010. *PLOS ONE* 5, e1 1049), this has not resulted in novel therapies.

No approved drug for the treatment of NASH is available at present, and consequently liver transplant remains the last option for end stage disease status. In the case of IPF for example, only two drugs have been approved despite their undesirable side effects (Brunnemer et al. 2018. *Respiration* 95, 301-309; Lancaster et al., 2017, *Eur. Respir. Rev.* 26, 170057; Richeldi et al., 2014, *N. Engl. J. Med.* 370, 2071-2082), and therefore there is clear need for improved therapies (Raghu, 2015, *Am J Respir Crit Care Med* 191(3) 252-4).

Potent and selective GPR84 inhibitor GLPG1205 at once-daily doses of 3 and 10 mg/kg, reduced disease activity index score and neutrophil infiltration in a mouse dextran sodium sulfate-induced chronic inflammatory bowel disease model, with efficacy similar to positive-control compound sulfasalazine. (Labéguére F, et al. 2020. *J Med Chem.* 63(22), 13526-13545)

A study by Nguyen et al. showed that PBI-4050 (a GPR84 antagonist/GPR40 agonist) reduces pulmonary hypertension, lung fibrosis, and right ventricular dysfunction in heart failure. This points to GPR84 antagonists being a novel promising therapy for targeting lung remodeling in group II pulmonary hypertension (Nguyen et al. 2020. *Cardiovasc Res.* 116(1), 171-182).

A study by Gagnon et al. showed that GPR40 and GPR84 may represent promising molecular targets in fibrosis pathways. Administering PBI-4050, an antagonist of GPR84 as well as an agonist of GPR40, significantly attenuated fibrosis in many injury contexts, as evidenced by the antifibrotic activity observed in kidney, liver, heart, lung, pancreas, and skin fibrosis models (Gagnon et al. 2018. *Am J Pathol.* 188(5)).

Studies have also linked GPR84 to acute lung injury and/or inflammation.

A review by Alavi et al. summarized studies on GPR17, GPR30, GPR37, GPR40, GPR50, GPR54, GPR56, GPR65, GPR68, GPR75, GPR84, GPR97, GPR109, GPR124, and GPR126 that reported considerable effects in the prevention and/or treatment of multiple sclerosis (MS) in preclinical studies (Alavi et al. 2019. *Life Sci.* 224, 33-40).

GPR84 expression in several murine tissues is enhanced under inflammatory stimuli, such as in endotoxemia, hyperglycemia and hypercholesterolemia. These stimuli also increase GPR84 expression in macrophages, while a selective GPR84 receptor agonist (6-OAU) triggered enhanced secretion of pro-inflammatory cytokines and phagocytosis in macrophages (Recio et al. 2018. *Front. Immunol.* 9, 1419). The results reveal that GPR84 functions as an enhancer of inflammatory signaling in macrophages once inflammation is established and that molecules that antagonize the GPR84 receptor may be potential therapeutic tools in inflammatory and metabolic diseases.

Discovery of DL-175, a potent and selective structurally novel molecule which leads to distinct functional effects in macrophages, compared to other GPR84 ligands (Lucy et al. 2019. *ACS Chem. Biol.* 14(9), 2055-2064). This study confirms GPR84 agonism leads to enhanced chemotaxis and/or phagocytosis in macrophages (aka macrophage activation)

GPR84 was among a few pro-inflammatory neutrophil-associated genes highly enriched in the analysis of RNA-seq data sets from BALF cells from COVID-19 patients (Didangelos, A. 2020. *mSphere.* 5(3), e00367-20).

In acute lung inflammation models, LPS-induced a switch of alveolar macrophages from $CD11^{lo}$ to more inflamed $CD11^{hi}$ status, worsening the lung injury process (Yin et al. 2020. *Mucosal Immunol.* 13(6), 892-907). GPR84 was highly expressed in diseased lung tissues and involved in cytokine release, phagocytosis, and the status switch of alveolar macrophages. GPR84 may represent a potential therapeutic target for acute respiratory distress syndrome.

Köse et al. prepared the first GPR84 agonist radioligand (tritiated) for studying the binding affinities of receptor ligands. They note that GPR84 was found to be involved in inflammatory processes relevant to gastroesophageal reflux disease, inflammatory bowel disease, multiple sclerosis, neuropathic pain, and Alzheimer's disease. Moreover, GPR84 has been linked to obesity and diabetes. Preliminary evidence indicates that GPR84 might be associated with leukemogenesis, osteoclastogenesis, as well as organ fibrosis, a pathological outcome of many inflammatory and metabolic diseases. (Köse M, et al. 2020. *J. Med. Chem.* 63(5), 2391-2410).

A global analysis of glycoproteins by Müller et al. identified markers of endotoxin tolerant monocytes and GPR84 as a modulator of TNFα expression. (Müller M M, et al. 2017 *Sci Rep.* 7(1), 838).

A study by Venkataraman et al. demonstrated that GPR84 regulates IL-4 production by T lymphocytes in response to CD3 crosslinking revealing a novel role for GPR84 in regulating early IL-4 gene expression in activated T cells (Venkataraman C, et al. 2005. *Immunol Lett.* 101(2), 144-53).

Additionally, GPR84 has been linked to neuropathic pain and/or neuropathy.

Gao et al. have shown that DOK3 is involved in microglial cell activation in neuropathic pain by interacting with GPR84, uncovering a physical association between DOK3 and GPR84 in the induction of inflammatory responses. They hypothesize that targeting the adaptor protein DOK3 may open new avenues for pharmaceutical approaches to the alleviation of neuropathic pain in the spinal cord (Gao W S, et al. 2020. *Aging* (Albany NY). 12.).

Studies by Kozela et al. on behavioral effects of CBD in a pharmacological model of schizophrenia-like cognitive deficits induced by repeated ketamine (KET) administration demonstrated that CBD reversed transcriptional changes induced by KET including the Gpr84 gene (Kozela E, et al. 2020. *Mol Neurobiol*. 57(3), 1733-1747).

A study by Wei et al. demonstrated that agonists for G-protein-coupled receptor 84 (GPR84) alter cellular morphology and motility but do not induce pro-inflammatory responses in microglia. The study suggests that micro-glial GPR84 could be a therapeutic target in microglia-associated diseases such as multiple sclerosis and Alzheimer's disease (Wei L, et al. 2017. *J Neuroinflammation*. 14(1), 198).

Nicol et al. studied the role of GPR84 in experimental neuropathic pain and demonstrated that GPR84 is a proinflammatory receptor that contributes to nociceptive signaling via the modulation of macrophages, whereas in its absence the response of these cells to an inflammatory insult is impaired (Nicol L S, et al. 2015. *J Neurosci*. 35(23), 8959-69).

Mededdu et al. found that expression of Gpr84 was induced in both microglia and astrocytes and was upregulated in the CNS following virus infection indicating that Gpr 84 expression may be a useful measurement of glial activation during insult or injury to the CNS (Madeddu S, et al. 2015. *PLoS One*. 10(7), e0127336).

Bouchard et al. found that mice suffering from endotoxemia express GPR84 in microglia in a strong and sustained manner, making GPR84 a sensitive marker of microglial activation, which may play an important regulatory role in neuroimmunological processes, acting downstream to the effects of proinflammatory mediators (Bouchard C, et al. 2007. *Glia*. 55(8), 790-800).

GPR84 has also been linked to inflammatory bowel disease as a potential disease target.

Planell et al. identified GPR84 as a transcriptional Blood Biomarker useful as a Non-invasive Surrogate Marker of Mucosal Healing and Endoscopic Response in Ulcerative Colitis. At 14 weeks of treatment, response to anti-TNF therapy induced alterations in blood HP, CD177, GPR84, and S100A12 transcripts that correlated with changes in endoscopic activity (Planell N, et al. 2017. *J Crohns Colitis*. 11(11), 1335-1346).

Studies by Abdel-Aziz et al. found that GPR84 and TREM-1 signaling contribute to the pathogenesis of reflux esophagitis, indicating that GPR84 plays an important role in the pathogenesis of Gastro-esophageal reflux disease (GERD), (Abdel-Aziz, et al. 2016 *Mol Med*. 21(1), 1011-1024).

Dietrich et al. demonstrated that GPR84 sustains aberrant β-catenin signaling in leukemic stem cells (LSCs) for maintenance of stem cell-derived mixed-lineage leukemia (MLL) leukemogenesis, a previously unrecognized role of GPR84 in maintaining fully developed acute myeloid leukemia (AML) by sustaining aberrant β-catenin signaling in LSCs, and suggesting that targeting the oncogenic GPR84/0-catenin signaling axis may represent a novel therapeutic strategy for AML (Dietrich P A, et al. 2014. *Blood*. 124(22), 3284-94).

By mining the Cancer Genome Atlas (TCGA) Database for tumor microenvironment-related genes of prognostic value in hepatocellular carcinoma (HCC), Deng et al. identified GPR84 among a set of differentially expressed genes (DEGs) useful as a candidate biomarker for HCC prognosis (Deng Z, et al. 2019. *Biomed Res Int*. 2019, 2408348).

GeneChip expression profiling by Wang et al. revealed the alterations of energy metabolism related genes including GPR84 in osteocytes under large gradient high magnetic fields. The identification of sensitive genes such as GPR84 to special environments may provide some potential targets for preventing and treating bone loss or osteoporosis (Wang Y, et al. 2015. *PLoS One*. 10(1), e0116359).

Studies by Park et al. demonstrated that GPR84 controls osteoclastogenesis through inhibition of NF-κB and MAPK signaling pathways, revealing that GPR84 functions as a negative regulator of osteoclastogenesis, suggesting that it may be a potential therapeutic target for osteoclast-mediated bone-destructive diseases (Park J W, et al. 2018. *J Cell Physiol*. 233(2), 1481-1489).

Whole-genome transcription and DNA methylation analysis of peripheral blood mononuclear cells by Zhu et al. identified aberrant gene regulation pathways in systemic lupus erythematosus. The gene expressions for MX1, GPR84, and E2F2 were increased in systemic lupus erythematosus (SLE) lupus nephritis (LN)+ as compared to SLE LN-patients (Zhu H, et al. 2016. *Arthritis Res Ther*. 18, 162).

In one embodiment, the subject matter disclosed herein is directed to a method of inhibiting GPR84, the method comprising contacting GPR84 with an effective amount of a compound of the invention or a pharmaceutical composition described herein.

In certain embodiments, the subject matter disclosed herein is directed to a method for modulating an immune response in a subject in need thereof, wherein the method comprises administering to the subject an effective amount of a compound of the invention or a pharmaceutical composition described herein.

The presently disclosed compounds bind directly to GPR84 and inhibit its signaling activity. In some embodiments, the presently disclosed compounds reduce, inhibit, or otherwise diminish the GPR84-mediated inflammatory response.

The presently disclosed compounds may or may not be a specific GPR84 antagonist. A specific GPR84 antagonist reduces the biological activity of GPR84 by an amount that is statistically greater than the inhibitory effect of the antagonist on any other protein (e.g., other GPCRs). In certain embodiments, the presently disclosed compounds specifically inhibit the signaling activity of GPR84. In some of these embodiments, the $IC_{50}$ of the GPR84 antagonist for GPR84 is about 90%, 80%, 70%, 60%, 50%, 40%, 30%, 20%, 10%, 0.1%, 0.01%, 0.001%, or less of the $IC_{50}$ of the GPR84 antagonist for another GPCR activated by free fatty acids (FFA) or other type of GPCR (e.g., Class A GPCR).

The presently disclosed compounds can be used in a method for inhibiting GPR84. Such methods comprise contacting GPR84 with an effective amount of a presently disclosed compound. By "contact" is intended bringing the compound within close enough proximity to an isolated GPR84 GPCR or a cell expressing GPR84 (e.g., T cell or B cell) such that the compound is able to bind to and inhibit the activity of GPR84. The compound can be contacted with GPR84 in vitro or in vivo via administration of the compound to a subject.

Any method known in the art to measure the signaling activity of GPR84 may be used to determine if GPR84 has been inhibited, including in vitro assays or the measurement of a downstream biological effect of GPR84 signaling activity.

The presently disclosed compounds can be used to treat a GPR84-dependent disorder. As used herein, a "GPR84-dependent disorder" is a pathological condition in which GPR84 activity is necessary for the genesis or maintenance of the pathological condition. In some embodiments, the GPR84-dependent disorder is an inflammatory condition.

The presently disclosed compounds also find use in modulating an immune response in a subject in need thereof. Such methods comprise administering an effective amount of a compound of the invention.

As used herein, "modulating an immune response" refers to modulation of any immunogenic response to an antigen.

In another aspect of the invention, this invention provides novel compounds of the invention for use in therapy.

In a further aspect of the invention, this invention provides a method of treating a mammal susceptible to or afflicted with a condition from among those listed herein, and particularly, such condition as may be associated with aberrant activity of GPR84 and/or aberrant GPR84 expression and/or aberrant GPR84 distribution, for example inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions, which method comprises administering a therapeutically effective amount of a compound of the invention, or one or more of the pharmaceutical compositions herein described.

In a further aspect, the present invention provides a compound of the invention for use in the treatment or prevention of a condition selected from those listed herein, particularly such conditions as may be associated with aberrant activity of GPR84 and/or aberrant GPR84 expression and/or aberrant GPR84 distribution expression such as inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions.

In additional aspects, this invention provides methods for synthesizing a compound of the invention, with representative synthetic protocols and pathways disclosed herein.

Accordingly, it is a principal object of this invention to provide a compound of the invention, which can modify the activity of GPR84 and thus prevent or treat any conditions that may be causally related thereto.

It is further an object of this invention to provide a compound of the invention that can treat or alleviate conditions or diseases or symptoms of same, such as inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions, that may be causally related to the activity and/or expression and/or distribution of GPR84.

A still further object of this invention is to provide pharmaceutical compositions that may be used in the treatment or prevention of a variety of disease states, including the diseases associated with aberrant activity of GPR84 and/or aberrant GPR84 expression and/or aberrant GPR84 distribution such as inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions.

Other objects and advantages will become apparent to those skilled in the art from a consideration of the ensuing detailed description.

The present disclosure provides methods of modulating (e.g., inhibiting) GPR84 activity, said method comprising administering to a patient a compound provided herein, or a pharmaceutically acceptable salt thereof.

In one aspect, provided herein is a method for treating of cancer in a subject in need thereof comprising administering to the subject an effective amount of a compound of the invention or a pharmaceutically acceptable salt, prodrug, metabolite, or derivative thereof.

In the methods described herein, a compound of the invention or a pharmaceutical composition thereof is administered to a subject that has cancer.

In certain embodiments, the subject matter disclosed herein is directed to a method for treating a GPR84-dependent disorder, the method comprising administering to a subject in need thereof an effective amount of a compound of the invention or a pharmaceutical composition described herein. In certain aspects of this embodiment, the GPR84-dependent disorder is a cancer.

In some embodiments, the subject matter disclosed herein is directed to a method for treatment of chronic viral infections. In some embodiments, the subject matter disclosed herein is directed to the use of an GPR84 inhibitor as an adjuvant treatment for increasing the efficacy of vaccination.

In some embodiments, the invention provides a pharmaceutical composition comprising an effective amount of a compound of the invention, or a pharmaceutically acceptable salt, hydrate, solvate, or prodrug thereof, and a pharmaceutically acceptable carrier.

In certain aspects, the invention provides a method of treating cell proliferation disorders, including cancers.

In one aspect, the invention provides a method of treating a cell proliferation disorder in a subject, comprising administering a therapeutically effective amount of a compound of the invention, or a pharmaceutically acceptable salt, hydrate, solvate, or prodrug thereof, to the subject.

In certain embodiments, the cell proliferation disorder is cancer.

Examples of cancers that are treatable using the compounds of the present disclosure include, but are not limited to, chronic or acute leukemias including acute myeloid leukemia, chronic myeloid leukemia, acute lymphoblastic leukemia, chronic lymphocytic leukemia, solid tumors of childhood, lymphocytic lymphoma, and combinations of said cancers.

In some embodiments, cancers that are treatable using the compounds of the present disclosure include, but are not limited to, hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, and combinations of said cancers.

In certain embodiments, the cancer is leukemia. In another embodiment the cancer is selected from the group consisting of acute myeloid leukemia and chronic myelogenous leukemia.

In certain embodiments, the cancer is selected from leukemia and cancers of the blood. In particular embodiments, the cancer is present in an adult patient; in additional embodiments, the cancer is present in a pediatric patient. In particular embodiments, the cancer is AIDS-related.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CMIL), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In some embodiments, diseases and indications that are treatable using the compounds of the present disclosure include, but are not limited to hematological cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, Waldenstrom's Macroglobulinemia, hairy cell lymphoma, chronic myelogenic lymphoma and Burkitt's lymphoma.

As used herein the term 'inflammatory condition(s)' refers to the group of conditions including inflammatory bowel diseases (IBD) (e.g., Crohn's disease, ulcerative colitis), rheumatoid arthritis, vasculitis, lung diseases (e.g., chronic obstructive pulmonary disease (COPD) and lung interstitial diseases (e.g., idiopathic pulmonary fibrosis (IPF))), psoriasis, gout, allergic airway disease (e.g., asthma, rhinitis), and endotoxin-driven disease states (e.g., complications after bypass surgery or chronic endotoxin states contributing to e.g., chronic cardiac failure). Particularly the term refers to rheumatoid arthritis, allergic airway disease (e.g., asthma) and inflammatory bowel diseases. In a further particular aspect, the term refers to uveitis, periodontitis, esophagitis, neutrophilic dermatoses (e.g., pyoderma gangrenosum, Sweet's syndrome), severe asthma, and skin and/or colon inflammation caused by oncology treatments aimed at activating the immune response.

As used herein the term 'pain' refers to diseases or disorders characterized by unpleasant feeling often caused by intense or damaging stimuli, and include but is not limited to nociceptive pain, inflammatory pain (associated with tissue damage and inflammatory cell infiltration) and neuropathic or dysfunctional pain (caused by damage to or abnormal function of the nervous system), and/or pain associated or caused by the conditions mentioned herein. Pain can be acute or chronic.

As used herein the term 'neuroinflammatory conditions' refers to diseases or disorders characterized by abrupt neurologic deficits associated with inflammation, demyelination, and axonal damage, and includes but is not limited to conditions such as Guillain-Barre syndrome (GBS), multiple sclerosis, axonal degeneration, and autoimmune encephalomyelitis.

As used herein the term 'neurodegenerative conditions' refers to diseases or disorders characterized by progressive loss of structure or function of neurons, including death of neurons, and includes but is not limited to conditions such as dementia, degenerative dementia, senile dementia, vascular dementia, dementia associated with intracranial space occupying lesions, mild cognitive impairment associated with ageing, age associated memory impairment, and/or peripheral neuropathies. In particular, the term refers to retinopathies, glaucoma, macular degeneration, stroke, cerebral ischemia, traumatic brain injury, Alzheimer's disease, Pick's disease, Huntingdon's chorea, Parkinson's disease, Creutzfeldt-Jakob disease, Amyotrophic lateral sclerosis (ALS), motor neurone disease (MND), Spinocerebellar ataxia (SCA), and/or Spinal muscular atrophy (SMA). More particularly, the term refers to retinopathies, glaucoma, macular degeneration, stroke, cerebral ischemia, traumatic brain injury, Alzheimer's disease, Pick's disease, Huntingdon's chorea, Parkinson's disease, Creutzfeldt-Jakob disease, and/or Amyotrophic lateral sclerosis (ALS).

As used herein, the term 'infectious diseases' refers to bacterial infectious diseases and includes but is not limited to conditions such as sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, or enterobacteria species.

As used herein the term 'autoimmune disease(s)' refers to the group of diseases including obstructive airways disease (including conditions such as COPD (chronic obstructive pulmonary disease)), psoriasis, asthma (e.g., intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), multiple sclerosis, type I diabetes mellitus and complications associated therewith, atopic eczema (atopic dermatitis), contact dermatitis and further eczematous dermatitis, vasculitis, inflammatory bowel disease (e.g., Crohn's disease and ulcerative colitis), atherosclerosis and amyotrophic lateral sclerosis. Particularly the term refers to COPD, asthma, psoriasis, systemic lupus erythematosus, type I diabetes mellitus, vasculitis and inflammatory bowel disease.

As used herein the term 'endocrine and/or metabolic disease(s)' refers to the group of conditions involving the body's over- or under-production of certain hormones, while metabolic disorders affect the body's ability to process certain nutrients and vitamins. Endocrine disorders include hypothyroidism, congenital adrenal hyperplasia, diseases of the parathyroid gland, diabetes mellitus, diseases of the adrenal glands (including Cushing's syndrome and Addison's disease), and ovarian dysfunction (including polycystic ovary syndrome), among others. Some examples of metabolic disorders include cystic fibrosis, phenylketonuria (PKU), diabetes, hyperlipidemia, gout, and rickets. A particular example of metabolic disorders is obesity.

As used herein the term "cardiovascular diseases" refers to diseases affecting the heart or blood vessels or both. In particular, cardiovascular disease includes arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; shock; vasoconstriction (including that associated with migraines);

vascular abnormality, inflammation, insufficiency limited to a single organ or tissue. Particularly, the term refers to atherosclerosis.

As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML) and acute lymphoblastic leukemia (ALL).

As used herein, the term 'diseases involving impairment of immune cell functions' includes conditions with symptoms such as recurrent and drawn out viral and bacterial infections, and slow recovery. Other invisible symptoms may be the inability to kill off parasites, yeasts and bacterial pathogens in the intestines or throughout the body.

As used herein the term 'fibrotic diseases' refers to diseases characterized by excessive scarring due to excessive production, deposition, and contraction of extracellular matrix, and are that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract. In particular, the term fibrotic diseases refers to idiopathic pulmonary fibrosis (IPF); cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage diseases, familial interstitial lung disease); radiation induced fibrosis; chronic obstructive pulmonary disease; scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; diabetic nephropathy, focal segmental glomerular sclerosis; IgA nephropathy; hypertension; Alport; gut fibrosis; liver fibrosis; cirrhosis; alcohol induced liver fibrosis; toxic/drug induced liver fibrosis; hemochromatosis; alcoholic steato hepatitis (ASH), nonalcoholic steatohepatitis (NASH), nonalcoholic fatty liver disease (NAFLD); cholestasis, biliary duct injury; primary sclerosing cholangitis (PSC), primary biliary cirrhosis (PBC); infection induced liver fibrosis; viral induced liver fibrosis; and autoimmune hepatitis; corneal scarring; hypertrophic scarring; Dupuytren disease, keloids, cutaneous fibrosis; cutaneous scleroderma; systemic sclerosis, spinal cord injury/fibrosis; myelofibrosis; Duchenne muscular dystrophy (DMD) associated musculoskeletal fibrosis, vascular restenosis; atherosclerosis; arteriosclerosis; Wegener's granulomatosis; Peyronie's disease, or chronic lymphocytic. More particularly, the term "fibrotic diseases" refers to idiopathic pulmonary fibrosis (IPF), Dupuytren disease, nonalcoholic steatohepatitis (NASH), nonalcoholic fatty liver disease (NAFLD), Alcoholic steatohepatitis, (ASH), portal hypertension, systemic sclerosis, renal fibrosis, and cutaneous fibrosis. Most particularly, the term "fibrotic diseases" refers to nonalcoholic steatohepatitis (NASH), and/or nonalcoholic fatty liver disease (NAFLD). Alternatively, most particularly, the term "fibrotic diseases" refers to IPF.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

The presently disclosed compounds may be administered in any suitable manner known in the art. In some embodiments, the compound of the invention or a pharmaceutically acceptable salt, prodrug, metabolite, or derivative thereof is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the GPR84 antagonist is administered continuously. In other embodiments, the GPR84 antagonist is administered intermittently. Moreover, treatment of a subject with an effective amount of a GPR84 antagonist can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of the invention or a pharmaceutically acceptable salt, prodrug, metabolite, or derivative thereof used for treatment may increase or decrease over the course of a particular treatment. Changes in dosage may result and become apparent from the results of diagnostic assays.

In some embodiments, the GPR84 antagonist is administered to the subject at a dose of between about 0.001 µg/kg and about 1000 mg/kg, including but not limited to about 0.001 µg/kg, 0.01 µg/kg, 0.05 µg/kg, 0.1 µg/kg, 0.5 µg/kg, 1 µg/kg, 10 µg/kg, 25 µg/kg, 50 µg/kg, 100 µg/kg, 250 µg/kg, 500 µg/kg, 1 mg/kg, 5 mg/kg, 10 mg/kg, 25 mg/kg, 50 mg/kg, 100 mg/kg, and 200 mg/kg.

In the methods described herein, the method can further comprise administering a chemotherapeutic agent to the subject. In certain aspects of this embodiment, the chemotherapeutic agent is administered to the subject simultaneously with the compound or the composition. In certain aspects of this embodiment, the chemotherapeutic agent is administered to the subject prior to administration of the compound or the composition. In certain aspects of this embodiment, the chemotherapeutic agent is administered to the subject after administration of the compound or the composition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "subject" refers to animals such as mammals, including, but not limited to, primates (e.g., humans), cows, sheep, goats, horses, dogs, cats, rabbits, rats, mice and the like. In certain embodiments, the subject is a human.

In one embodiment, the present invention provides compounds of the invention, or pharmaceutical compositions comprising a compound of the invention, for use in the prophylaxis and/or treatment of one or more fibrotic diseases. In a particular embodiment, the fibrotic disease is NASH and/or NAFLD. In a most particular embodiment, the fibrotic disease is NASH. In another most particular embodiment, the fibrotic disease is idiopathic pulmonary fibrosis (IPF).

In another embodiment, the present invention provides compounds of the invention, or pharmaceutical compositions comprising a compound of the invention for use in the manufacture of a medicament for use in the prophylaxis and/or treatment of one or more fibrotic diseases. In a particular embodiment, the fibrotic disease is NASH and/or NAFLD. In a most particular embodiment, the fibrotic disease is NASH. In another most particular embodiment, the fibrotic disease is idiopathic pulmonary fibrosis (IPF).

In additional method of treatment aspects, this invention provides methods of prophylaxis and/or treatment of a mammal afflicted with fibrotic diseases, which methods comprise the administration of an effective amount of a compound of the invention or one or more of the pharmaceutical compositions herein described for the treatment or prophylaxis of said condition. In a particular embodiment, the fibrotic disease is NASH and/or NAFLD. In a most particular embodiment, the fibrotic disease is NASH. In another most particular embodiment, the fibrotic disease is idiopathic pulmonary fibrosis (IPF).

In one embodiment, the present invention provides pharmaceutical compositions comprising a compound of the invention, and another therapeutic agent. In a particular embodiment, the other therapeutic agent is a fibrotic disease treatment agent. In a particular embodiment, the fibrotic disease is NASH and/or NAFLD. In a most particular embodiment, the fibrotic disease is NASH. In another most particular embodiment, the fibrotic disease is idiopathic pulmonary fibrosis (IPF).

In one embodiment, the present invention provides compounds of the invention, or pharmaceutical compositions comprising a compound of the invention, for use in the prophylaxis and/or treatment of a subject presenting a NAS score of at least 3, at least 4, at least 5, at least 6 or at least 7.

In another embodiment, the present invention provides compounds of the invention, or pharmaceutical compositions comprising a compound of the invention for use in the manufacture of a medicament for use in the prophylaxis and/or treatment of a subject presenting a NAS score >5.

In additional method of treatment aspects, this invention provides methods of prophylaxis and/or treatment of a mammal presenting a NAS score >5, which methods comprise the administration of an effective amount of a compound of the invention or one or more of the pharmaceutical compositions herein described for the treatment or prophylaxis of said fibrotic diseases, in particular NASH, and/or NAFLD, more particularly NASH.

In further method of treatment embodiments, the methods of prophylaxis and/or treatment of a mammal comprises measuring the forced vital capacity (FVC) in the subject, wherein the FVC does not decrease following treatment. In a particular embodiment, FVC does not decrease over a period of 12, 16, 20 or 26 weeks of treatment. In another embodiment, the method comprises measuring the FVC in the subject, wherein the FVC increases by at least 1 mL, at least 2 mL, at least 3 mL, at least 4 mL, at least 5 mL, at least 6 mL, at least 7 mL or at least 8 mL. In a particular embodiment, the FVC increases by at least 1 mL, at least 2 mL, at least 3 mL, at least 4 mL, at least 5 mL, at least 6 mL, at least 7 mL or at least 8 mL over a period of 12, 16, 20 or 26 weeks of treatment.

In one embodiment, the method comprises measuring the airway volume wherein said airway volume decrease is no more than 5 mL/L, no more than 4 mL/1, or no more than 3 mL/L. In a particular embodiment the airway volume decrease is no more than 5 mL/L, no more than 4 mL/1, or no more than 3 mL/L after 12, 16, 20 or 26 weeks of treatment.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

A compound of the invention may be used as a therapeutic agent for the treatment of conditions in mammals that are causally related or attributable to aberrant activity of GPR84 and/or aberrant GPR84 expression and/or aberrant GPR84 distribution.

Accordingly, a compound and pharmaceutical compositions of the invention find use as therapeutics for the prophylaxis and/or treatment of inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions, in mammals including humans.

Accordingly, in one aspect, the present invention provides the compound of the invention, or a pharmaceutical composition comprising the compound of the invention for use as a medicament.

In another aspect, the present invention provides the compound of the invention, or a pharmaceutical composition comprising the compound of the invention for use in the manufacture of a medicament.

In yet another aspect, the present invention provides a method of treating a mammal having, or at risk of having a disease disclosed herein. In a particular aspect, the present invention provides a method of treating a mammal having, or at risk of having inflammatory conditions, pain, neuroinflammatory conditions, neurodegenerative conditions, infectious diseases, autoimmune diseases, endocrine and/or metabolic diseases, cardiovascular diseases, leukemia, and/or diseases involving impairment of immune cell functions, in mammals including humans, said method comprising administering an effective amount of a compound of the invention, or one or more of the pharmaceutical compositions herein described.

In one aspect, the present invention provides the compound of the invention, or a pharmaceutical composition comprising the compound of the invention for use in the prophylaxis and/or treatment of inflammatory conditions. In a specific embodiment, the inflammatory condition is selected from inflammatory bowel disease (IBD), rheumatoid arthritis, vasculitis, chronic obstructive pulmonary disease (COPD), and idiopathic pulmonary fibrosis (IPF). In another specific embodiment, the inflammatory condition is selected from uveitis, periodontitis, esophagitis, neutrophilic dermatoses (e.g., pyoderma gangrenosum, Sweet's syndrome), severe asthma, and skin and/or colon inflammation caused by oncology treatments aimed at activating the immune response. In another aspect, the present invention provides the compound of the invention, or a pharmaceutical composition comprising the compound of the invention for use in the manufacture of a medicament for the prophylaxis and/or treatment of inflammatory conditions. In a specific embodiment, the inflammatory condition is selected from inflammatory bowel disease (IBD), rheumatoid arthritis, vasculitis, chronic obstructive pulmonary disease (COPD), and idiopathic pulmonary fibrosis (IPF). In another specific embodiment, the inflammatory condition is selected from uveitis, periodontitis, esophagitis, neutrophilic dermatoses (e.g., pyoderma gangrenosum, Sweet's syndrome), severe asthma, and skin and/or colon inflammation caused by oncology treatments aimed at activating the immune response.

In another aspect, the present invention provides a method of treating a mammal having, or at risk of having a disease selected from inflammatory conditions (for example inflammatory bowel diseases (IBD), rheumatoid arthritis, vasculitis), lung diseases (e.g., chronic obstructive pulmonary disease (COPD) and lung interstitial diseases (e.g., idiopathic pulmonary fibrosis (IPF))), neuroinflammatory conditions, infectious diseases, autoimmune diseases, endocrine and/or metabolic diseases, and/or diseases involving impairment of immune cell functions, which method comprises administering an effective amount of a compound of the invention, or one or more of the pharmaceutical compositions herein described.

In additional method of treatment aspects, this invention provides methods of treatment and/or prophylaxis of a mammal susceptible to or afflicted with inflammatory conditions, which method comprises administering an effective amount of a compound of the invention, or one or more of the pharmaceutical compositions herein described. In a specific embodiment, the inflammatory condition is selected from inflammatory bowel disease (IBD), rheumatoid arthritis, vasculitis, chronic obstructive pulmonary disease (COPD), and idiopathic pulmonary fibrosis (IPF). In another specific embodiment, the inflammatory condition is selected from uveitis, periodontitis, esophagitis, neutrophilic dermatoses (e.g., pyoderma gangrenosum, Sweet's syndrome), severe asthma, and skin and/or colon inflammation caused by oncology treatments aimed at activating the immune response.

In one aspect, the present invention provides the compound of the invention, or a pharmaceutical composition comprising the compound of the invention for use in the prophylaxis and/or treatment of pain. In a specific embodiment, the pain is acute or chronic and is selected from nociceptive pain, inflammatory pain, and neuropathic or dysfunctional pain.

In another aspect, the present invention provides the compound of the invention, or a pharmaceutical composition comprising the compound of the invention for use in the manufacture of a medicament for the prophylaxis and/or treatment of pain. In a specific embodiment, the pain is acute or chronic and is selected from nociceptive pain, inflammatory pain, and neuropathic or dysfunctional pain.

In additional method of treatment aspects, this invention provides methods of treatment and/or prophylaxis of a mammal susceptible to or afflicted with pain, which method comprises administering an effective amount of a compound of the invention, or one or more of the pharmaceutical compositions herein described. In a specific embodiment, the pain is acute or chronic and is selected from nociceptive pain, inflammatory pain, and neuropathic or dysfunctional pain.

In one aspect, the present invention provides a compound of the invention, or a pharmaceutical composition comprising the compound of the invention for use in the prophylaxis and/or treatment of neuroinflammatory conditions, Guillain-Barre syndrome (GBS), multiple sclerosis, axonal degeneration, autoimmune encephalomyelitis.

In another aspect, the present invention provides a compound of the invention, or a pharmaceutical composition comprising the compound of the invention for use in the manufacture of a medicament for the prophylaxis and/or treatment of neuroinflammatory conditions, Guillain-Barre syndrome (GBS), multiple sclerosis, axonal degeneration, autoimmune encephalomyelitis.

In additional method of treatment aspects, this invention provides methods of treatment and/or prophylaxis of a mammal susceptible to or afflicted with neuroinflammatory conditions, Guillain-Barré syndrome (GBS), multiple sclerosis, axonal degeneration, autoimmune encephalomyelitis, which method comprises administering an effective amount of a compound of the invention, or one or more of the pharmaceutical compositions herein described.

In one aspect, the present invention provides a compound of the invention, or a pharmaceutical composition comprising the compound of the invention for use in the prophylaxis and/or treatment of infectious disease(s). In a specific embodiment, the infectious disease(s) is selected from sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, enterobacteria species.

In another aspect, the present invention provides a compound of the invention, or a pharmaceutical composition comprising the compound of the invention for use in the manufacture of a medicament for the prophylaxis and/or treatment of infectious disease(s). In a specific embodiment, the infectious disease(s) is selected from sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, enterobacteria species.

In additional method of treatment aspects, this invention provides methods of treatment and/or prophylaxis of a mammal susceptible to or afflicted with infectious disease(s), which method comprises administering an effective amount of a compound of the invention, or one or more of the pharmaceutical compositions herein described. In a specific embodiment, the infectious disease is selected from sepsis, septicemia, endotoxemia, systemic inflammatory response syndrome (SIRS), gastritis, enteritis, enterocolitis, tuberculosis, and other infections involving, for example, *Yersinia, Salmonella, Chlamydia, Shigella*, enterobacteria species.

In one aspect, the present invention provides the compound of the invention, or a pharmaceutical composition comprising the compound of the invention for use in the prophylaxis and/or treatment of autoimmune diseases, and/or diseases involving impairment of immune cell functions. In a specific embodiment, the autoimmune diseases and/or diseases involving impairment of immune cell functions is selected from COPD, asthma, psoriasis, systemic lupus erythematosis, type I diabetes mellitus, vasculitis and inflammatory bowel disease.

In another aspect, the present invention provides the compound of the invention, or a pharmaceutical composition comprising the compound of the invention for use in the manufacture of a medicament for the prophylaxis and/or treatment of autoimmune diseases and/or diseases involving impairment of immune cell functions. In a specific embodiment, the autoimmune diseases, and/or diseases involving impairment of immune cell functions is selected from COPD, asthma, psoriasis, systemic lupus erythematosis, type I diabetes mellitus, vasculitis and inflammatory bowel disease.

In additional method of treatment aspects, this invention provides methods of treatment and/or prophylaxis of a mammal susceptible to or afflicted with autoimmune diseases and/or diseases involving impairment of immune cell functions, which method comprises administering an effective amount of a compound of the invention, or one or more of the pharmaceutical compositions herein described. In a specific embodiment, the autoimmune diseases and/or diseases involving impairment of immune cell functions is selected from COPD, asthma, psoriasis, systemic lupus erythematosis, type I diabetes mellitus, vasculitis and inflammatory bowel disease.

In one aspect, the present invention provides the compound of the invention, or a pharmaceutical composition comprising the compound of the invention for use in the prophylaxis and/or treatment of endocrine and/or metabolic diseases. In a specific embodiment, the endocrine and/or metabolic diseases is selected from hypothyroidism, congenital adrenal hyperplasia, diseases of the parathyroid gland, diabetes mellitus, diseases of the adrenal glands (including Cushing's syndrome and Addison's disease), ovarian dysfunction (including polycystic ovary syndrome), cystic fibrosis, phenylketonuria (PKU), diabetes, hyperlipidemia, gout, and rickets.

In another aspect, the present invention provides the compound of the invention, or a pharmaceutical composition comprising the compound of the invention for use in the manufacture of a medicament for the prophylaxis and/or treatment of endocrine and/or metabolic diseases. In a specific embodiment, the endocrine and/or metabolic diseases is selected from hypothyroidism, congenital adrenal hyperplasia, diseases of the parathyroid gland, diabetes mellitus, diseases of the adrenal glands (including Cushing's syndrome and Addison's disease), ovarian dysfunction (including polycystic ovary syndrome), cystic fibrosis, phenylketonuria (PKU), diabetes, hyperlipidemia, gout, and rickets.

In additional method of treatment aspects, this invention provides methods of treatment and/or prophylaxis of a mammal susceptible to or afflicted with endocrine and/or metabolic diseases, which method comprises administering an effective amount of a compound of the invention, or one or more of the pharmaceutical compositions herein described. In a specific embodiment, the endocrine and/or metabolic diseases is selected from hypothyroidism, congenital adrenal hyperplasia, diseases of the parathyroid gland, diabetes mellitus, diseases of the adrenal glands (including Cushing's syndrome and Addison's disease), ovarian dysfunction (including polycystic ovary syndrome), cystic fibrosis, phenylketonuria (PKU), diabetes, hyperlipidemia, gout, and rickets.

As a further aspect of the invention there is provided a compound of the invention for use as a medicament especially in the treatment or prevention of the aforementioned conditions and diseases. Also provided herein is the use of the compound in the manufacture of a medicament for the treatment or prevention of one of the aforementioned conditions and diseases.

A particular regimen of the present method comprises the administration to a subject in suffering from an inflammatory condition, of an effective amount of a compound of the invention for a period of time sufficient to reduce the level of inflammation in the subject, and preferably terminate, the processes responsible for said inflammation. A special embodiment of the method comprises administering of an effective amount of a compound of the invention to a subject suffering from or susceptible to the development of inflammatory condition, for a period of time sufficient to reduce or prevent, respectively, inflammation of said patient, and preferably terminate, the processes responsible for said inflammation.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compounds that demonstrate the same or a similar therapeutic activity, and that are determined to be safe and efficacious for such combined administration. In a specific embodiment, co-administration of two (or more) agents allows for significantly lower doses of each to be used, thereby reducing the side effects seen.

In one embodiment, a compound of the invention is co-administered with another therapeutic agent for the treatment and/or prevention of an inflammatory condition; particular agents include, but are not limited to, immunoregulatory agents e.g., azathioprine, corticosteroids (e.g., prednisolone or dexamethasone), cyclophosphamide, cyclosporin A, tacrolimus, Mycophenolate Mofetil, muromonab-CD3 (OKT3, e.g., Orthocolone®), ATG, aspirin, acetaminophen, ibuprofen, naproxen, and piroxicam.

In one embodiment, a compound of the invention is co-administered with another therapeutic agent for the treatment and/or prevention of arthritis (e.g., rheumatoid arthritis); particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, and cyclosporin), and biological DMARDS (for example but without limitation Infliximab, Etanercept, Adalimumab, Rituximab, Golimumab, Certolizumab pegol, Tocilizumab, Interleukin 1 blockers and Abatacept).

In one embodiment, a compound of the invention is co-administered with another therapeutic agent for the treatment and/or prevention of autoimmune diseases; particular agents include but are not limited to: glucocorticoids, cytostatic agents (e.g., purine analogs), alkylating agents, (e.g., nitrogen mustards (cyclophosphamide), nitrosoureas, platinum compounds, and others), antimetabolites (e.g., e.g., methotrexate, azathioprine and mercaptopurine), cytotoxic antibiotics (e.g., e.g., dactinomycin anthracyclines, mitomycin C, bleomycin, and mithramycin), antibodies (e.g., anti-CD20, anti-CD25 or anti-CD3 (OTK3) monoclonal antibodies, Atgam® and Thymoglobuline®), cyclosporin, tacrolimus, rapamycin (sirolimus), interferons (e.g., IFN-β), TNF binding proteins (e.g., infliximab (Remicade®), etanercept (Enbrel®), or adalimumab (Humira®)), mycophenolate, Fingolimod, and Myriocin.

In one embodiment, a compound of the invention is co-administered with another therapeutic agent for the treatment and/or prevention of infectious diseases; particular agents include but are not limited to antibiotics. In a particular embodiment, a compound of the invention is co-administered with another therapeutic agent for the treatment and/or prevention of infections of any organ of the human body; particular agents include but are not limited to: aminoglycosides, ansamycins, carbacephem, carbapenems, cephalosporins, glycopeptides, lincosamides, macrolides, monobactams, nitrofurans, penicillins, polypeptides, quinolones, sulfonamides, tetracyclins, anti-mycobacterial agents, as well as chloramphenicol, fosfomycin, linezolid, metronidazole, mupirocin, rifamycin, thiamphenicol and tinidazole.

In one embodiment, a compound of the invention is co-administered with another therapeutic agent for the treatment and/or prevention of vasculitis, particular agents include but are not limited to steroids (for example prednisone, prednisolone), cyclophosphamide and eventually antibiotics in case of cutaneous infections (for example cephalexin).

In one embodiment, a compound of the invention is co-administered with another therapeutic agent for the treatment and/or prevention of esophagitis; particular agents include but are not limited to: anti-acids (e.g., formulations containing aluminum hydroxide, magnesium hydroxide, and/or simethicone), H2-antagonists (e.g., cimetidine, ranitidine, famotidine), proton pump inhibitors (e.g., omeprazole, esomeprazole, lansoprazole, rabeprazole, pantoprazole), and glucocorticoids (e.g., prednisone, budesonide).

In one embodiment, a compound of the invention is co-administered with another therapeutic agent for the treatment and/or prevention of IPF, particular agents include but are not limited to pirfenidone and bosentan.

In one embodiment, a compound of the invention is co-administered with another therapeutic agent for the treatment and/or prevention of asthma and/or rhinitis and/or COPD; particular agents include but are not limited to: beta2-adrenoceptor agonists (e.g., salbutamol, levalbuterol, terbutaline and bitolterol), epinephrine (inhaled or tablets), anticholinergics (e.g., ipratropium bromide), glucocorticoids (oral or inhaled) Long-acting β2-agonists (e.g., salmeterol, formoterol, bambuterol, and sustained-release oral albuterol), combinations of inhaled steroids and long-acting bronchodilators (e.g., fluticasone/salmeterol, budesonide/formoterol), leukotriene antagonists and synthesis inhibitors (e.g., montelukast, zafirlukast and zileuton), inhibitors of mediator release (e.g., cromoglycate and ketotifen), phosphodiesterase-4 inhibitors (e.g., Roflumilast), biological regulators of IgE response (e.g., omalizumab), antihistamines (e.g., ceterizine, cinnarizine, fexofenadine), and vasoconstrictors (e.g., oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g., ipratropium), systemic steroids (oral or intravenous, e.g., prednisone, prednisolone, methylprednisolone, dexamethasone, or hydrocortisone), intravenous salbutamol, non-specific beta-agonists, injected or inhaled (e.g., epinephrine, isoetharine, isoproterenol, metaproterenol), anticholinergics (IV or nebulized, e.g., glycopyrrolate, atropine, ipratropium), methylxanthines (theophylline, aminophylline, bamiphylline), inhalation anesthetics that have a bronchodilatory effect (e.g., isoflurane, halothane, enflurane), ketamine, and intravenous magnesium sulfate.

In one embodiment, a compound of the invention is co-administered with another therapeutic agent for the treatment and/or prevention of inflammatory bowel disease (IBD); particular agents include but are not limited to: glucocorticoids (e.g., prednisone, budesonide) synthetic disease modifying, immunomodulatory agents (e.g., methotrexate, leflunomide, sulfasalazine, mesalazine, azathioprine, 6-mercaptopurine and ciclosporin) and biological disease modifying, immunomodulatory agents (infliximab, adalimumab, rituximab, and abatacept).

In one embodiment, a compound of the invention is co-administered with another therapeutic agent for the treatment and/or prevention of pain, such as non-narcotic and narcotic analgesics; particular agents include but are not limited to: paracetamol, acetylsalicylic acid, NSAID's, codeine, dihydrocodeine, tramadol, pentazocine, pethidine, tilidine, buprenorfine, fentanyl, hydromorfon, methadon, morphine, oxycodone, piritramide, tapentadol or combinations thereof.

Course of treatment for leukemia comprises chemotherapy, biological therapy, targeted therapy, radiation therapy, bone marrow transplantation and/or combinations thereof.

Examples of further therapeutic agents for Acute Lymphoblastic Leukemia (ALL) comprise methotrexate, nelarabine, asparaginase *Erwinia chrysanthemi*, blinatumomab, daunorubicin, clofarabine, cyclophosphamide, cytarabine, dasatinib, doxorubicin, imatinib, ponatinib vincristine, mercaptopurine, pegaspargase, and/or prednisone.

Examples of further therapeutic agents for Acute Myeloid Leukemia (AML) comprise arsenic trioxide, daunorubicin, cyclophosphamide, cytarabine, doxorubicin, idarubicin, mitoxantrone, and/or vincristine.

Examples of further therapeutic agents for Chronic Lymphocytic Leukemia (CLL) comprise alemtuzumab, chlorambucil, ofatumumab, bendamustine, cyclophosphamide, fludarabine, obinutuzumab, ibrutinib, idelalisib, mechlorethamine, prednisone, and/or rituximab.

Examples of further therapeutic agents for Chronic Myelogenous Leukemia (CML) comprise bosutinib, busulfan, cyclophosphamide, cytarabine, dasatinib, imatinib, ponatinib, mechlorethamine, nilotinib, and/or omacetaxine.

Examples of further therapeutic agents for Hairy Cell Leukemia comprise cladiribine, pentostatin, and/or interferon alfa-2b.

By co-administration is included any means of delivering two or more therapeutic-agents to the patient as part of the same treatment regime, as will be apparent to the skilled person. Whilst the two or more agents may be administered simultaneously in a single formulation this is not essential. The agents may be administered in different formulations and at different times.

In one embodiment, a compound of the invention is co-administered with one or more further therapeutic agents for the treatment and/or prophylaxis of a fibrotic disease. In a particular embodiment, a compound of the invention is co-administered with one or two further therapeutic agents for the treatment and/or prophylaxis of a fibrotic disease. In a more particular embodiment, a compound of the invention is co-administered with one further therapeutic agent for the treatment and/or prophylaxis of a fibrotic disease.

In one embodiment, the further therapeutic agent for the treatment and/or prophylaxis of a fibrotic disease include, but are not limited to 5-methyl-1-phenyl-2-(1H)-pyridone (pirfenidone); nintedanib (Ofev® or Vargatef®); STX-100 (ClinicalTrials.gov Identifier NCT01371305), FG-3019 (ClinicalTrials.gov Identifier NCT01890265), lebrikizumab (CAS n #953400-68-5); tralokinumab (CAS n #1044515-88-9), CC-90001 (ClinicalTrials.gov Identifier NCT03142191), tipelukast (MN-001; ClinicalTrials.gov Identifier NCT02503657), ND-L02-s0201 (ClinicalTrials.gov Identifier NCT03538301), KD025 (ClinicalTrials.gov Identifier NCT02688647), TD139 (ClinicalTrials.gov Identifier NCT02257177), VAY736 (ClinicalTrials.gov Identifier NCT03287414), PRM-151 (ClinicalTrials.gov Identifier NCT02550873) and PBI-4050 (ClinicalTrials.gov Identifier NCT02538536). In a particular embodiment, the further therapeutic agent for the treatment and/or prophylaxis of a fibrotic disease is an autotaxin (or ectonucleotide pyrophosphatase/phosphodiesterase 2 or NPP2 or ENPP2) inhibitor, examples of which are described in WO 2014/139882, such as GLPG1690.

In one embodiment, a compound of the invention is co-administered with another therapeutic agent for the treatment and/or prophylaxis of NASH, particular agents include but are not limited to weight loss treatment agents (for example Sibutramine, or Orlistat), insulin-sensitizing agents (for example Metformin, Thiazolidinedione, Rosiglitazone, or Pioglitazone), lipid-lowering agents (for example Gemfibrozil), Antioxidants (for example Vitamine E, N-acetylcysteine, Betaine, or Pentoxifylline), Angiotensin-converting enzyme inhibitors, Angiotensin-receptor blockers, Monounsaturated fatty acids, or Polyunsaturated fatty acids. FXR agonists (for example Obeticholic acid), LOXL2 antagonists (for example Simtuzumab), ASK1 antagonists (for example Selonsertib), PPAR agonists (for example clofibrate, gemfibrozil, ciprofibrate, bezafibrate, fenofibrate, thiazolidinediones, ibuprofen, GW-9662, aleglitazar, muraglitazar or tesaglitazar), Acetyl CoA-Carboxylase (ACC) antagonists (for example NDI-010976, PF-05221304), CCR2/CCR5 (for example Cenicriviroc), VAP1 antagonist.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex© and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-i" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-i" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating cutaneous lupus erythematosus or systemic lupus erythematosus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®, Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I and a BTK inhibitor, wherein the disease is selected from inflammatory bowel disease, arthritis, cutaneous lupus erythematosus, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, cutaneous lupus erythematosus, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), cutaneous lupus erythematosus, systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the disease is an autoimmune disorder, an inflammatory disorder, a proliferative disorder, an endocrine disorder, a neurological disorder, or a disorder associated with transplantation. In some embodiments the JH2 binding compound is a compound of formula I. Other suitable JH2 domain binding compounds include those described in WO2014074660A1, WO2014074661A1, WO2015089143A1, the entirety of each of which is incorporated herein by reference. Suitable JH1 domain binding compounds include those described in WO2015131080A1, the entirety of which is incorporated herein by reference.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting GPR84 activity in a biological sample comprising the step of contacting said biological sample with a compound of this invention, or a composition comprising said compound.

According to another embodiment, the invention relates to a method of inhibiting GPR84, or a mutant thereof, activity in a biological sample comprising the step of contacting said biological sample with a compound of this invention, or a composition comprising said compound.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition of GPR84 (or a mutant thereof) activity in a biological sample is useful for a variety of purposes that are known to one of skill in the art. Examples of such purposes include, but are not limited to, blood transfusion, organtransplantation, biological specimen storage, and biological assays.

Another embodiment of the present invention relates to a method of inhibiting GPR84 activity in a patient comprising the step of administering to said patient a compound of the present invention, or a composition comprising said compound.

According to another embodiment, the invention relates to a method of inhibiting activity of GPR84, or a mutant thereof, in a patient comprising the step of administering to said patient a compound of the present invention, or a composition comprising said compound. According to certain embodiments, the invention relates to a method of reversibly or irreversibly inhibiting one or more of GPR84, or a mutant thereof, activity in a patient comprising the step of administering to said patient a compound of the present invention, or a composition comprising said compound. In other embodiments, the present invention provides a method for treating a disorder mediated by GPR84, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™ Docetaxel is marketed under the trade name Taxotere™. Vinblastine sulfate is marketed under the trade name Vinblastin R.P™. Vincristine sulfate is marketed under the trade name Farmistin™

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C1-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MM1270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, 5-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™)

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787

(Parke-Davis), AWD-12-281 (Asta Medica), CDC-801 (Celgene), SeICID™CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-11B), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTOR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonist of activating receptors on NK cells. In some embodiments, an immuno-oncology agent is an antagonist of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgGI, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Ikena Oncology, formerly known as Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (OPDIVO©, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (POMALYST®, Celgene); lenalidomide (REVLIMID®, Celgene); ingenol mebutate (PICATO®, LEO Pharma).

In some embodiments, an immuno-oncology agent is a cancer vaccine. In some embodiments, the cancer vaccine is selected from sipuleucel-T (PROVENGE®, Dendreon/Valeant Pharmaceuticals), which has been approved for treatment of asymptomatic, or minimally symptomatic metastatic castrate-resistant (hormone-refractory) prostate cancer; and talimogene laherparepvec (IMLYGIC®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (REOLYSIN®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CGO070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June et al.; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCTO2124850) and ovarian cancer (NCT02431559).

Other immuno-oncology agents that can be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams et al., "Big opportunities for small molecules in immuno-oncology," Cancer Therapy 2015, Vol. 14, pages 603-622, the content of which is incorporated herein by reference in its entirety. In some embodiment, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams et al. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BITE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BITE®) antibody construct. In some embodiments, a bispecific T cell engager (BITE®) antibody construct is a CD19/CD3 bispecific antibody construct. In some embodiments, a bispecific T cell engager (BITE®) antibody construct is an EGFR/CD3 bispecific antibody construct. In some embodiments, a bispecific T cell engager (BITE®) antibody construct activates T cells. In some embodiments, a bispecific T cell engager (BITE®) antibody construct activates T cells, which release cytokines inducing upregulation of intercellular adhesion molecule 1 (ICAM-1) and FAS on bystander cells. In some embodiments, a bispecific T cell engager (BITE®) antibody construct activates T cells which result in induced bystander cell lysis. In some embodiments, the bystander cells are in solid tumors. In some embodiments, the bystander cells being lysed are in proximity to the BITE®-activated T cells. In some embodiment, the bystander cells comprise tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In some embodiments, the checkpoint inhibitor is a biologic therapeutic or a small molecule. In some embodiments, the checkpoint inhibitor is a monoclonal antibody, a humanized antibody, a fully human antibody, a fusion protein or a combination thereof. In some embodiments, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor is an immunostimulatory agent, a T cell growth factor, an interleukin, an antibody, a vaccine or a combination thereof. In some embodiments, the interleukin is IL-7 or IL-15. In some embodiments, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors can include small molecule inhibitors or can include antibodies, or antigen binding fragments thereof, that bind to and block or inhibit immune checkpoint receptors or antibodies that bind to and block or inhibit immune checkpoint receptor ligands. Illustrative checkpoint molecules that can be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, T6, and memory $CD8^+$ ($\alpha\beta$) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include, but are not limited to, Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (OPDIVO®), ipilimumab (YERVOY®), and pembrolizumab (KEYTRUDA®). In some embodiments, the checkpoint inhibitor is selected from nivolumab (anti-PD-1 antibody, OPDIVO®, Bristol-Myers Squibb); pembrolizumab (anti-PD-1 antibody, KEYTRUDA®, Merck); ipilimumab (anti-CTLA-4 antibody, YERVOY®, Bristol-Myers Squibb); durvalumab (anti-PD-L1 antibody, IMFINZI®, AstraZeneca); and atezolizumab (anti-PD-L1 antibody, TECENTRIQ®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (KEYTRUDA®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (BAVENCIO®, Pfizer/Merck KGaA), also known as MSB0010718C), a fully human IgGI anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that can be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that can be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981); and CTX-471 (Compass Therapeutics), an agonistic anti-CD137 antibody in metastatic or locally advanced malignancies (NCT03881488).

Checkpoint inhibitors that can be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that can be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that can be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that can be used in the present invention include killer IgG-like receptor (KTR) inhibitors. KTR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that can be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that can be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that can be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that can be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that can be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a GPR84 inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. Additional compounds of the invention were prepared by methods substantially similar to those described herein in the Examples and methods known to one skilled in the art.

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration. LCMS spectra were obtained on an Agilent 1200 series 6110 or 6120 mass spectrometer with electrospray ionization and excepted as otherwise indicated, * the general LCMS condition was as follows: Waters X Bridge C18 column (50 mm*4.6 mm*3.5 um); Flow Rate: 2.0 mL/min, the column temperature: 40° C.

Other methods: "A"=CSH C18, 3.5 m column (4.6 mm×30 mm); Flow Rate: 0.8 mL/min, the column temperature: 40° C. Eluting with MeCN in 10 mM aqueous ammonium formate; 5% MeCN for 0.5 min, 5% to 100% MeCN over 5 minutes; hold 100% MeCN for 1.5 minute Example 1: Synthesis of I-1

Synthetic Scheme of I-1

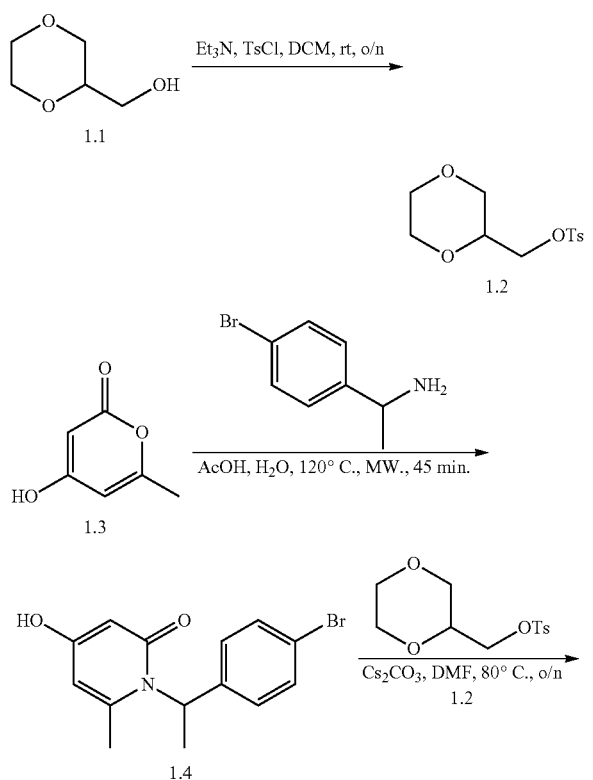

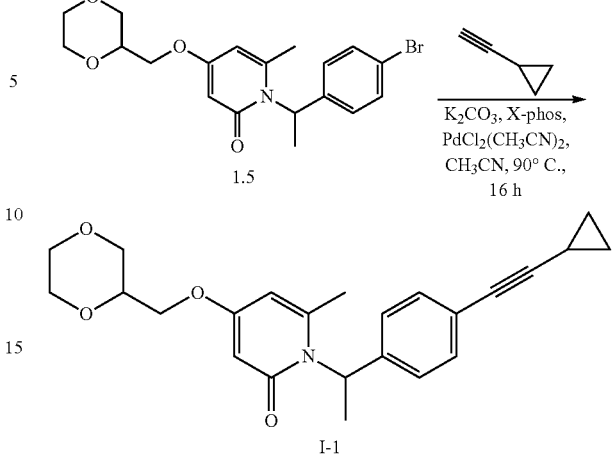

1. The Synthesis of Intermediate 1.2

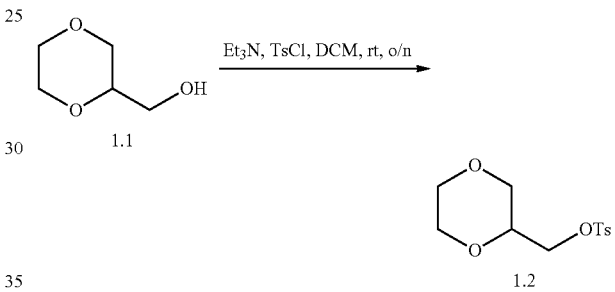

To a stirred solution of 1.1 (1.0 g, 8.4 mmol) in DCM (20 mL) was added Et₃N (2.5 g, 25.2 mmol) and TsCl (1.79 g, 10.08 mmol). The reaction mixture was stirred at RT overnight until the reaction was complete. The suspension was diluted with H₂O (30 mL) and extracted with DCM (20 mL×2), concentrated. The crude product was purified by column chromatography (silica gel, PE/EA=5:1) to give 1.2 (1.1 g, yield: 48%) as a white solid. LC-MS m/z: 373.3 [M+H]⁺.

2. The Synthesis of Intermediate 1.4

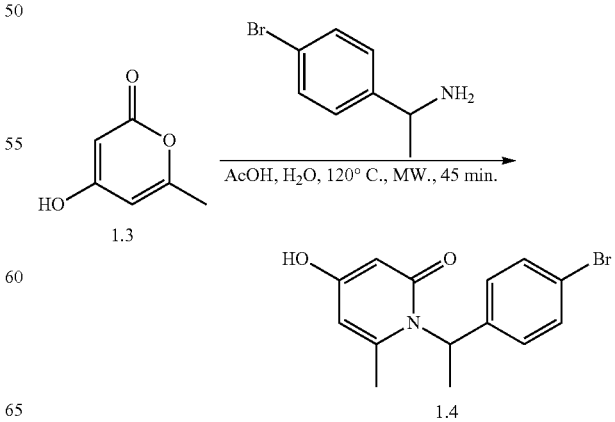

To a stirred solution of 1.3 (2.00 g, 15.8 mmol) in AcOH (20 m an water (10 mL) was added 1-(4-bromophenyl)ethanamine (3.17 g, 15.8 mmol). The reaction mixture was stirred at 120° C. for 45 min under microwave irradiation conditions. The suspension was diluted with H₂O (50 mL) and extracted with DCM (50 mL×2), concentrated. The crude product was purified by Prep-HPLC to give 1.4 (600 mg, yield: 12%) as brown oil. LC-MS m/z: 308.2 [M+H]⁺.

3. The Synthesis of Intermediate 1.5

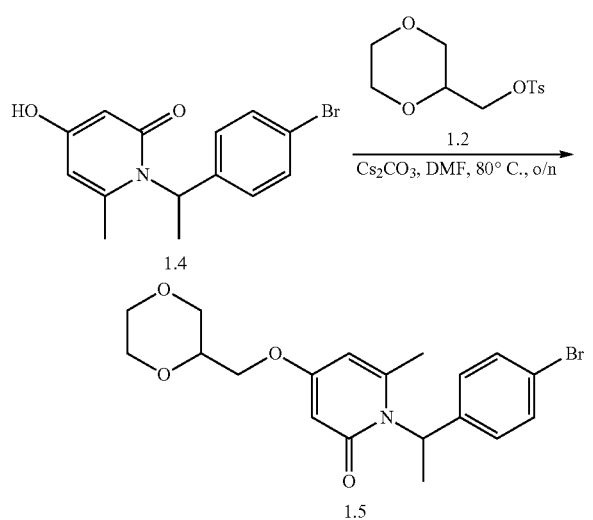

To a stirred solution of 1.4 (500 mg, 1.62 mmol), 1.2 (1.11 g, 4.87 mmol) in DMF (20 mL) was added K₂CO₃ (672 mg, 4.87 mmol). The reaction mixture was stirred at 80° C. overnight until the reaction was complete. The suspension was diluted with H₂O (20 mL) and extracted with DCM (20 mL×2), concentrated. The crude product was purified by Prep-HPLC to give 1.5 (200 mg, yield: 30%) as brown oil. LC-MS m/z: 408.0 [M+H]⁺.

4. The Synthesis of Target I-1

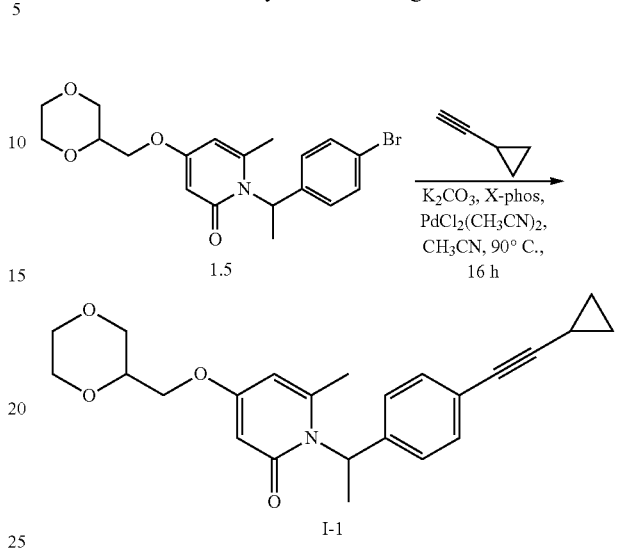

To a stirred solution of 1.5 (200 mg, 0.49 mmol) in CH₃CN (15 mL) was added K₂CO₃ (135 mg, 0.98 mmol), PdCl₂(CH₃CN)₂ (13 mg, 0.05 mmol) and X-phos (47 mg, 0.10 mmol), and then backfill with argon (three times). Add ethynylcyclopropane (49 mg, 0.73 mmol) to the resulting suspension and the reaction mixture was stirred at 90° C. for 16 hours until the reaction was completed. The reaction mixture was diluted with H₂O (20 mL) and extracted with DCM (20 mL×2), concentrated. The crude product was purified by Prep-HPLC to give I-1 (20 mg, yield: 10%) as a white solid.

Additional exemplary compounds were prepared following methods substantially similar to the method described above and herein. Data for these compounds are provided below.

TABLE 2

Characterization Data for Additional Exemplary Compounds

| Compound No. | Chemical Structure | [M + H] observed | ¹H NMR (400 MHz) |
|---|---|---|---|
| I-1 | 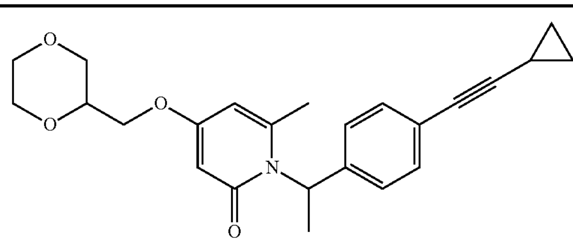 | 394.3 | ¹H NMR (400 MHz, DMSO-d₆): δ 7.30 (d, J = 7.2 Hz, 2 H), 7.07 (d, J = 8.4 Hz, 2 H), 5.87 (s, 1 H), 5.64 (br, 1 H), 3.89 (s, 2 H), 3.45-3.82 (m, 6 H), 3.30-3.37 (m, 1 H), 2.50 (s, 3 H), 2.33 (br, 1 H), 1.76 (d, J = 6.0 Hz, 3 H), 1.50-1.54 (m, 1 H), 0.85-0.88 (m, 2 H), 0.70-0.72 (m, 2 H). |
| I-89 | 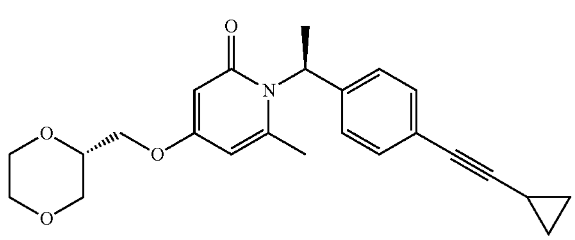 | 394.1 | ¹H NMR (400 MHz, DMSO-d₆): δ 7.31 (s, 2 H), 7.07 (d, J = 6.8 Hz, 2 H), 5.87 (s, 1 H), 5.63 (br, 1 H), 3.89 (s, 2 H), 3.73-3.78 (m, 3 H), 3.58-3.66 (m, 2 H), 3.45-3.50 (m, 1 H), 3.32-3.37 (m, 1 H), 2.23-2.39 (m, 4 H), 1.76 (s, 3 H), 1.52 (s, 1 H), 0.86 (d, J = 5.2 Hz, 2 H), 0.71 (s, 2 H). |

TABLE 2-continued

Characterization Data for Additional Exemplary Compounds

| Compound No. | Chemical Structure | [M + H] observed | $^1$H NMR (400 MHz) |
|---|---|---|---|
| I-6 | 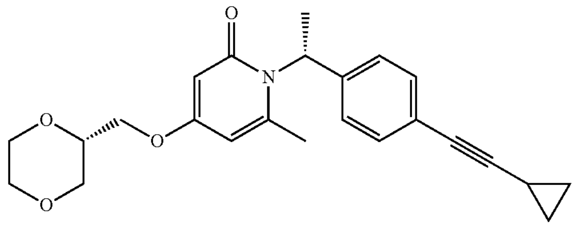 [SMILES: Cc1cc(OC[C@@H]2COCCO2)cc(=O)n1[C@H](C)c1ccc(C#CC2CC2)cc1] | 394.2 | $^1$H NMR (400 MHz, DMSO-$d_6$): δ 7.30 (d, J = 7.2 Hz, 2 H), 7.07 (d, J = 8.0 Hz, 2 H), 5.87 (s, 1 H), 5.63 (br, 1 H), 3.89 (s, 2 H), 3.73-3.82 (m, 3 H), 3.58-3.67 (m, 2 H), 3.45-3.50 (m, 1 H), 3.35-3.37 (m, 1 H), 2.50 (s, 3 H), 2.01-2.33 (m, 1H), 1.76 (d, J = 5.6 Hz, 3 H), 1.49-1.56 (m, 1 H), 0.84-0.89 (m, 2 H), 0.69-0.73 (m, 2 H). |
| I-44 | 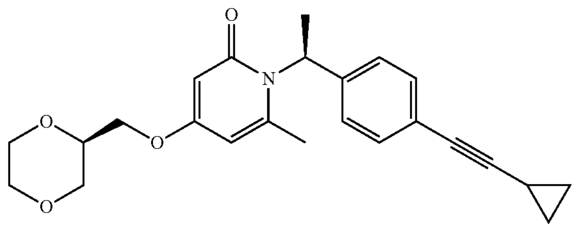 [SMILES: Cc1cc(OC[C@H]2COCCO2)cc(=O)n1[C@@H](C)c1ccc(C#CC2CC2)cc1] | 394.0 | $^1$H NMR (400 MHz, DMSO-$d_6$): δ 7.30 (d, J = 7.2 Hz, 2 H), 7.07 (d, J = 8.4 Hz, 2 H), 5.87 (s, 1 H), 5.40-5.75 (m, 1 H), 3.73-3.89 (m, 5 H), 3.57-3.67 (m, 2 H), 3.45-3.51 (m, 1 H), 3.30-3.39 (m, 1 H), 1.95-2.55 (m, 4 H), 1.76 (d, J = 6.0 Hz, 3 H), 1.50-1.54 (m, 1 H), 0.84-0.89 (m, 2 H), 0.69-0.73 (m, 2 H). |
| I-7 | 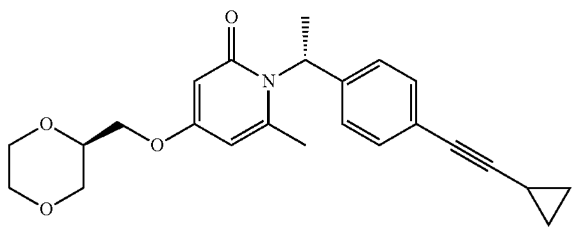 | 394.0 | $^1$H NMR (400 MHz, DMSO-$d_6$): δ 7.30 (d, J = 6.8 Hz, 2H), 7.07 (d, J = 7.6 Hz, 2H), 5.88 (s, 1H), 5.61 (br, 1H), 3.58-3.90 (m, 7H), 3.45-3.51 (m, 1H), 3.33-3.38 (m, 1H), 2.51 (s, 3H), 2.28 (br, 1H), 1.76 (d, J = 6.0 Hz, 3H), 1.49-1.56 (m, 1H), 0.85-0.90 (m, 2H), 0.69-0.73 (m, 2H). |
| I-63 | 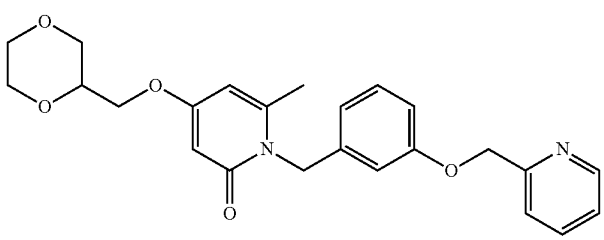 [SMILES: Cc1cc(OCC2COCCO2)cc(=O)n1Cc1cccc(OCc2ccccn2)c1] | 423.2 | $^1$H NMR (400 MHz, DMSO-$d_6$) δ 8.56 (d, J = 4.4 Hz, 1H), 7.79-7.83 (m, 1H), 7.47 (d, J = 8.0 Hz, 1H), 7.32-7.35 (m, 1H), 7.25 (t, J = 8.0 Hz, 1H), 6.91 (dd, J = 8.0 Hz, 2.0 Hz, 1H), 6.66-6.70 (m, 2H), 5.92 (d, J = 2.4 Hz, 1H), 5.79 (d, J = 2.8 Hz, 1H), 5.13-5.16 (m, 4H), 3.91-3.97 (m, 2H), 3.74-3.86 (m, 3H), 3.59-3.68 (m, 2H), 3.46-3.52 (m, 1H), 3.37-3.39 (m, 1H), 2.15 (s, 3H). |
| I-142 | 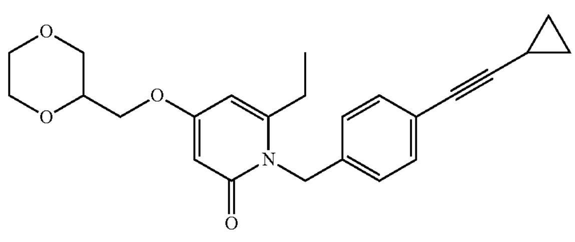 [SMILES: CCc1cc(OCC2COCCO2)cc(=O)n1Cc1ccc(C#CC2CC2)cc1] | 394.4 | $^1$H NMR (400 MHz, CDCl$_3$): δ 7.29 (d, J = 8.0 Hz, 2 H), 6.99 (d, J = 8.4 Hz, 2H), 5.85 (dd, J = 2.4 Hz, 14.4 Hz, 2 H), 5.26 (s, 2 H), 3.64-3.99 (m, 8 H), 3.51-3.56 (m, 1 H), 2.46 (q, J = 7.2 Hz, 2 H), 1.39-1.45 (m, 1 H), 1.12 (t, J = 7.2 Hz, 3 H), 0.76-0.88 (m, 4H). |
| I-141 | 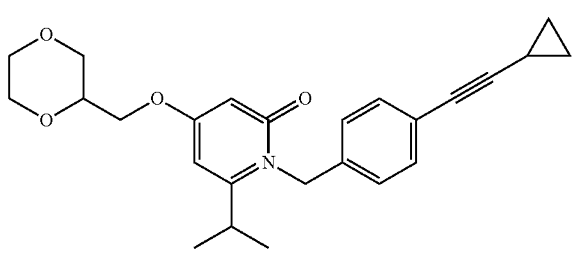 | 408.3 | $^1$H NMR (400 MHz, CDCl$_3$): δ 7.29 (d, J = 8.4 Hz, 2 H), 6.96 (d, J = 8.4 Hz, 2 H), 5.91-5.94 (m, 2 H), 5.32 (br, 2 H), 3.52-3.99 (m, 9 H), 2.79-2.85 (m, 1 H), 1.39-1.46 (m, 1 H), 1.11 (d, J = 6.4 Hz, 6 H), 0.76-0.88 (m, 4 H). |

TABLE 2-continued

Characterization Data for Additional Exemplary Compounds

| Compound No. | Chemical Structure | [M + H] observed | $^1$H NMR (400 MHz) |
|---|---|---|---|
| I-60 | 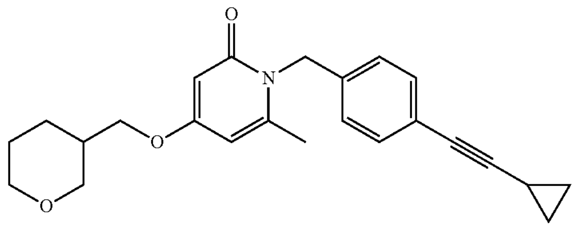 | 378.3 | $^1$H NMR (400 MHz, DMSO-$d_6$) δ 7.32 (d, J = 8.0 Hz, 2H), 7.04 (d, J = 8.0 Hz, 2H), 5.91 (d, J = 2.0 Hz, 1H), 5.79 (d, J = 2.8 Hz, 1H), 5.18 (s, 2H), 3.84 (d, J = 6.4 Hz, 3H), 3.72-3.75 (m, 1H), 3.31-3.34 (m, 1H), 3.23 (t, J = 9.2 Hz, 1H), 2.16 (s, 3H), 1.94-1.99 (m, 1H), 1.79-1.83 (m, 1H), 1.45-1.62 (m, 3H), 1.30-1.40 (m, 1H), 0.83-0.89 (m, 2H), 0.69-0.73 (m, 2H). |
| I-11 | 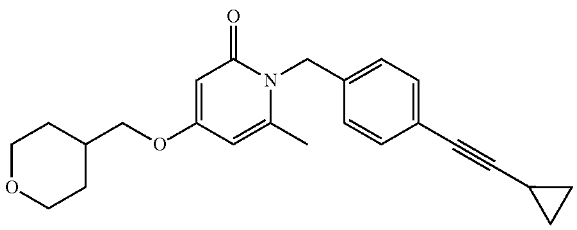 [SMILES: Cc1cc(OCC2CCOCC2)cc(=O)n1Cc1ccc(C#CC2CC2)cc1] | 378.2 | $^1$H NMR (400 MHz, DMSO-$d_6$) δ 7.32 (d, J = 8.4 Hz, 2H), 7.04 (d, J = 8.0 Hz, 2H), 5.91 (d, J = 2.4 Hz, 1H), 5.79 (d, J = 2.8 Hz, 1H), 5.18 (s, 2H), 3.87 (dd, J = 11.2 Hz, 2.8 Hz, 2H), 3.82 (d, J = 6.4 Hz, 2H), 3.29-3.35 (m, 2H), 2.16 (s, 3H), 1.93-2.00 (m, 1H), 1.61-1.64 (m, 2H), 1.49-1.55 (m, 1H), 1.25-1.36 (m, 2H), 0.84-0.89 (m, 2H), 0.69-0.73 (m, 2H). |
| I-2 | 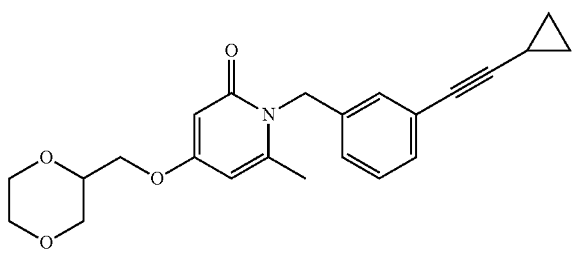 | 380.2 | $^1$H NMR (400 MHz, DMSO-$d_6$): δ 7.25-7.29 (m, 2 H), 7.03-7.07 (m, 2 H), 5.94 (d, J = 2.0 Hz, 1 H), 5.80 (d, J = 2.4 Hz, 1 H), 5.16 (s, 2 H), 3.94-3.96 (m, 2 H), 3.45-3.86 (m, 6 H), 3.37-3.39 (s, 1 H), 2.17 (s, 3 H), 1.49-1.53 (m, 1 H), 0.85-0.88 (m, 2 H), 0.70-0.72 (m, 2 H). |
| I-82 | 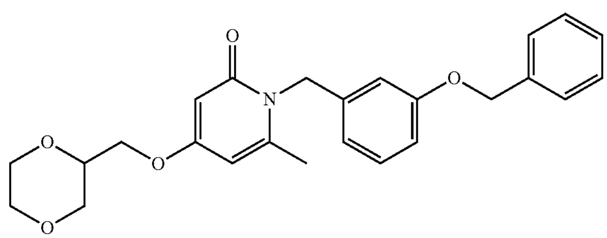 [SMILES: Cc1cc(OCC2COCCO2)cc(=O)n1Cc1cccc(OCc2ccccc2)c1] | 422.3 | $^1$H NMR (400 MHz, DMSO-$d_6$) δ 7.30-7.42 (m, 5H), 7.24 (t, J = 8.0 Hz, 1H), 6.90 (dd, J = 8.0 Hz, 2.0 Hz, 1H), 6.70 (s, 1H), 6.65 (d, J = 7.6 Hz, 1H), 5.92 (d, J = 2.4 Hz, 1H), 5.79 (d, J = 2.8 Hz, 1H), 5.16 (s, 2H), 5.05 (s, 2H), 3.91-3.97 (m, 2H), 3.74-3.86 (m, 3H), 3.58-3.67 (m, 2H), 3.46-3.51 (m, 1H), 3.36-3.39 (m, 1H), 2.16 (s, 3H). |
| I-99 | 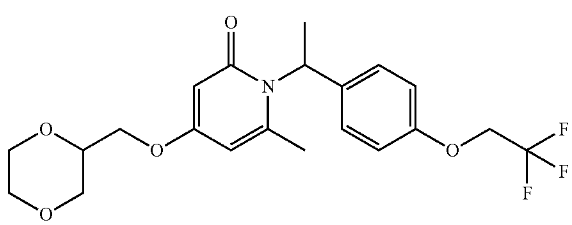 [SMILES: Cc1cc(OCC2COCCO2)cc(=O)n1C(C)c1ccc(OCC(F)(F)F)cc1] | 428.0 | $^1$H NMR (400 MHz, CDCl$_3$): δ 7.15 (d, J = 8.4 Hz, 2 H), 6.87-6.90 (m, 2 H), 5.79 (s, 1 H), 5.74 (s, 1 H), 4.32 (q, J = 8.0 Hz, 2 H), 3.75-3.97 (m, 7 H), 3.62-3.72 (m, 1 H), 3.47-3.52 (m, 1 H), 2.05 (br, 3 H), 1.84 (d, J = 6.0 Hz, 3 H), 1.68 (s, 1 H). |
| I-65 | 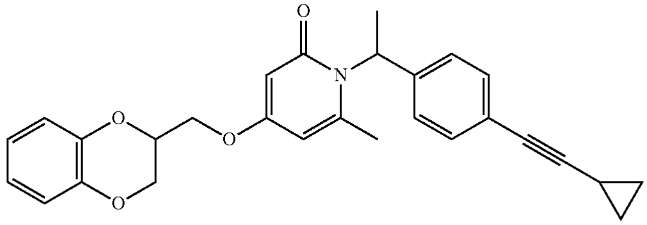 [SMILES: Cc1cc(OCC2COc3ccccc3O2)cc(=O)n1C(C)c1ccc(C#CC2CC2)cc1] | 442.0 | $^1$H NMR (400 MHz, CDCl$_3$): δ 7.32 (d, J = 8.4 Hz, 2 H), 7.08 (d, J = 8.0 Hz, 2 H), 6.85-6.93 (m, 4 H), 5.85 (s, 1 H), 5.73 (s, 1 H), 4.50-4.54 (m, 1 H), 4.35 (dd, J = 2.4 Hz, 11.6 Hz, 1 H), 4.09-4.19 (m, 3 H), 1.99 (br, 3 H), 1.82 (d, J = 6.4 Hz, 3 H), 1.64 (s, 1 H), 1.40-1.47 (m, 1 H), 0.77-0.88 (m, 4 H). |

TABLE 2-continued

Characterization Data for Additional Exemplary Compounds

| Compound No. | Chemical Structure | [M + H] observed | ¹H NMR (400 MHz) |
|---|---|---|---|
| I-106 | 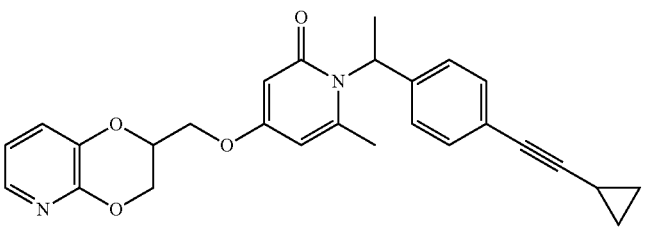 [SMILES: Cc1cc(OCC2COc3ncccc3O2)cc(=O)n1C(C)c1ccc(C#CC2CC2)cc1] | 442.9 | ¹H NMR (400 MHz, DMSO-$d_6$): δ 7.77 (dd, J = 1.6 Hz, 4.8 Hz, 1H), 7.36 (dd, J = 1.6 Hz, 8.0 Hz, 1H), 7.30 (d, J = 7.6 Hz, 2H), 7.08 (d, J = 8.4 Hz, 2H), 6.97 (dd, J = 4.8 Hz, 8.0 Hz, 1H), 5.92 (s, 1H), 5.68 (br, 1H), 4.55-4.58 (m, 2H), 4.18-4.29 (m, 3H), 3.36-3.46 (m, 1H), 2.33 (br, 4H), 1.77 (d, J = 6.0 Hz, 3H), 1.50-1.54 (m, 1H), 0.85-0.89 (m, 2H), 0.69-0.73 (m, 2H). |
| I-88 | 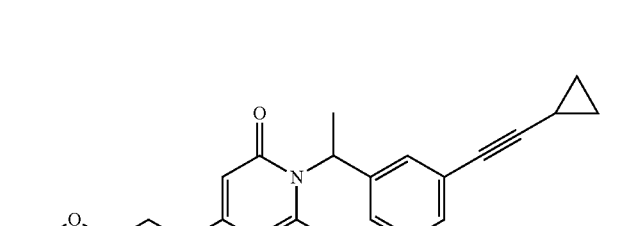 | 394.0 | ¹H NMR (400 MHz, DMSO-$d_6$): δ 7.18-7.32 (m, 2 H), 7.06-7.09 (m, 2 H) 5.89 (s, 1 H), 5.60 (br, 1 H), 3.88-3.90 (m, 2 H), 3.73-3.83 (m, 3 H), 3.58-3.67 (m, 2 H), 3.43-3.51 (m, 1 H), 3.35-3.40 (m, 1 H), 2.38 (br, 4 H), 1.77 (d, J = 5.6 Hz, 3 H), 1.50-1.54 (m, 1 H), 0.84-0.89 (m, 2 H), 0.70-0.74 (m, 2 H). |
| I-114 | 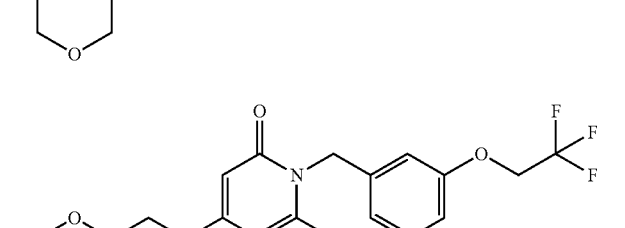 | 414.0 | ¹H NMR (400 MHz, DMSO-$d_6$): δ 7.30 (t, J = 8.0 Hz, 1 H), 6.96 (dd, J = 2.0 Hz, 8.4 Hz, 1 H), 6.78 (s, 1 H), 6.72 (d, J = 7.6 Hz, 1 H), 5.94 (d, J = 2.0 Hz, 1 H), 5.80 (d, J = 2.4 Hz, 1 H), 5.18 (s, 2 H), 4.73 (q, J = 8.8 Hz, 2 H), 3.92-3.98 (m, 2 H), 3.74-3.85 (m, 3 H), 3.59-3.68 (m, 2 H), 3.45-3.52 (m, 1 H), 3.34-3.38 (m, 1 H), 2.19 (s, 3 H). |
| I-49 | 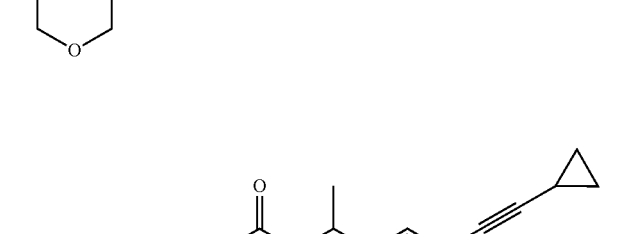 | 394.0 | ¹H NMR (400 MHz, DMSO-$d_6$) δ 7.23 (d, J = 7.6 Hz, 1H), 7.05 (t, J = 8.0 Hz, 1H), 6.34 (d, J = 7.6 Hz, 1H), 5.99 (d, J = 2.4 Hz, 1H), 5.80 (d, J = 2.8 Hz, 1H), 5.11 (s, 2H), 3.95-3.98 (m, 2H), 3.74-3.85 (m, 3H), 3.59-3.68 (m, 2H), 3.37-3.51 (m, 2H), 2.40 (s, 3H), 2.12 (s, 3H), 1.56-1.62 (m, 1H), 0.89-1.05 (m, 2H), 0.73-0.77 (m, 2H). |
| I-115 | 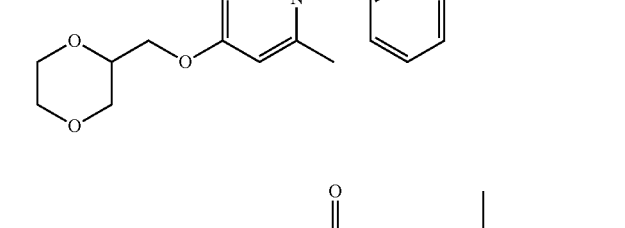 | 394.1 | ¹H NMR (400 MHz, CDCl₃): δ 7.16 (d, J = 7.2 Hz, 1H), 7.06 (d, J = 7.6 Hz, 1H), 6.61 (s, 1H), 5.89 (s, 2H), 5.14 (s, 2H), 3.64-4.04 (m, 8H), 3.52-3.57 (m, 1H), 2.33 (s, 3H), 2.13 (s, 3H), 1.36-1.42 (m, 1H), 0.74-0.84 (m, 4H). |

TABLE 2-continued

Characterization Data for Additional Exemplary Compounds

| Compound No. | Chemical Structure | [M + H] observed | $^1$H NMR (400 MHz) |
|---|---|---|---|
| I-30 | 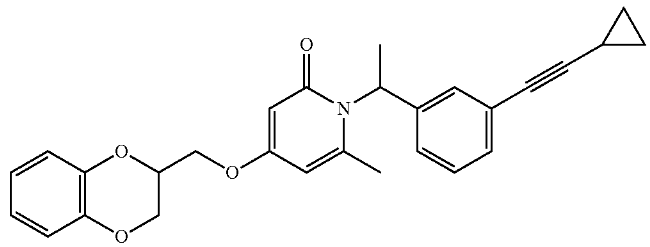 [SMILES: Cc1cc(OCC2COc3ccccc3O2)cc(=O)n1C(C)c1cccc(C#CC2CC2)c1] | 428.3 | $^1$H NMR (400 MHz, DMSO-$d_6$): δ 7.23-7.31 (m, 2H), 7.04-7.07 (m, 2H), 6.84-6.93 (m, 4H), 5.99 (d, J = 2.0 Hz, 1H), 5.87 (d, J = 6.8 Hz, 1H), 5.18 (s, 2H), 4.54-4.56 (m, 1H), 4.42 (dd, J = 11.6 Hz, 2.4 Hz, 1H), 4.20-4.31 (m, 2H), 4.07-4.12 (m, 1H), 2.18 (s, 3H), 1.49-1.56 (m, 1H), 0.84-0.89 (m, 2H), 0.70-0.73 (m, 2H). |
| I-118 | 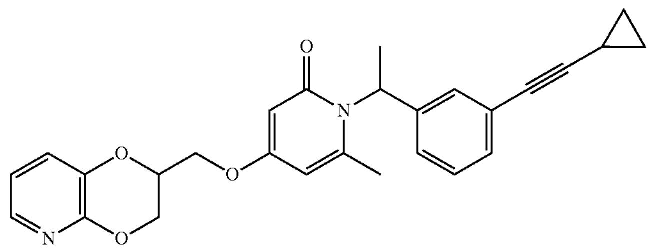 | 428.9 | $^1$H NMR (400 MHz, DMSO-$d_6$): δ 7.78 (dd, J = 1.6 Hz, 4.8 Hz, 1H), 7.36 (dd, J = 1.2 Hz, 7.6 Hz, 1H), 7.24-7.32 (m, 2H), 7.05-7.08 (m, 2H), 6.97 (dd, J = 4.8 Hz, 8.0 Hz, 1H), 5.98 (d, J = 2.0 Hz, 1H), 5.88 (d, J = 2.4 Hz, 1H), 5.18 (s, 2H), 4.57-4.63 (m, 2H), 4.22-4.34 (m, 3H), 2.18 (s, 3H), 1.50-1.55 (m, 1H), 0.84-0.89 (m, 2H), 0.70-0.74 (m, 2 H). |
| I-100 | 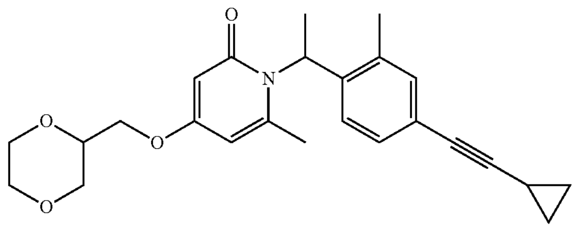 | 408.0 | $^1$H NMR (400 MHz, CDCl$_3$): δ 7.35 (d, J = 8.0 Hz, 1H), 7.23 (dd, J = 1.2 Hz, 8.0 Hz, 1H), 7.15 (s, 1H), 5.80 (d, J = 2.4 Hz, 1H), 5.63 (d, J = 2.4 Hz, 1H), 3.61-3.97 (m, 8H), 3.44-3.52 (m, 1H), 1.93 (s, 3H), 1.85-1.90 (m, 1H), 1.76-1.78 (m, 6H), 1.40-1.47 (m, 1H), 0.77-0.89 (m, 4 H). |
| I-21 | 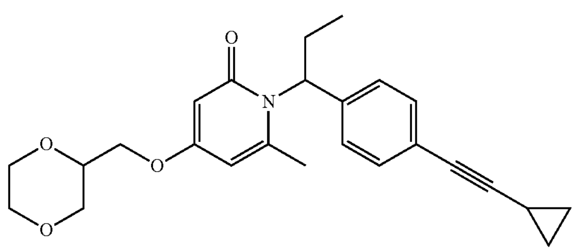 [SMILES: CCC(c1ccc(C#CC2CC2)cc1)n1c(C)cc(OCC2COCCO2)cc1=O] | 408.3 | $^1$H NMR (400 MHz, 333K, DMSO-$d_6$): δ 7.29 (d, J = 8.0 Hz, 2H), 7.14 (d, J - 7.6 Hz, 2H), 5.85 (s, 1H), 5.66 (s, 1H), 3.92-3.93 (m, 2H), 3.74-3.85 (m, 3H), 3.59-3.67 (m, 2H), 3.46-3.53 (m, 1H), 3.35-3.40 (m, 1H), 1.89-2.50 (m, 6H), 1.49-1.53 (m, 1H), 0.84-0.90 (m, 5H), 0.69-0.73 (m, 2H). |
| I-50 | 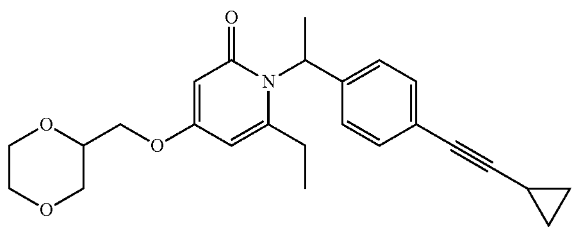 [SMILES: CCc1cc(OCC2COCCO2)cc(=O)n1C(C)c1ccc(C#CC2CC2)cc1] | 408.2 | $^1$H NMR (400 MHz, CDCl$_3$) δ 7.31 (d, J = 8.4 Hz, 2H), 7.06 (d, J = 8.0 Hz, 2H), 5.81 (s, 2H), 3.63-3.97 (m, 8H), 3.52 (t, J = 10.4 Hz, 1H), 2.42-2.65 (m, 2H), 1.85 (br, 3H), 1.72 (s, 1H), 1.38-1.46 (m, 1H), 0.80-1.31 (m, 7H). |
| I-68 | 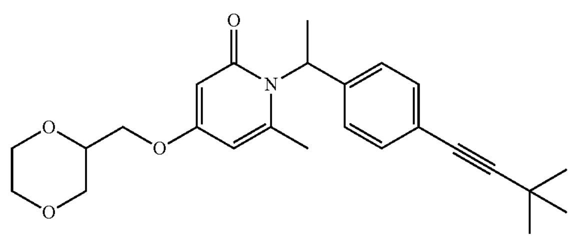 [SMILES: Cc1cc(OCC2COCCO2)cc(=O)n1C(C)c1ccc(C#CC(C)(C)C)cc1] | 410.0 | $^1$H NMR (400 MHz, CDCl$_3$): δ 7.33 (d, J = 8.4 Hz, 2 H), 7.07 (d, J = 8.0 Hz, 2 H), 5.81 (s, 1 H), 5.72 (s, 1 H), 3.65-3.97 (m, 8 H), 3.47-3.53 (m, 1 H), 1.96 (br, 3 H), 1.82 (d, J = 6.8 Hz, 3 H), 1.73 (s, 1 H), 1.30 (s, 9 H). |

TABLE 2-continued

Characterization Data for Additional Exemplary Compounds

| Compound No. | Chemical Structure | [M + H] observed | $^1$H NMR (400 MHz) |
|---|---|---|---|
| I-96 | 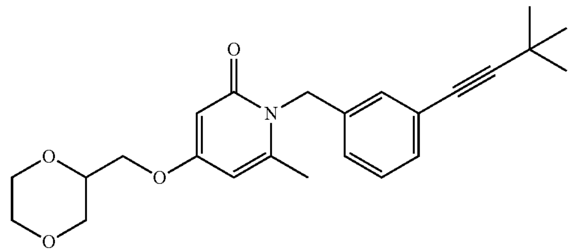 [SMILES: Cc1cc(OCC2COCCO2)cc(=O)n1Cc1cccc(C#CC(C)(C)C)c1] | 396.0 | $^1$H NMR (400 MHz, CDCl$_3$): δ 7.26 (s, 1 H), 7.20 (t, J = 7.6 Hz, 1 H), 7.16 (s, 1 H), 7.00 (d, J - 7.6 Hz, 1 H), 5.89 (d, J = 2.4 Hz, 1 H), 5.82 (d, J- 2.4 Hz, 1 H), 5.23 (s, 2 H), 3.66-3.99 (m, 8 H), 3.49-3.55 (m, 1 H), 2.19 (s, 3 H), 1.30 (s, 9 H). |
| I-20 | 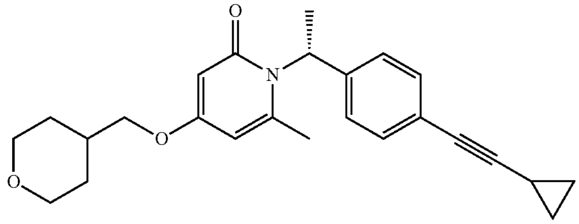 [SMILES: Cc1cc(OCC2CCOCC2)cc(=O)n1[C@H](C)c1ccc(C#CC2CC2)cc1] | 392.4 | $^1$H NMR (400 MHz, DMSO-d$_6$): δ 7.30 (d, J = 6.8 Hz, 2H), 7.08 (d, J = 8.0 Hz, 2H), 5.85 (s, 1H), 5.73 (br, 1H), 3.86 (dd, J - 2.8 Hz, 11.2 Hz, 2H), 3.77 (d, J = 5.6 Hz, 2H), 3.27-3.36 (m, 3H), 2.50 (s, 3H), 1.91-1.97 (m, 1H), 1.75 (d, J = 5.6 Hz, 3H), 1.60-1.63 (m, 2H), 1.49-1.56 (m, 1H), 1.24-1.34 (m, 2H), 0.85-0.89 (m, 2H), 0.69-0.73 (m, 2H). |
| I-22 | 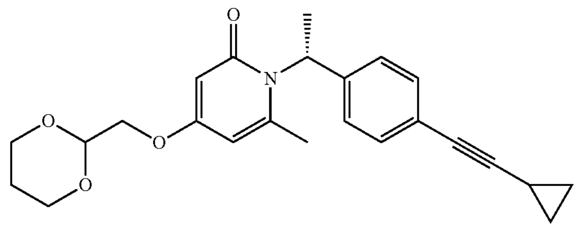 [SMILES: Cc1cc(OCC2OCCCO2)cc(=O)n1[C@H](C)c1ccc(C#CC2CC2)cc1] | 394.1 | $^1$H NMR (400 MHz, DMSO-d$_6$): δ 7.30 (d, J = 7.2 Hz, 2 H), 7.07 (d, J = 8.0 Hz, 2 H), 5.89 (s, 1 H), 5.56 (br, 1 H), 4.86 (t, J = 4.4 Hz, 1 H), 4.04 (dd, J = 4.8 Hz, 10.8 Hz, 2 H), 3.71-3.87 (m, 4 H), 2.47-2.55 (m, 3 H), 2.20-2.45 (m, 1 H), 1.85-1.97 (m, 1 H), 1.76 (d, J = 5.6 Hz, 3 H), 1.50-1.55 (m, 1 H), 1.36-1.40 (m, 1 H), 0.84-0.89 (m, 2 H), 0.68-0.73 (m, 2 H). |
| I-28 | 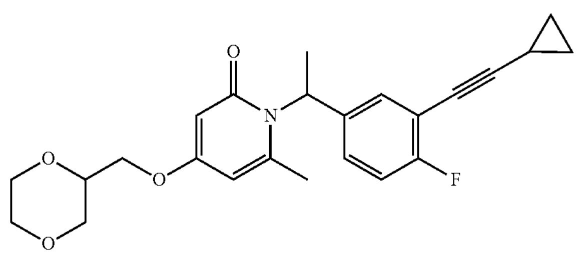 [SMILES: Cc1cc(OCC2COCCO2)cc(=O)n1C(C)c1ccc(F)c(C#CC2CC2)c1] | 398.2 | $^1$H NMR (400 MHz, DMSO-d$_6$) δ 7.71 (t, J = 8.8 Hz, 1H), 7.11-7.14 (m, 2H), 5.94 (d, J = 2.4 Hz, 1H), 5.80 (d, J = 2.8 Hz, 1H), 5.13 (s, 2H), 3.92-3.97 (m, 2H), 3.32-3.85 (m, 7H), 2.18 (s, 3H), 1.55-1.61 (m, 1H), 0.87-0.94 (m, 2H), 0.71-0.77 (m, 2H). |
| I-143 | 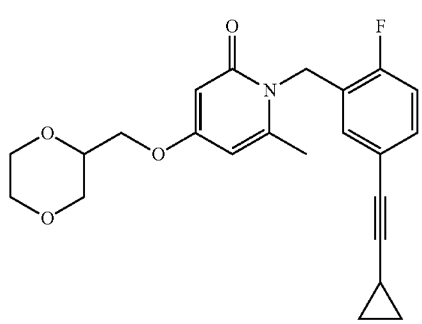 | 398.0 | $^1$HNMR (400 MHz, DMSO-d$_6$) δ 7.30-7.34 (m, 1H), 7.19-9.24 (m, 1H), 6.69 (d, J = 7.2 Hz, 1H), 6.00 (d, J = 2.4 Hz, 1H), 5.81 (d, J = 2.8 Hz, 1H), 5.16 (s, 2H), 3.96-4.00 (m, 2H), 3.75-3.84 (m, 3H), 3.59-3.68 (m, 2H), 3.46-3.52 (m, 1H), 3.34-3.39 (m, 1H), 2.20 (s, 3H), 1.46-1.53 (m, 1H), 0.81-0.86 (m, 2H), 0.68-0.71 (m, 2H). |

TABLE 2-continued

Characterization Data for Additional Exemplary Compounds

| Compound No. | Chemical Structure | [M + H] observed | ¹H NMR (400 MHz) |
|---|---|---|---|
| I-147 | 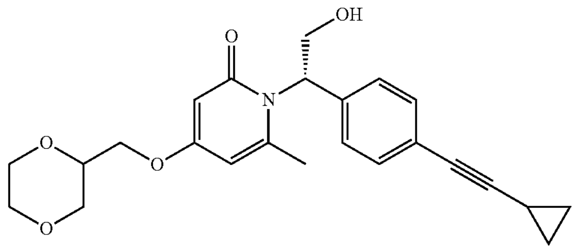 [SMILES: Cc1cc(OCC2COCCO2)cc(=O)n1[C@H](CO)c1ccc(C#CC2CC2)cc1] | 410.0 | ¹HNMR (400 MHz, CDCl₃) δ 7.30 (d, J = 8.4 Hz, 2H), 7.10 (d, J = 8.4 Hz, 2H), 5.89 (d, J = 2.0 Hz, 1H), 5.82 (d, J = 2.8 Hz, 1H), 5.51 (br., 1H), 4.47-4.56 (m, 1H), 4.25-4.28 (m, 1H), 3.92-3.98 (m, 2H), 3.79-3.89 (m, 4H), 3.74-3.77 (m, 1H), 3.63-3.69 (m, 1H), 3.48-3.54 (m, 1H), 2.24 (s, 3H), 1.40-1.46 (m, 1H), 0.82-0.88 (m, 2H), 0.76-0.80 (m, 2H). |
| I-76 | 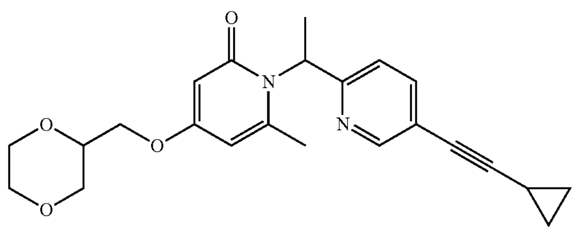 [SMILES: Cc1cc(OCC2COCCO2)cc(=O)n1C(C)c1ccc(C#CC2CC2)cn1] | 395.0 | ¹HNMR (400 MHz, DMSO-d₆) δ 8.43 (s, 1H), 7.71 (dd, J = 1.6 Hz, 8.0 Hz, 1H), 7.18 (d, J = 8.0 Hz, 1H), 5.89 (s, 1H), 5.55 (br, 2H), 3.73-3.89 (m, 5H), 3.57-3.67 (m, 2H), 3.43-3.50 (m, 1H), 3.31-3.37 (m, 1H), 2.00-2.42 (m, 3H), 1.78 (d, J = 6.8 Hz, 3H), 1.54-1.60 (m, 1H), 0.84-0.94 (m, 2H), 0.69-0.80 (m, 2H). |
| I-144 | 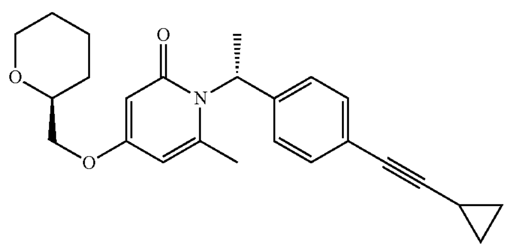 [SMILES: Cc1cc(OC[C@@H]2CCCCO2)cc(=O)n1[C@H](C)c1ccc(C#CC2CC2)cc1] | 392.0 | ¹HNMR (400 MHz, DMSO-d₆) δ 7.30 (d, J = 6.4 Hz, 2H), 7.07 (d, J = 8.4 Hz, 2H), 5.87 (s, 1H), 5.60 (br, 1H), 3.83-3.90 (m, 3H), 3.54-3.60 (m, 1H), 3.36-3.40 (m, 1H), 3.30-3.33 (m, 1H), 2.45-2.50 (m, 3H), 1.71-1.82 (m, 4H), 1.40-1.60 (m, 5H), 1.25-1.32 (m, 1H), 0.84-0.90 (m, 2H), 0.68-0.73 (m, 2H). |
| I-145 | 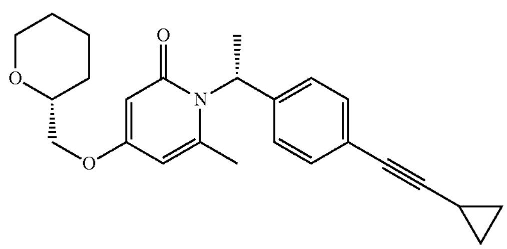 [SMILES: Cc1cc(OC[C@H]2CCCCO2)cc(=O)n1[C@H](C)c1ccc(C#CC2CC2)cc1] | 392.0 | ¹HNMR (400 MHz, DMSO-d₆) δ 7.30 (d, J = 7.2 Hz, 2H), 7.08 (d, J = 8.0 Hz 2H), 5.87 (s, 1H), 5.62 (br, 1H), 3.85-3.88 (m, 3H), 3.39-3.58 (m, 1H), 3.33-3.39 (m, 2H), 2.08-2.42 (m, 4H), 1.75-1.81 (m, 3H), 1.41-1.60 (m, 5H), 1.23-1.33 (m, 1H), 0.81-0.89 (m, 2H), 0.65-0.73 (m, 2H). |
| I-151 | 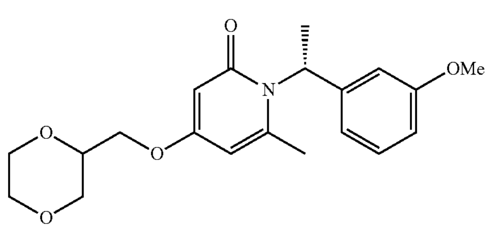 [SMILES: COc1cccc([C@@H](C)n2c(C)cc(OCC3COCCO3)cc2=O)c1] | 360.0 | ¹HNMR (400 MHz, DMSO-d₆) δ 7.24 (t, J = 7.6 Hz, 1H), 6.81 (d, J = 7.6 Hz, 1H), 6.67 (d, J = 7.6 Hz, 1H), 6.64 (s, 1H), 5.87 (s, 1H), 5.71 (br, 1H), 3.90-3.92 (m, 2H), 3.72-3.88 (m, 7H), 3.58-3.67 (m, 2H), 3.44-3.51 (m, 1H), 3.31-3.38 (m, 1H), 2.14 (br, 3H), 1.76 (d, J = 6.8 Hz, 3H). |
| I-152 | 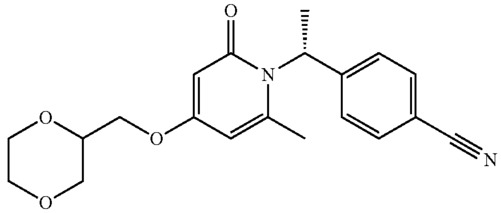 [SMILES: Cc1cc(OCC2COCCO2)cc(=O)n1[C@H](C)c1ccc(C#N)cc1] | 355.1 | ¹HNMR (400 MHz, DMSO-d₆) δ 7.77 (d, J = 7.2 Hz, 2H), 7.31 (d, J = 8.0 Hz, 2H), 5.94 (s, 1H), 5.57 (s, 1H), 3.89 (s, 2H), 3.73-3.82 (m, 3H), 3.58-3.67 (m, 2H), 3.45-3.51 (m, 1H), 3.32-3.37 (m, 2H), 2.39 (br, 3H), 1.80 (d, J = 6.8 Hz, 3H). |

TABLE 2-continued

Characterization Data for Additional Exemplary Compounds

| Compound No. | Chemical Structure | [M + H] observed | ¹H NMR (400 MHz) |
|---|---|---|---|
| I-35 | 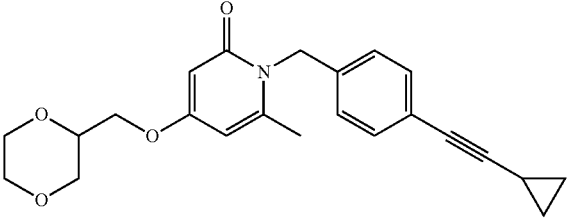 [SMILES: Cc1cc(OCC2COCCO2)cc(=O)n1Cc1ccc(C#CC2CC2)cc1] | 380.2 | ¹HNMR (400 MHz, CDCl₃) δ 7.29 (d, J = 8.0 Hz, 2H), 7.01 (d, J = 8.0 Hz, 2H), 5.86 (d, J = 2.3 Hz, 1H), 5.80 (d, J = 2.1 Hz, 1H), 5.23 (s, , 2H), 3.99 = 3.90 (m, 2H), 3.89 = 3.70 (m, 5H), 3.65 (td, J = 11.0, 3.2 Hz, 1H),3.55 -3.46 (m, 1H), 2.16 (s, 3H), 1.47 – 1.40 (m, 1H), 0.89 = 0.74 (m, 4H). |
| I-91 | 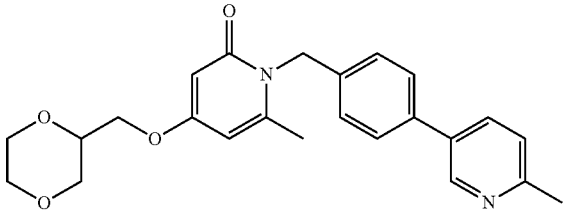 [SMILES: Cc1ccc(-c2ccc(Cn3c(C)cc(OCC4COCCO4)cc3=O)cc2)cn1] | 407.2 | ¹HNMR (400 MHz, CD₃OD) δ 8.63 (d, J = 1.9 Hz, 1H), 7.95 (dd, J = 8.1, 2.4 Hz, 1H), 7.61 (d, J = 8.5, 2H), 7.36 (d, J = 8.1 Hz, 1H), 7.25 (d, J = 8.4 Hz, 2H), 6.07 (d, J = 2.0 Hz, 1H), 5.94 (d, J = 2.7 Hz, 1H), 5.37 (s, 2H), 4.03 = 3.89 (m, 3H), 3.88 = 3.68 (m, 4H), 3.66 = 3.55 (m, 1H), 3.55 = 3.46 (m, 1H), 2.56 (s, 3H), 2.30 (s, 3H). |
| I-101 | 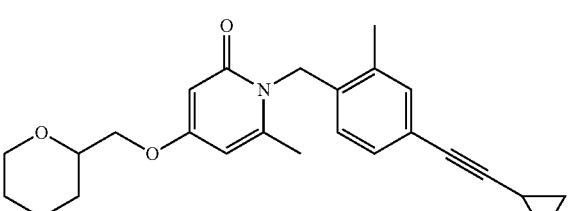 | 394.2 | ¹HNMR (400 MHz, CDCl₃) δ 7.20 (s, 1H), 7.10 (dd, J = 7.9, 1.3 Hz, 1H), 6.47 (d, J = 8.0 Hz, 1H), 6.06 (s, 1H), 5.94 (s, 1H), 5.18 (s, 2H), 4.01 = 3.90 (m, 3H), 3.89 = 3.72 (m, 4H), 3.66 (ddd, J = 15.3, 9.4, 4.1 Hz, 1H), 3.53 (dd, J = 11.4, 9.4 Hz, 1H), 2.31 (s, 3H), 2.14 (s, 3H), 1.42 (tt, J = 8.2, 5.1 Hz, 1H), 0.88 = 0.80 (m, 2H), 0.80 = 0.74 (m, 2). |
| I-73 | 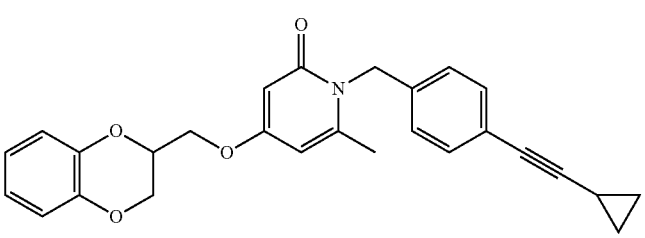 [SMILES: Cc1cc(OCC2COc3ccccc3O2)cc(=O)n1Cc1ccc(C#CC2CC2)cc1] | 428.2 | ¹HNMR (400 MHz, CDCl₃) δ 7.85 (s, 1H), 7.62 (d, J = 8.4 Hz, 1H), 6.51 = 6.46 (m, 2H), 4.41 (dd, J = 14.2, 3.8 Hz, 1H), 4.34 (dd, J = 14.2, 7.5 Hz, 1H), 4.24 (t, J = 12.1 Hz, 4H), 3.93 = 3.86 (m, 1H), 3.73 (dddd, J = 11.2, 7.4, 3.7, 2.2 Hz, 1H), 3.42 = 3.33 (m, 1H), 2.40 (s, 3H), 1.89= 1.80 (m, 1H), 1.70 = 1.61 (m, 1H), 1.57 = 1.44 (m, 3H), 1.31 – 1.18 (m, 1H). |
| I-31 | 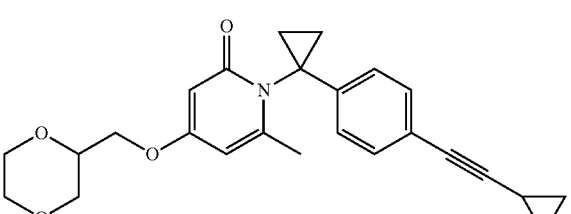 | 406.2 | ¹HNMR (400 MHz, CDCl₃) δ 7.25 (s, 2H), 6.77 (d, J = 8.4 Hz, 2H), 5.82 (dd, J = 2.4 Hz, 12.8 Hz, 2H), 3.65-3.97 (m, 8H), 3.53 (t, J = 10.0 Hz, 1H), 2.20 (s, 3H), 1.74-1.78 (m, 2H), 1.65-1.67 (m, 1H), 1.36-1.45 (m, 1H), 1.24-1.34 (m, 1H), 0.77-0.86 (m, 4 H). |
| I-153 | 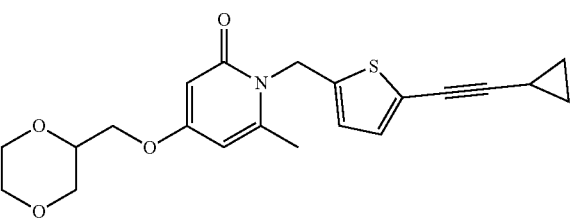 | 386.2 | ¹HNMR (400 MHz, DMSO-d₆) δ 7.77 (d, J = 7.2 Hz, 2H), 7.31 (d, J = 8.0 Hz, 2H), 5.94 (s, 1H), 5.57 (s, 1H), 3.89 (s, 2H), 3.73-3.82 (m, 3H), 3.58-3.67 (m, 2H), 3.45-3.51 (m, 1H), 3.32-3.37 (m, 2H), 2.39 (br, 3H), 1.80 (d, J = 6.8 Hz, 3H). |

TABLE 2-continued
Characterization Data for Additional Exemplary Compounds
| Compound No. | Chemical Structure | [M + H] observed | ¹H NMR (400 MHz) |
|---|---|---|---|
| I-154 | 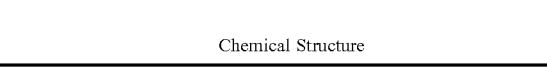 | 386.2 | ¹HNMR (400 MHz, DMSO-$d_6$) δ 7.48 (d, J = 1.4 Hz, 1H), 6.98 (d, J = 1.2 Hz, 1H), 5.90 (d, J = 2.1 Hz, 1H), 5.76 (d, J = 2.8 Hz, 1H), 5.20 (s, 2H), 3.97 – 3.87 (m, 2H), 3.85 – 3.71 (m, 3H), 3.68 – 3.56 (m, 2H), 3.53 – 3.43 (m, 1H), 3.40 – 3.29 (m, 1H, overlaps with H2O peak), 2.32 (s, 3H), 1.48 (tt, J = 8.2, 5.0 Hz, 1H), 0.89 – 0.81 (m, 2H), 0.72 – 0.64 (m, 2H). |
Example 2: Synthesis of I-61 and I-4
Synthetic Scheme of I-61 and I-4
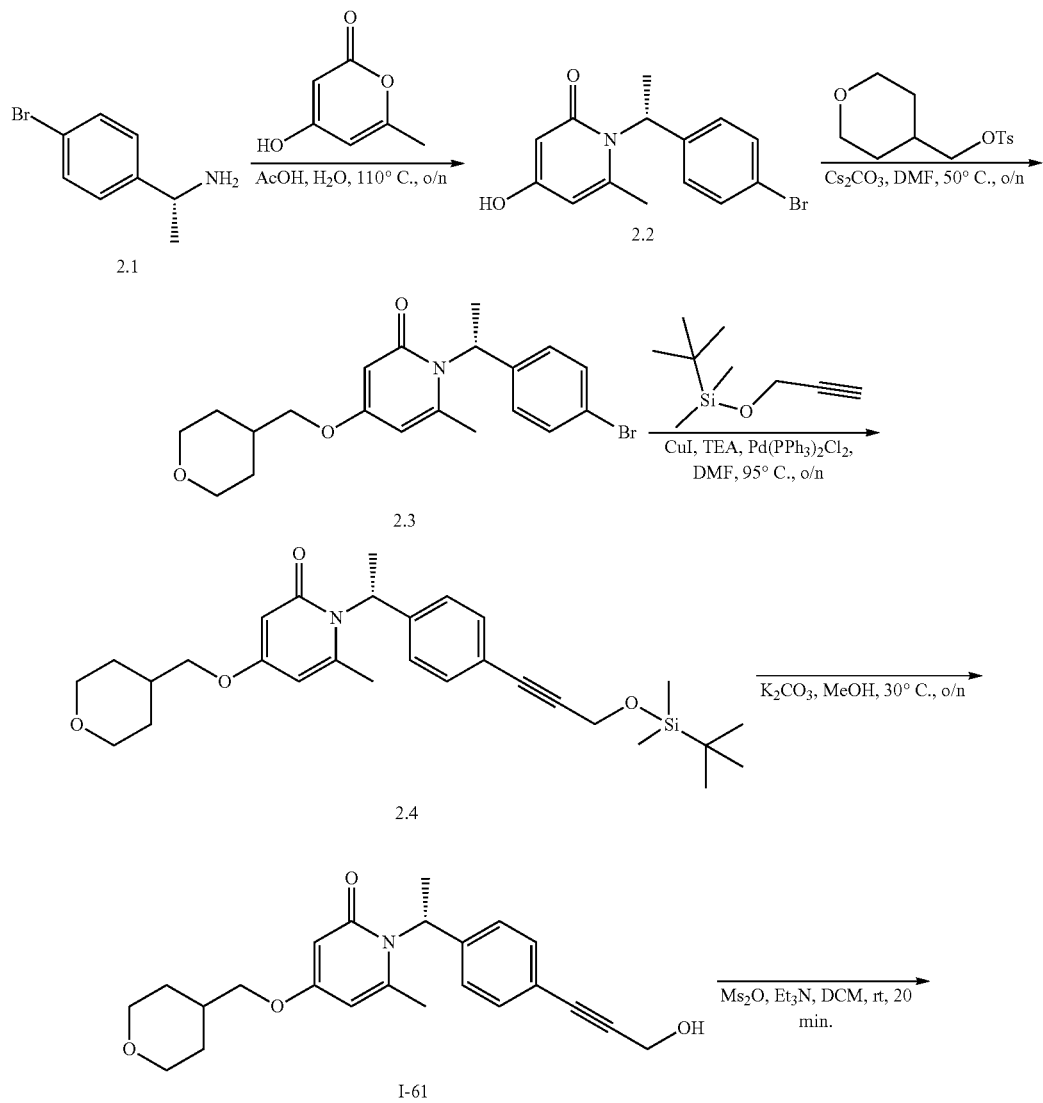

-continued

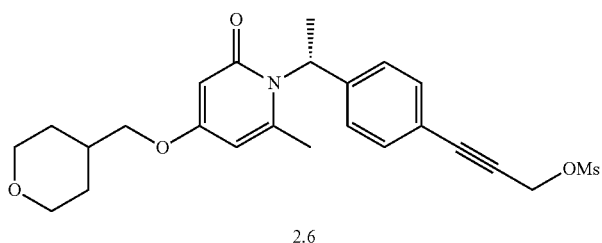 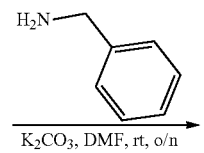

2.6

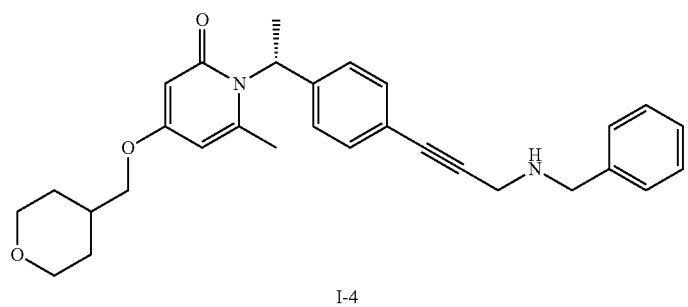

I-4

1. The Synthesis of Intermediate 2.2

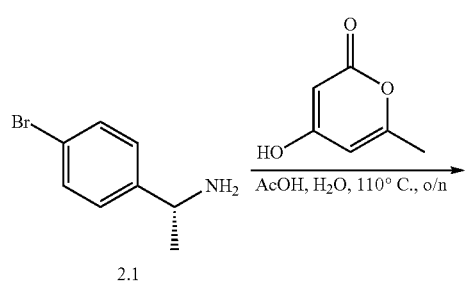

2.1

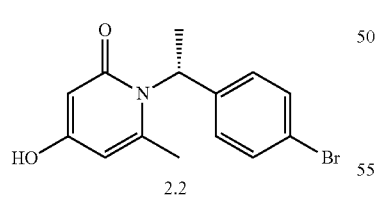

2.2

To a stirred solution of 2.1 (1.4 g, 7.0 mmol) in AcOH (20 mL) and water (10 mL) was added 4-hydroxy-6-methyl-2H-pyran-2-one (2.6 g, 21.0 mmol), the reaction mixture was stirred at 110° C. overnight. The suspension was diluted with H₂O (50 mL) and extracted with DCM (50 mL×2), concentrated. The crude product was purified by flash column chromatography (silica gel, DCM/MeOH=10:1) to give 2.2 (200 mg, yield: 9.2%) as a yellow solid. LC-MS m/z: 308.0 [M+H]⁺.

2. The Synthesis of Intermediate 2.3

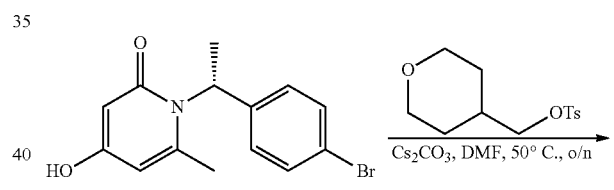

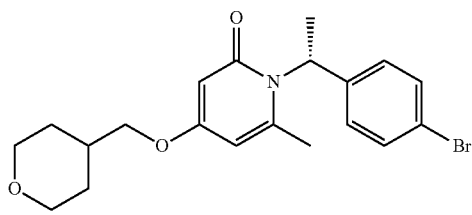

2.3

To a stirred solution of 2.2 (920 mg, 3.0 mmol), (tetrahydro-2H-pyran-4-yl)methyl 4-methylbenzenesulfonate (1.2 g, 4.5 mmol) in DMF (10 mL) was added Cs₂CO₃ (1.5 g, 4.5 mmol). The reaction mixture was stirred at 50° C. overnight until the reaction was complete (by LCMS). The suspension was diluted with H₂O (20 mL) and extracted with EA (20 mL×3), concentrated. The crude product was purified by flash column chromatography (silica gel, PE/EA=1:1) to give 2.3 (700 mg, yield: 57%) as a yellow solid. LC-MS m/z: 406.0 [M+H]⁺.

3. The Synthesis of Intermediate 2.4

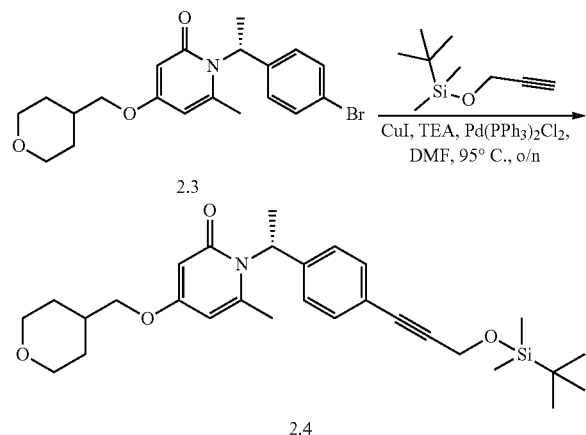 [SMILES: Cc1cc(OCC2CCOCC2)cc(=O)n1[C@H](C)c1ccc(Br)cc1 ; C#CCO[Si](C)(C)C(C)(C)C ; Cc1cc(OCC2CCOCC2)cc(=O)n1[C@H](C)c1ccc(C#CCO[Si](C)(C)C(C)(C)C)cc1]

To a stirred solution of 2.3 (450 mg, 1.1 mmol), tert-butyldimethyl(prop-2-yn-1-yloxy)silane (567 mg, 3.3 mmol) in DMF (5 mL) was added CuI (42 mg, 0.22 mmol) and Pd(PPh$_3$)$_2$Cl$_2$ (45 mg). The reaction mixture was stirred at 95° C. overnight. The suspension was diluted with H$_2$O (50 mL) and extracted with EA (10 mL×3), washed by NaCl (aq.), concentrated. The crude product was purified by flash column chromatography (silica gel, PE/EA=1:3) to give 2.4 (200 mg, yield: 36%) as brown oil. LC-MS m/z: 496.0 [M+H]$^+$.

4. The Synthesis of I-61

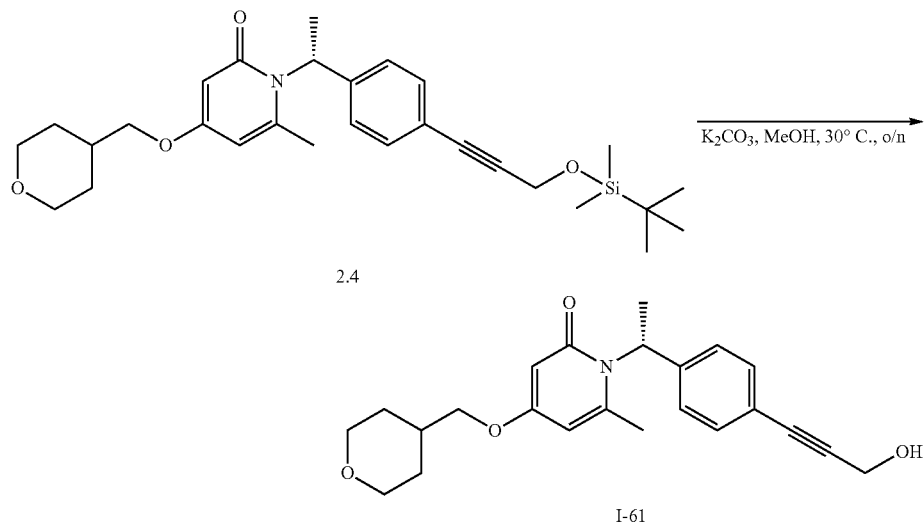

To a stirred solution of 2.4 (690 mg, 1.39 mmol) in MeOH (10 mL) was added K$_2$CO$_3$ (767 mg, 5.56 mmol). The reaction mixture was stirred at 30° C. overnight until the reaction was complete (by LCMS). The solvent was removed in vacuo, the suspension was diluted with H$_2$O (20 mL) and extracted with EA (20 mL×3), concentrated. The crude product was purified by flash column chromatography (silica gel, EA/PE=1:2) to give I-61 (400 mg, yield: 75%) as yellow oil.

5. The Synthesis of Intermediate 2.6

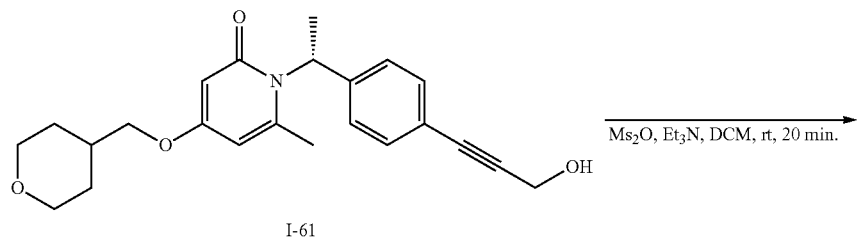

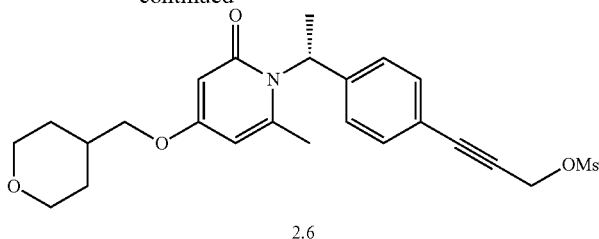

2.6

To a stirred solution of I-61 (100 mg, 0.26 mmol), TEA (80 mg, 0.79 mmol) in DCM (5 mL) was added Ms$_2$O (91 mg, 0.52 mmol). The reaction mixture was stirred at room temperature for 20 min. until the reaction was complete (by LCMS). The suspension was diluted with H$_2$O (10 mL) and extracted with DCM (10 mL×3), concentrated. The crude product was used to the next step directly without further purification.

6. The Synthesis of I-4

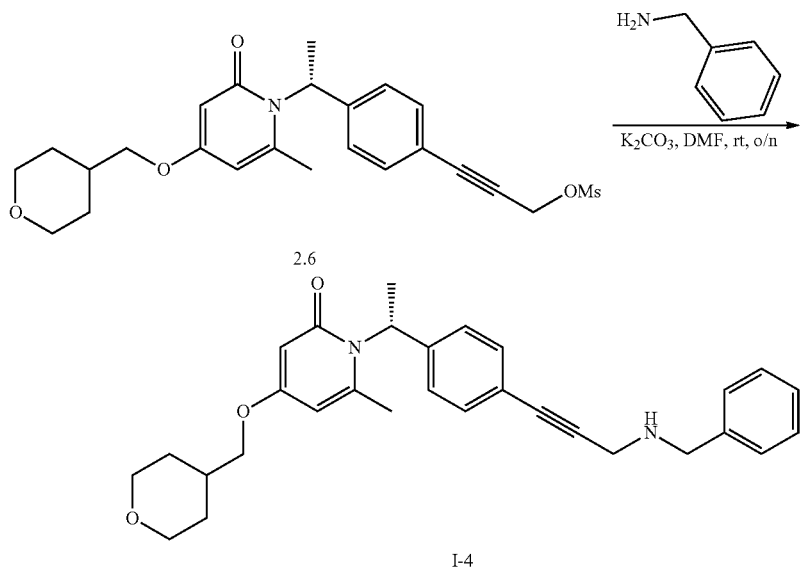

To a stirred solution of 2.6 (100 mg, 0.22 mmol), K$_2$CO$_3$ (90 mg, 0.65 mmol) in DMF (5 mL) was added phenylmethanamine (35 mg, 0.33 mmol). The reaction mixture was stirred at room temperature overnight until the reaction was complete (by LCMS). The suspension was diluted with H$_2$O (10 mL) and extracted with EA (20 mL×3), washed by NaCl (aq.), concentrated. The crude product was purified by Prep-PLC to give I-4 (40 mg, yield: 390) as a yellow solid.

Additional exemplary compounds were prepared following methods substantially similar to the method described above and herein. Data for these compounds are provided below.

TABLE 3

Characterization Data for Additional Exemplary Compounds

| Compound No. | Chemical Structure | [M + H] observed | $^1$H NMR (400 MHz) |
|---|---|---|---|
| I-117 | 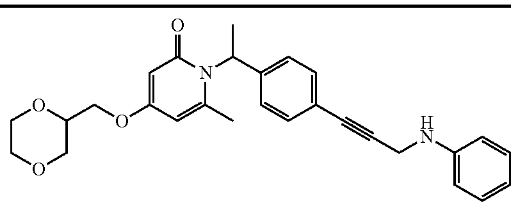 | 459.0 | $^1$H NMR (400 MHz, CDCl$_3$): δ 7.34 (d, J = 8.0 Hz, 2 H), 7.22 (t, J = 7.6 Hz, 2 H), 7.09 (d, J = 7.6 Hz, 2 H), 6.78 (t, J = 7.6 Hz, 1 H), 6.73 (d, J = 8.0 Hz, 2 H), 5.79 (s, 1 H), 5.73 (s, 1 H), 4.14 (s, 2 H), 3.62-3.96 (m, 9 H), 3.47-3.52 (m, 1 H), 2.05 (br, 3 H), 1.82 (s, 3 H). |

TABLE 3-continued

Characterization Data for Additional Exemplary Compounds

| Compound No. | Chemical Structure | [M + H] observed | $^1$H NMR (400 MHz) |
|---|---|---|---|
| I-14 | 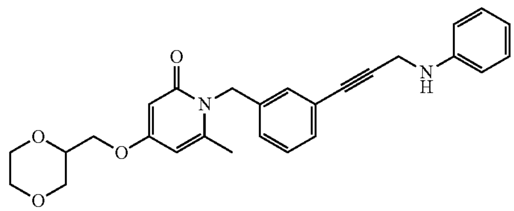 [SMILES: Cc1cc(OCC2COCCO2)cc(=O)n1Cc1cccc(C#CCNc2ccccc2)c1] | 445.0 | $^1$H NMR (400 MHz, CDCl$_3$): δ 7.20-7.28 (m, 4 H), 7.15 (s, 1 H), 7.07 (d, J = 8.0 Hz, 1 H), 6.78 (t, J = 7.2 Hz, 1 H), 6.72 (dd, J = 1.2 Hz, 8.4 Hz, 2 H), 5.87 (d, J = 2.8 Hz, 2 H), 5.82 (d, J = 2.0 Hz, 2 H), 5.22 (s, 2 H), 4.13 (s, 2 H), 3.73-4.00 (m, 8 H), 3.63-3.69 (m, 1 H), 3.49-3.54 (m, 1 H), 2.17 (s, 3 H). |
| I-4 | 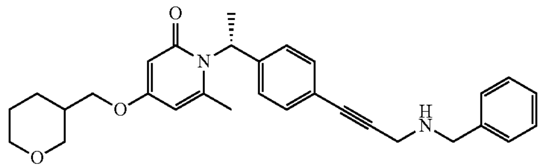 [SMILES: Cc1cc(OCC2CCCOC2)cc(=O)n1[C@H](C)c1ccc(C#CCNCc2ccccc2)cc1] | 471.0 | $^1$H NMR (400 MHz, DMSO-d$_6$): δ 7.31-7.40 (m, 6H), 7.24-7.27 (m, 1H), 7.13 (d, J = 8.0 Hz, 2H), 5.87 (s, 1H), 5.59 (br., 1H), 3.77-3.88 (m, 6H), 3.58 (s, 2H), 3.29-3.34. (m. 3H). 2.00-2.50. (m. 3H). 1.94-1.98 (ni, 1H), 1.77 (d, J = 6.4 Hz. 3H), 1.57-1.66 (m, 2H), 1.24-1.34 (m, 2H). |
| I-150 | 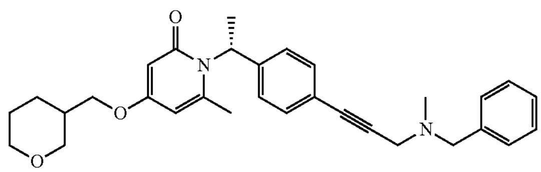 [SMILES: Cc1cc(OCC2CCCOC2)cc(=O)n1[C@H](C)c1ccc(C#CCN(C)Cc2ccccc2)cc1] | 485.0 | $^1$H NMR (400 MHz, DMSO-d$_6$): δ 7.42 (d, J = 7.2 Hz, 2H), 7.32-7.34 (m, 4H), 7.25-7.29 (m, 1H), 7.14 (d, J = 8.0 Hz, 2H), 5.87 (s, 1H), 5.60 (br., 1H), 3.86 (dd, J = 2.8 Hz, 11.2 Hz, 2H), 3.78 (d, J = 4.4 Hz, 2H), 3.57 (s, 2H), 3.49 (s, 2H), 3.24-3.34 (m, 3H), 2.49 (br., 3H), 2.26 (s, 3H), 1.92-2.01 (m, 1H), 1.78 (d, J = 5.6 Hz, 3H), 1.60-1.63 (m, 2H), 1.24-1.34 (m, 2H). |
| I-97 | 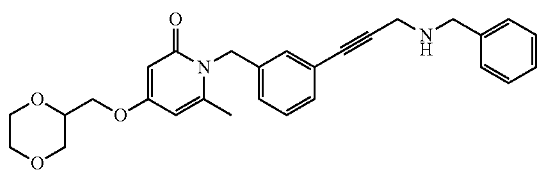 [SMILES: Cc1cc(OCC2COCCO2)cc(=O)n1Cc1cccc(C#CCNCc2ccccc2)c1] | 459.0 | $^1$HNMR (400 MHz, DMSO-d$_6$ + D$_2$O) δ 7.31-7.38 (m, 7H), 7.13-7.15 (m, 1H), 7.07 (s, 1H), 6.00 (d, J = 2.0 Hz, 1H), 5.83 (d, J = 2.8 Hz, 1H), 5.20 (s, 2H), 3.94-3.96 (m, 2H), 3.74-3.87 (m, 6H), 3.62 (d, J = 2.8 Hz, 1H), 3.49-3.52 (m, 3H), 3.35-3.40 (m, 1H), 2.20 (s, 3H). |
| I-123 | 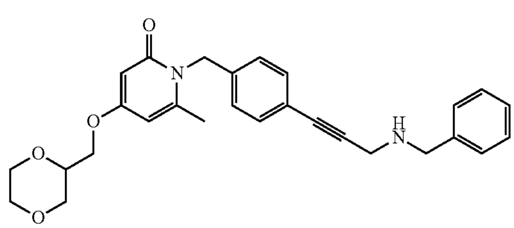 [SMILES: Cc1cc(OCC2COCCO2)cc(=O)n1Cc1ccc(C#CCNCc2ccccc2)cc1] | 459.3 | $^1$HNMR (400 MHz, DMSO-d$_6$) δ 7.29-7.40 (m, 6H), 7.21-7.24 (m, 1H), 7.08 (d, J = 8.0 Hz, 1H), 5.94 (d, J = 2 Hz, 1H), 5.80 (d, J = 2.8 Hz, 1H), 5.20 (s, 2H), 3.93-3.95 (m, 2H), 3.74-3.86 (m, 5H), 3.58-3.67 (m, 2H), 3.45-3.50 (m, 3H), 3.38 (d, J = 11.2 Hz, 1H), 2.63 (br, 1H), 2.18 (s, 3H). |
| I-61 | 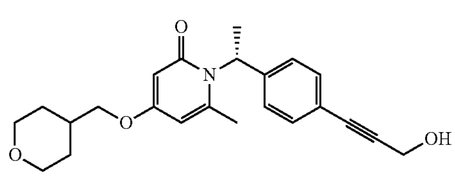 [SMILES: Cc1cc(OCC2CCOCC2)cc(=O)n1[C@H](C)c1ccc(C#CCO)cc1] | 382.3 | $^1$H NMR (400 MHz, CDCl$_3$): δ 7.38 (d, J = 8.0 Hz, 2H), 7.14 (d, J = 8.0 Hz, 2H), 5.82 (br., 1H), 5.70 (s, 1H), 4.49 (d, J = 6.4 Hz, 2H) 4.01 (dd, J = 3.2 Hz, 11.2 Hz, 2H), 3.75 (d, J = 6.0 Hz, 2H), 3.40-3.46 (m, 2H), 1.98-2.07 (m, 2H), 1.78-1.90 (m, 4H), 1.68-1.71 (m, 2H), 1.51 (s, 3H), 1.39-1.49 (m, 2H). |

TABLE 3-continued

Characterization Data for Additional Exemplary Compounds

| Compound No. | Chemical Structure | [M + H] observed | $^1$H NMR (400 MHz) |
|---|---|---|---|
| I-83 | 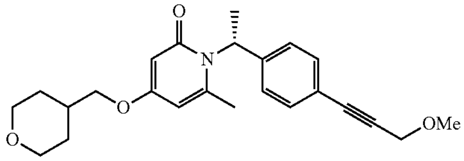 [SMILES: COCC#Cc1ccc([C@@H](C)n2c(C)cc(OCC3CCOCC3)cc2=O)cc1] | 396.3 | $^1$H NMR (400 MHz, DMSO-d$_6$): δ 7.41 (d, J = 7.6 Hz, 2H), 7.14 (d, J = 8.0 Hz, 2H), 5.87 (s, 1H), 5.53 (br., 1H), 4.31 (s, 2H), 3.86 (dd, J = 2.8 Hz, 11.2 Hz, 2H), 3.78 (d, J = 5.6 Hz, 2H), 3.28-3.34 (m, 6H), 2.50 (s, 3H), 1.93-1.98 (m, 1H), 1.78 (d, J = 6.4 Hz, 3H), 1.60-1.63 (m, 2H), 1.24-1.34 (m, 2H). |
| I-149 | 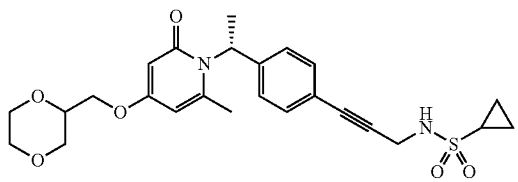 [SMILES: Cc1cc(OCC2COCCO2)cc(=O)n1[C@H](C)c1ccc(C#CCNS(=O)(=O)C2CC2)cc1] | 486.8 | $^1$HNMR (400 MHz, CDCl$_3$) δ 7.35 (d, J = 8.4 Hz, 2H), 7.14 (d, J = 8.0 Hz, 2H), 5.76 (s, 2H), 4.48 (t, J= 5.6 Hz, 1H), 4.18 (d, J = 6.4 Hz, 2H), 3.65-3.97 (m, 9H), 3.48-3.53 (m, 1H), 2.56-2.60 (m, 1H), 1.86 (d, J = 2.4 Hz, 3H), 1.56 (s, 3H), 1.22-1.27 (m, 2H), 1.02-1.07 (m, 2H). |

Example 3: Synthesis of I-148

1. The Synthesis of I-148

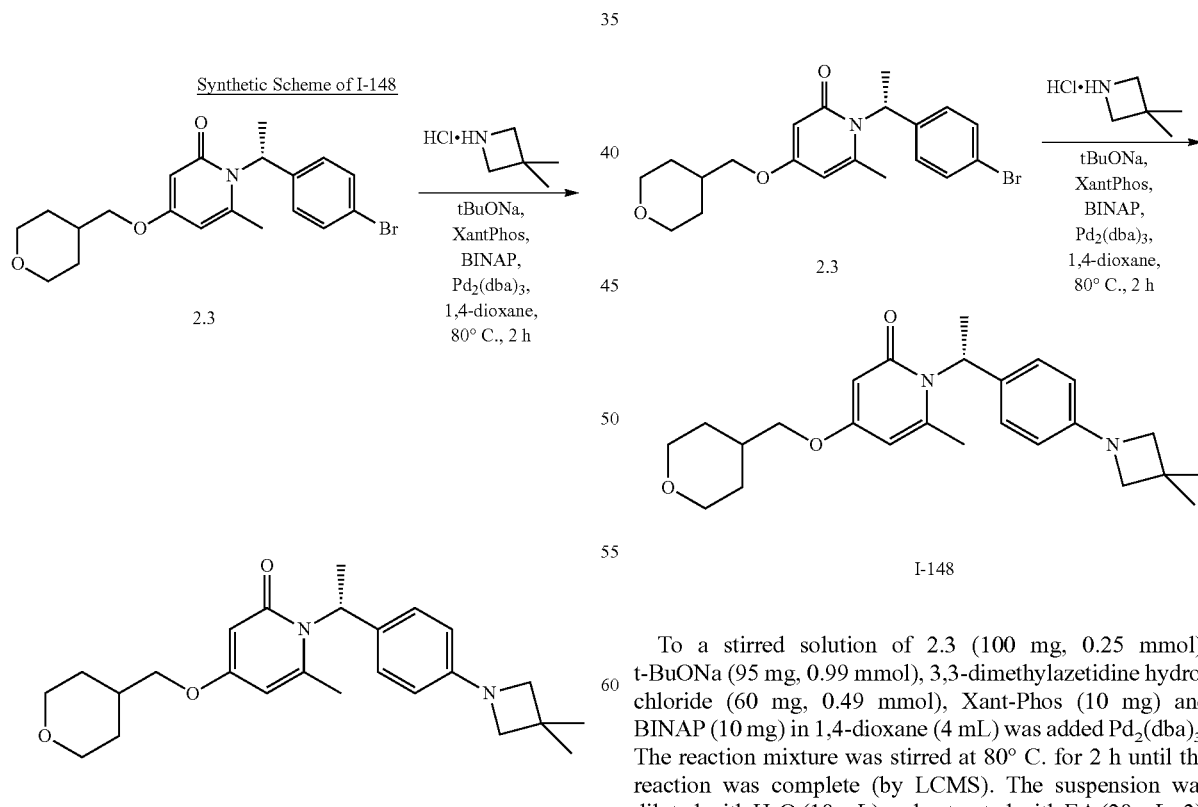

To a stirred solution of 2.3 (100 mg, 0.25 mmol), t-BuONa (95 mg, 0.99 mmol), 3,3-dimethylazetidine hydrochloride (60 mg, 0.49 mmol), Xant-Phos (10 mg) and BINAP (10 mg) in 1,4-dioxane (4 mL) was added Pd$_2$(dba)$_3$. The reaction mixture was stirred at 80° C. for 2 h until the reaction was complete (by LCMS). The suspension was diluted with H$_2$O (10 mL) and extracted with EA (20 mL×3), concentrated. The crude product was purified by Prep-HPLC to give I-148 (50 mg, yield: 49.5%) as a white solid.

Additional exemplary compounds were prepared following methods substantially similar to the method described above and herein. Data for these compounds are provided below.

TABLE 4

Characterization Data for Additional Exemplary Compounds

| Compound No. | Chemical Structure | [M + H] observed | $^1$H NMR (400 MHz) |
|---|---|---|---|
| I-148 | 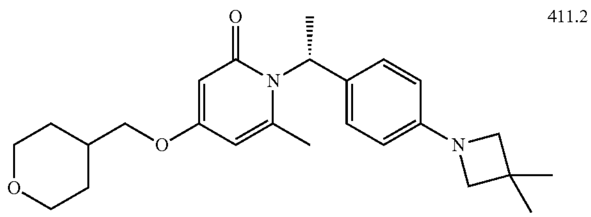 | 411.2 | $^1$H NMR (400 MHz, DMSO-d$_6$): δ 6.94 (d, J = 8.0 Hz, 2H), 6.35 (d, J = 8.0 Hz, 2H), 5.78 (s, 1H), 5.65 (br, 1H), 3.86 (dd, J = 3.2 Hz, 11.2 Hz, 2H), 3.78 (d, J = 6.0 Hz, 2H), 3.48 (s, 4H), 3.28-3.33 (m, 3H), 2.50 (s, 3H), 1.92-1.96 (m, 1H), 1.71 (d, J = 6.0 Hz, 3H), 1.60-1.63 (m, 2H), 1.24-1.34 (m, 8H). |
| I-146 | 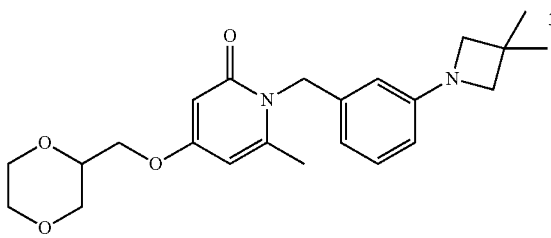 | 399.5 | $^1$HNMR (400 MHz, DMSO-d$_6$) δ 7.07 (t, J = 7.6 Hz, 1H), 6.25-6.30 (m, 2H), 6.13 (s, 1H), 5.91 (d, J = 2.4 Hz, 1H), 5.78 (d, J = 2.8 Hz, 1H), 5.11 (s, 2H), 3.93-3.96 (m, 2H), 3.80-3.84 (m, 3H), 3.67-3.77 (m, 2H), 3.45-3.51 (m, 1H), 3.39 (s, 4H), 3.37 (d, J = 11.2 Hz, 1H), 2.18 (s, 3H) , 1.26 (s, 6H). |
| I-116 | 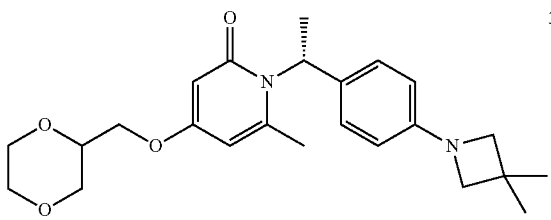 | 399.0 | $^1$HNMR (400 MHz, DMSO-d$_6$) δ 6.94 (d, J = 8.4 Hz, 2H), 6.33 (d, J = 8.4 Hz, 2H), 5.87 (d, J = 2.4 Hz, 1H), 5.76 (d, J = 2.8 Hz, 1H), 5.05 (s, 2H), 3.91-3.93 (m, 2H), 3.73-3.80 (m, 3H), 3.60-3.67 (m, 2H), 3.46-3.50 (m, 5H), 3.35-3.37 (m, 1H), 2.20(s, 3H), 1.25 (s, 6H). |

Example 4: Synthesis of I-113

Synthetic Scheme of I-113

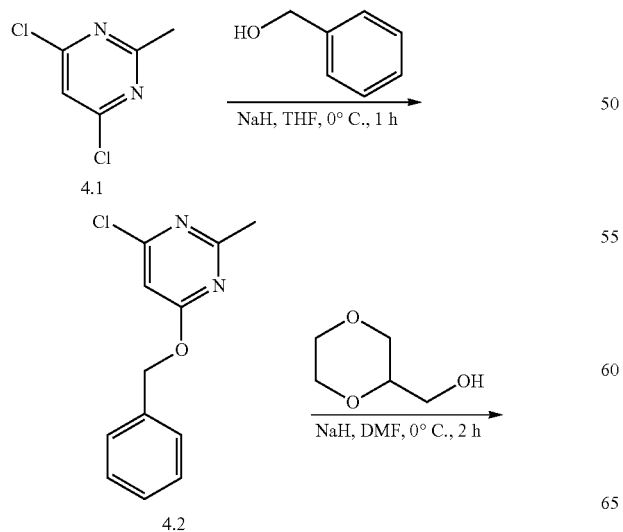

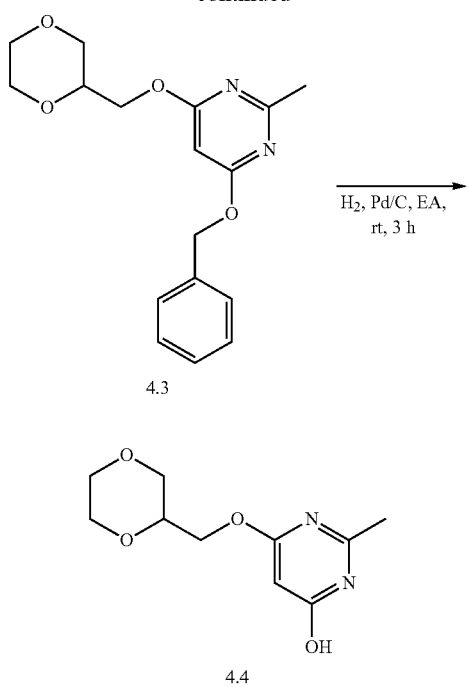

2. The Synthesis of Intermediate 4.3

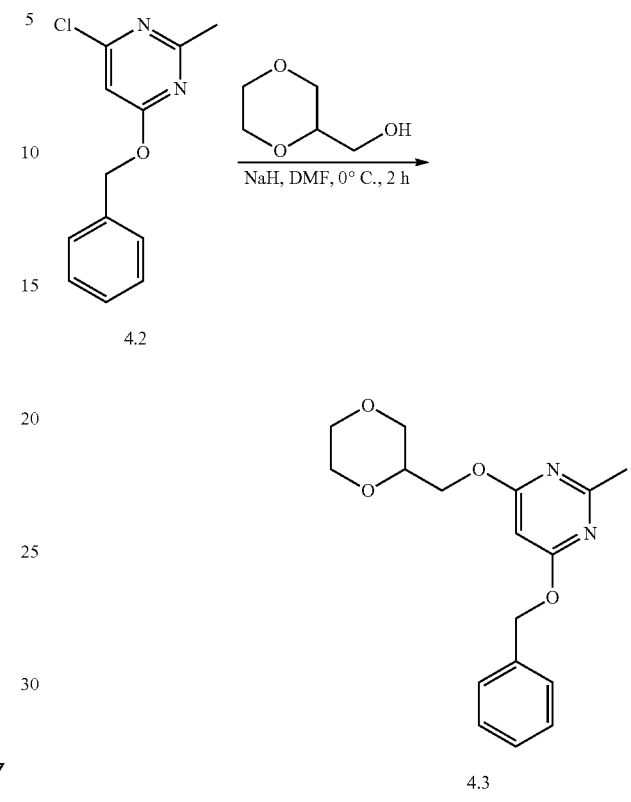

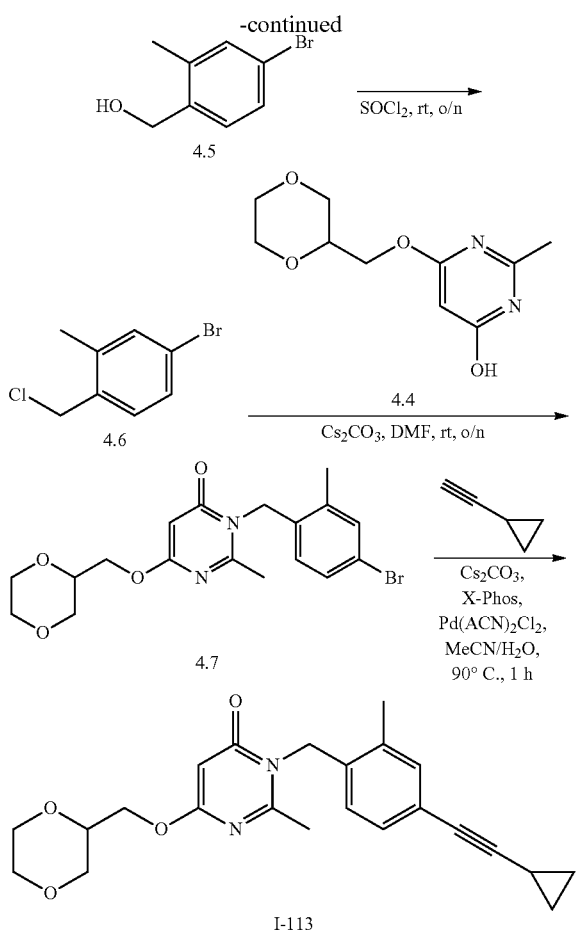

To a stirred solution of (1,4-dioxan-2-yl)methanol (392 mg, 3.3 mmol) in DMF (5 mL) was added NaH (60%, 222 mg, 5.5 mmol) at 0° C. The solution was stirred at 0° C. for 10 min then a solution of 4.2 (650 mg, 2.8 mmol) in DMF (5 mL) was added slowly and the mixture stirred at 0° C. for 2 h. The suspension was diluted with H₂O (30 mL) and extracted with DCM (30 mL×2), concentrated. The residue was purified by Prep-HPLC to give 4.3 (200 mg, yield: 23%) as a white solid. LC-MS m/z: 317.3 [M+H]⁺.

3. The Synthesis of Intermediate 4.4

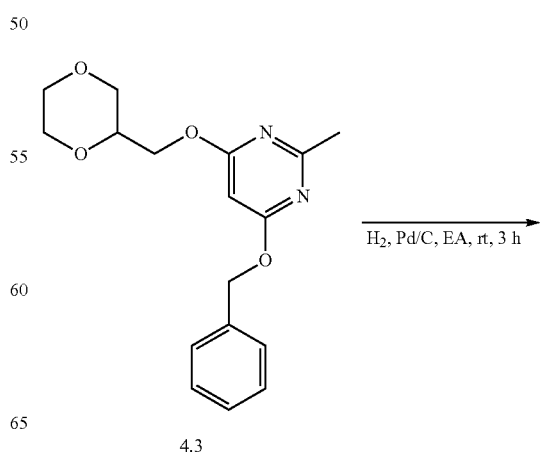

1. The Synthesis of Intermediate 4.2

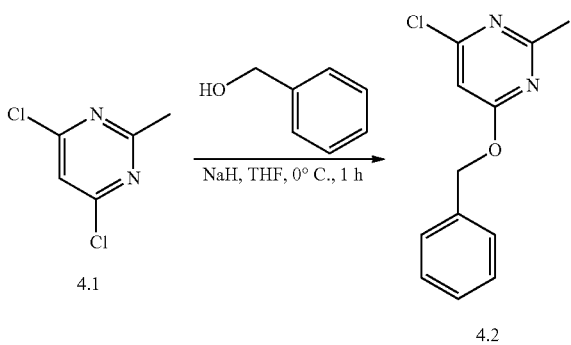

To a stirred solution of phenylmethanol (1.3 g, 12.3 mmol) in THF (20 mL) was added NaH (60%, 736 mg, 18.4 mmol) at 0° C. The mixture was stirred at 0° C. for 10 min then a solution of 4.1 (2.0 g, 12.3 mmol) in THF (10 mL) was added slowly and the mixture was stirred at 0° C. for 1 h until the reaction was complete (by LCMS). The suspension was diluted with H₂O (30 mL) and extracted with DCM (30 mL×2), concentrated. The residue was purified by Prep-HPLC to give 4.2 (850 mg, yield: 28%) as a white solid. LC-MS m/z: 235.2 [M+H]⁺.

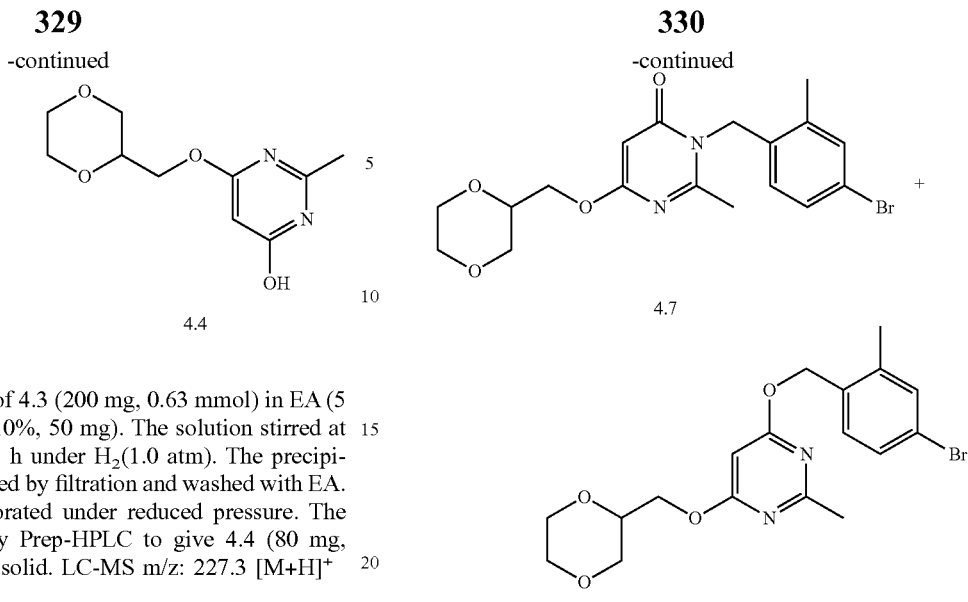

To a stirred solution of 4.3 (200 mg, 0.63 mmol) in EA (5 mL) was added Pd/C (10%, 50 mg). The solution stirred at room temperature for 3 h under $H_2$ (1.0 atm). The precipitated solids were removed by filtration and washed with EA. The organic was evaporated under reduced pressure. The residue was purified by Prep-HPLC to give 4.4 (80 mg, yield: 56%) as a white solid. LC-MS m/z: 227.3 $[M+H]^+$

4. The Synthesis of Intermediate 4.6

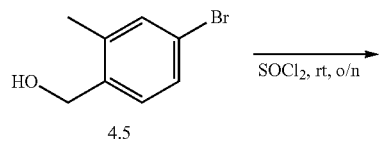

A solution of 4.5 (1.0 g, 4.97 mmol) in $SOCl_2$ (20 mL) was stirred at room temperature overnight. The mixture was evaporated under reduced pressure. $H_2O$ (30 mL) and EA (30 mL) were added and the organic phase was evaporated under reduced pressure to give 4.6 (800 mg crude). The crude resulting mixture was used in the next step directly without further purification.

5. The Synthesis of Intermediate 4.7

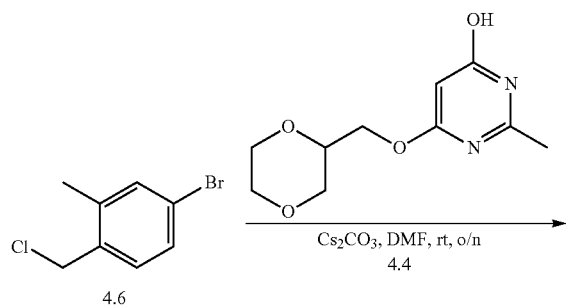

To a stirred solution of 4.6 (466 mg, 2.1 mmol) in DMF (10 mL) was added 4.4 (400 mg, 1.8 mmol) and $Cs_2CO_3$ (1600 mg, 4.9 mmol). The solution was stirred at RT overnight. $H_2O$ (10 mL) and EA (20 mL) was added and the organic phase was evaporated under reduced pressure. The residue was purified by Prep-HPLC to give 4.7 (160 mg, yield: 22%) as yellow oil and 4.7a (400 mg, yield: 56%) as yellow oil.

6. The Synthesis of Intermediate I-113

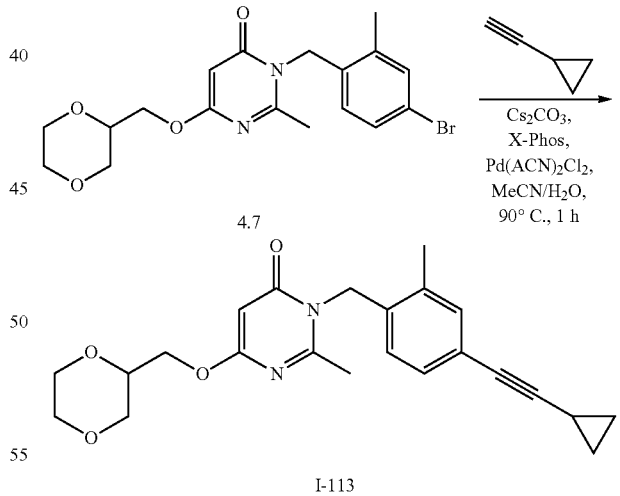

To a stirred solution of 4.7 (160 mg, 0.39 mmol) in MeCN (2 mL) and $H_2O$ (1 mL) was added $Cs_2CO_3$ (381 mg, 1.17 mmol), X-Phos (37.2 mg, 0.078 mmol) and $Pd(ACN)_2Cl_2$ (10.1 mg, 0.039 mmol). The solution was stirred at 90° C. for 1 h until the reaction was complete (by LCMS). The suspension was diluted with $H_2O$ (10 mL) and extracted with DCM (20 mL×2), concentrated. The residue was purified by Prep-HPLC to give I-113 (80.17 mg, yield: 52.00%) as brown oil.

Additional exemplary compounds were prepared following methods substantially similar to the method described above and herein. Data for these compounds are provided below.

TABLE 5

Characterization Data for Additional Exemplary Compounds

| Compound No. | Chemical Structure | [M + H] observed | $^1$H NMR (400 MHz) |
|---|---|---|---|
| I-34 | 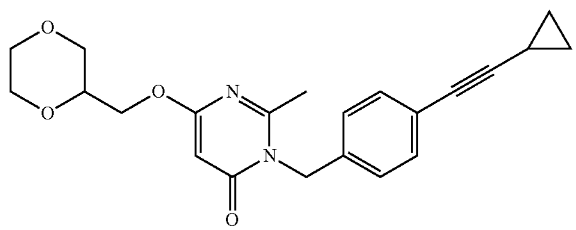 | 381.3 | $^1$H NMR (400 MHz, CDCl$_3$) δ 7.33 (d, J = 8.0 Hz, 2H), 7.07 (d, J = 8.4 Hz, 2H), 5.73 (s, 1H), 5.23 (s, 2H), 4.08-4.19 (m, 2H), 3.93-3.99 (m, 1H), 3.62-3.89 (m, 5H), 3.48-3.53 (m, 1H), 2.38 (s, 3H), 1.40-1.47 (m, 1H), 0.77-0.89 (m, 4H). |
| I-113 | 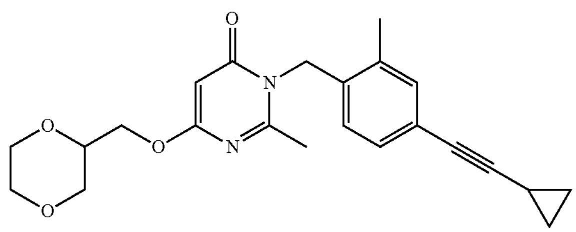 [SMILES: Cc1cc(C#CC2CC2)ccc1Cn1c(C)nc(OCC2COCCO2)cc1=O] | 395.0 | $^1$H NMR (400 MHz, CDCl$_3$) δ 7.22 (s, 1 H), 7.13 (dd, J = 1.2 Hz, 6.8 Hz, 1 H), 6.55 (d, J = 8.0 Hz, 1 H), 5.74 (s, 1 H), 5.18 (s, 2 H), 4.10-4.21 (m, 2 H), 3.97-4.00 (m, 1 H), 3.64-3.90 (m, 5 H), 3.50-3.55 (m, 1 H), 2.32 (s, H), 1.39-1.45 (m, 1 H), 0.76-0.88 (m, 4 H). |
| I-13 | 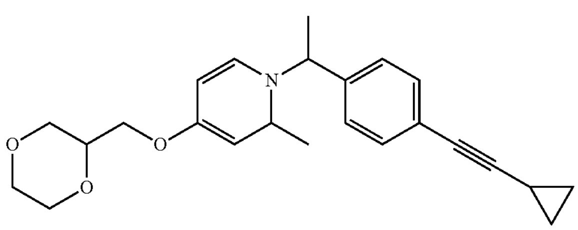 [SMILES: CC1C=C(OCC2COCCO2)C=CN1C(C)c1ccc(C#CC2CC2)cc1] | 380.3 | $^1$H NMR (400 MHz, DMSO-d$_6$) δ 7.46 (d, J = 7.6 Hz, 1H), 7.33 (d, J = 8.4 Hz, 2H), 7.19 (d, J = 8.4 Hz, 2H), 6.05 (q, J = 7.2 Hz, 1H), 5.97 (dd, J = 8.0 Hz, 2.8 Hz, 1H), 5.81 (d, J = 2.8 Hz, 1H), 3.90-3.95 (m, 2H), 3.32-3.85 (m, 7H), 1.62 (d, J = 11.2 Hz, 3H), 1.48-1.55 (m, 1H), 0.86-0.88 (m, 2H), 0.70-0.73 (m, 2H). |
| I-23 | 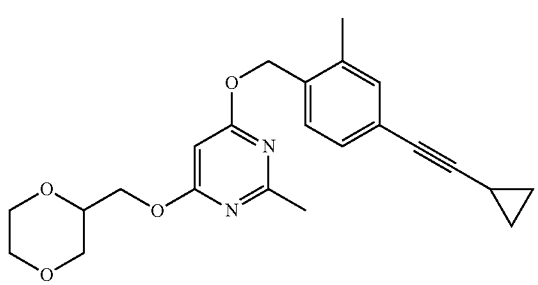 [SMILES: Cc1nc(OCc2ccc(C#CC3CC3)cc2C)cc(OCC2COCCO2)n1] | 395.1 | $^1$H NMR (400 MHz, CDCl$_3$) δ 7.27 (d, J = 3.6 Hz, 1 H), 7.18-7.22 (m, 2 H), 5.94 (s, 1 H), 5.31 (s, 2 H), 4.26-4.35 (m, 2 H), 3.92-3.97 (m, 1 H), 3.61-3.86 (m, 5 H), 3.46-3.51 (m, 1 H), 2.50 (s, 3 H), 2.32 (s, 3 H), 1.40-1.46 (m, 1 H), 0.77-0.88 (m, 4 H). |
| I-77 | 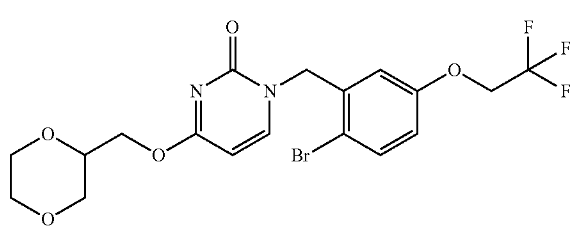 [SMILES: O=c1nc(OCC2COCCO2)ccn1Cc1cc(OCC(F)(F)F)ccc1Br] | 479.2 | $^1$H NMR (400 MHz, DMSO-d$_6$) δ 8.00 (d, J = 7.2 Hz, 1 H), 7.64 (d, J = 8.8 Hz, 1 H), 7.02 (d, J = 8.8 Hz, 1 H), 6.61 (d, J = 2.8 Hz, 1 H), 6.11 (d, J = 6.8 Hz, 1 H), 4.98 (s, 2 H), 4.76 (q, J = 8.8 Hz, 2 H), 4.24 (d, J = 4.8 Hz, 2 H), 3.71-3.89 (m, 3 H), 3.56-3.69 (m, 2 H), 3.45-3.52 (m, 1 H), 3.35-3.40 (m, 1 H). |

TABLE 5-continued
Characterization Data for Additional Exemplary Compounds
| Compound No. | Chemical Structure | {M + H} observed | $^1$H NMR (400 MHz) |
|---|---|---|---|
| I-92 | 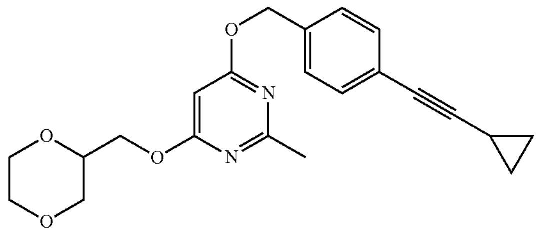 [SMILES: Cc1nc(OCc2ccc(C#CC3CC3)cc2)cc(OCC2COCCO2)n1] | 381.3 | $^1$H NMR (400 MHz, CDCl$_3$) δ 7.30-7.38 (m, 4H), 5.95 (s, 1H), 5.32 (s, 2H), 4.27-4.35 (m, 2H), 3.92-3.98 (m, 1H), 3.62 – 3.86 (m, 5H), 3.46-3.51 (m, 1H), 2.50 (s, 3H), 1.41-1.48 (m, 1H), 0.78-0.89 (m, 4H). |
Example 5: Synthesis of I-155
Synthetic Scheme of I-155
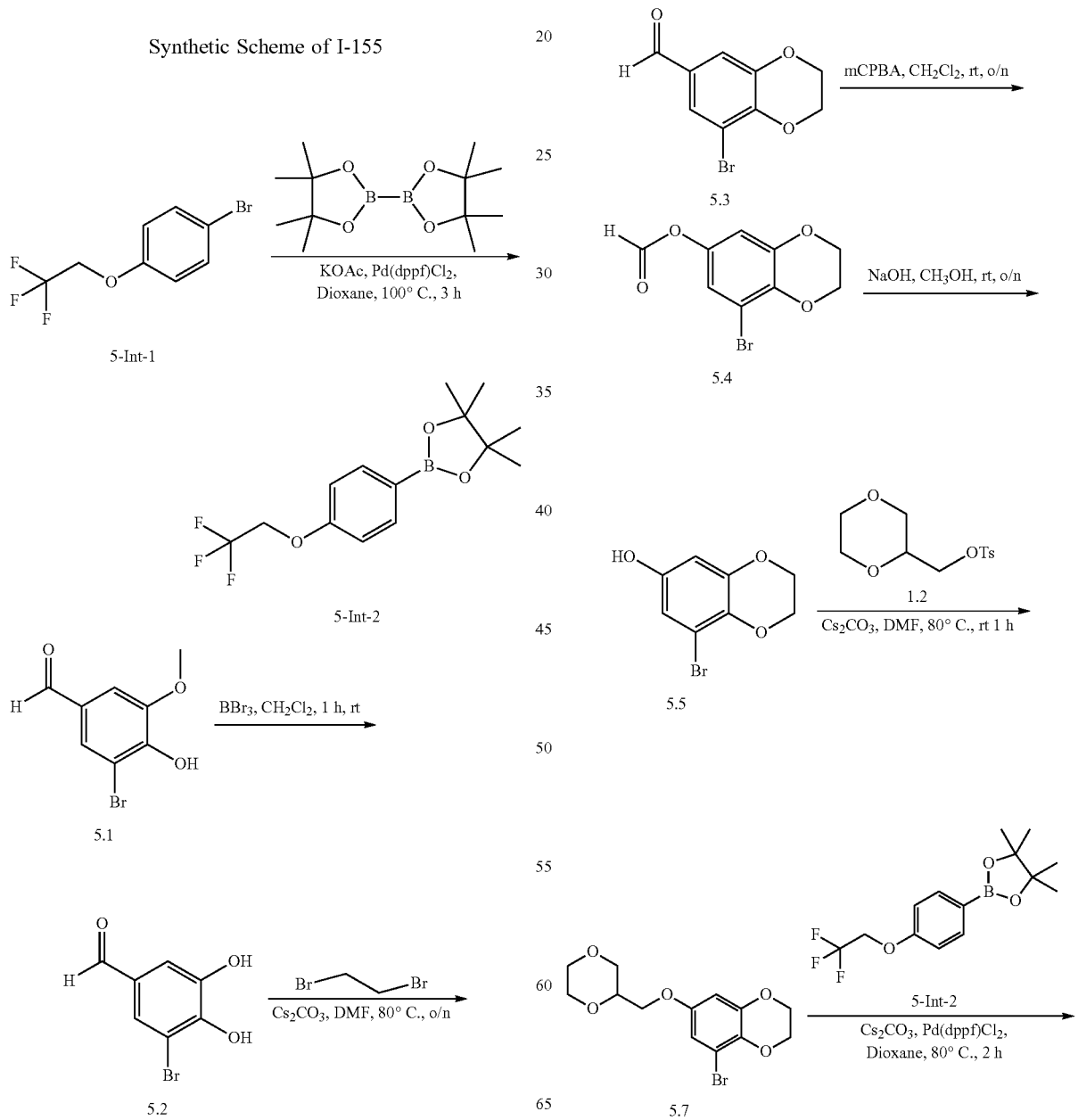

1. The Synthesis of Intermediate 5-Int-2

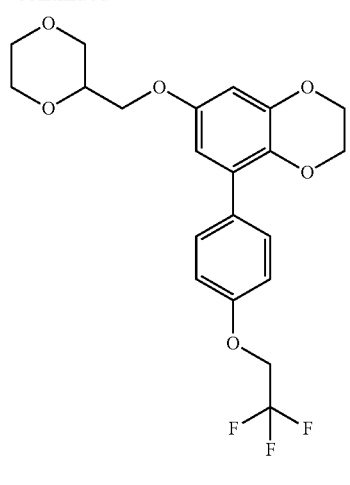

I-155

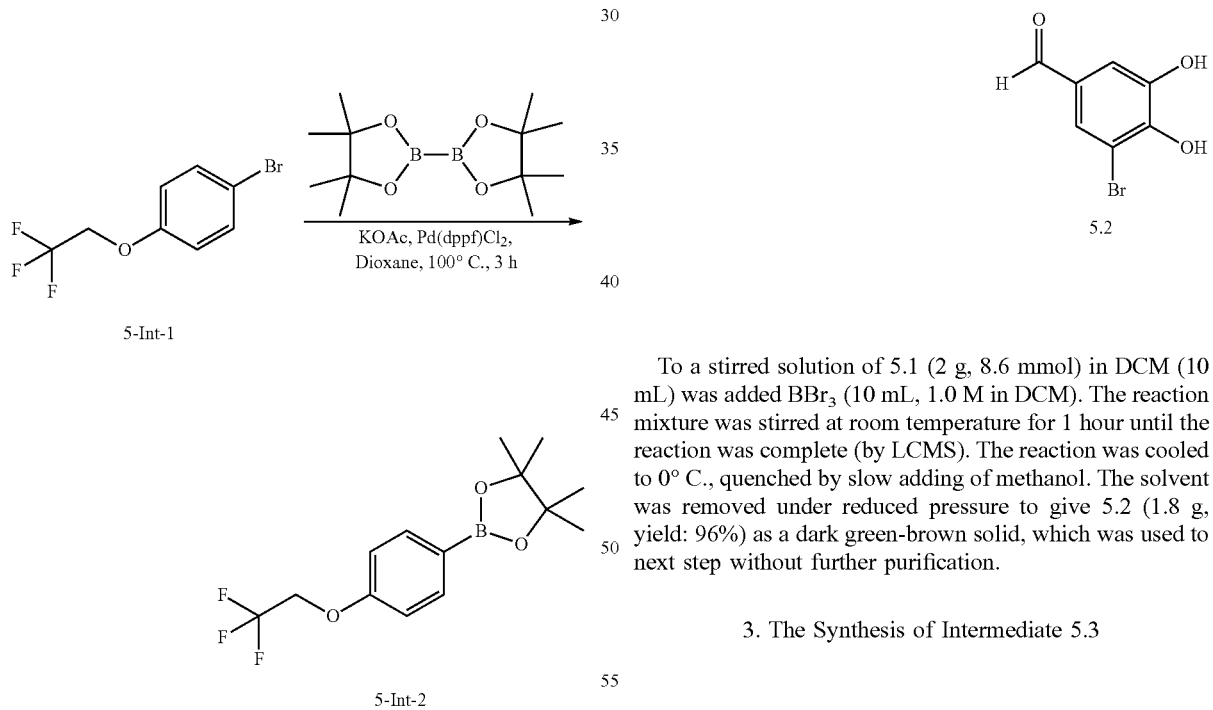

5-Int-1

5-Int-2

To a stirred solution of compound 5-Int-1 (15.0 g, 58.8 mmol) in dioxane (150 mL) was added 4,4,4',4',5,5,5',5'-octamethyl-2,2'-bi(1,3,2-dioxaborolane) (29.9 g, 117.6 mmol), KOAc (17.3 g, 176.4 mmol) and Pd(dppf)Cl$_2$ (2.15 g, 2.94 mmol) under N$_2$ atmosphere. The resulting reaction mixture was heated to 100° C. and stirred for 3 h, then concentrated in vacuo to remove the solvent. Water (500 mL) was added, the mixture was extracted with EA (500 mL×2). The combined organic layers were washed with brine (250 mL×2), dried over anhydrous Na$_2$SO$_4$, filtered and concentrated. The residue was purified by column chromatography (silica gel, PE/EA=5:1) to give 5-Int-2 (14.2 g, yield: 79.9%) as yellow oil. LC-MS m/z: 303.2 [M+H]$^+$.

2. The Synthesis of Intermediate 5.2

To a stirred solution of 5.1 (2 g, 8.6 mmol) in DCM (10 mL) was added BBr$_3$ (10 mL, 1.0 M in DCM). The reaction mixture was stirred at room temperature for 1 hour until the reaction was complete (by LCMS). The reaction was cooled to 0° C., quenched by slow adding of methanol. The solvent was removed under reduced pressure to give 5.2 (1.8 g, yield: 96%) as a dark green-brown solid, which was used to next step without further purification.

3. The Synthesis of Intermediate 5.3

5. The Synthesis of Intermediate 5.5

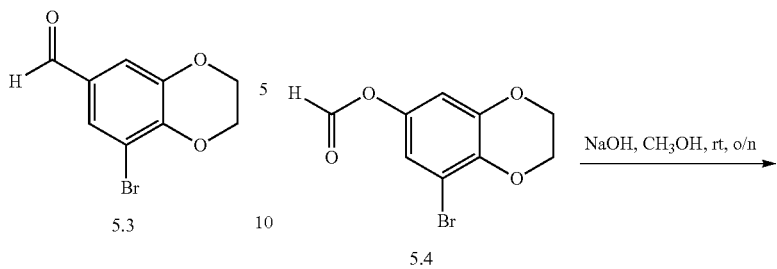

To a solution of 5.2 (1.8 g, 8.3 mmol) in DMF (20 ml) was added cesium carbonate (8.1 g, 24.9 mol). The mixture was stirred at ambient temperature for 30 min, then 1,2-dibromoethane (1.85 g, 9.96 mol) was added. After heating at 80° C. overnight, the solvent was removed under reduced pressure. The residue was partitioned between water and ethyl acetate, and the organic layer was washed with brine and dried. The crude product was purified by flash column chromatography (silica gel, PE/EA=4:1) to give 5.3 (650 mg, yield: 32%) as an off-white solid.

4. The Synthesis of Target 5.4

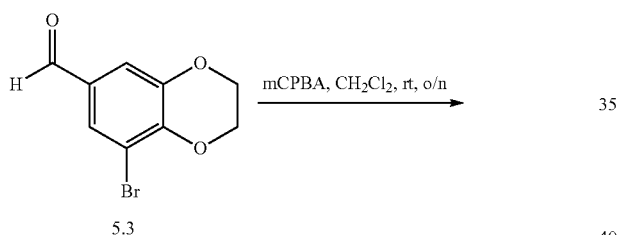

To a stirred solution of 5.3 (550 mg, 2.27 mmol) in DCM (10 mL) was added mCPBA (586 mg, 3.4 mmol). The reaction mixture was stirred at room temperature overnight until the reaction was complete (by LCMS). The suspension was diluted with Na$_2$SO$_3$ (10 mL, aq.) and extracted with DCM (20 mL×2), concentrated to give 5.4 as yellow oil (crude, 600 mg, yield: 100%), which was used to next step without further purification.

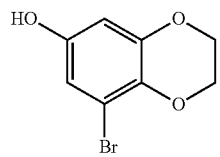

To a stirred solution of 5.4 (600 mg, 2.3 mmol) in CH$_3$OH (10 mL) was added NaOH (4.0 M, 2 mL). The reaction mixture was stirred at room temperature overnight until the reaction was complete (by LCMS). The suspension was diluted with 1N HCl to pH=5-6, extracted with DCM (20 mL×2), concentrated. The crude product was purified by flash column chromatography (silica gel, PE/EA=2:1) to give 5.5 (240 mg, yield: 45%) as an off-white solid. $^1$H NMR (400 MHz, CDCl$_3$): δ 6.57 (s, 1H), 6.30 (s, 1H), 4.63 (br, 1H), 4.16-4.25 (m, 4H).

6. The Synthesis of Intermediate 5.7

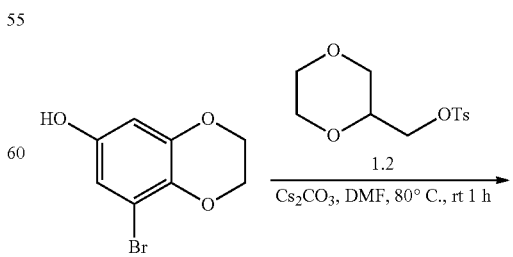

339 / 340

-continued

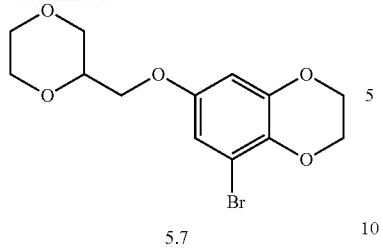

5.7

To a stirred solution of 5.5 (240 mg, 1.03 mmol), 1.2 (340 mg, 1.25 mmol) in DMF (5 mL) was added Cs₂CO₃ (1 g, 3.09 mmol). The reaction mixture was stirred at 80° C. for 1 hour until the reaction was complete (by LCMS). The suspension was diluted with H₂O (20 mL) and extracted with DCM (20 mL×2), concentrated. The crude product was purified by flash column chromatography (silica gel, PE/EA=5:1) to give 5.7 (220 mg, yield: 65%) as yellow oil.

7. The Synthesis of Target I-155

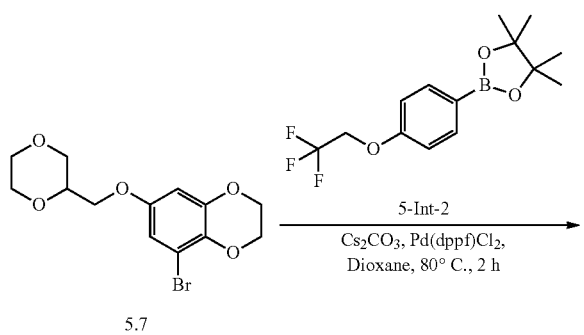

-continued

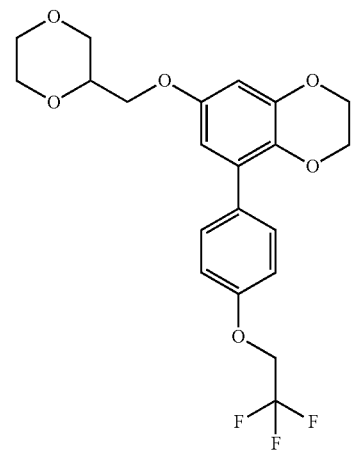

I-155

To a stirred solution of 5.7 (220 mg, 0.66 mmol), 5-Int-2 (199 mg, 0.66 mmol) and Cs₂CO₃ (645 mg, 1.98 mmol) in dioxane (10 mL) was added Pd(dppf)Cl₂ (22 mg). The reaction mixture was stirred at 80° C. for 2 hours until the reaction was complete (by LCMS). The suspension was diluted with H₂O (20 mL) and extracted with EA (20 mL×2), concentrated. The crude product was purified by Prep-HPLC to give I-155 (108 mg, yield: 38%) as a white solid.

Additional exemplary compounds were prepared following methods substantially similar to the method described above and herein. Data for these compounds are provided below.

TABLE 6

Characterization Data for Additional Exemplary Compounds

| Compound No. | Chemical Structure | {M + H} observed | ¹H NMR (400 MHz) |
|---|---|---|---|
| 1-155 | 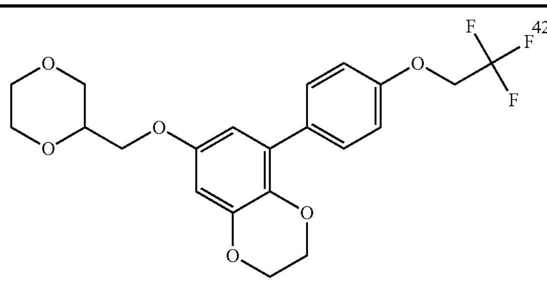 | 427.3 | ¹H NMR (400 MHz, CDCl₃): δ 7.46-7.49 (m, 2 H), 6.96-6.99 (m, 2 H), 6.45-6.48 (m, 2 H), 4.37 (q, J = 8.0 Hz, 2 H), 4.25-4.27 (m, 2 H), 4.19-4.21 (m, 2 H), 3.65-3.97 (m, 8 H), 3.49-3.55 (m, 1 H). |
| 1-156 | 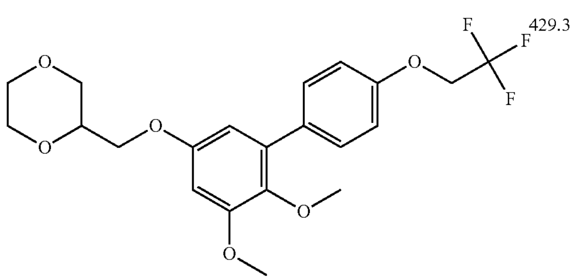 | 429.3 | ¹H NMR (400 MHz, CDCl₃): δ 7.51 (d, J = 8.8 Hz, 2H), 6.98 (d, J = 8.8 Hz, 2H), 6.54 (d, J = 2.8 Hz, 1H), 6.40 (d, J = 2.8 Hz, 1H), 4.40 (q, J = 8.0 Hz, 2H), 3.98-4.01 (m, 2H), 3.89-3.94 (m, 2H), 3.87 (s, 3H), 3.78-3.86 (m, 2H), 3.70-3.74 (m, 1H), 3.65-3.69 (m, 1H), 3.52-3.57 (m, 1H), 3.49 (s, 3H). |

TABLE 6-continued
Characterization Data for Additional Exemplary Compounds
| Compound No. | Chemical Structure | {M + H} observed | ¹H NMR (400 MHz) |
|---|---|---|---|
| 1-157 | 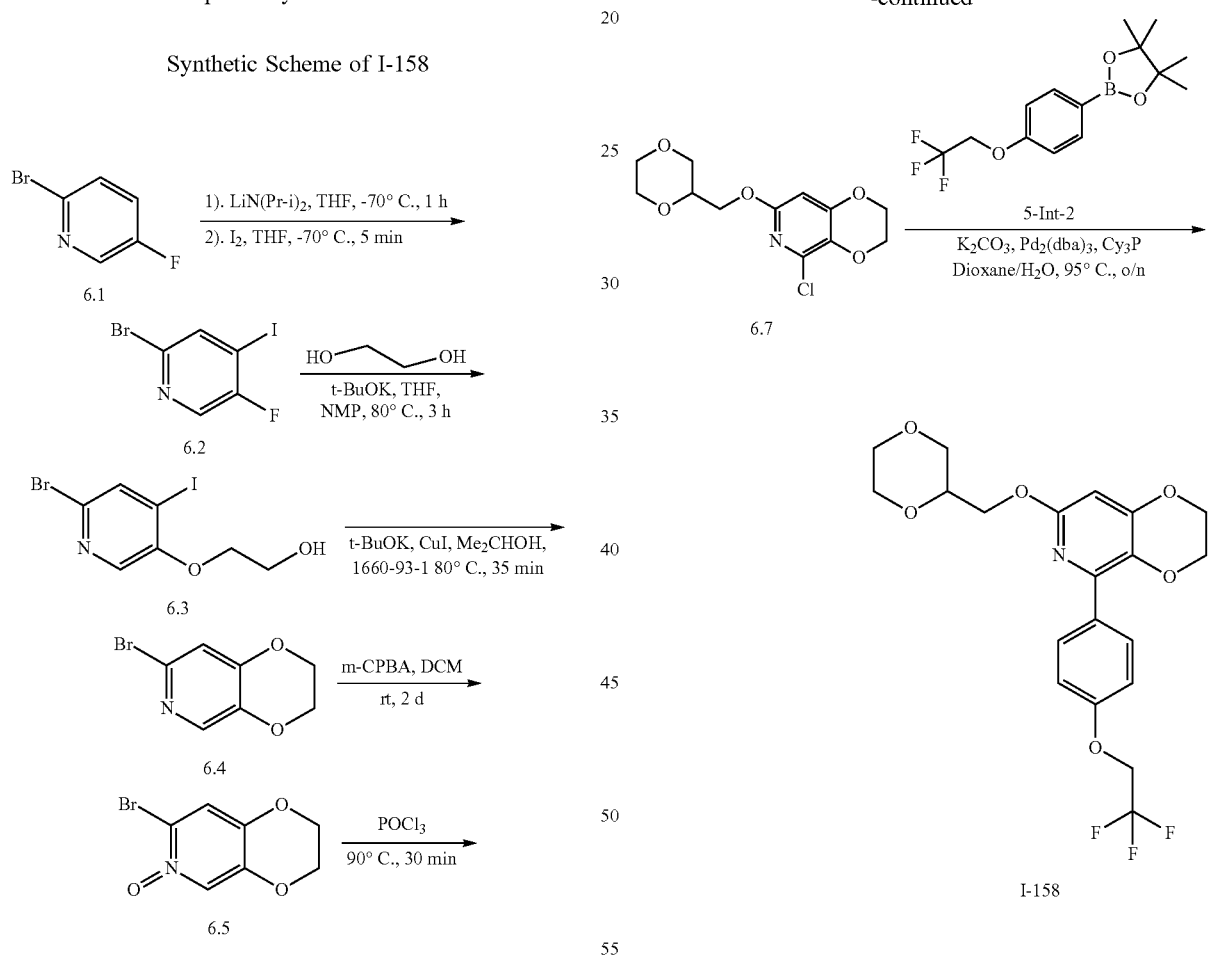 | 413.3 | ¹H NMR (400 MHz, DMSO-d$_6$) δ 7.27 (d, J = 8.4 Hz, 2H), 7.10 (d, J = 8.8 Hz, 2H), 6.55 (d, J = 2.4 Hz, 1H), 6.34 (d, J = 2.4 Hz, 1H), 4.80 (q, J = 9.2 Hz, 2H), 3.95 (d, J = 4.8 Hz, 2H), 3.74-3.82 (m, 6H), 3.62-3.65 (m, 2H), 3.47-3.51 (m, 1H), 3.36-3.43 (m, 1H), 1.94 (s, 3H). |
Example 6: Synthesis of I-158
Synthetic Scheme of I-158
1. The Synthesis of Intermediate 6.2
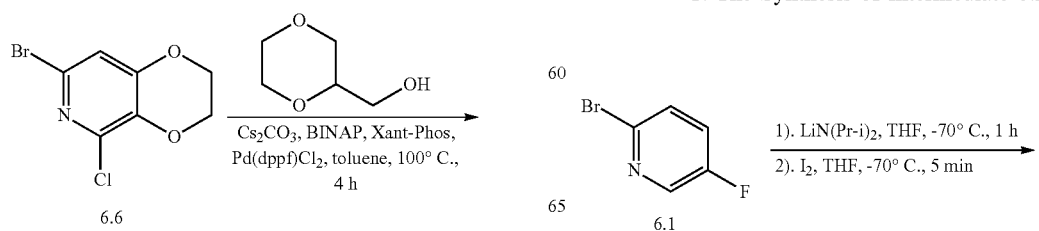

-continued

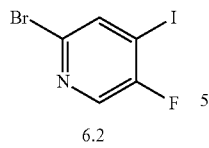

6.2

To a stirred solution of 6.1 (10.0 g, 56.8 mmol) in dry THF (100 mL) was slowly added LDA (2 M in THF, 31.25 mL, 62.5 mmol) at −70° C., keeping the internal temperature below −65° C. The solution stirred at −70° C. for another 1 h. A solution of iodine (15.2 g, 59.7 mmol) in THF (25 mL) was added slowly over 5 minutes keeping the internal temperature below −50° C. and the mixture stirred at −70° C. for another 5 minutes. Saturated NH$_4$Cl (80 mL) and EA (200 mL) were added and the organic phase was separated, washed with aq. NaHSO$_3$ (100 mL) and brine (75 mL), evaporated to dryness under reduced pressure. The residue was purified by flash column chromatography (silica gel, PE/EA=15/1) to give 6.2 (14.7 g, yield: 86%) as a yellow solid. $^1$H NMR (400 MHz, CDCl$_3$) δ 8.13 (s, 1H), 7.91 (d, J=4.4 Hz, 1H).

2. The Synthesis of Intermediate 6.3

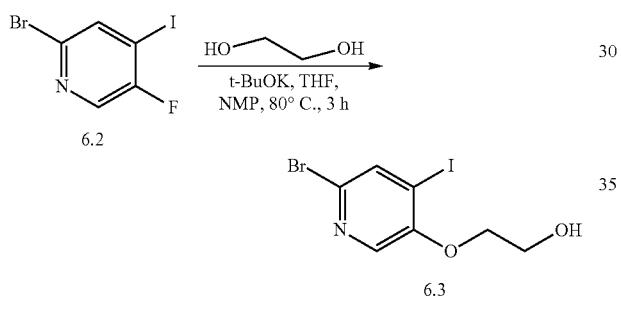

A mixture of 6.2 (11.6 g, 38.3 mmol), ethane-1,2-diol (11.9 g, 191.4 mmol) and t-BuOK (4.7 g, 42.1 mmol) in NMP (20 mL) and THF (40 mL) was heated to 60° C. and stirred for 40 min, the mixture was removed from the oil bath and allowed to stir at room temperature for 16 h. The mixture was concentrated under reduced pressure. Additional t-BuOK (2.14 g, 19.14 mmol) and ethane-1,2-diol (2.37 g, 38.28 mmol) was added and the reaction heated in an 80° C. bath for another 3 h. When it cooled to RT, EA (100 mL) and H$_2$O (80 mL) was added, the organic phase was collected and washed with brine (50 mL×3), dried over anhydrous Na$_2$SO$_4$ and concentrated. The residue was purified by flash column chromatography (silica gel, PE/EA=10/3) to give 6.3 (3.0 g, yield: 23%) as a white solid. LC-MS m/z: 344.0 [M+H]$^+$.

3. The Synthesis of Intermediate 6.4

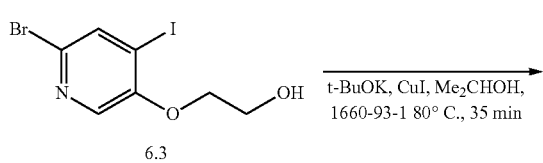

-continued

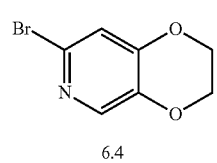

6.4

The solution of 6.3 (3.0 g, 8.8 mmol), t-BuOK (1.1 g, 9.7 mmol), CuI (84 mg, 0.44 mmol) and 3,4,7,8-tetramethyl-1,10-phenanthroline (145 mg, 0.62 mmol) in isopropanol (60 mL) was stirred at 80° C. for 35 min under nitrogen. When it cooled to RT, the solvent was removed under reduced pressure. The residue was dissolved in EA (60 mL) and washed by brine (30 mL×2). The organic phase was dried over anhydrous Na$_2$SO$_4$ and concentrated. The residue was purified by flash column chromatography (silica gel, PE/EA=10/3) to give 6.4 (1.4 g, yield: 75%) as a white solid. LC-MS m/z: 216.1 [M+H]$^+$.

4. The Synthesis of Intermediate 6.55

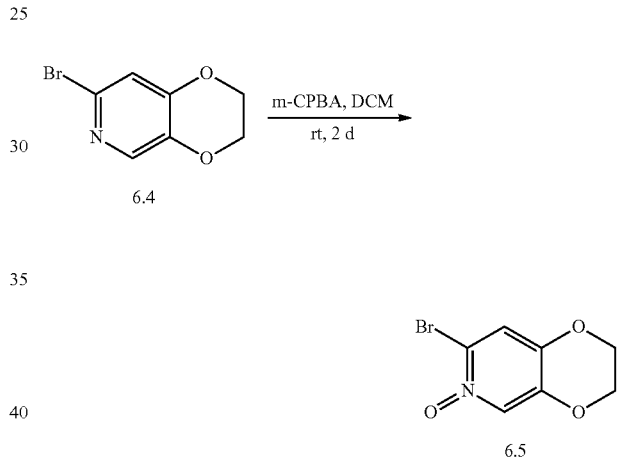

To a stirred solution of 6.4 (1.0 g, 4.6 mmol) in dry DCM (20 mL) was added m-CPBA (1.6 g, 9.3 mmol) at 0° C. The solution was stirred at RT for 2 days. Then the mixture was filtered, the filtrate was washed with 10% NaOH (10 mL) and extracted with DCM (20 mL×3). The combined organic phase was dried over anhydrous Na$_2$SO$_4$, and concentrated. The residue was purified by flash column chromatography (silica gel, DCM/MeOH=3/10) to give 6.5 (778 mg, yield: 72%) as a white solid. $^1$H NMR (400 MHz, CDCl$_3$) δ 8.16 (s, 1H), 7.15 (s, 1H), 4.32-4.36 (m, 4H).

5. The Synthesis of Intermediate 6.6

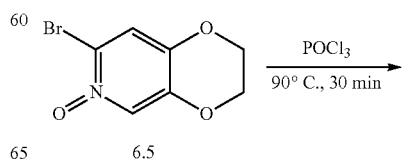

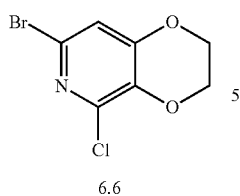

6.6

The solution of 6.5 (700 mg, 3.03 mmol) in POCl₃ (15 mL) was stirred at 90° C. for 30 min. When it cooled to room temperature, the solvent was removed under reduced pressure. The residue was purified by flash column chromatography (silica gel, PE/DCM=1/1) to give 6.6 (450 mg, yield: 60%) as a white solid. ¹H NMR (400 MHz, CDCl₃) δ 6.97 (s, 1H), 4.36-4.39 (m, 4H).

6. The Synthesis of Intermediate 6.7

7. The Synthesis of Target I-158

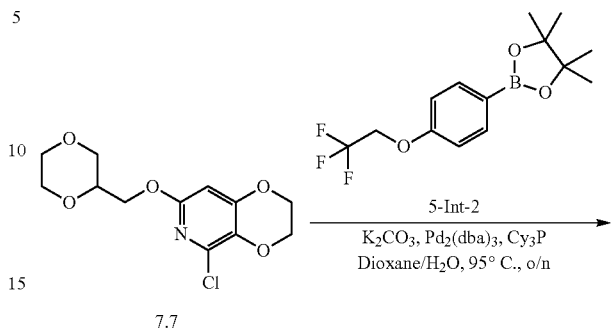

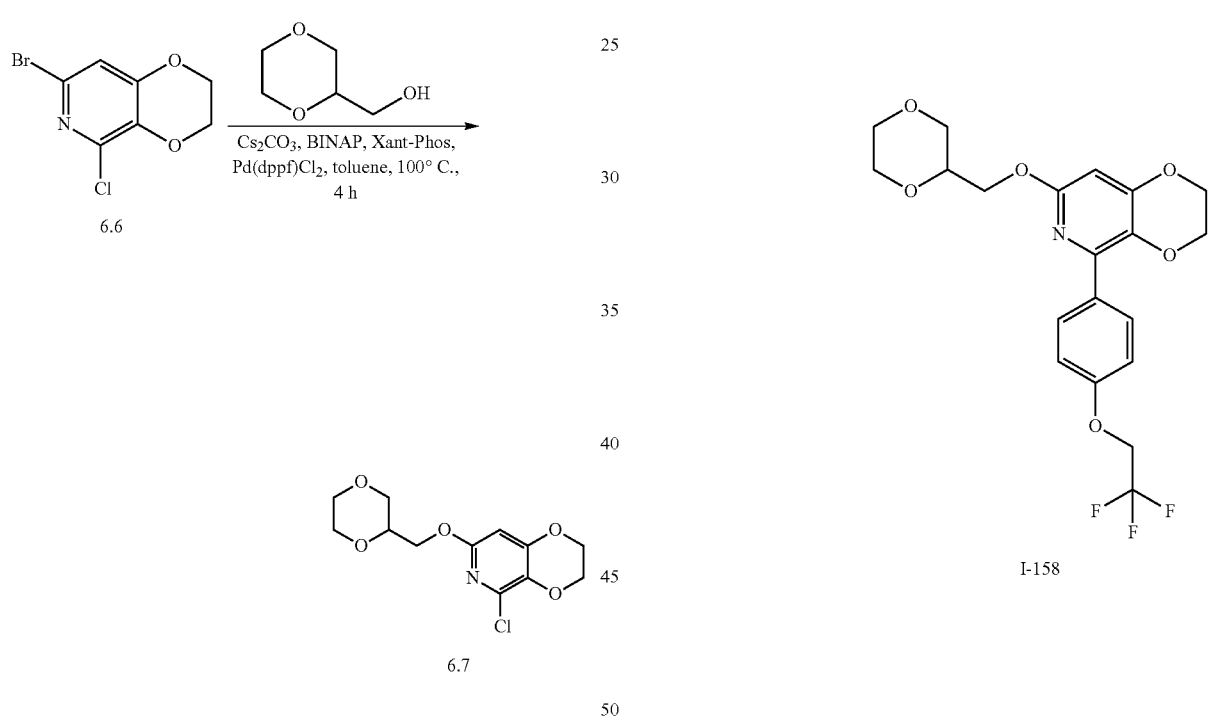

To a solution of 6.6 (275 mg, 1.1 mmol), (1,4-dioxan-2-yl)methanol (137 mg, 1.2 mmol), Cs₂CO₃ (717 mg, 2.2 mmol), BINAP (68 mg, 0.11 mmol) and Xant-Phos (64 mg, 0.11 mmol) in dry toluene (10 mL) was added Pd(dppf)Cl₂ (27 mg). The reaction mixture was stirred at 100° C. for 4 h under nitrogen. When it cooled to RT, water (20 mL) was added. The mixture was extracted by EA (20 mL×2), dried over anhydrous Na₂SO₄ and concentrated. The residue was purified by flash column chromatography (silica gel, PE/EA=3/1) to give 6.7 (146 mg, yield: 46%) as a white solid. ¹H NMR (400 MHz, CDCl₃) δ 6.27 (s, 1H), 4.32 (s, 4H), 4.22-4.23 (m, 2H), 3.64-3.95 (m, 6H), 3.46-3.52 (m, 1H).

To a stirred solution of 6.7 (80 mg, 0.28 mmol), 5-Int-2 (100 mg, 0.33 mmol) and K₂CO₃ (77 mg, 0.56 mmol) in dioxane (5 mL) and H₂O (1 mL) were added Pd₂(dba)₃ (25 mg, 0.03 mmol) and Cy₃P (19 mg, 0.07 mmol). The reaction mixture was stirred at 95 MC overnight until the reaction was completed (by LCMS). The suspension was diluted with H₂O (20 mL) and extracted with EA (20 mL×2). The organic phase was washed by brine, dried over anhydrous Na₂SO₄ and concentrated. The residue was purified by Prep-HPLC to give I-158 (51 mg, yield: 430%) as a white solid.

Additional exemplary compounds were prepared following methods substantially similar to the method described above and herein. Data for these compounds are provided below.

TABLE 7

Characterization Data for Additional Exemplary Compounds

| Compound No. | Chemical Structure | [M + H] observed | $^1$H NMR (400 MHz) |
|---|---|---|---|
| I-158 | 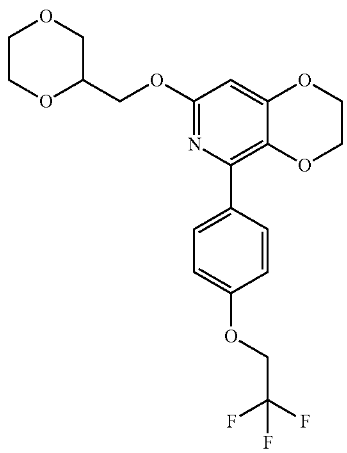 [SMILES: FC(F)(F)COc1ccc(-c2nc(OCC3COCCO3)cc3c2OCCO3)cc1] | 428.0 | $^1$H NMR (400 MHz, CDCl$_3$): δ 8.01 (dd, J = 2.0 Hz, 6.8 Hz, 2H), 6.99 (dd, J = 2.0 Hz, 7.2 Hz, 2H), 6.28 (s, 1H), 4.27-4.43 (m, 8H), 3.97-4.03 (m, 1H), 3.80-3.90 (m, 3H), 3.63-3.75 (m, 2H), 3.49-3.55 (m, 1H). |
| I-94 | 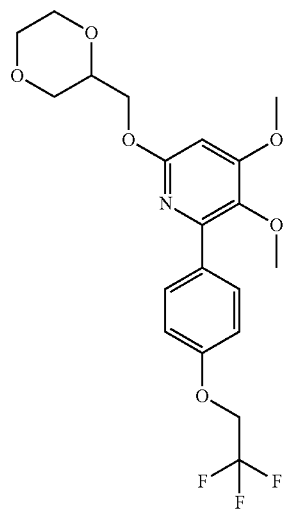 [SMILES: COc1cc(OCC2COCCO2)nc(-c2ccc(OCC(F)(F)F)cc2)c1OC] | 430.3 | $^1$H NMR (400 MHz, DMSO-d$_6$) δ 7.95 (d, J = 9.2 Hz, 2 H), 7.14 (d, J = 8.8 Hz, 2 H), 6.48 (s, 1 H), 4.82 (q, J = 8.8 Hz, 2 H), 4.24-4.26 (m, 2 H), 3.84-3.91 (m, 4 H), 3.74-3.82 (m, 2 H), 3.57-3.69 (m, 2 H), 3.56 (s, 3 H), 3.46-3.54 (m, 1 H), 3.37-3.44 (m, 1 H). |
| I-39 | 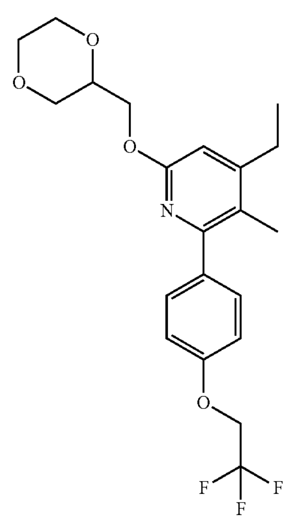 [SMILES: CCc1cc(OCC2COCCO2)nc(-c2ccc(OCC(F)(F)F)cc2)c1C] | 414.1 | $^1$H NMR (400 MHz, DMSO-d$_6$) d$_6$): δ 7.49 (d, J = 8.8 Hz, 2 H), 7.12 (d, J = 8.4 Hz, 2 H), 6.40 (s, 1 H), 4.82 (q, J = 9.2 Hz, 2 H), 4.18-4.21 (m, 2 H), 3.80-3.88 (m, 4 H), 3.71-3.79 (m, 2 H), 3.56-3.68 (m, 2 H), 3.44-3.52 (m, 1 H), 3.36-3.41 (m, 1 H), 2.05 (s, 3 H). |

TABLE 7-continued
Characterization Data for Additional Exemplary Compounds
| Compound No. | Chemical Structure | [M + H] observed | $^1$H NMR (400 MHz) |
|---|---|---|---|
| I-78 | 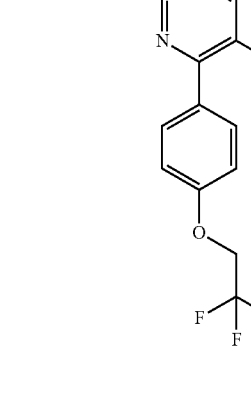 | 414.3 | $^1$H NMR (400 MHz, DMSO-d$_6$) δ 7.97 (d, J = 8.8 Hz, 2 H), 7.15 (d, J = 8.8 Hz, 2 H), 6.68 (s, 1 H), 4.83 (q, J = 8.8 Hz, 2 H), 4.22-4.24 (m, 2 H), 3.84-3.92 (m, 1 H), 3.74-3.81 (m, 2 H), 3.57-3.67 (m, 2 H), 3.46-3.52 (m, 1 H), 3.37-3.42 (m, 4 H), 2.27 (s, 3 H). |
| I-52 | 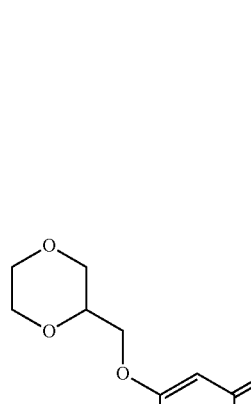 | 414.2 | $^1$H NMR (400 MHz, CDCl$_3$): δ 7.17 (d, J = 8.4 Hz, 2 H), 7.07 (d, J = 8.8 Hz, 2 H), 5.92 (s, 1 H), 4.42 (q, J = 8.0 Hz, 2 H), 3.99-4.08 (m, 3 H), 3.75-3.89 (m, 4 H), 3.64-3.68 (m, 1 H), 3.49-3.55 (m, 1 H), 3.15 (s, 3 H), 1.72 (s, 3 H). |

TABLE 7-continued

Characterization Data for Additional Exemplary Compounds

| Compound No. | Chemical Structure | [M + H] observed | ¹H NMR (400 MHz) |
|---|---|---|---|
| I-140 | 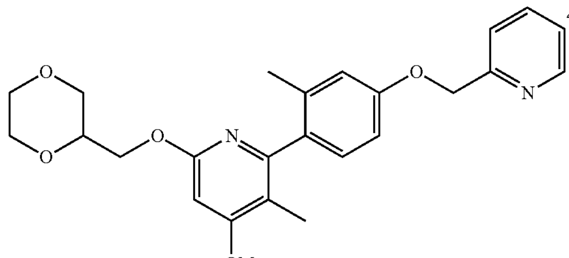 | 437.3 | ¹H NMR (400 MHz, CDCl$_3$): δ 8.61 (d, J = 4.8 Hz, 1 H), 7.70-7.76 (m, 1 H), 7.56 (d, J = 8.0 Hz, 1 H), 7.20-7.25 (m, 1 H), 7.07 (d, J = 8.4 Hz, 1 H), 6.90 (d, J = 2.4 Hz, 1 H), 6.84 (dd, J = 2.8 Hz, 8.4 Hz, 1 H), 6.26 (s, 1 H), 5.23 (s, 2 H), 4.27 (d, J = 4.8 Hz, 2 H), 3.90-3.98 (m, 1 H), 3.61-3.88 (m, 8 H), 3.44-3.52 (m, 1 H), 2.10 (s, 3 H), 1.85 (s, 3 H). |
| I-112 | 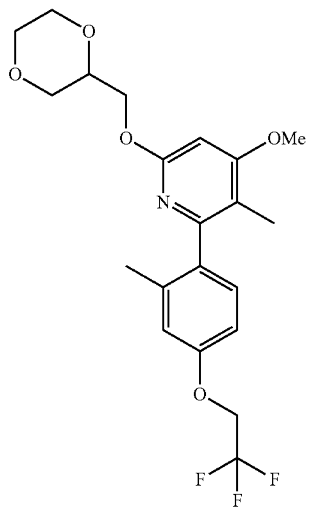 [SMILES: COc1cc(OCC2COCCO2)nc(-c2ccc(OCC(F)(F)F)cc2C)c1C] | 428.3 | ¹H NMR (400 MHz, DMSO-d$_6$) δ 7.07 (d, J = 8.4 Hz, 1H), 7.00 (d, J = 2.4 Hz, 1 H), 6.90-6.93 (m, 1 H), 6.41 (s, 1 H), 4.79 (q, J = 8.8 Hz, 2 H), 4.06-4.15 (m, 2 H), 3.86 (s, 3 H), 3.72-3.84 (m, 3 H), 3.54-3.66 (m, 2H), 3.45-3.50 (m, 1H), 3.30-3.32 (m, 1H), 2.04 (s, 3H), 1.78 (s, 3H). |
| I-69 | 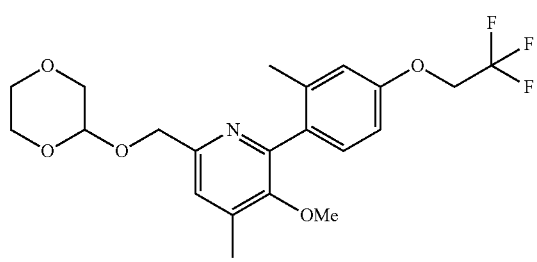 [SMILES: COc1c(C)cc(COC2COCCO2)nc1-c1ccc(OCC(F)(F)F)cc1C] | 428.2 | ¹H NMR (400 MHz, CDCl$_3$): δ 7.32 (d, J = 8.4 Hz, 1 H), 6.86 (d, J = 2.4 Hz, 1 H), 6.82 (dd, J = 2.4 Hz, 8.4 Hz, 1 H), 6.62 (s, 1 H), 4.38 (q, J = 8.0 Hz, 2 H), 4.23-4.25 (m, 2 H), 3.92-3.98 (m, 1 H), 3.61-3.86 (m, 5 H), 3.45-3.51 (m, 1 H), 3.28 (s, 3 H), 2.28 (s, 3 H), 2.24 (s, 3 H). |

Example 7: Synthesis of I-159

Synthetic Scheme of I-159

-continued

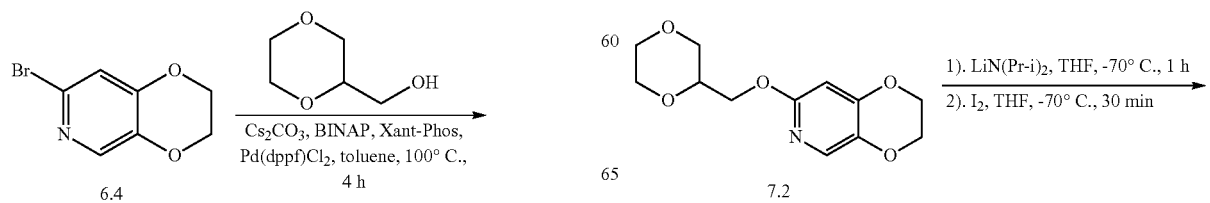

2. The Synthesis of Intermediate 7.3

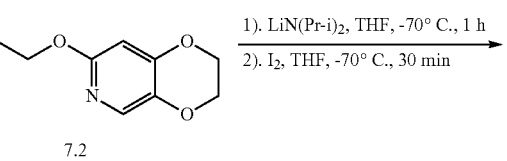
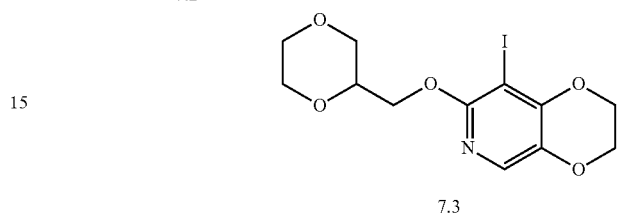

To a stirred solution of 7.2 (300 mg, 1.2 mmol) in dry THF (10 mL) was slowly added LDA (2 M in THF, 0.65 mL, 1.3 mmol) at −70° C. The solution stirred at −70° C. for another 1 h. A solution of iodine (316 mg, 1.25 mmol) in THF (5 mL) was added slowly over 2 minutes and the mixture stirred at −70° C. for another 30 minutes. Saturated NH$_4$Cl (10 mL), H$_2$O (10 mL) and EA (20 mL) were added and the organic phase was separated, washed with aq. NaHSO$_3$ (20 mL) and brine (20 mL), evaporated to dryness under reduced pressure. The residue was purified by flash column chromatography (silica gel, PE/EA=4/1) to give 7.3 (339 mg, yield: 71%) as a white solid. LC-MS m/z: 380.0 [M+H]$^+$.

3. The Synthesis of Target I-159

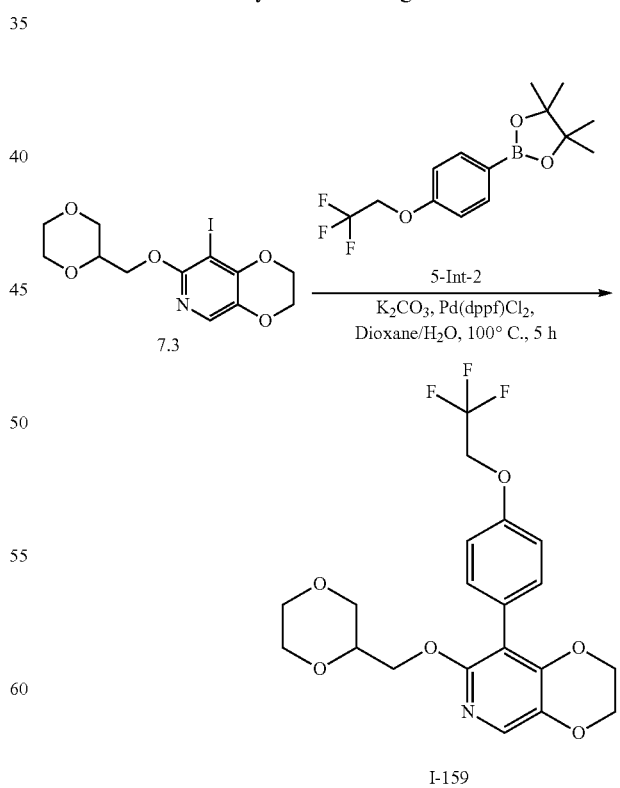

To a stirred solution of 7.3 (250 mg, 0.66 mmol), 5-Int-2 (239 mg, 0.79 mmol) and K$_2$CO$_3$ (273 mg, 1.98 mmol) in

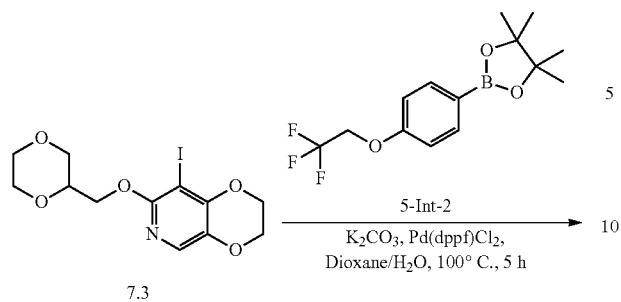

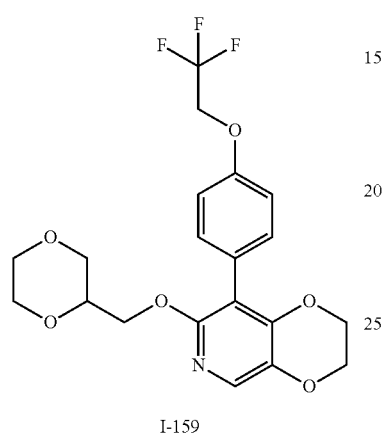

1. The Synthesis of Intermediate 7.2

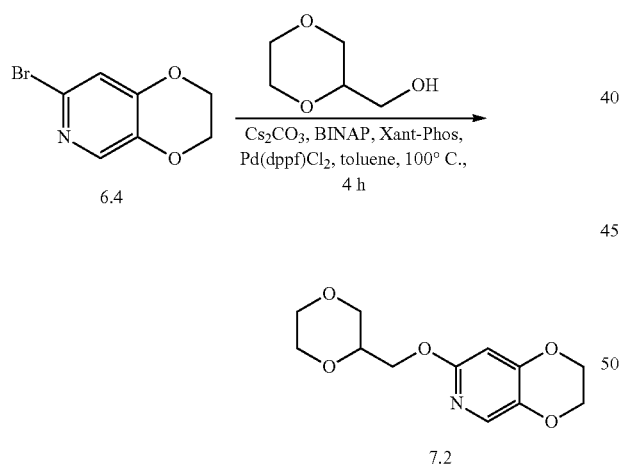

To a solution of 6.4 (797 mg, 3.7 mmol), (1,4-dioxan-2-yl)methanol (525 mg, 4.4 mmol), Cs$_2$CO$_3$ (2.4 g, 7.4 mmol), BINAP (231 mg, 0.37 mmol) and Xant-Phos (215 mg, 0.37 mmol) in dry toluene (20 mL) was added Pd(dppf)Cl$_2$ (80 mg). The reaction mixture was stirred at 100° C. for 4 h under nitrogen. When it cooled to RT, water (20 mL) was added. The mixture was extracted by EA (20 mL×2), dried over anhydrous Na$_2$SO$_4$ and concentrated. The residue was purified by flash column chromatography (silica gel, PE/EA=3/1) to give 7.2 (300 mg, yield: 32%) as a yellow solid. LC-MS m/z: 254.2 [M+H]$^+$.

dioxane (10 mL) and H₂O (2 mL) was added Pd(dppf)Cl₂ (25 mg). The reaction mixture was stirred at 100° C. for 5 hours until the reaction was complete (by LCMS). The suspension was diluted with H₂O (20 mL) and extracted with EA (20 mL×2). The organic phase was washed by brine, dried over anhydrous Na₂SO₄ and concentrated. The residue was purified by Prep-HPLC to give 1-159 (70 mg, yield: 25%) as a white solid.

Additional exemplary compounds were prepared following methods substantially similar to the method described above and herein. Data for these compounds are provided below.

-continued

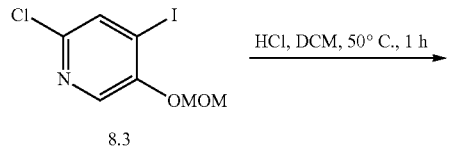

8.3

TABLE 8

Characterization Data for Additional Exemplary Compounds

| Compound No. | Chemical Structure | [M + H] observed | ¹H NMR (400 MHz) |
|---|---|---|---|
| I-159 | 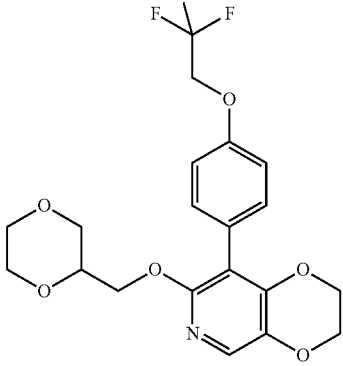 | 428.2 | ¹H NMR (400 MHz, CDCl₃): δ 7.72 (s, 1H), 7.37-7.40 (m, 2H), 6.96-7.00 (m, 2H), 4.39 (q, J = 8.4 Hz, 2H), 4.27-4.31 (m, 3H), 4.16-4.23 (m, 3H), 3.84-3.87 (m, 1H), 3.66-3.79 (m, 4H), 3.54-3.60 (m, 1H), 3.35-3.40 (m, 1H). |
| I-131 | 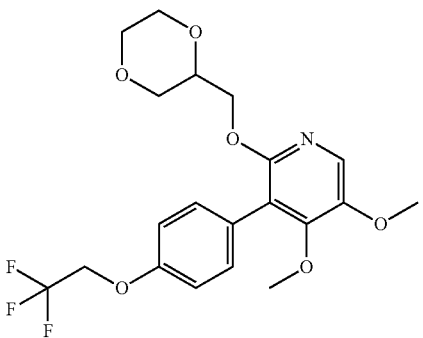 [SMILES: COc1cnc(OCC2COCCO2)c(-c2ccc(OCC(F)(F)F)cc2)c1OC] | 430.2 | ¹H NMR (400 MHz, DMSO-d₆) δ 7.87 (s, 1 H), 7.30 (d, J = 8.8 Hz, 2 H), 7.10 (d, J = 8.8 Hz, 2 H), 4.81 (q, J = 8.8 Hz, 2 H), 4.08-4.20 (m, 2 H), 3.86 (s, 3 H), 3.51-3.77 (m, 8 H), 3.39-3.43 (m, 1 H), 3.25 (t, J = 10.8 Hz, 1 H). |

Example 8: Synthesis of I-160

Synthetic Scheme of I-160

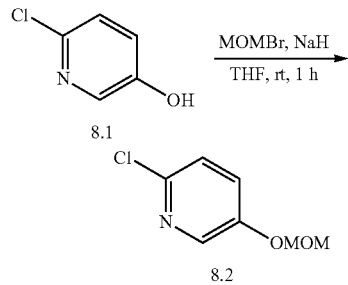

-continued

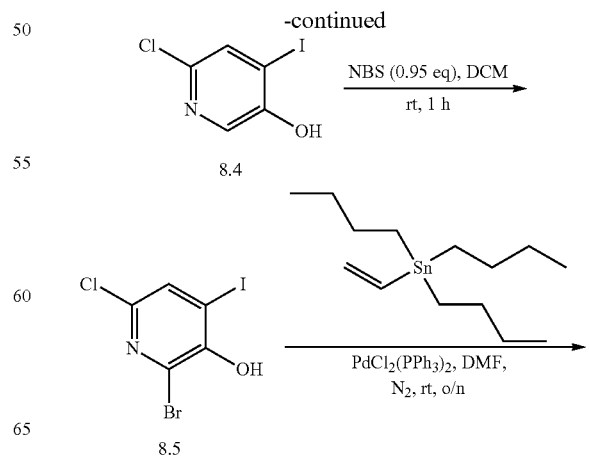

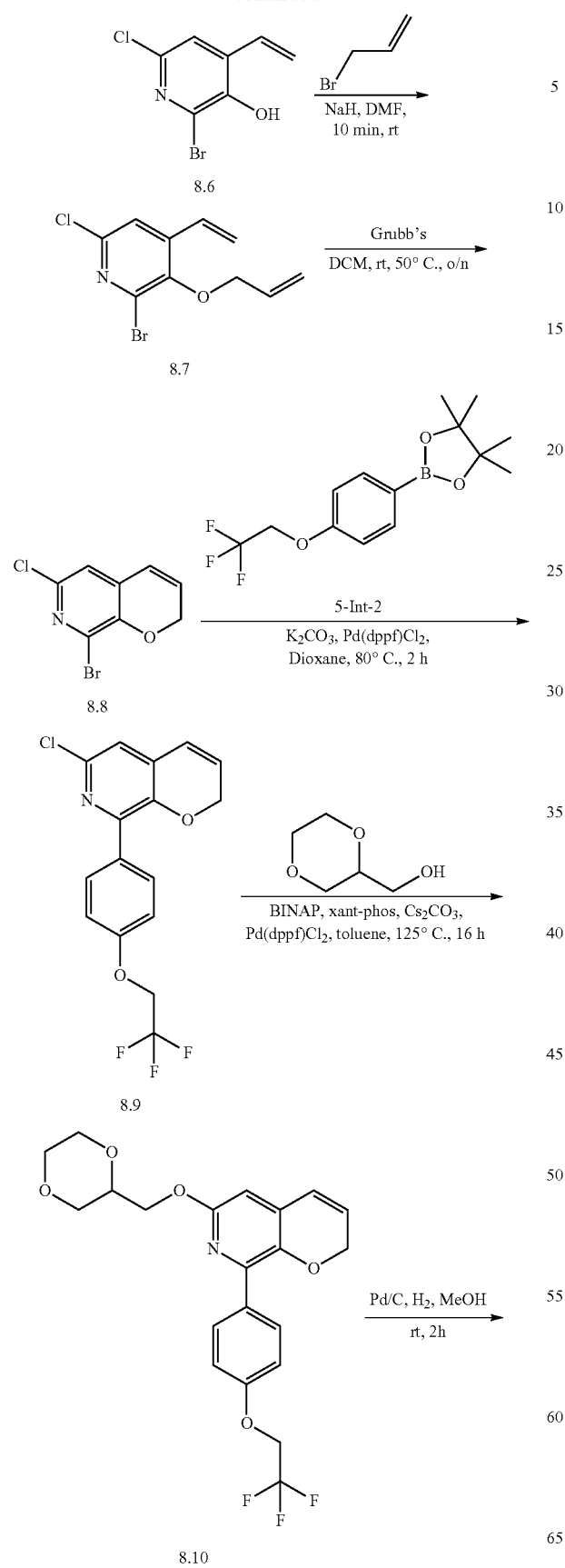

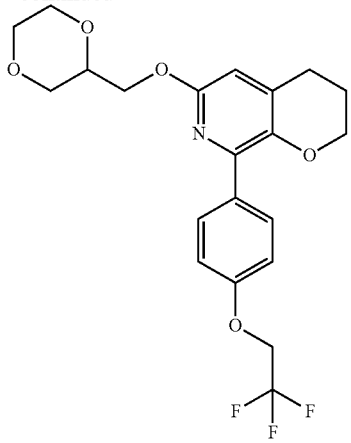 [SMILES: FC(F)(F)COc1ccc(-c2nc(OCC3COCCO3)cc3c2OCCC3)cc1]

1. The Synthesis of Intermediate 8.2

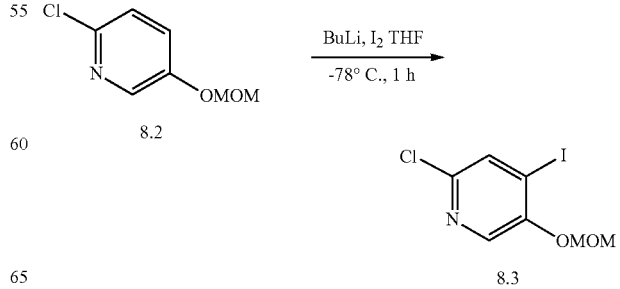

To a stirred solution of 8.1 (10 g, 77.5 mmol) in THF (100 ml) was added NaH (4.6 g, 116.2 mmol, 60% in mineral oil). The reaction mixture was stirred at RT for 30 min then MOMBr (10.6 g, 93 mmol) was added. The reaction mixture was stirred at RT for 30 min. Ice water (100 mL) was added dropwise and the reaction was extracted with EtOAc (100 mL×2). The organic phase was combined, washed with brine, dried over anhydrous $Na_2SO_4$. The solvent was removed under reduced pressure and purified by flash column chromatography (silica gel, PE/EA=2:1) to give 8.2 (12.4 g, yield: 92%) as yellow oil.

2. The Synthesis of Intermediate 8.3

To a stirred solution of 8.2 (12.4 g, 71.6 mmol) in THF (100 mL) was added n-BuLi (43 mL, 107.4 mmol) dropwise at −78° C. The reaction mixture was stirred at −78° C. for 30 min. Then the solution of I$_2$ (9.8 g, 71.6 mmol) in THF (50 mL) was added dropwise. The reaction mixture was stirred at −78° C. for 30 min. Ice water (100 mL) was added and the reaction mixture was extracted with EtOAc (100 mL×2). The organic phase was combined, washed with brine, dried over anhydrous Na$_2$SO$_4$, The solvent was removed under reduced pressure and purified by flash column chromatography (silica gel, PE/EA=5:1) to give 8.3 (6 g, yield: 28%) as a white solid. $^1$H NMR (400 MHz, CDCl$_3$): δ 8.00 (s, 1H), 7.68 (s, 1H), 5.18 (s, 2H), 3.44 (s, 3H).

3. The Synthesis of Intermediate 8.4

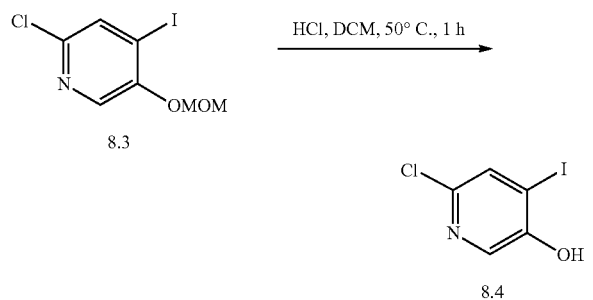

To a solution of 8.3 (6 g, 20.1 mmol) in DCM (50 mL) was added HCl (2.0 M, 5 mL). The mixture was stirred at 50° C. for 1 h. The solvent was removed under reduced pressure to give 8.4 (4.4 g, yield: 85%) as a white solid.

4. The Synthesis of Intermediate 8.5

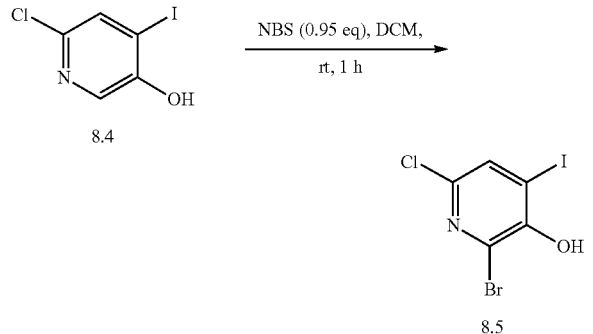

To a stirred solution of 8.4 (4.4 g, 17.2 mmol) in DCM (50 mL) was added NBS (2.9 g, 16.3 mmol). The reaction mixture was stirred at room temperature for 1 h. Water (50 ml) was added and the reaction mixture was extracted with DCM (50 mL×2). The organic phase was combined, washed with brine, dried over anhydrous Na$_2$SO$_4$, The solvent was removed under reduced pressure and purified by flash column chromatography (silica gel, PE/EA=2:1) to give 8.5 (1 g, yield: 17.5%) as a yellow solid. $^1$H NMR (400 MHz, CDCl$_3$): δ 7.59 (s, 1H), 5.89 (br, 1H).

5. The Synthesis of Intermediate 8.6

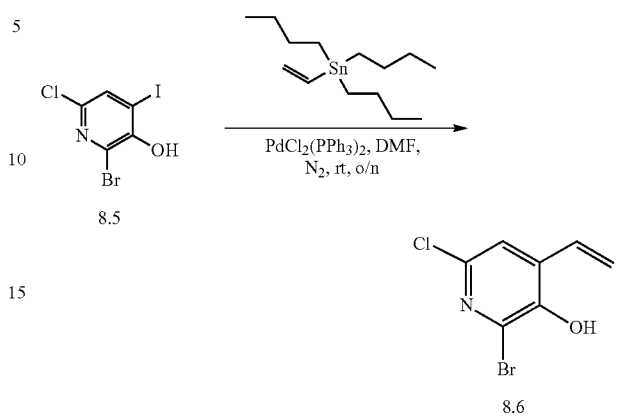

To a stirred solution of 8.5 (3 g, 9.0 mmol) in DMF (20 mL) was added tributyl(vinyl)stannane (4.3 g, 13.5 mmol) and PdCl$_2$(PPh$_3$)$_2$ (300 mg). The reaction mixture was stirred at RT overnight under N$_2$. Water (50 ml) was added and the reaction was extracted with EA (50 mL×3). The organic phase was combined, washed with brine, dried over anhydrous Na$_2$SO$_4$. The solvent was removed under reduced pressure and purified by flash column chromatography (silica gel, PE/EA=2:1) to give 8.6 (1.8 g, yield: 85.8%) as a yellow solid. $^1$H NMR (400 MHz, CDCl$_3$): δ 7.30 (s, 1H), 6.88 (dd, J 11.2 Hz, 18.0 Hz, 1H), 6.02 (d, J 17.6 Hz, 1H), 5.70 (br, 1H), 5.65 (d, J 5.2 Hz, 1H).

6. The Synthesis of Intermediate 8.7

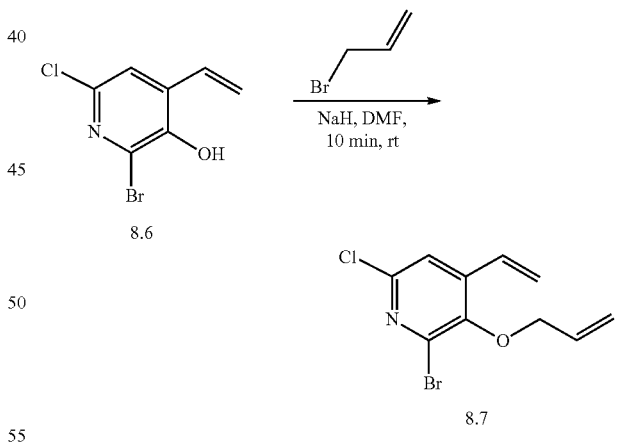

To a solution of 8.6 (1.8 g, 7.7 mmol) in DMF (10 mL) was added NaH (465 mg, 11.5 mmol, 60% in mineral oil). The reaction mixture was stirred at RT for 5 min. Then 3-bromoprop-1-ene (1.1 g, 9.24 mmol) was added. The reaction mixture was stirred at room temperature for 5 min. Ice water (50 mL) was added and the reaction mixture was extracted with EtOAc (50 mL×2). The organic phase was combined, washed with brine, dried over Na$_2$SO$_4$. The solvent was removed under reduced pressure and purified by flash column chromatography (silica gel, PE/EA=5:1) to give 8.7 (1.6 g, yield: 76.1%) as yellow oil. $^1$H NMR (400

MHz, CDCl$_3$): δ 7.35 (s, 1H), 6.88 (dd, J 11.2 Hz, 17.6 Hz, 1H), 6.04-6.14 (m, 1H), 5.98 (d, J 17.6 Hz, 1H), 5.62 (d, J 10.8 Hz, 1H), 5.40-5.45 (m, 1H), 5.30-5.33 (m, 1H), 4.45-4.47 (m, 2H).

7. The Synthesis of Intermediate 8.8

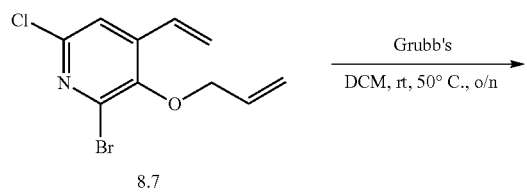

To a solution of 8.7 (1.6 g, 5.9 mmol) in DCM (20 mL) was added Grubb's catalyst (160 mg). The reaction mixture was stirred at 50° C. overnight. Ice water (50 mL) was added and the reaction was extracted with DCM (30 mL×2). The organic phase was combined, washed with brine, dried over anhydrous Na$_2$SO$_4$, The solvent was removed under reduced pressure and purified by flash column chromatography (silica gel, PE/EA=5:1) to give 8.8 (0.7 g, yield: 48.7%) as yellow oil. $^1$H NMR (400 MHz, CDCl$_3$): δ 6.84 (s, 1H), 6.32-6.36 (m, 1H), 6.06-6.10 (m, 1H), 5.06-5.07 (m, 2H).

8. The Synthesis of Intermediate 8.9

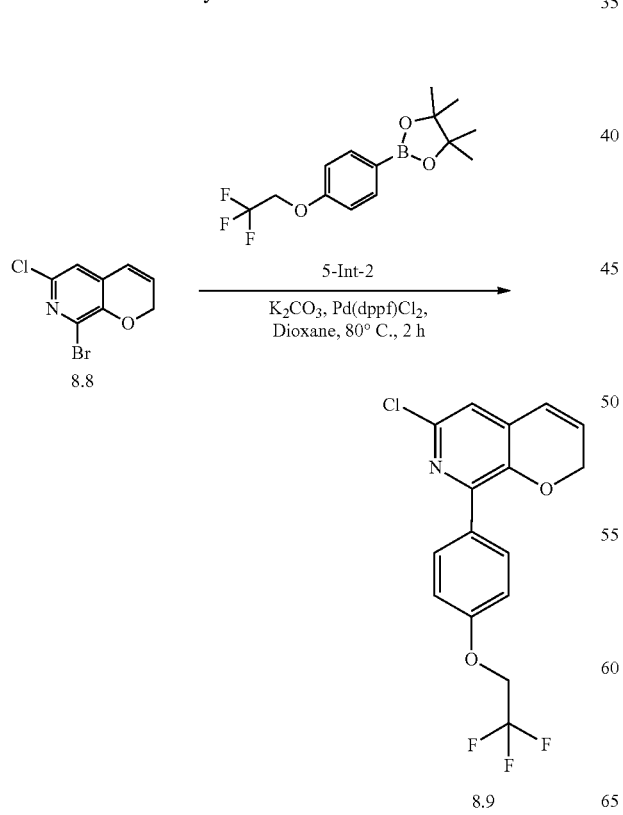

To a stirred solution of 8.8 (400 mg, 1.63 mmol), 5-Int-2 (575 mg, 1.9 mmol) and K$_2$CO$_3$ (680 mg, 4.89 mmol) in dioxane (15 mL) was added Pd(dppf)Cl$_2$ (40 mg). The reaction mixture was stirred at 80° C. for 2 hours under Ar atmosphere until the reaction was complete (by LCMS). The suspension was diluted with H$_2$O (20 mL) and extracted with EA (20 mL×2), the organic phase was concentrated. The crude product was purified by flash column chromatography (silica gel, PE/EA=2:1) to give 8.9 (300 mg, yield: 54%) as a yellow solid.

9. The Synthesis of Intermediate 8.10

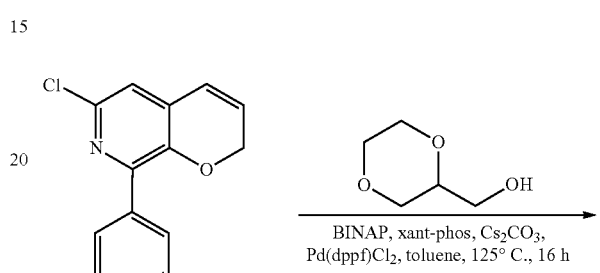

To a stirred solution of 8.9 (300 mg, 0.9 mmol), (1,4-dioxan-2-yl)methanol (128 mg, 1.1 mmol) and Cs$_2$CO$_3$ (880 mg, 2.7 mmol) in toluene (15 mL) was added Xant-phos (56 mg, 0.09 mmol), BINAP (56 mg, 0.09 mmol), Pd(dppf)Cl$_2$ (33 mg, 0.045 mmol). The reaction mixture was stirred at 125° C. for 16 hours under Ar atmosphere until the reaction was complete. The suspension was diluted with H₂O (20 mL) and extracted with EA (20 mL×2), the organic phase was concentrated. The crude product was purified by flash column chromatography (silica gel, PE/EA=5:1) to give 8.10 (200 mg, yield: 52%) as colorless oil.

10. The Synthesis of Intermediate I-160

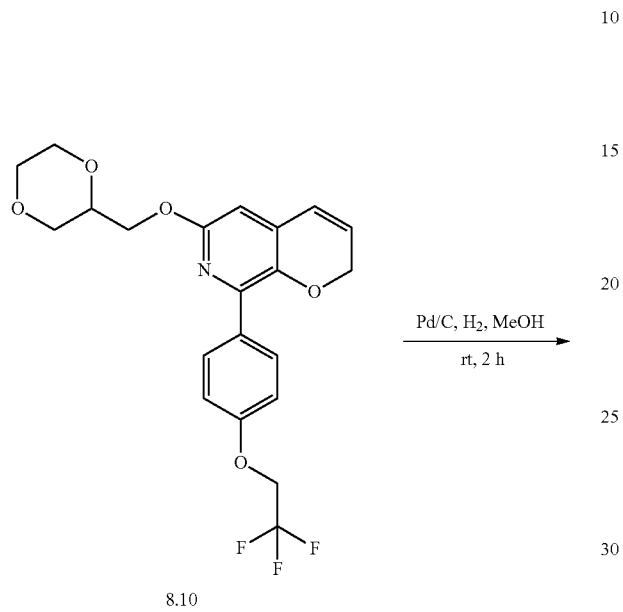

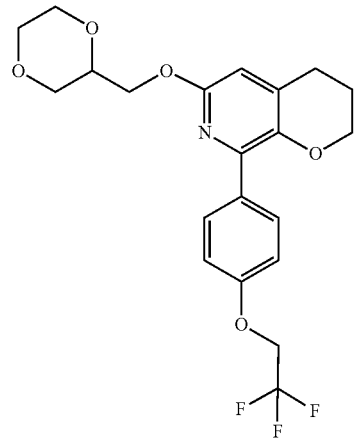

I-160

To a stirred solution of 8.10 (200 mg, 0.47 mmol) in MeOH (15 mL) was added Pd/C (50 mg). The reaction mixture was stirred at rt for 2 hours under H₂ (1.0 atm) until the reaction was complete (by LCMS). The suspension was filtered, and the filtrate was concentrated. The crude product was purified by Prep-HPLC to give I-160 (40.62 mg, yield: 20%) as a colorless oil.

Data for I-160 is provided below.

TABLE 9

Characterization Data for Additional Exemplary Compounds

| Compound No. | Chemical Structure | [M + H] observed | ¹H NMR (400 MHz) |
|---|---|---|---|
| I-160 | 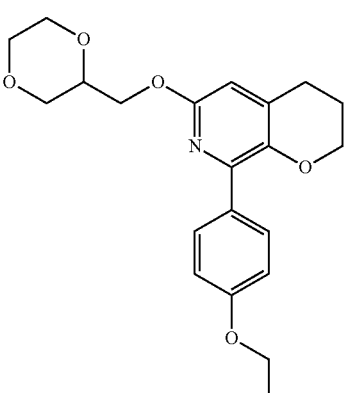 | 426.3 | ¹H NMR (400 MHz, DMSO-d₆) δ 7.95-7.99 (m, 2 H), 7.08-7.12 (m, 2 H), 6.54 (s, 1 H), 4.80 (q, J = 8.8 Hz, 2 H), 4.17-4.24 (m, 4 H), 3.73-3.88 (m, 3 H), 3.57-3.66 (m, 2 H), 3.45-3.51 (m, 1 H), 3.34-3.40 (m, 1 H), 2.81 J = 6.8 Hz, 2 H), 1.91-1.96 (m, 2 H). |

Example 9: Synthesis of I-161
Synthetic Scheme of I-161
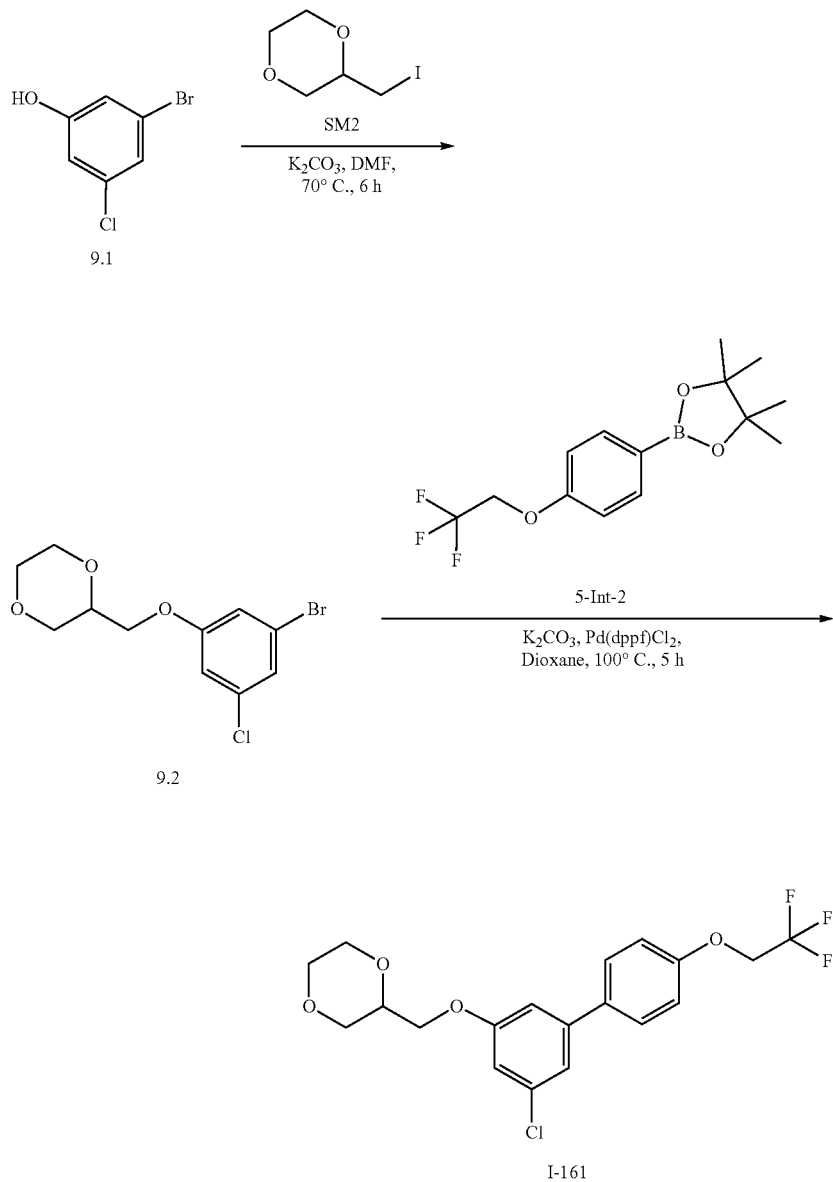
1. The Synthesis of Intermediate 9.2
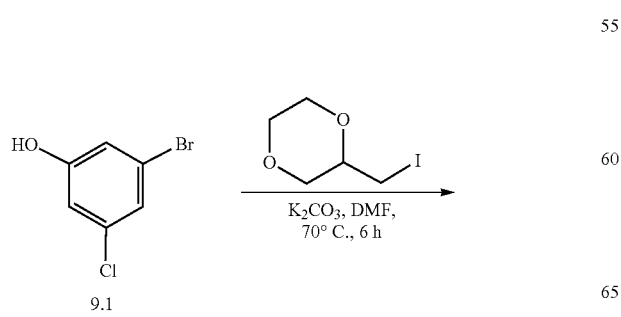
To a stirred solution of 9.1 (412 mg, 2.0 mmol), 2-(iodomethyl)-1,4-dioxane (2.3 g, 10.0 mmol) in DMF (5 mL)

was added K₂CO₃ (1.1 g, 8.0 mmol). The reaction mixture was stirred at 70° C. for 6 hours until the reaction was complete (by LCMS). The suspension was diluted with H₂O (20 mL) and extracted with DCM (20 mL×2), the combined organic phase was concentrated. The crude product was purified by flash column chromatography (silica gel, PE/EA=5:1) to give 9.2 (500 mg, yield: 82%) as brown oil. LC-MS m/z: 307.2 [M+H]⁺.

2. The Synthesis of Target I-161

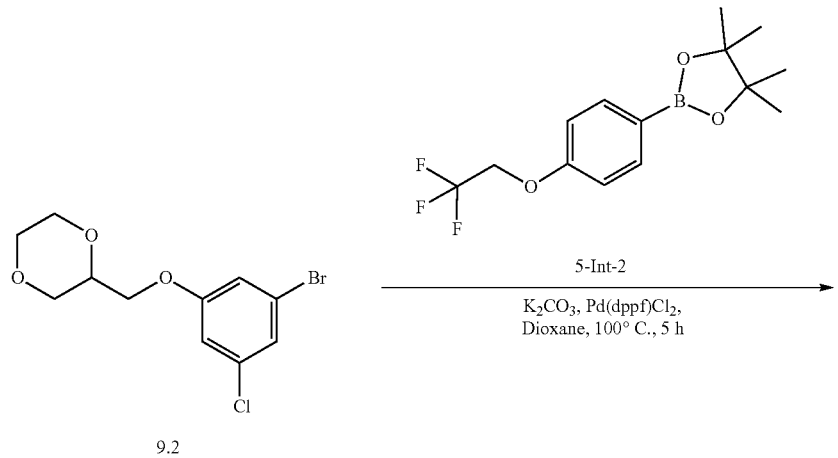

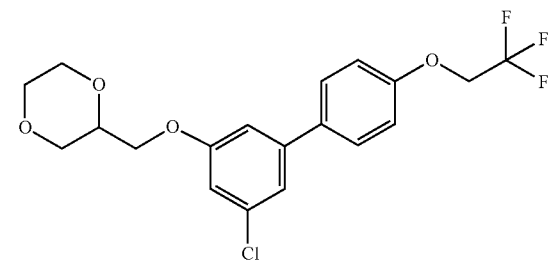

I-161

To a stirred solution of 9.2 (130 mg, 0.42 mmol), 5-Int-2 (127 mg, 0.42 mmol) and K₂CO₃ (174 mg, 1.26 mmol) in dioxane (10 mL) was added Pd(dppf)Cl₂ (25 mg). The reaction mixture was stirred at 100° C. for 5 hours until the reaction was complete (by LCMS). The suspension was diluted with H₂O (20 mL) and extracted with EA (20 mL×2), the combine organic phase was concentrated. The crude product was purified by Prep-HPLC to give I-161 (108 mg, yield: 640R) as a yellow solid.

Additional exemplary compounds were prepared following methods substantially similar to the method described above and herein. Data for these compounds are provided below.

TABLE 10

Characterization Data for Additional Exemplary Compounds

| Compound No. | Chemical Structure | [M + H] observed | ¹H NMR (400 MHz) |
|---|---|---|---|
| I-161 | 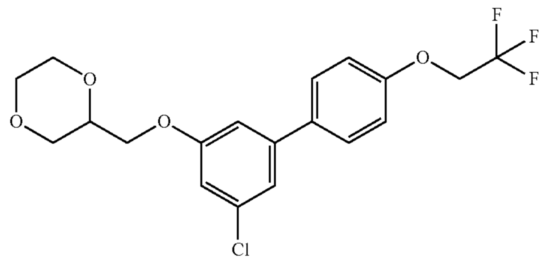 [SMILES: FC(F)(F)COc1ccc(-c2cc(Cl)cc(OCC3COCCO3)c2)cc1] | 403.1 | ¹H NMR (400 MHz, CDCl₃): δ 7.71 (d, J = 8.8 Hz, 2 H), 7.28 (d, J = 1.6 Hz, 1 H), 7.14-7.17 (m, 3 H), 7.00 (t, J = 2.0 Hz, 1 H), 4.83 (q, J = 9.2 Hz, 2 H), 4.07 (d, J = 3.2 Hz, 2 H), 3.76-3.86 (m, 3 H), 3.63-3.69 (m, 2 H), 3.36-3.54 (m, 2 H). |
| I-53 | 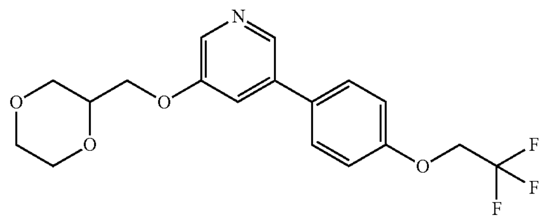 [SMILES: FC(F)(F)COc1ccc(-c2cncc(OCC3COCCO3)c2)cc1] | 370.1 | ¹H NMR (400 MHz, DMSO-d₆) δ 8.48 (d, J = 1.6 Hz, 1H), 8.26 (d, J = 2.8 Hz, 1H), 7.74-7.77 (m, 2H), 7.62-7.64 (m, 1H), 7.17-7.20 (m, 2H), 4.84 (q, J = 8.8 Hz, 2H), 4.14 (d, J = 5.2 Hz, 2H), 3.76-3.89 (m, 3H), 3.64-3.70 (m, 2H), 3.40-3.54 (m, 2H). |
| I-162 | 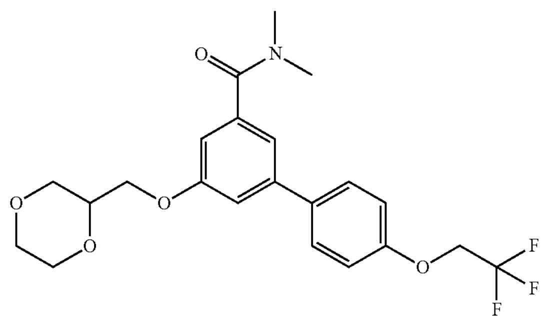 [SMILES: CN(C)C(=O)c1cc(OCC2COCCO2)cc(-c2ccc(OCC(F)(F)F)cc2)c1] | 440.2 | ¹H NMR (400 MHz, DMSO-d₆) δ 7.68-7.72 (m, 2 H), 7.13-7.25 (m, 4 H), 6.89-6.90 (m, 1 H), 4.82 (q, J = 8.8 Hz, 2 H), 4.07 (d, J = 5.2 Hz, 2 H), 3.31-3.91 (m, 7 H), 2.99 (s, 3H), 2.93 (s, 3H). |
| I-163 | 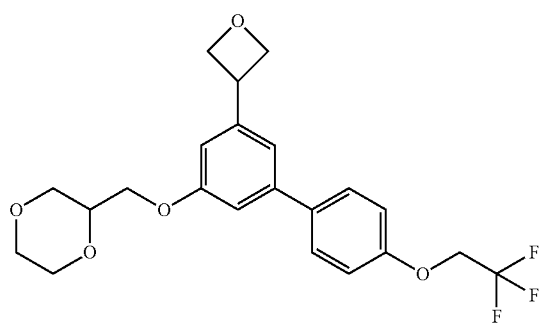 [SMILES: FC(F)(F)COc1ccc(-c2cc(OCC3COCCO3)cc(C3COC3)c2)cc1] | 425.1 | ¹H NMR (400 MHz, CDCl₃): δ 7.54 (d, J = 8.8 Hz, 2H), 7.15 (s, 1H), 6.99-7.02 (m, 3H), 6.95 (s, 1H), 5.09 (dd, J = 6.0 Hz, 8.4 Hz, 2H), 4.80 (t, J = 6.4 Hz, 2H), 4.40 (q, J = 9.2 Hz, 2H), 4.22-4.26 (m, 1H), 3.98-4.09 (m, 3H), 3.68-3.93 (m, 5H), 3.55-3.60 (m, 1H). |
| I-29 | 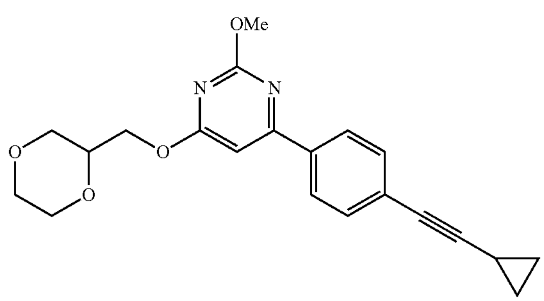 [SMILES: COc1nc(OCC2COCCO2)cc(-c2ccc(C#CC3CC3)cc2)n1] | 367.2 | ¹HNMR (400 MHz, DMSO-d₆) δ 8.14 (d, J = 8.4 Hz, 2H), 7.47 (d, J = 8.4 Hz, 2H), 7.17 (s, 1H), 4.33 (d, J = 4.8 Hz, 2H), 3.97 (s, 3H), 3.86-3.90 (m, 1H), 3.74-3.83 (m, 2H), 3.58-3.68 (m, 2H), 3.47-3.53 (m, 1H), 3.67-3.42 (m, 1H), 1.56-1.61 (m, 1H), 0.89-0.93 (m, 2H), 0.76-0.79 (m, 2H). |

TABLE 10-continued

Characterization Data for Additional Exemplary Compounds

| Compound No. | Chemical Structure | [M + H] observed | $^1$H NMR (400 MHz) |
|---|---|---|---|
| I-103 | 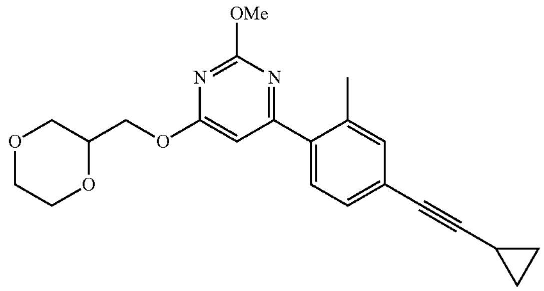 [SMILES: COc1nc(OCC2COCCO2)cc(-c2ccc(C#CC3CC3)cc2C)n1] | 381.3 | $^1$H NMR (400 MHz, DMSO-$d_6$) δ 7.44 (d, J = 7.6 Hz, 1H), 7.32 (s, 1H), 7.27 (d, J = 8.0 Hz, 1H), 6.71 (s, 1H), 4.32 (d, J = 4.8 Hz, 2H), 3.91 (s, 4H), 3.74-3.82 (m, 2H), 3.54-3.67 (m, 2H), 3.46-3.52 3.52 (m, 1H), 3.38 (t, J = 10.4 Hz, 1H), 2.37 (s, 3H), 1.53-1.60 (m, 1 H), 0.88-0.93 (m, 2H), 0.73-0.77 (m, 2 H). |
| I-87 | 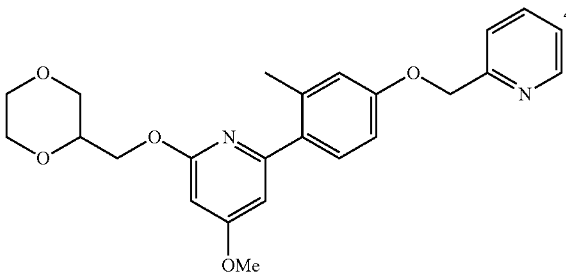 [SMILES: COc1cc(OCC2COCCO2)nc(-c2ccc(OCc3ccccn3)cc2C)c1] | 423.3 | $^1$H NMR (400 MHz, DMSO-$d_6$) δ 8.58-8.60 (m, 1H), 7.82-7.87 (m, 1H), 7.52 (d, J = 8.0 Hz, 1H), 7.34-7.38 (m, 2H), 6.89-6.98 (m, 2H), 6.65 (d, J = 2.0 Hz, 1H), 6.32 (d, J = 2.0 Hz, 1H), 5.22 (s, 2H), 4.17-4.25 (m, 2H), 3.73-3.87 (m, 6H), 3.57-3.67 (m, 2H), 3.45-3.51 (m, 1H), 3.34-3.40 (m, 1H), 2.35 (s, 3H). |
| I-164 | 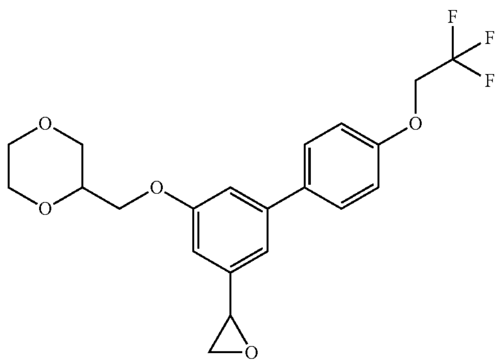 [SMILES: FC(F)(F)COc1ccc(-c2cc(OCC3COCCO3)cc(C3CO3)c2)cc1] | 411.2 | $^1$H NMR (400 MHz, DMSO-$d_6$) δ 7.67 (d, J = 8.8 Hz, 2 H), 7.12-7.16 (m, 4 H), 6.80 (s, 1 H), 4.82 (q, J = 8.8 Hz, 2 H), 4.00-4.04 (m, 2 H), 3.96-3.98 (m, 1 H), 3.38-3.88 (m, 7 H), 3.12 (t, J = 3.6 Hz, 1 H), 2.90-2.96 (m, 1 H). |
| I-165 | 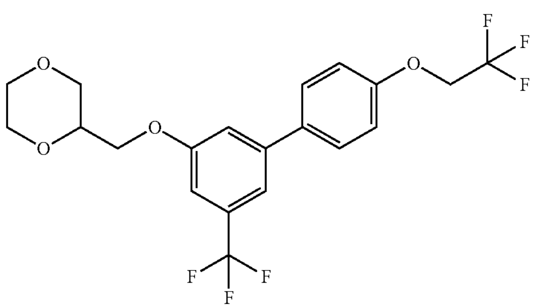 [SMILES: FC(F)(F)COc1ccc(-c2cc(OCC3COCCO3)cc(C(F)(F)F)c2)cc1] | 437.2 | $^1$H NMR (400 MHz, DMSO-$d_6$) δ 7.76 (d, J = 8.8 Hz, 2 H), 7.50 (d, J = 8.8 Hz, 2 H), 7.22 (s, 1 H), 7.16-7.18 (m, 2 H), 4.84 (q, J = 8.8 Hz, 2 H), 4.14 (d, J = 5.2 Hz, 2 H), 3.40-3.88 (m, 7 H). |
| I-166 | 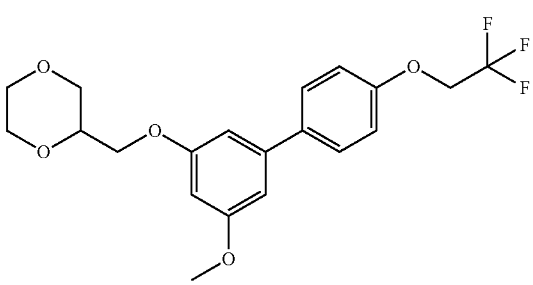 [SMILES: COc1cc(OCC2COCCO2)cc(-c2ccc(OCC(F)(F)F)cc2)c1] | 399.1 | $^1$H NMR (400 MHz, DMSO-$d_6$) δ 7.65 (d, J = 8.8 Hz, 2H), 7.12 (d, J = 8.8 Hz, 2H), 6.76 (d, J = 2.4 Hz, 2H), 6.48 (t, J = 2.0 Hz, 1H), 4.81 (q, J = 8.8 Hz, 2H), 4.01 (d, J = 4.8 Hz, 2H), 3.74-3.89 (m, 6H), 3.59-3.69 (m, 2H), 3.37-3.54 (m, 2H). |

TABLE 10-continued

Characterization Data for Additional Exemplary Compounds

| Compound No. | Chemical Structure | [M + H] observed | $^1$H NMR (400 MHz) |
|---|---|---|---|
| I-132 | | 424.3 | $^1$H NMR (400 MHz, CDCl$_3$): δ 8.61(d, J = 4.8 Hz, 1H), 8.03-8.05 (m, 1H), 7.69-7.74 (m, 1H), 7.52 (d, J = 8.0 Hz, 1H), 7.21-7.24 (m, 1H), 6.88-6.90 (m, 2H), 6.00 (s, 1H), 5.26 (s, 2H), 4.36-4.45 (m, 2H), 3.89-4.02 (m, 4H), 3.74-3.89 (m, 3H), 3.62-3.72 (m, 2H), 3.48-3.54 (m, 1H), 2.67 (s, 3H). |
| I-132 | | 424.4 | $^1$H NMR (400 MHz, CDCl$_3$): δ 8.60-8.62 (m, 1H), 7.70-7.74 (m, 1H), 7.52 (d, J = 8.0 Hz, 1H), 7.41 (d, J = 8.8 Hz, 1H), 7.22-7.25 (m, 1H), 6.86-6.90 (m, 2H), 6.46 (s, 1H), 5.24 (s, 2H), 4.43 (dd, J = 6.0 Hz, 11.2 Hz, 1H), 4.32 (dd, J = 4.8 Hz, 11.2 Hz, 1H), 4.03-4.09 (m, 1H), 4.00 (s, 3H), 3.92 (dd, J = 2.4 Hz, 11.2 Hz, 1H), 3.55-3.85 (m, 4H), 3.49-3.55 (m, 1H), 2.43 (s, 1H). |
| I-55 | 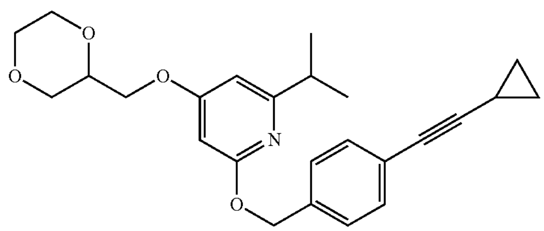 [SMILES: CC(C)c1cc(OCC2COCCO2)cc(OCc2ccc(C#CC3CC3)cc2)n1] | 408.3 | $^1$H NMR (400 MHz, CDCl$_3$): δ 7.32-7.37 (m, 4 H), 6.35 (d, J = 2.0 Hz, 1 H), 6.04 (d, J = 2.0 Hz, 1 H), 5.34 (s, 2 H), 3.48-3.99 (m, 9 H), 2.81-2.88 (m, 1 H), 1.41-1.47 (m, 1 H), 1.22 (d, J = 6.8 Hz, 6 H), 0.77-0.89 (m, 4 H). |
| I-33 | 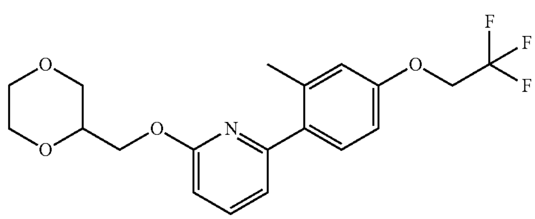 | 384.1 | $^1$H NMR (400 MHz, DMSO-d$_6$) δ 7.77 (t, J = 7.6 Hz, 1H), 7.40 (d, J = 8.4 Hz, 1H), 7.10 (d, J = 7.2 Hz, 1H), 7.02 (d, J = 2.4 Hz, 1H), 6.97 (dd, J = 2.8 Hz, 8.4 Hz, 1H), 6.78 (d, J = 8.0 Hz, 1H), 4.80 (q, J = 8.8 Hz, 2H), 4.20-4.26 (m, 2H), 3.84-3.90 (m, 1H), 3.74-3.81 (m, 2H), 3.58-3.67 (m, 2H), 3.46-3.51 (m, 1H), 3.39 (m, 1H), 2.38 (s, 3H). |
| I-59 | 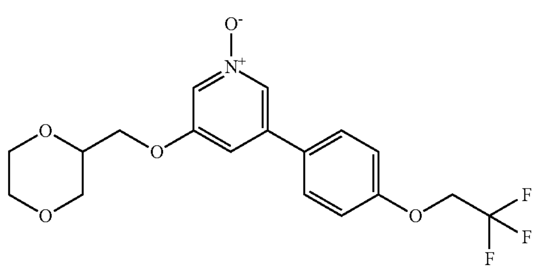 [SMILES: [O-][n+]1cc(OCC2COCCO2)cc(-c2ccc(OCC(F)(F)F)cc2)c1] | 386.2 | $^1$H NMR (400 MHz, DMSO-d$_6$) δ 8.25 (s, 1H), 8.04 (s, 1H), 7.78 (d, J = 8.8 Hz, 2H), 7.33 (s, 1H), 7.17 (d, J = 8.8 Hz, 2H), 4.85 (q, = 9.2 Hz, 2H), 4.13 (d, J = 4.8 Hz, 2H), 3.75-3.88 (m, 3H), 3.60-3.69 (m, 2H), 3.37-3.53 (m, 2H). |
| I-24 | 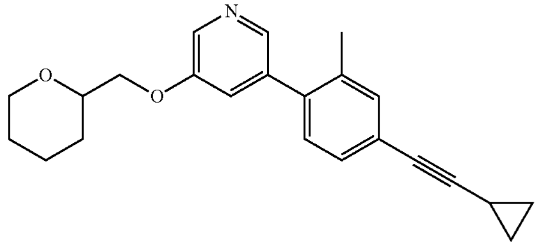 [SMILES: Cc1cc(C#CC2CC2)ccc1-c1cncc(OCC2CCCCO2)c1] | 348.1 | $^1$H NMR (400 MHz, CDCl$_3$): δ 8.33 (br, 1H), 8.19 (br, 1H), 7.31 (s, 1H), 7.27 (s, 1H), 7.17 (s, 1H), 7.10 (d, J = 8.0 Hz, 1H), 4.02-4.08 (m, 2H), 3.94-3.98 (m, 1H), 3.71-3.77 (m, 1H), 3.49-3.55 (m, 1H), 2.22 (s, 3H), 1.90-1.93 (m, 1H), 1.43-1.67 (m, 6H), 0.80-0.91 (m, 4H). |

TABLE 10-continued

Characterization Data for Additional Exemplary Compounds

| Compound No. | Chemical Structure | [M + H] observed | ¹H NMR (400 MHz) |
|---|---|---|---|
| I-43 | 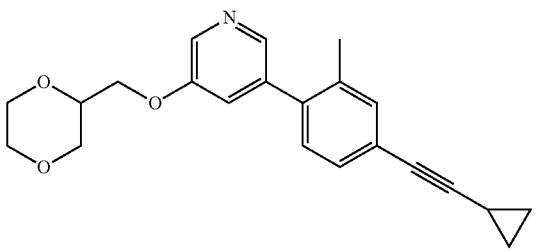 [SMILES: Cc1cc(C#CC2CC2)ccc1-c1cncc(OCC2COCCO2)c1] | 350.0 | ¹H NMR (400 MHz, CDCl₃): δ 8.30 (d, J = 2.8 Hz, 1H), 8.18 (d, J = 1.6 Hz, 1H), 7.31 (s, 1H), 7.25 (d, J = 0.8 Hz, 1H), 7.15-7.16 (m, 1H), 7.10 (d, J = 7.6 Hz, 1H), 3.98-4.10 (m, 3H), 3.75-3.93 (m, 4H), 3.64-3.70 (m, 1H), 3.54-3.59 (m, 1H), 2.22 (s, 3H), 1.43-1.50 (m, 1H), 0.80-0.91 (m, 4H). |
| I-56 | 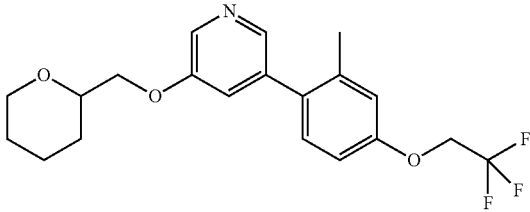 [SMILES: Cc1cc(OCC(F)(F)F)ccc1-c1cncc(OCC2CCCCO2)c1] | 382.2 | ¹H NMR (400 MHz, CDCl₃): δ 8.31 (d, J = 2.4 Hz, 1H), 8.15 (s, 1H), 7.15-7.17 (m, 2H), 6.89 (d, J = 2.4 Hz, 1H), 6.84 (dd, J = 2.4 Hz, 8.4 Hz, 1H), 4.39 (q, J = 8.0 Hz, 2H), 4.03-4.08 (m, 2H), 3.97 (dd, J = 3.6 Hz, 10.0 Hz, 1H), 3.73-3.77 (m, 1H), 3.49-3.55 (m, 1H), 2.26 (s, 3H), 1.91-1.94 (m, 1H), 1.43-1.68 (m, 5H). |
| I-32 | 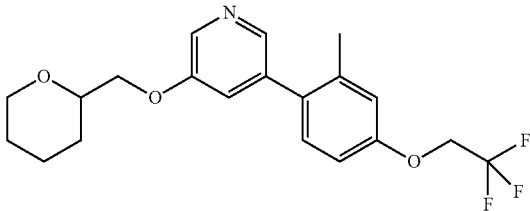 [SMILES: Cc1cc(OCC(F)(F)F)ccc1-c1cncc(OCC2CCCCO2)c1] | 384.0 | ¹H NMR (400 MHz, CDCl₃): δ 8.30 (d, J = 2.8 Hz, 1H), 8.18 (d, J = 1.6 Hz, 1H), 7.15-7.17 (m, 2H), 6.89 (d, J = 2.8 Hz, 1H), 6.84 (dd, J = 2.4 Hz, 8.0 Hz, 1H), 4.39 (q, J = 8.0 Hz, 2H), 3.99-4.11 (m, 3H), 3.75-3.94 (m, 4H), 3.54-3.71 (m, 2H), 2.26 (s, 3H). |
| I-111 | 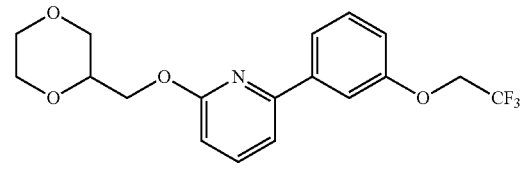 [SMILES: FC(F)(F)COc1cccc(-c2cccc(OCC3COCCO3)n2)c1] | 370.1 | ¹H NMR (400 MHz, CDCl₃): δ 7.72-7.57 (m, 3H), 7.40 (t, J = 8.0 Hz, 1H), 7.34 (d, J = 7.4 Hz, 1H), 6.97 (ddd, J = 8.2, 2.6, 0.8 Hz 1H) 6.77 (d, J = 8.2 Hz, 1H), 4.55-4.34 (m, 4H), 4.07 (dddd, J = 10.2, 5.6, 4.7, 2.6 Hz, 1H), 10.2, 1H). |
| I-129 | 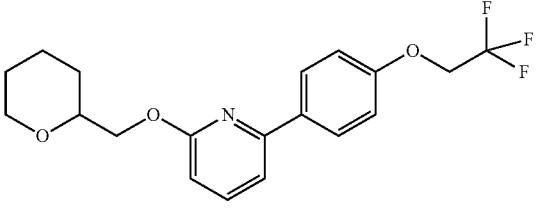 [SMILES: FC(F)(F)COc1ccc(-c2cccc(OCC3CCCCO3)n2)cc1] | 368.1 | ¹H NMR (400 MHz, CDCl₃): δ 8.00 (d, J = 9.0 Hz, 1H), 7.60 (dd, J = 8.2, 7.5 Hz, 1H), 7.33-7.20 (m, 1H), 7.01 (d, J = 9.0 Hz, 1H), 6.73 (dd, J = 8.2, 0.6 Hz, 1H), 4.49-4.34 (m, 4H)), 4.09 (ddd, J = 11.4, 4.0, 1.9 Hz, 2H), 3.77 (dddd, J = 10.6, 6.0, 3.8, 2.1 Hz, 2H), 3.52 (td, J = 11.6, 2.3 Hz, 1H), 1.96-1.87 (m, 1H), 1.76-1.41 (m, 5H). |
| I-104 | 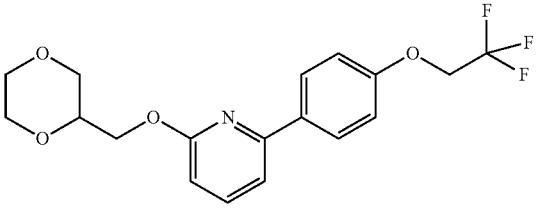 [SMILES: FC(F)(F)COc1ccc(-c2cccc(OCC3COCCO3)n2)cc1] | 307.1 | ¹H NMR (400 MHz, CDCl₃): δ 7.98 (d, J = 9.0 Hz, 1H), 7.62 (dd, J = 8.2, 7.5 Hz, 1H), 7.29 (dd, J = 7.5, 0.6 Hz, 1H), 7.01 (d, J = 9.0 Hz, 1H), 6.72 (dd, J = 8.2, 0.6 Hz, 1H), 4.68-4.31 (m, 4H), 4.06 (dddd, J = 10.3, 5.7, 4.7, 2.7 Hz, 1H), 3.98-3.64 (m, 5H), 3.56 (dd, J = 11.5, 10.1 Hz, 1H). |

TABLE 10-continued

Characterization Data for Additional Exemplary Compounds

| Compound No. | Chemical Structure | [M + H] observed | ¹H NMR (400 MHz) |
|---|---|---|---|
| I-167 | 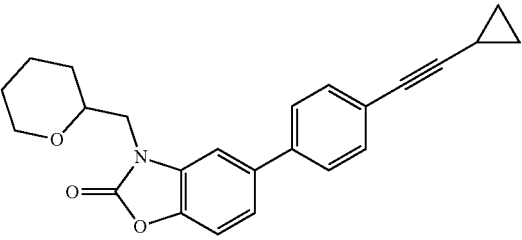 [SMILES: O=c1oc2ccc(-c3ccc(C#CC4CC4)cc3)cc2n1CC1CCCCO1] | 374.2 | ¹H NMR (400 MHz, CDCl₃): δ 7.51-7.17 (m, 7H), 3.98-3.77 (m, 3H), 3.70 (dddd, J = 11.0, 6.2, 4.0, 2.1 Hz, 1H), 3.36 (td, J = 11.6, 2.3 Hz, 1H), 1.87 (dd, J = 9.0, 3.5 Hz, 1H), 1.70 (d, J = 12.4 Hz, 1H), 1.63-1.23 (m, 5H), 0.93-0.85 (m, 2H), 0.83 (tt, J = 5.2, 2.3 Hz, 2H). |
| I-168 | 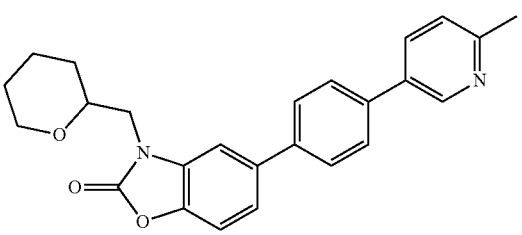 [SMILES: Cc1ccc(-c2ccc(-c3ccc4oc(=O)n(CC5CCCCO5)c4c3)cc2)cn1] | 401.2 | ¹H NMR (400 MHz, CDCl₃): δ 8.81-8.75 (m, 1H), 7.82 (dd, J = 8.0, 2.4 Hz, 1H), 7.66 (br s, 4H), 7.40-7.31 (m, 2H), 7.29-7.21 (m, 2H), 3.99-3.90 (m, 1H), 3.90-3.79 (m, 2H), 3.71 (tdd, J = 9.2, 3.8, 2.1 Hz, 1H), 3.37 (td, J = 11.6, 2.5 Hz, 1H), 2.62 (s, 3H), 1.87 (dt, J = 9.0, 3.1 Hz, 1H), 1.75-1.67 (m, 1H), 1.64-1.32 (m, 4H). |
| I-169 | 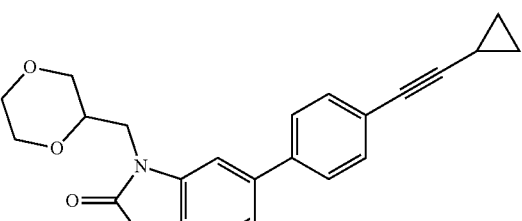 | 376.2 | ¹H NMR (400 MHz, CDCl₃): δ 7.46-7.40 (m, 4H), 7.27 (dd, J = 8.3, 1.8 Hz, 1H), 7.25-7.19 (m, 2H), 4.00-3.92 (m, 1H), 3.89-3.81 (m, 3H), 3.76 (dd, J = 11.2, 2.5 Hz, 1H), 3.71-3.62 (m, 2H), 3.57 (td, J = 11.8, 11.3, 2.7 Hz, 1H), 3.41 (dd, J = 11.6, 9.9 Hz, 1H), 1.57-1.37 (m, 1H), 0.94-0.83 (m, 2H), 0.83-0.75 (m, 2H). |
| I-25 | 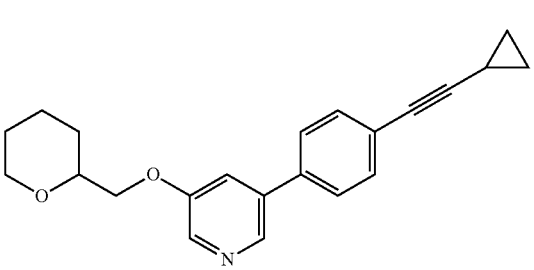 [SMILES: C(#CC1CC1)c1ccc(-c2cncc(OCC3CCCCO3)c2)cc1] | 334.2 | ¹H NMR (400 MHz, CDCl₃): δ 8.42 (d, J = 1.8 Hz, 1H), 8.29 (d, J = 2.7 Hz, 1H), 7.49-7.42 (m, 4H), 7.38 (dd, J = 2.7, 7.9 Hz, 1H), 4.11-4.03 (m, 2H), 3.98 (dd, J = 9.8, 3.7 Hz, 1H), 3.73 (dtd, J = 10.1, 3.7, 1.9 Hz, 2H), 3.51 (td, J = 11.7, 2.5 Hz, 1H), 1.97-1.86 (m, 1H), 1.73-1.40 (m, 6H), 0.93-0.85 (m, 2H), 0.85-0.78 (m, 2H). |
| I-54 | 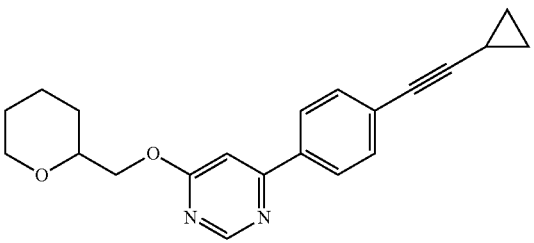 | 335.2 | ¹H NMR (400 MHz, CDCl₃): δ 8.79 (d, J = 1.1 Hz, 1H), 7.93 (d, J = 8.7 Hz, 2H), 7.46 (d, J = 8.6 Hz, 2H), 7.16 (d, J = 1.1 Hz, 1H), 4.43 (dd, J = 11.4, 3.1 Hz, 1H), 4.35 (dd, J = 11.4, 7.0 Hz, 1H), 4.10-4.02 (m, 1H), 3.78-3.68 (m, 1H), 3.50 (td, J = 11.6, 2.4 Hz, 1H), 1.95-1.86 (m, 1H), 1.75-1.27 (m, 6H), 0.98-0.86 (m, 2H), 0.86-0.80 (m, 2H). |
| I-124 | 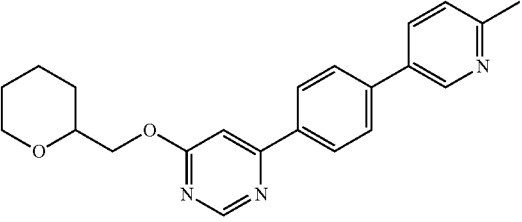 [SMILES: Cc1ccc(-c2ccc(-c3cc(OCC4CCCCO4)ncn3)cc2)cn1] | 362.2 | ¹H NMR (400 MHz, CDCl₃): δ 8.84 (d, J = 1.1 Hz, 1H), 8.79 (dd, J = 2.4, 0.6 Hz, 2H), 8.16-8.09 (m, 2H), 7.83 (dd, J = 8.0, 2.4 Hz, 1H), 7.73-7.66 (m, 2H), 7.29-7.22 (m' 2H)' 4.46 (dd, J = 11.4, 3.1 Hz, 1H), 4.37 (dd, J = 11.4, 7.1 Hz, 1H), 4.12-4.04 (m, 1H), 3.81-3.70 (m, 1H), 3.52 (td, J = 11.5, 2.3 Hz, 1H), 2.62 (s, 3H), 1.97-1.88 (m, 1H), 1.77-1.35 (m, 5H). |

TABLE 10-continued
Characterization Data for Additional Exemplary Compounds
| Compound No. | Chemical Structure | [M + H] observed | ¹H NMR (400 MHz) |
|---|---|---|---|
| I-16 | 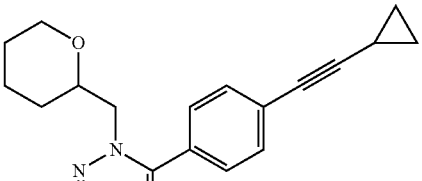 | 335.2 | ¹H NMR (CD$_3$OD, 400 MHz) δ 8.03 (d, J = 3.0 Hz, 1H), 7.49 (d, J = 8.5 Hz, 2H), 7.44 (d, J = 8.5 Hz, 2H), 6.42 (d, J = 3.0 Hz, 1H), 4.06 (dd, J = 13.7, 8.90 Hz, 1H), 3.99 (dd, J = 13.7, 3.6 Hz, 1H), 3.90-3.82 (m, 1H), 3.29-3.19 (m, 1H), 1.85-1.76 (m, 1H), 1.69-1.41 (m, 5H), 1.20-1.04 (m, 1H), 1.00-0.86 (m, 2H), 0.86-0.70 (m, 2H). |
| I-135 | 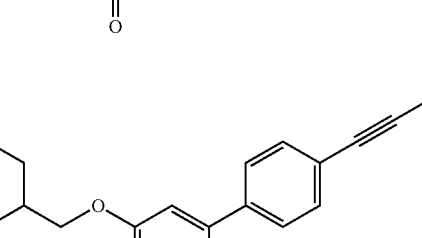 | 335.2 | ¹H NMR (CD$_3$OD, 400 MHz) δ 8.91 (d, J = 2.8 Hz, 1H), 7.95 (d, J = 8.7 Hz, 2H), 7.50 (d, J = 8.6 Hz, 2H), 7.25 (d, J = 2.8 Hz, 1H), 4.14 (dd, J = 10.0, 6.4 Hz, 1H), 4.10-4.02 (m, 2H), 3.85-3.73 (m, 1H), 3.52 (td, J = 11.6, 2.8 Hz, 1H), 2.03-1.88 (m, 1H), 1.76-1.60 (m, 2H), 1.57-1.42 (m, 4H), 0.98-0.87 (m, 2H), 0.87-0.79 (m, 2H). |
Example 10: Synthesis of I-45
Synthetic Scheme of I-45
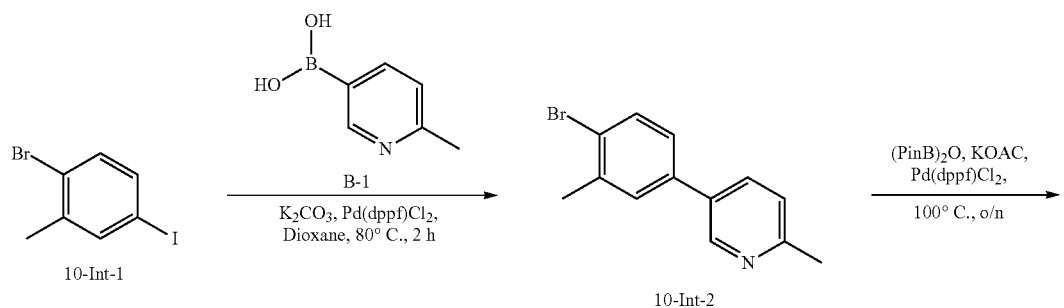
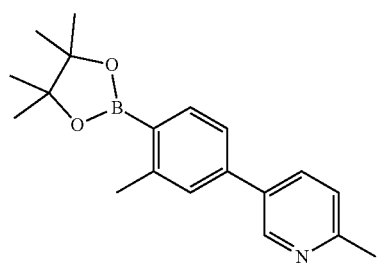

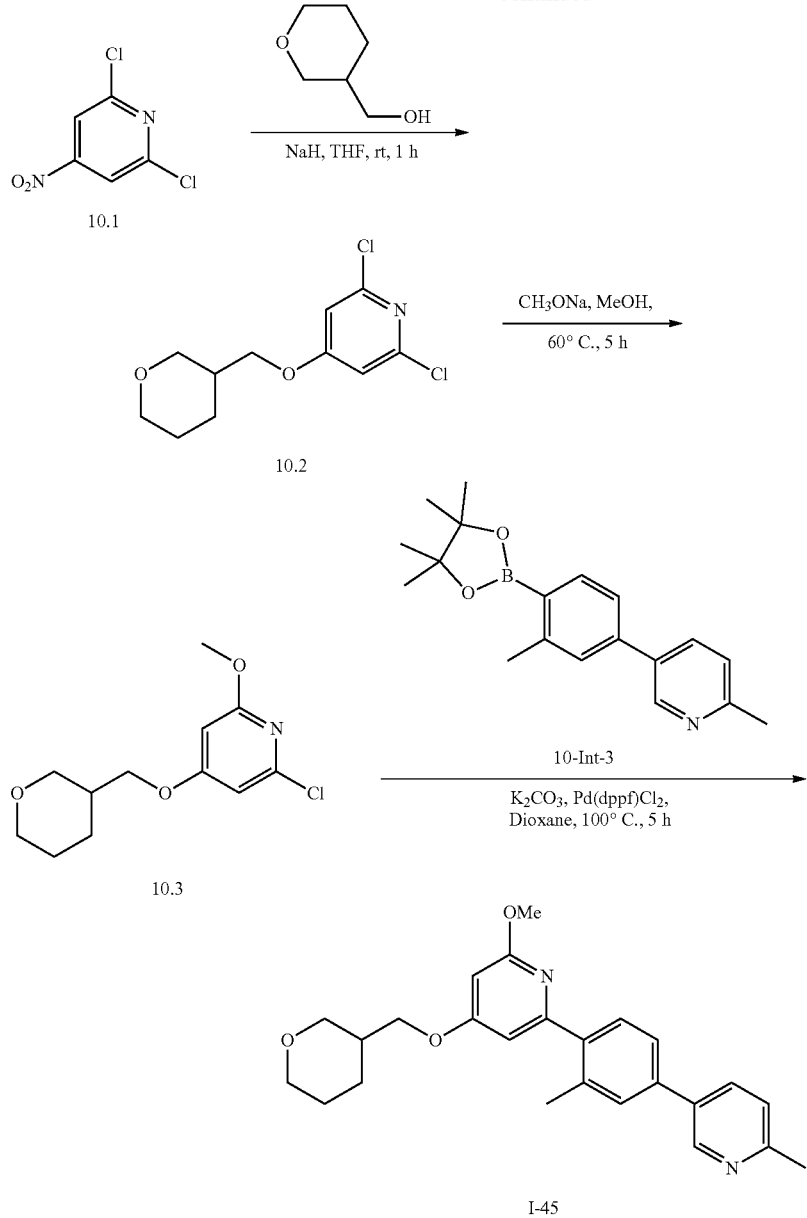

I-45

1. The Synthesis of 5-(4-bromo-3-methylphenyl)-2-methylpyridine (10-Int-2)

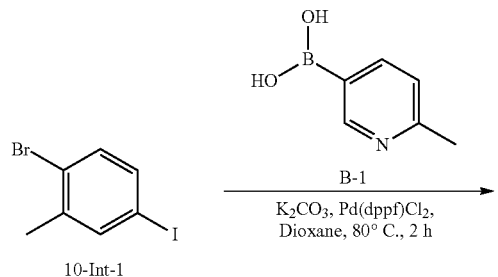

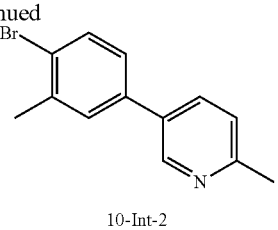

10-Int-2

To a stirred solution of 10-Int-1 (5.66 g, 19.11 mmol), compound B-1 (2.38 g, 17.37 mmol) and $K_2CO_3$ (8.50 g, 26.06 mmol) in a mixture of 1,4-dioxane and $H_2O$ (10:1, 10 mL) was added Pd(dppf)Cl$_2$ (240 mg), then the reaction mixture was stirred at 80° C. for 2 hours until the reaction was completed. The suspension was diluted with NaCl (aq.), extracted with EtOAc (15 mL×3), concentrated, the crude product was purified by flash column chromatography (silica gel, PE/EA=4:1) to give 10-Int-2 (3.07 g, 64% yield) as a yellow solid. LC-MS m/z: 262.2 [M+H]+. LCMS Purity (214 nm):98.24%; $t_R$=2.068 min.

2. The Synthesis of 2-methyl-5-(3-methyl-4-(4,4,5,5-tetramethyl-1,3,2-dioxaborolan-2-yl)phenyl)pyridine (10-Int-3)

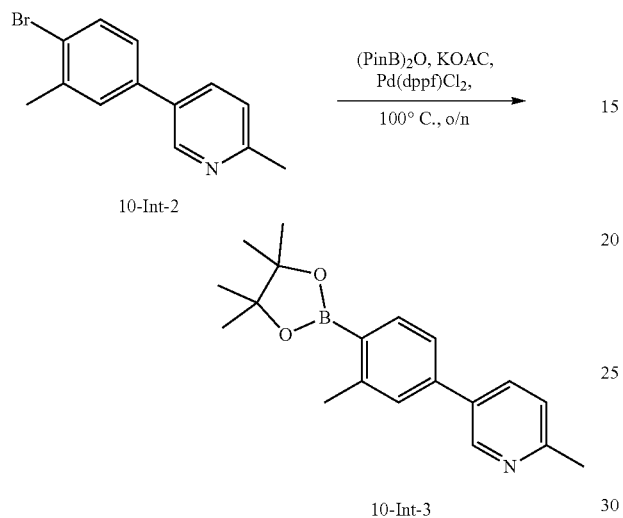

To a stirred solution of 10-Int-2 (2.00 g, 7.66 mmol), (PinB)₂O (9.73 g, 38.3 mmol) and KOAc (1.13 g, 11.49 mmol) in 1,4-dioxane (20 mL) was added Pd(dppf)Cl₂ (200 mg), then the mixture was stirred at 100° C. overnight until the reaction was completed. The suspension was diluted with NaCl (aq.), extracted with EtOAc (50 mL×3), concentrated, the crude product was purified by flash column chromatography (silica gel, PE/EA=8:1) to give 10-Int-3 (1.8 g, 76% yield) as a white solid. LC-MS m/z: 310.2 [M+H]+. LCMS Purity (214 nm):95.93%; $t_R$=1.969 min.

3. The Synthesis of Intermediate 10.2

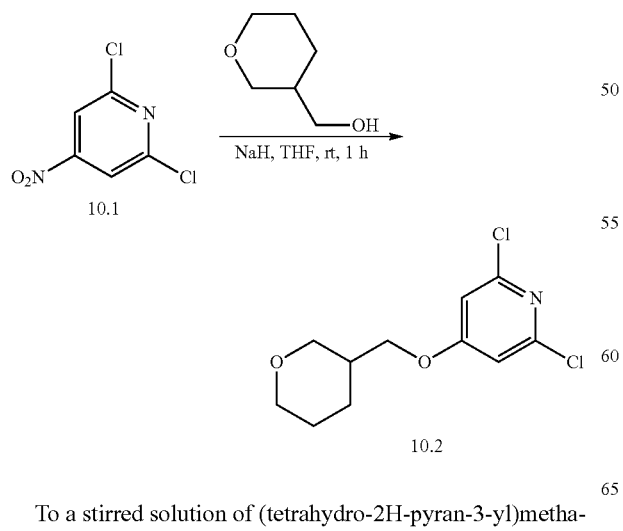

To a stirred solution of (tetrahydro-2H-pyran-3-yl)methanol (332 mg, 2.9 mmol) in THF (10 ml) was added NaH (312 mg, 7.8 mmol, 60% in mineral oil). The reaction mixture was stirred at RT for 30 min, then 10.1 (500 mg, 2.6 mmol) was added. The reaction mixture was stirred at room temperature for 1 h until the reaction was complete (by LCMS). Ice water (10 mL) was added and the reaction was extracted with EtOAc (10 mL×2). The organic phase was combined, washed with brine, dried over anhydrous Na₂SO₄, The solvents was removed under reduced pressure and purified by flash column chromatography (silica gel, PE/EA=2:1) to give 10.2 (624 mg, yield: 84%) as yellow oil.

4. The Synthesis of Intermediate 10.3

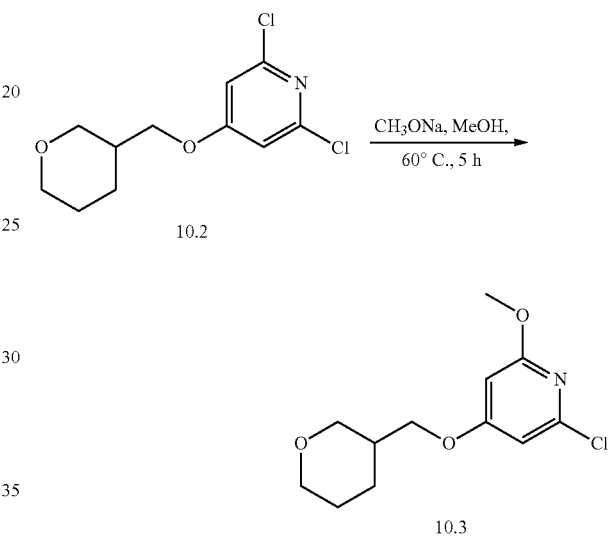

To a stirred solution of CH₃ONa (205 mg, 3.8 mmol) in CH₃OH (10 ml) was added 10.2 (500 mg, 1.9 mmol). The reaction mixture was stirred at 60° C. for 5 h. Ice water (10 mL) was added and the reaction mixture was extracted with EtOAc (10 mL×2). The organic phase was combined, washed with brine, dried over anhydrous Na₂SO₄, The solvent was removed under reduced pressure and purified by flash column chromatography (silica gel, PE/EA=2:1) to give 10.3 (342 mg, yield: 70%) as yellow oil.

5. The Synthesis of Target I-45

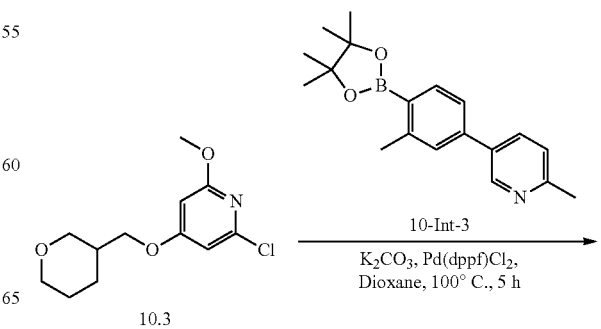

-continued

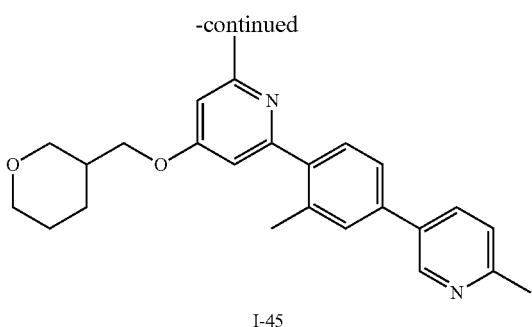

I-45

To a stirred solution of 10.3 (200 mg, 0.76 mmol), 10-Int-3 (352 mg, 1.14 mmol) and K$_2$CO$_3$ (316 mg, 2.28 mmol) in dioxane (15 mL) was added Pd(dppf)Cl$_2$ (20 mg). The reaction mixture was stirred at 100° C. for 5 hours under Ar atmosphere until the reaction was complete (by LCMS). The suspension was diluted with H$_2$O (20 mL) and extracted with EA (20 mL×2), the combine organic phase was concentrated. The crude product was purified by Prep-HPLC to give I-45 (64.99 mg, yield: 21%) as colorless oil.

Additional exemplary compounds were prepared following methods substantially similar to the method described above and herein. Data for these compounds are provided below.

TABLE 11

Characterization Data for Additional Exemplary Compounds

| Compound No. | Chemical Structure | [M + H] observed | $^1$H NMR (400 MHz) |
|---|---|---|---|
| I-12 | 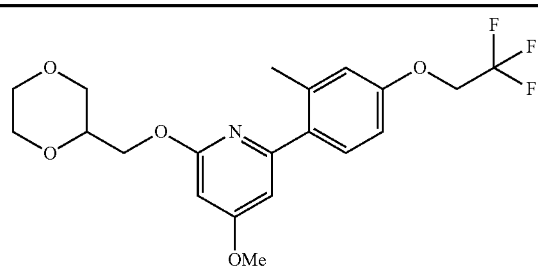 | 414.3 | $^1$H NMR (400 MHz, DMSO-d$_6$) δ 7.38 (d, J = 8.4 Hz, 1H), 7.00 (d, J = 2.8 Hz, 1H), 6.95 (dd, J = 2.4 Hz, 8.4 Hz, 1H), 6.66 (d, J = 2.0 Hz, 1H), 6.34 (d, J = 1.6 Hz, 1H), 4.79 (q, J = 8.8 Hz, 2H), 4.18-4.25 (m, 2H), 3.82-3.88 (m, 4H), 3.74-3.80 (m, 2H), 3.57-3.67 (m, 2H), 3.45-3.51 (m, 1H), 3.34-3.40 (m, 1H), 2.36 (s, 3H). |
| I-46 | 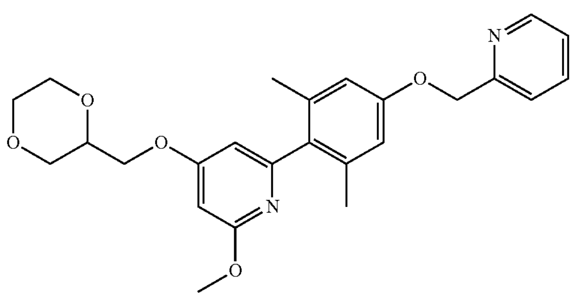 [SMILES: COc1cc(OCC2COCCO2)cc(-c2c(C)cc(OCc3ccccn3)cc2C)n1] | 437.3 | $^1$H NMR (400 MHz, DMSO-d$_6$): δ 8.60-8.61 (m, 1 H), 7.71-7.73 (m, 1 H), 7.54-7.56 (m, 1 H), 7.23-7.26 (m, 1 H), 6.72 (s, 2 H), 6.40 (d, J = 2.0 Hz, 1 H), 6.15 (d, J = 2.0 Hz, 1 H), 5.22 (s, 2 H), 3.93-4.03 (m, 3 H), 3.88-3.91 (m, 4 H), 3.69-3.85 (m, 4 H), 3.53-3.56 (m, 1 H), 2.08 (s, 6 H). |
| I-57 | 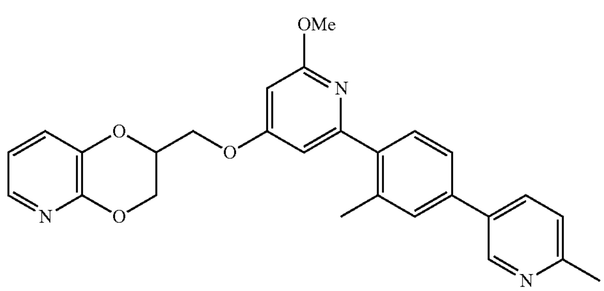 [SMILES: COc1cc(OCC2COc3ncccc3O2)cc(-c2ccc(-c3ccc(C)nc3)cc2C)n1] | 456.3 | $^1$H NMR (400 MHz, CDCl$_3$) δ 8.76 (d, J = 2.4 Hz, 1H), 7.86 (dd, J = 1.6 Hz, 4.8 Hz, 1H), 7.81 (dd, J = 2.4 Hz, 8.0 Hz, 1H), 7.45-7.53 (m, 3H), 7.23-7.26 (m, 2H), 6.91 (dd, J = 4.8 Hz, 8.0 Hz, 1H), 6.67 (d, J = 2.0 Hz, 1H), 6.21 (d, J = 2.0 Hz, 1H), 4.58-4.62 (m, 2H), 4.39-4.44 (m, 1H), 4.31 (dd, J = 4.8 Hz, 10.4 Hz, 1H), 4.24 (dd, J = 6.0 Hz, 10.4 Hz, 1H), 3.96 (s, 3H), 2.62 (s, 3H), 2.52 (s, 3H). |
| I-64 | 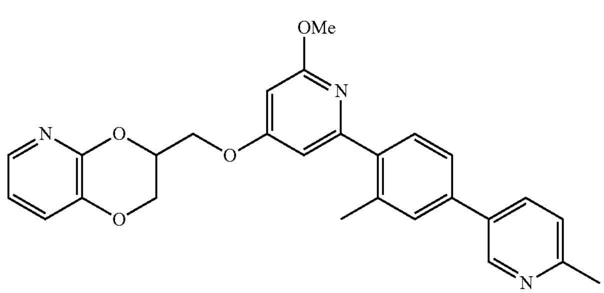 [SMILES: COc1cc(OCC2COc3cccnc3O2)cc(-c2ccc(-c3ccc(C)nc3)cc2C)n1] | 456.3 | $^1$H NMR (400 MHz, CDCl$_3$) δ 8.76 (d, J = 1.6 Hz, 1H), 7.86 (dd, J = 1.6 Hz, 4.8 Hz, 1H), 7.81 (dd, J = 2.4 Hz, 8.0 Hz, 1H), 7.45-7.53 (m, 3H), 7.22-7.25 (m, 2H), 6.91 (dd, J = 4.8 Hz, 8.0 Hz, 1H), 6.66 (d, J = 2.0 Hz, 1H), 6.21 (d, J = 2.0 Hz, 1H), 4.75-4.80 (m, 1H), 4.43 (dd, J = 2.4 Hz, 11.6 Hz, 1H), 4.38 (dd, J = 4.4 Hz, 9.6 Hz, 1H), 4.22-4.29 (m, 2H), 3.95 (s, 3H), 2.62 (s, 3H), 2.52 (s, 3H). |

TABLE 11-continued

Characterization Data for Additional Exemplary Compounds

| Compound No. | Chemical Structure | [M + H] observed | $^1$H NMR (400 MHz) |
|---|---|---|---|
| I-19 | 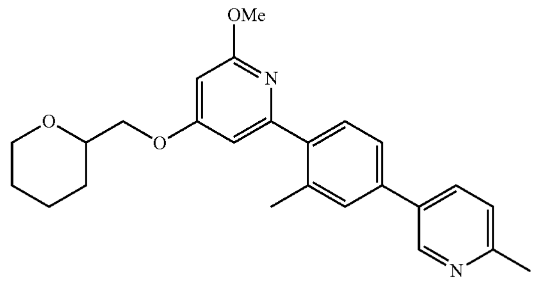 [SMILES: COc1cc(OCC2CCCCO2)cc(-c2ccc(-c3ccc(C)nc3)cc2C)n1] | 405.3 | $^1$H NMR (400 MHz, CDCl$_3$): δ 8.76 (d, J = 2.0 Hz, 1 H), 7.81 (dd, J = 2.0 Hz, 7.6 Hz, 1 H), 7.51 (d, J = 8.0 Hz, 1 H), 7.43-7.45 (m, 2 H), 7.23 (d, J = 8.0 Hz, 1 H), 6.68 (d, J = 2.0 Hz, 1 H), 6.19 (d, J = 2.0 Hz, 1 H), 4.00-4.08 (m, 2 H), 3.92-3.96 (m, 4 H), 3.70-3.76 (m, 1 H), 3.49-3.55 (m, 1 H), 2.61 (s, 3 H), 2.51 (s, 3 H), 1.90-1.93 (m, 1 H), 1.41-1.70 (m, 5 H). |
| I-45 | 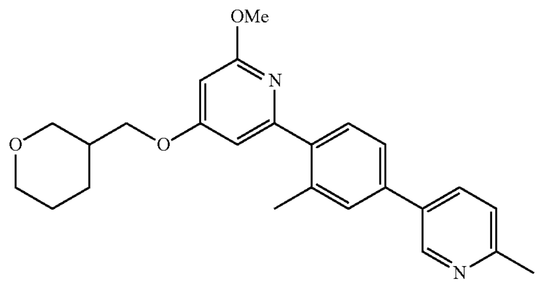 [SMILES: COc1cc(OCC2CCCOC2)cc(-c2ccc(-c3ccc(C)nc3)cc2C)n1] | 405.3 | $^1$H NMR (400 MHz, CDCl$_3$): δ 8.76 (d, J = 2.0 Hz, 1 H), 7.81 (dd, J = 2.4 Hz, 8.0 Hz, 1 H), 7.52 (d, J = 7.6 Hz, 1 H), 7.43-7.46 (m, 2 H), 7.23 (d, J =8.0 Hz, 1 H), 6.62 (d, J = 2.0 Hz, 1 H), 6.17 (d, J = 2.0 Hz, 1 H), 4.00-4.03 (m, 1 H), 3.94 (s, 3 H), 3.84-3.92 (m, 3 H), 3.45-3.51 (m, 1 H), 3.36-3.41 (m, 1 H), 2.61 (s, 3 H), 2.52 (s, 3 H), 2.14-2.19 (m, 1 H), 1.89-1.93 (m, 1 H), 1.63-1.70 (m, 2 H), 1.43-1.50 (m, 1 H). |
| I-3 | 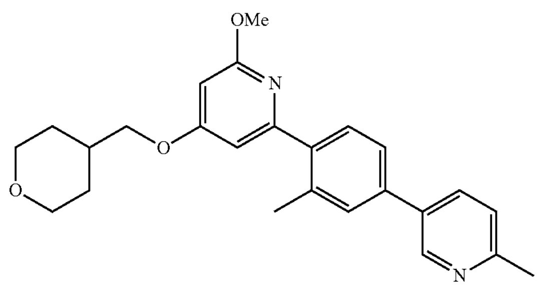 [SMILES: COc1cc(OCC2CCOCC2)cc(-c2ccc(-c3ccc(C)nc3)cc2C)n1] | 405.3 | $^1$H NMR (400 MHz, CDCl$_3$): δ 8.76 (d, J = 2.0 Hz, 1 H), 7.81 (dd, J = 2.4 Hz, 8.0 Hz, 1 H), 7.52 (d, J = 7.6 Hz, 1 H), 7.44-7.46 (m, 2 H), 7.23 (d, J = 8.4 Hz, 1 H), 6.62 (d, J = 2.0 Hz, 1 H), 6.17 (d, J = 2.0 Hz, 1 H), 4.03 (dd, J = 3.2 Hz, 11.2 Hz, 2 H), 3.95 (s, 3 H), 3.86 (d, J = 6.4 Hz, 2 H), 3.41-3.48 (m, 2 H), 2.61 (s, 3 H), 2.52 (s, 3 H), 2.06-2.12 (m, 1 H), 1.74-1.77 (m, 2 H), 1.41-1.52 (m, 2 H). |
| I-70 | 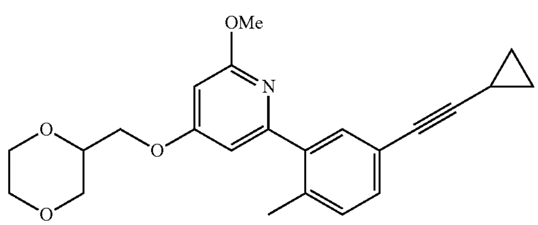 [SMILES: COc1cc(OCC2COCCO2)cc(-c2cc(C#CC3CC3)ccc2C)n1] | 380.3 | $^1$H NMR (400 MHz, DMSO-d$_6$): δ 7.37 (d, J = 1.6 Hz, 1H), 7.23-7.30 (m, 2H), 6.72 (d, J = 2.0 Hz, 1H), 6.33 (d, J = 2.0 Hz, 1H), 4.08 (d, J = 4.8 Hz, 2H), 3.75-3.89 (m, 6H), 3.59-3.68 (m, 2H), 3.47-3.52 (m, 1H), 3.36-3.41 (m, 1H), 2.34 (s, 3H), 1.50-1.56 (m, 1H), 0.85-0.90 (m, 2H), 0.70-0.74 (m, 2H). |
| I-95 | 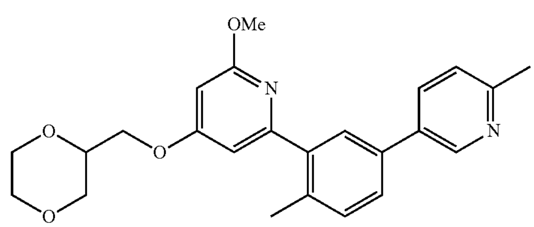 [SMILES: COc1cc(OCC2COCCO2)cc(-c2cc(-c3ccc(C)nc3)ccc2C)n1] | 407.3 | $^1$H NMR (400 MHz, DMSO-d$_6$): δ 8.80 (d, J = 2.0 Hz, 1 H), 8.00 (dd, J = 2.4 Hz, 8.0 Hz, 1 H), 7.70 (d, J = 2.0 Hz, 1 H), 7.63 (dd, J = 1.6 Hz, 8.0 Hz, 1 H), 7.39 (d, J = 8.0 Hz, 1 H), 7.32 (d, J = 8.0 Hz, 1 H), 6.86 (d, J = 2.0 Hz, 1 H), 6.36 (d, J = 1.6 Hz, 1 H), 4.09 (d, J = 4.8 Hz, 2 H), 3.74-3.92 (m, 6 H), 3.58-3.70 (m, 2 H), 3.45-3.53 (m, 1 H), 3.40-3.44 (m, 4 H), 2.41 (s, 3 H). |
| I-79 | 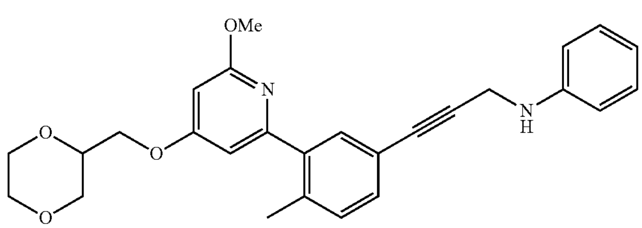 [SMILES: COc1cc(OCC2COCCO2)cc(-c2cc(C#CCNc3ccccc3)ccc2C)n1] | 445.3 | $^1$H NMR (400 MHz, DMSO-d$_6$): δ 7.38 (s, 1H), 7.25-7.32 (m, 2H), 7.10-7.14 (m, 2H), 6.68-6.72 (m, 4H), 6.60 (t, J = 7.2 Hz, 1H), 6.33-6.34 (m, 1H), 6.05 (t, J = 6.0 Hz, 1H), 4.09 (dd, J = 6.0 Hz, 14.4 Hz, 4H), 3.74-3.89 (m, 6H), 3.59-3.68 (m, 2H), 3.34-3.52 (m, 2H), 2.35 (s, 3H). |

TABLE 11-continued

Characterization Data for Additional Exemplary Compounds

| Compound No. | Chemical Structure | [M + H] observed | ¹H NMR (400 MHz) |
|---|---|---|---|
| I-66 | 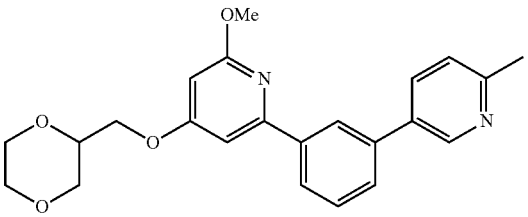 [SMILES: COc1cc(OCC2COCCO2)cc(-c2cccc(-c3ccc(C)nc3)c2)n1] | 393.3 | ¹H NMR (400 MHz, DMSO-d$_6$): δ 8.86 (d, J = 2.4 Hz, 1H), 8.35 (s, 1H), 8.14 (d, J = 8.0 Hz, 1H), 8.08 (d, J = 8.0 Hz, 1H), 7.75 (d, J = 8.0 Hz, 1H), 7.58 (t, J = 8.0 Hz, 1H), 7.36-7.38 (m, 2H), 6.36 (s, 1H), 4.12 (d, J = 5.2 Hz, 2H), 3.95 (s, 3H), 3.35-3.86 (m, 8H), 2.53 (s, 2H). |
| I-48 | 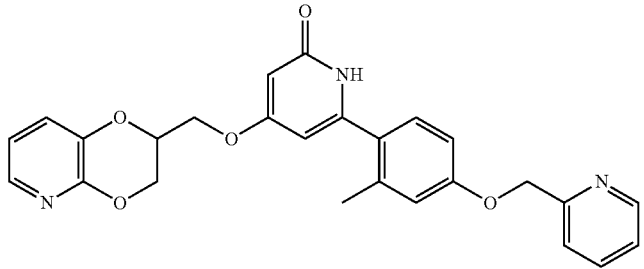 [SMILES: Cc1cc(OCc2ccccn2)ccc1-c1cc(OCC2COc3ncccc3O2)cc(=O)[nH]1] | 458.2 | ¹H NMR (400 MHz, DMSO-d$_6$) δ 10.66 (s, 1H), 8.59 (d, J = 4.4 Hz, 1H), 7.83-7.86 (m, 1H), 7.75 (d, J = 4.8 Hz, 1H), 7.52 (d, J = 7.6 Hz, 1H), 7.29-7.37 (m, 3H), 6.89-6.98 (m, 3H), 6.52 (s, 1H), 6.11 (s, 1H), 5.21 (s, 2H), 4.47-4.60 (m, 4H), 4.28-4.33 (m, 1H), 2.32 (s, 3H). |
| I-120 | 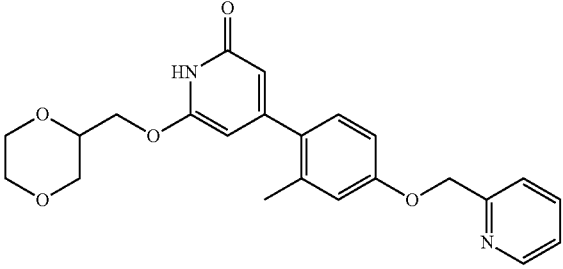 [SMILES: Cc1cc(OCc2ccccn2)ccc1-c1cc(OCC2COCCO2)[nH]c(=O)c1] | 409.0 | ¹H NMR (400 MHz, DMSO-d$_6$) δ 10.65 (br, 1H), 8.59 (d, J = 4.4 Hz, 1H), 7.83-7.87 (m, 1H), 7.53 (d, J = 7.6 Hz, 1H), 7.34-7.37 (m, 1H), 7.13 (d, J = 8.4 Hz, 1H), 6.98 (d, J = 2.4 Hz, 1H), 6.90 (dd, J = 2.4 Hz, 8.4 Hz, 1H), 6.15 (s, 1H), 6.09 (s, 1H), 5.20 (s, 2H), 4.12-4.22 (m, 2H), 3.74-3.88 (m, 3H), 3.58-3.67 (m, 2H), 3.45-3.52 (m, 1H), 3.34-3.40 (m, 1H) 2.23 (s, 3H). |
| I-121 | 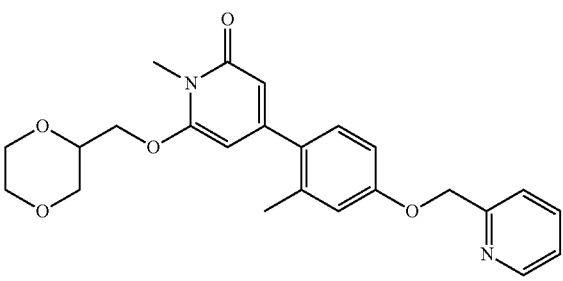 [SMILES: Cc1cc(OCc2ccccn2)ccc1-c1cc(OCC2COCCO2)n(C)c(=O)c1] | 423.0 | ¹H NMR (400 MHz, DMSO-d$_6$): δ 8.58 (d, J = 4.4 Hz, 1 H), 7.80-7.88 (m, 1H), 7.51 (d, J = 7.6 Hz, 1 H), 7.32-7.37 (m, 1 H), 7.16 (d, J = 8.4 Hz, 1 H), 6.97 (d, J = 2.4 Hz, 1 H), 6.90 (dd, J = 2.4 Hz, 8.4 Hz, 1 H), 5.89 (d, J = 1.2 Hz, 1 H), 5.71 (d, J = 1.2 Hz, 1 H), 5.20 (s, 2 H), 4.13 (d, J = 4.4 Hz, 2 H), 3.85-3.95 (m, 1 H), 3.75-3.83 (m, 2 H), 3.59-3.70 (m, 2 H), 3.41-3.53 (m, 2 H), 3.35 (s, 3 H), 2.27 (s, 3 H). |
| I-40 | 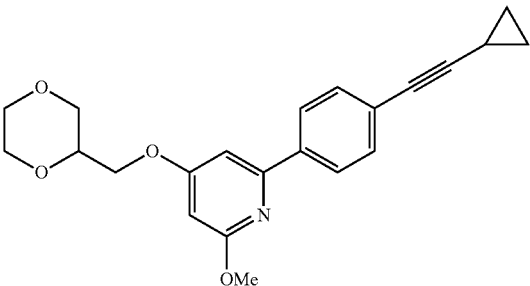 [SMILES: COc1cc(OCC2COCCO2)cc(-c2ccc(C#CC3CC3)cc2)n1] | 366.2 | ¹H NMR (400 MHz, CDCl$_3$) δ 7.92 (d, J = 8.4 Hz, 2H), 7.43 (d, J = 8.4 Hz, 2H), 6.94 (d, J = 1.9 Hz, 1H), 6.13 (d, J = 1.8 Hz, 1H), 4.00 (s, 3H), 4.08-3.93 (m, 3H), 3.93-3.61 (m, 5H), 3.60-3.48 (m1H), 1.47 (tt, J = 8.2, 5.1 Hz, 1H), 0.92-0.78 (m, 4H). |

TABLE 11-continued

Characterization Data for Additional Exemplary Compounds

| Compound No. | Chemical Structure | [M + H] observed | $^1$H NMR (400 MHz) |
|---|---|---|---|
| I-74 | 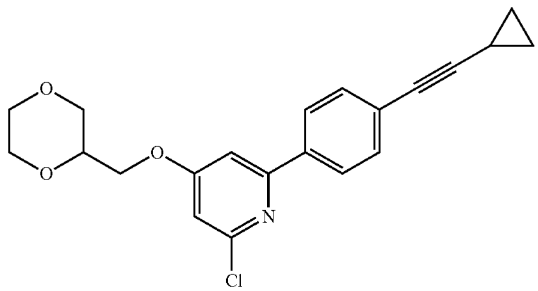 [SMILES: Clc1cc(OCC2COCCO2)cc(-c2ccc(C#CC3CC3)cc2)n1] | 369.2 | $^1$H NMR (400 MHz, CDCl$_3$) δ 7.88-7.83 (m, 2H), 7.47-7.40 (m, 2H), 7.16 (d, J = 2.0 Hz, 1H), 6.77 (d, J = 2.0 Hz, 1H), 4.11-3.97 (m, 3H), 3.92-3.72 (m, 4H), 3.66 (ddd, J = 11.7, 10.3, 3.4 Hz, 1H), 3.54 (dd, J = 11.5, 9.5 Hz, 1H), 1.50-1.42 (m, 1H), 0.93-0.78 (m, 4H). |
| I-108 | 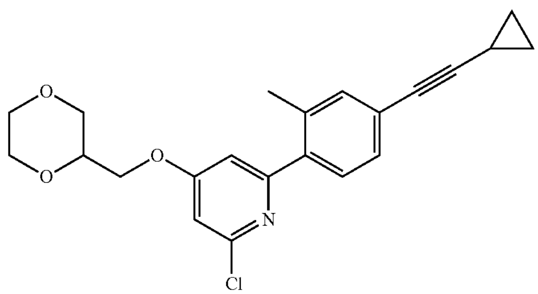 [SMILES: Cc1cc(C#CC2CC2)ccc1-c1cc(OCC2COCCO2)cc(Cl)n1] | 384.2 | $^1$H NMR (400 MHz, CDCl$_3$) δ 7.28 (dd, J = 2.6, 2.0 Hz, 1H), 7.26 (s, 2H), 6.84 (d, J = 2.1 Hz, 1H), 6.82 (d, J = 2.1 Hz, 1H), 4.11-3.97 (m, 3H), 3.92-3.73 (m, 4H), 3.71-3.62 (m, 1H), 3.54 (dd, J = 11.5, 9.4 Hz, 1H), 2.32 (s, 3H), 1.50-1.41 (m, 1H), 0.91-0.78 (m, 4H). |
| I-90 | 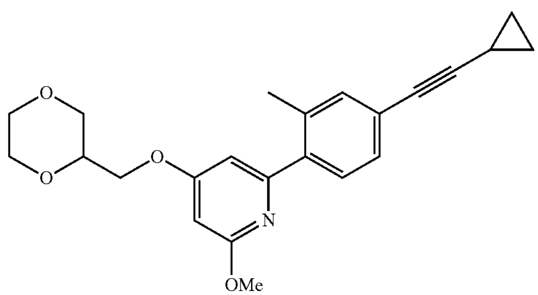 [SMILES: COc1cc(OCC2COCCO2)cc(-c2ccc(C#CC3CC3)cc2C)n1] | 380.2 | $^1$H NMR (400 MHz, CDCl$_3$) δ 7.32 (d, J = 7.9 Hz, 1H), 7.28 (br s, 1H), 7.24 (dd, J = 7.9, 1.2 Hz, 1H), 6.59 (d, J = 2.0 Hz, 1H), 6.15 (d, J = 2.0 Hz, 1H), 4.05-3.88 (m, 3H), 3.92 (s, 3H), 3.89-3.70 (m, 4H), 3.66 (ddd, J = 11.7, 10.4, 3.4 Hz, 1H), 3.53 (dd, J = 11.4, 9.4 Hz, 1H), 2.38 (s, 3H), 1.46 (tt, J = 8.2, 5.1 Hz, 1H), 0.91-0.77 (m, 4H). |
| I-109 | 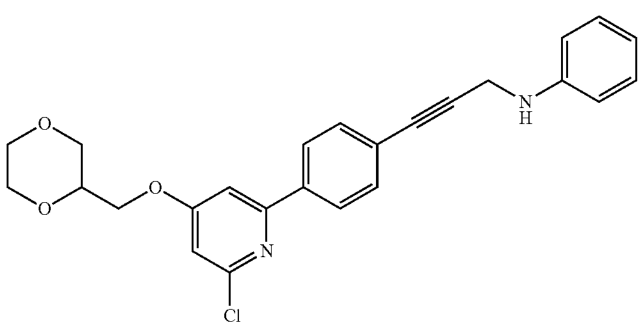 [SMILES: Clc1cc(OCC2COCCO2)cc(-c2ccc(C#CCNc3ccccc3)cc2)n1] | 435.2 | $^1$H NMR (400 MHz, CDCl$_3$) δ 7.92-7.85 (m, 2H), 7.50-7.44 (m, 2H), 7.28-7.21 (m, 2H), 7.17 (d, J = 2.0 Hz, 1H), 6.84-z 6.79 (m, 1H), 6.79-6.76 (m, 3H), 4.19 (s, 2H), 4.12-3.98 (m, 3H), 3.92-3.72 (m, 4H), 3.67 (ddd, J = 11.7, 10.3, 3.4 Hz, 1H), 3.55 (dd, J = 11.5, 9.5 Hz, 1H) [N—H proton not observed]. |
| I-93 | 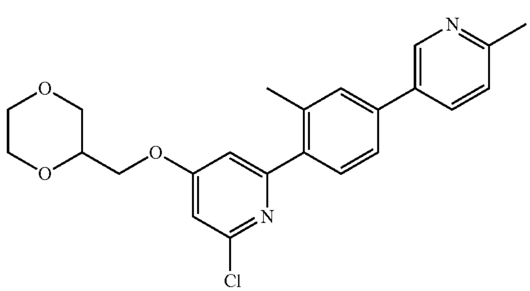 [SMILES: Cc1ccc(-c2ccc(-c3cc(OCC4COCCO4)cc(Cl)n3)c(C)c2)cn1] | 411.2 | $^1$H NMR (400 MHz, DMSO-d$_6$) δ 8.81 (d, J = 2.4 Hz, 1H), 8.02 (dd, J = 8.1, 2.4 Hz, 1H), 7.67 (d, J = 1.7 Hz, 1H), 7.62 (dd, J = 8.0, 1.7 Hz, 1H), 7.51 (d, J = 8.0 Hz, 1H), 7.36 (d, J = 8.1 Hz, 1H), 7.17 (d, J = 2.1 Hz, 1H), 7.15 (d, J = 2.1 Hz, 1H), 4.17-4.15 (m, 2H), 3.93-3.85 (m, 1H), 3.82 (dd, J = 11.5, 2.6 Hz, 1H), 3.79-3.74 (m, 1H), 3.70-3.64 (m, 1H), 3.61 (dd, J = 11.5, 2.5 Hz, 1H), 3.50 (dd, J = 12.2, 9.6 Hz, 1H), 3.39 (dd, J = 11.3, 10.1 Hz, 1H), 2.52 (s, 3H), 2.41 (s, 3H). |

TABLE 11-continued

Characterization Data for Additional Exemplary Compounds

| Compound No. | Chemical Structure | [M + H] observed | $^1$H NMR (400 MHz) |
|---|---|---|---|
| I-58 | 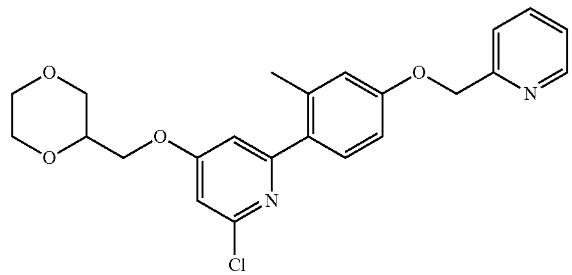 [SMILES: Cc1cc(OCc2ccccn2)ccc1-c1cc(OCC2COCCO2)cc(Cl)n1] | 427.2 | $^1$H NMR (400 MHz, DMSO-d$_6$) δ 8.59 (ddd, J = 4.8, 1.8, 0.9 Hz, 1H), 7.84 (td, J = 7.7, 1.8 Hz, 1H), 7.52 (app. dt, J = 7.7, 1.2 Hz, 1H), 7.36 (overlapped ddd, J = 7.7, 4.8, 1.2 Hz, 1H), 7.35 (overlapped d, J = 8.4 Hz, 1H), 7.07 (d, J = 2.1 Hz, 1H), 7.06 (d, J = 2.1 Hz, 1H), 6.98 (d, J = 2.5 Hz, 1H), 6.93 (dd, J = 8.4, 2.5 Hz, 1H), 5.22 (s, 2H), 4.19-4.10 (m, 2H), 3.91-3.84 (m, 1H), 3.80 (dd, J = 11.3, 2.5 Hz, 1H), 3.78-3.73 (m, 1H), 3.67 (dd, J = 11.6, 2.5 Hz, 1H), 3.60 (dd, J = 11.6, 2.5 Hz, 1H), 3.50 (dd, J = 10.4, 3.4 Hz, 1H), 3.38 (dd, J = 11.4, 10.0 Hz, 1H), 2.32 (s, 3H). |
| I-105 | 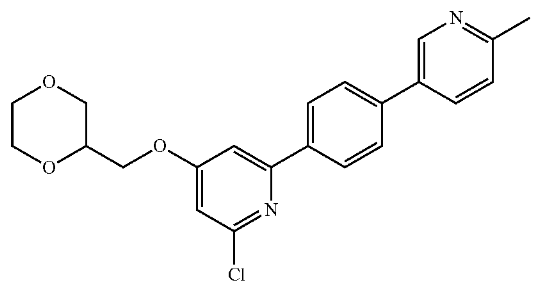 [SMILES: Cc1ccc(-c2ccc(-c3cc(OCC4COCCO4)cc(Cl)n3)cc2)cn1] | 397.2 | $^1$H NMR (400 MHz, DMSO-d$_6$) δ 8.84 (d, J = 2.5 Hz, 1H), 8.23-8.17 (m, 2H), 8.06 (dd, J = 8.1, 2.5 Hz, 1H), 7.87-7.81 (m, 2H), 7.64 (d, J = 1.9 Hz, 1H), 7.37 (d, J = 8.1 Hz, 1H), 7.13 (d, J = 1.9 Hz, 1H), 4.26-4.17 (m, 2H), 3.95-3.87 (m, 1H), 3.84 (dd, J = 11.3, 2.6 Hz, 1H), 3.81-3.75 (m, 1H), 3.71-3.65 (m, 1H), 3.63 (dd, J = 11.5, 2.5 Hz, 1H), 3.55-3.47 (m, 1H), 3.41 (dd, J = 11.3, 10.1 Hz, 1H), 2.53 (s, 3H). |
| I-107 | 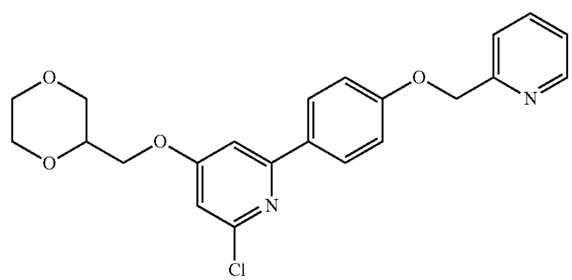 [SMILES: Clc1cc(OCC2COCCO2)cc(-c2ccc(OCc3ccccn3)cc2)n1] | 413.2 | $^1$H NMR (400 MHz, DMSO-d$_6$) δ 8.59 (ddd, J = 4.8, 1.8, 0.9 Hz, 1H), 8.06-8.00 (m, 2H), 7.85 (td, J = 7.7, 1.8 Hz, 1H), 7.54 (app dt, J = 7.7, 0.9 Hz, 1H), 7.49 (d, J = 2.0 Hz, 1H), 7.36 (ddd, J = 7.7, 4.8, 1.1 Hz, 1H), 7.15-7.10 (m, 2H), 7.03 (d, J = 2.0 Hz, 1H), 5.26 (s, 2H), 4.22-4.13 (m, 2H), 3.93-3.85 (m, 1H), 3.82 (dd, J = 11.3, 2.6 Hz, 1H), 3.77 (dd, J = 11.0, 2.6 Hz, 1H), 3.68 (dd, J = 11.3, 2.2 Hz, 1H), 3.62 (dd, J = 11.6, 2.5 Hz, 1H), 3.50 (dd, J = 10.5, 7.7 Hz, 1H), 3.40 (dd, J = 11.3, 10.0 Hz, 1H). |
| I-15 | 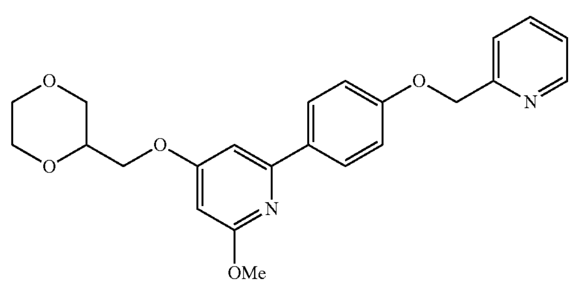 [SMILES: COc1cc(OCC2COCCO2)cc(-c2ccc(OCc3ccccn3)cc2)n1] | 409.2 | $^1$H NMR (400 MHz, DMSO-d$_6$) δ 8.60 (ddd, J = 4.8, 1.7, 0.9 Hz, 1H), 8.08-8.03 (m, 2H), 7.85 (td, J = 7.7, 1.7 Hz, 1H), 7.54 (app dt, J = 7.7, 0.9 Hz, 1H), 7.36 (ddd, J = 7.7, 4.8, 1.1 Hz, 1H), 7.13-7.08 (m, 3H), 6.26 (d, J = 1.8 Hz, 1H), 5.24 (s, 2H), 4.11-4.05 (m, 2H), 3.91 (s, 3H), 3.90-3.84 (m, 1H), 3.82 (dd, J = 11.3, 2.6 Hz, 1H), 3.77 (dd, J = 11.2, 3.1 Hz, 1H), 3.67 (dd, J = 11.2, 2.5 Hz, 1H), 3.61 (dd, J = 11.3, 2.3 Hz, 1H), 3.54-3.46 (m, 1H), 3.39 (dd, J = 11.2, 10.0 Hz, 1H). |

TABLE 11-continued

Characterization Data for Additional Exemplary Compounds

| Compound No. | Chemical Structure | [M + H] observed | $^1$H NMR (400 MHz) |
|---|---|---|---|
| I-130 | 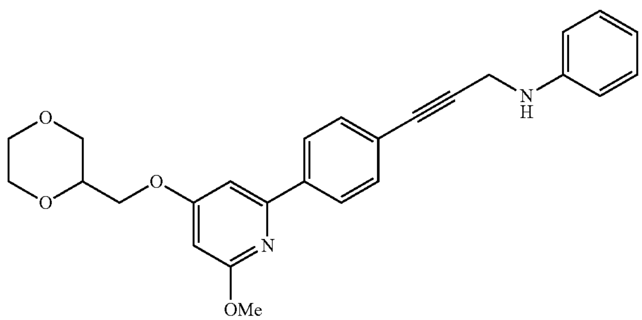 [SMILES: COc1cc(OCC2COCCO2)cc(-c2ccc(C#CCNc3ccccc3)cc2)n1] | 431.2 | $^1$H NMR (400 MHz, DMSO-d$_6$) δ 7.93 (d, J = 8.4 Hz, 2H), 7.45 (d, J = 8.4 Hz, 2H), 7.27-7.21 (m, 2H), 6.94 (d, J = 1.9 Hz, 1H), 6.80 (t, J = 7.4 Hz, 1H), 6.76 (d, J = 7.7 Hz, 2H), 6.13 (d, J = 1.8 Hz, 1H), 4.17 (s, 2H), 3.99 (s, 3H), 4.06-3.93 (m, 3H), 3.92-3.72 (m, 4H), 3.70-3.62 (m, 1H), 3.54 (dd, J = 11.4, 9.3 Hz, 1H) [N—H proton not observed]. |
| I-36 | 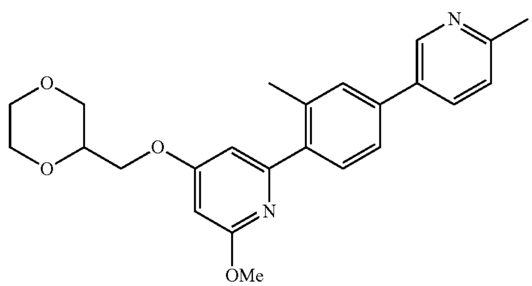 [SMILES: COc1cc(OCC2COCCO2)cc(-c2ccc(-c3ccc(C)nc3)cc2C)n1] | 407.2 | $^1$H NMR (400 MHz, DMSO-d$_6$) δ 8.76 (d, J = 2.1 Hz, 1H), 7.80 (dd, J = 8.0, 2.4 Hz, 1H), 7.51 (d, J = 7.7 Hz, 1H), 7.47-7.43 (m, 2H), 7.23 (d, J = 8.0 Hz, 1H), 6.66 (d, J = 2.0 Hz, 1H), 6.18 (d, J = 2.0 Hz, 1H), 4.08-3.95 (m, 3H), 3.94 (s, 3H), 3.93-3.73 (m, 4H), 3.68 (ddd, J = 11.7, 10.3, 3.4 Hz, 1H), 3.55 (dd, J = 11.3, 9.3 Hz, 1H), 2.61 (s, 3H), 2.51 (s, 3H). |
| I-37 | 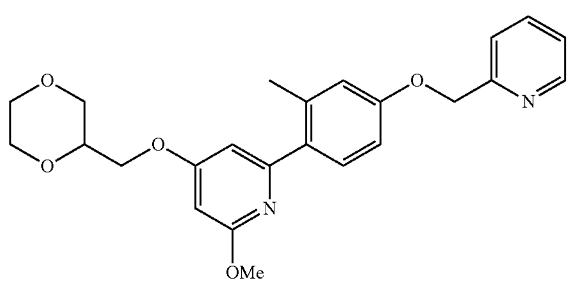 [SMILES: COc1cc(OCC2COCCO2)cc(-c2ccc(OCc3ccccn3)cc2C)n1] | 423.2 | $^1$H NMR (400 MHz, CDCl$_3$) δ 8.61 (ddd, J = 4.9, 1.7, 0.9 Hz, 1H), 7.72 (td, J = 7.7, 1.8 Hz, 1H), 7.53 (br. d, J = 7.9 Hz, 1H), 7.36 (d, J = 8.4 Hz, 1H), 7.25-7.20 (m, 1H), 6.90 (d, J = 2.6 Hz, 1H), 6.85 (dd, J = 8.5, 2.7 Hz, 1H), 6.58 (d, J = 2.0 Hz, 1H), 6.13 (d, J = 2.0 Hz, 1H), 5.24 (s, 2H), 4.06-3.94 (m, 3H), 3.92 (s, 3H), 3.91-3.72 (m, 4H), 3.67 (ddd, J = 11.7, 10.3, 3.5 Hz, 1H), 3.53 (dd, J = 11.5, 9.5 Hz, 1H), 2.42 (s, 3H). |
| I-51 | 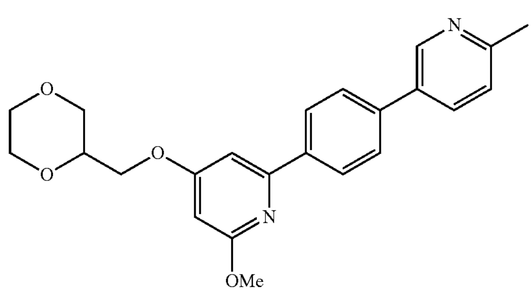 [SMILES: COc1cc(OCC2COCCO2)cc(-c2ccc(-c3ccc(C)nc3)cc2)n1] | 393.2 | $^1$H NMR (400 MHz, CDCl$_3$) δ 8.78 (br. s, 1H), 8.13-8.08 (m, 2H), 7.86-7.79 (m, 1H), 7.66-7.64 (m, 2H), 7.26-7.23 (m, submerged by solvent signal, 1H), 7.02 (d, J = 1.7 Hz, 1H), 6.17 (d, J = 1.7 Hz, 1H), 4.10-4.04 (m, 1H), 4.03 (s, 3H), 4.01-3.64 (m, 7H), 3.57 (dd, J = 11.1, 8.5 Hz, 1H), 2.62 (s, 3H). |
| I-71 | 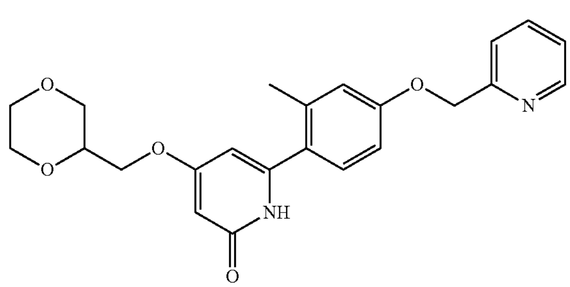 [SMILES: Cc1cc(OCc2ccccn2)ccc1-c1cc(OCC2COCCO2)cc(=O)[nH]1] | 409.2 | $^1$H NMR (400 MHz, CDCl$_3$) δ 9.03 (br. s, 1H), 8.65-8.59 (m, 1H), 7.74 (td, J = 7.7, 1.7 Hz, 1H), 7.51 (br. d, J = 7.8 Hz, 1H), 7.24 (br. d, J = 5.4 Hz, 1H), 7.19 (d, J = 8.4 Hz, 1H), 6.91 (d, J = 2.6 Hz, 1H), 6.87 (dd, J = 8.4, 2.6 Hz, 1H), 5.89 (d, J = 2.4 Hz, 1H), 5.78 (d, J = 2.4 Hz, 1H), 5.22 (s, 2H), 3.97 (m, 2H), 3.94-3.62 (m, 6H), 3.52 (dd, J = 11.5, 9.6 Hz, 1H), 2.32 (s, 3H). |

TABLE 11-continued

Characterization Data for Additional Exemplary Compounds

| Compound No. | Chemical Structure | [M + H] observed | 1H NMR (400 MHz) |
|---|---|---|---|
| I-127 | 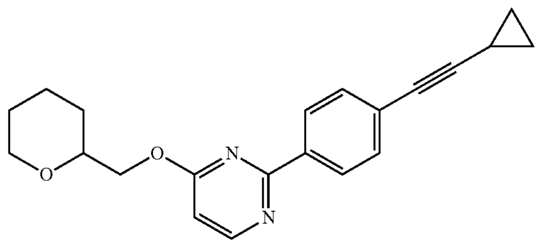 [SMILES: C(#CC1CC1)c1ccc(-c2nccc(OCC3CCCCO3)n2)cc1] | 335.1 | 1H NMR (400 MHz, CDCl3) δ 8.48 (d, J = 5.7 Hz, 1H), 8.32 (d, J = 8.7 Hz, 2H), 7.46 (d, J = 8.7 Hz, 2H), 6.67 (d, J = 5.7 Hz, 1H), 4.49 (dd, J = 11.4, 3.7 Hz, 1H), 4.43 (dd, J = 11.4, 6.6 Hz, 1H), 4.11-4.02 (m, 1H), 3.75 (tdd, J = 8.6, 3.6, 2.2 Hz, 1H), 3.50 (td, J = 11.7, 2.4 Hz, 1H), 1.95-1.87 (m, 1H), 1.80-1.43 (m, 6H), 0.95-0.86 (m, 2H), 0.96-0.79 (m, 2H). |
| I-133 | 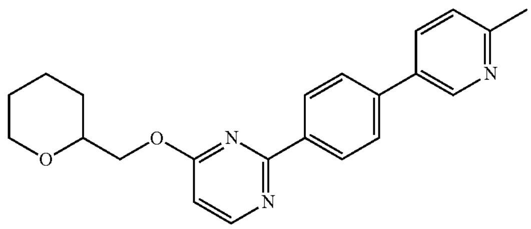 [SMILES: Cc1ccc(-c2ccc(-c3nccc(OCC4CCCCO4)n3)cc2)cn1] | 362.2 | 1H NMR (400 MHz, CDCl3) δ 8.80 (d, J = 1.9 Hz, 1H), 8.61-8.44 (m, 3H), 7.85 (dd, J = 8.0, 2.4 Hz, 1H), 7.74-7.62 (m, 2H), 7.28-7.22 (m, 1H), 6.72 (d, J = 5.7 Hz, 1H), 4.54 (dd, J = 11.4, 3.6 Hz, 1H), 4.47 (dd, J = 11.4, 6.7 Hz, 1H), 4.14-3.95 (m, 1H), 3.89-3.73 (m, 1H), 3.63-3.47 (m, 1H), 2.62 (s, 3H), 1.98-1.90 (m, 1H), 1.82-1.60 (m, 2H), 1.57-1.43 (m, 3H). |
| I-128 | 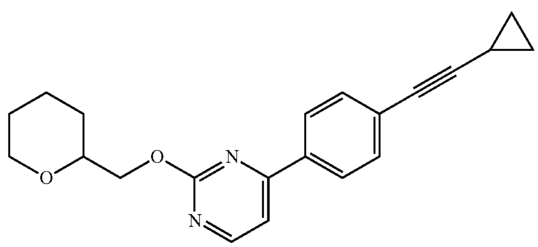 [SMILES: C(#CC1CC1)c1ccc(-c2ccnc(OCC3CCCCO3)n2)cc1] | 335.1 | 1H NMR (400 MHz, CDCl3) δ 8.52 (d, J = 5.2 Hz, 1H), 8.02 (d, J = 8.5 Hz, 2H), 7.46 (d, J = 8.5 Hz, 2H), 7.32 (d, J = 5.2 Hz, 1H), 4.48 (dd, J = 11.1, 6.6 Hz, 1H), 4.35 (dd, J = 11.1, 4.3 Hz, 1H), 4.08-4.00 (m, 1H), 3.80 (dddd, J = 10.8, 6.3, 4.2, 2.1 Hz, 1H), 3.50 (td, J = 11.6, 2.3 Hz, 1H), 1.95-1.86 (m, 1H), 1.76 (d, J = 12.0 Hz, 1H), 1.71-1.60 (m, 1H), 1.59-1.39 (m, 4H), 0.94-0.87 (m, 2H), 0.87-0.81 (m, 2H). |
| I-8 | 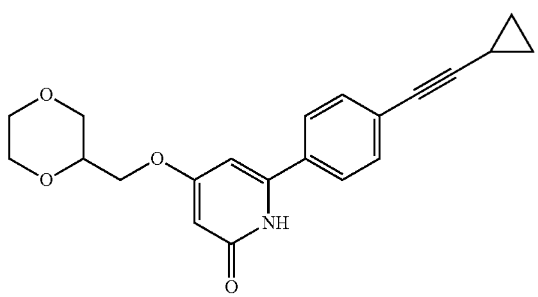 [SMILES: O=c1cc(OCC2COCCO2)cc(-c2ccc(C#CC3CC3)cc2)[nH]1] | 352.1 | 1H NMR (400 MHz, DMSO-d6) δ 11.31 (br s, 1H), 7.71 (d, J = 8.4 Hz, 2H), 7.41 (d, J = 8.4 Hz, 2H), 6.30 (s, 1H), 5.76 (d, J = 1.8 Hz, 1H), 4.00-3.96 (m, 2H), 3.85 (ddd, J = 9.9, 5.1, 2.7 Hz, 1H), 3.82-3.73 (m, 2H), 3.63 (ddd, J = 14.0, 11.5, 5.7 Hz, 2H), 3.53-3.45 (m, 1H), 3.38 (dd, J = 11.2, 10.0 Hz, 1H), 1.57 (tt, J = 8.2, 5.0 Hz, 1H), 0.94-0.88 (m, 2H), 0.78-0.72 (m, 2H) |
| I-75 | 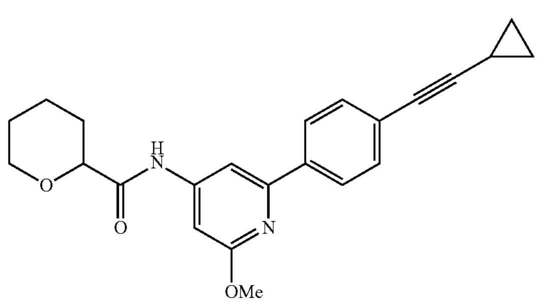 | 377.2 | 1H NMR (400 MHz, CDCl3) δ 8.48 (s, 1H), 7.95 (d, J = 8.4 Hz, 2H), 7.56 (d, J = 1.5 Hz, 1H), 7.42 (d, J = 8.4 Hz, 2H), 6.98 (d, J = 1.4 Hz, 1H), 4.18-4.08 (m, 1H), 4.00 (s, 3H), 3.89 (dd, J = 11.4, 2.5 Hz, 1H), 3.54 (td, J = 11.1, 3.7 Hz, 1H), 2.18 (d, J = 12.8 Hz, 1H), 2.04 (s, 0H), 1.95 (d, J = 6.1 Hz, 1H), 1.73-1.52 (m, 2H), 1.47 (tdt, J = 11.7, 8.2, 4.1 Hz, 2H), 1.29-1.21 (m, 1H), 0.87 (dt, J = 8.1, 2.7 Hz, 2H), 0.83 (td, J = 5.0, 2.1 Hz, 2H). |

TABLE 11-continued

Characterization Data for Additional Exemplary Compounds

| Compound No. | Chemical Structure | [M + H] observed | $^1$H NMR (400 MHz) |
|---|---|---|---|
| I-84 | 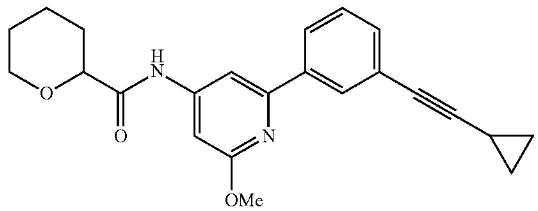 [SMILES: COc1cc(NC(=O)C2CCCCO2)cc(-c2cccc(C#CC3CC3)c2)n1] | 377.2 | $^1$H NMR (400 MHz, CDCl$_3$) δ 8.48 (s, 1H), 8.05-7.99 (m, 1H), 7.94 (dt, J = 7.7, 1.5 Hz, 1H), 7.54 (d, J = 1.5 Hz, 1H), 7.42-7.28 (m, 2H), 7.01 (d, J = 1.5 Hz, 1H), 4.19-4.04 (m, 2H), 4.01 (s, 3H), 3.89 (dd, J = 11.3, 2.5 Hz, 1H), 3.54 (td, J = 11.1, 3.7 Hz, 1H), 2.18 (d, J = 12.7 Hz, 1H), 2.03 (s, 1H), 1.95 (d, J = 6.0 Hz, 1H), 1.46 (ddt, J = 11.5, 8.1, 4.0 Hz, 2H), 1.25 (t, J = 7.1 Hz, 1H), 0.85 (ddt, J = 13.9, 7.5, 2.5 Hz, 4H). |
| I-67 | 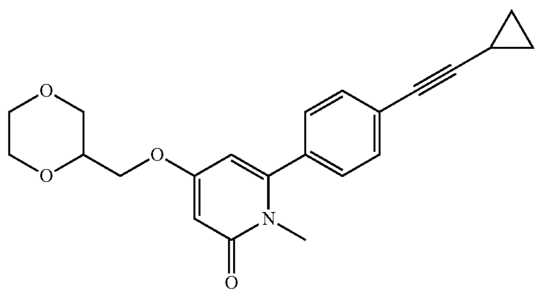 [SMILES: Cn1c(-c2ccc(C#CC3CC3)cc2)cc(OCC2COCCO2)cc1=O] | 366.2 | $^1$H NMR (400 MHz, CDCl$_3$) δ 7.48-7.39 (m, 4H), 5.88 (d, J = 2.8 Hz, 1H), 5.84 (d, J = 2.8 Hz, 1H), 3.98-3.93 (m, 2H), 3.86-3.80 (m, 1H), 3.80-3.71 (m, 2H), 3.68-3.55 (m, 2H), 3.51-3.43 (m, 1H), 3.38-3.30 (m, 1H [partially hidden by water peak], 3.13 (s, 3H), 1.57 (tt, J =8.2, 5.0 Hz, 1H), 0.95-0.88 (m, 2H), 0.79-0.72 (m, 2H). |
| I-98 | 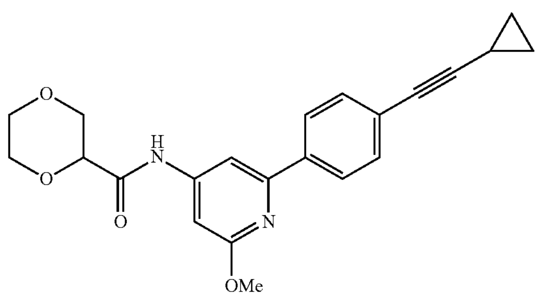 [SMILES: COc1cc(NC(=O)C2COCCO2)cc(-c2ccc(C#CC3CC3)cc2)n1] | 379.2 | $^1$H NMR (400 MHz, CDCl$_3$) δ 8.39 (s, 1H), 8.05-7.87 (m, 2H), 7.54 (d, J = 1.5 Hz, 1H), 7.43 (d, J = 8.5 Hz, 2H), 6.95 (d, J = 1.5 Hz, 1H), 4.31-4.18 (m, 2H), 4.00 (s, 3H), 3.96 (dd, J = 11.7, 2.2 Hz, 1H), 3.91-3.72 (m, 2H), 3.64 (td, J = 11.5, 2.9 Hz, 1H), 3.59-3.45 (m, 1H), 1.52-1.42 (m, 1H), 0.95-0.76 (m, 4H). |
| I-42 | 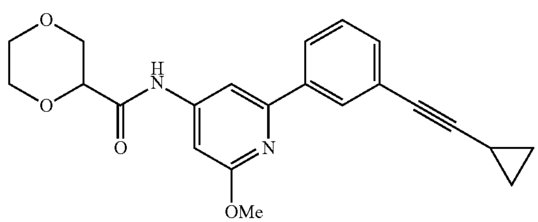 [SMILES: COc1cc(NC(=O)C2COCCO2)cc(-c2cccc(C#CC3CC3)c2)n1] | 379.2 | $^1$H NMR (400 MHz, CDCl$_3$) δ 8.39 (s, 1H), 8.01 (t, J = 1.5 Hz, 1H), 7.94 (dt, J = 7.7, 1.5 Hz, 1H), 7.52 (d, J = 1.6 Hz, 1H), 7.39 (dt, J = 7.6, 1.4 Hz, 1H), 7.34 (t, J = 7.7 Hz, 1H), 6.98 (d, J = 1.5 Hz, 1H), 4.33-4.21 (m, 2H), 4.01 (s, 3H), 4.01-3.76 (m, 3H), 3.66 (dd, J = 11.5, 2.9 Hz, 1H), 3.61-3.48 (m, 1H), 1.55-1.41 (m, 1H), 0.97-0.72 (m, 4H). |
| I-26 | 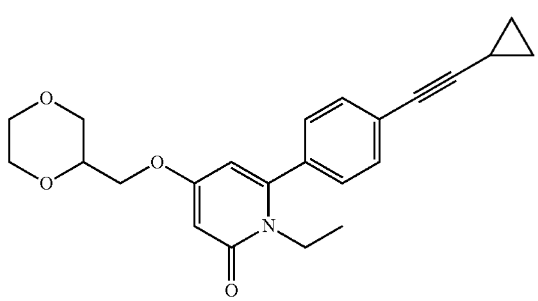 [SMILES: CCn1c(-c2ccc(C#CC3CC3)cc2)cc(OCC2COCCO2)cc1=O] | 380.2 | $^1$H NMR (400 MHz, DMSO-d$_6$) δ 7.46 (d, J = 8.4 Hz, 2H), 7.40 (d, J = 8.4 Hz, 2H), 5.86 (d, J = 2.8 Hz, 1H), 5.78 (d, J = 2.8 Hz, 1H), 3.95 (d, J = 4.6 Hz, 2H), 3.85-3.79 (m, 1H), 3.79-3.71 (m, 2H), 3.71-3.55 (m, 4H), 3.51-3.43 (m, 1H), 3.41-3.25 (m, 1H), 1.57 (tt, J = 8.2, 5.0 Hz, 1H), 0.98-0.88 (m, 5H), 0.79-0.73 (m, 2H). |

TABLE 11-continued

Characterization Data for Additional Exemplary Compounds

| Compound No. | Chemical Structure | [M + H] observed | $^1$H NMR (400 MHz) |
|---|---|---|---|
| I-17 | 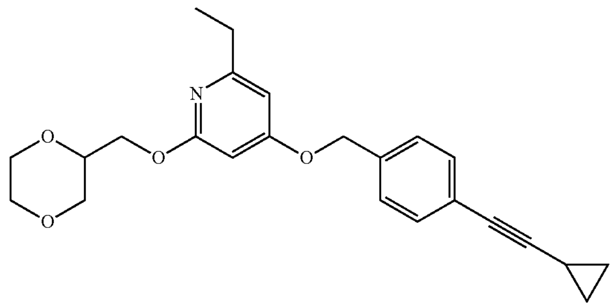 [SMILES: CCc1cc(OCc2ccc(C#CC3CC3)cc2)cc(OCC2COCCO2)n1] | 394.3 | $^1$H NMR (400 MHz, CDCl$_3$) δ 7.38 (d, J = 8.0 Hz, 2 H), 7.28 (d, J = 8.4 Hz, 2 H), 6.38 (d, J = 2.0 Hz, 1 H), 6.12 (d, J = 2.0 Hz, 1 H), 5.00 (s, 2 H), 4.30-4.32 (m, 2 H), 3.47-3.88 (m, 7 H), 2.61 (q, J = 8.0 Hz, 2 H), 1.41-1.47 (m, 1 H), 1.22 (t, J = 7.6 Hz, 3 H), 0.80-0.88 (m, 4 H). |
| I-72 | 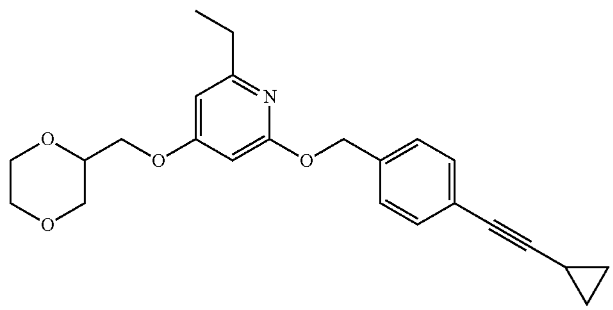 [SMILES: CCc1cc(OCC2COCCO2)cc(OCc2ccc(C#CC3CC3)cc2)n1] | 394.3 | $^1$H NMR (400 MHz, CDCl$_3$) δ 7.32-7.37 (m, 4 H), 6.35 (d, J = 2.0 Hz, 1 H), 6.05 (d, J = 2.0 Hz, 1 H), 5.32 (s, 2 H), 3.48-3.99 (m, 9 H), 2.63 (q, J = 7.2 Hz, 2 H), 1.41-1.47 (m, 1 H), 1.23 (t, J = 7.6 Hz, 3 H), 0.77-0.88 (m, 4 H). |
| I-125 | 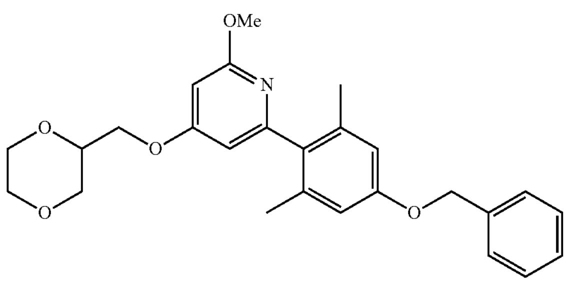 [SMILES: COc1cc(OCC2COCCO2)cc(-c2c(C)cc(OCc3ccccc3)cc2C)n1] | 436.4 | $^1$H NMR (400 MHz, DMSO-d$_6$): δ 7.31-7.46 (m, 5 H), 6.72 (s, 2 H), 6.41 (d, J = 2.0 Hz, 1 H), 6.15 (d, J = 2.0 Hz, 1 H), 5.07 (s, 2 H), 3.93-4.04 (m, 3 H), 3.89-3.91 (m, 4 H), 3.66-3.85 (m, 4 H), 3.51-3.56 (m, 1 H), 2.09 (s, 6 H). |

Example 11: Synthesis of I-18

Synthetic Scheme of I-18

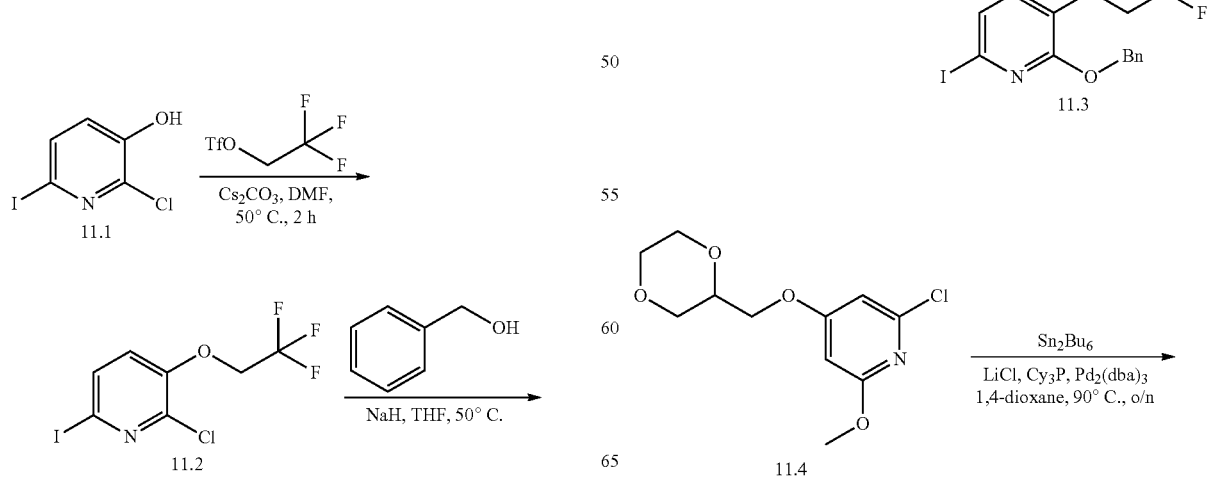

-continued

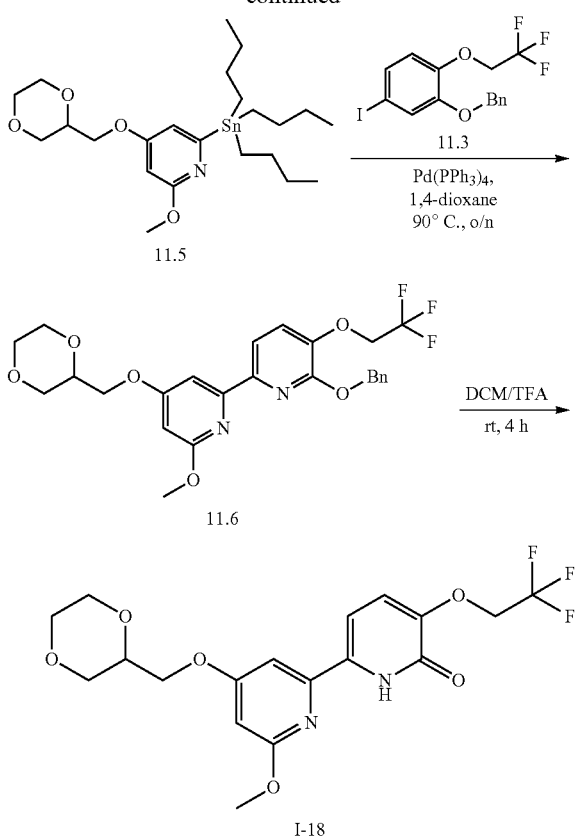

1. The Synthesis of Intermediate 11.2

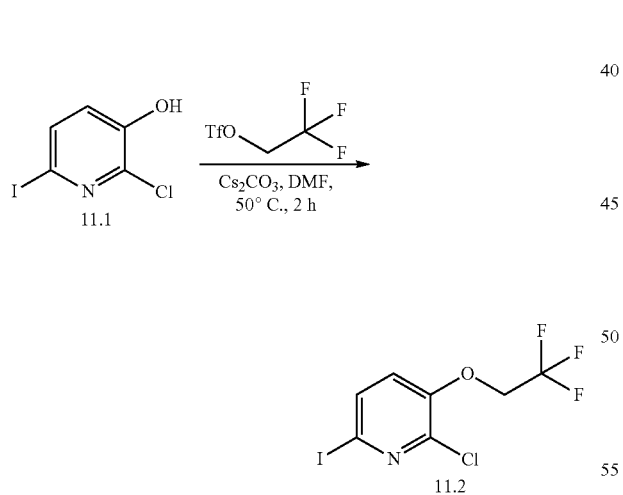

The solution of 11.1 (2.0 g, 7.8 mmol), 2,2,2-trifluoroethyl trifluoromethanesulfonate (1.9 g, 8.2 mmol) and Cs$_2$CO$_3$ (5.1 g, 15.8 mmol) in DMF (30 mL) was stirred at 50° C. for 2 h. When it cooled to RT, water (50 mL) was added. The mixture was extracted with EA (20 mL×3). The organic phase was washed by brine, dried over anhydrous Na$_2$SO$_4$ and concentrated to give 11.2 (2.6 g, yield: 98%) as colorless oil, which was directly used to the next step without further purification. LC-MS m/z: 338.0 [M+H]$^+$.

2. The Synthesis of Intermediate 11.3

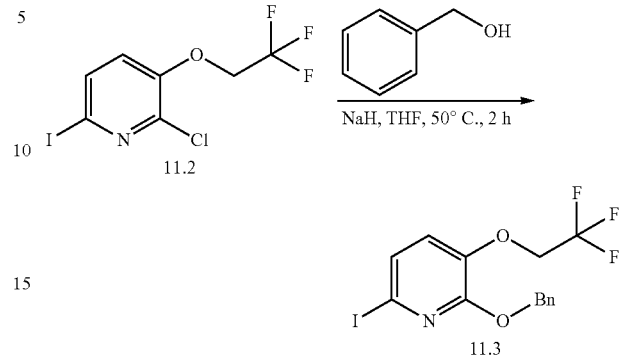

To a stirred solution of 11.2 (2.4 g, 7.2 mmol) in dry THF (40 mL) was added NaH (868 mg, 21.7 mmol, 60% in mineral oil) at 0° C. The reaction mixture was stirred at 0° C. for 20 min, then phenylmethanol (859 mg, 7.9 mmol) was added. The solution was stirred at RT for 2 h. Then water (60 mL) was added, the mixture was extracted with EA (30 mL×3). The combined organic phase was washed by brine, dried over anhydrous Na$_2$SO$_4$ and concentrated. The residue was purified by column chromatography (PE/EA=10/1) to give 11.3 (2.30 g, yield: 78%) as colorless oil. $^1$H NMR (400 MHz, CDCl$_3$) δ 7.46-7.49 (m, 2H), 7.26-7.41 (m, 3H), 7.24 (s, 1H), 6.92 (d, J 7.6 Hz, 1H), 5.43 (s, 2H), 4.35 (dd, J 16.4, 8.4 Hz, 1H).

3. The Synthesis of Intermediate 11.5

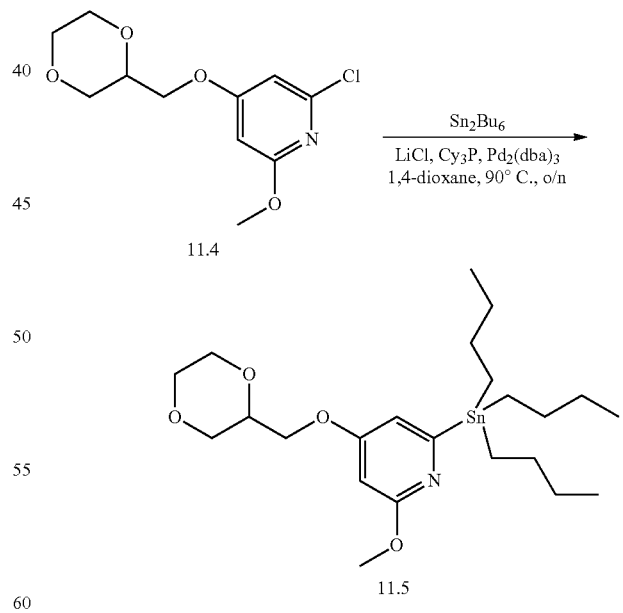

To a mixture of 11.4 (500 mg, 1.9 mmol, prepared in the same manner as intermediate 10.3 of example 10, using (1,4-dioxan-2-yl)methanol in place of (tetrahydropyran-2-yl)methanol), Sn$_2$Bu$_6$ (1.7 g, 2.9 mmol), LiCl (491 mg, 11.6 mmol) and Cy$_3$P (108 mg, 0.39 mmol) in 1,4-dioxane (15 mL) was added Pd$_2$(dba)$_3$ (177 mg, 0.19 mmol) under Ar atmosphere, then the mixture was stirred at 90° C. overnight. The reaction mixture was cooled to room temperature and crude 11.5 was used directly to next step without further purification. LC-MS m/z: 516.3 [M+H]+.

4. The Synthesis of Intermediate 11.6

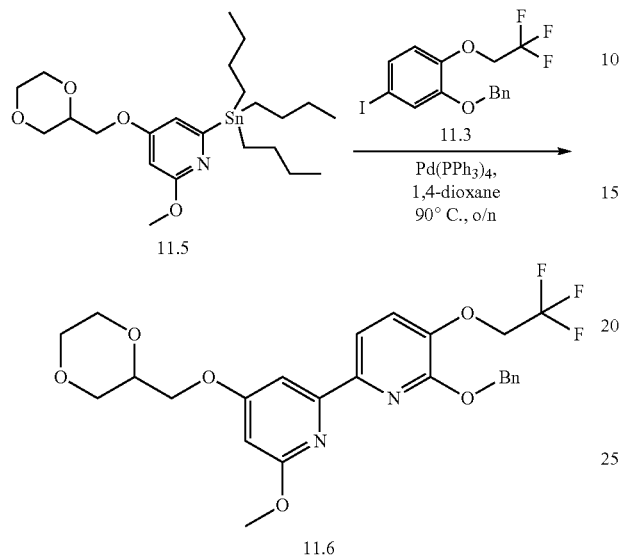

To the above solution of 11.5 in 1, 4-dioxane (15 mL) was added 11.3 (395 mg, 0.97 mmol) and Pd(PPh$_3$)$_4$ (70 mg, 0.06 mmol). The reaction mixture was stirred at 90° C. overnight under Ar atmosphere. The solvent was removed and the residue was purified by column chromatography on silica gel (PE/EA=9/2) to give 11.6 (135 mg, yield: 38%) as a yellow solid. LC-MS m/z: 507.3 [M+H]+.

5. The Synthesis of Target I-18

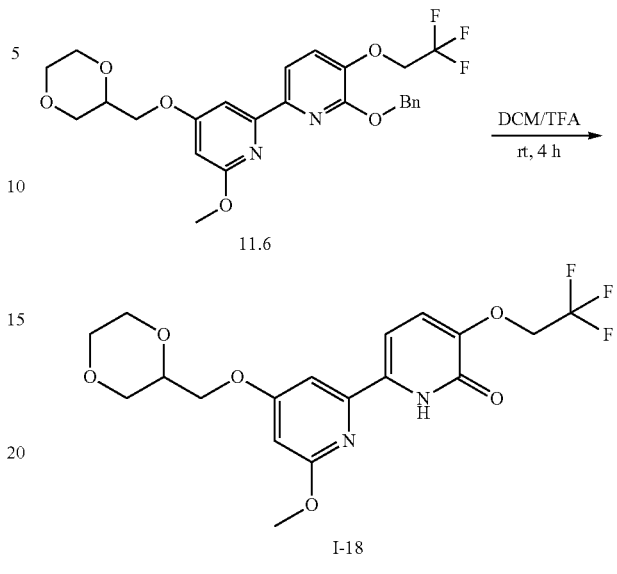

To a solution of 11.6 (135 mg, 0.27 mmol) in DCM (5 mL) was added TFA (2.5 mL). The reaction mixture was stirred at RT for 4 h. The solvent was removed, the residue was dissolved in DCM (10 mL), washed by sat. NaHCO$_3$ (5 mL×3), dried over anhydrous Na$_2$SO$_4$ and concentrated. The residue was purified by Prep-HPLC to give I-18 (41 mg, yield: 37%) as a white solid.

Additional exemplary compounds were prepared following methods substantially similar to the method described above and herein. Data for these compounds are provided below.

TABLE 12

Characterization Data for Additional Exemplary Compounds

| Compound No. | Chemical Structure | [M + H] observed | $^1$H NMR (400 MHz) |
|---|---|---|---|
| I-18 | 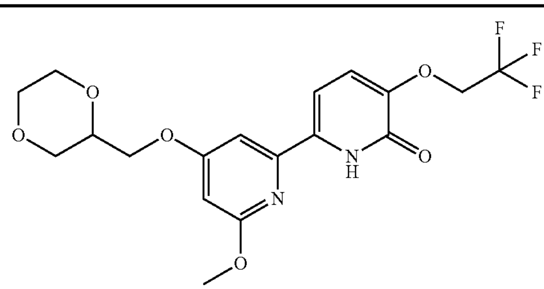 | 417.1 | $^1$H NMR (400 MHz, DMSO-d$_6$) δ 11.36 (s, 1H), 7.34 (d, J = 2.0 Hz, 1H), 7.17-7.19 (m, 1H), 7.07-7.09 (m, 1H), 6.38 (d, J = 2.0 Hz, 1H), 4.78 (q, J = 8.8 Hz, 2H), 4.10 (d, J = 5.2 Hz, 2H), 3.96 (s, 3H), 3.75-3.89 (m, 3H), 3.60-3.69 (m, 2H), 3.48-3.53 (m, 1H), 3.37-3.40 (m, 1H). |
| I-5 | 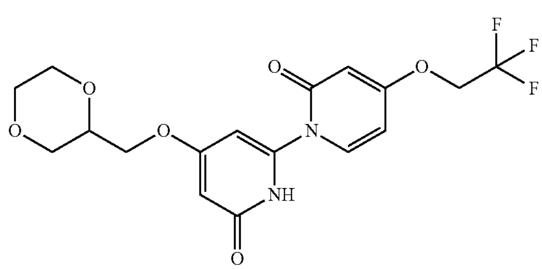 [SMILES: O=c1cc(OCC2COCCO2)cc(-n2ccc(OCC(F)(F)F)cc2=O)[nH]1] | 403.1 | $^1$HNMR (400 MHz, DMSO-d$_6$) δ 11.32 (br, 1H), 7.77 (d, J = 8.0 Hz, 1H), 6.64 (s, 1H), 6.16-6.18 (m, 2H), 6.06 (d, J = 2.4 Hz, 1H), 4.81-4.88 (m, 2H), 4.00-4.04 (m, 2H), 3.74-3.87 (m, 3H), 3.60-3.68 (m, 2H), 3.46-3.52 (m, 1H), 3.38-3.41 (m, 1H). |

Example 12: Synthesis of I-126

Synthetic Scheme of I-126

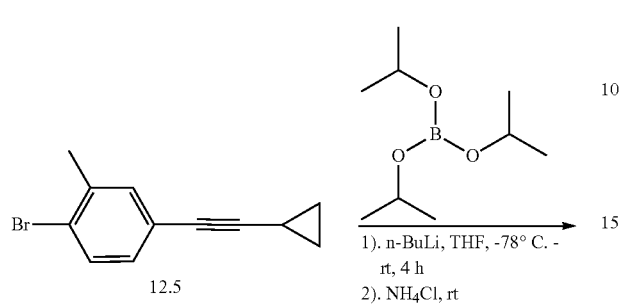

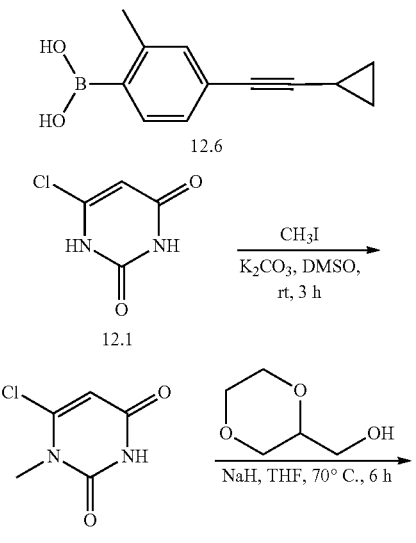

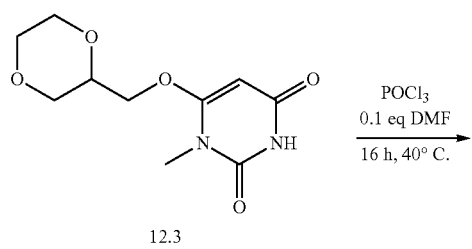

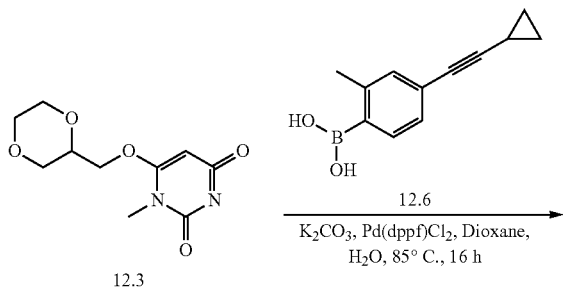

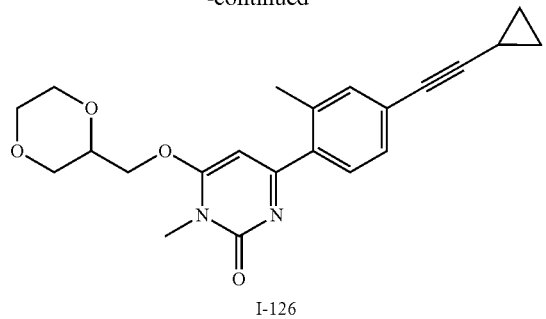

I-126

1. The Synthesis of Intermediate 12.6

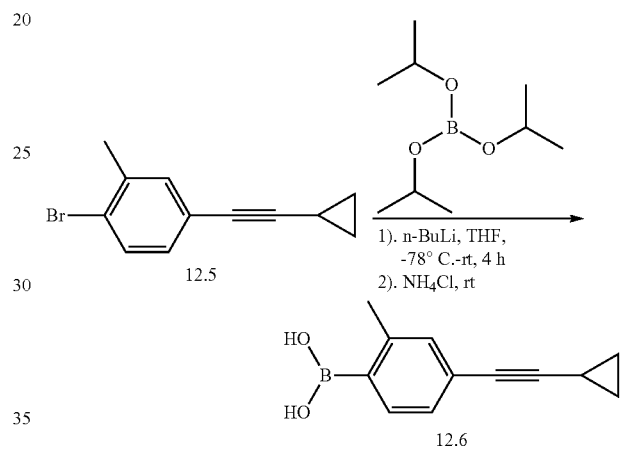

To a stirred solution of 12.5 (500 mg, 2.13 mmol) in THF (10 mL) was added n-BuLi (1.3 mL, 3.2 mmol, 2.5 M) at −78° C. and the reaction mixture was stirred at −78° C. for 1 h, then triisopropyl borate (800 mg, 4.25 mmol) was added to the reaction mixture at −78° C. The reaction mixture was allowed to warm to RT and stirred at room temperature for 4 h. The reaction mixture was quenched with aqueous NH$_4$Cl solution (10 mL) and extracted with EA (20 mL×2), concentrated to give 12.6 (300 mg, crude) as yellow oil. LC-MS m/z: 199.1 [M−H]$^−$.

2. The Synthesis of Intermediate 12.2

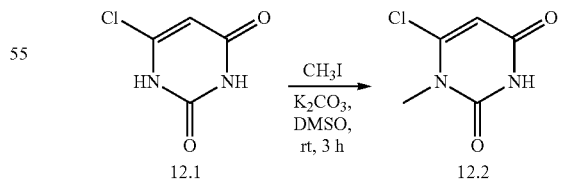

To a stirred solution of 12.1 (5.0 g, 34.1 mmol), CH$_3$I (5.8 g, 40.9 mmol) in DMSO (30 ml) was added K$_2$CO$_3$ (2.4 g, 17.1 mmol), and the reaction mixture was stirred at rt for 3 hours until the reaction was complete (by LCMS). The suspension was added H$_2$O (30 mL) and stirred at 0° C. for another 3 h, the solid was collected by filtration to get 12.2

(4.2 g, 77%) as a white solid. $^1$H NMR (400 MHz, CDCl$_3$): δ 9.35 (s, 1H), 5.92 (s, 1H), 3.55 (s, 3H).

3. The Synthesis of Intermediate 12.3

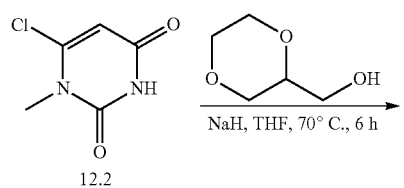

A solution of (1,4-dioxan-2-yl)methanol (3.3 g, 28 mmol) and NaH (1.2 g, 30 mmol, 60% in mineral oil) in anhydrous THF (30 mL) was stirred for 1 h at 70° C. Then 12.2 (3.2 g, 20 mmol) was added and the reaction mixture was stirred for 6 h at 70° C. Saturated NH$_4$Cl was added, the reaction mixture was extracted with EA (30 mL×2) and the combined organic layer was washed with water, dried over anhydrous Na$_2$SO$_4$ and evaporated to dryness. The crude product was purified by flash chromatography on silica gel (silica gel, PE/EA=1:1) to give 12.3 (2.8 g, yield: 58%) as a yellow solid. $^1$H NMR (400 MHz, DMSO-d$_6$): δ 11.01 (s, 1H), 5.08 (s, 1H), 4.03-4.08 (m, 2H), 3.76-3.90 (m, 3H), 3.60-3.68 (m, 2H), 3.45-3.51 (m, 1H), 3.36-3.41 (m, 1H), 3.15 (s, 3H).

4. The Synthesis of Intermediate 12.4

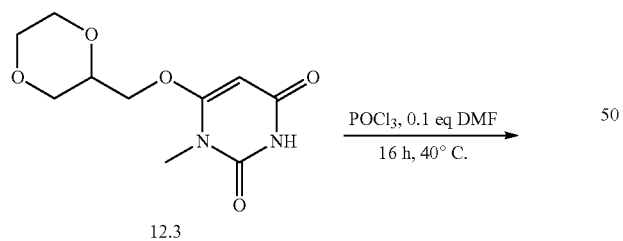

To a stirred solution of 12.3 (800 mg, 3.3 mmol) in POCl$_3$ (10 mL) was added DMF (30 mg, 0.33 mmol). The reaction mixture was stirred at 40° C. for 16 hours until the reaction was complete (by LCMS). The suspension was diluted with aqueous NaHCO$_3$ solution and extracted with DCM (50 mL×3), concentrated. The crude product was recrystallized from MeOH to give 12.4 (400 mg, yield: 46%) as a yellow solid. $^1$H NMR (400 MHz, DMSO-d$_6$): δ 6.37 (s, 1H), 4.25-4.32 (m, 2H), 3.90-3.93 (m, 1H), 3.76-3.89 (m, 2H), 3.60-3.70 (m, 2H), 3.36-3.52 (m, 2H), 3.28 (s, 3H).

5. The Synthesis of Target I-126

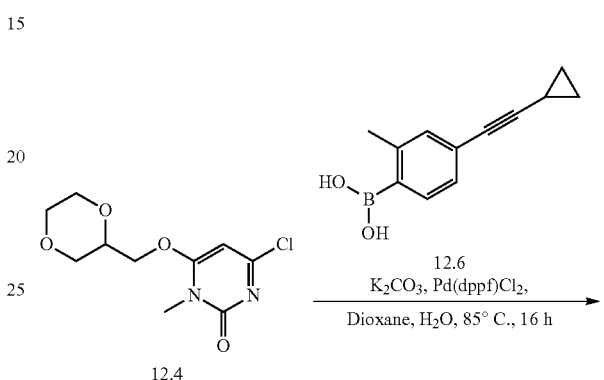

To a stirred solution of 12.4 (300 mg, 1.15 mmol), 12.6 (460 mg, 2.3 mmol) and K$_2$CO$_3$ (477 mg, 3.45 mmol) in dioxane (30 mL) and H$_2$O (3 mL) was added Pd(dppf)Cl$_2$ (84 mg, 0.115 mmol). The reaction mixture was stirred at 85° C. for 16 hours until the reaction was complete (by LCMS). The suspension was diluted with H$_2$O (20 mL) and extracted with EA (40 mL×2), the combined organic phase was concentrated. The crude product was purified by Prep-HPLC to give I-126 (50 mg, yield: 11%) as a white solid.

Additional exemplary compounds were prepared following methods substantially similar to the method described above and herein. Data for these compounds are provided below.

TABLE 13

Characterization Data for Additional Exemplary Compounds

| Compound No. | Chemical Structure | [M + H] observed | ¹H NMR (400 MHz) |
|---|---|---|---|
| I-136 | 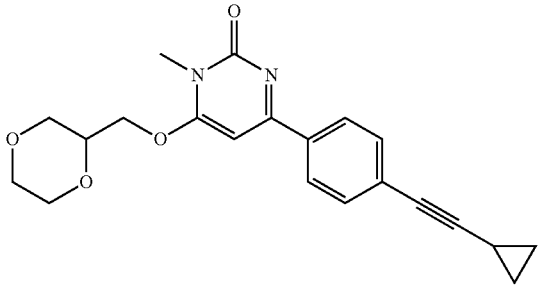 [SMILES: Cn1c(OCC2COCCO2)cc(-c2ccc(C#CC3CC3)cc2)nc1=O] | 367.1 | ¹H NMR (400 MHz, CDCl₃): δ 7.96 (d, J = 8.4 Hz, 2H), 7.44 (d, J = 8.4 Hz, 2H), 6.18 (s, 1H), 4.17-4.26 (m, 2H), 4.02-4.09 (m, 1H), 3.76-3.94 (m, 4H), 3.53-3.71 (m, 2H), 3.52 (s, 3H), 1.46-1.49 (m, 1H), 0.80-0.93 (m, 4H). |
| I-126 | 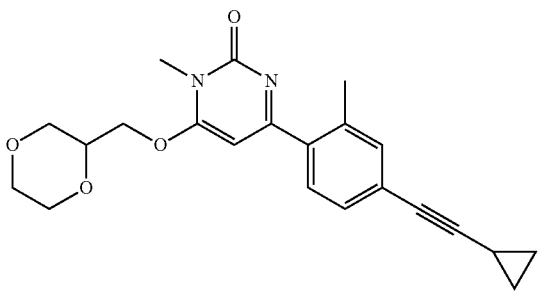 [SMILES: Cc1cc(C#CC2CC2)ccc1-c1cc(OCC2COCCO2)n(C)c(=O)n1] | 381.3 | ¹H NMR (400 MHz, DMSO-d₆): δ 7.38 (d, J = 8.0 Hz, 1H), 7.26-7.30 (m, 2H), 6.25 (s, 1H), 4.26-4.32 (m, 2H), 3.89-3.94 (m, 1H), 3.77-3.85 (m, 2H), 3.61-3.69 (m, 2H), 3.38-3.52 (m, 2H), 3.35 (s, 3H), 2.35 (s, 3H), 1.53-1.59 (m, 1H), 0.88-0.93 (m, 2H), 0.73-0.77 (m, 2H). |
| I-137 | 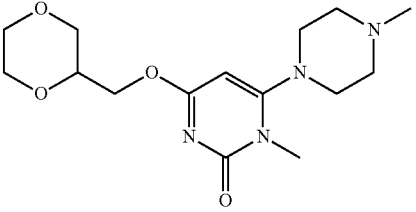 [SMILES: CN1CCN(c2cc(OCC3COCCO3)nc(=O)n2C)CC1] | 325.4 | ¹H NMR (400 MHz, DMSO-d₆) δ 5.51 (s, 1H), 4.15-4.17 (m, 2H), 3.73-3.80 (m, 3H), 3.56-3.66 (m, 2H), 3.44-3.50 (m, 1H), 3.31 (s, 1H), 3.26 (s, 3H), 2.99 (s, 4H), 2.44 (s, 4H), 2.22 (s, 3H). |
| I-138 | 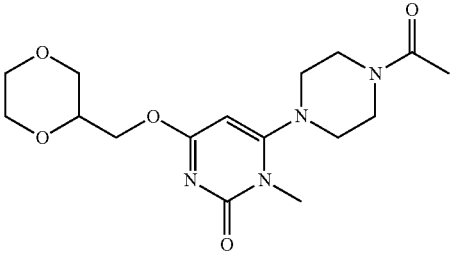 [SMILES: CC(=O)N1CCN(c2cc(OCC3COCCO3)nc(=O)n2C)CC1] | 353.2 | ¹H NMR (400 MHz, CDCl₃ + D2O): δ 5.65 (s, 1 H), 4.41-4.45 (m, 1 H), 4.15-4.39 (m, 2 H), 3.92-3.97 (m, 1 H), 3.45-3.80 (m, 9 H), 3.36 (s, 3 H), 3.01-3.09 (m, 4 H), 2.05 (s, 3 H). |
| I-86 | 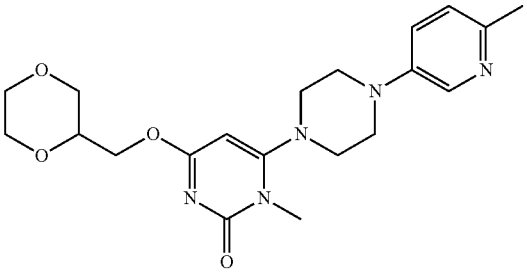 [SMILES: Cc1ccc(N2CCN(c3cc(OCC4COCCO4)nc(=O)n3C)CC2)cn1] | 402.3 | ¹H NMR (400 MHz, DMSO-d₆) δ 8.20 (d, J = 2.8 Hz, 1H), 7.31 (dd, J = 2.8 Hz, 8.4 Hz, 1H), 7.11 (d, J = 8.4 Hz, 1H), 5.58 (s, 1H), 4.16-4.19 (m, 2H), 3.73-3.83 (m, 3H), 3.56-3.67 (m, 2H), 3.45-3.51 (m, 1H), 3.35-3.37 (m, 4H), 3.26-3.27 (m, 4H), 3.15-3.16 (m, 4H), 2.37 (s, 3H). |

TABLE 13-continued

Characterization Data for Additional Exemplary Compounds

| Compound No. | Chemical Structure | [M + H] observed | ¹H NMR (400 MHz) |
|---|---|---|---|
| I-22 | 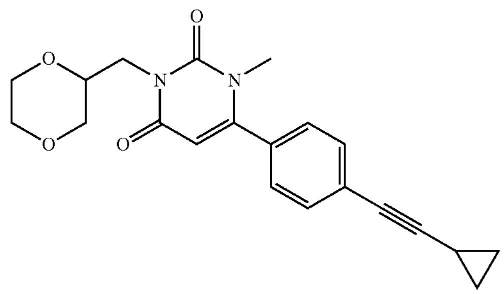 [SMILES: Cn1c(-c2ccc(C#CC3CC3)cc2)cc(=O)n(CC2COCCO2)c1=O] | 367.0 | ¹H NMR (400 MHz, DMSO-d6): δ 7.44-7.50 (m, 4 H), 5.61 (s, 1 H), 4.01-4.06 (m, 1 H), 3.69-3.77 (m, 4 H), 3.60-3.63 (m, 1 H), 3.48-3.50 (m, 2 H), 3.27-3.31 (m, 1 H), 3.07 (s, 3 H), 1.52-1.61 (m, 1 H), 0.87-0.94 (m, 2 H), 0.74-0.79 (m, 2 H). |
| I-62 | 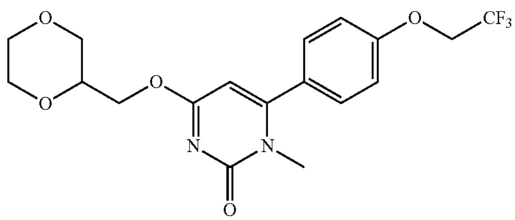 [SMILES: Cn1c(-c2ccc(OCC(F)(F)F)cc2)cc(OCC2COCCO2)nc1=O] | 401.2 | ¹H NMR (400 MHz, CDCl₃): δ 7.36-7.29 (m, 2H), 7.09-7.02 (m, 2H), 5.87 (s, 1H), 4.49-4.34 (m, 4H), 4.02-3.92 (m, 1H), 3.88-3.70 (m, 4H), 3.69-3.59 (m, 1H), 3.47 (dd, J = 11.5, 10.1 Hz, 1H), 3.34 (s, 3H). |
| I-110 | 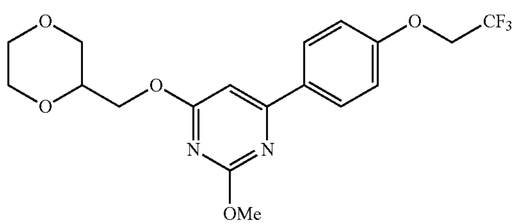 [SMILES: COc1nc(OCC2COCCO2)cc(-c2ccc(OCC(F)(F)F)cc2)n1] | 401.2 | ¹H NMR (400 MHz, CDCl₃): δ 8.05 (d, J = 8.5 Hz, 2H), 7.02 (d, J = 8.5 Hz, 2H), 6.81 (s, 1H), 4.47-4.36 (m, 4H), 4.07 (s, 3H), 4.01 (m, 4H), 3.91-3.72 (m, 1H), 3.67 (td, J = 11.1, 2.9 Hz, 1H), 3.52 (t, J = 10.8 Hz, 1H). |
| I-41 | 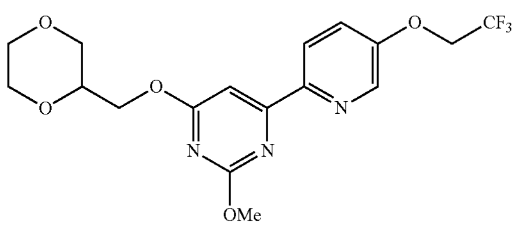 [SMILES: COc1nc(OCC2COCCO2)cc(-c2ccc(OCC(F)(F)F)cn2)n1] | 402.2 | ¹H NMR (400 MHz, DMSO-d₆): δ 8.55-8.52 (m, 1H), 8.39-8.34 (m, 1H), 7.71 (dd, J = 8.8, 3.0 Hz, 1H), 7.26 (s, 1H), 4.99 (q, J = 8.8 Hz, 2H), 4.36-4.32 (m, 2H), 3.99 (s, 3H), 3.94-3.86 (m, 1H), 3.84-3.73 (m, 2H), 3.69-3.57 (m, 2H), 3.54-3.46 (m, 1H), 3.40 (dd, J = 11.4, 10.0 Hz, 1H). |
| I-81 | 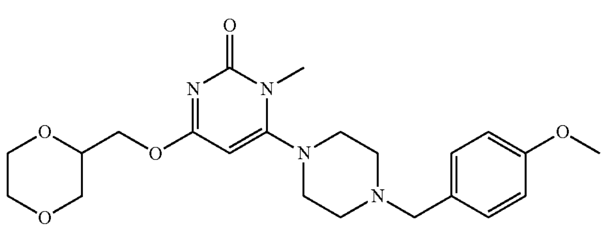 [SMILES: COc1ccc(CN2CCN(c3cc(OCC4COCCO4)nc(=O)n3C)CC2)cc1] | 431.3 | ¹H NMR (400 MHz, DMSO-d6): δ 7.22 (d, J = 8.8 Hz, 2 H), 6.89 (d, J = 8.8 Hz, 2 H), 5.50 (s, 1 H), 4.15-4.16 (m, 2 H), 3.72-3.81 (m, 6 H), 3.55-3.66 (m, 2 H), 3.44-3.50 (m, 3 H), 3.30-3.35 (m, 1 H), 3.25 (s, 3 H), 2.98 (s, 4 H), 2.47 (s, 4 H). |

Example 13: Synthesis of I-38

Synthetic Scheme of I-38

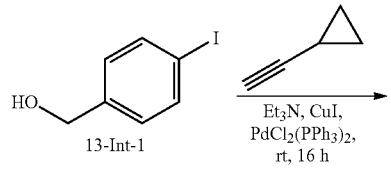

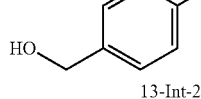

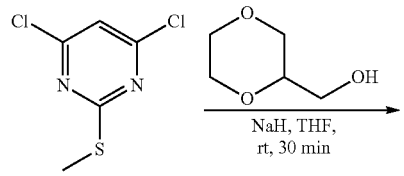

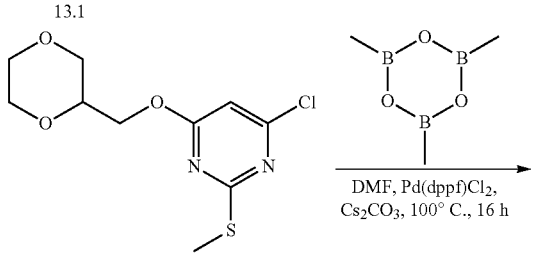

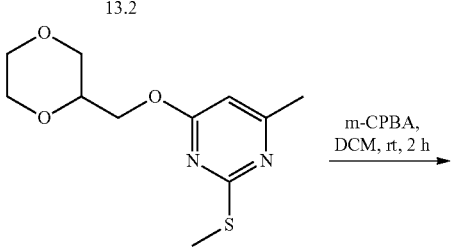

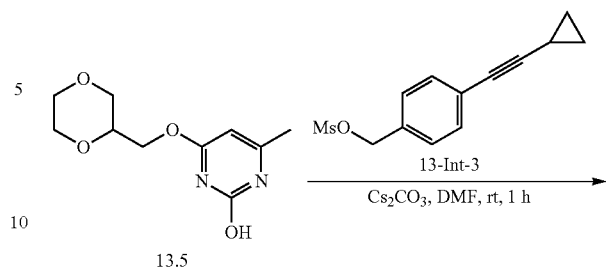

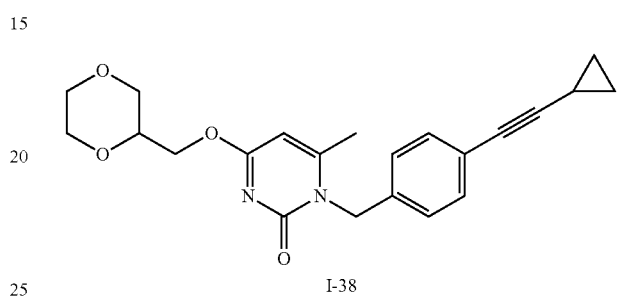

1. The synthesis of (4-(cyclopropylethynyl)phenyl)methanol (13-Int-2)

To a stirred solution of 13-Int-1 (2 g, 8.5 mmol), ethynylcyclopropane (1.68 g, 25.5 mmol) and CuI (400 mg) in Et₃N (20 mL) was added PdCl₂(PPh₃)₂ (200 mg). The reaction mixture was stirred at rt for 16 hours until the reaction was complete. The suspension was diluted with H₂O (40 mL) and extracted with EA (40 mL×2), concentrated. The crude product was purified by flash column chromatography (silica gel, PE/EA=20:1) to give 13-Int-2 (1.2 g, yield: 82.1%) as yellow oil.

$^1$H NMR (400 MHz, CDCl$_3$): δ 7.33 (dd, J=1.6 Hz, 6.4 Hz, 2H), 7.21 (d, J=8.4 Hz, 2H), 4.59 (s, 2H), 2.65 (s, 1H), 1.40-1.46 (m, 1H), 0.77-0.88 (m, 4H).

2. The Synthesis of 4-(cyclopropylethynyl)benzyl methanesulfonate (13-Int-3)

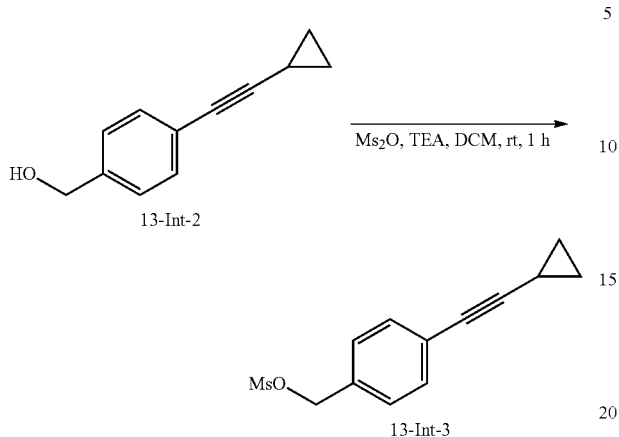

To a stirred solution of 13-Int-2 (400 mg, 2.3 mmol) in DCM (10 mL) was added TEA (697 mg, 6.9 mmol) and Ms$_2$O (800 mg, 4.6 mmol). The reaction mixture was stirred at rt for 1 h. H$_2$O (15 mL) and DCM (10 mL) were added and the organic phases was collected and evaporated under reduced pressure to give 13-Int-3 (450 mg, crude) as yellow oil. This compound was used immediately in the next reaction without purification.

3. The Synthesis of Intermediate 13.2

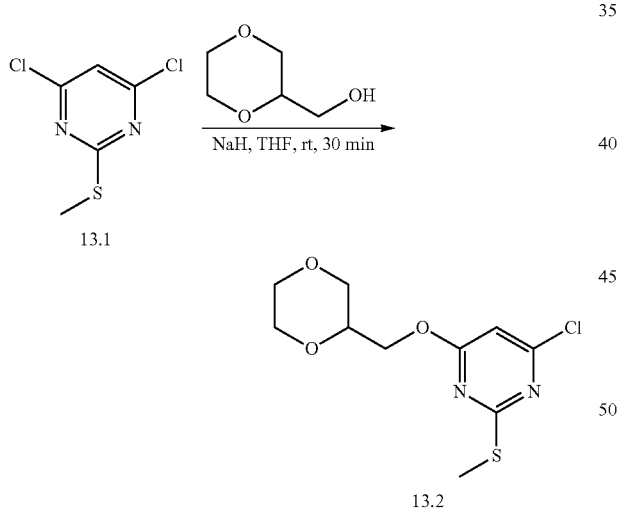

To a stirred solution of 13.1 (500 mg, 2.6 mmol) in THF (10 ml) was added NaH (312 mg, 7.8 mmol, 60% in mineral oil). The reaction mixture was stirred at room temperature for 30 min, then (1,4-dioxan-2-yl)methanol (337 mg, 2.9 mmol) was added. The reaction mixture was stirred at RT for 30 min. Ice water (10 mL) was added and the reaction mixture was extracted with EtOAc (10 mL×2). The organic phase was combined, washed with brine, dried over anhydrous Na$_2$SO$_4$. The solvent was removed under reduced pressure and purified by flash column chromatography (silica gel, PE/EA=2:1) to give 13.2 (600 mg, yield: 84%) as yellow oil.

4. The Synthesis of Intermediate 13.3

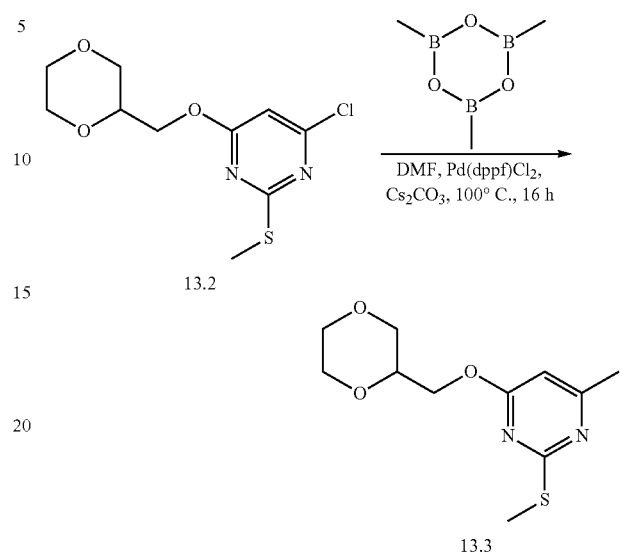

To a stirred solution of 13.2 (550 mg, 2.0 mmol), 2,4,6-trimethyl-1,3,5,2,4,6-trioxatriborinane (756 mg, 6.0 mmol) and Cs$_2$CO$_3$ (1.956 g, 6 mmol) in DMF (15 mL) was added Pd(dppf)Cl$_2$ (60 mg). The reaction mixture was stirred at 100° C. for 16 hours under Ar atmosphere until the reaction was complete (by LCMS). The suspension was diluted with H$_2$O (20 mL) and extracted with EA (20 mL×2), the combined organic phase was concentrated. The crude product was purified by flash column chromatography (silica gel, PE/EA=2:1) to give 13.3 (400 mg, yield: 78%) as a yellow solid.

5. The Synthesis of Intermediate 13.4

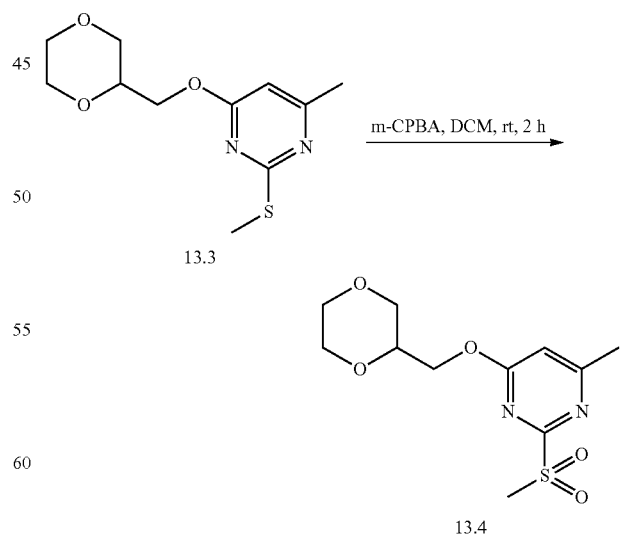

To a stirred solution of 13.3 (400 mg, 1.6 mmol) in DCM (20 mL) was added m-CPBA (537 mg, 3.1 mmol). The reaction mixture was stirred at RT for 2 h then Na$_2$SO$_3$ (aq.

20 mL) was added and the reaction mixture was extracted with DCM (50 mL×2). The organic phase was combined, washed with brine, dried over anhydrous Na₂SO₄, the solvent was removed under reduced pressure and purified by flash column chromatography (silica gel, PE/EA=5:1) to give 13.4 (410 mg, yield: 91%) as a yellow solid.

6. The Synthesis of Intermediate 13.5

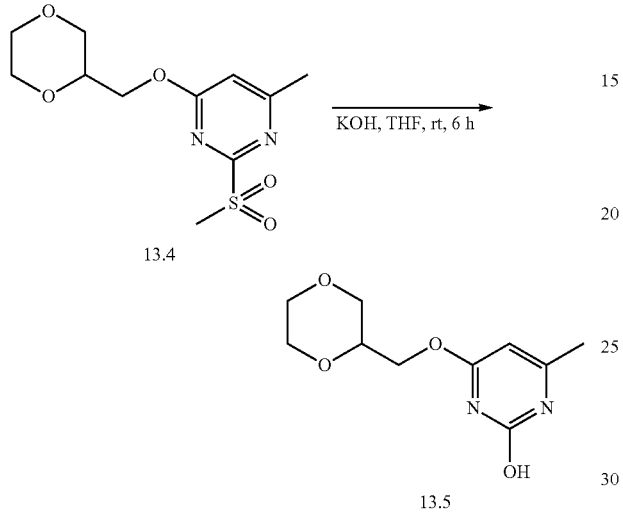

To a solution of 13.4 (410 mg, 1.4 mmol) in THF (10 mL) was added KOH (2.0 M, 10 mL). The mixture was stirred at rt for 6 h then HCl (1.0 M) was added to adjust pH=5-6. The reaction mixture was extracted with EA (30 mL×2), the combined organic phase was washed with brine, dried over anhydrous Na₂SO₄. The solvent was removed under reduced pressure to give 13.5 (300 mg, yield: 93.5%) as yellow oil. ¹H NMR (400 MHz, DMSO-d₆): δ 11.31 (br, 1H), 5.77 (s, 1H), 4.13-4.24 (m, 2H), 3.72-3.83 (m, 3H), 3.55-3.66 (m, 2H), 3.43-3.51 (m, 1H), 3.32-3.37 (m, 1H), 2.11 (s, 3H).

7. The Synthesis of Target I-38

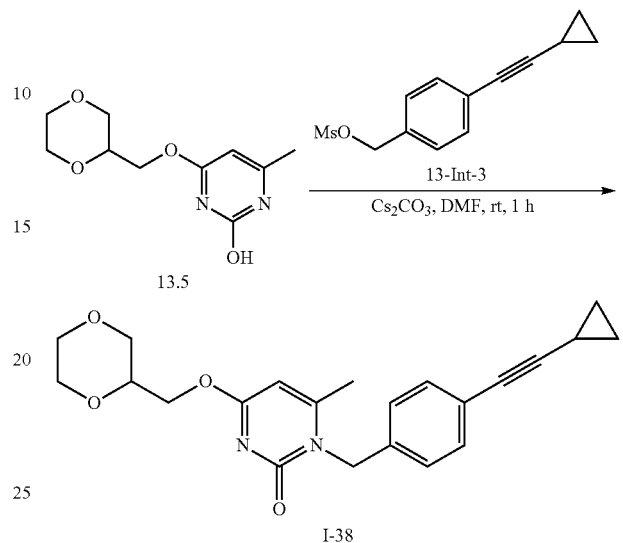

To a solution of 13.5 (300 mg, 1.3 mmol) in DMF (5 mL) was added 13-Int-3 and Cs₂CO₃ (1.3 g, 4.0 mmol). The reaction mixture was stirred at RT for 1 h. Water (30 mL) was added and the reaction mixture was extracted with EtOAc (30 mL×2). The organic phase was combined, washed with brine, dried over anhydrous Na₂SO₄. The solvent was removed under reduced pressure and purified by Prep-HPLC to give I-38 (27.53 mg, yield: 5b %) as a white solid.

Additional exemplary compounds were prepared following methods substantially similar to the method described above and herein. Data for these compounds are provided below.

TABLE 14

Characterization Data for Additional Exemplary Compounds

| Compound No. | Chemical Structure | [M + H] observed | ¹H NMR (400 MHz) |
|---|---|---|---|
| I-38 | 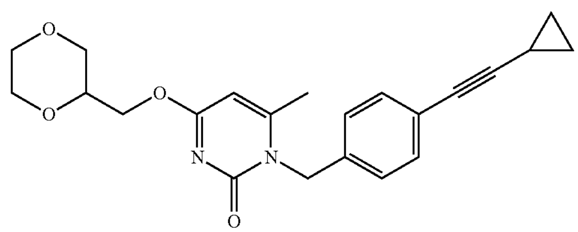 [SMILES: Cc1cc(OCC2COCCO2)nc(=O)n1Cc1ccc(C#CC2CC2)cc1] | 381.3 | ¹H NMR (400 MHz, CDCl₃): δ 7.32 (d, J = 8.4 Hz, 2 H), 7.09 (d, J = 8.4 Hz, 2 H), 5.82 (s, 1 H), 5.21 (s, 2 H), 4.33-4.42 (m, 2 H), 3.92-3.98 (m, 1 H), 3.49-3.86 (m, 5 H), 3.43-3.46 (m, 1 H), 2.19 (s, 3 H), 1.39-1.46 (m, 1 H), 0.77-0.88 (s, 4 H). |
| I-10 | 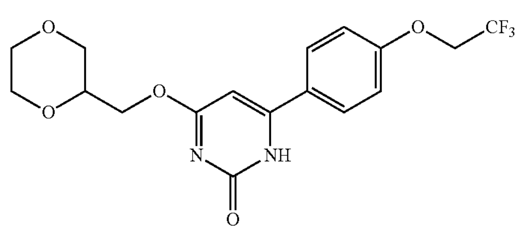 | 387.2 | ¹H NMR (400 MHz, DMSO-d₆): δ 12.38 (br s, 1H), 7.81 (d, J = 8.3 Hz, 2H), 7.10 (d, J = 8.2 Hz, 2H), 6.22 (br s, 1H), 4.53-4.33 (m, 4H), 4.03-3.94 (m, 1H), 3.92-3.70 (m, 4H), 3.70-3.60 (m, 1H), 3.53-3.44 (m, 1H) |

TABLE 14-continued

Characterization Data for Additional Exemplary Compounds

| Compound No. | Chemical Structure | [M + H] observed | ¹H NMR (400 MHz) |
|---|---|---|---|
| I-102 | 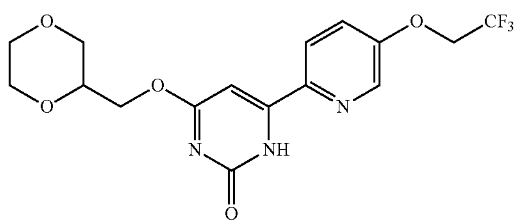 [SMILES: O=c1nc(OCC2COCCO2)cc(-c2ccc(OCC(F)(F)F)cn2)[nH]1] | 388.2 | ¹H NMR (400 MHz, DMSO-d$_6$): δ 11.06 (br s, 1H), 8.54 (d, J = 2.9 Hz, 1H), 8.25 (d, J = 8.9 Hz, 1H), 7.75 (dd, J = 8.9, 3.0 Hz, 1H), 6.69 (s, 1H), 5.01 (q, J = 8.8 Hz, 2H), 4.27 (d, J = 4.7 Hz, 2H), 3.91-3.82 (m, 1H), 3.7 (td, J = 11.7, 2.7 Hz, 2H), 3.71-3.57 (m, 2H), 3.49 (td, J = 10.7, 2.6 Hz, 1H), 3.38 (dd, J = 11.4, 10.0 Hz, 1H). |
| I-9 | 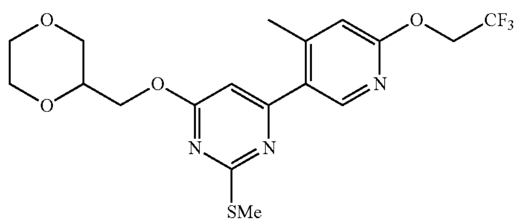 [SMILES: CSc1nc(OCC2COCCO2)cc(-c2cnc(OCC(F)(F)F)cc2C)n1] | 432.2 | ¹H NMR (400 MHz, CDCl$_3$): δ 8.18 (s, 1H), 6.77 (s, 1H), 6.55 (s, 1H), 4.78 (q, J = 8.5 Hz, 2H), 4.42 (d, J = 5.0 Hz, 2H), 4.01 (dtd, J = 10.0, 5.0, 2.6 Hz, 1H), 3.87 (dd, J = 11.5, 2.5 Hz, 2H), 3.82 (dd, J = 10.6, 2.6 Hz, 1H), 3.78-3.72 (m, 1H), 3.70-3.62 (m, 1H), 3.52 (dd, J = 11.2, 10.3 Hz, 1H), 2.56 (s, 3H), 2.44 (s, 3H). |
| I-85 | 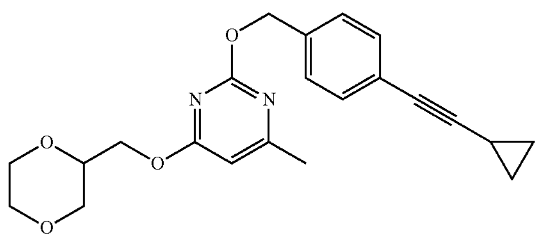 [SMILES: Cc1cc(OCC2COCCO2)nc(OCc2ccc(C#CC3CC3)cc2)n1] | 381.2 | ¹H NMR (400 MHz, CDCl$_3$): δ 7.33 (s, 4 H), 6.27 (s, 1 H), 5.34 (s, 2 H), 4.26-4.35 (m, 2 H), 3.91-3.96 (m, 1 H), 3.49-3.86 (m, 5 H), 3.44-3.47 (m, 1 H), 2.35 (s, 3 H), 1.41-1.47 (m, 1 H), 0.77-0.89 (m, 4H). |

Example 14: Synthesis of I-80

Synthetic Scheme of I-80

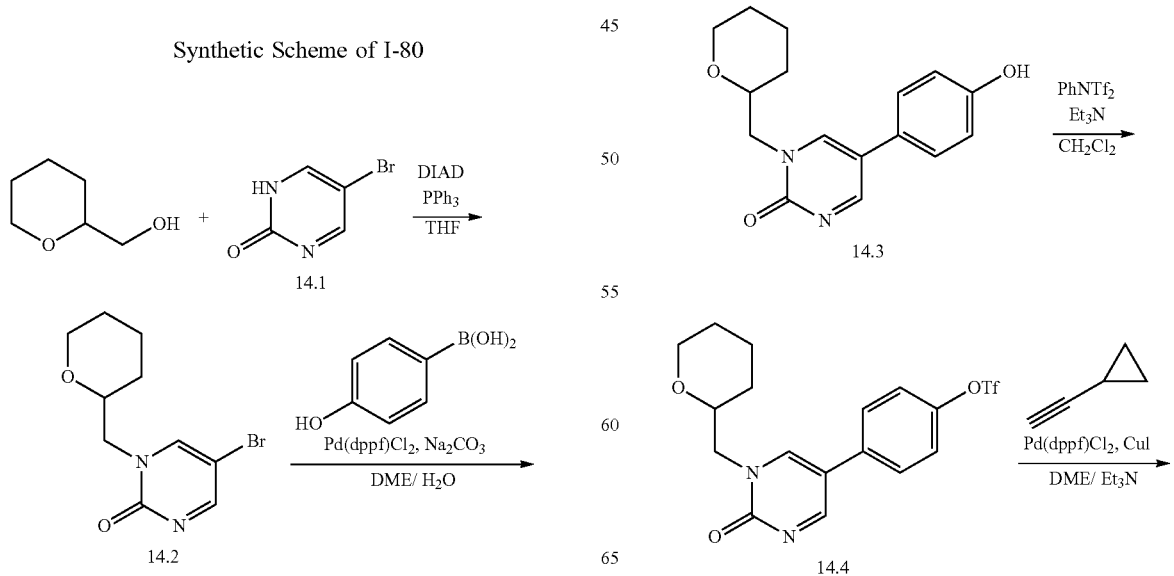

423

-continued

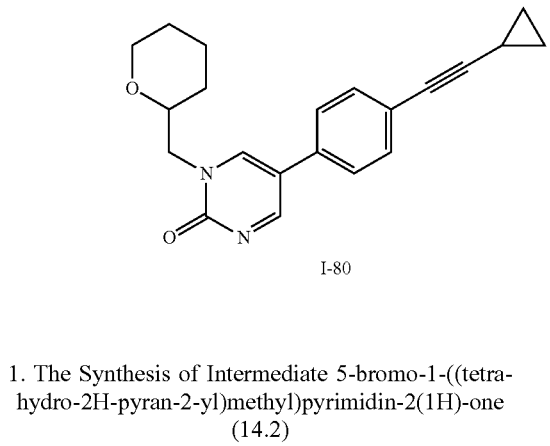

I-80

1. The Synthesis of Intermediate 5-bromo-1-((tetrahydro-2H-pyran-2-yl)methyl)pyrimidin-2(1H)-one (14.2)

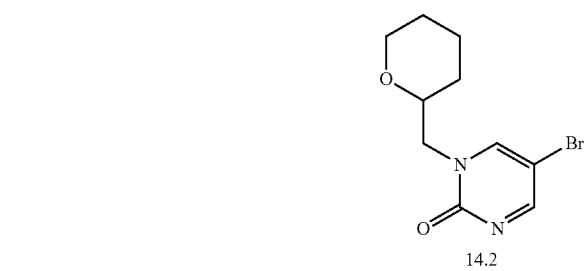

DIAD (1.13 mL, 5.71 mmol, 2.00 eq.) and PPh₃ (1.48 g, 5.71 mmol, 2.00 eq.) were stirred in THF (30 mL) for 10 minutes at RT. 5-Bromopyrimidin-2(1H)-one, 14.1 (1.00 g, 5.71 mmol, 2.00 eq.) was added and the mixture was stirred for 5 minutes. (Tetrahydro-2H-pyran-2-yl)methanol (332 mg, 2.86 mmol, 1.00 eq.) was added and the mixture was stirred at RT for 24 hours. Water was added and the mixture was extracted twice with EtOAc. The combined organic layers were washed with brine, dried over Na₂SO₄, filtered and concentrated under reduced pressure to give a crude mixture containing O-alkylated (major) and N-alkylated (minor) products. The residue was purified by silica gel chromatography (0-4% MeOH in CH₂Cl₂) to provide 5-bromo-1-((tetrahydro-2H-pyran-2-yl)methyl)pyrimidin-2 (1H)-one (14.2) as a white solid (143 mg, 9%).

424

2. The Synthesis of Intermediate 5-(4-hydroxyphenyl)-1-((tetrahydro-2H-pyran-2-yl)methyl)pyrimidin-2(1H)-one (14.3)

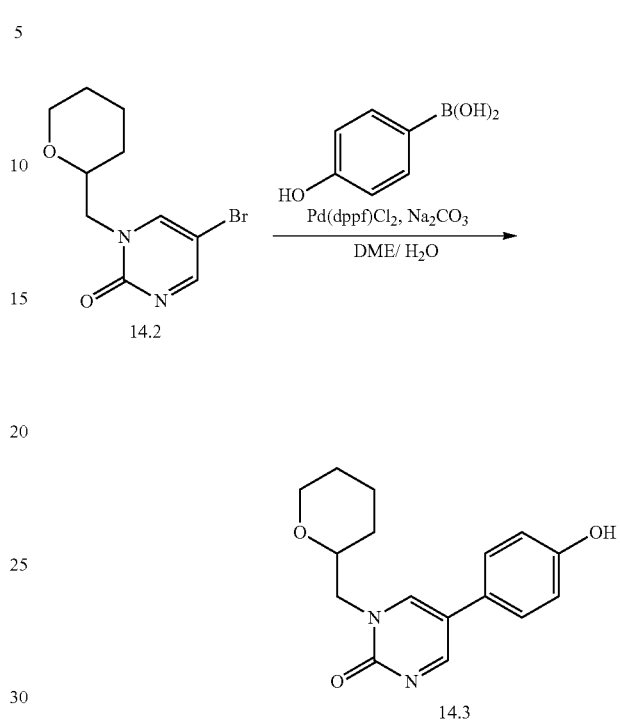

A mixture of 5-bromo-1-((tetrahydro-2H-pyran-2-yl) methyl)pyrimidin-2(1H)-one, 14.2 (143 mg, 0.526 mmol, 1.00 eq.), 4-hydroxyphenylboronic acid (109 mg, 0.789 mmol, 1.50 eq.) and Na₂CO₃ (123 mg, 1.16 mmol, 2.20 eq.) in DME (2.0 mL) and water (0.5 mL) was degassed with N₂ for 10 minutes. Pd(dppf)Cl₂ (38 mg, 0.0526 mmol, 0.10 eq.) was added and the mixture was stirred at 90° C. for 18 hours. The mixture was cooled to RT, poured into a saturated NH₄Cl solution and extracted twice with EtOAc. The combined organic layers were washed with brine, dried over Na₂SO₄, filtered and concentrated under reduced pressure. The residue was purified by silica gel chromatography (0-30% MeOH in CH₂Cl₂) to provide 5-(4-hydroxyphenyl)-1-((tetrahydro-2H-pyran-2-yl)methyl)pyrimidin-2(1H)-one (14.3) as a brown gum (90 mg, 60%).

3. The Synthesis of Intermediate 4-(2-oxo-1-((tetrahydro-2H-pyran-2-yl)methyl)-1,2-dihydropyrimidin-5-yl)phenyl trifluoromethylsulfonate (14.4)

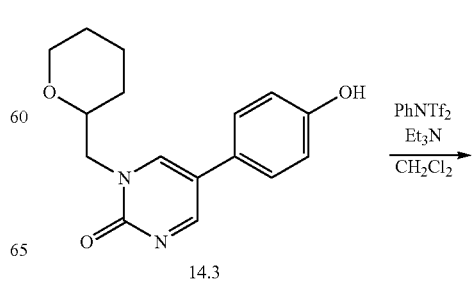

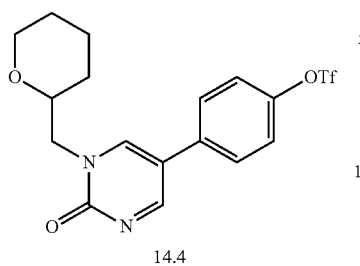

14.4

A mixture of 5-(4-hydroxyphenyl)-1-((tetrahydro-2H-pyran-2-yl)methyl)pyrimidin-2(1H)-one, 14.3 (90 mg, 0.315 mmol, 1.00 eq.), PhNTf$_2$ (124 mg, 0.346 mmol, 1.10 eq.) and Et$_3$N (88 µL, 0.63 mmol, 2.0 eq.) in CH$_2$Cl$_2$ (2.0 mL) was stirred at RT for 60 hours. The mixture was concentrated under reduced pressure and the residue was purified by silica gel chromatography (0-20% MeOH in CH$_2$Cl$_2$) to provide 4-(2-oxo-1-((tetrahydro-2H-pyran-2-yl)methyl)-1,2-dihydropyrimidin-5-yl)phenyl trifluoromethylsulfonate (14.4) as a brown solid (99 mg, 75%).

4. The Synthesis of Target I-80

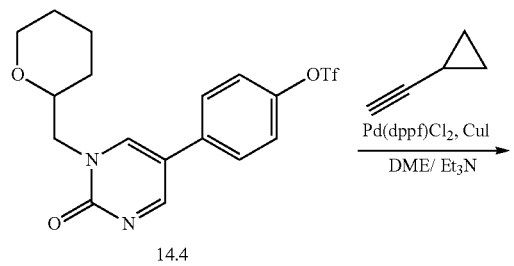

14.4

Pd(dppf)Cl$_2$, CuI
DME/ Et$_3$N

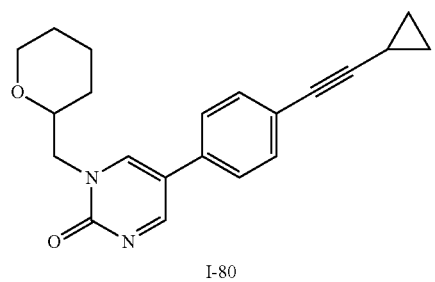

I-80

A mixture of 4-(2-oxo-1-((tetrahydro-2H-pyran-2-yl)methyl)-1,2-dihydropyrimidin-5-yl)phenyl trifluoromethylsulfonate, 14.4 (99 mg, 0.237 mmol, 1.00 eq.), Pd(dppf)Cl$_2$ (17 mg, 0.024 mmol, 0.10 eq.) and CuI (4.5 mg, 0.024 mmol, 0.10 eq.) in DME (1.0 mL) and Et$_3$N (0.25 mL) was degassed with N$_2$ for 10 minutes. Cyclopropylacetylene (200 µL, 2.37 mmol, 10 eq.) was added and the mixture was stirred at 90° C. for 18 hours. The mixture was cooled to RT, poured into a saturated NH$_4$Cl solution and extracted twice with EtOAc. The combined organic layers were washed with brine, dried over Na$_2$SO$_4$, filtered and concentrated under reduced pressure. The residue was purified by silica gel chromatography (20-100% EtOAc in hexanes) to provide 5-(4-(cyclopropylethynyl)phenyl)-1-((tetrahydro-2H-pyran-2-yl)methyl)pyrimidin-2(1H)-one, I-80, as a beige solid (10 mg, 13%).

Additional exemplary compounds were prepared following methods substantially similar to the method described above and herein. Data for these compounds are provided below.

TABLE 15

| Compound No. | Chemical Structure | [M + H] observed | $^1$H NMR (400 MHz) |
|---|---|---|---|
| I-80 | 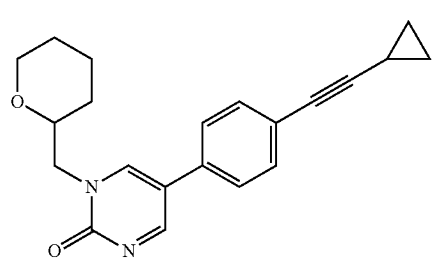 [SMILES: O=c1ncc(-c2ccc(C#CC3CC3)cc2)cn1CC1CCCCO1] | 335.2 | $^1$H NMR (400 MHz, CDCl$_3$): δ 8.85 (d, J = 3.4 Hz, 1H), 7.90 (d, J = 3.4 Hz, 1H), 7.43 (d, J = 8.5 Hz, 2H), 7.32 (d, J = 8.6 Hz, 2H), 4.42 (dd, J = 13.3, 2.1 Hz, 1H), 3.92 (dd, J = 10.8, 2.1 Hz, 1H), 3.71 (tt, J = 11.2, 2.0 Hz, 1H), 3.47 (dd, J = 13.4, 9.1 Hz, 1H), 3.33 (td, J = 10.9, 10.4, 3.5 Hz, 1H), 1.88 (d, J = 3.8 Hz, 1H), 1.76 (d, J = 12.5 Hz, 1H), 1.61-1.42 (m, 4H), 1.35-1.25 (m, 1H), 1.05-0.86 (m, 2H), 0.86-0.77 (m, 2H). |

Characterization Data for Additional Exemplary Compounds

Example 15: Synthesis of I-139

S Synthetic Scheme of I-139

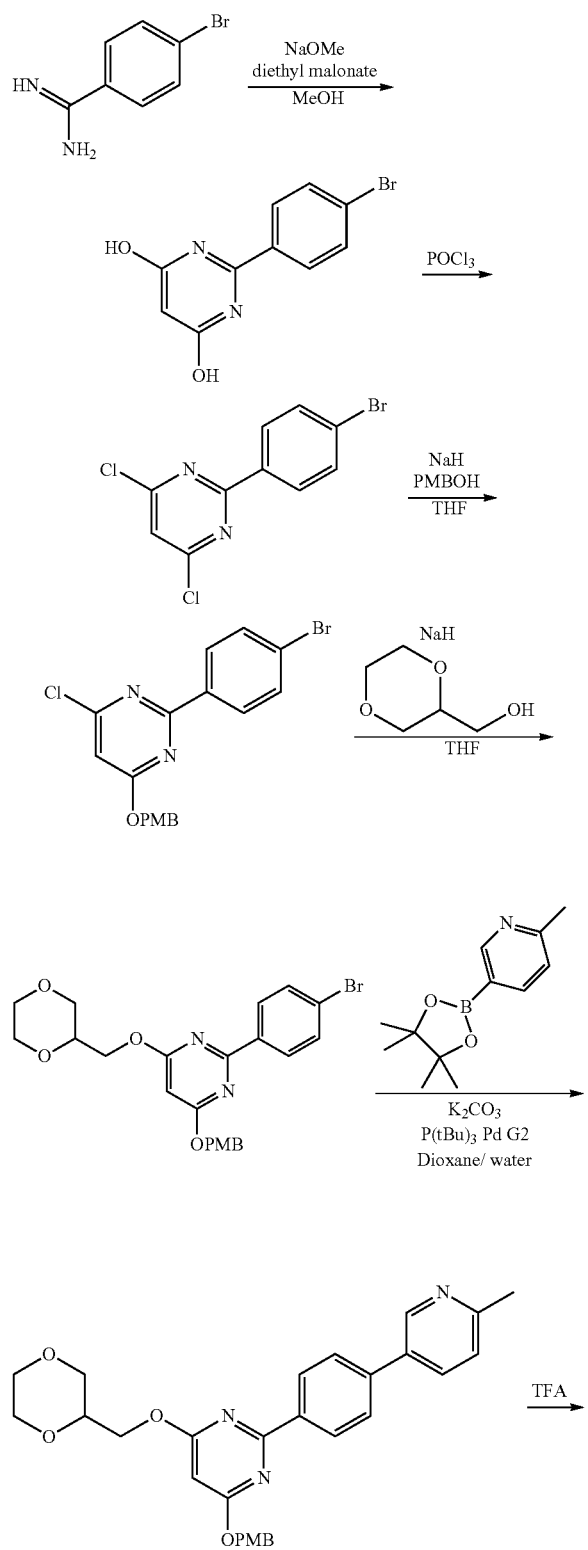

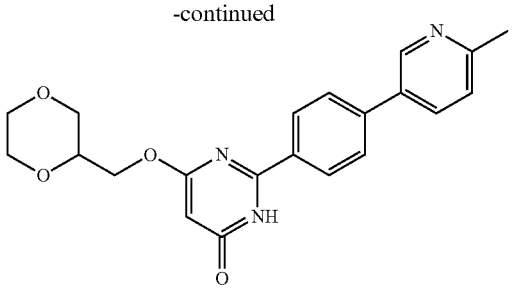

1. The Synthesis of Intermediate 2-(4-bromophenyl)pyrimidine-4,6-diol

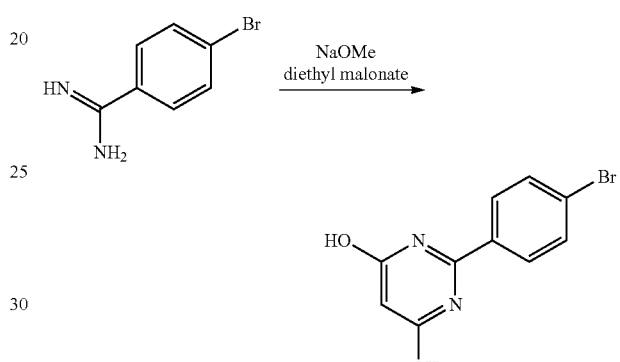

To a solution of 4-Bromobenzimidamide hydrochloride (1 g, 4.16 mmol, 1 eq) in MeOH (25.0 mL) were added at 0° C. a 25% solution of sodium methoxide (2.22 mL, 8.32 mmol, 2 eq) and diethyl malonate (708 μL, 746 mg, 4.66 mmol, 1.12 eq). The reaction mixture was stirred at RT overnight and acidified with a 10% aqueous solution of hydrogen chloride. The obtained white precipitate was dried and washed with methanol to afford 2-(4-bromophenyl) pyrimidine-4,6-diol (880 mg, 79%) as a white solid.

2. The synthesis of intermediate 2-(4-bromophenyl)-4,6-dichloropyrimidine

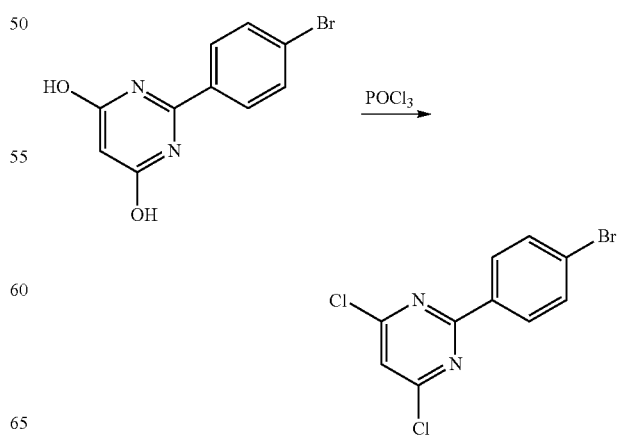

A solution of 2-(4-bromophenyl)pyrimidine-4,6-diol (880 mg, 3.29 mmol, 1 eq) in phosphorus oxychloride (4 mL, 42.5 mmol, 13 eq) was stirred at 100° C. overnight. The mixture was cooled to RT, carefully added to cold water and extracted with methylene chloride. The organic layer was washed, dried over MgSO₄ and concentrated to afford the desired product 2-(4-bromophenyl)-4,6-dichloropyrimidine (450 mg, 45%) used in the next step without further purification.

3. The Synthesis of Intermediate 2-(4-bromophenyl)-4-chloro-6-((4-methoxybenzyl) oxy)pyrimidine

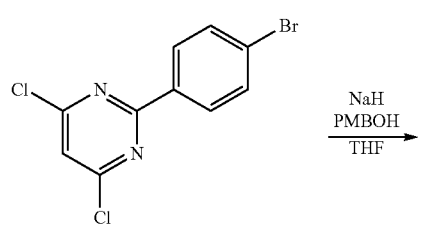

To a solution of 4-Methoxybenzyl alcohol (162 mg, 1.15 mmol, 1 eq) in THF (5 mL) was added sodium hydride (46.1 mg, 1.15 mmol, 1 eq). The reaction mixture was stirred at RT for 10 min before the addition of 2-(4-bromophenyl)-4,6-dichloropyrimidine (350 mg, 1.15 mmol, 1 eq). The stirring was continued for 45 min. The reaction mixture was quenched with cold water and extracted with ethyl acetate. The organic layer was washed, dried over MgSO4 and concentrated to afford the desired product 2-(4-bromophenyl)-4-chloro-6-((4-methoxybenzyl) oxy)pyrimidine (460 mg, 98%) used in the next step without further purification.

4. The Synthesis of Intermediate 4-((1,4-dioxan-2-yl)methoxy)-2-(4-bromophenyl)-6-((4-methoxybenzyl)oxy)pyrimidine

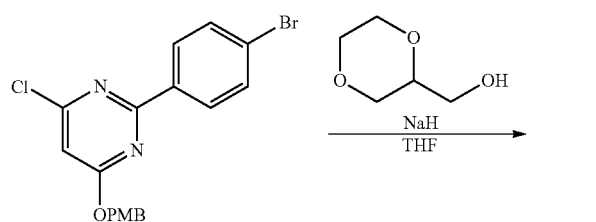

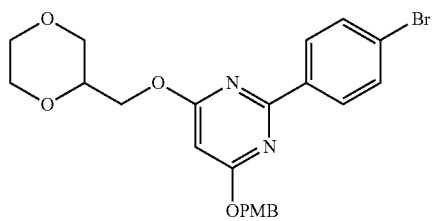

To a solution of (1,4-Dioxan-2-yl)methanol (134 mg, 1.13 mmol, 1 eq) in THF (5.00 mL) was added sodium hydride (45.4 mg, 1.13 mmol, 1 eq). The reaction mixture was stirred at RT for 10 min before the addition of 2-(4-bromophenyl)-4-chloro-6-((4-methoxybenzyl)oxy)pyrimidine (460 mg, 1.13 mmol, 1 eq). The stirring was continued overnight. The reaction mixture was quenched with cold water and extracted with ethyl acetate. The organic layer was washed, dried over MgSO₄ and concentrated to afford the desired product 4-((1,4-dioxan-2-yl)methoxy)-2-(4-bromophenyl)-6-((4-methoxybenzyl)oxy)pyrimidine (480 mg, 52%) used in the next step without further purification.

5. The Synthesis of Intermediate 4-((1,4-dioxan-2-yl)methoxy)-6-((4-methoxybenzyl)oxy)-2-(4-(6-methylpyridin-3-yl)phenyl)pyrimidine

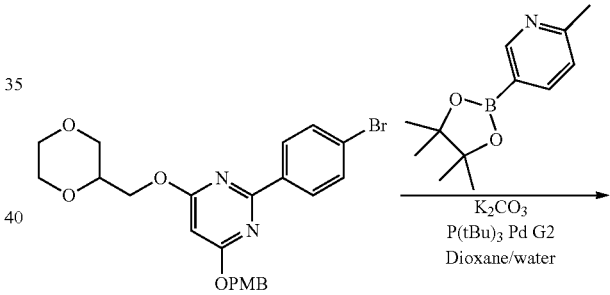

A mixture of 4-((1,4-dioxan-2-yl)methoxy)-2-(4-bromophenyl)-6-((4-methoxybenzyl)oxy) pyrimidine (100 mg, 123 μmol, 1 eq), 2-methylpyridine-5-boronic acid, pinacol ester (42.1 mg, 185 μmol, 1.5 eq), P(tBu)₃ Pd G2 (6.31 mg, 12.3 μmol, 0.1 eq) and K₂CO₃ (51 mg, 369 μmol, 3 eq) in dioxane (450 μL) and water (50 μL) was degassed with nitrogen for 5 minutes. The reaction mixture was stirred at 100° C. for 1 h and partitioned between ethyl acetate (20 mL) and an aqueous solution of ammonium chloride (10 mL). The layers were separated and the organic one was washed, dried over MgSO₄, concentrated and purified by reverse phase FCC (30 g C18 cartridge, 5 to 95% ACN in 10 mM AmF) to afford the desired product 4-((1,4-dioxan-2-yl)methoxy)-6-((4-methoxybenzyl)oxy)-2-(4-(6-methylpyridin-3-yl)phenyl)pyrimidine (61 mg, 100%) as a white powder.

6. The Synthesis of Target I-139

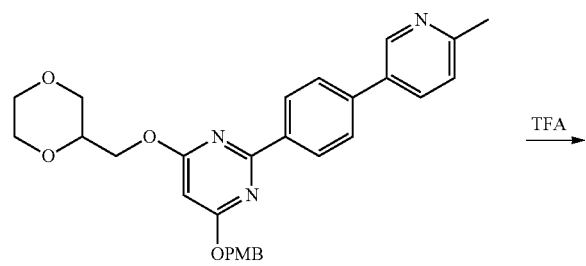

A solution of 4-((1,4-dioxan-2-yl)methoxy)-6-((4-methoxybenzyl)oxy)-2-(4-(6-methylpyridin-3-yl)phenyl)pyrimidine (61 mg, 123 μmol, 1 eq) in trifluoroacetic acid (1 mL, 1.22 mmol, 10 eq) was stirred at RT for 35 min and partitioned between an aqueous solution of sodium hydrogenocarbonate and ethyl acetate. The layers were separated and the organic one was washed, dried over MgSO₄, concentrated purified by reverse phase FCC (30 g C18 cartridge, 5 to 25% ACN in 10 mM AmF) to afford the desired product 6-((1,4-dioxan-2-yl)methoxy)-2-(4-(6-methylpyridin-3-yl)phenyl)pyrimidin-4(3H)-one, I-139 (15 mg, 32%) as a white solid.

Additional exemplary compounds were prepared following methods substantially similar to the method described above and herein. Data for these compounds are provided below.

TABLE 16

Characterization Data for Additional Exemplary Compounds

| Compound No. | Chemical Structure | [M + H] observed | $^1$H NMR (400 MHz) |
|---|---|---|---|
| I-139 | 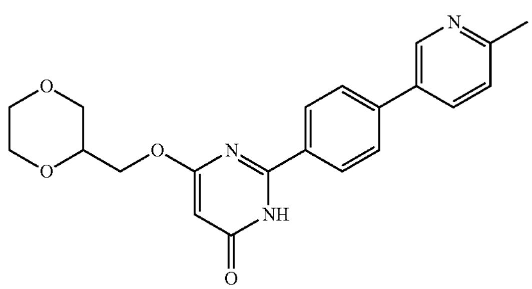 [SMILES: Cc1ccc(-c2ccc(-c3nc(OCC4COCCO4)cc(=O)[nH]3)cc2)cn1] | 380.2 | $^1$H NMR (400 MHz, DMSO-$d_6$): δ 12.43 (br. s, 1H), 8.85 (d, J = 2.4 Hz, 1H), 8.31-8.27 (m, 2H), 8.07 (dd, J = 8.1, 2.4 Hz, 1H), 7.89-7.87 (m, 2H), 7.38 (d, J = 8.1 Hz, 1H), 5.68 (s, 1H), 4.28 (d, J = 4.9 Hz, 2H), 3.91-3.85 (m, 1H), 3.82 (dd, J = 11.3, 2.6 Hz, 1H), 3.79-3.74 (m, 1H), 3.69-3.64 (m, 1H), 3.61 (dd, J = 11.3, 2.6 Hz, 1H), 3.50 (dd, J = 12.1, 9.5 Hz, 1H), 3.40 (dd, J = 11.2, 10.2 Hz, 1H), 2.53 (s, 3H). |
| I-47 | 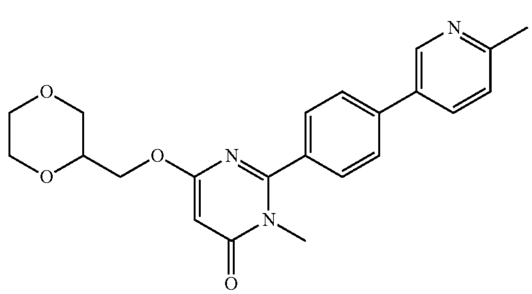 [SMILES: Cc1ccc(-c2ccc(-c3nc(OCC4COCCO4)cc(=O)n3C)cc2)cn1] | 394.2 | $^1$H NMR (400 MHz, CD$_3$CN): δ 8.79 (d, J = 1.9 Hz, 1H), 7.96 (dd, J = 8.1, 1.9 Hz, 1H), 7.82-7.78 (m, 2H), 7.71-7.66 (m, 2H), 7.34 (d, J = 8.1 Hz, 1H), 5.64 (s, 1H), 4.19-4.07 (m, 2H), 3.91-3.82 (m, 1H), 3.79-3.74 (m, 2H), 3.71-3.62 (m, 2H), 3.56-3.49 (m, 1H), 3.40 (dd, J = 11.5, 10.1 Hz, 1H), 3.35 (s, 3H), 2.56 (s, 3H). |

TABLE 16-continued
Characterization Data for Additional Exemplary Compounds
| Compound No. | Chemical Structure | [M + H] observed | 1H NMR (400 MHz) |
|---|---|---|---|
| I-27 | 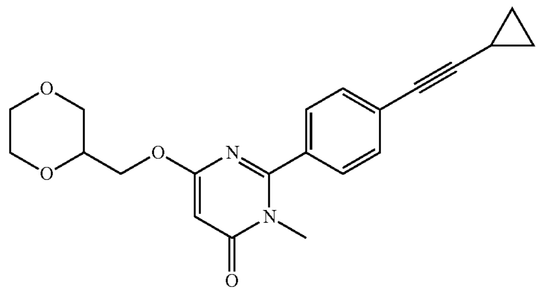 [SMILES: Cn1c(-c2ccc(C#CC3CC3)cc2)nc(OCC2COCCO2)cc1=O] | 367.2 | 1H NMR (400 MHz, CD3CN): δ 7.52-7.46 (m, 4H), 5.60 (s, 1H), 4.16-4.05 (m, 2H), 3.89-3.81 (m, 1H), 3.77-3.73 (m, 2H), 3.69-3.63 (m, 2H), 3.55-3.49 (m, 1H), 3.39 (dd, J = 11.5, 10.1 Hz, 1H), 3.28 (s, 3H), 1.50 (tt, J = 8.3, 5.0 Hz, 1H), 0.95-0.88 (m, 2H), 0.81-0.75 (m, 2H). |
| I-119 | 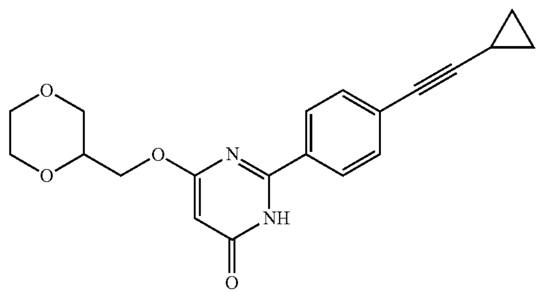 [SMILES: O=c1cc(OCC2COCCO2)nc(-c2ccc(C#CC3CC3)cc2)[nH]1] | 353.2 | 1H NMR (400 MHz, DMSO-d6): δ 8.20-8.10 (m, 2H), 7.50-7.47 (m, 2H), 5.69 (br. s, 1H), 4.30-4.25 (m, 2H), 3.89-3.74 (m, 3H), 3.68-3.58 (m, 2H), 3.55-3.45 (m, 2H), 3.38 (dd, J = 11.3, 10.0 Hz, 1H), 1.62-1.55 (m, 1H), 0.96-0.89 (m, 2H), 0.80-0.75 (m, 2H). |
| I-134 | 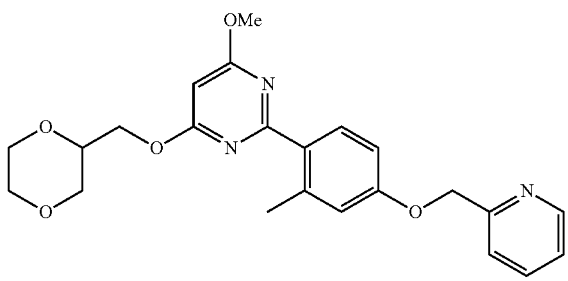 [SMILES: COc1cc(OCC2COCCO2)nc(-c2ccc(OCc3ccccn3)cc2C)n1] | 424.3 | 1H NMR (400 MHz, CDCl3): δ 8.61 (dd, J = 4.8 Hz, 0.4 Hz, 1H), 8.03-8.05 (m, 1H), 7.69-7.74 (m, 1H), 7.52 (d, J = 8.0 Hz, 1H), 7.21-7.24 (m, 1H), 6.88-6.90 (m, 2H), 6.00 (s, 1H), 5.26 (s, 2H), 4.36-4.45 (m, 2H), 3.89-4.02 (m, 4H), 3.74-3.89 (m, 3H), 3.62-3.72 (m, 2H), 3.48-3.54 (m, 1H), 2.67 (s, 3H). |
Example 16: Synthesis of I-228
Scheme of I-228
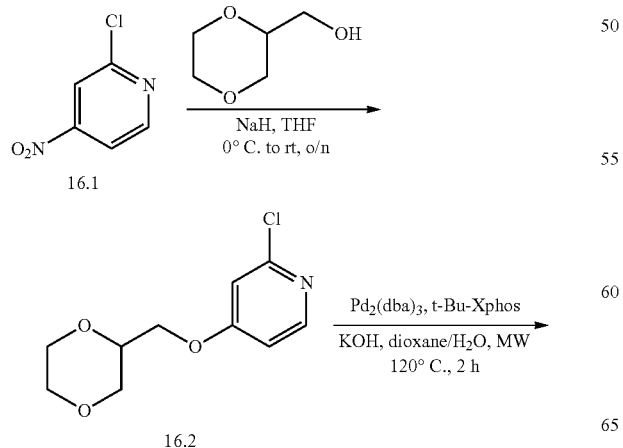
-continued
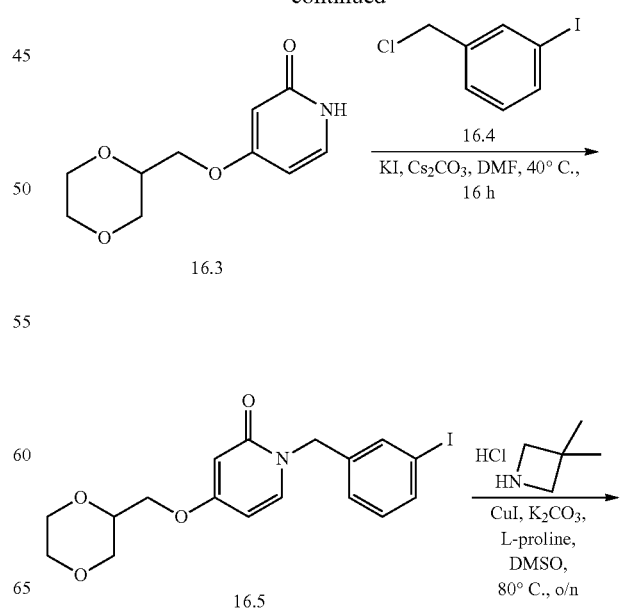

-continued

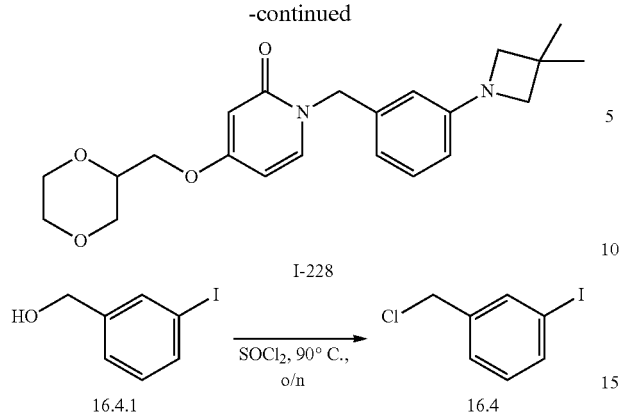

I-228

1. The Synthesis of Intermediate 16.2

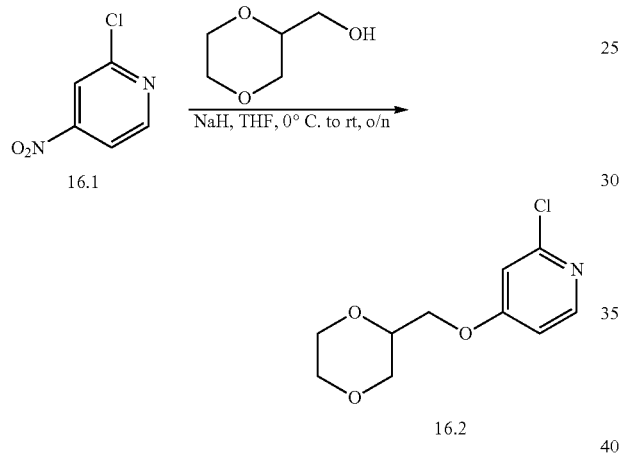

To a stirred solution of (1,4-dioxan-2-yl)methanol (447 mg, 3.79 mmol) and NaH (99 mg, 4.11 mmol) in dry THF (10 mL), 16.1 (500 mg, 3.16 mmol) was added at 0° C. and the mixture was stirred at room temperature overnight until the reaction was complete (by LCMS). The suspension was diluted with H$_2$O (20 mL), extracted with ethyl acetate (EA) (20 mL×2) and concentrated. The crude product was purified by flash column chromatography (silica gel, EA/DCM=10:1) to give 16.2 (500 mg, yield: 69%) as a yellow solid. LC-MS m/z: 229 [M+H]$^+$.

2. The Synthesis of Intermediate 16.3

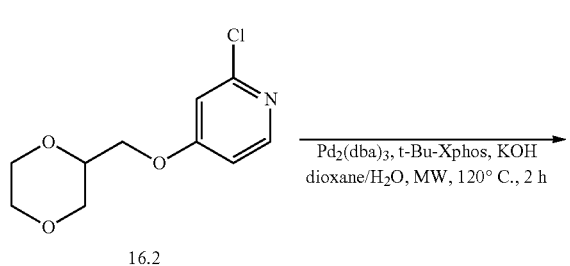

-continued

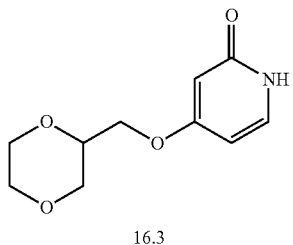

16.3

To a stirred solution of 16.2 (500 mg, 2.17 mmol) in dioxane/H$_2$O (20:1) (5 mL), KOH (243 mg, 4.34 mmol), Pd$_2$(dba)$_3$ (50 mg, 0.05 mmol) and t-Bu-Xphos (50 mg, 0.12 mmol) were added and the mixture was stirred at 120° C. for 2 hours under microwave condition until the reaction was complete (by LCMS). The suspension was diluted with H$_2$O (20 mL) and extracted with EA (20 mL×2), concentrated. The crude product was purified by flash column chromatography (silica gel, DCM/CH$_3$OH=20:1) to give 16.3 (400 mg, yield: 87%) as a yellow solid. LC-MS m/z: 211 [M+H]$^+$.

3. The Synthesis of Intermediate 16.4

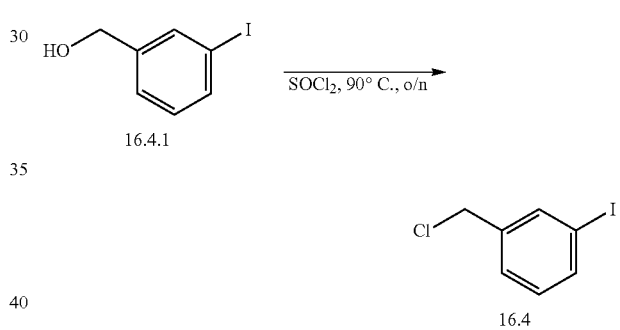

To a stirred solution of 16.4.1 (550 mg, 1.71 mmol) was added SOCl$_2$ (10 mL), the mixture was stirred at 90° C. overnight until the reaction was complete (by LCMS). The suspension was concentrated and the crude product was purified by flash column chromatography (silica gel, PE/DCM=10:1) to give 16.4 (524 mg, yield: 89%) as brown oil. LC-MS m/z: 252 [M+H]$^+$.

4. The Synthesis of Intermediate 16.5

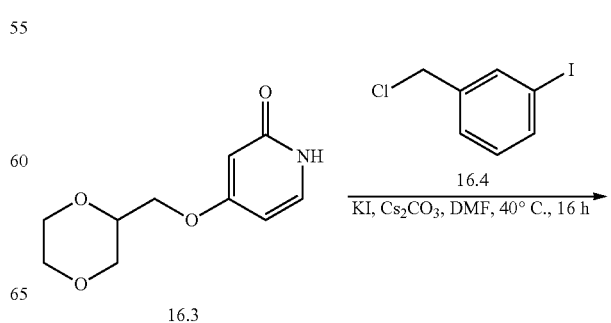

437
-continued

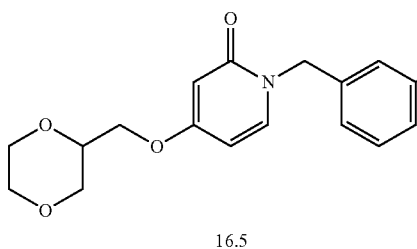

16.5

To a stirred solution of 16.3 (400 mg, 1.89 mmol) and KI (126 mg, 0.76 mmol) in DMF (10 mL), 16.4 (524 mg, 2.08 mmol) and Cs$_2$CO$_3$ (1.86 g, 5.67 mmol) were added and the mixture was stirred at 40° C. for 16 hours until the reaction was complete (by LCMS). The suspension was diluted with H$_2$O (20 mL), extracted with EA (20 mL×2) and concentrated. The crude product was purified by flash column chromatography (silica gel, DCM/CH$_3$OH=20:1) to give 16.5 (370 mg, yield: 46%) as yellow oil. LC-MS m/z: 427 [M+H]$^+$.

5. The Synthesis of Target I-228

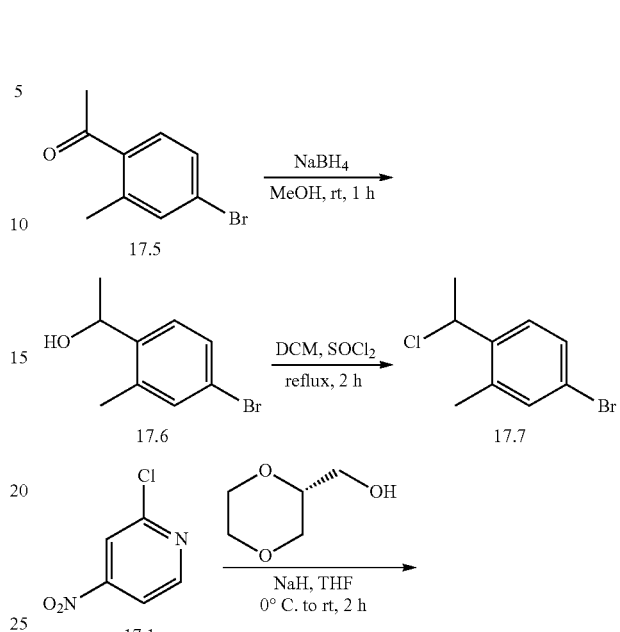

I-228

To a stirred solution of 16.5 (370 mg, 0.87 mmol) and 3,3-dimethylazetidine hydrochloride (159 mg, 1.31 mmol) in DMSO (10 mL), CuI (50 mg, 0.26 mmol), K$_2$CO$_3$ (240 mg, 1.74 mmol) and L-proline (50 mg, 0.43 mmol) were added and the mixture was stirred at 80° C. overnight until the reaction was complete (by LCMS). The suspension was diluted with H$_2$O (20 mL), extracted with EA (20 mL×2) and concentrated. The crude product was purified by Prep-HPLC to give I-228 (35.58 mg, yield: 11%) as a yellow solid.

Additional exemplary compounds were prepared following methods substantially similar to the method described above and herein. Data for these compounds are provided in Table 17, Following Example 27.

438
Example 17: Synthesis of I-239

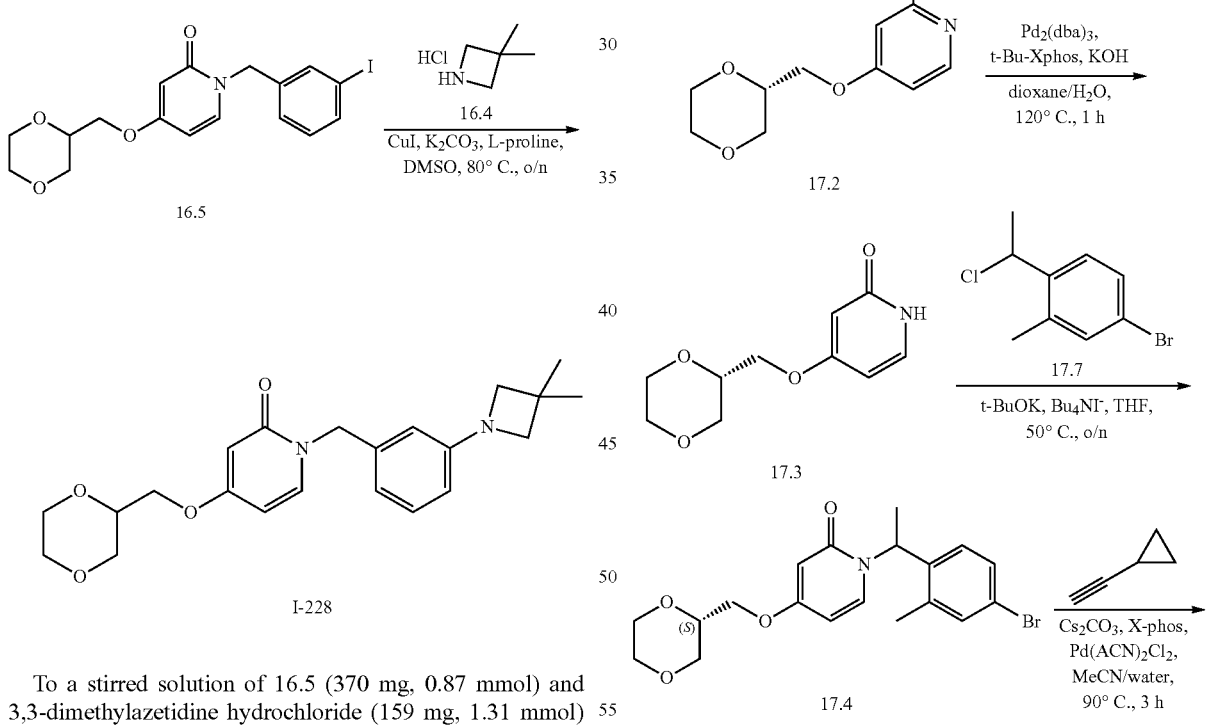

1. The Synthesis of Intermediate 17.2

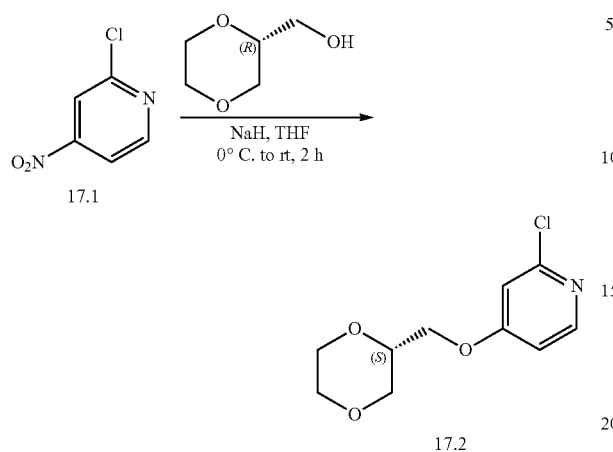

To a stirred solution of (R)-(1,4-dioxan-2-yl)methanol (1.3 g, 11.4 mmol) in THF (30 mL) was added NaH (684 mg, 17.1 mmol), the reaction mixture was stirred at 0° C. for 1 h then 17.1 (1.5 g, 9.5 mmol) was added. The solution was stirred at room temperature for 1 h. Then ice water (40 mL) was added, the solution was extracted with DCM (40 mL×3), the combined organic phase was dried over anhydrous sodium sulfate, filtered and concentrated in vacuo. The residue was purified by flash column chromatography (silica gel, PE/EA=10:1) to give 17.2 (2 g, yield: 92%) as yellow oil. LC-MS m/z: 230.2 [M+H]$^+$.

2. The Synthesis of Intermediate 17.3

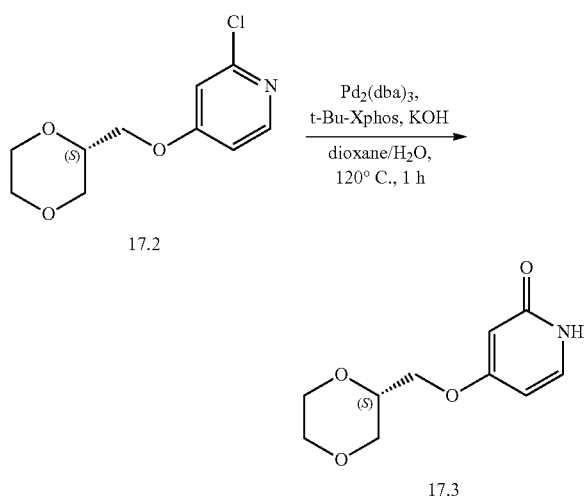

To a stirred solution of 17.2 (1 g, 4.3 mmol) and KOH (482 mg, 8.6 mmol) in dioxane (20 mL) was added Pd$_2$(dba)$_3$ (100 mg), t-Bu-Xphos (200 mg) and water (10 mL). The reaction mixture was stirred at 120° C. for 1 hour until the reaction was complete (by LCMS). The suspension was concentrated. The crude product was purified by flash column chromatography (silica gel, DCM/CH$_3$OH=10:1) to give 17.3 (0.9 g, yield: 99%) as yellow oil.

3. The Synthesis of Intermediate 17.4

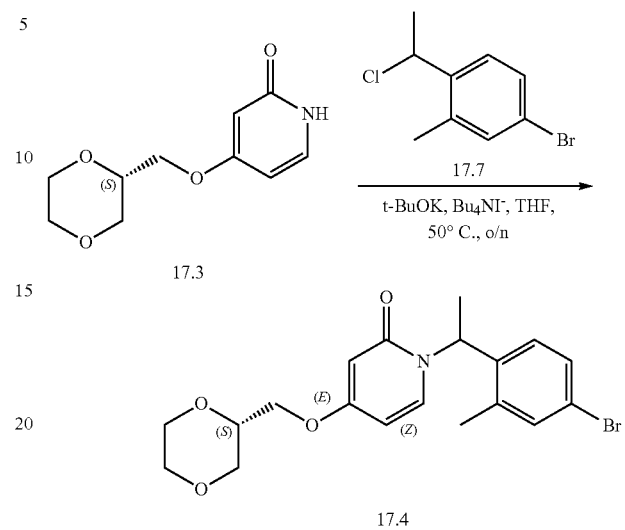

To a stirred solution of 17.3 (400 mg, 1.9 mmol) in THF (10 mL) was added t-BuOK (302 mg, 2.7 mmol), Bu$_4$NI$^-$ (701 mg, 1.9 mmol) and 17.7 (882 mg, 3.8 mmol). The reaction mixture was stirred at 50° C. overnight until the reaction was complete. Water (30 mL) was added, the solution was extracted with DCM (40 mL×3) and the combined organic phase was dried over anhydrous sodium sulfate, filtered, and concentrated in vacuo. The residue was purified by flash column chromatography (silica gel, DCM/CH$_3$OH=10:1) to give 17.4 (100 mg, yield: 13%) as yellow oil. LC-MS m/z: 407.9 [M+H]$^+$.

4. The Synthesis of I-239

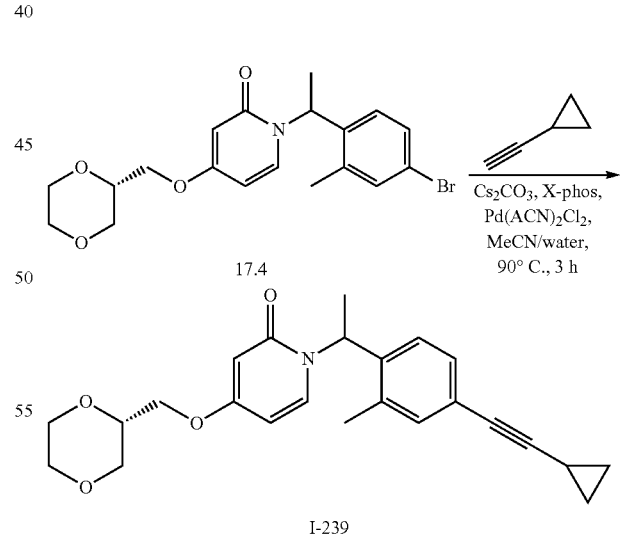

To a stirred solution of 17.4 (100 mg, 0.24 mmol) in CH$_3$CN (15 mL) was added Cs$_2$CO$_3$ (100 mg, 0.72 mmol), H$_2$O (15 mL), Pd(ACN)$_2$Cl$_2$ (10 mg) and X-phos (20 mg), then backfill with argon (three times). Added ethynylcyclopropane (49 mg, 0.72 mmol) to the resulting suspension and the reaction mixture was stirred at 90° C. for 3 hours until the reaction was complete (by LCMS). The reaction mixture was diluted with H₂O (20 mL) and extracted with DCM (20 mL×2), concentrated. The crude product was purified by Prep-HPLC to give 1-239 (44.46 mg, yield: 47%) as a white solid.

5. The Synthesis of Intermediate 17.6

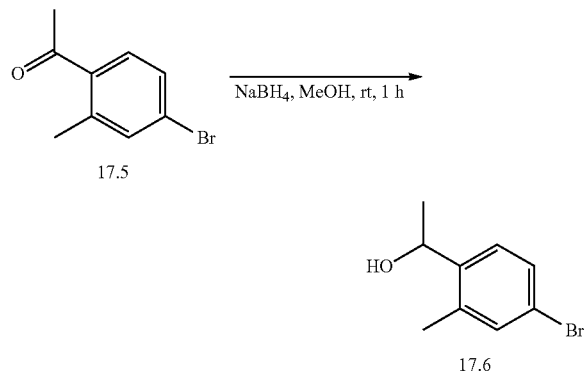

To a stirred solution of 17.5 (500 mg, 2.3 mmol) in MeOH (10 mL), was added NaBH₄ (435 mg, 6.9 mmol). The reaction mixture was stirred for 1 h at rt. The reaction mixture was diluted with H₂O (40 mL), extracted with EA (50 mL×2) and concentrated to dryness. The crude product was purified by flash column chromatography (silica gel, PE/EA=10:1) to give 17.6 (400 mg, yield: 81%) as yellow oil.

6. The Synthesis of Intermediate 17.7

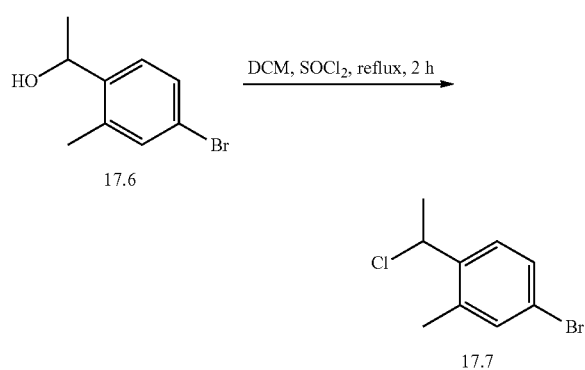

To a stirred solution of 17.6 (400 mg, 1.8 mmol) in DCM (15 mL) was added SOCl₂ (432 mg, 3.6 mmol). The reaction mixture was stirred at 70° C. for 2 h until the reaction was complete. The suspension was diluted with H₂O (30 mL), extracted with DCM (30 mL×2) and concentrated. The crude product was used to the next step directly.

Additional exemplary compounds were prepared following methods substantially similar to the method described above and herein. Data for these compounds are provided in Table 17, Following Example 27.

Example 18: Synthesis of I-225

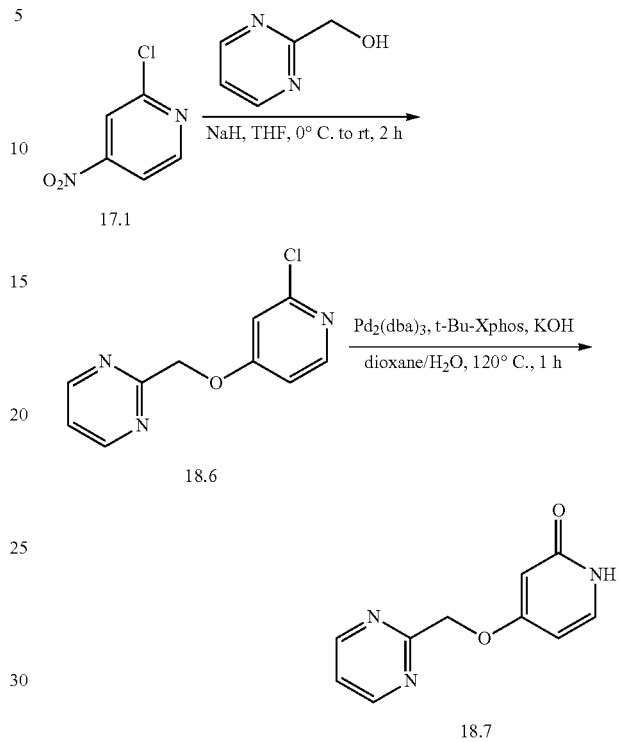

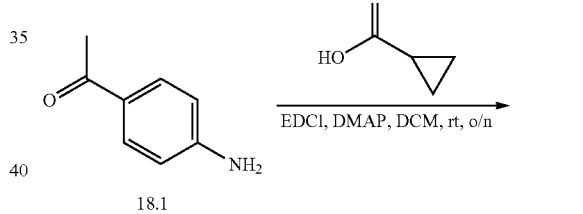

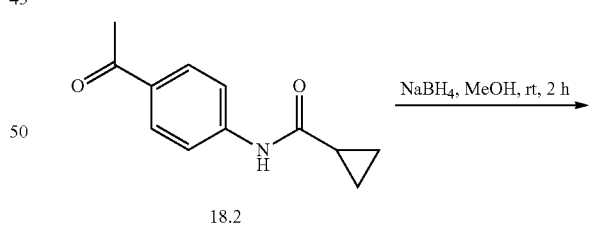

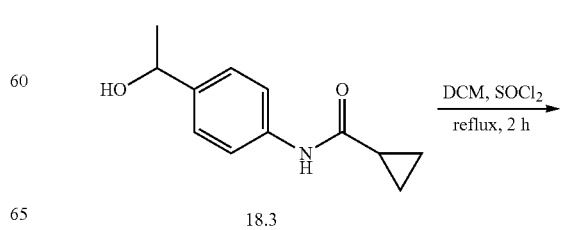

-continued

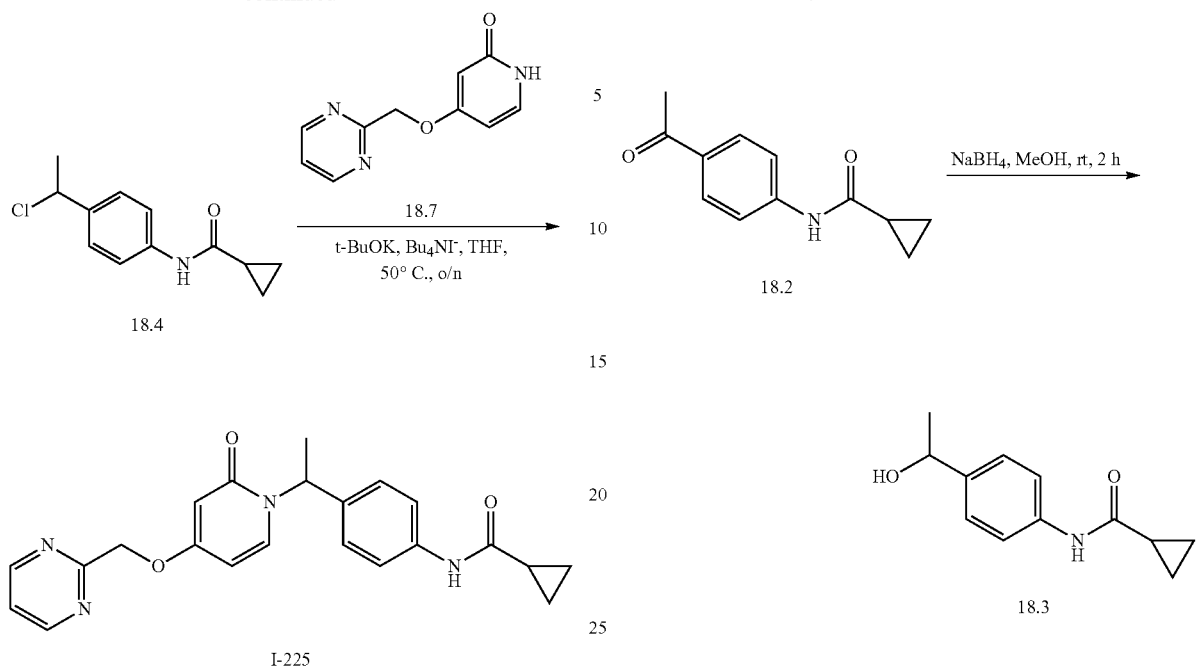

I-225

1. The Synthesis of Intermediate 18.2

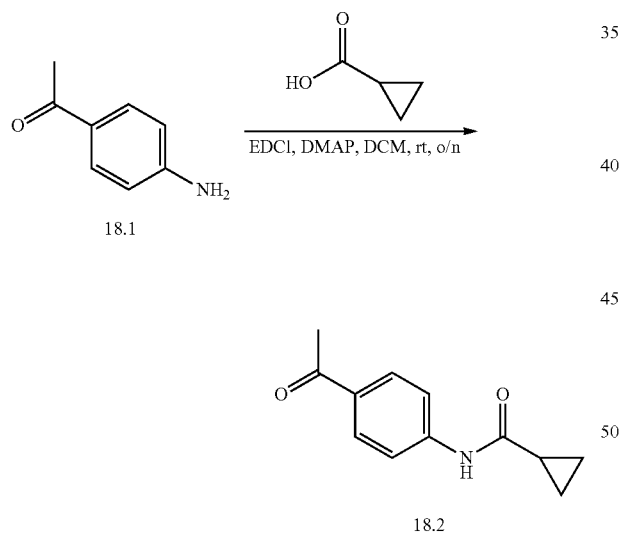

2. The Synthesis of Intermediate 18.3

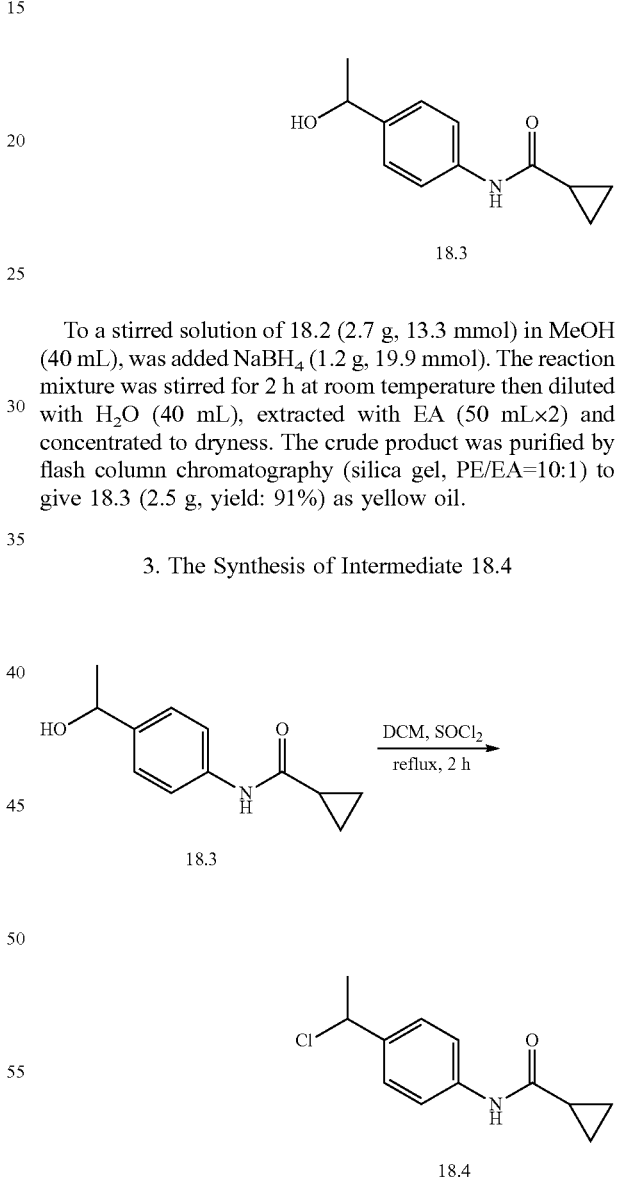

To a stirred solution of 18.2 (2.7 g, 13.3 mmol) in MeOH (40 mL), was added NaBH$_4$ (1.2 g, 19.9 mmol). The reaction mixture was stirred for 2 h at room temperature then diluted with H$_2$O (40 mL), extracted with EA (50 mL×2) and concentrated to dryness. The crude product was purified by flash column chromatography (silica gel, PE/EA=10:1) to give 18.3 (2.5 g, yield: 91%) as yellow oil.

3. The Synthesis of Intermediate 18.4

To a stirred solution of 18.1 (2 g, 14.8 mmol) in DCM (30 mL) was added cyclopropanecarboxylic acid (1.9 g, 22.2 mmol), EDCI (4.2 g, 22.2 mmol) and DMAP (5.4 g, 44.4 mmol). The reaction mixture was stirred at room temperature overnight until the reaction was complete. Water (30 mL) was added, the solution was extracted with DCM (40 mL×3), the combined organic phase was dried over anhydrous sodium sulfate, filtered and concentrated in vacuo. The residue was purified by flash column chromatography (silica gel, PE/EA=10:1) to give 18.2 (2.7 g, yield: 90%) as yellow oil.

To a stirred solution of 18.3 (300 mg, 1.46 mmol) in DCM (15 mL) was added SOCl$_2$ (347 mg, 2.92 mmol). The reaction mixture was stirred at 70° C. for 2 h until the reaction was complete. The suspension was diluted with H$_2$O (30 mL), extracted with DCM (30 mL×2) and concentrated. The crude product was used to the next step directly.

4. The Synthesis of I-225

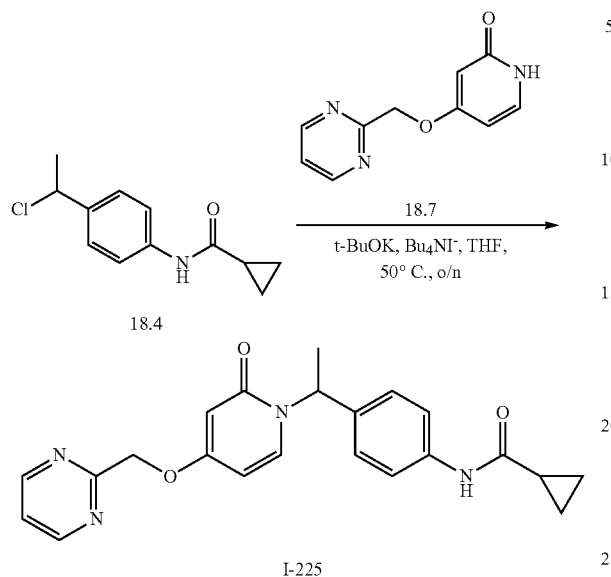

To a stirred solution of 18.7 (424 mg, 1.9 mmol) in THF (10 mL) was added t-BuOK (302 mg, 2.7 mmol), Bu$_4$NI$^-$ (701 mg, 1.9 mmol) and 18.4 (882 mg, 3.8 mmol). The reaction mixture was stirred at 50° C. overnight until the reaction was complete. Water (30 mL) was added, extracted with DCM (40 mL×3), the combined organic phase was dried over anhydrous sodium sulfate, filtered and concentrated in vacuo. The residue was purified by Prep-HPLC to give I-225 (45.86 mg, yield: 6.2%) as a white solid.

5. The Synthesis of Intermediate 18.6

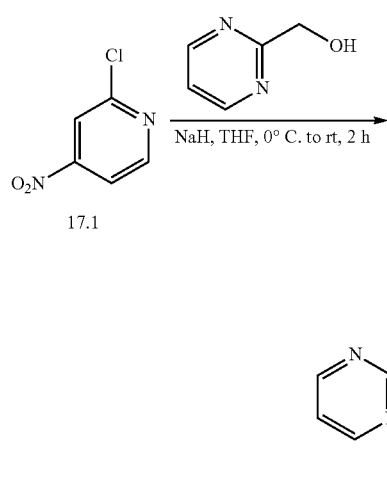

To a stirred solution of pyrimidin-2-ylmethanol (1.2 g, 11.4 mmol) in THF (30 mL) was added NaH (684 mg, 17.1 mmol), the reaction mixture was stirred at 0° C. for 1 h then 17.1 (1.5 g, 9.5 mmol) was added. The solution was stirred at room temperature for another 1 h. Then ice water (40 mL) was added, the solution was extracted with DCM (40 mL×3), the combined organic phase was dried over anhydrous sodium sulfate, filtered and concentrated in vacuo. The residue was purified by flash column chromatography (silica gel, PE/EA=10:1) to give 18.6 (1.9 g, yield: 92%) as yellow oil. LC-MS m/z: 230.2 [M+H]$^+$.

6. The Synthesis of Intermediate 18.7

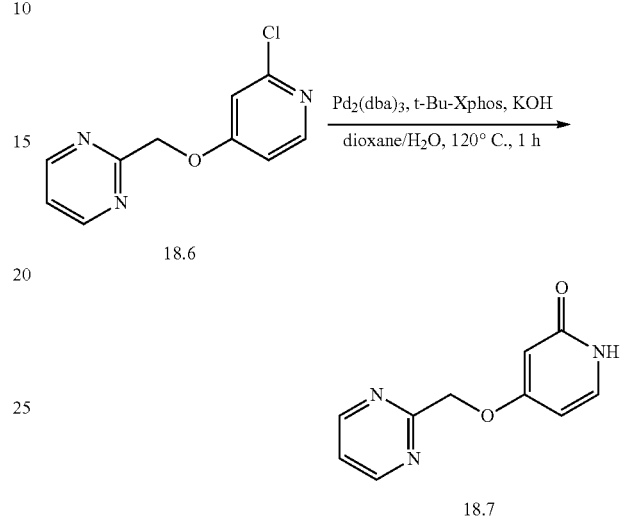

To a stirred solution of 18.6 (950 mg, 4.3 mmol) and KOH (482 mg, 8.6 mmol) in dioxane (20 mL) was added Pd$_2$(dba)$_3$ (100 mg), t-Bu-Xphos (200 mg) and water (10 mL). The reaction mixture was stirred at 120° C. for 1 hour until the reaction was complete (by LCMS). The suspension was concentrated. The crude product was purified by flash column chromatography (silica gel, DCM/CH$_3$OH=10:1) to give 18.7 (0.8 g, yield: 91%) as yellow oil.

Additional exemplary compounds were prepared following methods substantially similar to the method described above and herein. Data for these compounds are provided in Table 17, Following Example 27.

Example 19: Synthesis of I-242

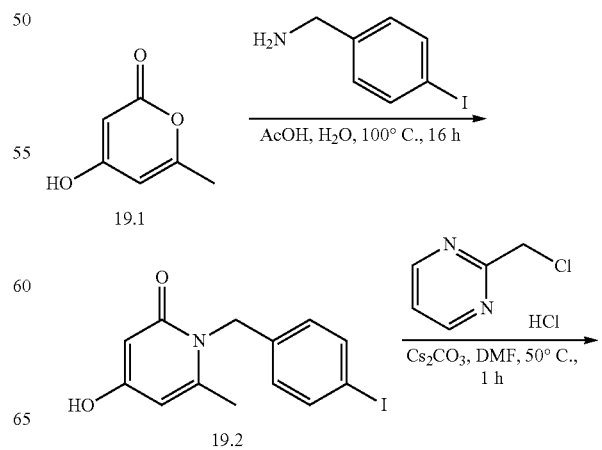

447
-continued

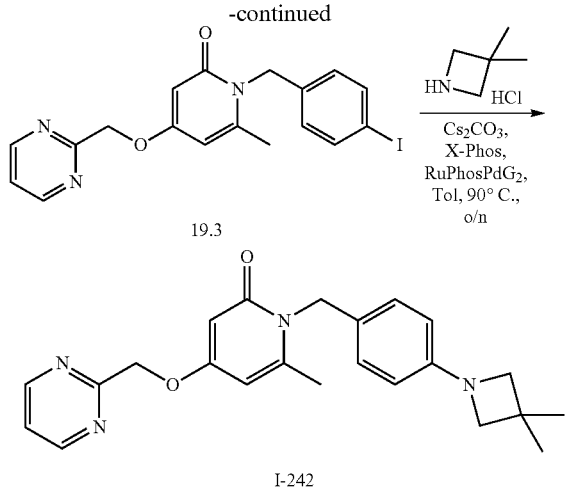

1. The Synthesis of Intermediate 19.2

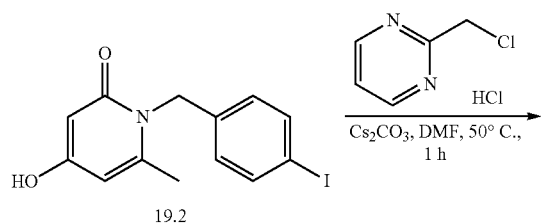

To a stirred solution of 19.1 (2.5 g, 20.0 mmol) in AcOH (20 mL) and water (10 mL) was added (4-iodophenyl) methanamine (14 g, 60.0 mmol), the reaction mixture was stirred at 110° C. overnight until the reaction was complete (by LCMS). The suspension was diluted with $H_2O$ (50 mL), extracted with EA (50 mL×2) and concentrated. The crude product was purified by flash column chromatography (silica gel, PE/EA=2:1) to give 19.2 (680 mg, yield: 9.9%) as yellow oil.

2. The Synthesis of Intermediate 19.3

448
-continued

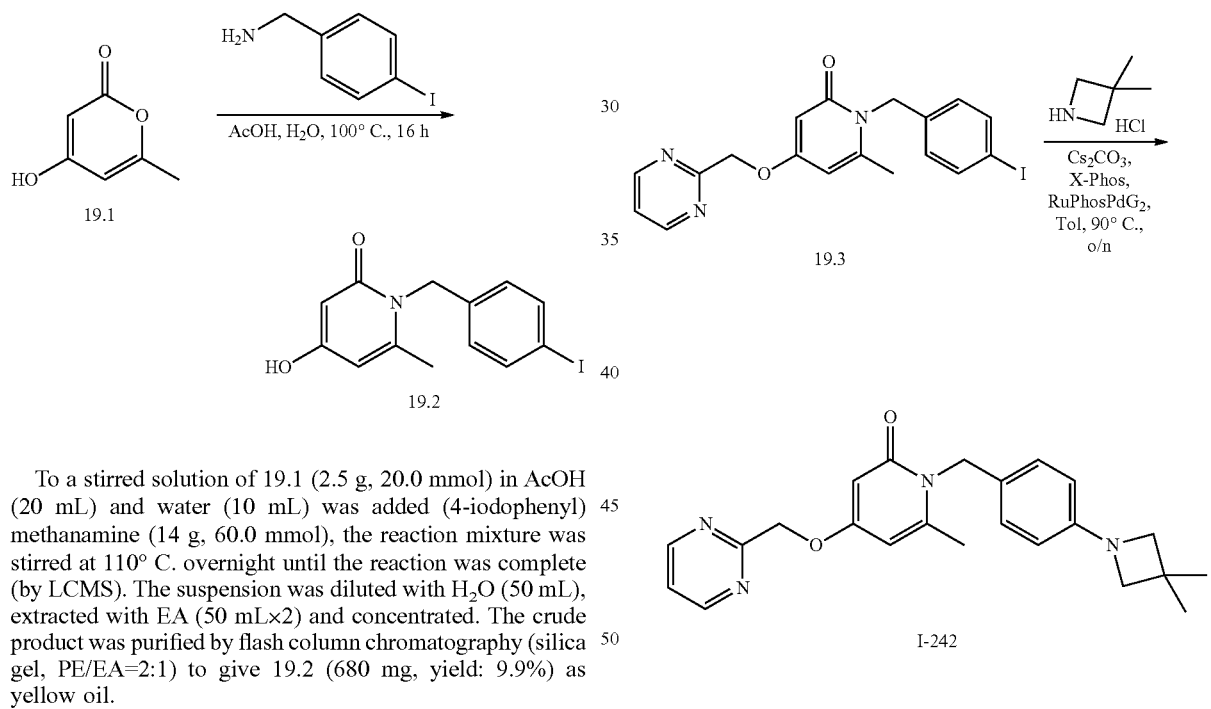

To a stirred solution of 19.2 (680 mg, 1.99 mmol), 2-(chloromethyl)pyrimidine hydrochloride (330 mg, 1.99 mmol) in DMF (10 mL) was added $Cs_2CO_3$ (1.9 g, 5.97 mmol). The reaction mixture was stirred at 50° C. for 1 hour until the reaction was complete (by LCMS). The suspension was diluted with $H_2O$ (20 mL), extracted with EA (30 mL×2) and concentrated. The crude product was purified by flash column chromatography (silica gel, PE/EA=3:1) to give 19.3 (800 mg, yield: 92%) as yellow oil.

3. The Synthesis of Target I-242

To a stirred solution of 19.3 (200 mg, 0.46 mmol), $Cs_2CO_3$ (450 mg, 1.38 mmol), 3,3-dimethylazetidine hydrochloride (56 mg, 0.46 mmol), X-Phos (88 mg, 0.18 mmol) in toluene (10 mL) was added $RuPhosPdG_2$ (72 mg, 0.09 mmol). The reaction mixture was stirred at 90° C. for 12 h until the reaction was complete (by LCMS). The suspension was diluted with $H_2O$ (10 mL), extracted with EA (30 mL×3) and concentrated. The crude product was purified by Prep-HPLC to give I-242 (58 mg, yield: 32%) as a white solid.

Additional exemplary compounds were prepared following methods substantially similar to the method described above and herein. Data for these compounds are provided in Table 17, Following Example 27.

Example 20: Synthesis of I-350

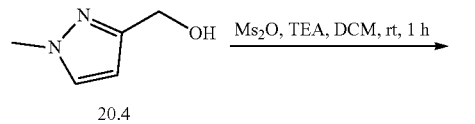

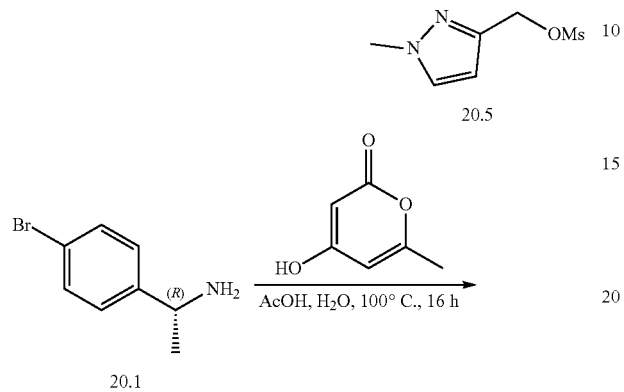

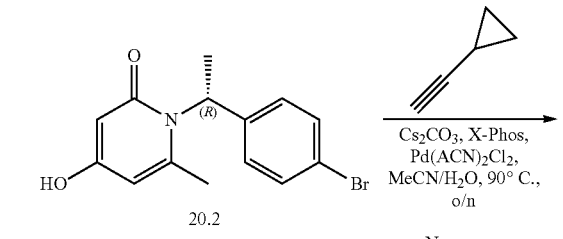

I-350

1. The Synthesis of Intermediate 20.2

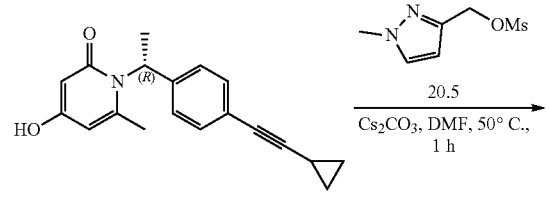

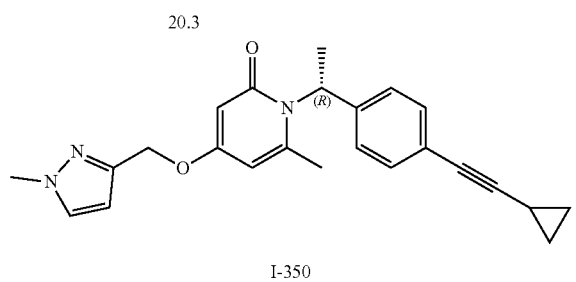

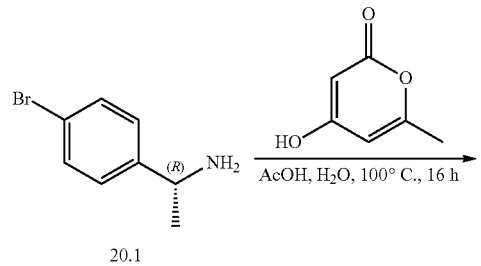

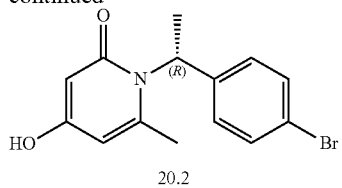

20.2

To a solution of 20.1 (700 mg, 3.52 mmol) in AcOH/H$_2$O (2:1, 12 mL) was added 4-hydroxy-6-methyl-2H-pyran-2-one (532 mg, 4.22 mmol), then the reaction mixture was stirred at 110° C. overnight. The solvent was concentrated to dryness, then the crude product was purified by flash column chromatography (silica gel, MeOH/DCM=5%) to give 20.2 (94 mg, yield: 7%) as a yellow solid. LC-MS m/z: 308.2 [M+H]$^+$.

2. The Synthesis of Intermediate 20.3

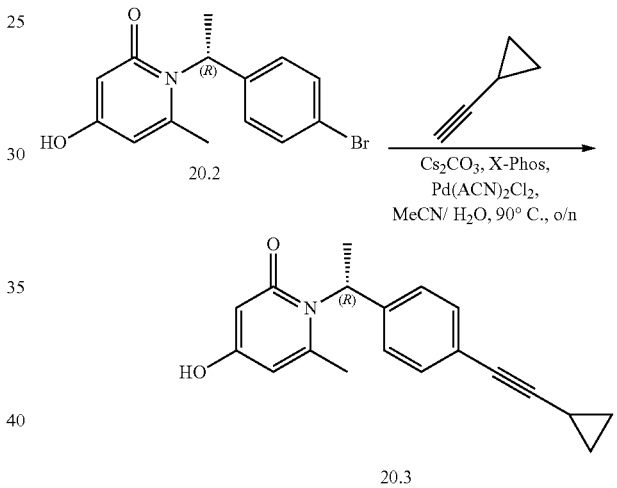

To a solution of of 20.2 (5 g, 16.29 mmol), ethynylcyclopropane (3.22 mg, 48.86 mmol), Cs$_2$CO$_3$ (7.96 g, 24.43 mmol), X-Phos (500 mg) in MeCN/H$_2$O (10:1, 30 mL) was added Pd(ACN)$_2$Cl$_2$ (500 mg), the mixture was stirred at 90° C. for 16 h until the reaction was complete (by LCMS). The suspension was diluted with H$_2$O (30 mL), extracted with EA (50 mL×3) and the combined organic layer was dried over anhydrous Na$_2$SO$_4$, concentrated to dryness, then the crude product was purified by flash column chromatography (silica gel, MeOH/DCM=5%) to give 20.3 as a yellow solid. LC-MS m/z: 294.4 [M+H]$^+$.

3. The Synthesis of Intermediate 20.5

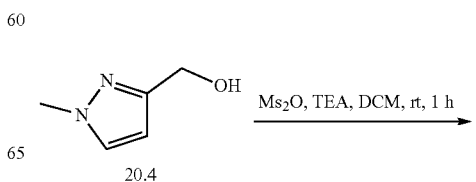

451
-continued

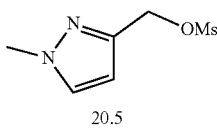
20.5

To a solution of 20.4 (100 mg, 0.89 mmol) and TEA (271 mg, 2.68 mmol) in DCM (3 mL) was added Ms₂O (311 mg, 1.79 mmol), then reaction mixture was stirred at room temperature for 1 h until the reaction was complete. The reaction mixture was diluted with H₂O (10 mL) and extracted with DCM (10 mL×3). The combined organic phases were dried over anhydrous Na₂SO₄ and concentrated to dryness. The crude product was used to the next step directly without further purification.

4. The Synthesis of Target I-350

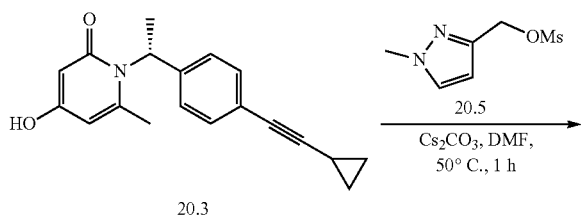

452
-continued

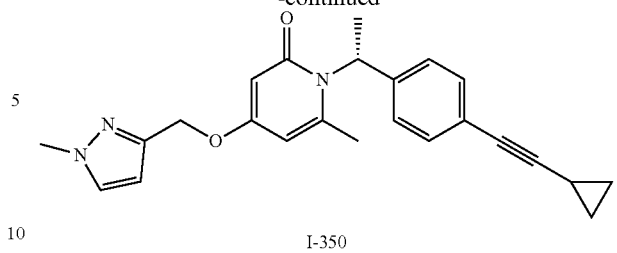
I-350

To a solution of 20.3 (100 mg, 0.34 mmol) and Cs₂CO₃ (167 mg, 0.51 mmol) in DMF (3 mL) was added 20.5 (78 mg, 0.41 mmol), then the reaction mixture was stirred at 50° C. for 1 h until the reaction was complete (by LCMS). The reaction mixture was diluted with H₂O (10 mL) and extracted with EtOAc (10 mL×3). The combined organic phase was washed with brine (10 ml×3), dried over anhydrous Na₂SO₄ and concentrated to dryness. The crude product was purified Prep-HPLC to give I-350 (26.05 mg, 20%) as a yellow solid.

Additional exemplary compounds were prepared following methods substantially similar to the method described above and herein. Data for these compounds are provided in Table 17, Following Example 27.

Example 21: Synthesis of I-258

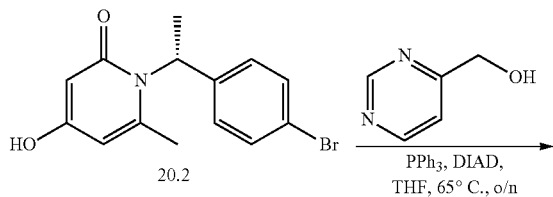

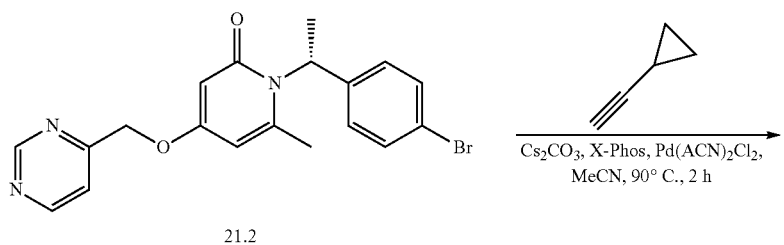
21.2

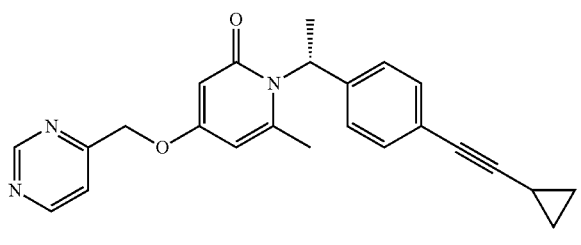
I-258

1. The Synthesis of Intermediate 21.2

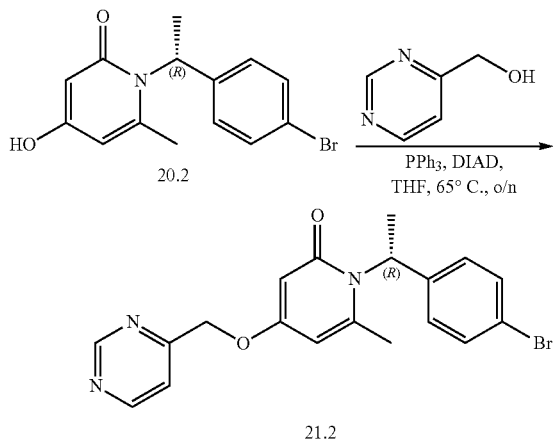

To a solution of 20.2 (300 mg, 0.99 mmol), pyrimidin-4-ylmethanol (172 mg, 1.50 mmol) and PPh₃ (263 mg, 0.99 mmol) in THF (10 mL) was added DIAD (302 mg, 1.50 mmol), then the mixture was stirred at 65° C. overnight until the reaction was complete (by LCMS). The reaction mixture was diluted with H₂O (10 mL) and extracted with EA (10 mL×3). The combined organic phase was dried over anhydrous Na₂SO₄ and concentrated to dryness. The crude product was purified by Prep-HPLC to give 21.2 (220 mg, yield: 53%) as a yellow solid.

2. The Synthesis of Target I-258

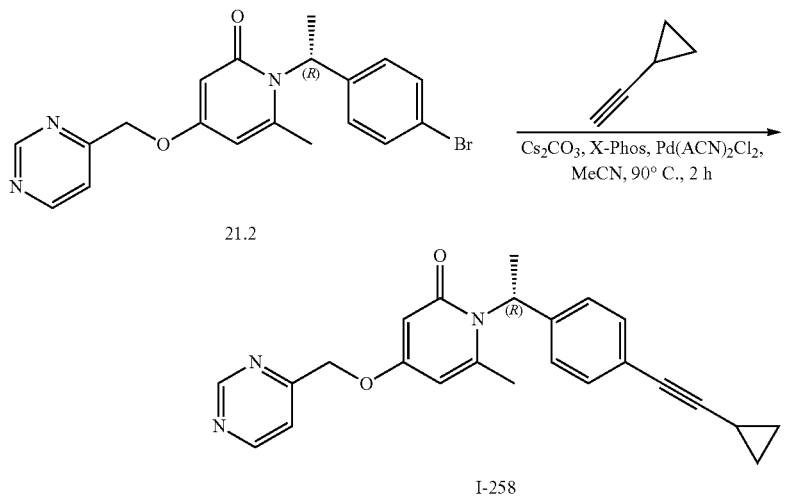

To a stirred solution of 21.2 (220 mg, 0.55 mmol) in MeCN (10 mL) was added ethynylcyclopropane (112 mg, 1.65 mmol), Cs₂CO₃ (536 mg, 1.65 mmol), X-Phos (48 mg, 0.1 mmol) and Pd(ACN)₂Cl₂ (13 mg). The mixture was stirred at 90° C. for 2 h. After the consumption of starting material (by LCMS), concentrated the mixture to oil, then water (10 mL) was added, extracted with ethyl acetate (10 mL×3), washed with water (10 mL×3), dried over anhydrous Na₂SO₄ and concentrated. The crude was purified by prep-HPLC to get I-258 (40 mg, 19% yield) as yellow oil.

Additional exemplary compounds were prepared following methods substantially similar to the method described above and herein. Data for these compounds are provided in Table 17, Following Example 27.

Example 22: Synthesis of I-322

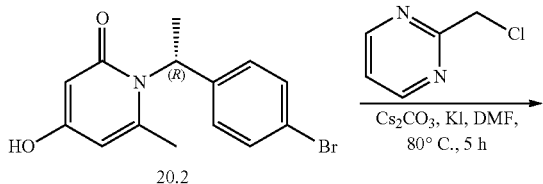

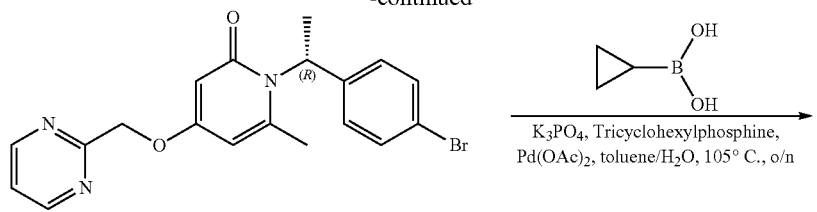

22.2

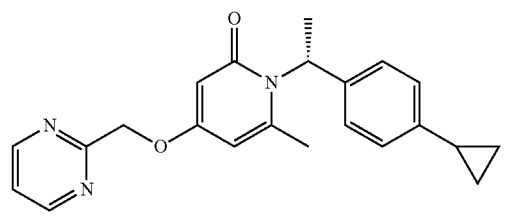

I-322

1. The Synthesis of Intermediate 22.2

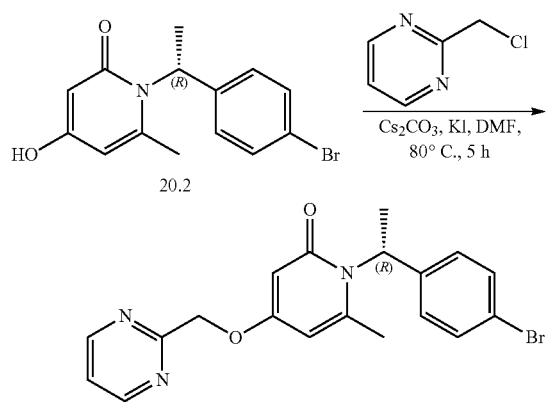

To a stirred solution of 20.2 (200 mg, 0.65 mmol) in DMF (10 mL) was added 2-(chloromethyl)pyrimidine (160 mg, 0.98 mmol) and $Cs_2CO_3$ (633 mg, 1.95 mmol). The mixture was stirred at 80° C. for 5 h. After the consumption of starting material (by LCMS), water (15 mL) was added, extracted with ethyl acetate (15 mL×3), washed with water (15 mL×3), dried over anhydrous $Na_2SO_4$ and concentrated. The crude was purified by prep-HPLC to get 22.2 (220 mg, 84% yield) as a yellow solid.

2. The Synthesis of Target I-322

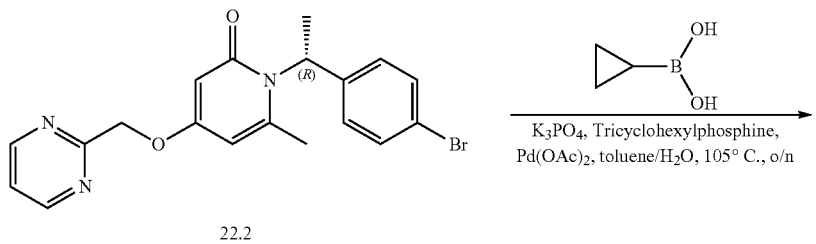

22.2

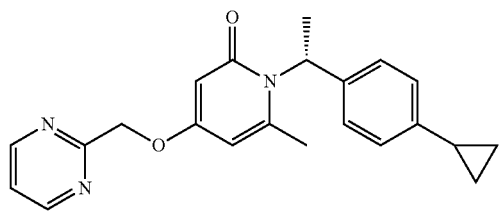

I-322

To a stirred solution of 22.2 (220 mg, 0.55 mmol) in toluene (10 mL) was added cyclopropylboronic acid (95 mg, 1.1 mmol), K$_3$PO$_4$ (350 mg, 1.65 mmol), tricyclohexylphosphine (32 mg, 0.11 mmol) and Pd(OAc)$_2$ (14 mg, 0.06 mmol). The mixture was stirred at 105° C. for 16 h. After the consumption of starting material (by LCMS), concentrated the mixture to oil, then water (10 mL) was added, extracted with ethyl acetate (10 mL×3), washed with water (10 mL×3), dried over anhydrous Na$_2$SO$_4$ and concentrated. The crude was purified by prep-HPLC to get I-322 (40 mg, 20% yield) as yellow oil.

Additional exemplary compounds were prepared following methods substantially similar to the method described above and herein. Data for these compounds are provided in Table 17, Following Example 27.

Example 23: Synthesis of I-342

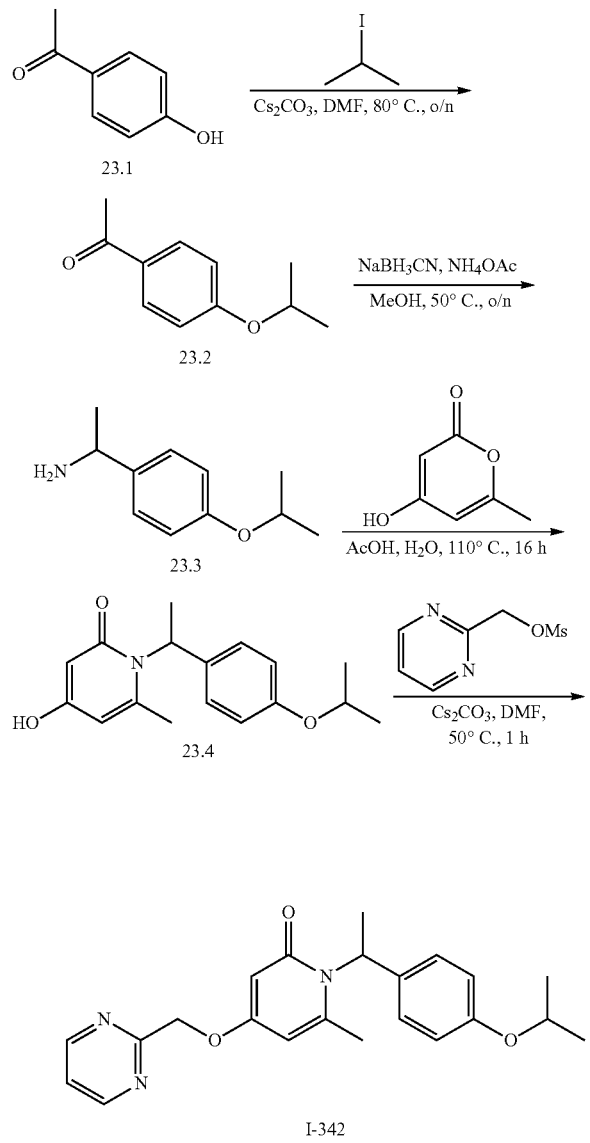

1. The Synthesis of Intermediate 23.2

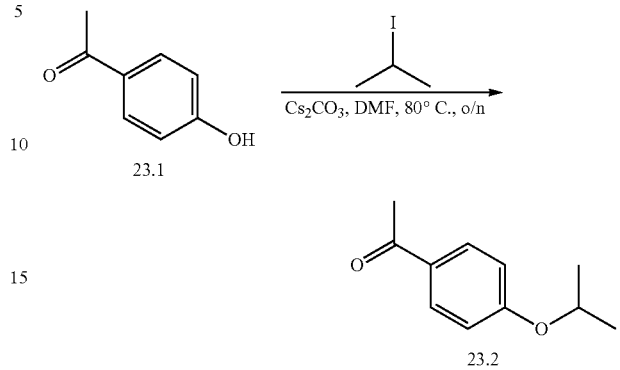

To a stirred solution of 23.1 (8.0 g, 58.82 mmol) and Cs$_2$CO$_3$ (28.76 g, 88.24 mmol) in DMF (80 mL) was added 2-iodopropane (12.0 g, 70.59 mmol). The reaction mixture was stirred at 80° C. overnight until the reaction was complete (by LCMS). The reaction mixture was diluted with H$_2$O (50 mL) and extracted with EA (100 mL×3). The combined organic layer was washed with brine (100 mL×3), dried over anhydrous Na$_2$SO$_4$ and concentrated to dryness. The crude product was purified by flash column chromatography (silica gel, PE/EA=20:1) to give 23.2 (10 g, yield: 96%) as colorless oil. LC-MS m/z: 179.4 [M+H]$^+$.

2. The Synthesis of Intermediate 23.3

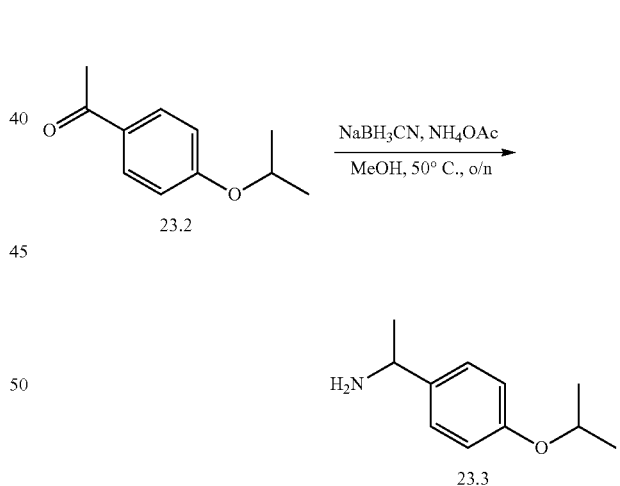

To a solution of 23.2 (5 g, 28.09 mmol), NH$_4$OAc (10.8 g, 140.45 mmol) and HOAc (catalytic amount) in MeOH (40 mL) was added NaBH$_3$CN (5.3 g, 84.27 mmol) in portion at room temperature, then the reaction mixture was stirred at 50° C. overnight until the reaction was complete (by LCMS), the reaction mixture was concentrated to dryness, the crude product was washed with brine (20 mL×3), dried over anhydrous Na$_2$SO$_4$ and concentrated to dryness. The crude product was purified by flash column chromatography (silica gel, DCM/MeOH=10:1) to give 23.3 (4.9 g, yield: 98%) as yellow oil. LC-MS m/z: 163.4 [M−NH$_2$]$^+$.

3. The Synthesis of Intermediate 23.4

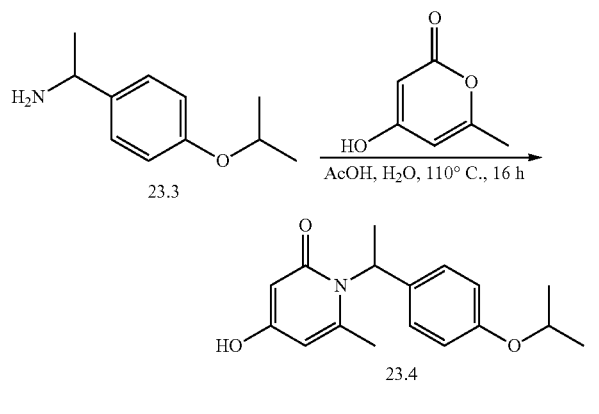

To a solution of 23.3 (700 mg, 3.91 mmol) in AcOH/H₂O (2:1, 12 mL) was added 4-hydroxy-6-methyl-2H-pyran-2-one (591 mg, 4.69 mmol), then the reaction mixture was stirred at 110° C. overnight. The solvent was concentrated to dryness, then the crude product was purified by flash column chromatography (silica gel, MeOH/DCM=5%) to give 23.4 (130 mg, 12%) as a yellow solid. LC-MS m/z: 575.4 [2M+H]⁺.

4. The Synthesis of Intermediate I-342

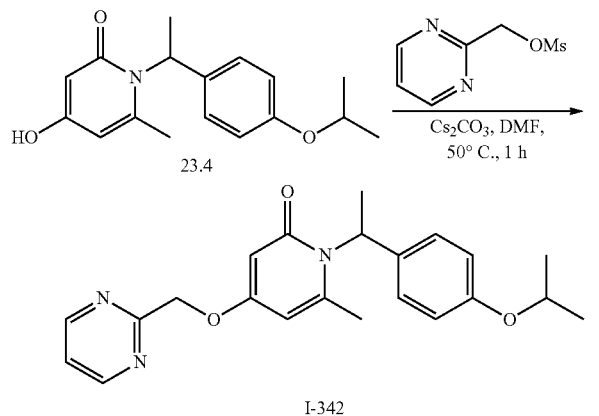

To a stirred solution of 23.4 (40 mg, 0.14 mmol), Cs₂CO₃ (68 mg, 0.21 mmol) in DMF (2 mL) was added pyrimidin-2-ylmethyl methanesulfonate (31 mg, 0.17 mmol). The reaction mixture was stirred at 50° C. for 1 h until the reaction was complete (by LCMS). The suspension was diluted with H₂O (5 mL) and extracted with EA (10 mL×3), the combined organic phase was washed with brine (10 ml×3), dried over anhydrous Na₂SO₄ and concentrated to dryness. The crude product was purified Prep-HPLC to give I-342 (15 mg, yield: 28%) as a white solid.

Additional exemplary compounds were prepared following methods substantially similar to the method described above and herein. Data for these compounds are provided in Table 17, Following Example 27.

Example 24: Synthesis of I-349

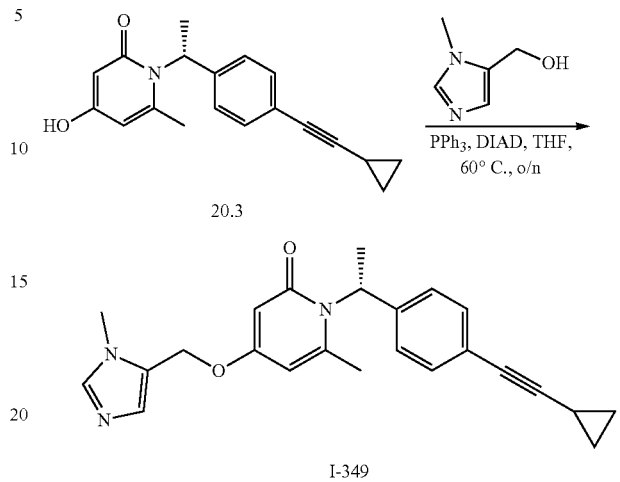

1. The Synthesis of Target I-349

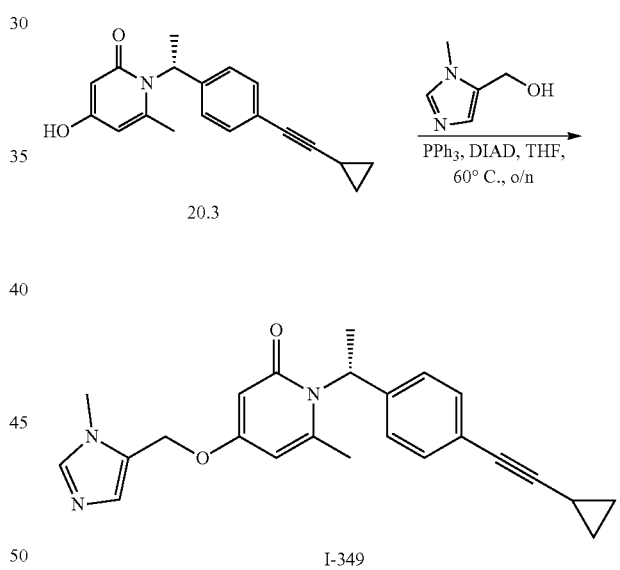

To a solution of 20.3 (100 mg, 0.34 mmol), (1-methyl-1H-imidazol-5-yl)methanol (57 mg, 0.51 mmol) and PPh₃ (89 mg, 0.34 mmol) in THF (2 mL) was added DIAD (103 mg, 0.51 mmol), then the mixture was stirred at 60° C. overnight until the reaction was complete (by LCMS). The reaction mixture was diluted with H₂O (10 mL) and extracted with EA (10 mL×3). The combined organic phase was dried over anhydrous Na₂SO₄ and concentrated to dryness. The crude product was purified by Prep-HPLC to give I-349 (17.33 mg, yield: 13%) as a white solid.

Additional exemplary compounds were prepared following methods substantially similar to the method described above and herein. Data for these compounds are provided in Table 17, Following Example 27.

Example 25: Synthesis of I-353

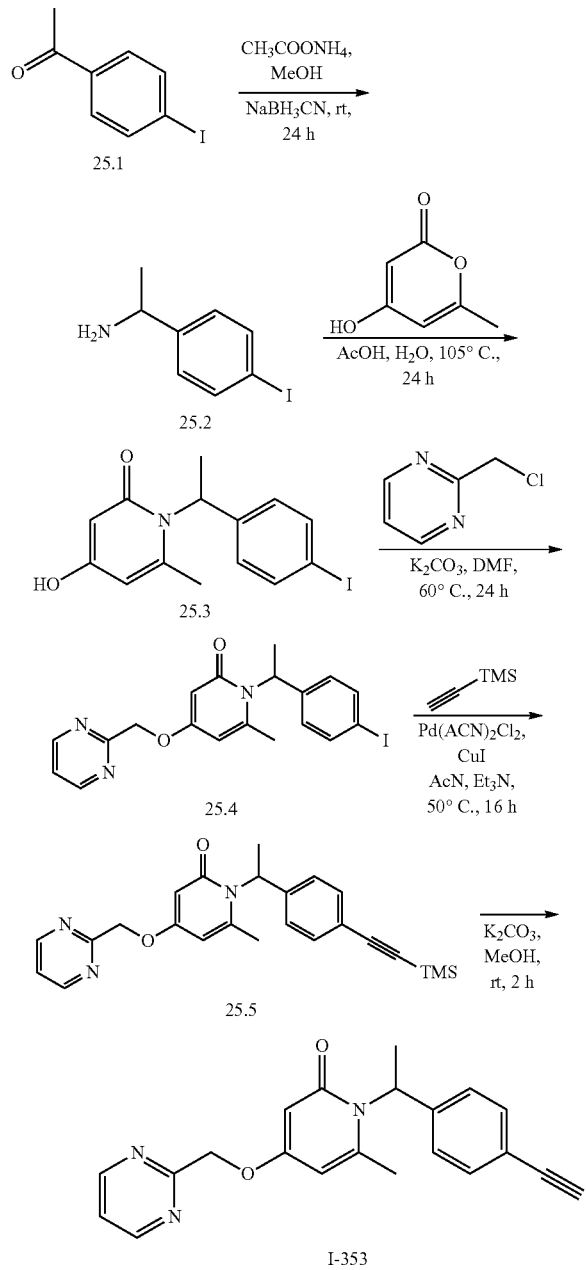

1. The Synthesis of Intermediate 25.2

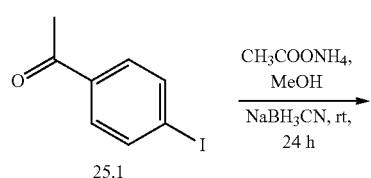

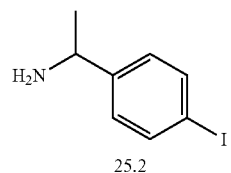

To a solution of 25.1 (5 g, 20.4 mmol), NH₄OAc (15.7 g, 204 mmol) and HOAc (catalytic amount) in MeOH (60 mL) was added NaBH₃CN (5.1 g, 81.6 mmol) in portion at room temperature, then the reaction mixture was stirred at room temperature overnight until the reaction was complete (by LCMS), the reaction mixture was concentrated to dryness, the crude product was washed with brine (20 mL×3), dried over anhydrous Na₂SO₄ and concentrated to dryness. The crude product was purified by flash column chromatography (silica gel, DCM/MeOH=10:1) to give 25.2 (2.5 g, yield: 50%) as yellow oil. LC-MS m/z: 231.0 [M−NH₂]⁺.

2. The Synthesis of Intermediate 25.3

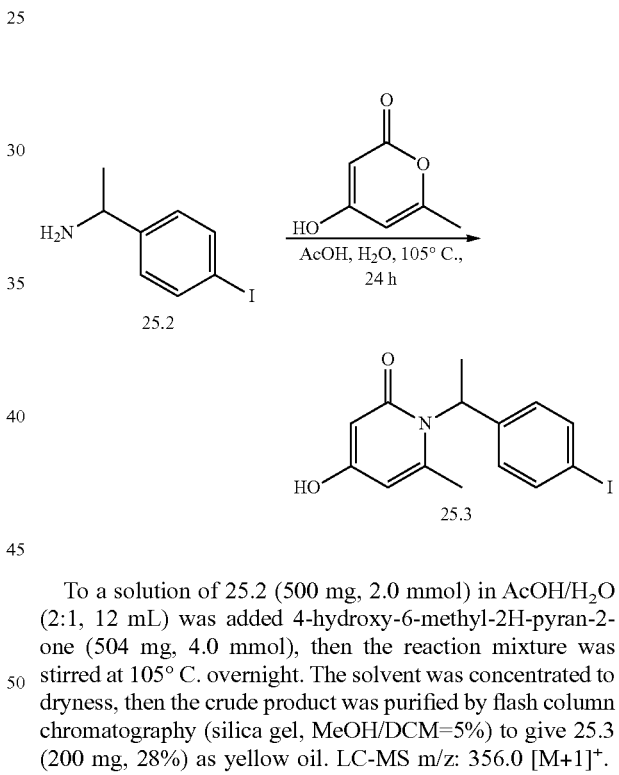

To a solution of 25.2 (500 mg, 2.0 mmol) in AcOH/H₂O (2:1, 12 mL) was added 4-hydroxy-6-methyl-2H-pyran-2-one (504 mg, 4.0 mmol), then the reaction mixture was stirred at 105° C. overnight. The solvent was concentrated to dryness, then the crude product was purified by flash column chromatography (silica gel, MeOH/DCM=5%) to give 25.3 (200 mg, 28%) as yellow oil. LC-MS m/z: 356.0 [M+1]⁺.

3. The Synthesis of Intermediate 25.4

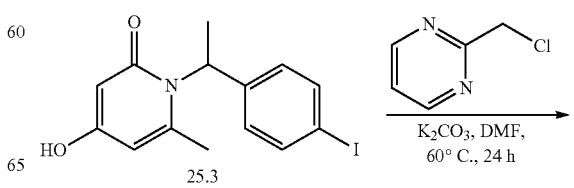

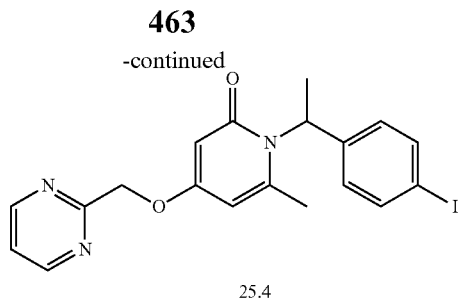

25.4

To a stirred solution of 25.3 (1.0 g, 2.82 mmol), K₂CO₃ (1.2 g, 8.5 mmol) in DMF (10 mL) was added 2-(chloromethyl)pyrimidine (384 mg, 3.0 mmol). The reaction mixture was stirred at 60° C. for 24 h until the reaction was complete (by LCMS). The suspension was diluted with H₂O (5 mL) and extracted with EA (10 mL×3), the combined organic phase was washed with brine (10 ml×3), dried over anhydrous Na₂SO₄ and concentrated to dryness. The crude product was purified Prep-HPLC to give 25.4 (360 mg, yield: 29%) as yellow oil.

4. The Synthesis of Intermediate 25.5

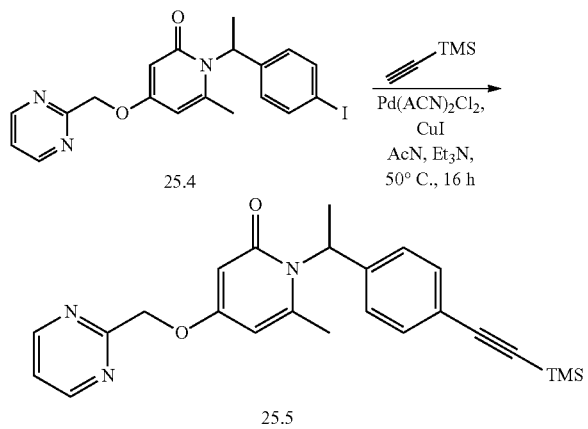

To a stirred solution of 25.4 (360 mg, 0.8 mmol), ethynyltrimethylsilane (235 mg, 2.4 mmol) and TEA (3 mL) in ACN (10 mL) was added PdCl₂(ACN)₂ (30 mg) and CuI (30 mg). The reaction mixture was stirred at 50° C. for 16 hours until the reaction was complete. The suspension was diluted with H₂O (20 mL), extracted with EA (20 mL×2) and concentrated. The crude product was purified by flash column chromatography (silica gel, PE/EA=100:1) to give 25.5 (100 mg, yield: 30%) as brown oil.

5. The Synthesis of Target I-353

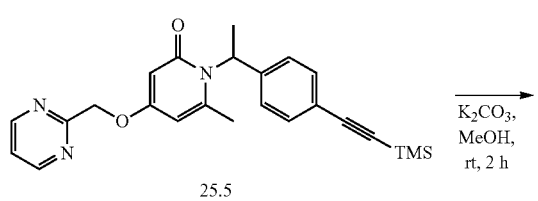

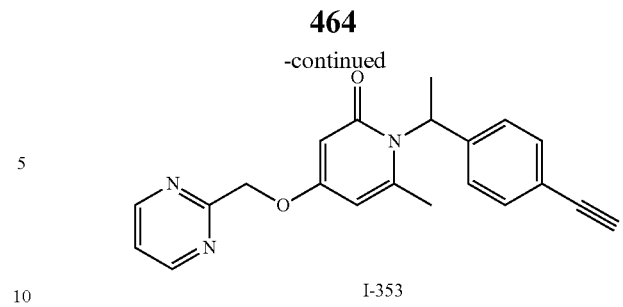

I-353

To a stirred solution of 25.5 (100 mg, 0.24 mmol) in MeOH (5 mL) was added K₂CO₃ (138 mg, 1.0 mmol). The reaction mixture was stirred at room temperature for 2 h until the reaction was complete. The reaction mixture was concentrated and the crude product was purified by prep-HPLC to give I-353 (4 mg, yield: 5%) as a yellow solid.

Additional exemplary compounds were prepared following methods substantially similar to the method described above and herein. Data for these compounds are provided in Table 17, Following Example 27.

Example 26: Synthesis of I-360

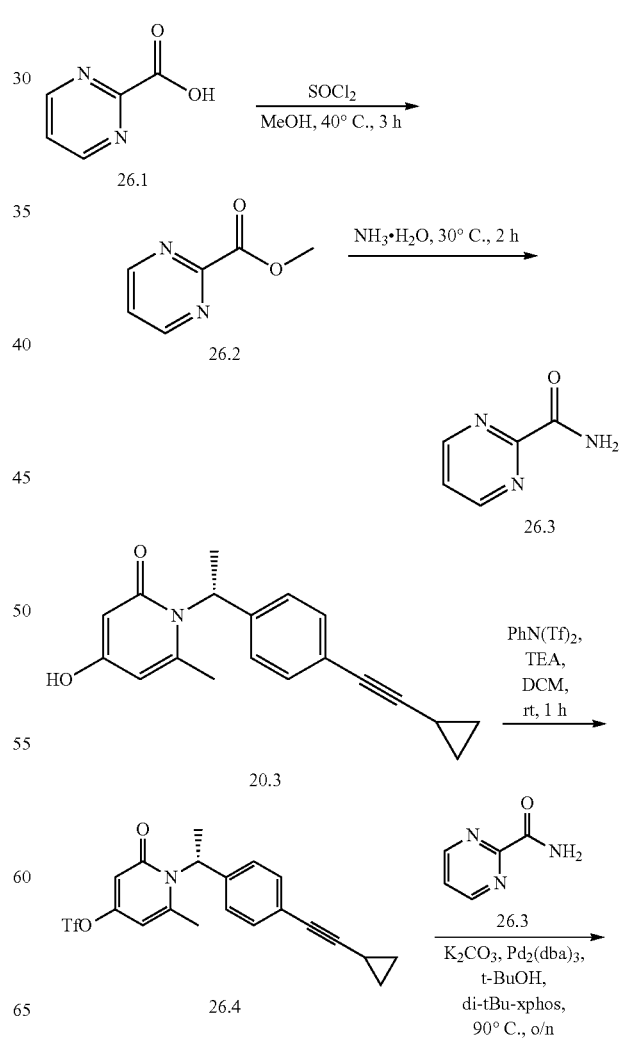

1. The Synthesis of Intermediate 26.2

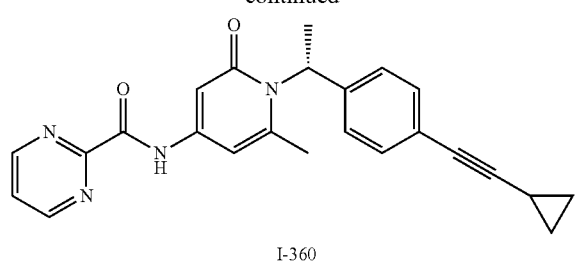

I-360

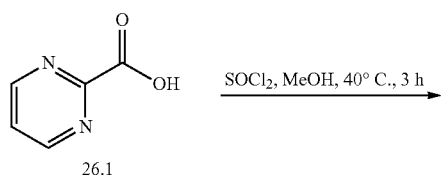

To a solution of 26.1 (300 mg, 2.42 mmol) in MeOH (5 mL) was added SOCl₂ (2 mL), then the mixture was stirred at 40° C. for 3 h until the reaction was complete (by LCMS). The reaction mixture was concentrated to dryness. The crude product was used to the next step directly without further purification.

2. The Synthesis of Intermediate 26.3

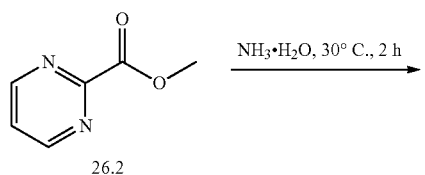

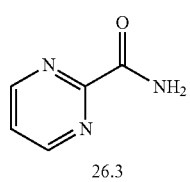

A solution of 26.2 (330 mg, 2.39 mmol) in NH₃·H₂O (2 mL) was stirred at 30° C. for 2 h until the reaction was complete (by LCMS). The reaction mixture was concentrated to dryness. The crude product was used to the next step directly without further purification.

3. The Synthesis of Intermediate 26.4

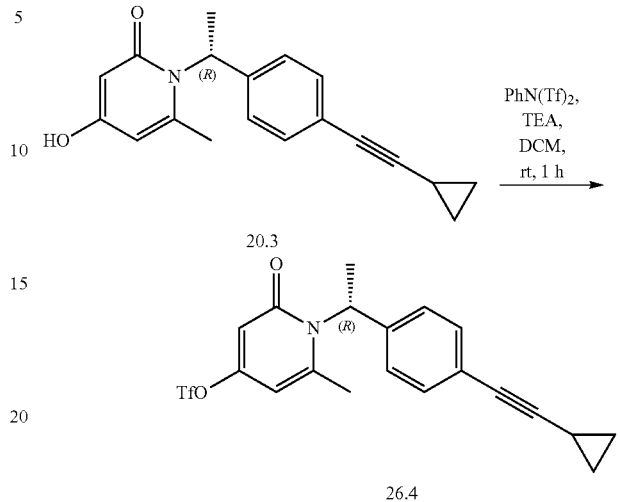

To a solution of 20.3 (200 mg, 0.68 mmol) and TEA (103 mg, 1.02 mmol) in DCM (2 mL) was added PhN(Tf)₂ (292 mg, 0.82 mmol), then the mixture was stirred at room temperature for 1 h until the reaction was complete (by LCMS). The reaction mixture was diluted with H₂O (10 mL) and extracted with DCM (10 mL×3). The combined organic phase was dried over anhydrous Na₂SO₄ and concentrated to dryness. The crude product was purified by flash column chromatography (silica gel, PE/EA=4:1) to give 26.4 (240 mg, yield: 83%) as a yellow solid. LC-MS m/z: 851.2 [2M+H]⁺.

4. The Synthesis of Intermediate I-360

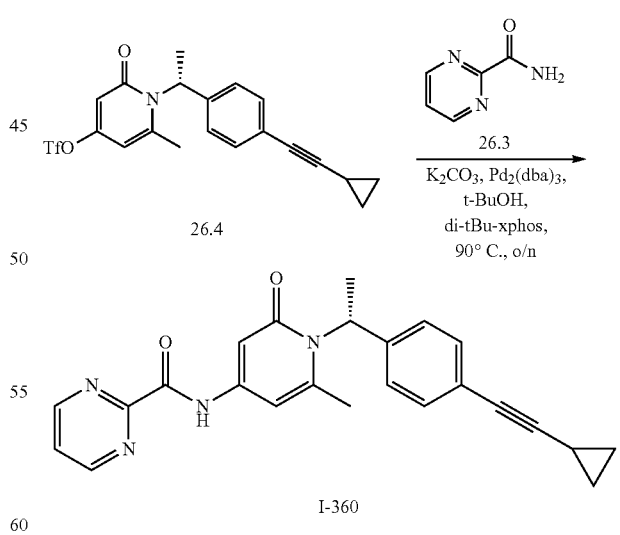

To a solution of 26.4 (240 mg, 0.56 mmol), 26.3 (83 mg, 0.68 mmol), K₂CO₃ (234 mg, 1.70 mmol) and di-tBu-xphos (24 mg) in t-BuOH (5 mL) was added and Pd₂(dba)₃ (24 mg), then the mixture was stirred at 90° C. overnight until the reaction was complete (by LCMS). The reaction mixture was diluted with brine (10 mL) and extracted with EtOAc (15 mL×3). The combined organic phase was dried over anhydrous Na₂SO₄ and concentrated to dryness. The crude product was purified by Prep-HPLC to give I-360 (15.63 mg, yield: 7%) as a yellow solid.

Example 27: Synthesis of I-379

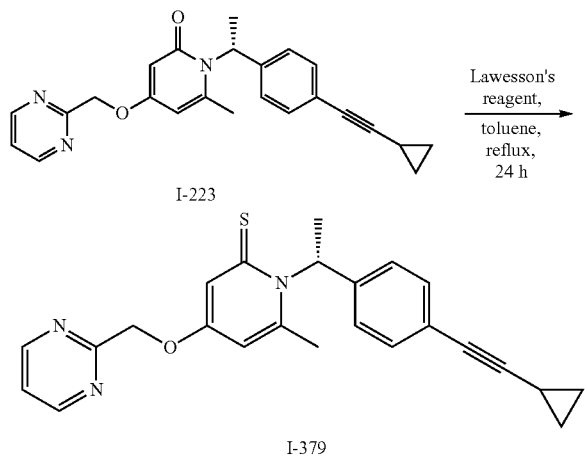

To a stirred solution oF I-223 (150 mg, 0.39 mmol in toluene 3 mL was added Lawesson's reagent (189 mg, 0.47 mmol), the mixture was stirred at reflux for 24 h. Then the reaction mixture was treated with K₂CO₃ (a.q., 1 mL) and stirred at room temperature for 1 h. The reaction mixture was diluted with water (10 mL) and extracted with EtOAc (10 mL×3), the combined organic layer was washed with brine (10 mL) and concentrated. The crude product was purified by Prep-HPLC to I-379 (12.3 mg, yield: 7.9%) as a yellow solid. ¹HNMR (400 MHz, DMSO-d₆) δ 8.87 (d, J=4.8 Hz, 2H), 8.38 (q, J=7.2 Hz, 1H), 7.52 (t, J=4.8 Hz, 1H), 7.37 (d, J=8.4 Hz, 2H), 7.13 (d, J=3.2 Hz, 1H), 7.05 (d, J=8.0 Hz, 2H), 6.48 (d, J=2.8 Hz, 1H), 5.39 (s, 2H), 2.01 (s, 3H), 1.78 (d, J=7.2 Hz, 3H), 1.50-1.57 (m, 1H), 0.85-0.90 (m, 2H), 0.70-0.74 (m, 2H). LC-MS m/z: 402.3 [M+H]⁺. $t_R$=1.925 min. HPLC Purity (254 nm): 99.1%; $t_R$=9.777 min.

Additional exemplary compounds were prepared following methods substantially similar to the method described above and herein. Data for these compounds are provided in Table 17.

TABLE 17

Characterization Data for Additional Exemplary Compounds

| Compound No. | Chemical Structure | M + 1 | ¹H NMR (400 MHz) |
|---|---|---|---|
| I-220 | 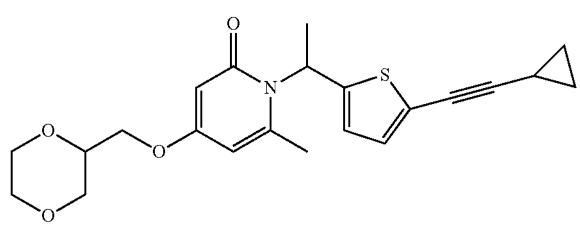 | 798.8 (2M + 1) | ¹HNMR (400 MHz, CDCl₃) δ 6.91 (d, J = 3.6 Hz, 1H), 6.65 (s, 1H), 5.7-3.577 (m, 2H), 3.92-3.95 (m, 2H), 3.71-3.89 (m, 5H), 3.61-3.67 (m, 1H), 3.45-3.51 (m, 1H), 2.10 (br, 3H), 1.85 (br, 3H), 1.71 (br, 1H), 1.38-1.44 (m, 1H), 0.82-0.87 (m, 2H), 0.74-0.81 (m, 2H). |
| I-221 | 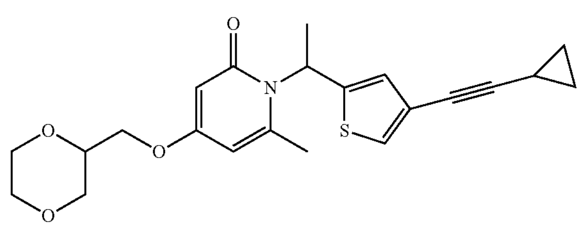 [SMILES: Cc1cc(OCC2COCCO2)cc(=O)n1C(C)c1cc(C#CC2CC2)cs1] | 399.9 | ¹HNMR (400 MHz, CDCl₃) δ 7.18 (s, 1H), 6.80 (s, 1H), 5.73-5.76 (m, 2H), 3.71-3.97 (m, 7H), 3.61-3.67 (m, 1H), 3.48 (dd, J = 9.6 Hz, 11.2 Hz, 1H), 2.08 (br., 3H), 1.86 (br., 3H), 1.60-1.70 (m, 1H), 1.35-1.41 (m, 1H), 0.79-0.85 (m, 2H), 0.73-0.77 (m, 2H). |
| I-222 | 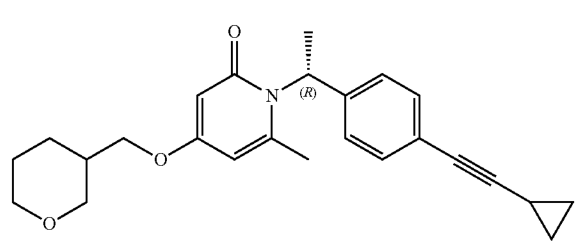 | 392.0 | ¹HNMR (400 MHz, CDCl₃) δ 7.31 (d, J = 8.0 Hz, 2H), 7.07 (d, J = 8.0 Hz, 2H), 5.83 (s, 1H), 5.68 (s, 1H), 3.96 (dd, J = 2.8 Hz, 11.2 Hz, 1H), 3.74-3.87 (m, 3H), 3.41-3.47 (m, 1H), 3.28-3.33 (m, 1H), 1.80-2.09 (m, 8H), 1.61-1.67 (m, 2H), 1.35-1.46 (m, 2H), 0.82-0.87 (m, 2H), 0.76-0.81 (m, 2H). |

TABLE 17-continued

Characterization Data for Additional Exemplary Compounds

| Compound No. | Chemical Structure | M + 1 | $^1$H NMR (400 MHz) |
|---|---|---|---|
| I-223 | 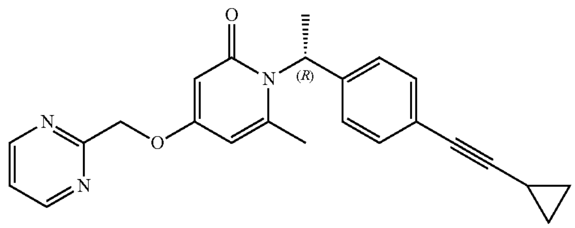 | 386.0 | $^1$HNMR (400 MHz, CDCl$_3$) δ 8.76 (d, J = 8.8 Hz, 2H), 7.30 (d, J = 8.4 Hz, 2H), 7.25 (t, J = 4.4 Hz, 1H), 7.06 (d, J = 8.0 Hz, 2H), 5.87 (s, 1H), 5.82 (br., 1H), 5.23 (s, 2H), 1.79-1.99 (m, 6H), 1.38-1.43 (m, 1H), 0.80-0.86 (m, 2H), 0.75-0.79 (m, 2H). |
| I-224 | 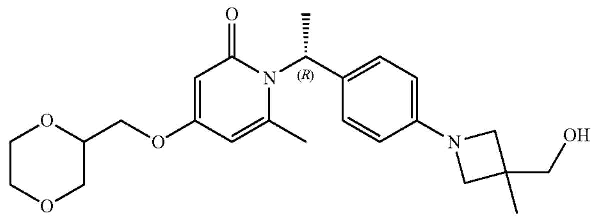 | 429.2 | $^1$HNMR (400 MHz, CDCl$_3$) δ 7.02 (d, J = 8.4 Hz, 2H), 6.39 (d, J = 8.4 Hz, 2H), 5.80 (s, 1H), 5.70 (s, 1H), 3.62-3.98 (m, 12H), 3.48-3.52 (m, 3H), 2.01-2.07 (m, 3H), 1.79 (d, J = 6.4 Hz, 3H), 1.62-1.74 (m, 1H), 1.31 (s, 3H). |
| I-225 | 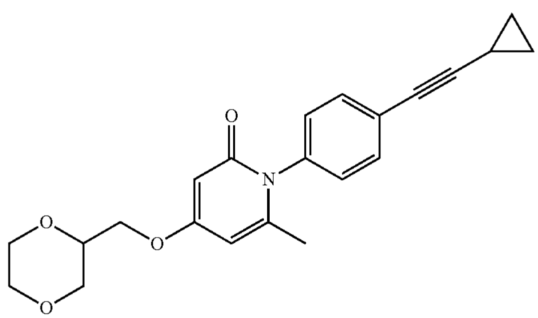 [SMILES: Cc1cc(OCC2COCCO2)cc(=O)n1-c1ccc(C#CC2CC2)cc1] | 366.1 | $^1$HNMR (400 MHz, CDCl$_3$) δ 7.48 (d, J = 8.4 Hz, 2H), 7.08 (d, J = 8.4 Hz, 2H), 5.87-5.92 (m, 2H), 3.94-4.00 (m, 2H), 3.80-3.91 (m, 4H), 3.73-3.76 (m, 1H), 3.63-3.69 (m, 1H), 3.49-3.54 (m, 1H), 1.87 (s, 3H), 1.42-1.48 (m, 1H), 0.87-0.91 (m, 2H), 0.79-0.83 (m, 2H). |
| I-226 | 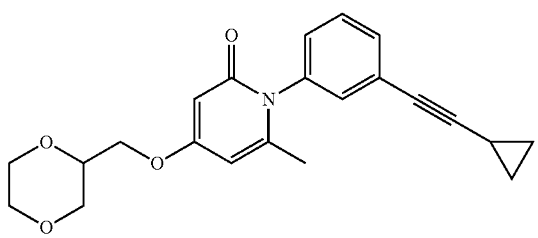 [SMILES: Cc1cc(OCC2COCCO2)cc(=O)n1-c1cccc(C#CC2CC2)c1] | 366.1 | $^1$HNMR (400 MHz, CDCl$_3$) δ 7.37-7.44 (m, 2H), 7.17-7.22 (m, 1H), 7.06-7.08 (m, 1H), 5.87 (d, J = 7.6 Hz, 1H), 5.84 (d, J = 2.4 Hz, 1H), 3.66-4.00 (m, 8H), 3.49-3.55 (m, 1H), 1.90 (s, 3H), 1.38-1.45 (m, 1H), 0.85-0.89 (m, 2H), 0.76-0.80 (m, 2H). |
| I-228 | 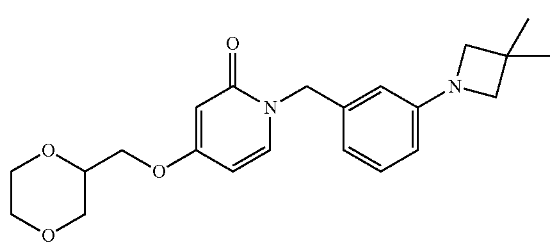 [SMILES: CC1(C)CN(c2cccc(Cn3ccc(OCC4COCCO4)cc3=O)c2)C1] | 385.1 | $^1$HNMR (400 MHz, DMSO-d$_6$) δ 7.59 (d, J = 7.6 Hz, 1H), 7.06-7.10 (m, 1H), 6.49 (d, J = 7.6 Hz, 1H), 6.28-6.30 (m, 2H), 5.97 (dd, J = 2.4, 7.6 Hz, 1H), 5.81 (d, J = 2.8 Hz, 1H), 4.91 (s, 2H), 3.92-3.95 (m, 2H), 3.73-3.89 (m, 3H), 3.57-3.67 (m, 2H), 3.46-3.51 (m, 5H), 3.35-3.38 (m, 1H), 1.26 (s, 6H). |

TABLE 17-continued

Characterization Data for Additional Exemplary Compounds

| Compound No. | Chemical Structure | M + 1 | $^1$H NMR (400 MHz) |
|---|---|---|---|
| I-229 | 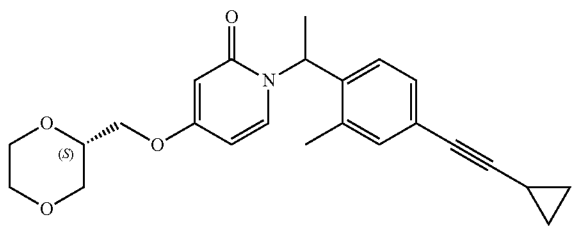 | 394.0 | $^1$HNMR (400 MHz, DMSO-d$_6$) δ 7.36 (d, J = 8.0 Hz, 1H), 7.24 (d, J = 8.0 Hz, 1H), 7.19 (s, 1H), 7.12 (d, J = 8.0 Hz, 1H), 6.03-6.08 (m, 1H), 5.92 (dd, J = 2.8 Hz, 7.6 Hz, 1H), 5.80 (d, J = 2.8 Hz, 1H), 3.88-3.92 (m, 2H), 3.72-3.81 (m, 3H), 3.57-3.66 (m, 2H), 3.45-3.50 (m, 1H), 3.32-3.37 (m, 1H), 2.07 (s, 3H), 1.49-1.55 (m, 4H), 0.85-0.90 (m, 2H), 0.69-0.73 (m, 2H). |
| I-227 | 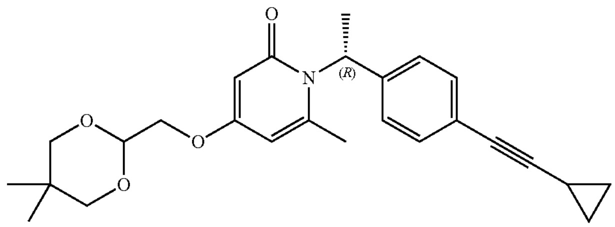 | 422.1 | $^1$HNMR (400 MHz, DMSO-d$_6$) δ 7.30 (d, J = 7.6 Hz, 2H), 7.08 (d, J = 8.0 Hz, 2H), 5.87 (s, 1H), 5.62 (br., 1H), 3.93-3.99 (m, 4H), 3.69 (dd, J = 6.0 Hz, 12.0 Hz, 2H), 2.50 (s, 3H), 1.96-2.06 (m, 2H), 1.76 (d, J = 6.0 Hz, 3H), 1.50-1.54 (m, 1H), 1.35 (s, 3H), 1.31 (s, 3H), 0.85-0.89 (m, 2H), 0.69-0.73 (m, 2H). |
| I-246 | 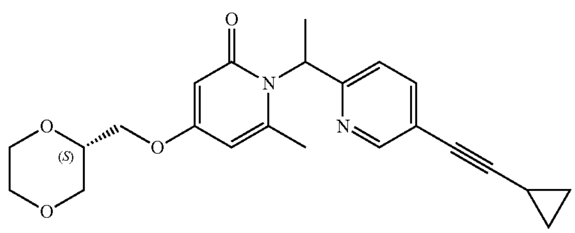 | 395.0 | $^1$H NMR (400 MHz, DMSO-d$_6$) δ 8.43 (s, 1H), 7.70 (dd, J = 1.6 Hz, 8.0 Hz, 1H), 7.18 (d, J = 8.4 Hz, 1H), 5.89 (s, 1H), 5.55 (s, 1H), 3.88 (d, J = 4.4 Hz, 2H), 3.73-3.79 (m, 3H), 3.60-3.67 (m, 2H), 3.47-3.50 (m, 1H), 3.32-3.37 (m, 1H), 2.11-2.51 (br., 3H), 1.78 (d, J = 6.8 Hz, 3H), 1.51-1.52 (m, 1H), 0.88-0.91 (m, 2H), 0.74-0.77 (m, 2H). |
| I-240 | 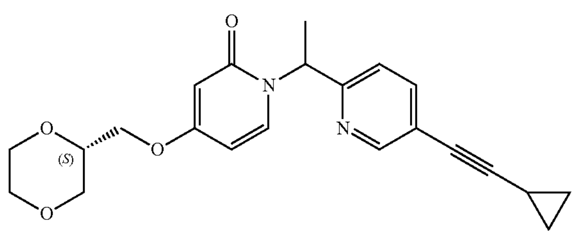 | 381.1 | $^1$HNMR (400 MHz, DMSO-d$_6$) δ 8.50 (d, J = 1.6 Hz, 1H), 7.75 (dd, J = 2.0 Hz, 8.0 Hz, 1H), 7.54 (d, J = 8.0 Hz, 1H), 7.21 (d, J = 8.0 Hz, 1H), 5.97-6.06 (m, 2H), 5.79 (d, J = 2.4 Hz, 1H), 3.89-3.96 (m, 2H), 3.73-3.84 (m, 3H), 3.57-3.67 (m, 2 H), 3.45-3.51 (m, 1H), 3.33-3.38 (m, 1H), 1.64 (d, J = 7.2 Hz, 3H), 1.54-1.61 (m, 1H), 0.88-0.93 (m, 2H), 0.73-0.77 (m, 2H). |
| I-285 | 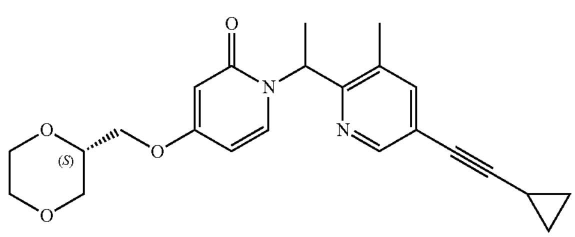 | 395.4 | $^1$HNMR (400 MHz, DMSO-d$_6$) δ 8.37 (d, J = 2.0 Hz, 1H), 7.61 (d, J = 1.6 Hz, 1H), 7.40 (d, J = 8.0 Hz, 1H), 6.21 (q, J = 6.8 Hz, 1H), 5.95 (dd, J = 2.8 Hz, 7.6 Hz, 1H), 5.77 (d, J = 2.8 Hz, 1H), 3.90-3.92 (m, 2H), 3.72-3.83 (m, 3H), 3.57-3.66 (m, 2H), 3.45-3.50 (m, 1H), 3.31-3.37 (m, 1H), 2.25 (s, 3H), 1.53-1.60 (m, 4H), 0.88-0.93 (m, 2H), 0.72-0.76 (m, 2H). |
| I-233 | 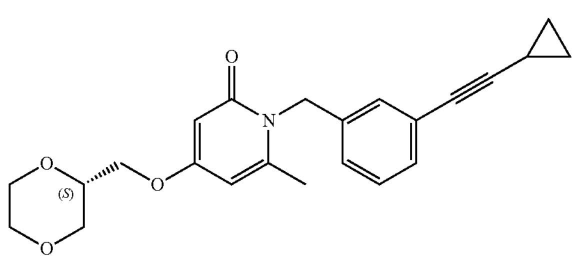 | 380.0 | $^1$H NMR (400 MHz, DMSO-d$_6$) δ 7.23-7.31 (m, 2H), 7.03-7.07 (m, 2H), 5.94 (d, J = 2.0 Hz, 1H), 5.80 (d, J = 2.4 Hz, 1H), 5.16 (s, 2H), 3.94-3.96 (m, 2H), 3.74-3.84 (m, 3H), 3.59-3.68 (m, 2H), 3.48-3.51 (m, 1H), 3.33-3.39 (m, 1H), 2.17 (s, 3H), 1.50-1.54 (m, 1H), 0.84-0.89 (m, 2H), 0.69-0.73 (m, 2H). |

TABLE 17-continued

Characterization Data for Additional Exemplary Compounds

| Compound No. | Chemical Structure | M + 1 | ¹H NMR (400 MHz) |
|---|---|---|---|
| I-231 | 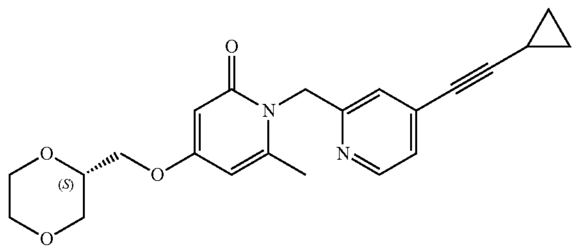 | 381.1 | ¹H NMR (400 MHz, DMSO-d$_6$) δ 8.42 (d, J = 5.2 Hz, 1H), 7.21 (dd, J = 1.6 Hz, 4.8 Hz, 1H), 7.05 (s, 1H), 5.94 (d, J = 2.4 Hz, 1H), 5.73 (d, J = 2.4 Hz, 1H), 5.18 (s, 2H), 3.93 (d, J = 3.2 Hz, 2H), 3.74-3.84 (m, 3H), 3.58-3.67 (m, 2H), 3.46-3.51 (m, 1H), 3.36-3.39 (m, 1H), 2.25 (s, 3H), 1.57-1.61 (m, 1H), 0.90-0.95 (m, 2H), 0.77-0.81 (m, 2H). |
| I-286 | 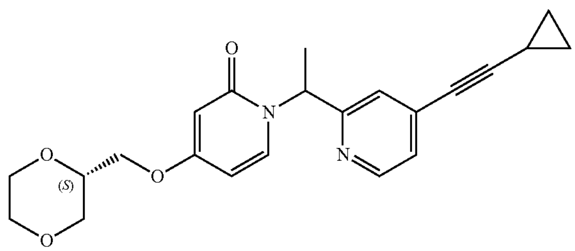 | 381.0 | ¹HNMR (400 MHz, CDCl$_3$) δ 8.45 (d, J = 5.2 Hz, 1H), 7.42 (d, J = 8.0 Hz, 1H), 7.12 (d, J = 5.2 Hz, 1H), 6.30 (q, J = 7.2 Hz, 1H), 5.93 (dd, J = 2.8 Hz, 8.0 Hz, 1H), 5.86 (d, J = 2.4 Hz, 1H), 3.72-3.96 (m, 8H), 3.64-3.68 (m, 1H), 3.46-3.52 (m, 1H), 1.72 (d, J = 7.2 Hz, 3H), 1.41-1.47 (m, 1H), 0.87-0.94 (m, 2H), 0.81-0.86 (m, 2H). |
| I-229 | 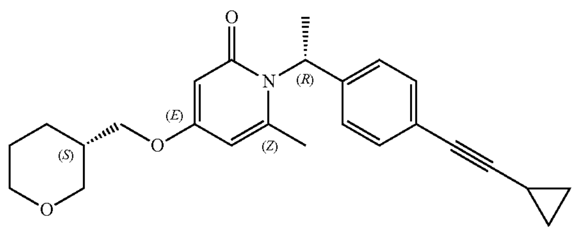 | 392.0 | ¹HNMR (400 MHz, DMSO-d$_6$) δ 7.30 (d, J = 7.2 Hz, 2H), 7.07 (d, J = 8.0 Hz, 2H), 5.85 (s, 1H), 5.60 (br., 1H), 3.71-3.84 (m, 4H), 3.33-3.35 (m, 1H), 3.19-3.24 (m, 1H), 2.50 (s, 3H), 1.92-2.01 (m, 2H), 1.75-1.81 (m, 4H), 1.48-1.61 (m, 3H), 1.30-1.37 (m, 1H), 0.85-0.89 (m, 2H), 0.69-0.73 (m, 2H). |
| I-232 | 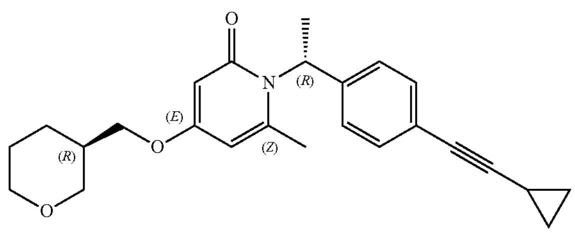 | 392.1 | ¹HNMR (400 MHz, DMSO-d$_6$) δ 7.30 (d, J = 7.2 Hz, 2H), 7.07 (d, J = 8.0 Hz, 2H), 5.85 (s, 1H), 5.64 (br., 1H), 3.71-3.84 (m, 4H), 3.33-3.36 (m, 1H), 3.19-3.24 (m, 1H), 2.50 (s, 3H), 1.94-2.01 (m, 2H), 1.75-1.81 (m, 4H), 1.48-1.61 (m, 3H), 1.32-1.37 (m, 1H), 0.85-0.89 (m, 2H), 0.69-0.73 (m, 2H). |
| I-230 | 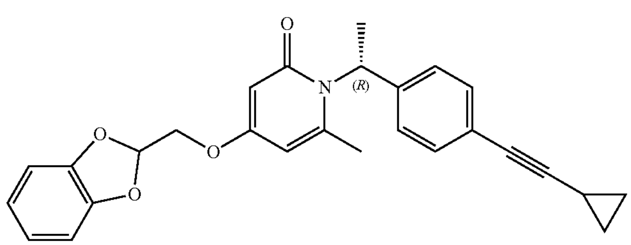 | 428.0 | ¹HNMR (400 MHz, DMSO-d$_6$) δ 7.30 (d, J = 7.6 Hz, 2H), 7.07 (d, J = 8.0 Hz, 2H), 6.90-6.94 (m, 2H), 6.83-6.86 (m, 2H), 6.54 (t, J = 3.2 Hz, 1H), 5.84 (s, 1H), 5.69 (br., 1H), 4.31 (s, 2H), 2.51 (s, 3H), 2.10-2.26 (m, 1H), 1.76 (d, J = 5.6 Hz, 3H), 1.50-1.54 (m, 1H), 0.840.89 (m, 2H), 0.69-0.73 (m, 2H). |
| I-274 | 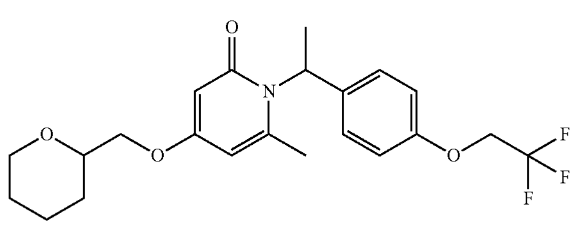 [SMILES: Cc1cc(OCC2CCCCO2)cc(=O)n1C(C)c1ccc(OCC(F)(F)F)cc1] | 426.3 | ¹HNMR (400 MHz, CDCl$_3$) δ 7.15 (d, J = 8.0 Hz, 2H), 6.88-6.90 (m, 2H), 5.85 (s, 1H), 5.79 (s, 1H), 4.33 (q, J = 8.0 Hz, 2H), 4.02-4.05 (m, 1H), 3.83-3.92 (m, 2H), 3.65-3.70 (m, 1H), 3.45-3.51 (m, 1H), 1.84-2.09 (m, 7H), 1.40-1.64 (m, 5H). |

TABLE 17-continued

Characterization Data for Additional Exemplary Compounds

| Compound No. | Chemical Structure | M + 1 | ¹H NMR (400 MHz) |
|---|---|---|---|
| I-234 | 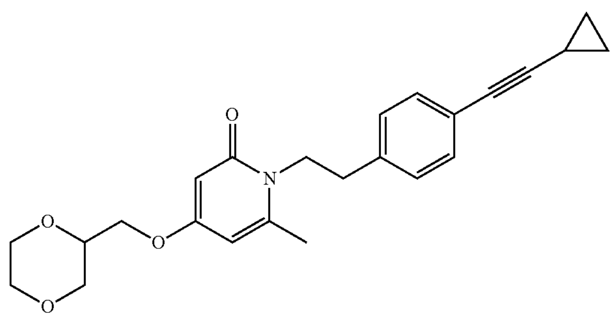 [SMILES: Cc1cc(OCC2COCCO2)cc(=O)n1CCc1ccc(C#CC2CC2)cc1] | 394.1 | ¹H NMR (400 MHz, DMSO-d$_6$) δ 7.29 (d, J = 8.0 Hz, 2H), 7.16 (d, J = 8.0 Hz, 2H), 5.83 (d, J = 2.4 Hz, 1H), 5.72 (d, J = 2.8 Hz, 1H), 4.00 (t, J = 7.6 Hz, 2H), 3.89-3.91 (m, 2H), 3.73-3.84 (m, 3H), 3.57-3.67 (m, 2H), 3.45-3.51 (m, 1H), 3.33-3.37 (m, 1H), 2.83 (t, J = 8.0 Hz, 2H), 2.15 (s, 3H), 1.49-1.54 (m, 1H), 0.85-0.89 (m, 2H), 0.69-0.73 (m, 2H). |
| I-259 | 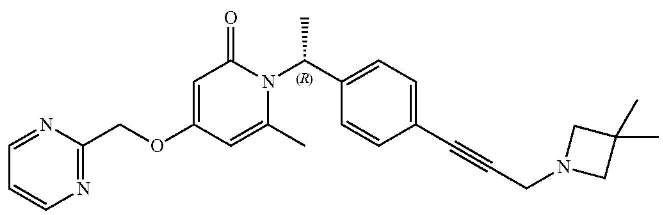 | 443.0 | ¹HNMR (400 MHz, DMSO-d$_6$) δ 8.85 (d, J = 5.2 Hz, 2H), 7.49 (t, J = 4.8 Hz, 1H), 7.39 (d, J = 7.2 Hz, 2H), 7.13 (d, J = 8.0 Hz, 2H), 5.97 (s, 1H), 5.62 (br., 2H), 5.23 (s, 2H), 3.42 (s, 2H), 3.00 (s, 4H), 2.21 (br., 3H), 1.78 (d, J = 6.4 Hz, 3H), 1.17 (s, 6H). |
| I-288 | 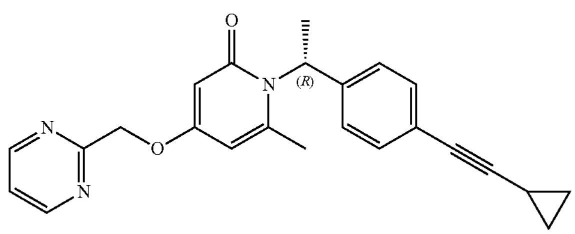 | 387.3 | ¹H NMR (400 MHz, DMSO-d$_6$) δ 8.84 (d, J = 4.8 Hz, 2H), 8.30 (d, J = 2.0 Hz, 1H), 7.47-7.51 (m, 2H), 7.34 (d, J = 8.0 Hz, 1H), 6.00 (s, 1H), 5.55 (br., 2H), 5.22 (s, 2H), 2.16-2.51 (m, 3H), 1.79 (d, J = 6.8 Hz, 3H), 1.55-1.59 (m, 1H), 0.89-0.94 (m, 2H), 0.74-0.78 (m, 2H). |
| I-247 | 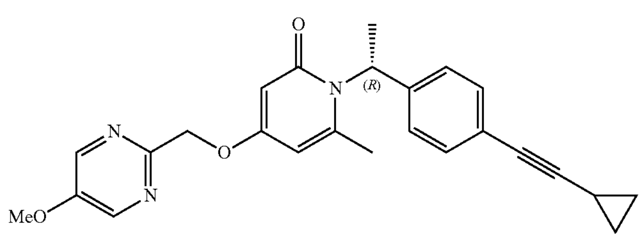 | 416.0 | ¹H NMR (400 MHz, DMSO-d$_6$) δ 8.59 (s, 2H), 7.30 (d, J = 6.8 Hz, 2H), 7.08 (d, J = 8.0 Hz, 2H), 5.92 (s, 1H), 5.63 (br., 1H), 5.14 (s, 2H), 3.92 (s, 3H), 2.08-2.50 (m, 3H), 1.75 (d, J = 6.0 Hz, 3H), 1.49-1.56 (m, 1H), 0.85-0.89 (m, 2H), 0.69-0.73 (m, 2H). |
| I-235 | 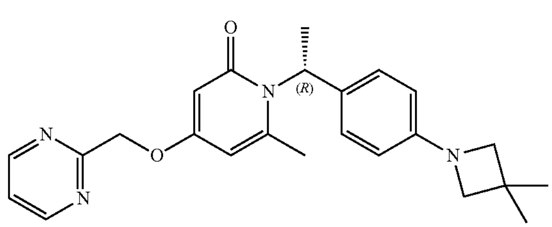 | 188.2 | ¹HNMR (400 MHz, DMSO-d$_6$) δ 8.85 (d, J = 4.8 Hz, 2H), 7.49 (t, J = 4.8 Hz, 1H), 6.95 (d, J = 7.2 Hz, 2H), 6.34 (d, J = 8.4 Hz, 2H), 5.88 (s, 1H), 5.64 (br., 1H), 5.23 (s, 2H), 3.47 (s, 4H), 2.50 (s, 3H), 2.08-2.18 (m, 1H), 1.71 (d, J = 6.0 Hz, 3H), 1.26 (s, 6H). |
| I-236 | 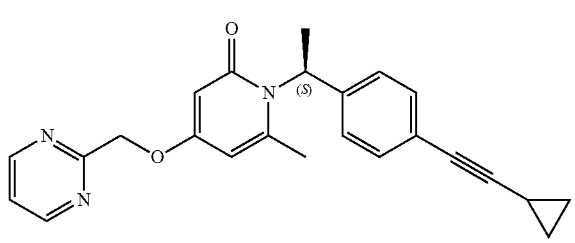 | 386.0 | ¹HNMR (400 MHz, DMSO-d$_6$) δ 8.85 (d, J = 4.8 Hz, 2H), 7.49 (t, J = 4.8 Hz, 1H), 7.30 (d, J = 5.2 Hz, 2H), 7.08 (d, J = 8.0 Hz, 2H), 5.96 (s, 1H), 5.41-5.74 (m, 1H), 5.23 (s, 2H), 1.88-1.50 (m, 4H), 1.76 (d, J = 6.0 Hz, 3H), 1.49-1.56 (m, 1H), 0.85-0.89 (m, 2H), 0.69-0.73 (m, 2H). |

TABLE 17-continued

Characterization Data for Additional Exemplary Compounds

| Compound No. | Chemical Structure | M + 1 ¹H NMR (400 MHz) |
|---|---|---|
| I-275 | 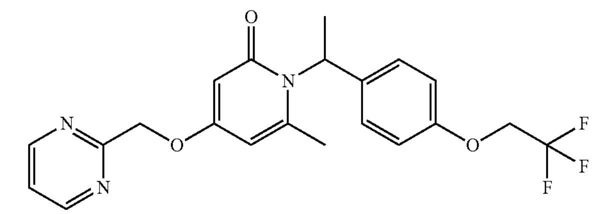 [SMILES: Cc1cc(OCc2ncccn2)cc(=O)n1C(C)c1ccc(OCC(F)(F)F)cc1] | 420.2 ¹HNMR (400 MHz, CDCl₃) δ 8.78 (d, J = 4.8 Hz, 2H), 7.27-7.29 (m, 2H), 7.15 (d, J = 8.4 Hz, 2H), 6.89 (d, J = 8.4 Hz, 2H), 5.94 (s, 2H), 5.26 (s, 2H), 4.33 (q, J = 8.0 Hz, 2H), 1.67-2.11 (m, 6H). |
| I-252 | 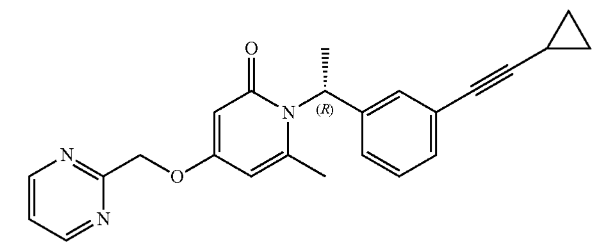 | 386.0 ¹HNMR (400 MHz, DMSO-d₆) δ 8.85 (d, J = 4.8 Hz, 2H), 7.49 (t, J = 4.8 Hz, 1H), 7.22-7.27 (m, 2H), 7.08 (s, 2H), 5.97 (s, 1H), 5.46-5.64 (m, 2H), 5.24 (s, 2H), 2.22-2.46 (br., 3H), 1.76 (d, J = 6.0 Hz, 3H), 1.51-1.55 (m, 1H), 0.84-0.89 (m, 2H), 0.70-0.74 (m, 2H). |
| I-260 | 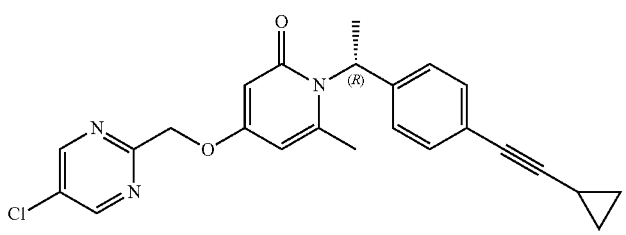 | 420.0 ¹HNMR (400 MHz, DMSO-d₆) δ 8.99 (s, 2H), 7.30 (d, J = 6.4 Hz, 2H), 7.08 (d, J = 8.0 Hz, 2H), 5.95 (s, 1H), 5.57 (br., 2H), 5.26 (s, 2H), 2.27 (br., 3H), 1.76 (d, J = 5.6 Hz, 3H), 1.50-1.54 (m, 2H), 0.85-0.89 (m, 2H), 0.69-0.73 (m, 2H). |
| I-279 | 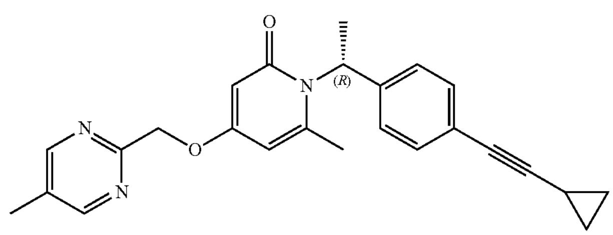 | 400.0 ¹HNMR (400 MHz, CDCl₃) δ 8.60 (s, 2H), 7.31 (d, J = 8.4 Hz, 2H), 7.07 (d, J = 8.0 Hz, 2H), 5.78-5.91 (m, 2H), 5.21 (s, 2H), 2.34 (s, 3H), 1.89-2.14 (m, 3H), 1.81 (d, J = 6.0 Hz, 3H), 1.41-1.45 (m, 1H), 0.85-0.88 (m, 2H), 0.77-0.81 (m, 2H). |
| I-237 | 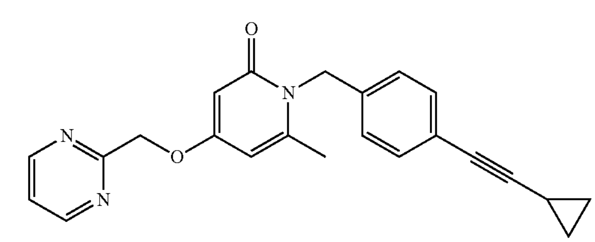 [SMILES: Cc1cc(OCc2ncccn2)cc(=O)n1Cc1ccc(C#CC2CC2)cc1] | 372.1 ¹HNMR (400 MHz, DMSO-d₆) δ 8.86 (d, J = 4.8 Hz, 2H), 7.50 (t, J = 4.8 Hz, 1H), 7.32 (d, J = 8.0 Hz, 2H), 7.04 (d, J = 8.0 Hz, 2H), 6.01 (d, J = 2.4 Hz, 1H), 5.78 (d, J = 2.8 Hz, 1H), 5.27 (s, 2H), 5.17 (s, 2H), 2.18 (s, 3H), 1.50-1.54 (m, 1H), 0.84-0.89 (m, 2H), 0.69-0.73 (m, 2H). |
| I-267 | 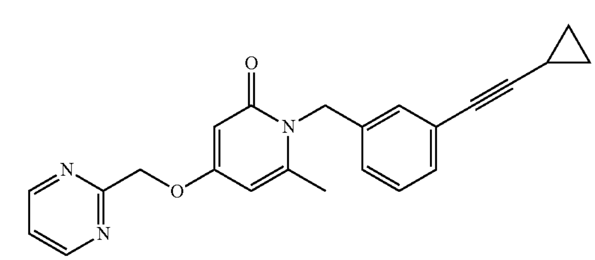 | 372.0 ¹HNMR (400 MHz, DMSO-d₆) δ 8.86 (d, J = 4.8 Hz, 2H), 7.50 (t, J = 4.8 Hz, 1H), 7.23-7.31 (m, 2H), 7.03-7.08 (m, 2H), 6.02 (d, J = 2.0 Hz, 1H), 5.78 (d, J = 2.8 Hz, 1H), 5.28 (s, 2H), 5.08-5.19 (m, 2H), 2.19 (s, 3H), 1.49-1.56 (m, 1H), 0.85-0.89 (m, 2H), 0.70-0.74 (m, 2H). |

TABLE 17-continued

Characterization Data for Additional Exemplary Compounds

| Compound No. | Chemical Structure | M + 1 | $^1$H NMR (400 MHz) |
|---|---|---|---|
| I-312 | 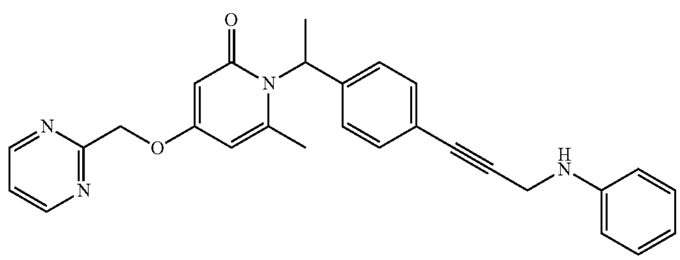 [SMILES: Cc1cc(OCc2ncccn2)cc(=O)n1C(C)c1ccc(C#CCNc2ccccc2)cc1] | 451.1 | $^1$H NMR (400 MHz, DMSO-d$_6$) δ 8.85 (d, J = 5.2 Hz, 2H), 7.49 (t, J = 4.8 Hz, 1H), 7.32 (d, J = 6.8 Hz, 2H), 7.10-7.14 (m, 4H), 6.68 (d, J = 8.4 Hz, 2H), 6.60 (t, J = 7.2 Hz, 1H), 6.04 (t, J = 5.6 Hz, 1H), 5.95 (s, 1H), 5.62 (br., 2H), 5.22 (s, 2H), 4.10 (d, J = 6.0 Hz, 2H), 2.16-2.51 (m, 3H), 1.75 (d, J = 6.4 Hz, 3H). |
| I-261 | 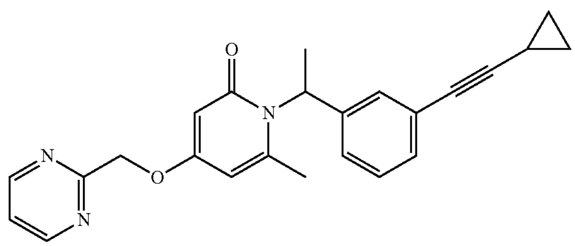 | 386.2 | $^1$HNMR (400 MHz, DMSO-d$_6$) δ 8.85 (d, J = 4.8 Hz, 2H), 7.49 (t, J = 4.4 Hz, 1H), 7.22-.27 (m, 2H), 7.08 (s, 2H), 5.97 (s, 1H), 5.58 (br., 2H), 5.24 (s, 2H), 2.34 (br., 3H), 1.76 (d, J = 5.2 Hz, 3H), 1.49-1.56 (m, 1H), 0.85-0.87 (m, 2H), 0.72-0.73 (m, 2H). |
| I-262 | 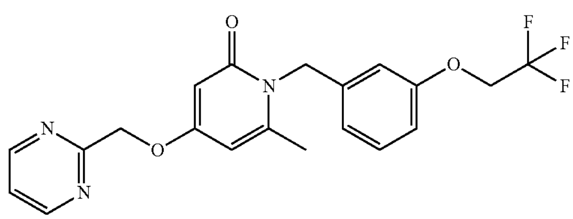 [SMILES: Cc1cc(OCc2ncccn2)cc(=O)n1Cc1cccc(OCC(F)(F)F)c1] | 406.1 | $^1$HNMR (400 MHz, CDCl$_3$) δ 8.78 (d, J = 4.8 Hz, 2H), 7.27-7.29 (m, 1H), 7.23-7.25 (m, 1H), 6.79-6.84 (m, 2H), 6.73 (s, 1H), 6.00 (s, 1H), 5.93 (s, 1H), 5.25-5.28 (m, 4H), 4.30 (q, J = 8.0 Hz, 2H), 2.23 (s, 3H). |
| I-280 | 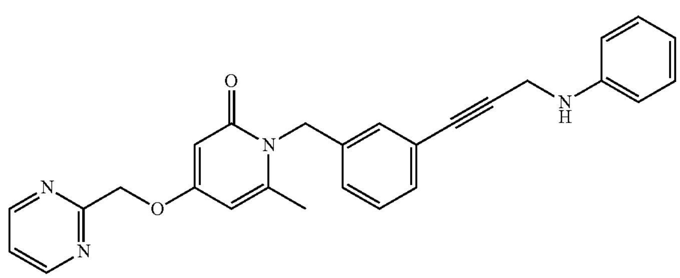 [SMILES: Cc1cc(OCc2ncccn2)cc(=O)n1Cc1cccc(C#CCNc2ccccc2)c1] | 437.0 | $^1$HNMR (400 MHz, DMSO-d$_6$) δ 8.86 (d, J = 4.8 Hz, 2H), 7.50 (t, J = 4.8 Hz, 1H), 7.32 (t, J = 7.6 Hz, 1H), 7.25 (d, J = 7.6 Hz, 1H), 7.09-7.13 (m, 3H), 7.04 (s, 1H), 6.67 (d, J = 7.6 Hz, 2H), 6.60 (t, J = 7.2 Hz, 1H), 6.01-6.06 (m, 2H), 5.78 (d, J = 2.8 Hz, 1H), 5.28 (s, 2H), 5.16 (s, 2H), 4.09 (d, J = 6.4 Hz, 2H), 2.18 (s, 3H). |
| I-241 | 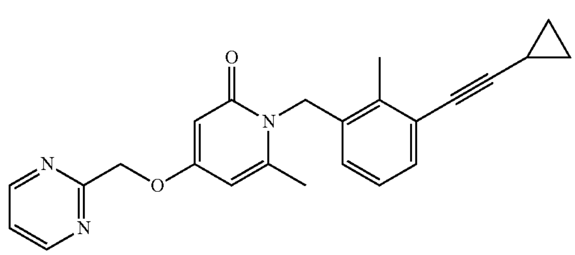 [SMILES: Cc1c(C#CC2CC2)cccc1Cn1c(C)cc(OCc2ncccn2)cc1=O] | 386.0 | $^1$HNMR (400 MHz, DMSO-d$_6$) δ 8.87 (d, J = 4.8 Hz, 2H), 7.50 (t, J = 4.8 Hz, 1H), 7.23 (d, J = 7.2 Hz, 1H), 7.06 (t, J = 7.6 Hz, 1H), 6.35 (d, J = 8.0 Hz, 1H), 6.07 (d, J = 2.0 Hz, 1H), 5.79 (d, J = 2.4 Hz, 1H), 5.29 (s, 2H), 5.11 (s, 2H), 2.40 (s, 3H), 2.13 (s, 3H), 1.56-1.62 (m, 1H), 0.89-0.94 (m, 2H), 0.73-0.77 (m, 2H). |

TABLE 17-continued

Characterization Data for Additional Exemplary Compounds

| Compound No. | Chemical Structure | M + 1 | $^1$H NMR (400 MHz) |
|---|---|---|---|
| I-289 | 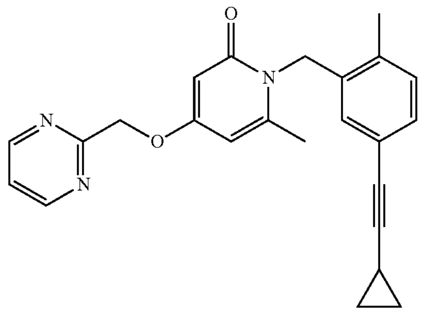 | 386.3 | $^1$H NMR (400 MHz, DMSO-d$_6$) δ 8.87 (d, J = 4.8 Hz, 2H), 7.51 (t, J = 4.8 Hz, 1H), 7.13-7.19 (m, 2H), 6.35 (s, 1H), 6.10 (d, J = 2.4 Hz, 1H), 5.80 (d, J = 2.8 Hz, 1H), 5.32 (s, 2H), 5.08 (s, 2H), 2.32 (s, 3H), 2.15 (s, 3H), 1.46-1.52 (m, 1H), 0.81-0.86 (m, 2H), 0.66-0.70 (m, 2H). |
| I-263 | 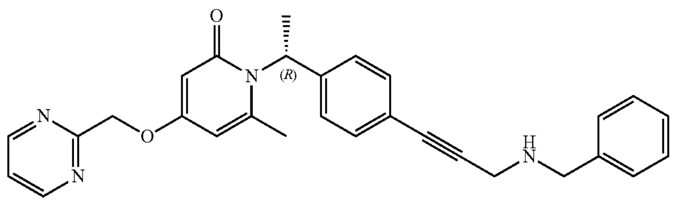 | 465.3 | $^1$HNMR (400 MHz, CDCl$_3$) δ 8.78 (d, J = 4.8 Hz, 2H), 7.27-7.43 (m, 8H), 7.13 (d, J = 8.0 Hz, 2H), 5.91 (s, 1H), 5.88 (br., 1H), 5.25 (s, 2H), 4.01 (s, 2H), 3.68 (s, 2H), 2.10 (br., 3H), 1.84 (d, J = 4.8 Hz, 3H). |
| I-264 | 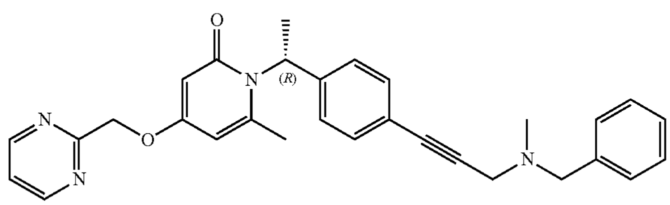 | 479.0 | $^1$HNMR (400 MHz, DMSO-d$_6$) δ 8.85 (d, J = 4.8 Hz, 2H), 7.49 (t, J = 4.8 Hz, 1H), 7.40-7.42 (m, 2H), 7.26-7.36 (m, 5H), 7.14 (d, J = 7.6 Hz, 2H), 5.97 (s, 1H), 5.59 (br., 2H), 5.23 (s, 2H), 3.57 (s, 2H), 3.49 (s, 2H), 2.40 (br., 3H), 2.26 (s, 3H), 1.78 (d, J = 5.6 Hz, 3H). |
| I-268 | 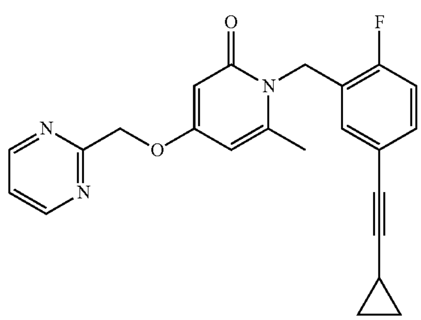 | 390.1 | $^1$HNMR (400 MHz, DMSO-d$_6$) δ 8.86 (d, J = 4.8 Hz, 2H), 7.50 (t, J = 4.8 Hz, 1H), 7.30-7.34 (m, 1H), 7.19-7.24 (m, 1H), 6.68-6.70 (m, 1H), 6.08 (d, J = 2.4 Hz, 1H), 5.79 (d, J = 2.8 Hz, 1H), 5.31 (s, 2H), 5.15 (s, 2H), 2.22 (s, 3H), 1.47-1.52 (m, 1H), 0.83-0.87 (m, 2H), 0.68-0.72 (m, 2H). |
| I-271 | 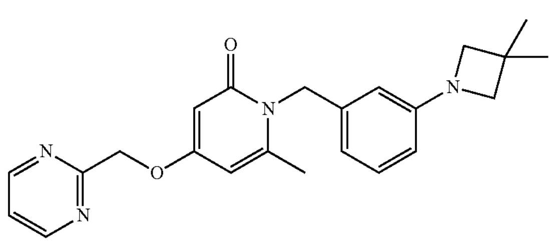 [SMILES: Cc1cc(OCc2ncccn2)cc(=O)n1Cc1cccc(N2CC(C)(C)C2)c1] | 391.0 | $^1$HNMR (400 MHz, DMSO-d$_6$) δ 8.85 (d, J = 4.8 Hz, 2H), 7.50 (t, J = 4.8 Hz, 1H), 7.07 (t, J = 8.0 Hz, 1H), 6.25-6.31 (m, 2H), 6.12 (s, 1H), 5.99 (d, J = 2.4 Hz, 1H), 5.76 (d, J = 2.8 Hz, 1H), 5.27 (s, 2H), 5.10 (s, 2H), 3.44 (s, 4H), 2.20 (s, 3H), 1.26 (s, 6H). |

TABLE 17-continued

Characterization Data for Additional Exemplary Compounds

| Compound No. | Chemical Structure | M + 1 | $^1$H NMR (400 MHz) |
|---|---|---|---|
| I-242 | 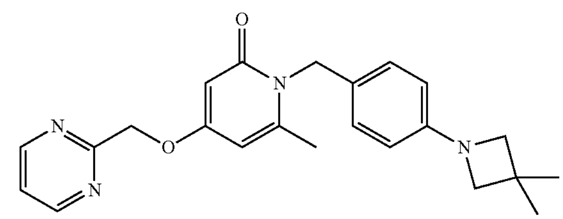 [SMILES: Cc1cc(OCc2ncccn2)cc(=O)n1Cc1ccc(N2CC(C)(C)C2)cc1] | 781.1 | $^1$HNMR (400 MHz, DMSO-d$_6$) δ 8.85 (d, J = 4.8 Hz, 2H), 7.49 (t, J = 4.8 Hz, 1H), 6.95 (d, J = 8.4 Hz, 2H), 6.34 (d, J = 8.4 Hz, 2H), 5.95 (d, J = 2.0 Hz, 1H), 5.74 (d, J = 2.8 Hz, 1H), 5.26 (s, 2H), 5.04 (s, 2H), 3.46 (s, 4H), 2.22 (s, 3H), 1.25 (s, 6H). |
| I-287 | 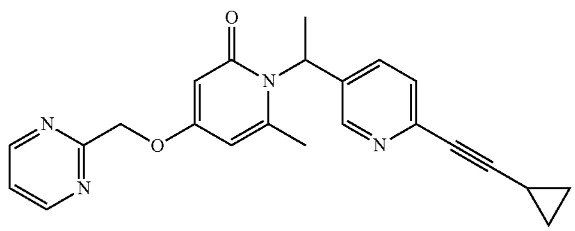 | 387.2 | 1HNMR (400 MHz, CDCl$_3$) δ 8.77 (d, J = 4.8 Hz, 2H), 8.37-8.38 (m, 1H), 7.37-7.50 (m, 1H), 7.27-7.30 (m, 2H), 5.93 (s, 1H), 5.69-5.85 (m, 1H), 5.24 (s, 2H), 2.12-2.53 (m, 3H), 1.72 (s, 3H), 1.43-1.50 (m, 1H), 0.86-0.90 (m, 4H). |
| I-253 | 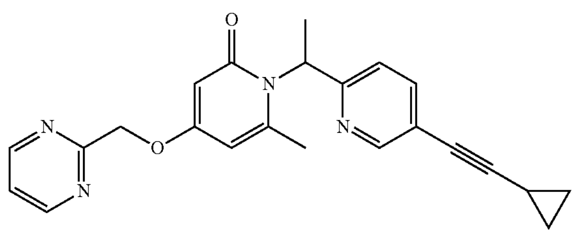 | 387.0 | $^1$HNMR (400 MHz, DMSO-d$_6$) δ 8.84 (d, J = 4.8 Hz, 2H), 8.43 (s, 1H), 7.70 (d, J = 7.2 Hz, 1H), 7.48 (t, J = 5.2 Hz, 1H), 7.19 (t, J = 8.4 Hz, 1H), 5.97 (s, 1H), 5.54 (br., 2H), 5.21 (s, 2H), 2.33 (br., 3H), 1.77 (d, J = 6.8 Hz, 3H), 1.54-1.59 (m, 1H), 0.88-0.92 (m, 2H), 0.73-0.77 (m, 2H). |
| I-243 | 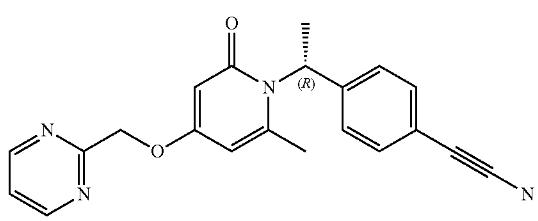 | 347.0 | $^1$HNMR (400 MHz, DMSO-d$_6$) δ 8.85 (d, J = 4.8 Hz, 2H), 7.77 (d, J = 7.6 Hz, 2H), 7.49 (t, J = 4.8 Hz, 1H), 7.32 (d, J = 8.0 Hz, 2H), 6.01 (s, 1H), 5.57 (br., 1H), 5.23 (s, 2H), 2.50 (s, 3H), 2.34-2.38 (m, 1H), 1.80 (d, J = 6.8 Hz, 3H). |
| I-292 | 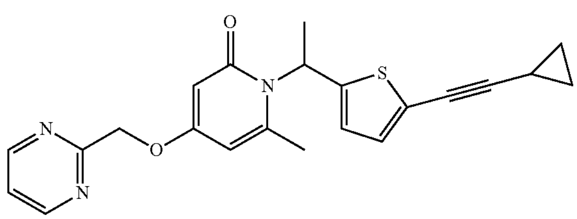 [SMILES: Cc1cc(OCc2ncccn2)cc(=O)n1C(C)c1ccc(C#CC2CC2)s1] | 783.3 | $^1$H NMR (400 MHz, DMSO-d$_6$) δ 8.85 (d, J = 4.8 Hz, 2H), 7.49 (t, J = 4.4 Hz, 1H), 6.97-6.99 (m, 1H), 6.84 (d, J = 3.6 Hz, 1H), 5.95 (s, 1H), 5.56-5.61 (m, 2H), 5.23 (s, 2H), 2.00-2.38 (m, 3H), 1.79 (d, J = 4.4 Hz, 3H), 1.52-1.56 (m, 1H), 0.86-0.90 (m, 2H), 0.68-0.72 (m, 2H). |
| I-265 | 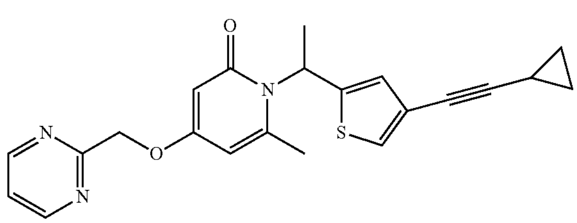 [SMILES: Cc1cc(OCc2ncccn2)cc(=O)n1C(C)c1cc(C#CC2CC2)cs1] | 392.3 | $^1$HNMR (400 MHz, CDCl$_3$) δ 8.78 (d, J = 4.8 Hz, 2H), 7.33-7.40 (m, 1H), 7.19 (s, 1H), 6.82 (s, 1H), 5.90 (s, 1H), 5.81 (br., 1H), 5.24 (s, 2H), 2.18 (br., 3H), 1.81-1.94 (m, 3H), 1.36-1.43 (m, 1H), 0.80-0.88 (m, 2H), 0.74-0.78 (m, 2H). |

TABLE 17-continued

Characterization Data for Additional Exemplary Compounds

| Compound No. | Chemical Structure | M + 1 | $^1$H NMR (400 MHz) |
|---|---|---|---|
| I-276 | 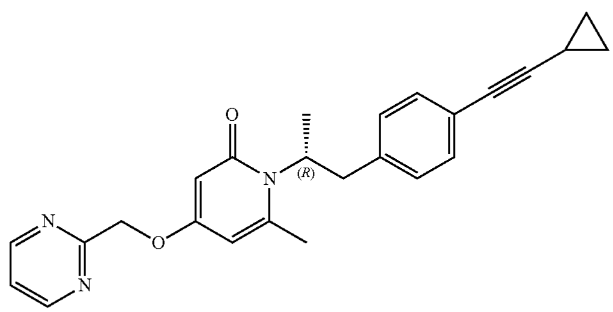 | 400.3 | $^1$H NMR (400 MHz, DMSO-$d_6$) δ 8.84 (d, J = 4.8 Hz, 2H), 7.49 (t, J = 4.8 Hz, 1H), 7.19 (d, J = 8.0 Hz, 2H), 7.06 (d, J = 8.0 Hz, 2H), 5.70 (d, J = 2.8 Hz, 1H), 5.58 (d, J = 2.8 Hz, 1H), 5.18 (s, 2H), 4.32-4.38 (m, 1H), 3.59-3.64 (m, 1H), 2.93 (dd, J = 5.2 Hz, 12.8 Hz, 1H), 1.94 (s, 3H), 1.47-1.54 (m, 4H), 0.83-0.88 (m, 2H), 0.69-0.72 (m, 2H). |
| I-277 | 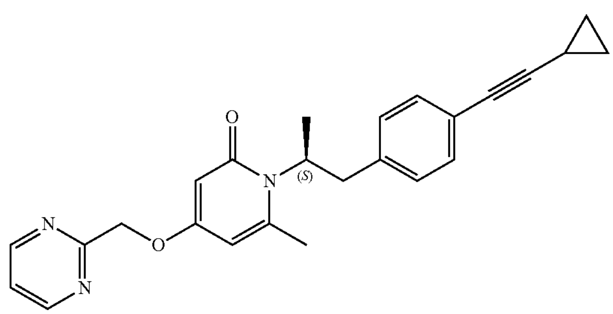 | 400.3 | $^1$H NMR (400 MHz, DMSO-$d_6$) δ 8.85 (d, J = 4.8 Hz, 2H), 7.49 (t, J = 4.8 Hz, 1H), 7.19 (d, J = 7.6 Hz, 2H), 7.06 (d, J = 7.6 Hz, 2H), 5.70 (d, J = 2.4 Hz, 1H), 5.59 (d, J = 2.8 Hz, 1H), 5.18 (s, 2H), 4.32-4.38 (m, 1H), 3.59-3.65 (m, 1H), 2.93 (dd, J = 4.8 Hz, 2.8 Hz, 1H), 1.94 (s, 3H), 1.47-1.52 (m, 4H), 0.83-0.88 (m, 2H), 0.69-0.72 (m, 2H). |
| I-281 | 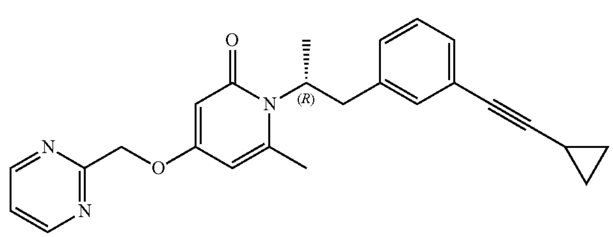 | 400.3 | $^1$H NMR (400 MHz, DMSO-$d_6$) δ 8.84 (d, J = 5.2 Hz, 2H), 7.49 (t, J = 4.8 Hz, 1H), 7.13-7.18 (m, 3H), 7.03-7.05 (m, 1H), 5.72 (d, J = 2.8 Hz, 1H), 5.60 (d, J = 3.2 Hz, 1H), 5.18 (s, 2H), 4.34-4.39 (m, 1H), 3.54-3.59 (m, 1H), 2.94 (dd, J = 5.6 Hz, 13.2 Hz, 1H), 1.97 (s, 3H), 1.49-1.55 (m, 4H), 0.85-0.89 (m, 2H), 0.69-0.72 (m, 2H). |
| I-282 | 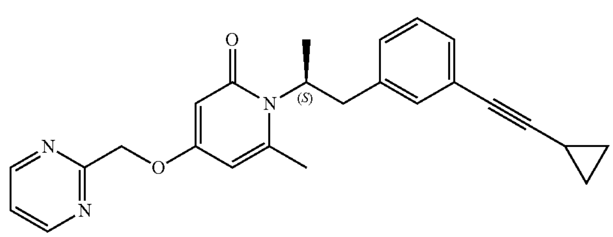 | 400.3 | $^1$H NMR (400 MHz, DMSO-$d_6$) δ 8.84 (d, J = 5.2 Hz, 2H), 7.49 (t, J = 4.8 Hz, 1H), 7.13-7.18 (m, 3H), 7.03-7.05 (m, 1H), 5.72 (d, J = 2.4 Hz, 1H), 5.60 (d, J = 2.8 Hz, 1H), 5.18 (s, 2H), 4.34-4.39 (m, 1H), 3.54-3.59 (m, 1H), 2.94 (dd, J = 5.6 Hz, 12.8 Hz, 1H), 1.97 (s, 3H), 1.40-1.55 (m, 4H), 0.85-0.89 (m, 2H), 0.69-0.72 (m, 2H). |
| I-244 | 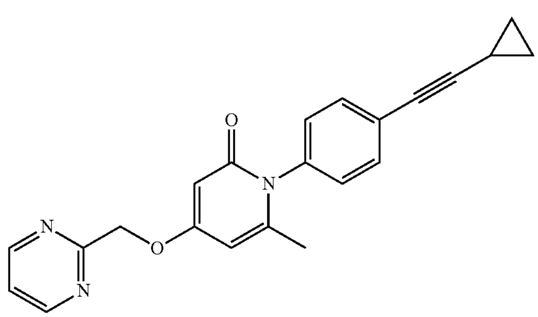 [SMILES: Cc1cc(OCc2ncccn2)cc(=O)n1-c1ccc(C#CC2CC2)cc1] | 358.0 | $^1$HNMR (400 MHz, DMSO-$d_6$) 8.87 (d, J = 3.2 Hz, 2H), 7.50 (t, J = 5.2 Hz, 1H), 7.44-7.48 (m, 2H), 7.13-7.23 (m, 2H), 6.09 (d, J = 1. Hz, 1H), 5.73 (d, J = 2.4 Hz, 1H), 5.29 (s, 2H), 1.85 (s, 3H), 1.52-1.61 (m, 1H), 0.86-0.94 (m, 2H), 0.74-0.76 (m, 2H). |

TABLE 17-continued

Characterization Data for Additional Exemplary Compounds

| Compound No. | Chemical Structure | M + 1 | $^1$H NMR (400 MHz) |
|---|---|---|---|
| I-245 | 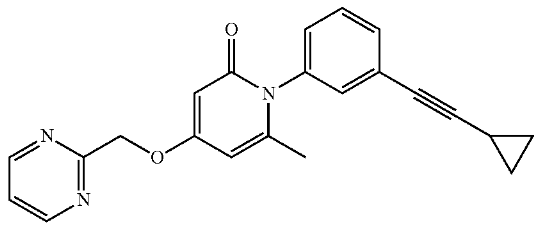 [SMILES: Cc1cc(OCc2ncccn2)cc(=O)n1-c1cccc(C#CC2CC2)c1] | 358.0 | $^1$HNMR (400 MHz, CDCl$_3$) δ 8.79 (d, J = 4.8 Hz, 2H), 7.36-7.43 (m, 2H), 7.29 (d, J = 4.8 Hz, 1H), 7.19 (t, J = 1.6 Hz, 1H), 7.06-7.09 (m, 1H), 6.04 (dd, J = 0.8 Hz, 2.8 Hz, 1H), 5.86 (d, J = 2.4 Hz, 1H), 5.29 (s, 2H), 1.91 (s, 3H), 1.41-1.45 (m, 1H), 0.84-0.89 (m, 2H), 0.77-0.80 (m, 2H). |
| I-248 | 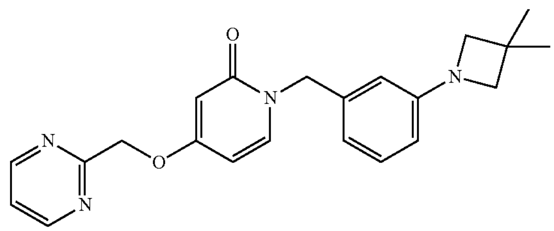 [SMILES: CC1(C)CN(c2cccc(Cn3ccc(OCc4ncccn4)cc3=O)c2)C1] | 377.0 | $^1$HNMR (400 MHz, DMSO-d$_6$) δ 8.85 (d, J = 4.8 Hz, 2H), 7.62 (d, J = 7.6 Hz, 1H), 7.49 (t, J = 4.8 Hz, 1H), 7.08 (t, J = 7.6 Hz, 1H), 6.51 (d, J = 7.6 Hz, 1H), 6.28-6.30 (m, 2H), 6.05 (dd, J = 2.4 Hz, 7.2 Hz, 1H), 5.80 (d, J = 2.4 Hz, 1H), 5.26 (s, 2H), 4.91 (s, 2H), 3.46 (s, 4H), 1.26 (s, 6H). |
| I-251 | 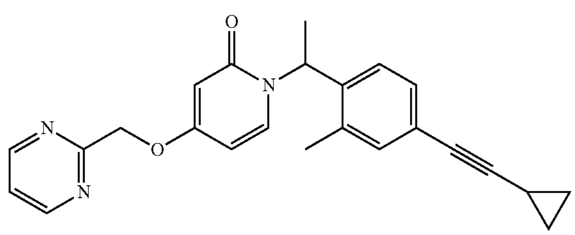 | 386.2 | $^1$HNMR (400 MHz, DMSO-d$_6$) δ 8.84 (d, J = 5.2 Hz, 2H), 7.49 (t, J = 4.8 Hz, 1H), 7.37 (d, J = 8.0 Hz, 1H), 7.25 (d, J = 7.6 Hz, 1H), 7.16-7.19 (m, 2H), 5.99-6.07 (m, 2H), 5.80 (d, J = 2.8 Hz, 1H), 5.25 (s, 2H), 2.07 (s, 3H), 1.50-1.55 (m, 4H), 0.87-0.90 (m, 2H), 0.70-0.73 (m, 2H). |
| I-249 | 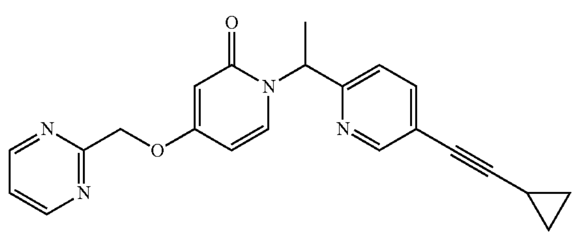 [SMILES: CC(c1ccc(C#CC2CC2)cn1)n1ccc(OCc2ncccn2)cc1=O] | 373.3 | $^1$HNMR (400 MHz, DMSO-d$_6$) δ 8.85 (d, J = 5.2 Hz, 2H), 8.51 (d, J = 1.6 Hz, 1H), 7.75 (dd, J = 2.4 Hz, 8.4 Hz, 1H), 7.57 (d, J = 7.6 Hz, 1H), 7.49 (t, J = 4.8 Hz, 1H), 7.23 (d, J = 8.0 Hz, 1H), 6.01-6.07 (m, 2H), 5.77 (d, J = 2.8 Hz, 1H), 5.26 (s, 2H), 1.63 (d, J = 7.2 Hz, 3H), 1.55-1.64 (m, 1H), 0.88-0.93 (m, 2H), 0.74-0.77 (m, 2H). |
| I-254 | 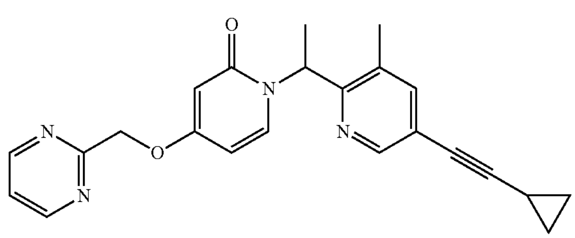 [SMILES: Cc1cc(C#CC2CC2)cnc1C(C)n1ccc(OCc2ncccn2)cc1=O] | 387.3 | $^1$HNMR (400 MHz, CDCl$_3$) δ 8.77 (d, J = 4.8 Hz, 2H), 8.42 (d, J = 1.6 Hz, 1H), 7.43 (d, J = 1.2 Hz, 1H), 7.33 (d, J = 8.0 Hz, 1H), 7.26 (d, J = 4.8 Hz, 1H), 6.45 (q, J = 6.8 Hz, 1H), 6.03 (dd, J = 2.8 Hz, 8.0 Hz, 1H), 5.89 (d, J = 2.8 Hz, 1H), 5.23 (s, 2H), 2.27 (s, 3H), 1.66 (d, J = 6.8 Hz, 3H), 1.42-1.49 (m, 1H), 0.80-0.92 (m, 4H). |
| I-266 | 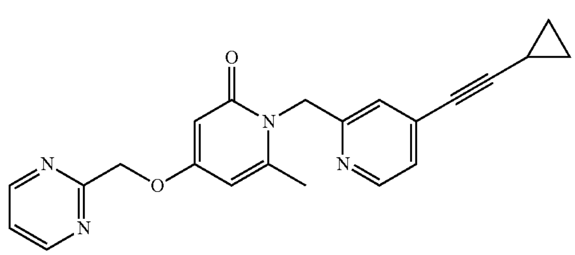 | 373.3 | $^1$H NMR (400 MHz, DMSO-d$_6$) δ 8.85 (d, J = 4.8 Hz, 2H), 8.42 (d, J = 4.8 Hz, 1H), 7.49 (t, J = 4.8 Hz, 1H), 7.21 (d, J = 4.0 Hz, 1H), 7.06 (s, 1H), 6.02 (d, J = 2.0 Hz, 1H), 5.70 (d, J = 2.4 Hz, 1H), 5.27 (s, 2H), 5.17 (s, 2H), 2.27 (s, 3H), 1.56-1.63 (m, 1H), 0.91-0.96 (m, 2H), 0.77-0.81 (m, 2H). |

TABLE 17-continued

Characterization Data for Additional Exemplary Compounds

| Compound No. | Chemical Structure | M + 1 | $^1$H NMR (400 MHz) |
|---|---|---|---|
| I-250 | 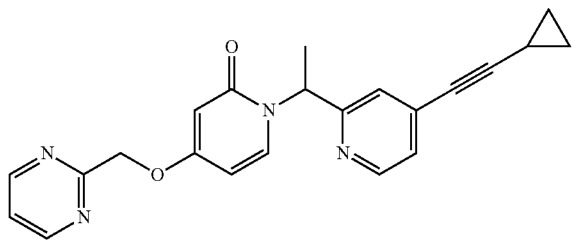 [SMILES: CC(c1cc(C#CC2CC2)ccn1)n1ccc(OCc2ncccn2)cc1=O] | 373.1 | $^1$HNMR (400 MHz, DMSO-d$_6$) δ 8.85 (d, J = 4.8 Hz, 2H), 8.46 (d, J = 5.2 Hz, 1H), 7.61 (d, J = 8.0 Hz, 1H), 7.49 (t, J = 4.8 Hz, 1H), 7.23 (dd, J = 1.6 Hz, 4.8 Hz, 1H), 7.19 (s, 1H), 6.07 (dd, J = 2.8 Hz, 7.6 Hz, 1H), 5.99 (q, J = 7.6 Hz, 1H), 5.76 (d, J = 2.8 Hz, 1H), 5.26 (s, 2H), 1.64 (d, J = 7.2 Hz, 3H), 1.56-1.62 (m, 1H), 0.91-0.96 (m, 2H), 0.78-0.82 (m, 2H). |
| I-238 | 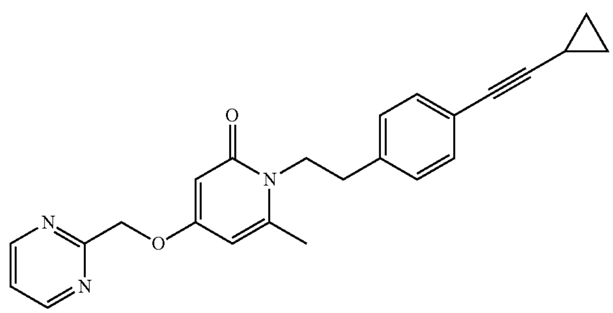 [SMILES: Cc1cc(OCc2ncccn2)cc(=O)n1CCc1ccc(C#CC2CC2)cc1] | 386.0 | $^1$H NMR (400 MHz, DMSO-d$_6$) δ 8.85 (d, J = 4.8 Hz, 2H), 7.49 (t, J = 4.8 Hz, 1H), 7.29 (d, J = 8.0 Hz, 2H), 7.16 (d, J = 8.0 Hz, 2H), 5.91 (d, J = 2.4 Hz, 1H), 5.69 (d, J = 2.8 Hz, 1H), 5.24 (s, 2H), 3.99 (t, J = 7.6 Hz, 2H), 2.83 (t, J = 7.6 Hz, 2H), 2.19 (s, 3H), 1.50-1.54 (m, 1H), 0.85-0.89 (m, 2H), 0.70-0.73 (m, 2H). |
| I-269 | 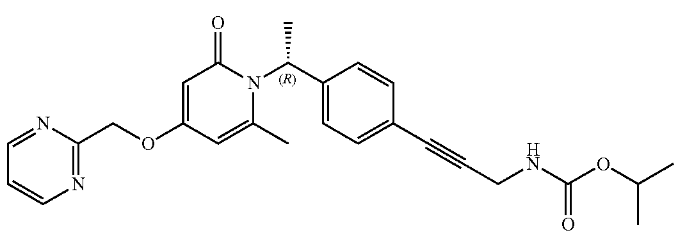 | 461.3 | $^1$HNMR (400 MHz, CDCl$_3$) δ 8.78 (d, J = 4.8 Hz, 2H), 7.36 (d, J = 8.4 Hz, 2H), 7.26-7.29 (m, 1H), 7.12 (d, J = 7.6 Hz, 2H), 5.90 (s, 1H), 5.83 (br., 1H), 5.25 (s, 2H), 4.89-4.98 (m, 1H), 4.76-4.82 (m, 1H), 4.19 (d, J = 4.4 Hz, 2H), 2.03 (br., 3H), 1.84 (d, J = 6.4 Hz, 3H), 1.25 (d, J = 6.4 Hz, 6H). |
| I-255 | 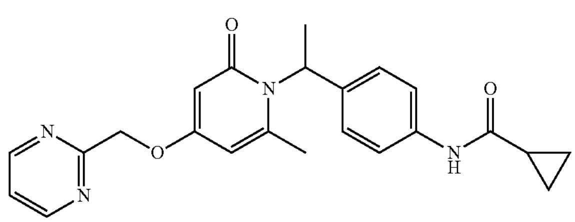 [SMILES: Cc1cc(OCc2ncccn2)cc(=O)n1C(C)c1ccc(NC(=O)C2CC2)cc1] | 391.2 | $^1$HNMR (400 MHz, DMSO-d$_6$) δ 10.21 (s, 1H), 8.85 (d, J = 5.2 Hz, 2H), 7.55 (d, J = 8.8 Hz, 2H), 7.49 (t, J = 4.8 Hz, 1H), 7.43 (d, J = 7.6 Hz, 1H), 7.21 (d, J = 8.8 Hz, 2H), 6.01-6.05 (m, 2H), 5.79 (d, J = 2.8 Hz, 1H), 5.26 (s, 2H), 1.72-1.79 (m, 1H), 1.60 (d, J = 6.8 Hz, 3H), 0.77-0.79 (m, 4H). |
| I-290 | 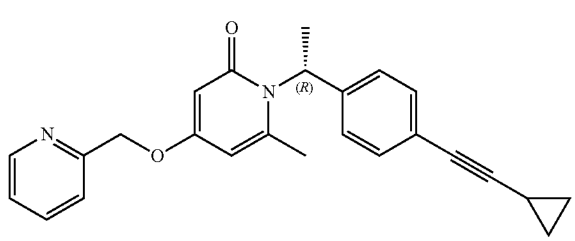 | 385.3 | $^1$HNMR (400 MHz, DMSO-d$_6$) δ 8.58 (d, J = 4.4 Hz, 1H), 7.83-7.88 (m, 1H), 7.49 (d, J = 7.6 Hz, 1H), 7.35-7.38 (m, 1H), 7.30 (d, J = 6.8 Hz, 2H), 7.08 (d, J = 8.0 Hz, 2H), 5.96 (s, 1H), 5.24-5.86 (m, 2H), 5.11 (s, 2H), 2.16-2.40 (m, 3H), 1.76 (d, J = 6.0 Hz, 3H), 1.49-1.56 (m, 1H), 0.85-0.89 (m, 2H), 0.69-0.73 (m, 2H). |

TABLE 17-continued

Characterization Data for Additional Exemplary Compounds

| Compound No. | Chemical Structure | M + 1 ¹H NMR (400 MHz) |
|---|---|---|
| I-278 | 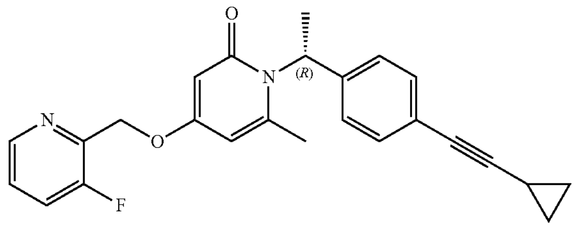 | 403.3 ¹HNMR (400 MHz, DMSO-d₆) δ 8.47 (d, J = 4.8 Hz, 1H), 7.81 (t, J = 9.2 Hz, 1H), 7.54-7.57 (m, 1 H), 7.30 (d, J = 7.2 Hz, 2H), 7.09 (d, J = 8.0 Hz, 2H), 5.44-5.90 (m, 3H), 5.17 (s, 2H), 2.29 (br., 3H), 1.77 (d, J = 6.0 Hz, 3H), 1.51-1.55 (m, 1H), 0.85-0.89 (m, 2H), 0.69-073 (m, 2H). |
| I-256 | 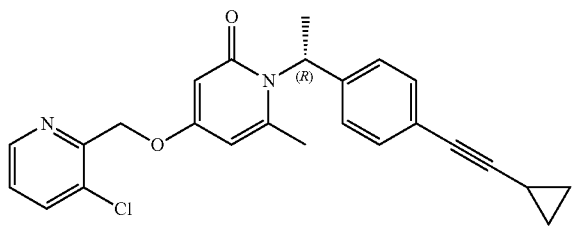 | 419.2 ¹HNMR (400 MHz, CDCl₃) δ 8.57 (dd, J = 1.2 Hz, 4.8 Hz, 1H), 7.78 (dd, J = 1.2 Hz, 8.0 Hz, 1H), 7.30-7.34 (m, 3H), 7.08 (d, J = 8.0 Hz, 2H), 6.29 (s, 1H), 6.00 (s, 1H), 5.33-5.37 (m, 1H), 5.29 (s, 2H), 2.33 (br., 3H), 1.86 (d, J = 4.8 Hz, 3H, 1.40-1.46 (m, 1H), 0.85-0.89 (m, 2H), 1.77-0.81 (m, 2H). |
| I-257 | 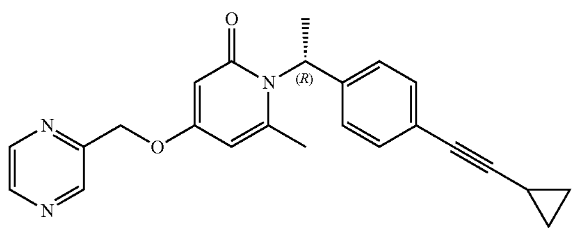 | 386.1 ¹HNMR (400 MHz, CDCl₃) δ 8.75 (s, 1H), 8.58 (d, J = 3.6 Hz, 2H), 7.33 (d, J = 8.4 Hz, 2H), 7.09 (d, J = 8.0 Hz, 2H), 5.89-6.19 (m, 1H), 5.83 (s, 1H), 5.17 (s, 2H), 2.05 (br., 3H), 1.84 (t, J = 6.4 Hz, 3H), 1.42-1.46 (m, 1H), 0.83-0.89 (m, 2H), 0.77-0.81 (m, 2H). |
| I-258 | 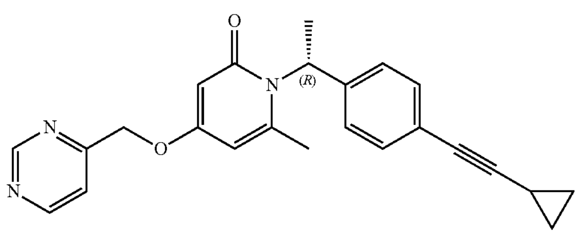 | 386.0 ¹H NMR (400 MHz, DMSO-d₆) δ 9.19 (d, J = 1.2 Hz, 1H), 8.86 (d, J = 5.2 Hz, 1H), 7.59 (d, J = 4.8 Hz, 1H), 7.29-7.31 (m, 2H), 7.08 (d, J = 8.4 Hz, 2H), 6.02 (s, 1H), 5.71 (br., 2H), 5.18 (s, 2H), 2.30 (br., 3H), 1.77 (d, J = 6.4 Hz, 3H), 1.50-1.55 (m, 1H), 0.85-0.89 (m, 2H), 0.69-0.73 (m, 2H). |
| I-291 | 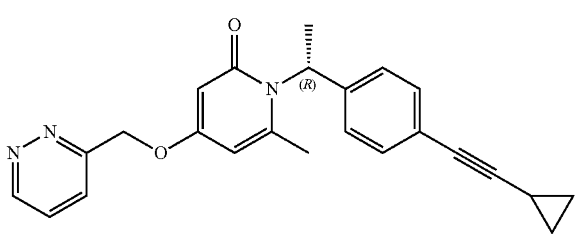 | 386.3 ¹H NMR (400 MHz, DMSO-d₆) δ 9.24 (dd, J = 2.0 Hz, 4.4 Hz, 1H), 7.76-7.82 (m, 2H), 7.31 (d, J = 8.0 Hz, 2H), 7.09 (d, J = 8.4 Hz, 2H), 5.97 (s, 1H), 5.76 (br., 1H), 5.35 (s, 2H), 2.16-2.51 (m, 3H), 1.77 (d, J = 6.0 Hz, 3H), 1.49-1.55 (m, 1H), 0.85-0.88 (m, 2H), 0.69-0.73 (m, 2H). |
| I-272 | 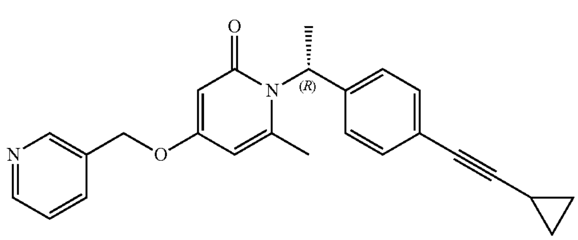 | 385.3 ¹HNMR (400 MHz, CDCl₃) δ 8.67 (s, 1H), 8.62 (d, J = 4.8 Hz, 1H), 7.74-7.76 (m, 1H), 7.35-7.37 (m, 1H), 7.33 (d, J = 8.4 Hz, 2H), 7.09 (d, J = 8.0 Hz, 2H), 5.93 (s, 1H), 5.76 (s, 1H), 5.01 (s, 2H), 2.00 (s, 4H), 1.84 (d, J = 6.8 Hz, 3H), 1.40-1.47 (m, 1H), 0.83-0.89 (m, 2H), 0.77-0.81 (m, 2H). |

TABLE 17-continued

Characterization Data for Additional Exemplary Compounds

| Compound No. | Chemical Structure | M + 1 | $^1$H NMR (400 MHz) |
|---|---|---|---|
| I-283 | 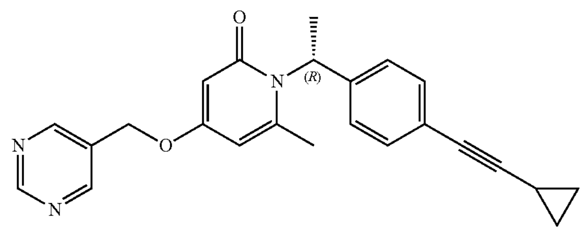 | 386.3 | $^1$H NMR (400 MHz, DMSO-d$_6$) δ 9.20 (s, 1H), 8.90 (s, 1H), 7.31 (d, J = 7.6 Hz, 2H), 7.08 (d, J = 8.0 Hz, 2H), 5.95 (s, 1H), 5.75 (br., 1H), 5.13 (s, 2H), 2.33 (br., 3H), 1.77 (d, J = 6.0 Hz, 3H), 1.49-1.56 (m, 1H), 0.85-0.90 (m, 2H), 0.69-0.73 (m, 2H). |
| I-293 | 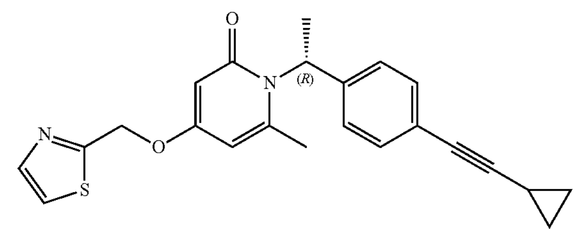 | 391.2 | $^1$H NMR (400 MHz, DMSO-d$_6$) δ 7.86 (d, J = 3.2 Hz, 1H), 7.82 (d, J = 3.2 Hz, 1H), 7.31 (d, J = 7.2 Hz, 2H), 7.08 (d, J = 8.0 Hz, 2H), 5.96 (s, 1H), 5.81 (br., 1H), 5.39 (s, 2H), 2.16-2.51 (m, 3H), 1.77 (d, J = 6.4 Hz, 3H), 1.50-1.55 (m, 1H), 0.85-0.89 (m, 2H), 0.69-0.73 (m, 2H). |
| I-294 | 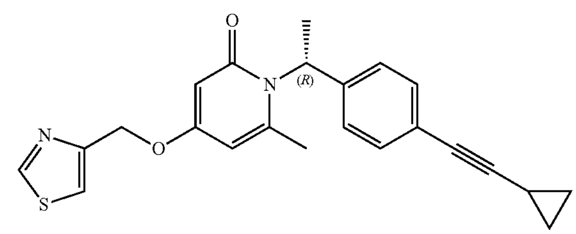 | 391.0 | $^1$H NMR (400 MHz, DMSO-d$_6$) δ 9.13 (d, J = 2.0 Hz, 1H), 7.83 (d, J = 1.6 Hz, 1H), 7.31 (d, J = 8.0 Hz, 2H), 7.08 (d, J = 8.4 Hz, 2H), 5.90 (s, 1H), 5.67 (br., 1H), 5.15 (s, 2H), 2.16-2.51 (m, 3H), 1.77 (d, J = 6.4 Hz, 3H), 1.50-1.55 (m, 1H), 0.85-0.89 (m, 2H), 0.69-0.73 (m, 2H). |
| I-296 | 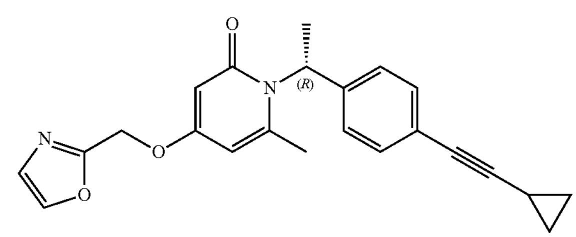 | 375.3 | $^1$H NMR (400 MHz, DMSO-d$_6$) δ 8.20 (s, 1H), 7.30-7.31 (m, 3H), 7.08 (d, J = 8.0 Hz, 2H), 5.92 (s, 1H), 5.79 (br., 2H), 5.20 (s, 2H), 2.16-2.51 (m, 3H), 1.77 (d, J = 6.0 Hz, 3H), 1.50-1.55 (m, 1H), 0.85-0.89 (m, 2H), 0.69-0.73 (m, 2H). |
| I-284 | 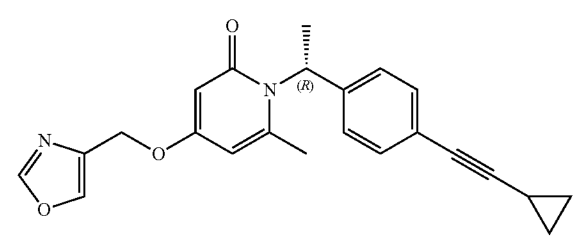 | 375.3 | $^1$H NMR (400 MHz, DMSO-d$_6$) δ 8.42 (s, 1H), 8.24 (s, 1H), 7.31 (d, J = 7.2 Hz, 2H), 7.08 (d, J = 8.0 Hz, 2H), 5.51-5.94 (m, 2H), 4.95 (s, 2H), 2.16-2.51 (m, 3H), 1.77 (d, J = 6.4 Hz, 3H), 1.49-1.56 (m, 1H), 0.85-0.89 (m, 2H), 0.69-0.73 (m, 2H). |
| I-295 | 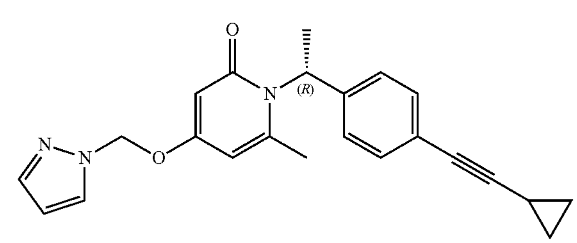 | 374.3 | $^1$H NMR (400 MHz, DMSO-d$_6$) δ 8.02 (s, 1H), 7.60 (s, 1H), 7.31 (d, J = 7.2 Hz, 2H), 7.08 (d, J = 8.0 Hz, 2H), 6.37 (s, 1H), 5.95-6.31 (m, 3H), 5.90 (s, 1H), 2.16-2.51 (m, 3H), 1.77 (d, J = 6.0 Hz, 3H), 1.51-1.55 (m, 1H), 0.85-0.89 (m, 2H), 0.70-0.73 (m, 2H). |

TABLE 17-continued

Characterization Data for Additional Exemplary Compounds

| Compound No. | Chemical Structure | M + 1 | ¹H NMR (400 MHz) |
|---|---|---|---|
| I-372 | 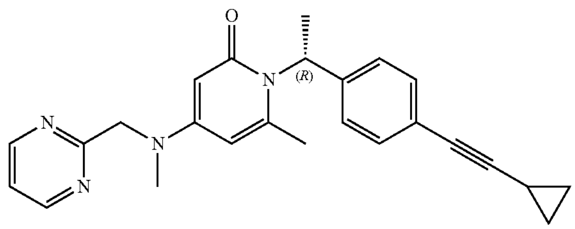 | 399.3 | ¹H NMR (400 MHz, DMSO-d$_6$) δ 8.78 (d, J = 3.2 Hz, 2H), 7.42 (t, J = 4.8 Hz, 1H), 7.29 (d, J = 2.4 Hz, 2H), 7.05 (d, J = 8.0 Hz, 2H), 5.88 (s, 1H), 5.18 (br, 1H), 4.71 (s, 2H), 3.08 (s, 3H), 2.03-2.49 (m, 3H), 1.70-1.71 (m, 3H), 1.50-1.54 (m, 1H), 0.84-0.89 (m, 2H), 0.69-0.72 (m, 2H). |
| I-324 | 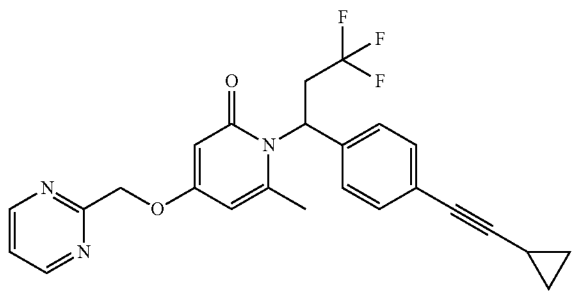 [SMILES: Cc1cc(OCc2ncccn2)cc(=O)n1C(CC(F)(F)F)c1ccc(C#CC2CC2)cc1] | 454.3 | ¹HNMR (400 MHz, CDCl$_3$) δ 8.77 (d, J = 4.8 Hz, 2H), 7.26-7.33 (m, 3H), 7.17 (d, J = 7.2 Hz, 2H), 6.01 (s, 1H), 5.69 (s, 1H), 5.47-5.48 (m, 1H), 5.21 (s, 2H), 3.88-3.96 (m, 1H), 3.03-3.08 (m, 1H), 2.45 (s, 3H), 1.39-1.46 (m, 1H), 0.76-0.88 (m, 4H). |
| I-273 | 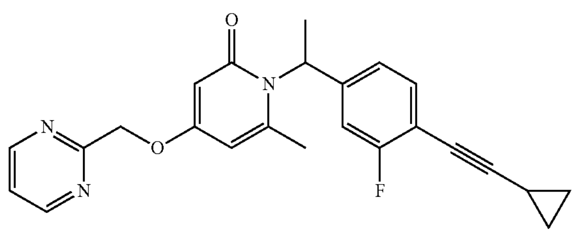 [SMILES: Cc1cc(OCc2ncccn2)cc(=O)n1C(C)c1ccc(C#CC2CC2)c(F)c1] | 404.3 | ¹H NMR (400 MHz, DMSO-d$_6$) δ 8.85 (d, J = 4.8 Hz, 2H), 7.49 (t, J = 4.8 Hz, 1H), 7.35 (t, J = 4.8 Hz, 1H), 6.99 (d, J = 11.2 Hz, 1H), 6.88 (d, J = 7.6 Hz, 1H), 5.98 (s, 1H), 5.58 (br., 2H), 5.23 (s, 2H), 2.25 (br., 3H), 1.75 (d, J = 6.8 Hz, 3H), 1.55-1.61 (m, 1H), 0.84-0.93 (m, 2H), 0.72-0.79 (m, 2H). |
| I-325 | 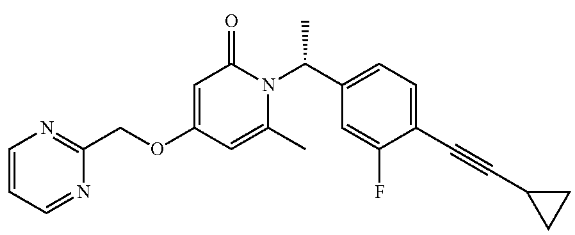 | 404.3 | ¹H NMR (400 MHz, DMSO-d$_6$) δ 8.85 (d, J = 5.2 Hz, 2H), 7.49 (t, J = 4.8 Hz, 1H), 7.34-7.37 (m, 1H), 6.99 (d, J = 11.2 Hz, 1H), 6.88 (d, J = 8.0 Hz, 1H), 5.98 (s, 1H), 5.57-5.64 (m, 2H), 5.23 (s, 2H), 2.08-2.38 (m, 3H), 1.75 (d, J = 6.4 Hz, 3H), 1.54-1.60 (m, 1H), 0.88-0.93 (m, 2H), 0.71-0.75 (m, 2H). |
| I-326 | 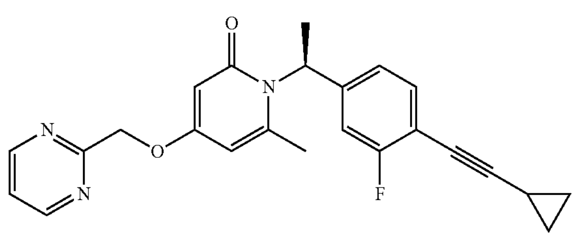 | 404.3 | ¹H NMR (400 MHz, DMSO-d$_6$) δ 8.85 (d, J = 4.8 Hz, 2H), 7.49 (t, J = 4.8 Hz, 1H), 7.35 (t, J = 4.8 Hz, 1H), 6.99 (d, J = 10.8 Hz, 1H), 6.88 (d, J = 7.6 Hz, 1H), 5.98 (s, 1H), 5.58 (br., 2H), 5.23 (s, 2H), 2.27-2.39 (m, 3H), 1.75 (d, J = 6.8 Hz, 3H), 1.54-1.61 (m, 1H), 0.88-0.93 (m, 2H), 0.71-0.75 (m, 2H). |
| I-270 | 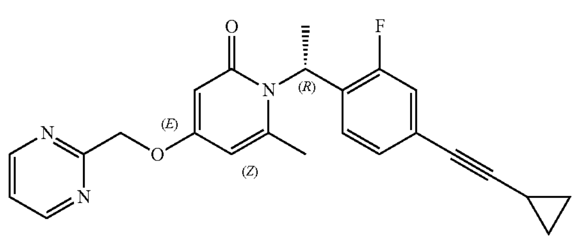 | 404.3 | ¹HNMR (400 MHz, DMSO-d$_6$) δ 8.83 (d, J = 4.8 Hz, 2H), 7.44-7.48 (m, 2H), 7.16 (d, J = 7.6 Hz, 1H), 7.08 (d, J = 11.6 Hz, 1H), 5.93 (s, 1H), 5.48 (br, 2H), 5.18 (s, 2H), 2.36 (br., 3H), 1.75 (d, J = 6.8 Hz, 3H), 1.52-1.56 (m, 1H), 0.86-0.91 (m, 2H), 0.71-0.75 (m, 2H). |

TABLE 17-continued

Characterization Data for Additional Exemplary Compounds

| Compound No. | Chemical Structure | M + 1 ¹H NMR (400 MHz) |
|---|---|---|
| I-320 | 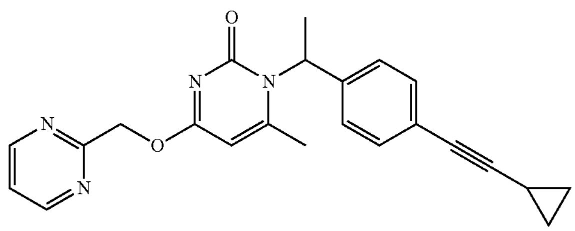 | 387.4 ¹HNMR (400 MHz, DMSO-d$_6$) δ 8.79 (d, J = 4.8 Hz, 2H), 7.44 (t, J = 5.2 Hz, 1H), 7.30 (d, J = 8.0 Hz, 2H), 7.14 (d, J = 8.0 Hz, 2H), 6.09 (s, 1H), 5.70 (br., 1H), 5.45 (s, 2H), 2.35 (br., 3H), 1.76 (d, J = 6.8 Hz, 3H), 1.49-1.55 (m, 1H), 0.85-0.89 (m, 2H), 0.69-0.73 (m, 2H). |
| I-340 | 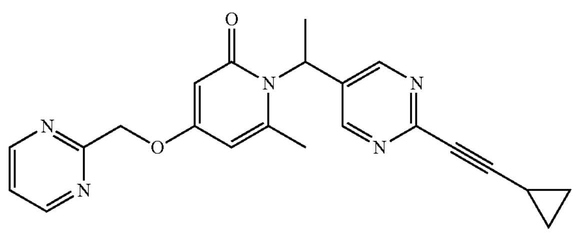 | 388.4 ¹H NMR (400 MHz, DMSO-d$_6$) δ 8.83 (d, J = 5.2 Hz, 2H), 8.54 (s, 2H), 7.48 (t, J = 4.8 Hz, 1H), 6.03 (d, J = 2.4 Hz, 1H), 5.52 (s, 2H), 5.21 (s, 2H), 2.46-2.50 (m, 3H), 1.79 (d, J = 6.8 Hz, 3H), 1.57-1.63 (m, 1H), 0.93-0.98 (m, 2H), 0.79-0.83 (m, 2H). |
| I-302 | 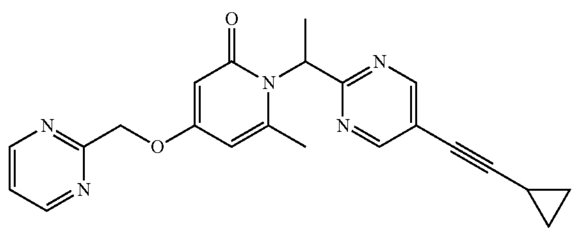 [SMILES: Cc1cc(OCc2ncccn2)cc(=O)n1C(C)c1ncc(C#CC2CC2)cn1] | 388.3 ¹HNMR (400 MHz, DMSO-d$_6$) δ 8.84 (d, J = 4.8 Hz, 2H), 8.69 (s, 2H), 7.49 (t, J = 4.8 Hz, 1H), 5.99 (d, J = 2.0 Hz, 1H), 5.50-5.76 (m, 2H), 5.21 (s, 2H), 2.33 (s, 3H), 1.75 (d, J = 6.4 Hz, 3H), 1.58-1.64 (m, 1H), 0.91-0.94 (m, 2H), 0.77-0.80 (m, 2H). |
| I-318 | 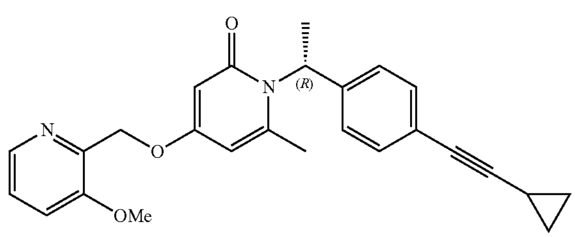 | 415.0 ¹HNMR (400 MHz, CDCl$_3$) 8.24 (d, J = 4.0 Hz, 1H), 7.22-7.33 (m, 4H), 7.08 (d, J = 8.0 Hz, 2H), 5.98 (s, 1H), 5.82 (s, 1H), 5.17 (s, 2H), 3.89 (s, 3H), 1.89-2.26 (m, 3H), 1.82 (d, J = 6.0 Hz, 3H), 1.41-1.45 (m, 1H), 0.83-0.88 (m, 2H), 0.77-0.81 (m, 2H). |
| I-297 | 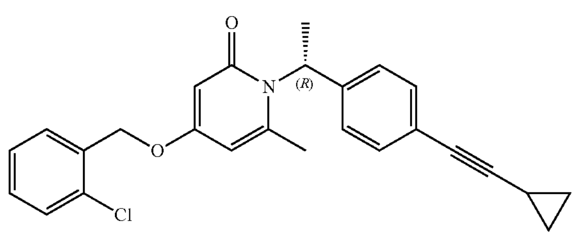 | 418.0 ¹HNMR (400 MHz, CDCl$_3$) 7.39-7.41 (m, 1H), 7.31-7.35 (m, 1H), 7.22-7.27 (m, 4H), 7.03 (d, J = 8.0 Hz, 2H), 5.99 (s, 1H), 5.75 (s, 1H), 5.03 (s, 2H), 1.87-2.01 (m, 3H), 1.77 (d, J = 5.2 Hz, 3H), 1.33-1.40 (m, 1H), 0.76-0.82 (m, 2H), 0.72-0.74 (m, 2H). |
| I-303 | 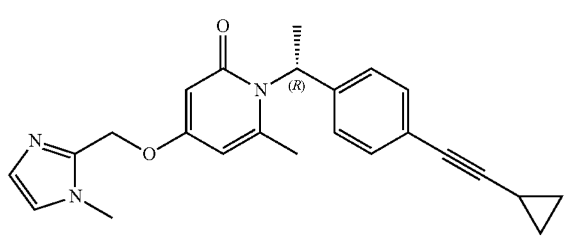 | 388.2 ¹HNMR (400 MHz, DMSO-d$_6$) 7.31 (d, J = 4.4 Hz, 2H), 7.19 (s, 1H), 7.09 (d, J = 7.2 Hz, 2H), 6.88 (s, 1H), 5.89 (br., 2H), 5.51 (br., 1H), 5.08 (s, 2H), 3.65 (s, 3H), 2.22 (br., 3H), 1.77 (s, 3H), 1.44-1.54 (m, 1H), 0.86-0.98 (m, 2H), 0.63-0.80 (m, 2H). |

TABLE 17-continued

Characterization Data for Additional Exemplary Compounds

| Compound No. | Chemical Structure | M + 1 | $^1$H NMR (400 MHz) |
|---|---|---|---|
| I-313 | 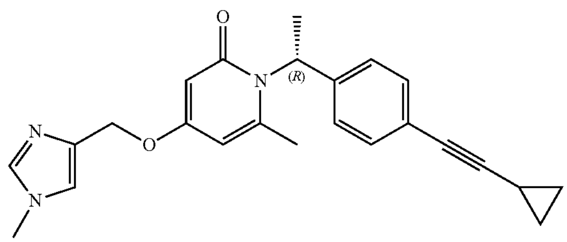 | 388.2 | $^1$HNMR (400 MHz, CDCl$_3$) 7.43 (s, 1H), 7.32 (d, J = 8.0 Hz, 2H), 7.08 (d, J = 8.0 Hz, 2H), 6.97 (s, 1H), 5.97 (s, 1H), 5.74 (s, 1H), 4.93 (s, 2H), 3.69 (s, 3H), 1.82-2.20 (m, 3H), 1.75-1.77 (m, 3H), 1.40-1.47 (m, 1H), 0.81-0.88 (m, 2H), 0.77-0.79 (m, 2H). |
| I-308 | 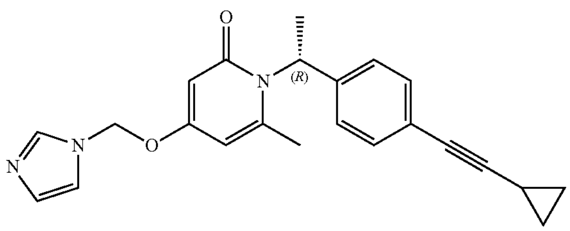 | 374.3 | $^1$HNMR (400 MHz, CDCl$_3$) 7.75 (s, 1H), 7.33 (d, J = 8.4 Hz, 2H), 7.13 (d, J = 7.2 Hz, 2H), 7.08 (d, J = 8.0 Hz, 2H), 5.93 (s, 1H), 5.75 (s, 2H), 5.68 (s, 1H), 2.05-2.17 (m, 3H), 1.83 (d, J = 6.8 Hz, 3H), 1.42-1.46 (m, 1H), 0.84-0.88 (m, 2H), 0.78-0.81 (m, 2H). |
| I-298 | 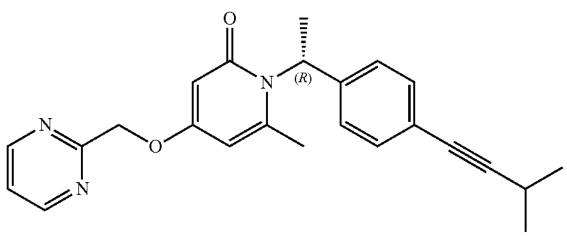 | 388.4 | $^1$H NMR (400 MHz, DMSO-d$_6$) δ 8.85 (d, J = 4.8 Hz, 2H), 7.49 (t, J = 4.8 Hz, 1H), 7.31 (d, J = 6.8 Hz, 2H), 7.09 (d, J = 8.0 Hz, 2H), 5.95 (s, 1H), 5.68 (br., 2H), 5.23 (s, 2H), 2.75-2.82 (m, 1H), 2.16-2.51 (m, 3H), 1.76 (d, J = 6.4 Hz, 3H), 1.20 (d, J = 6.8 Hz, 6H). |
| I-314 | 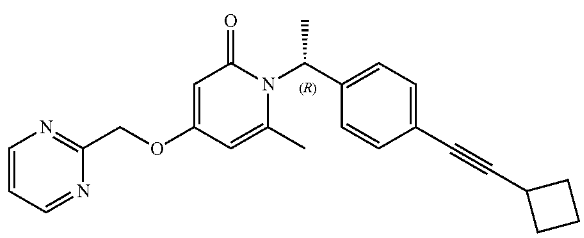 | 400.0 | $^1$H NMR (400 MHz, DMSO-d$_6$) δ 8.85 (d, J = 4.8 Hz, 2H), 7.49 (t, J = 4.8 Hz, 1H), 7.32 (d, J = 7.2 Hz, 2H), 7.09 (d, J = 8.0 Hz, 2H), 5.96 (s, 1H), 5.60 (br., 2H), 5.23 (s, 2H), 3.22-3.30 (m, 1H), 2.25-2.33 (m, 3H), 2.06-2.13 (m, 3H), 1.83-1.97 (m, 3H), 1.76 (d, J = 6.4 Hz, 3H). |
| I-385 | 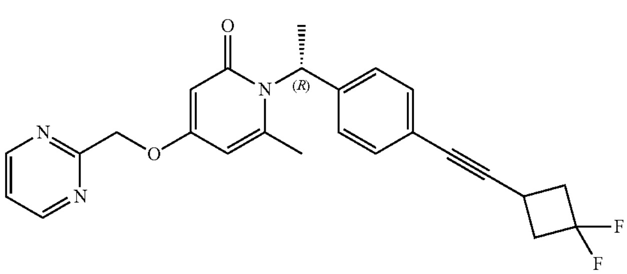 | 436.3 | $^1$HNMR (400 MHz, DMSO-d$_6$) δ 8.85 (d, J = 4.8 Hz, 2H), 7.49 (t, J = 4.8 Hz, 1H), 7.35-7.37 (m, 2H), 7.12 (d, J = 7.6 Hz, 2H), 5.97 (s, 1H), 5.60 (br., 2H), 5.23 (s, 2H), 3.23-3.27 (m, 1H), 2.99-3.06 (m, 2H), 2.68-2.75 (m, 2H), 2.16-2.51 (m, 3H), 1.76 (d, J = 5.2 Hz, 3H). |
| I-341 | 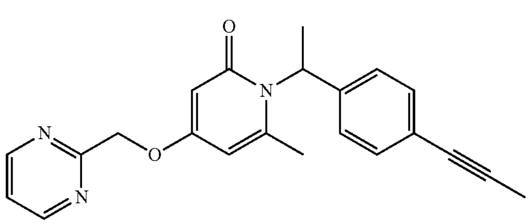 [SMILES: CC#Cc1ccc(C(C)n2c(C)cc(OCc3ncccn3)cc2=O)cc1] | 360.2 | $^1$H NMR (400 MHz, DMSO-d$_6$) δ 8.85 (d, J = 4.8 Hz, 2H), 7.49 (t, J = 4.8 Hz, 1H), 7.33 (d, J = 7.2 Hz, 2H), 7.09 (d, J = 8.0 Hz, 2H), 5.96 (s, 1H), 5.60 (br., 2H), 5.23 (s, 2H), 2.02-2.44 (m, 3H), 1.96 (s, 3H), 1.76 (d, J = 6.0 Hz, 3H). |

TABLE 17-continued

Characterization Data for Additional Exemplary Compounds

| Compound No. | Chemical Structure | M + 1 | $^1$H NMR (400 MHz) |
|---|---|---|---|
| I-341 | 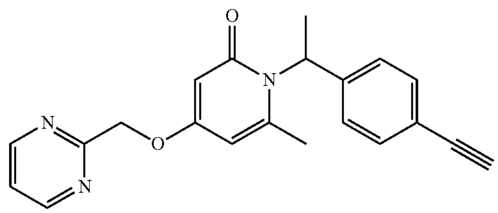 [SMILES: C#Cc1ccc(C(C)n2c(C)cc(OCc3ncccn3)cc2=O)cc1] | 346.2 | $^1$H NMR (400 MHz, DMSO-d$_6$) δ 8.85 (d, J = 4.8 Hz, 2H), 7.49 (t, J = 4.8 Hz, 1H), 7.42 (d, J = 7.2 Hz, 2H), 7.14 (d, J = 8.0 Hz, 2H), 5.97 (s, 1H), 5.63 (br., 2H), 5.23 (s, 2H), 4.15 (s, 1H), 1.84-2.44 (m, 3H), 1.77 (d, J = 6.8 Hz, 3H). |
| I-299 | 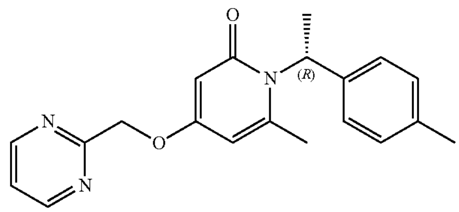 | 336.4 | $^1$H NMR (400 MHz, DMSO-d$_6$) δ 8.85 (d, J = 4.8 Hz, 2H), 7.49 (t, J = 4.8 Hz, 1H), 7.12 (d, J = 7.6 Hz, 2H), 7.02 (d, J = 8.0 Hz, 2H), 5.92 (s, 1H), 5.41-5.88 (m, 1H), 5.23 (s, 2H), 2.27 (s, 3H), 1.85-2.22 (m, 3H), 1.75 (d, J = 6.8 Hz, 3H). |
| I-309 | 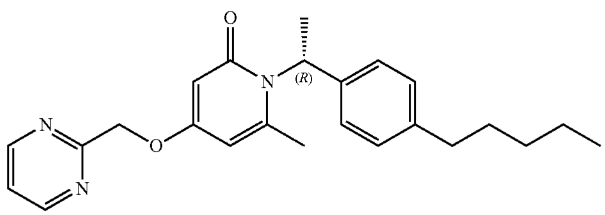 | 392.4 | $^1$HNMR (400 MHz, CDCl$_3$) δ 8.78 (d, J = 4.8 Hz, 2H), 7.26-7.28 (m, 1H), 7.07-7.13 (m, 4H), 5.92 (s, 2H), 5.26 (s, 2H), 2.56 (t, J = 7.6 Hz, 2H), 2.06 (br., 3H), 1.84 (d, J = 6.4 Hz, 3H), 1.55-1.62 (m, 2H), 1.25-1.35 (m, 4H), 0.88 (t, J = 6.8 Hz, 3H). |
| I-310 | 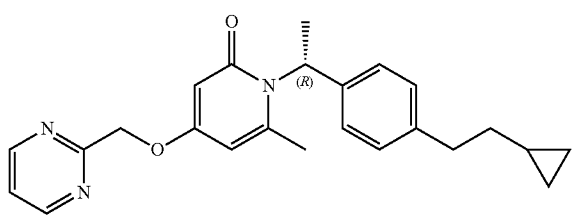 | 390.4 | $^1$HNMR (400 MHz, CDCl$_3$) δ 8.78 (d, J = 4.8 Hz, 2H), 7.26-7.27 (m, 1H), 7.08-7.14 (m, 4H), 5.92 (s, 2H), 5.25 (s, 2H), 2.66-2.69 (m, 2H), 2.05 (br., 3H), 1.78-1.83 (m, 3H), 1.45-1.50 (m, 2H), 0.63-0.72 (m, 1H), 0.39-0.41 (m, 2H), 0.00-0.01 (m, 2H). |
| I-300 | 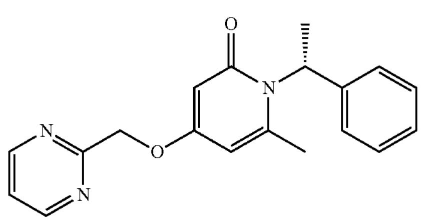 [SMILES: Cc1cc(OCc2ncccn2)cc(=O)n1[C@H](C)c1ccccc1] | 322.1 | $^1$HNMR (400 MHz, DMSO-d$_6$) δ 8.85 (d, J = 5.2 Hz, 2H), 7.49 (t, J = 5.2 Hz, 1H), 7.30-7.34 (m, 2H), 7.20-7.24 (m, 1H), 7.14 (d, J = 7.6 Hz, 2H), 5.94 (s, 1H), 5.64 (s, 1H), 5.23 (s, 2H), 2.06-2.21 (m, 3H), 1.78 (d, J = 6.8 Hz, 3H). |
| I-304 | 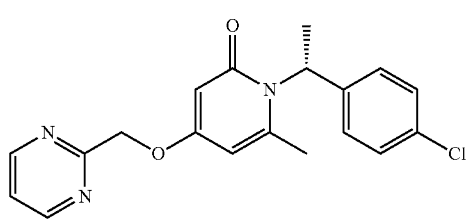 [SMILES: Cc1cc(OCc2ncccn2)cc(=O)n1[C@H](C)c1ccc(Cl)cc1] | 356.3 | $^1$H NMR (400 MHz, DMSO-d$_6$) δ 8.85 (d, J = 5.2 Hz, 2H), 7.49 (t, J = 4.8 Hz, 1H), 7.36 (d, J = 7.6 Hz, 2H), 7.16 (d, J = 8.4 Hz, 2H), 5.97 (s, 1H), 5.61 (br., 2H), 5.22 (s, 2H), 2.29 (br., 3H), 1.77 (d, J = 6.8 Hz, 3H). |

TABLE 17-continued

Characterization Data for Additional Exemplary Compounds

| Compound No. | Chemical Structure | M + 1 | ¹H NMR (400 MHz) |
|---|---|---|---|
| I-386 | 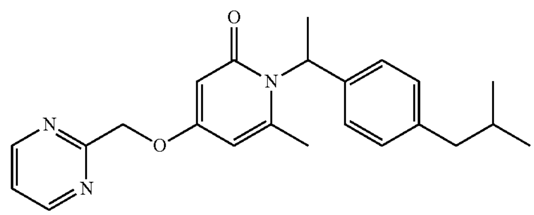 [SMILES: Cc1cc(OCc2ncccn2)cc(=O)n1C(C)c1ccc(CC(C)C)cc1] | 378.4 | ¹HNMR (400 MHz, CDCl₃) δ 8.78 (d, J = 4.8 Hz, 2H), 7.26-7.29 (m, 1H), 7.08 (s, 4H), 5.88 (s, 1H), 5.85 (s, 1H), 5.25 (s, 2H), 2.44 (d, J = 7.6 Hz, 2H), 1.96-2.21 (m, 3H), 1.75-1.88 (m, 4H), 0.87 (d, J = 6.8 Hz, 6H). |
| I-311 | 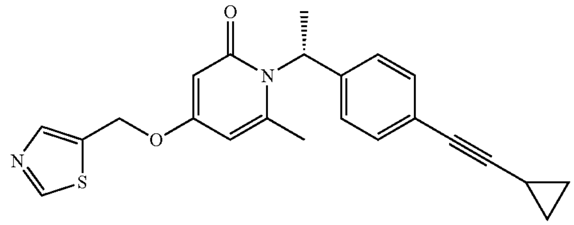 [SMILES: Cc1cc(OCc2cncs2)cc(=O)n1[C@H](C)c1ccc(C#CC2CC2)cc1] | 391.2 | ¹HNMR (400 MHz, CDCl₃) 8.85 (s, 1H), 7.92 (s, 1H), 7.33 (d, J = 8.4 Hz, 2H), 7.09 (d, J = 8.0 Hz, 2H), 5.96 (s, 1H), 5.73 (s, 1H), 5.20 (s, 2H), 2.00-2.51 (m, 3H), 1.84 (d, J = 6.4 Hz, 3H), 1.42-1.46 (m, 1H), 0.83-0.88 (m, 2H), 0.77-0.81 (m, 2H). |
| I-315 | 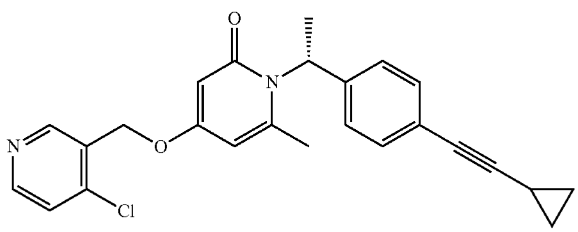 [SMILES: Cc1cc(OCc2cnccc2Cl)cc(=O)n1[C@H](C)c1ccc(C#CC2CC2)cc1] | 419.2 | ¹HNMR (400 MHz, CDCl₃) δ 8.75 (s, 1H), 8.58 (d, J = 5.2 Hz, 1H), 7.65 (d, J = 5.2 Hz, 1H), 7.31 (d, J = 6.8 Hz, 2H), 7.10 (d, J = 7.6 Hz, 2H), 5.82-5.93 (m, 2H), 5.15 (s, 2H), 2.20 (br., 3H), 1.78 (d, J = 6.0 Hz, 3H), 1.51-1.55 (m, 1H), 0.85-0.90 (m, 2H), 0.69-0.73 (m, 2H). |
| I-305 | 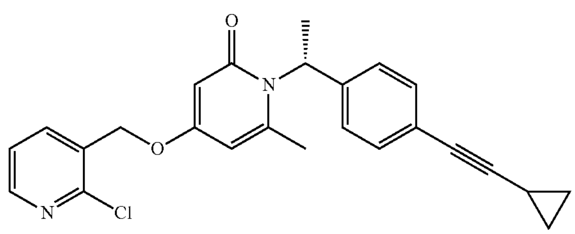 [SMILES: Cc1cc(OCc2cccnc2Cl)cc(=O)n1[C@H](C)c1ccc(C#CC2CC2)cc1] | 419.4 | ¹HNMR (400 MHz, DMSO-d₆) δ 8.44 (dd, J = 1.2 Hz, 4.4 Hz, 1H), 8.02 (d, J = 6.4 Hz, 1H), 7.51 (dd, J = 4.8 Hz, 7.2 Hz, 1H), 7.31 (d, J = 7.2 Hz, 2H), 7.09 (d, J = 8.4 Hz, 2H), 5.96 (s, 1H), 5.78 (br., 2H), 5.11 (s, 2H), 2.25 (br., 3H), 1.78 (d, J = 6.0 Hz, 3H), 1.49-1.55 (m, 1H), 0.85-0.89 (m, 2H), 0.69-0.73 (m, 2H). |
| I-306 | 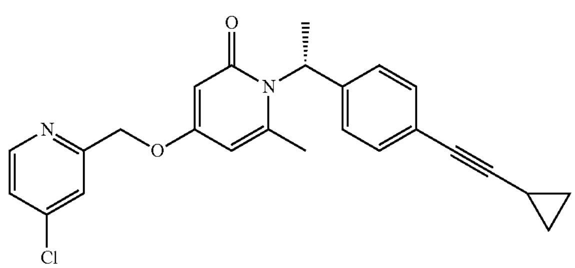 [SMILES: Cc1cc(OCc2cc(Cl)ccn2)cc(=O)n1[C@H](C)c1ccc(C#CC2CC2)cc1] | 419.3 | ¹H NMR (400 MHz, DMSO-d₆) δ 8.57 (d, J = 5.6 Hz, 1H), 7.63 (s, 1H), 7.53 (dd, J = 1.2 Hz, 5.2 Hz, 1H), 7.31 (d, J = 7.2 Hz, 2H), 7.08 (d, J = 8.0 Hz, 2H), 6.00 (s, 1H), 5.31-5.92 (m, 2H), 5.13 (s, 2H), 2.16-2.51 (m, 3H), 1.77 (d, J = 6.0 Hz, 3H), 1.50-1.54 (m, 1H), 0.85-0.89 (m, 2H), 0.69-0.73 (m, 2H). |
| I-301 | 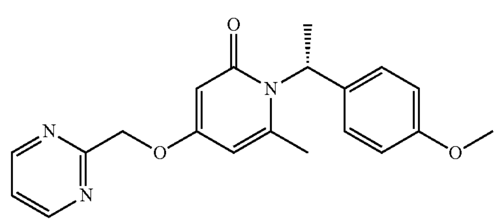 [SMILES: COc1ccc([C@@H](C)n2c(C)cc(OCc3ncccn3)cc2=O)cc1] | 352.1 | ¹HNMR (400 MHz, CDCl₃) δ 8.70 (d, J = 5.2 Hz, 2H), 7.18-7.21 (m, 1H), 7.04 (d, J = 8.4 Hz, 2H), 6.76 (d, J = 8.8 Hz, 2H), 5.80 (s, 1H), 5.76 (s, 1H), 5.17 (s, 2H), 3.70 (s, 3H), 1.98-2.08 (m, 3H), 1.75 (d, J = 6.4 Hz, 3H). |

TABLE 17-continued

Characterization Data for Additional Exemplary Compounds

| Compound No. | Chemical Structure | M + 1 | $^1$H NMR (400 MHz) |
|---|---|---|---|
| I-342 | 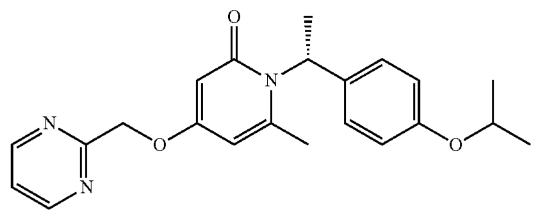 | 759.4 | $^1$HNMR (400 MHz, CDCl$_3$) δ 8.78 (d, J = 4.8 Hz, 2H), 7.28-7.33 (m, 1H), 7.09 (d, J = 8.0 Hz, 2H), 6.82 (d, J = 8.4 Hz, 2H), 5.89 (s, 2H), 5.25 (s, 2H), 4.48-4.54 (m, 1H), 2.10 (br., 3H), 1.82 (d, J = 4.8 Hz, 3H), 1.32 (d, J = 6.0 Hz, 6H). |
| I-343 | 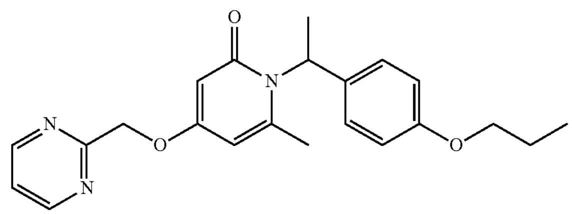 [SMILES: CCCOc1ccc(C(C)n2c(C)cc(OCc3ncccn3)cc2=O)cc1] | 759.3 | $^1$HNMR (400 MHz, CDCl$_3$) δ 8.79 (d, J = 4.8 Hz, 2H), 7.28-7.31 (m, 1H), 7.09 (d, J = 8.8 Hz, 2H), 6.82-6.85 (m, 2H), 6.52-6.54 (m, 1H), 6.15-6.16 (m, 1H), 5.33 (s, 2H), 3.90 (t, J = 6.8 Hz, 2H), 1.87-2.03 (m, 5H), 1.71-1.84 (m, 3H), 1.03 (t, J = 7.6 Hz, 3H). |
| I-345 | 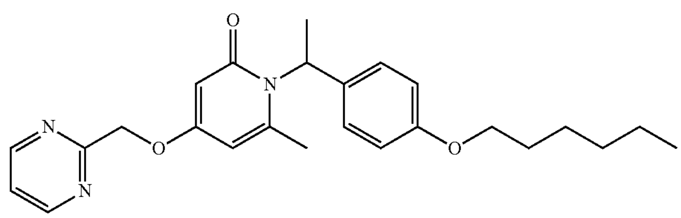 [SMILES: CCCCCCOc1ccc(C(C)n2c(C)cc(OCc3ncccn3)cc2=O)cc1] | 843.4 | $^1$H NMR (400 MHz, DMSO-d$_6$) δ 8.87 (dd, J = 4.8 Hz, 12.8 Hz, 2H), 7.49 (t, J = 4.8 Hz, 1H), 7.05 (d, J = 7.6 Hz, 2H), 6.86 (d, J = 7.6 Hz, 2H), 5.91 (s, 1H), 5.64 (br., 2H), 5.23 (s, 2H), 3.92 (t, J = 6.8 Hz, 2H), 1.93-2.33 (m, 3H), 1.70-1.75 (m, 3H), 1.65-1.68 (m, 2H), 1.33-1.41 (m, 2H), 1.27-1.30 (m, 4H), 0.87 (t, J = 6.8 Hz, 3H). |
| I-307 | 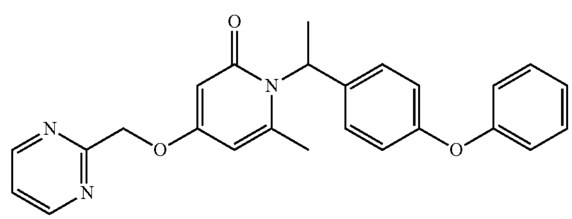 [SMILES: Cc1cc(OCc2ncccn2)cc(=O)n1C(C)c1ccc(Oc2ccccc2)cc1] | 414.1 | $^1$H NMR (400 MHz, DMSO-d$_6$) δ 8.85 (d, J = 4.8 Hz, 2H), 7.49 (t, J = 4.8 Hz, 1H), 7.38 (t, J = 7.2 Hz, 2H), 7.12-7.18 (m, 3H), 6.97-6.99 (m, 4H), 5.95 (s, 1H), 5.63 (br., 2H), 5.23 (s, 2H), 2.20-2.33 (m, 3H), 1.78 (d, J = 5.2 Hz, 3H). |
| I-316 | 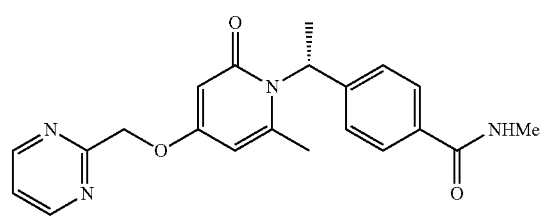 [SMILES: CNC(=O)c1ccc([C@@H](C)n2c(C)cc(OCc3ncccn3)cc2=O)cc1] | 379.2 | $^1$HNMR (400 MHz, DMSO-d$_6$) δ 8.85 (d, J = 5.2 Hz, 2H), 8.39 (s, 1H), 7.76 (d, J = 6.8 Hz, 2H), 7.49 (t, J = 4.8 Hz, 1H), 7.20 (d, J = 8.0 Hz, 2H), 5.98 (s, 1H), 5.49-5.68 (m, 2H), 5.23 (s, 2H), 2.77 (d, J = 4.4 Hz, 3H), 1.89-2.33 (m, 3H), 1.80 (d, J = 6.4 Hz, 3H). |
| I-317 | 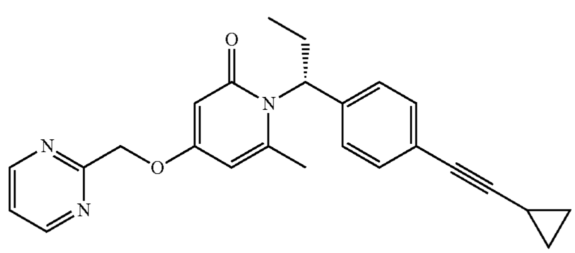 [SMILES: CC[C@H](c1ccc(C#CC2CC2)cc1)n1c(C)cc(OCc2ncccn2)cc1=O] | 400.3 | $^1$HNMR (400 MHz, CDCl$_3$) δ 8.78 (d, J = 4.8 Hz, 2H), 7.28-7.32 (m, 3H), 7.11-7.16 (m, 2H), 5.93-6.10 (m, 2H), 5.28 (s, 2H), 2.41-2.47 (m, 2H), 2.05-2.19 (m, 3H), 1.40-1.47 (m, 1H), 0.96 (t, J = 6.8 Hz, 3H), 0.78-0.88 (m, 4H). |

TABLE 17-continued

Characterization Data for Additional Exemplary Compounds

| Compound No. | Chemical Structure | M + 1 | ¹H NMR (400 MHz) |
|---|---|---|---|
| I-321 | 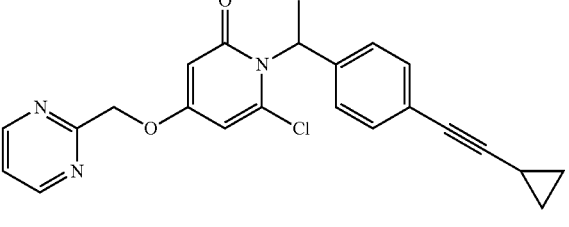 | 811.3 | ¹HNMR (400 MHz, CDCl₃) δ 8.78 (d, J = 4.8 Hz, 2H), 7.27-7.32 (m, 3H), 7.12 (d, J = 6.8 Hz, 2H), 6.50 (br., 1H), 6.16 (s, 1H), 5.87 (s, 1H), 5.25 (s, 2H), 1.89 (d, J = 6.8 Hz, 3H), 1.40-1.47 (m, 1H), 0.82-0.88 (m, 2H), 0.77-0.81 (m, 2H). |
| I-322 | 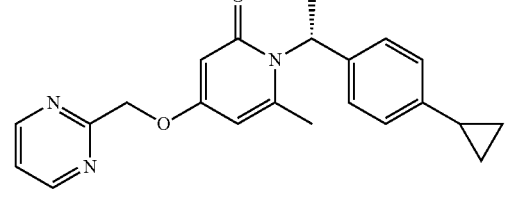 | 362.4 | ¹H NMR (400 MHz, DMSO-d₆) δ 8.85 (d, J = 4.8 Hz, 2H), 7.49 (t, J = 4.8 Hz, 1H), 7.01 (s, 4H), 5.92 (s, 1H), 5.62 (br., 1H), 5.23 (s, 2H), 2.16-2.51 (m, 3H), 1.84-1.89 (m, 1H), 1.74 (d, J = 6.4 Hz, 3H), 0.89-0.94 (m, 2H), 0.60-0.64 (m, 2H). |
| I-387 | 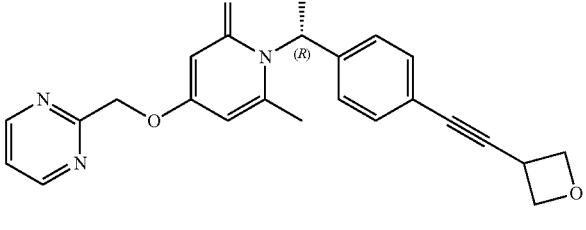 | 402.3 | ¹HNMR (400 MHz, CDCl₃) δ 8.79 (d, J = 5.2 Hz, 2H), 7.36 (d, J = 8.4 Hz, 2H), 7.26-7.29 (m, 1H), 7.13 (d, J = 7.6 Hz, 2H), 5.92 (s, 1H), 5.87 (s, 1H), 5.26 (s, 2H), 4.82-4.89 (m, 2H), 4.79-4.81 (m, 2H), 4.04-4.09 (m, 1H), 1.96-2.21 (m, 3H), 1.85 (d, J = 4.4 Hz, 3H). |
| I-389 | 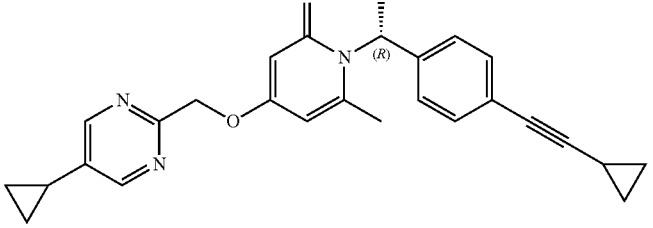 | 426.3 | ¹HNMR (400 MHz, DMSO-d₆) δ 8.60 (s, 2H), 7.30 (d, J = 5.6 Hz, 2H), 7.07 (d, J = 8.0 Hz, 2H), 5.93 (s, 1H), 5.54 (br., 2H), 5.16 (s, 2H), 2.36 (br., 3H), 1.92-1.99 (m, 1H), 1.75 (d, J = 5.6 Hz, 3H), 1.49-1.56 (m, 1H), 1.02-1.07 (m, 2H), 0.85-0.89 (m, 4H), 0.69-0.73 (m, 2H). |
| I-323 | 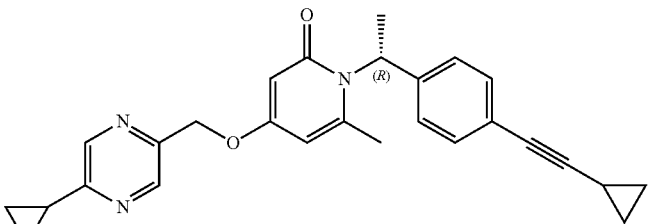 | 425.4 | ¹HNMR (400 MHz, DMSO-d₆) δ 8.64 (d, J = 0.8 Hz, 1H), 8.58 (s, 1H), 7.31 (d, J = 7.6 Hz, 1H), 7.08 (d, J = 8.0 Hz, 1H), 5.93 (s, 1H), 5.71-5.88 (m, 2H), 5.12 (s, 2H), 2.29-2.50 (m, 3H), 2.20-2.26 (m, 1H), 1.77 (d, J = 6.0 Hz, 3H), 1.49-1.56 (m, 1H), 1.02-1.09 (m, 2H), 0.93-0.98 (m, 2H), 0.83-0.91 (m, 2H), 0.69-0.73 (m, 2H). |
| I-327 | 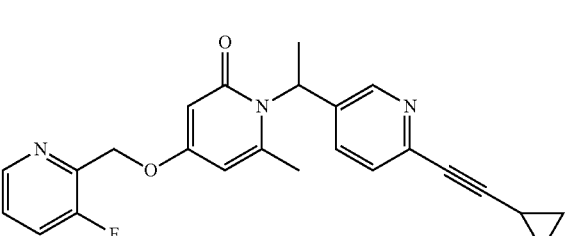 | 404.3 | ¹H NMR (400 MHz, DMSO-d₆) δ 8.46 (d, J = 4.4 Hz, 1H), 8.31 (d, J = 2.0 Hz, 1H), 7.81 (t, J = 9.6 Hz, 1H), 7.50-7.57 (m, 2H), 7.35 (d, J = 8.4 Hz, 1H), 5.94 (s, 1H), 5.74 (s, 1H), 5.48 (br., 1H), 5.16 (s, 2H), 2.26-2.51 (m, 3H), 1.81 (d, J = 6.8 Hz, 3H), 1.55-1.59 (m, 1H), 0.89-0.94 (m, 2H), 0.74-0.78 (m, 2H). |

TABLE 17-continued

Characterization Data for Additional Exemplary Compounds

| Compound No. | Chemical Structure | M + 1 | ¹H NMR (400 MHz) |
|---|---|---|---|
| I-375 | 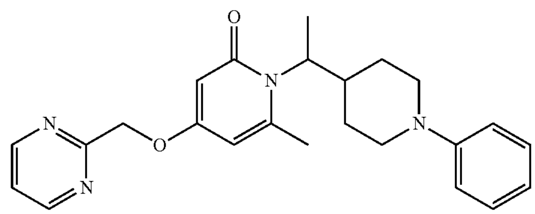 [SMILES: Cc1cc(OCc2ncccn2)cc(=O)n1C(C)C1CCN(c2ccccc2)CC1] | 405.3 | ¹HNMR (400 MHz, DMSO-d6) δ 8.85 (d, J = 5.2 Hz, 2H), 7.49 (t, J = 5.2 Hz, 1H), 7.18 (t, J = 8.8 Hz, 2H), 6.90 (d, J = 8.0 Hz, 2H), 6.74 (t, J = 7.6 Hz, 1H), 5.92 (d, J = 2.8 Hz, 1H), 5.58 (d, J = 2.8 Hz, 1H), 5.22 (s, 2H), 3.79-3.83 (m, 1H), 3.73 (d, J = 12.0 Hz, 1H), 3.62 (d, J = 12.0 Hz, 1H), 2.54-2.64 (m, 2H), 2.39-2.45 (m, 1H), 2.29 (s, 3H), 1.87 (d, J = 12.4 Hz, 1H), 1.46 (d, J = 6.8 Hz, 3H), 1.25-1.38 (m, 2H), 1.13-1.19 (m, 1H). |
| I-376 | 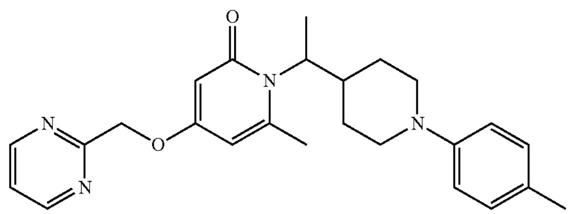 [SMILES: Cc1ccc(N2CCC(C(C)n3c(C)cc(OCc4ncccn4)cc3=O)CC2)cc1] | 419.4 | ¹HNMR (400 MHz, DMSO-d6) δ 8.85 (d, J = 4.8 Hz, 2H), 7.49 (t, J = 5.2 Hz, 1H), 6.99 (d, J = 8.4 Hz, 2H), 6.80 (d, J = 8.4 Hz, 2H), 5.92 (d, J = 2.4 Hz, 1H), 5.58 (d, J = 2.8 Hz, 1H), 5.21 (s, 2H), 3.77-3.83 (m, 1H), 3.64 (d, J = 11.6 Hz, 1H), 3.53 (d, J = 12.0 Hz, 1H), 2.54-2.64 (m, 1H), 2.48-2.50 (m, 1H), 2.34-2.42 (m, 1H), 2.29 (s, 3H), 2.18 (s, 3H), 1.86 (d, J = 12.4 Hz, 1H), 1.45 (d, J = 6.8 Hz, 3H), 1.10-1.37 (m, 3H). |
| I-360 | 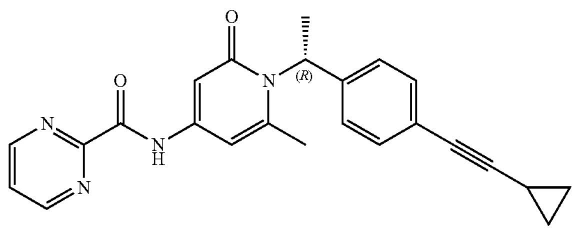 | 399.2 | ¹HNMR (400 MHz, DMSO-d₆) δ 10.74 (s, 1H), 9.05 (d, J = 4.8 Hz, 2H), 7.77 (t, J = 4.8 Hz, 1H), 7.32 (d, J = 7.2 Hz, 2H), 7.12 (d, J = 8.0 Hz, 2H), 6.91 (br., 1H), 6.63 (s, 1H), 2.31 (br., 3H), 1.80 (d, J = 6.4 Hz, 3H), 1.50-1.56 (m, 1H), 0.85-0.89 (m, 2H), 0.69-0.73 (m, 2H). |
| I-395 | 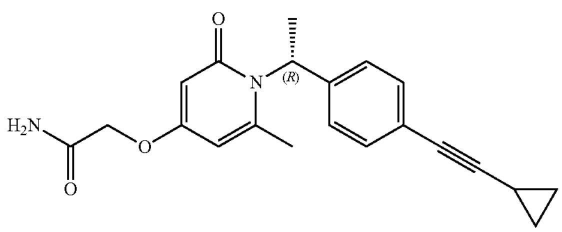 | 351.4 | ¹HNMR (400 MHz, DMSO-d₆) δ 7.54 (s, 1H), 7.39 (s, 1H), 7.31 (d, J = 7.2 Hz, 2H), 7.08 (d, J = 8.0 Hz, 2H), 5.92 (s, 1H), 5.54 (br., 2H), 4.40 (s, 2H), 2.33 (br., 3H), 1.76 (d, J = 6.0 Hz, 3H), 1.49-1.56 (m, 1H), 0.85-0.89 (m, 2H), 0.69-0.73 (m, 2H). |
| I-394 | 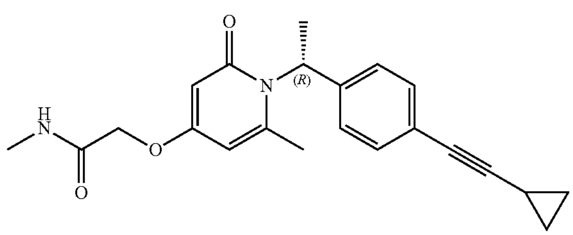 | 365.4 | ¹HNMR (400 MHz, DMSO-d₆) δ 8.01-8.08 (m, 1H), 7.31 (d, J = 7.2 Hz, 2H), 7.08 (d, J = 8.0 Hz, 2H), 5.92 (s, 1H), 5.55 (br., 2H), 4.43 (s, 2H), 2.64 (d, J = 4.4 Hz, 3H), 2.32 (br., 3H), 1.76 (d, J = 5.6 Hz, 3H), 1.50-1.55 (m, 1H), 0.85-0.89 (m, 2H), 0.69-0.73 (m, 2H). |
| I-393 | 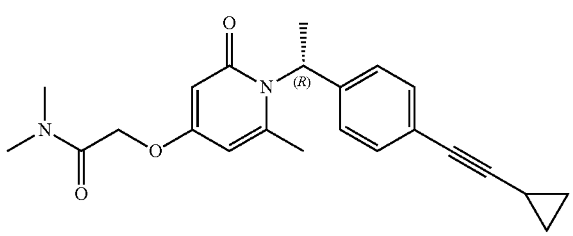 | 379.4 | ¹HNMR (400 MHz, DMSO-d₆) δ 7.31 (d, J = 6.0 Hz, 2H), 7.08 (d, J = 8.0 Hz, 2H), 5.91 (s, 1H), 5.59 (br., 2H), 4.79 (s, 2H), 2.95 (s, 3H), 2.84 (s, 3H), 2.38 (br., 3H), 1.76 (d, J = 5.2 Hz, 3H), 1.50-1.55 (m, 1H), 0.85-0.89 (m, 2H), 0.69-0.73 (m, 2H). |

TABLE 17-continued

Characterization Data for Additional Exemplary Compounds

| Compound No. | Chemical Structure | M + 1 | $^1$H NMR (400 MHz) |
|---|---|---|---|
| I-329 | 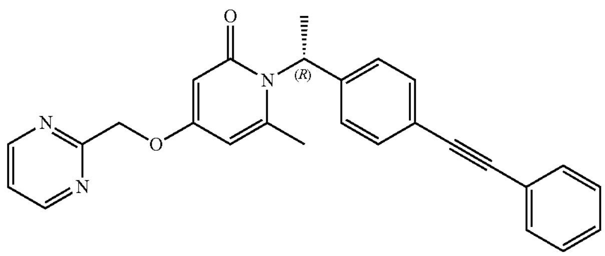 | 422.4 | $^1$H NMR (400 MHz, DMSO-d$_6$) δ 8.86 (d, J = 4.8 Hz, 2H), 7.48-7.56 (m, 5H), 7.41-7.44 (m, 3H), 7.19 (d, J = 8.0 Hz, 2H), 5.98 (s, 1H), 5.85 (br., 1H), 5.24 (s, 2H), 2.26-2.51 (m, 3H), 1.79 (d, J = 6.8 Hz, 3H). |
| I-374 | 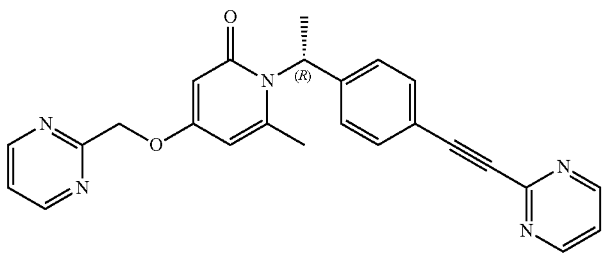 | 424.3 | $^1$HNMR (400 MHz, CDCl$_3$) δ 8.79 (d, J = 4.8 Hz, 2H), 8.76 (d, J = 5.2 Hz, 2H), 7.64 (s, 1H), 7.62 (s, 1H), 7.20-7.29 (m, 4H), 5.93 (s, 1H), 5.84 (br., 1H), 5.26 (s, 2H), 2.00-2.35 (m, 3H), 1.86-1.88 (m, 3H). |
| I-346 | | 388.3 | $^1$H NMR (400 MHz, DMSO-d$_6$) δ 8.86 (d, J = 4.4 Hz, 2H), 7.49 (t, J = 4.8 Hz, 1H), 7.27 (d, J = 6.4 Hz, 2H), 7.04 (d, J = 7.6 Hz, 2H), 6.43 (d, J = 16.0 Hz, 1H), 5.93 (s, 1H), 5.79 (dd, J = 9.2 Hz, 15.6 Hz, 1H), 5.63 (br., 1H), 5.23 (s, 2H), 2.26-2.51 (m, 3H), 1.75 (d, J = 5.6 Hz, 3H), 1.54-1.58 (m, 1H), 0.76-0.80 (m, 2H), 0.47-0.51 (m, 2H). |
| I-346 | | 438.3 | $^1$H NMR (400 MHz, DMSO-d$_6$) δ 8.86 (d, J = 4.8 Hz, 2H), 7.48-7.57 (m, 5H), 7.20 (d, J = 8.0 Hz, 2H), 7.15 (d, J = 8.4 Hz, 2H), 5.97 (s, 1H), 5.64 (br., 2H), 5.24 (s, 2H), 2.26-2.51 (m, 3H), 1.92-1.96 (m, 1H), 1.82 (s, 3H), 0.94-0.99 (m, 2H), 0.68-0.72 (m, 2H). |
| I-347 | 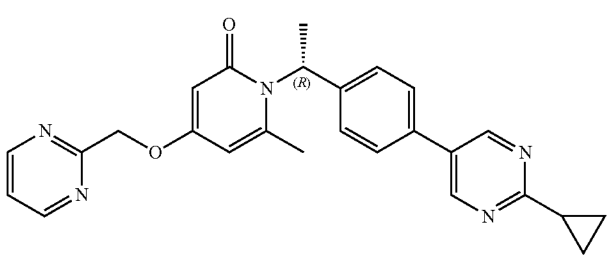 | 440.1 | $^1$H NMR (400 MHz, DMSO-d$_6$) δ 8.93 (s, 2H), 8.85 (d, J = 4.8 Hz, 2H), 7.69 (d, J = 3.6 Hz, 2H), 7.49 (t, J = 4.8 Hz, 1H), 7.26 (d, J = 8.0 Hz, 2H), 5.98 (s, 1H), 5.64 (br., 2H), 5.24 (s, 2H), 2.23-2.49 (m, 4H), 1.83 (d, J = 4.8 Hz, 3H), 1.02-1.09 (m, 4H). |
| I-344 | 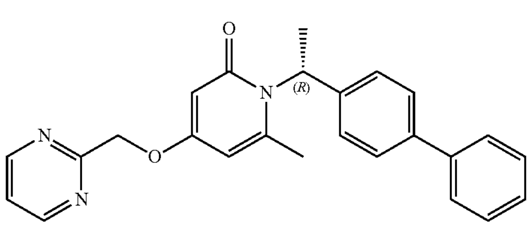 | 398.4 | $^1$H NMR (400 MHz, DMSO-d$_6$) δ 8.86 (d, J = 4.4 Hz, 2H), 7.61-7.69 (m, 4H), 7.43-7.49 (m, 3H), 7.33-7.37 (m, 1H), 7.23 (d, J = 7.2 Hz, 2H), 5.98 (s, 1H), 5.63 (br., 2H), 5.25 (s, 2H), 2.26-2.51 (m, 3H), 1.83 (s, 3H). |

TABLE 17-continued

Characterization Data for Additional Exemplary Compounds

| Compound No. | Chemical Structure | M + 1 | $^1$H NMR (400 MHz) |
|---|---|---|---|
| I-368 | 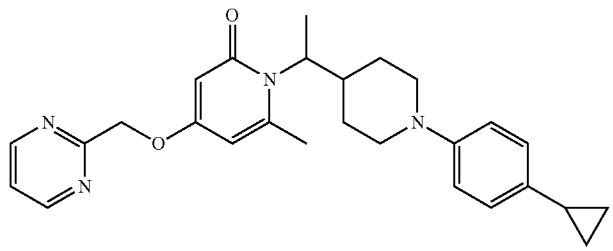 [SMILES: Cc1cc(OCc2ncccn2)cc(=O)n1C(C)C1CCN(c2ccc(C3CC3)cc2)CC1] | 445.3 | $^1$H NMR (400 MHz, DMSO-d$_6$) δ 8.85 (d, J = 4.8 Hz, 2H), 7.49 (t, J = 4.8 Hz, 1H), 6.90 (d, J = 8.8 Hz, 2H), 6.79 (d, J = 8.8 Hz, 2H), 5.92 (d, J = 2.8 Hz, 1H), 5.57 (d, J = 2.8 Hz, 1H), 5.21 (s, 2H), 3.79-3.83 (m, 1H), 3.63 (d, J = 11.6 Hz, 1H), 3.52 (d, J = 12.4 Hz, 1H), 2.51-2.60 (m, 1H), 2.33-2.50 (m, 2H), 2.29 (s, 3H), 1.75-1.87 (m, 2H), 1.45 (d, J = 6.4 Hz, 3H), 1.23-1.30 (m, 2H), 1.13-1.17 (m, 1H), 0.81-0.86 (m, 2H), 0.51-0.55 (m, 2H). |
| I-377 | 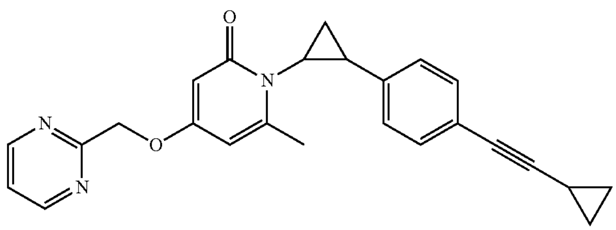 [SMILES: Cc1cc(OCc2ncccn2)cc(=O)n1C1CC1c1ccc(C#CC2CC2)cc1] | 398.3 | $^1$HNMR (400 MHz, DMSO-d$_6$) δ 8.85 (d, J = 4.8 Hz, 2H), 7.49 (t, J = 4.8 Hz, 1H), 7.28 (d, J = 8.4 Hz, 2H), 7.20 (d, J = 8.4 Hz, 2H), 5.95 (d, J = 2.4 Hz, 1H), 5.60 (d, J = 2.8 Hz, 1H), 5.22 (s, 2H), 2.91-2.95 (m, 1H), 2.30 (s, 3H), 2.24-2.28 (m, 1H), 1.49-1.63 (m, 2H), 1.41-1.46 (m, 1H), 0.85-0.89 (m, 2H), 0.69-0.73 (m, 2H). |
| I-354 | 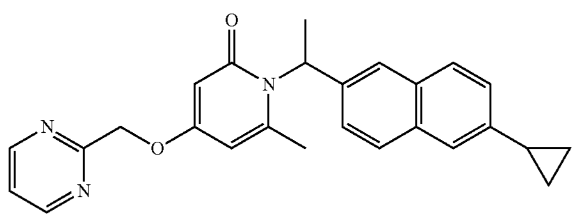 [SMILES: Cc1cc(OCc2ncccn2)cc(=O)n1C(C)c1ccc2cc(C3CC3)ccc2c1] | 412.3 | $^1$H NMR (400 MHz, DMSO-d$_6$) δ 8.86 (d, J = 4.8 Hz, 2H), 7.67-7.79 (m, 3H), 7.56 (s, 1H), 7.49 (t, J = 4.8 Hz, 1H), 7.14-7.22 (m, 2H), 5.96 (s, 1H), 5.65 (br., 2H), 5.24 (s, 2H), 2.03-2.51 (m, 4H), 1.87 (d, J = 4.8 Hz, 3H), 0.99-1.03 (m, 2H), 0.77-0.78 (m, 2H). |
| I-355 | 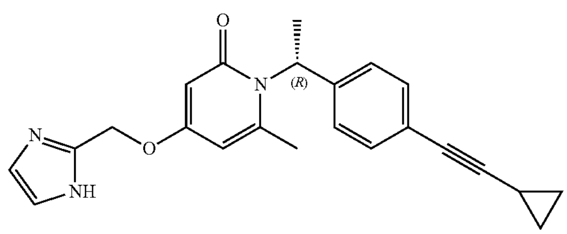 | 374.3 | $^1$HNMR (400 MHz, DMSO-d$_6$) δ 7.26-7.32 (m, 2H), 7.08 (d, J = 7.6 Hz, 2H), 6.88 (s, 2H), 5.81 (s, 1H), 5.38 (br., 1H), 3.83 (s, 2H), 2.20 (br., 3H), 1.71-1.77 (m, 3H), 1.49-1.55 (m, 1H), 0.85-0.89 (m, 2H), 0.69-0.72 (m, 2H). |
| I-356 | 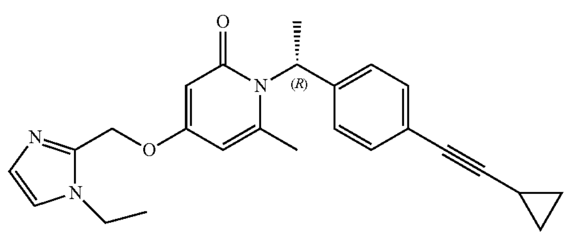 | 402.4 | $^1$HNMR (400 MHz, CDCl$_3$) δ 7.33 (d, J = 8.0 Hz, 2H), 7.06-7.11 (m, 3H), 6.99 (s, 1H), 6.01 (s, 1H), 5.71 (s, 1H), 5.04 (s, 2H), 4.01 (q, J = 7.2 Hz, 2H), 1.98 (br., 3H), 1.83 (d, J = 5.6 Hz, 3H), 1.40-1.46 (m, 4H), 0.77-0.89 (m, 4H). |
| I-348 | 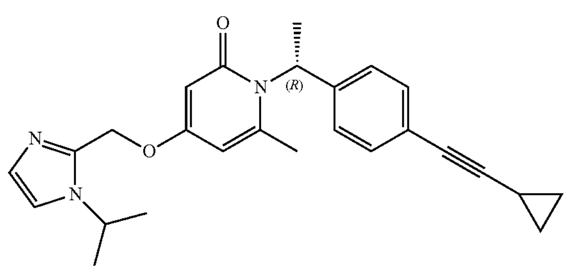 | 416.3 | $^1$HNMR (400 MHz, CDCl$_3$) δ 7.33 (d, J = 8.4 Hz, 2H), 7.05-7.11 (m, 4H), 6.02 (s, 1H), 5.71 (s, 1H), 5.05 (s, 2H), 4.40-4.47 (m, 1H), 1.91-1.98 (m, 3H), 1.83 (d, J = 6.0 Hz, 3H), 1.47 (d, J = 6.8 Hz, 6H), 1.40-1.44 (m, 1H), 0.77-0.89 (m, 4H). |

TABLE 17-continued

Characterization Data for Additional Exemplary Compounds

| Compound No. | Chemical Structure | M + 1 | ¹H NMR (400 MHz) |
|---|---|---|---|
| I-349 | 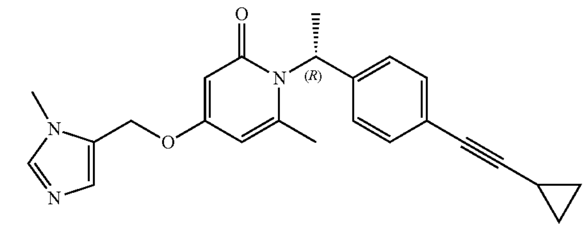 | 388.3 | ¹HNMR (400 MHz, DMSO-d$_6$) δ 7.66 (s, 1H), 7.31 (d, J = 7.6 Hz, 2H), 7.09 (d, J = 8.0 Hz, 2H), 7.02 (s, 1H), 5.77-5.87 (m, 2H), 5.05 (s, 2H), 3.61 (s, 3H), 2.33 (br., 3H), 1.77 (d, J = 5.2 Hz, 3H), 1.49-1.56 (m, 1H), 0.85-0.89 (m, 2H), 0.69-0.73 (m, 2H). |
| I-350 | 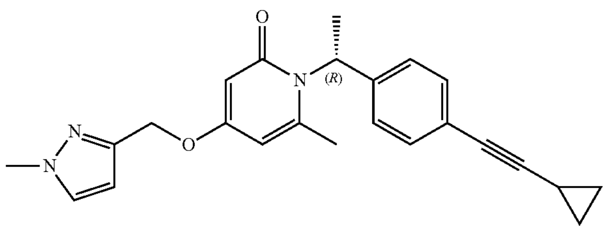 | 388.4 | ¹HNMR (400 MHz, CDCl$_3$) δ 7.31-7.35 (m, 3H), 7.08 (d, J = 8.0 Hz, 2H), 6.32 (d, J = 2.0 Hz, 1H), 6.04 (s, 1H), 5.76 (s, 1H), 4.99 (s, 2H), 3.91 (s, 3H), 1.98 (br., 3H), 1.83 (d, J = 5.6 Hz, 3H), 1.40-1.47 (m, 1H), 0.77-0.88 (m, 4H). |
| I-351 | 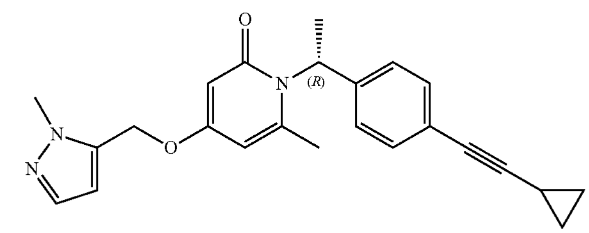 | 388.4 | ¹HNMR (400 MHz, DMSO-d$_6$) δ 7.39 (d, J = 2.0 Hz, 1H), 7.31 (d, J = 7.6 Hz, 2H), 7.09 (d, J = 8.0 Hz, 2H), 6.38 (d, J = 1.6 Hz, 1H), 5.73-5.90 (m, 2H), 5.12 (s, 2H), 3.80 (s, 3H), 2.26 (br., 3H), 1.77 (d, J = 6.0 Hz, 3H), 1.51-1.55 (m, 1H), 0.85-0.89 (m, 2H), 0.69-0.73 (m, 2H). |
| I-352 | 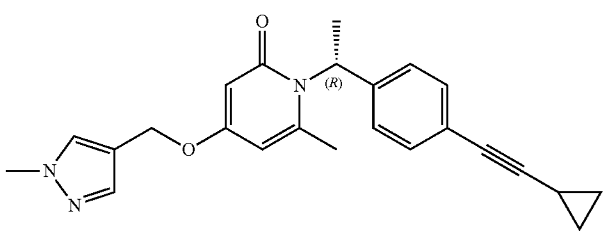 | 388.4 | ¹HNMR (400 MHz, DMSO-d$_6$) δ 7.79 (s, 1H), 7.48 (s, 1H), 7.31 (d, J = 7.2 Hz, 2H), 7.08 (d, J = 8.0 Hz, 2H), 5.71-5.82 (m, 2H), 4.88 (s, 2H), 3.82 (s, 3H), 2.31 (br., 3H), 1.76 (d, J = 5.6 Hz, 3H), 1.49-1.56 (m, 1H), 0.85-0.89 (m, 2H), 0.69-0.73 (m, 2H). |
| I-357 | 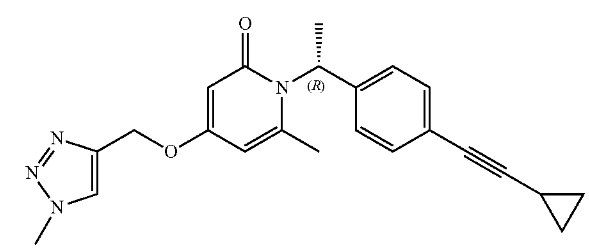 | 389.3 | ¹HNMR (400 MHz, CDCl$_3$) δ 7.63 (s, 1H), 7.32 (d, J = 8.4 Hz, 2H), 7.09 (d, J = 8.0 Hz, 2H), 5.98 (s, 1H), 5.72 (s, 1H), 5.13 (s, 2H), 4.12 (s, 3H), 1.98-2.06 (m, 3H), 1.90 (d, J = 8.0 Hz, 3H), 1.40-1.47 (m, 1H), 0.77-0.89 (m, 4H). |
| I-358 | 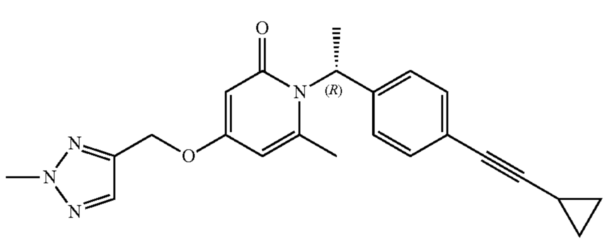 | 389.3 | ¹HNMR (400 MHz, DMSO-d$_6$) δ 7.83 (s, 1H), 7.31 (d, J = 7.6 Hz, 2H), 7.08 (d, J = 8.0 Hz, 2H), 5.71-5.87 (m, 3H), 5.09 (s, 2H), 4.16 (s, 3H), 2.15-2.41 (m, 3H), 1.77 (d, J = 5.2 Hz, 3H), 1.51-1.55 (m, 1H), 0.85-0.89 (m, 2H), 0.69-0.73 (m, 2H). |

TABLE 17-continued

Characterization Data for Additional Exemplary Compounds

| Compound No. | Chemical Structure | M + 1 ¹H NMR (400 MHz) |
|---|---|---|
| I-359 | 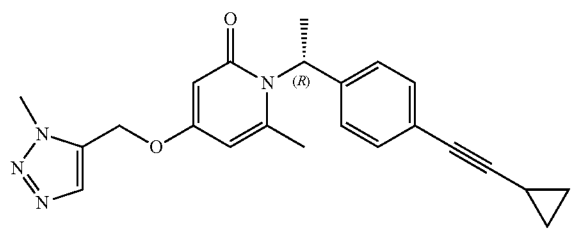 | 389.4 ¹HNMR (400 MHz, CDCl₃) δ 7.75 (s, 1H), 7.33 (d, J = 8.4 Hz, 2H), 7.09 (d, J = 8.0 Hz, 2H), 5.97 (s, 1H), 5.70 (s, 1H), 5.04 (s, 2H), 4.09 (m, 3H), 2.01-2.07 (m, 3H), 1.84 (d, J = 6.4 Hz, 3H), 1.40-1.47 (m, 1H), 0.77-0.89 (m, 4H). |
| I-361 | 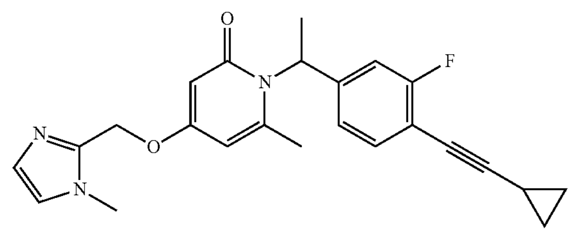 [SMILES: Cc1cc(OCc2nccn2C)cc(=O)n1C(C)c1ccc(C#CC2CC2)c(F)c1] | 406.4 ¹H NMR (400 MHz, DMSO-d₆) δ 7.35 (t, J = 7.2 Hz, 1H), 7.20 (d, J = 0.8 Hz, 1H), 7.01 (d, J = 10.8 Hz, 1H), 6.88-6.90 (m, 2H), 5.92 (s 1H), 5.40 (br., 2H), 5.08 (s, 2H), 3.65 (s, 3H), 2.27-2.37 (m, 3H), 1.76 (d, J = 6.4 Hz, 3H), 1.55-1.61 (m, 1H), 0.88-0.94 (m, 2H), 0.72-0.76 (m, 2H). |
| I-362 | 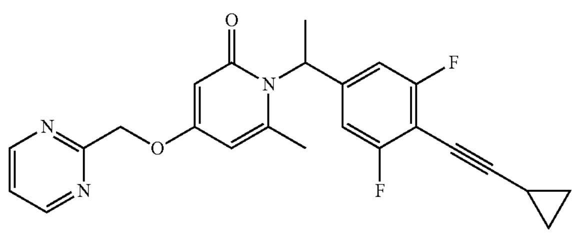 | 422.2 ¹HNMR (400 MHz, CDCl₃) δ 8.78 (d, J = 4.8 Hz, 2H), 7.26-7.28 (m, 1H), 6.69 (d, J = 8.0 Hz, 2H), 5.94 (s, 1H), 5.80-5.82 (m, 1H), 5.25 (s, 2H), 1.91-2.26 (m, 3H), 1.71-1.81 (m, 3H), 1.48-1.54 (m, 1H), 0.84-0.93 (m, 4H). |
| I-378 | 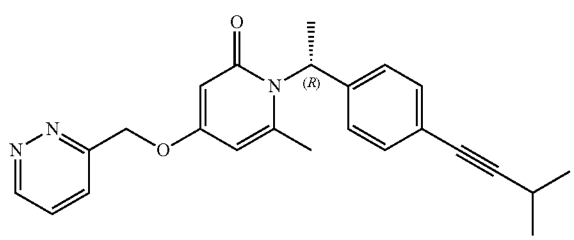 | 388.3 ¹HNMR (400 MHz, DMSO-d₆) δ 9.24 (dd, J = 2.0 Hz, 4.8 Hz, 1H), 7.76-7.82 (m, 2H), 7.32 (d, J = 6.8 Hz, 2H), 7.10 (d, J = 8.4 Hz, 2H), 5.98 (s, 1H), 5.41-5.85 (m, 1H), 5.35 (s, 2H), 2.77-2.81 (m, 1H), 2.16-2.51 (m, 3H), 1.77 (d, J = 5.6 Hz, 3H), 1.20 (d, J = 6.8 Hz, 6H). |
| I-363 | 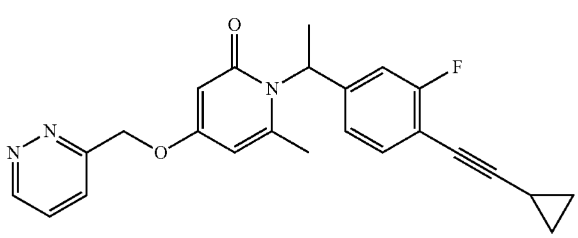 [SMILES: Cc1cc(OCc2cccnn2)cc(=O)n1C(C)c1ccc(C#CC2CC2)c(F)c1] | 404.3 ¹H NMR (400 MHz, DMSO-d₆) δ 9.23-9.25 (m, 1H), 7.76-7.82 (m, 2H), 7.35-7.37 (m, 1H), 7.01 (d, J = 11.2 Hz, 1H), 6.89 (d, J = 7.6 Hz, 1H), 6.00 (s, 1H), 5.76 (br., 2H), 5.35 (s, 2H), 2.39 (br., 3H), 1.77 (d, J = 6.4 Hz, 3H), 1.55-1.61 (m, 1H), 0.88-0.93 (m, 2H), 0.72-0.78 (m, 2H). |
| I-390 | 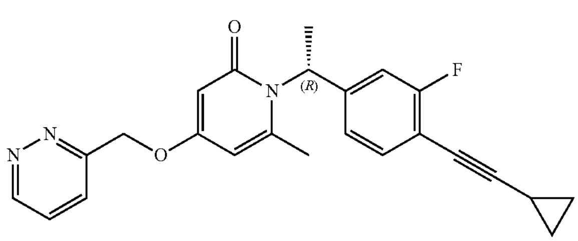 | 404.3 ¹HNMR (400 MHz, DMSO-d6) δ 9.24 (dd, J = 4.4 Hz, 2.0 Hz, 1H), 7.76-7.82 (m, 2H), 7.36 (t, J = 6.8 Hz, 1H), 7.01 (d, J = 10.8 Hz, 1H), 6.89 (d, J = 7.6 Hz, 1H), 6.00 (s, 1H), 5.63-5.90 (m, 2H), 5.35 (s, 2H), 2.14-2.40 (m, 3H), 1.77 (d, J = 6.8 Hz, 3H), 1.55-1.62 (m, 1H), 0.85-0.94 (m, 2H), 0.72-0.78 (m, 2H). |

TABLE 17-continued

Characterization Data for Additional Exemplary Compounds

| Compound No. | Chemical Structure | M + 1 | ¹H NMR (400 MHz) |
|---|---|---|---|
| I-369 | 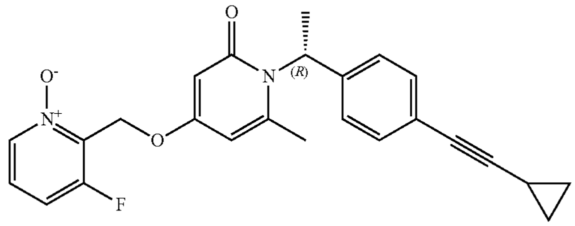 | 419.3 | ¹HNMR (400 MHz, DMSO-d₆) δ 8.31 (d, J = 6.4 Hz, 1H), 7.53-7.59 (m, 1H), 7.45 (t, J = 8.4 Hz, 1H), 7.31 (d, J = 6.8 Hz, 2H), 7.09 (d, J = 8.0 Hz, 2H), 6.09 (br., 2H), 5.22 (s, 2H), 2.27 (br., 3H), 1.77 (d, J = 5.6 Hz, 3H), 1.50-1.56 (m, 1H), 0.85-0.89 (m, 2H), 0.69-0.73 (m, 2H). |
| I-364 | 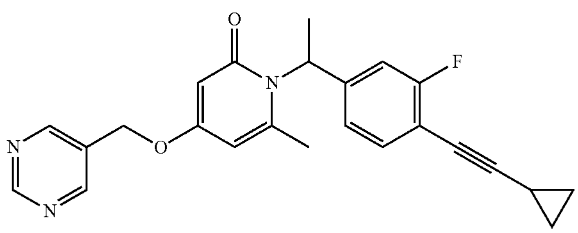 [SMILES: Cc1cc(OCc2cncnc2)cc(=O)n1C(C)c1ccc(C#CC2CC2)c(F)c1] | 404.3 | ¹H NMR (400 MHz, DMSO-d₆) δ 9.20 (s, 1H), 8.90 (s, 2H), 7.38 (t, J = 6.8 Hz, 1H), 7.00 (d, J = 11.2 Hz, 1H), 6.89 (d, J = 8.0 Hz, 1H), 5.98 (s, 1H), 5.41-5.82 (m, 2H), 5.13 (s, 2H), 2.13-2.45 (m, 3H), 1.77 (d, J = 6.4 Hz, 3H), 1.55-1.62 (m, 1H), 0.85-0.97 (m, 2H), 0.72-0.80 (m, 2H). |
| I-365 | 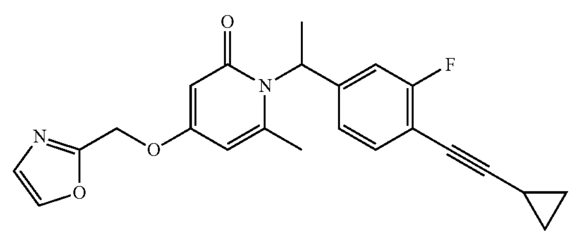 [SMILES: Cc1cc(OCc2ncco2)cc(=O)n1C(C)c1ccc(C#CC2CC2)c(F)c1] | 393.3 | ¹H NMR (400 MHz, DMSO-d₆) δ 8.20 (d, J = 0.4 Hz, 1H), 7.36 (t, J = 6.8 Hz, 1H), 7.30 (s, 1H), 7.00 (d, J = 11.2 Hz, 1H), 6.89 (d, J = 7.2 Hz, 1H), 5.95 (s, 1H), 5.36-5.86 (m, 2H), 5.20 (s, 2H), 1.91-2.37 (m, 3H), 1.76 (d, J = 6.4 Hz, 3H), 1.55-1.61 (m, 1H), 0.85-0.94 (m, 2H), 0.72-0.79 (m, 2H). |
| I-366 | 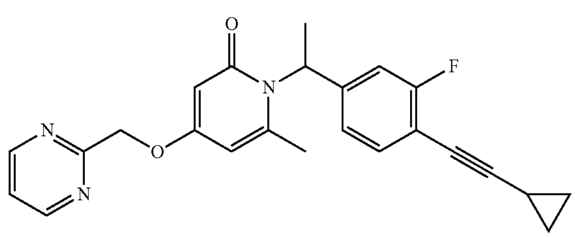 | 418.3 | ¹H NMR (400 MHz, DMSO-d₆) δ 8.85 (d, J = 4.8 Hz, 2H), 7.49 (t, J = 4.8 Hz, 1H), 7.38 (s, 1H), 7.01 (d, J = 11.2 Hz, 1H), 6.90 (d, J = 7.2 Hz, 1H), 5.99 (s, 1H), 5.55 (br., 2H), 5.23 (s, 2H), 3.29-3.32 (m, 1H), 2.27-2.51 (m, 4H), 2.08-2.17 (m, 2H), 1.81-2.00 (m, 3H), 1.76 (d, J = 6.8 Hz, 3H). |
| I-373 | 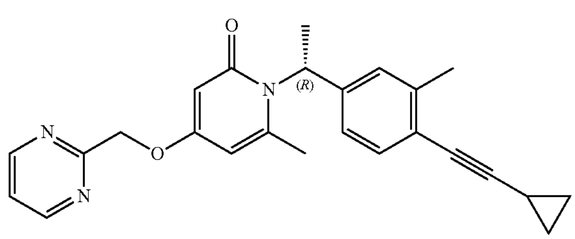 | 400.3 | ¹HNMR (400 MHz, DMSO-d₆) δ 8.85 (d, J = 4.8 Hz, 2H), 7.49 (t, J = 4.8 Hz, 1H), 7.25 (d, J = 6.8 Hz, 1H), 7.00 (s, 1H), 6.87 (d, J = 8.0 Hz, 1H), 5.95 (s, 1H), 5.39-5.76 (m, 2H), 5.23 (s, 2H), 2.29 (s, 3H), 1.87-2.20 (m, 3H), 1.74 (d, J = 5.6 Hz, 3H), 1.52-1.58 (m, 1H), 0.87-0.92 (m, 2H), 0.70-0.73 (m, 2H). |
| I-382 | 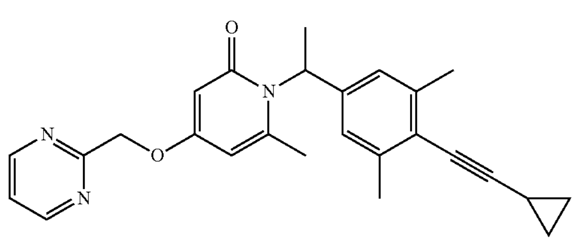 [SMILES: Cc1cc(C(C)n2c(C)cc(OCc3ncccn3)cc2=O)cc(C)c1C#CC1CC1] | 414.3 | ¹HNMR (400 MHz, DMSO-d₆) δ 8.85 (d, J = 4.8 Hz, 1H), 7.49 (t, J = 4.8 Hz, 1H), 6.81 (s, 2H), 5.94 (s, 1H), 5.64 (br, 1H), 5.23 (s, 2H), 2.49-2.51 (m, 3H), 2.27-2.33 (m, 6H), 1.72 (d, J = 5.2 Hz, 3H), 1.57-1.61 (m, 1H), 0.90-0.95 (m, 2H), 0.70-0.74 (m, 2H). |

TABLE 17-continued

Characterization Data for Additional Exemplary Compounds

| Compound No. | Chemical Structure | M + 1 | $^1$H NMR (400 MHz) |
|---|---|---|---|
| I-379 | 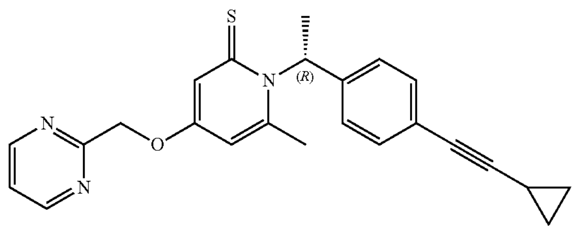 | 402.3 | $^1$HNMR (400 MHz, DMSO-d$_6$) δ 8.87 (d, J = 4.8 Hz, 2H), 8.38 (q, J = 7.2 Hz, 1H), 7.52 (t, J = 4.8 Hz, 1H), 7.37 (d, J = 8.4 Hz, 2H), 7.13 (d, J = 3.2 Hz, 1H), 7.05 (d, J = 8.0 Hz, 2H), 6.48 (d, J = 2.8 Hz, 1H), 5.39 (s, 2H), 2.01 (s, 3H), 1.78 (d, J = 7.2 Hz, 3H), 1.50-1.57 (m, 1H), 0.85-0.90 (m, 2H), 0.70-0.74 (m, 2H). |
| I-383 | 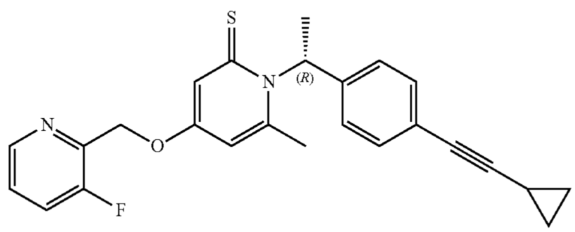 | 419.2 | $^1$HNMR (400 MHz, CDCl$_3$) δ 8.51-8.56 (m, 1H), 8.48-8.49 (m, 1H), 7.47-7.52 (m, 2H), 7.36-7.40 (m, 1H), 7.34 (d, J = 8.4 Hz, 2H), 7.07 (d, J = 7.6 Hz, 2H), 6.15 (d, J = 2.4 Hz, 1H), 5.25 (d, J = 1.6 Hz, 2H), 1.99 (s, 3H), 1.87 (d, J = 7.2 Hz, 3H), 1.41-1.48 (m, 1H), 0.83-0.89 (m, 2H), 0.78-0.82 (m, 2H). |
| I-380 | 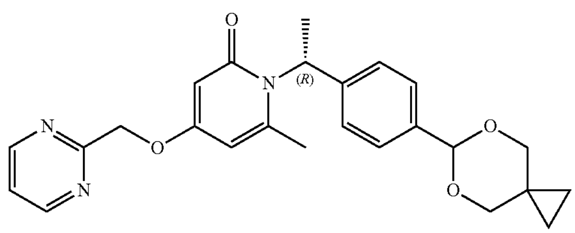 | 434.3 | $^1$HNMR (400 MHz, CDCl$_3$) δ 8.79 (d, J = 4.8 Hz, 2H), 7.49 (t, J = 8.0 Hz, 2H), 7.28 (d, J = 5.2 Hz, 1H), 7.18 (d, J = 8.0 Hz, 2H), 6.04 (s, 1H), 5.93 (s, 1H), 5.67 (s, 1H), 5.28 (s, 2H), 4.32 (d, J = 11.6 Hz, 2H), 3.40 (d, J = 11.6 Hz, 2H), 2.05 (br, 3H), 1.84 (d, J = 6.0 Hz, 3H), 0.73-0.77 (m, 2H), 0.37-0.41 (m, 2H). |
| I-381 | 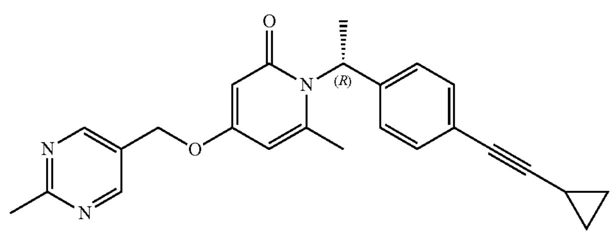 | 400.4 | $^1$HNMR (400 MHz, DMSO-d$_6$) δ 8.77 (s, 2H), 7.31 (d, J = 7.2 Hz, 2H), 7.08 (d, J = 8.0 Hz, 2H), 5.92 (s, 1H), 5.76 (br., 1H), 5.08 (s, 2H), 2.64 (s, 3H), 2.29 (br., 3H), 1.77 (d, J = 6.0 Hz, 3H), 1.51-1.55 (m, 1H), 0.85-0.89 (m, 2H), 0.69-0.73 (m, 2H). |
| I-384 | 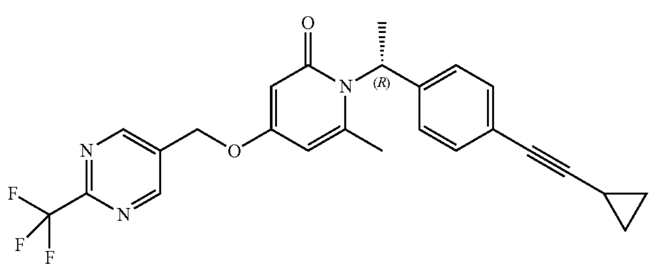 | 907.2 | $^1$HNMR (400 MHz, DMSO-d$_6$) δ 9.15 (s, 2H), 7.31 (d, J = 7.6 Hz, 2H), 7.09 (d, J = 8.0 Hz, 2H), 5.98 (s, 1H), 5.79 (br., 1H), 5.26 (s, 2H), 2.34 (br., 3H), 1.78 (d, J = 6.0 Hz, 3H), 1.50-1.56 (m, 1H), 0.85-0.90 (m, 2H), 0.69-0.73 (m, 2H). |
| I-391 | 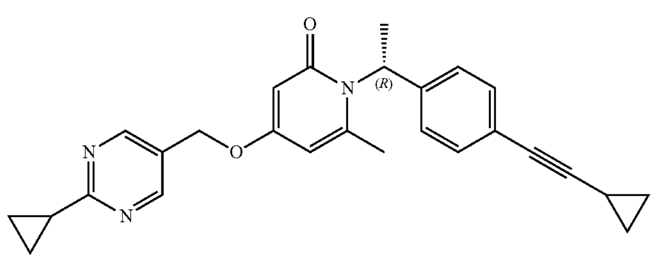 | 426.3 | $^1$HNMR (400 MHz, DMSO-d$_6$) δ 8.71 (s, 2H), 7.31 (d, J = 7.6 Hz, 2H), 7.08 (d, J = 8.4 Hz, 2H), 5.91 (s, 1H), 5.76 (br., 1H), 5.04 (s, 2H), 2.41 (br., 3H), 2.19-2.25 (m, 1H), 1.77 (d, J = 6.0 Hz, 3H), 1.49-1.56 (m, 1H), 0.99-1.09 (m, 4H), 0.85-0.89 (m, 2H), 0.69-0.73 (m, 2H). |

TABLE 17-continued

Characterization Data for Additional Exemplary Compounds

| Compound No. | Chemical Structure | M + 1 | $^1$H NMR (400 MHz) |
|---|---|---|---|
| I-392 | 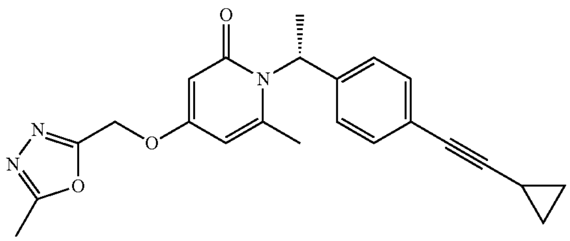 [SMILES: Cc1nnc(COc2cc(C)n([C@H](C)c3ccc(C#CC4CC4)cc3)c(=O)c2)o1] | 390.3 | $^1$HNMR (400 MHz, DMSO-d$_6$) δ 7.31 (d, J = 6.8 Hz, 2H), 7.09 (d, J = 8.0 Hz, 2H), 5.94 (s, 1H), 5.78 (br., 1H), 5.33 (s, 2H), 2.54 (s, 3H), 2.35 (br., 3H), 1.77 (d, J = 5.2 Hz, 3H), 1.49-1.55 (m, 1H), 0.85-0.89 (m, 2H), 0.69-0.73 (m, 2H). |
| I-388 | 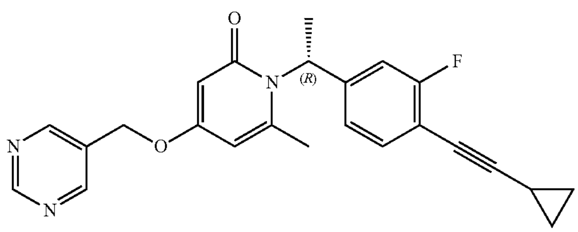 | 403.3 | $^1$HNMR (400 MHz, DMSO-d6) δ 8.65 (d, J = 1.6 Hz, 1H), 8.57 (dd, J = 4.8 Hz, 1.6 Hz, 1H), 7.85 (d, J = 8.0 Hz, 1H), 7.43-7.46 (m, 1H), 7.35-7.39 (m, 1H), 7.00 (d, J = 11.2 Hz, 1H), 6.89 (d, J = 7.6 Hz, 1H), 5.96 (s, 1H), 5.36-5.89 (m, 2H), 5.09 (s, 2H), 2.33-2.39 (m, 3H), 1.77 (d, J = 6.8 Hz, 3H), 1.55-1.62 (m, 1H), 0.88-0.93 (m, 2H), 0.72-0.76 (m, 2H). |

Example 28: BRET Assays

Background—The following assays can be used for determination of GPR84 activation in living HEK293 cells. The Gα$_i$ BRET biosensor (Gagnon et al., 2018; Gales et al., 2006. Nat Struct Mol Biol. 13, 778-86; Saulieres et al., 2012. Nat Chem Biol. 8, 622-30) allows to directly monitor GPR84-mediated activation of Gα$_i$. The Gα$_i$ biosensor consists of a Rluc8-tagged Gα$_{i2}$ subunit, a GFP10-tagged Gγ$_2$ subunit, and an untagged Gβ$_1$. Agonist stimulation and GPR84 activation triggers a physical separation between the RLuc8-Gα$_i$ donor and the GFP10-Gγ$_2$ acceptor, resulting in a decrease in BRET signal whose amplitude is correlated to ligand efficacy (Gales et al., 2006). Moreover, signaling functions of GPCRs are tightly regulated by endocytosis, the targeting of receptors to endosomes and their sorting to lysosomes or recycling to the plasma membrane. The early endosomes (EEs) trafficking assay (Namkung et al., 2016. Nat Commun. 7, 12178) uses Rluc8-tagged GPR84 and Renilla GFP (rGFP) attached to the FYVE domain from human endofin/zinc finger FYVE domain-containing protein 16, which binds phosphatidylinositol 3-phosphate in EEs. Agonist stimulation of GPR84-Rluc8 leads to trafficking of the receptor to EEs, and ensuing increase of the donor concentration relative to the rGFP-FYVE acceptor anchored in the same cellular compartment, and thus results in an increase in BRET signal.

Plasmids—The cDNA clones for human GPR84 receptor, human Gα$_{i2}$, Gβ$_1$, and Gγ$_2$ were obtained from the cDNA Resource Center (www.cdna.org). GFP10 (F64L, S147P, S202F and H231L variant of Aequorea victoria Green Fluorescent Protein) gBlocks gene fragments (Integrated DNA Technologies, IA) and linker were inserted in frame at the N-terminus of human Gγ$_2$. Rluc8 (A55T, C124A, S130A, K136R, A143M, M185V, M253L, and S287L variant of the Renilla renformis luciferase) gBlocks gene fragment was inserted with linkers in frame in between residues 91 and 92 of Gα$_{i2}$ or at the C-terminus of GPR84. The FYVE domain from human endofin (residues Q739 to K806) attached in frame at the C terminus of a humanized Renilla GFP (rGFP), were synthesized as gBlocks gene fragments.

Bioluminescence Resonance Energy Transfer (BRET) Measurement—HEK293 cells were transfected with GPR84-Rluc8 and rGFP-FYVE for the EEs trafficking biosensor or with GPR84, Gα$_{i2}$-Rluc8, GFP10-Gγ$_2$, and Gβ$_1$ for the Gα$_i$ biosensor. The following day, transiently transfected cells were seeded in 96-well white clear bottom microplates coated with poly-D-lysine and left in culture for 24 hours. Cells were washed once with Tyrode's buffer (140 mmol/L NaCl, 1 mmol/L CaCl$_2$, 2.7 mmol/L KCl, 0.49 mmol/L MgCl$_2$, 0.37 mmol/L NaH$_2$PO$_4$, 5.6 mmol/L glucose, 12 mmol/L NaHCO$_3$, and 25 mmol/L HEPES, pH 7.5) before performing assays in Tyrode's buffer. Test compounds were incubated with cells for 5 (Gα$_i$) or 15 (EEs) minutes at 37° C. before addition of 200 nmol/L of the GPR84 agonist ZQ-16 (2-(Hexylthio)-6-hydroxy-4(3H)-pyrimidinone) for 5 minutes at room temperature (Gα$_i$) or 30 minutes at 37° C. (EEs). The Rluc8 substrate coelenterazine 400A (Prolume, Lakeside, AZ) was added at a final concentration of 5 μmol/L and BRET readings were collected using an Infinite M1000 microplate reader (Tecan, Morrisville, NC). BRET$^2$ readings between Rluc8 and GFP10 or rGFP were collected by sequential integration of the signals detected in the 370 to 450 nm (Rluc8) and 510 to 540 nm (GFP10, rGFP) windows. The BRET signal was calculated as the ratio of light emitted by acceptor (GFP10, rGFP) over the light emitted by donor (Rluc8). The values were corrected to net BRET by subtracting the background BRET signal obtained in cells transfected with Rluc8 constructs alone. Ligand-promoted net BRET values were calculated by subtracting vehicle-induced net BRET from ligand-induced net BRET.

Table 18 shows the activity of selected compounds of this invention in the Gα$_i$ biosensor BRET assay when tested at a single concentration. The compound numbers correspond to the compound numbers in Table 1. Compounds tested at a concentration of 1 μM are designated "A*"; Compounds tested at a concentration of 2 μM are designated "A"; compounds tested at a concentration of 3 μM are designated "B"; compounds tested at a concentration of 4 μM are designated "C*"; compounds tested at a concentration of 5 μM are designated "C"; compounds tested at a concentration of 10 μM are designated "D"; compounds tested at a concentration of 12.5 μM are designated "E"; compounds tested at a concentration of 15 μM are designated "F"; compounds tested at a concentration of 25 μM are designated "G"; compounds tested at a concentration of 50 μM are designated "H". Compounds having an activity designated as "*" provided a percent inhibition of ≤25; compounds having an activity designated as "" provided a percent inhibition of ≥25-≤50; compounds having an activity designated as "*" provided a percent inhibition of >50-≤75; and compounds having an activity designated as "****" provided a percent inhibition of >75.

TABLE 18

BRET Assay (% Inhibition)

| Compound | Concentration | % Inhibition |
|---|---|---|
| I-1 | G | **** |
| I-2 | G | **** |
| I-4 | D | * |
| I-5 | G | * |
| I-6 | D | **** |
| I-7 | D | **** |
| I-8 | G | * |
| I-9 | G | * |
| I-10 | G | * |
| I-13 | D | **** |
| I-14 | D | * |
| I-15 | E | * |
| I-16 | G | * |
| I-17 | G | * |
| I-19 | G | *** |
| I-20 | D | *** |
| I-21 | D | *** |
| I-22 | D | *** |
| I-23 | D | * |
| I-24 | G | *** |
| I-25 | E | *** |
| I-26 | G | *** |
| I-27 | G | ** |
| I-28 | D | * |
| I-29 | G | * |
| I-30 | A | ** |
| I-31 | D | * |
| I-32 | D | ** |
| I-33 | G | ** |
| I-34 | G | ** |
| I-35 | G | ** |
| I-36 | G | ** |
| I-37 | G | ** |
| I-38 | G | ** |
| I-39 | G | ** |
| I-40 | G | * |
| I-41 | G | * |
| I-43 | D | ** |
| I-44 | D | ** |
| I-45 | G | ** |
| I-46 | G | ** |
| I-47 | G | ** |
| I-48 | D | ** |
| I-49 | D | ** |
| I-50 | D | ** |
| I-51 | G | ** |
| I-52 | E | ** |
| I-53 | G | ** |
| I-54 | G | * |
| I-55 | G | * |
| I-56 | D | ** |
| I-57 | A | ** |
| I-58 | E | ** |
| I-59 | G | ** |
| I-61 | D | ** |
| I-62 | G | * |
| I-63 | G | * |
| I-64 | C | * |
| I-65 | D | * |
| I-66 | F | * |
| I-67 | G | * |
| I-68 | D | * |
| I-69 | G | * |
| I-70 | G | * |
| I-71 | G | * |
| I-72 | G | * |
| I-73 | E | * |
| I-74 | G | * |
| I-75 | G | * |
| I-76 | D | * |
| I-77 | G | * |
| I-78 | G | * |
| I-79 | G | * |
| I-80 | G | * |
| I-81 | G | * |
| I-82 | D | * |
| I-83 | D | * |
| I-84 | G | * |
| I-85 | F | * |
| I-86 | G | * |
| I-88 | D | * |
| I-89 | D | * |
| I-90 | G | * |
| I-91 | G | * |
| I-92 | G | * |
| I-93 | G | * |
| I-94 | G | * |
| I-95 | G | * |
| I-96 | D | * |
| I-97 | D | * |
| I-98 | G | * |
| I-99 | D | * |
| I-100 | D | * |
| I-101 | G | * |
| I-102 | G | * |
| I-103 | G | * |
| I-104 | G | * |
| I-105 | G | * |
| I-106 | D | **** |
| I-107 | E | * |
| I-108 | G | * |
| I-109 | G | * |
| I-110 | G | * |
| I-111 | G | * |
| I-112 | G | * |
| I-113 | D | * |
| I-114 | D | * |
| I-115 | D | * |
| I-116 | D | * |
| I-117 | D | * |
| I-118 | D | * |
| I-119 | D | * |
| I-120 | D | * |
| I-121 | D | * |
| I-122 | D | * |
| I-123 | D | * |
| I-124 | E | * |
| I-125 | G | * |
| I-126 | G | * |
| I-127 | G | * |
| I-128 | G | * |
| I-129 | G | * |
| I-130 | G | * |
| I-131 | G | * |
| I-132 | G | * |
| I-133 | G | * |
| I-134 | G | * |
| I-135 | G | * |
| I-136 | G | * |

TABLE 18-continued

BRET Assay (% Inhibition)

| Compound | Concentration | % Inhibition |
|---|---|---|
| I-137 | G | * |
| I-138 | G | * |
| I-139 | G | * |
| I-143 | D | * |
| I-144 | D | **** |
| I-145 | D | **** |
| I-146 | D | * |
| I-147 | D | ** |
| I-148 | D | ** |
| I-149 | D | * |
| I-150 | D | * |
| I-155 | G | * |
| I-156 | G | * |
| I-157 | G | * |
| I-158 | G | * |
| I-159 | G | * |
| I-160 | G | * |
| I-161 | G | * |
| I-162 | G | * |
| I-163 | G | * |
| I-164 | F | * |
| I-165 | G | * |
| I-166 | C | * |
| I-167 | G | * |
| I-168 | C | * |
| I-169 | G | * |
| I-173 | H | * |
| I-174 | G | * |
| I-175 | G | * |
| I-176 | G | * |
| I-177 | G | * |
| I-178 | G | * |
| I-179 | G | * |
| I-180 | G | *** |
| I-181 | F | ** |
| I-182 | G | * |
| I-183 | A* | * |
| I-184 | A* | * |
| I-186 | G | ** |
| I-187 | D | ** |
| I-188 | G | * |
| I-197 | G | * |
| I-203 | G | ** |
| I-206 | G | ** |
| I-210 | F | * |
| I-211 | G | ** |
| I-214 | G | **** |
| I-215 | C | * |
| I-216 | D | * |
| I-217 | D | * |
| I-218 | D | ** |
| I-219 | D | *** |
| I-220 | D | * |
| I-221 | D | ** |
| I-222 | D | **** |
| I-223 | D | **** |
| I-224 | D | * |
| I-225 | D | ** |
| I-226 | D | *** |
| I-227 | D | *** |
| I-228 | D | * |
| I-229 | D | *** |
| I-230 | D | * |
| I-231 | D | * |
| I-232 | D | **** |
| I-233 | D | ** |
| I-234 | D | *** |
| I-235 | D | * |
| I-236 | D | * |
| I-237 | D | *** |
| I-238 | D | **** |
| I-239 | D | * |
| I-240 | D | ** |
| I-241 | A | * |
| I-242 | D | * |
| I-243 | D | * |
| I-244 | D | * |
| I-245 | D | * |
| I-246 | D | * |
| I-247 | D | **** |
| I-248 | D | ** |
| I-249 | D | ** |
| I-250 | D | ** |
| I-251 | D | * |
| I-252 | A | * |
| I-253 | D | *** |
| I-254 | D | * |
| I-255 | D | * |
| I-256 | A | **** |
| I-257 | A | **** |
| I-258 | A | **** |
| I-259 | D | * |
| I-260 | D | **** |
| I-261 | D | * |
| I-262 | D | * |
| I-263 | D | * |
| I-264 | D | ** |
| I-265 | D | * |
| I-266 | D | * |
| I-267 | D | * |
| I-268 | D | * |
| I-269 | D | * |
| I-270 | D | * |
| I-271 | D | * |
| I-272 | A | **** |
| I-273 | D | **** |
| I-274 | D | * |
| I-275 | D | * |
| I-276 | D | **** |
| I-277 | D | * |
| I-278 | A | **** |
| I-279 | D | **** |
| I-280 | D | * |
| I-281 | D | * |
| I-282 | D | * |
| I-283 | A | **** |
| I-284 | A | **** |
| I-285 | D | * |
| I-286 | D | * |
| I-287 | D | ** |
| I-288 | D | ** |
| I-289 | A | * |
| I-290 | A | **** |
| I-291 | A | **** |
| I-292 | D | ** |
| I-293 | A | **** |
| I-294 | D | **** |
| I-295 | D | **** |
| I-296 | D | **** |
| I-297 | D | * |
| I-298 | D | *** |
| I-299 | D | * |
| I-300 | D | * |
| I-301 | D | * |
| I-303 | A | **** |
| I-304 | D | * |
| I-305 | D | **** |
| I-306 | D | ** |
| I-307 | D | * |
| I-308 | D | **** |
| I-309 | D | * |
| I-310 | D | ** |
| I-311 | A | **** |
| I-312 | D | * |
| I-313 | D | **** |
| I-314 | D | **** |
| I-315 | A | **** |
| I-316 | D | * |
| I-317 | D | **** |
| I-318 | D | **** |
| I-319 | D | **** |
| I-320 | D | *** |

TABLE 18-continued

BRET Assay (% Inhibition)

| Compound | Concentration | % Inhibition |
|---|---|---|
| I-321 | D | **** |
| I-322 | D | * |
| I-323 | D | **** |
| I-324 | D | **** |
| I-325 | D | **** |
| I-326 | A* | ** |
| I-327 | D | *** |
| I-328 | D | *** |
| I-329 | D | * |
| I-340 | D | * |
| I-341 | D | * |
| I-342 | D | * |
| I-343 | D | * |
| I-344 | D | * |
| I-345 | D | * |
| I-346 | D | * |
| I-346 | D | * |
| I-347 | D | * |
| I-348 | D | **** |
| I-349 | A | **** |
| I-350 | D | **** |
| I-351 | D | **** |
| I-352 | D | **** |
| I-353 | D | * |
| I-354 | A | * |
| I-355 | D | ** |
| I-356 | A | **** |
| I-357 | A | **** |
| I-358 | D | **** |
| I-359 | D | **** |
| I-360 | D | **** |
| I-361 | A | **** |
| I-362 | D | **** |
| I-363 | A | **** |
| I-364 | D | **** |
| I-365 | D | **** |
| I-366 | D | **** |
| I-368 | D | * |
| I-369 | D | **** |
| I-372 | D | **** |
| I-373 | D | **** |

Table 19 shows the activity of selected compounds of this invention in the Gαi biosensor BRET assay. The compound numbers correspond to the compound numbers in Table 1. Compounds having an activity designated as "A" provided an $IC_{50} \leq 5$ µM; compounds having an activity designated as "B" provided an $IC_{50}$ of 5-10 µM; compounds having an activity designated as "C" provided an $IC_{50}$ of 10-15 µM; compounds having an activity designated as "D" provided an $IC_{50}$ of >12.5 µM; and compounds having an activity designated as "E" provided an $IC_{50}$ of ≥25 µM.

TABLE 19

BRET Assay ($IC_{50}$)

| Compound | hGPR84 $IC_{50}$ (µM) |
|---|---|
| I-1 | A |
| I-2 | A |
| I-3 | A |
| I-6 | A |
| I-7 | A |
| I-25 | B |
| I-26 | C |
| I-35 | A |
| I-36 | A |
| I-37 | A |
| I-51 | E |
| I-58 | D |

TABLE 19-continued

BRET Assay ($IC_{50}$)

| Compound | hGPR84 $IC_{50}$ (µM) |
|---|---|
| I-180 | E |
| I-181 | E |
| I-211 | B |
| I-214 | A |
| I-223 | A |
| I-232 | A |
| I-256 | A |
| I-257 | A |
| I-258 | A |
| I-272 | A |
| I-273 | A |
| I-278 | A |
| I-283 | A |
| I-290 | A |
| I-291 | A |
| I-293 | A |
| I-294 | A |
| I-296 | A |
| I-303 | A |
| I-315 | A |
| I-318 | A |
| I-319 | A |
| I-324 | A |
| I-325 | A |
| I-326 | C |
| I-328 | B |
| I-351 | A |
| I-356 | A |
| I-357 | A |
| I-359 | A |
| I-360 | A |
| I-361 | A |
| I-363 | A |
| I-364 | A |
| I-396 | A |

Example 29: Neutrophil Migration Assay

Neutrophil migration assay. After isolation, neutrophils were resuspended in chemotaxis buffer (DMEM supplemented with 10 mM HEPES) at a concentration of $8.9 \times 10^6$ cells/ml. In a 96-well plate, 20 µl of compound solution in chemotaxis buffer is added to 180 µl of cell suspension. After incubation at 37° C. for 30 minutes, 75 uL of cell suspension is transferred in the upper chamber of a 5 µm pore size Corning HTS transwell. 235 uL of chemotaxis buffer containing the chemotactic agent (embelin) is added to the lower chamber of the transwell. After a 60-minute incubation time at 37° C. in 5% $CO_2$, the upper chamber of the transwell is removed and the plate is centrifuged at 1500 rpm for 6 minutes. Supernatant is removed and cells resuspended in 100 ul of PBS. ATP content was assessed using ATPlite Luminescence Assay System® according to manufacturer instructions (Perkin Elmer, Buckinghamshire, UK). Briefly, 50 uL of ATPlite buffer and 50 uL of lysis solution is added to the lower chamber of the Transwells. After incubation at room temperature, in the dark with constant agitation for 5 minutes, 150 µL of cell lysate is transferred in a 96 wells white plate and incubated for 10 minutes in the dark. Luminescence is read on a TECAN plate reader, Infinite M1000 (Tecan, Morrisville, NC).

Table 20 shows the activity of selected compounds of this invention in the neutrophil migration assay. The compound numbers correspond to the compound numbers in Table 1. Neutrophil migration results are normalized to a GPR84 antagonist Control Compound which provided an average $IC_{50}$ value of 131 nM and an $IC_{50}$ range of 15 nM to 553 nM in the neutrophil migration assay (n=26). Normalization of the results takes the donor's variation into account. Compounds having an activity designated as "A" provided an $IC_{50} \leq 300$ nM; compounds having an activity designated as "B" provided an $IC_{50}$ of >300-≤1,000 nM; compounds having an activity designated as "C" provided an $IC_{50}$ of >1,000-3,000 nM; and compounds having an activity designated as "D" provided an $IC_{50}$ of >3,000 nM. Compounds having a migration inhibition potency relative to Control Compound designated as "C" provided an $IC_{50} \leq 0.5$-fold relative to Control Compound; compounds having an activity designated as "B" provided an $IC_{50}$ of >0.5-≤1.0-fold relative to Control Compound; and compounds having an activity designated as "A" provided an $IC_{50}$ of >1.0-fold relative to Control Compound.

TABLE 20

Neutrophil Migration Assay

| Compound No. | Human Neutrophil migration inhibition $IC_{50}$ (nM) | Human Neutrophil migration inhibition - fold potency to Control Compound |
| --- | --- | --- |
| I-2 | D | C |
| I-30 | C | C |
| I-222 | C | — |
| I-223 | A | B |

While we have described a number of embodiments of this invention, it is apparent that our examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I:

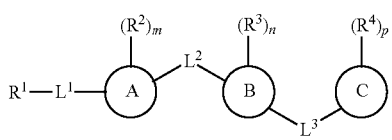

I or an N-oxide, or a pharmaceutically acceptable salt thereof, wherein:

Ring A taken together with $(R^2)_m$ is

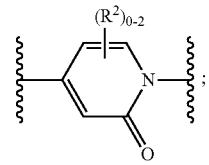

Ring B is phenyl;
Ring C is a 3-7 membered saturated or partially unsaturated monocyclic carbocyclic ring;
$R^1$ is selected from (i) a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 4-8 membered saturated or partially unsaturated monocyclic heterocyclic ring having 1-2 heteroatoms independently selected from nitrogen, oxygen, and sulfur; phenyl; or a $C_{1-6}$ aliphatic; each of which is substituted with q instances of $R^5$; and (ii) hydrogen, —CN, or —OR;

each instance of $R^2$, $R^4$, and $R^5$ is independently hydrogen, deuterium, $R^z$, halogen, —CN, —NO$_2$, —OR, —SR, —NR$_2$, —S(O)$_2$R, —S(O)$_2$NR$_2$, —S(O)R, —S(O)NR$_2$, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —Si(OR)R$_2$, —SiR$_3$, —P(O)(R)NR$_2$, —P(O)(R)OR or —P(O)R$_2$; or two $R^2$ groups are optionally taken together to form =O;

two $R^4$ groups are optionally taken together to form =O;

two $R^5$ groups are optionally taken together to form =O;

two $R^2$ groups are optionally taken together with their intervening atoms to form a 5-8 membered saturated, partially unsaturated, or aryl fused ring having 0-3 heteroatoms independently selected from nitrogen, oxygen and sulfur;

two $R^4$ groups are optionally taken together with their intervening atoms to form an optionally substituted 5-8 membered saturated, partially unsaturated, or aryl fused ring having 0-3 heteroatoms independently selected from nitrogen, oxygen and sulfur; or two $R^5$ groups are optionally taken together with their intervening atoms to form a 5-8 membered saturated, partially unsaturated, or aryl fused ring having 0-3 heteroatoms independently selected from nitrogen, oxygen and sulfur; or two $R^5$ groups are taken together with their intervening atoms to form a 3-7 membered saturated or partially unsaturated monocyclic carbocyclic ring;

each $R^z$ is independently selected from an optionally substituted group selected from $C_{1-6}$ aliphatic; phenyl; a 3-7 membered saturated or partially unsaturated monocyclic carbocyclic ring; a 4-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur;

each instance of $R^3$ is independently selected from:

(a) hydrogen, deuterium, halogen, —OR, —SR, —NR$_2$, —S(O)$_2$R, —S(O)$_2$NR$_2$, —S(O)R, —S(O)NR$_2$, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$^2$, —S(NR)(O)R, —N(R)S(O)R, or —N(R)CN; or (b) an optionally substituted group selected from $C_{1-6}$ aliphatic; phenyl; a 3-7 membered saturated or partially unsaturated heterocyclic ring having 1-2 heteroatoms independently selected from nitrogen, oxygen, and sulfur; and a 5-6 membered heteroaryl ring having 1-4 heteroatoms independently selected from nitrogen, oxygen, and sulfur; or two R³ groups are optionally taken together to form =O or =S; or two R³ groups are optionally taken together with their intervening atoms to form a 5-8 membered saturated, partially unsaturated, or aryl fused ring having 0-3 heteroatoms independently selected from nitrogen, oxygen and sulfur; or L¹ is a $C_{1-5}$ bivalent straight or branched saturated or unsaturated hydrocarbon chain wherein 1-2 methylene units of the chain are independently and optionally replaced with —O—, —C(O)—, —C(S)—, —C(R)₂—, —CH(R)—, —CH(OR)—, —C(F)₂—, —N(R)—, —S—, —S(O)—, or —S(O)₂—;

L² is a $C_{1-3}$ bivalent straight or branched saturated or unsaturated hydrocarbon chain wherein 1-2 methylene units of the chain are independently and optionally replaced with —O—, —C(O)—, —C(S)—, —C(R)₂—, —CH(R)—, —CH(OR)—, —C(F)₂—, —N(R)—, —S—, —S(O)—, or —S(O)₂—;

L³ is

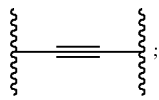

each R is independently hydrogen, or an optionally substituted group selected from $C_{1-6}$ aliphatic; phenyl; an 8-10 membered bicyclic aryl ring, a 3-7 membered saturated or partially unsaturated monocyclic carbocyclic ring; a 4-8 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; and an 8-10 membered bicyclic heteroaryl ring having 1-5 heteroatoms independently selected from nitrogen, oxygen, and sulfur; and/or two R groups on the same nitrogen are optionally taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur; and/or two R groups on vicinal carbons are taken together with the vicinal carbons to form an optionally substituted 3-7 membered monocyclic saturated or partially unsaturated carbocyclic ring or heterocyclic ring, wherein the heterocyclic ring has, in addition to the vicinal carbons, 0-3 heteroatoms independently selected from nitrogen, oxygen, and sulfur;

n is 0, 1, 2, 3, or 4;

p is 0, 1, 2, 3, or 4; and q is 0, 1, 2, 3, or 4.

2. A compound of formula III-f-1:

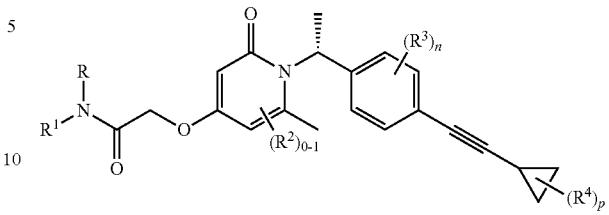

III-f-1 or a pharmaceutically acceptable salt thereof; wherein

R¹ is $C_{1-6}$ aliphatic;

R is hydrogen or $C_{1-6}$ aliphatic;

R², R³, and R⁴ are independently hydrogen, deuterium, or halogen;

n is 0, 1, 2, 3, or 4; and p is 0, 1, 2, 3, or 4.

3. The compound of claim 1, wherein Ring A and its R² substituents is

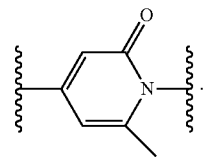 [SMILES: *c1cc(C)n(*)c(=O)c1]

4. The compound of claim 1, wherein Ring C and its R⁴ substituents is

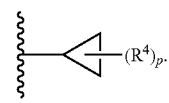

5. The compound of claim 1, wherein R¹ is a $C_{1-6}$ aliphatic substituted with q instances of R⁵.

6. The compound of claim 1, wherein R¹ is methyl, —OMe, —CN,

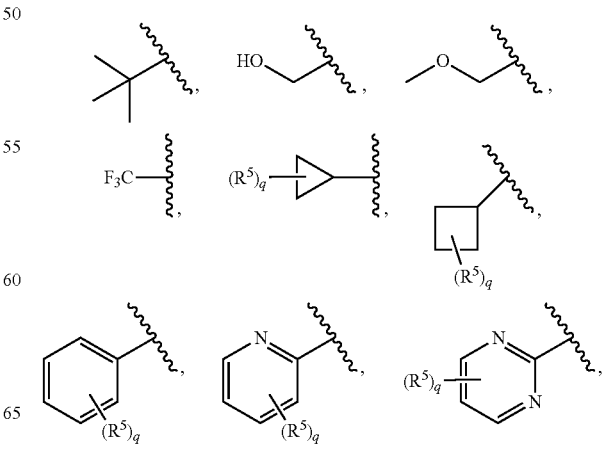

535
-continued
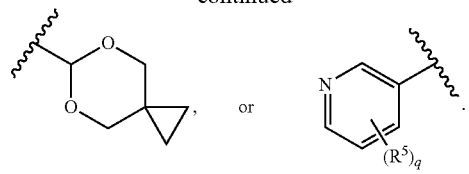, or
7. The compound of claim 1, wherein L² is
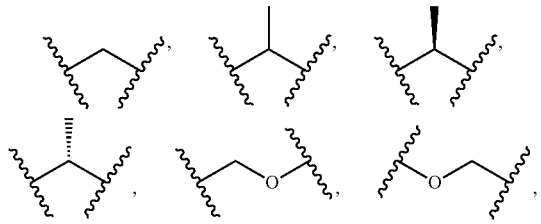,
536
-continued
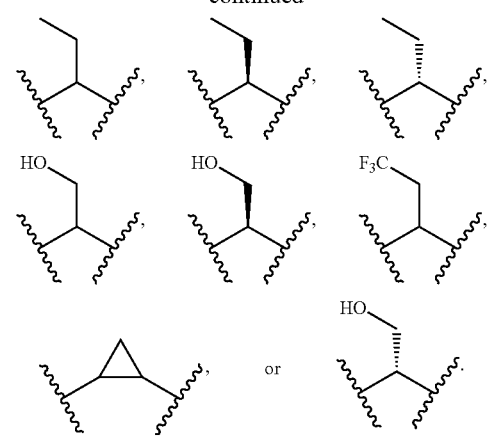
8. A compound selected from the following or a pharmaceutically acceptable salt thereof:
| Compound No. | Structure |
|---|---|
| I-1 | 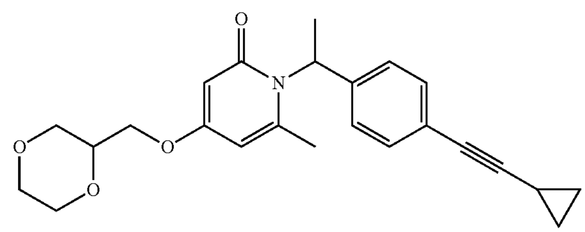 [SMILES: Cc1cc(OCC2COCCO2)cc(=O)n1C(C)c1ccc(C#CC2CC2)cc1] |
| I-2 | 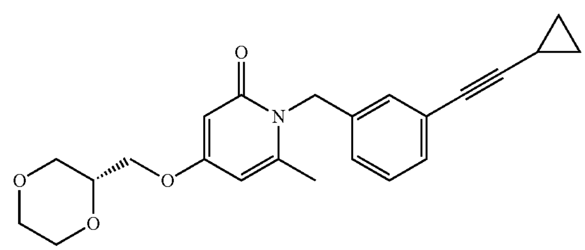 [SMILES: Cc1cc(OC[C@H]2COCCO2)cc(=O)n1Cc1cccc(C#CC2CC2)c1] |
| I-3 | 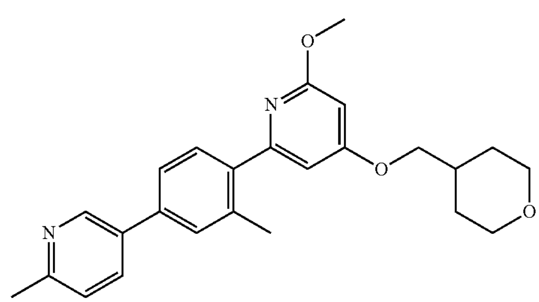 [SMILES: COc1cc(OCC2CCOCC2)cc(-c2ccc(-c3ccc(C)nc3)cc2C)n1] |
| I-4 | 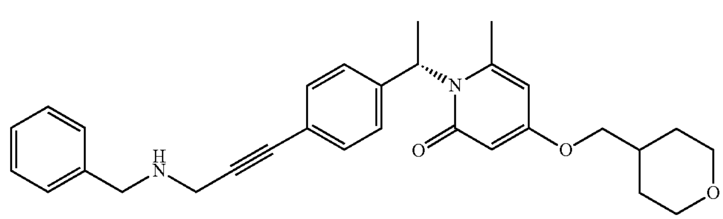 [SMILES: Cc1cc(OCC2CCOCC2)cc(=O)n1[C@@H](C)c1ccc(C#CCNCc2ccccc2)cc1] |

-continued
| Compound No. | Structure |
|---|---|
| I-5 | 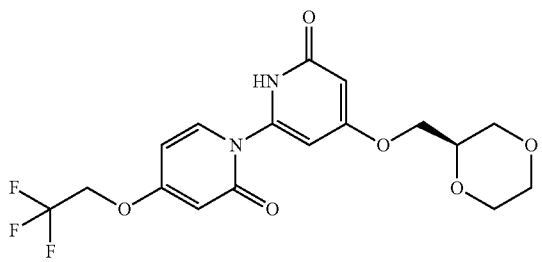 [SMILES: O=c1cc(OC[C@H]2COCCO2)cc(-n2ccc(OCC(F)(F)F)cc2=O)[nH]1] |
| I-6 | 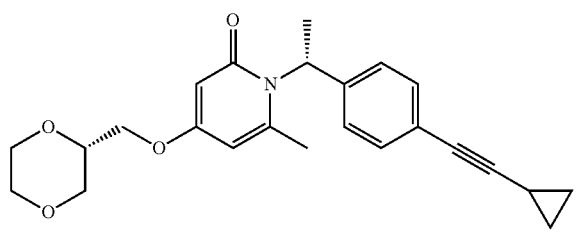 |
| I-7 | 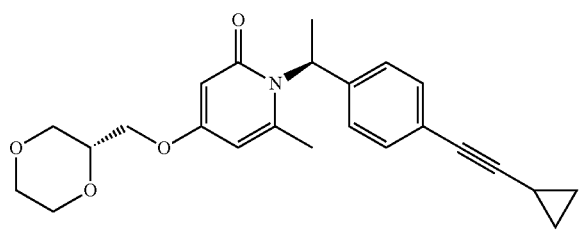 [SMILES: Cc1cc(OC[C@H]2COCCO2)cc(=O)n1[C@@H](C)c1ccc(C#CC2CC2)cc1] |
| I-8 | 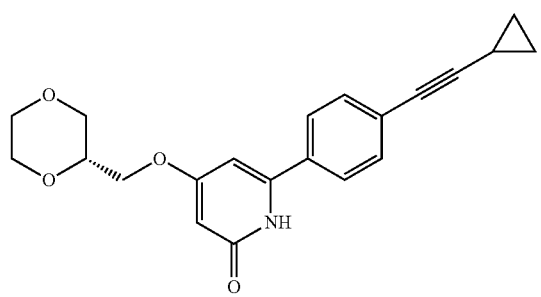 [SMILES: O=c1cc(OC[C@H]2COCCO2)cc(-c2ccc(C#CC3CC3)cc2)[nH]1] |
| I-9 | 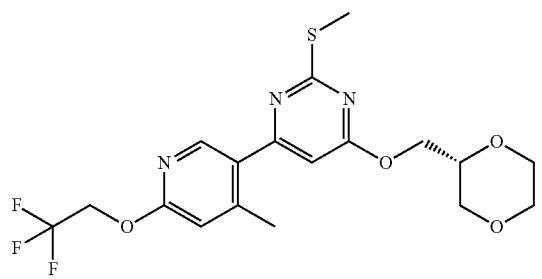 [SMILES: CSc1nc(OC[C@H]2COCCO2)cc(-c2cnc(OCC(F)(F)F)cc2C)n1] |
| I-10 | 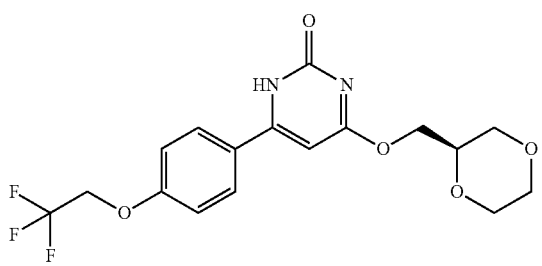 [SMILES: O=c1nc(OC[C@H]2COCCO2)cc(-c2ccc(OCC(F)(F)F)cc2)[nH]1] |

-continued
| Compound No. | Structure |
|---|---|
| I-11 | 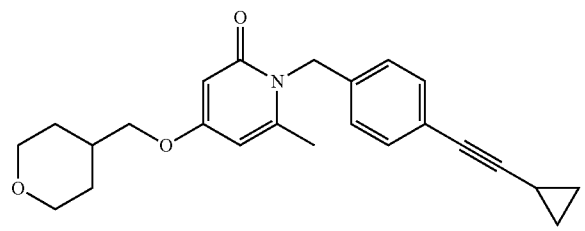 [SMILES: Cc1cc(OCC2CCOCC2)cc(=O)n1Cc1ccc(C#CC2CC2)cc1] |
| I-12 | 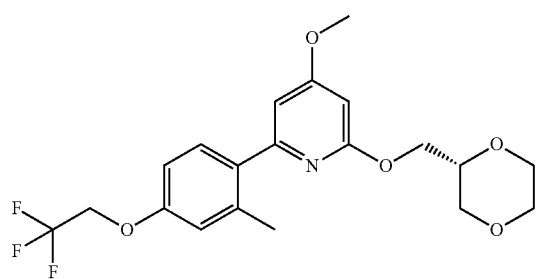 |
| I-13 | 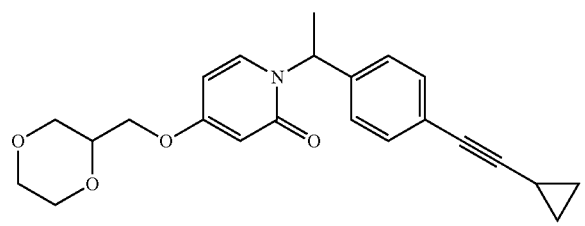 [SMILES: CC(c1ccc(C#CC2CC2)cc1)n1ccc(OCC2COCCO2)cc1=O] |
| I-14 | 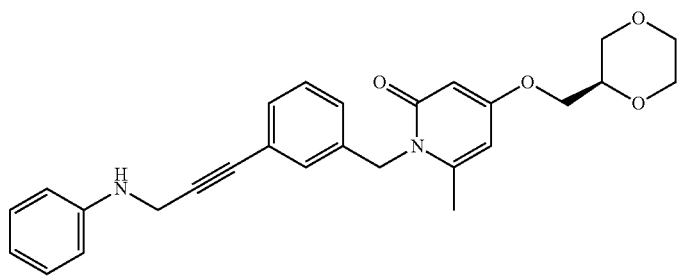 [SMILES: Cc1cc(OC[C@H]2COCCO2)cc(=O)n1Cc1cccc(C#CCNc2ccccc2)c1] |
| I-15 | 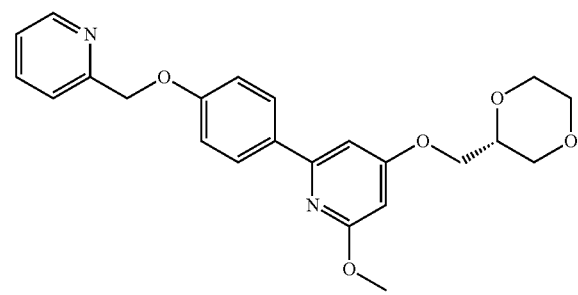 [SMILES: COc1cc(OC[C@H]2COCCO2)cc(-c2ccc(OCc3ccccn3)cc2)n1] |

-continued
| Compound No. | Structure |
|---|---|
| I-16 | 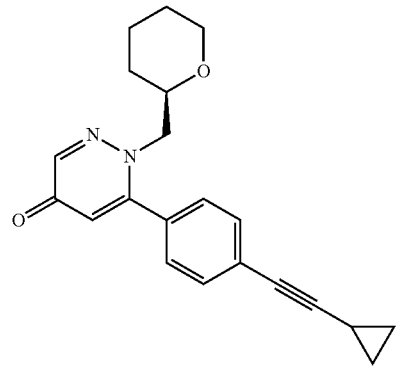 [SMILES: O=c1cnn(C[C@H]2CCCCO2)c(-c2ccc(C#CC3CC3)cc2)c1] |
| I-17 | 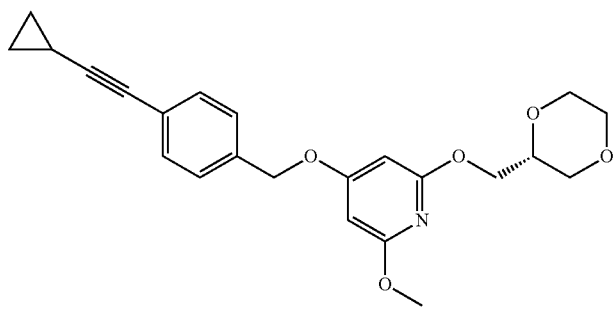 [SMILES: COc1cc(OCc2ccc(C#CC3CC3)cc2)cc(OC[C@H]2COCCO2)n1] |
| I-18 | 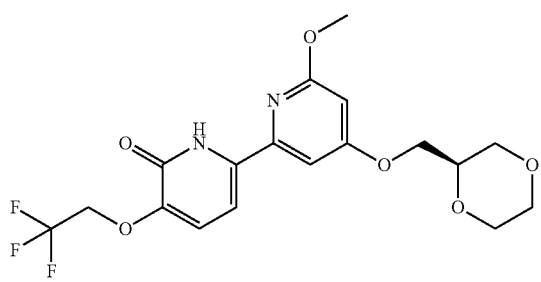 |
| I-19 | 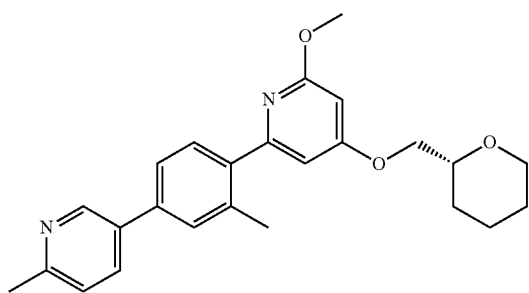 [SMILES: COc1cc(OC[C@H]2CCCCO2)cc(-c2ccc(-c3ccc(C)nc3)cc2C)n1] |
| I-20 | 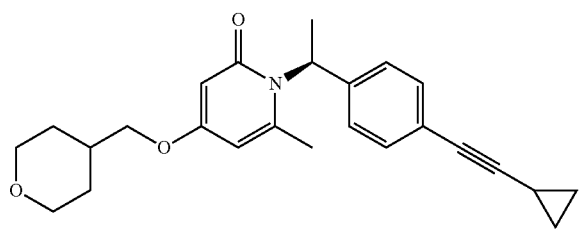 [SMILES: Cc1cc(OCC2CCOCC2)cc(=O)n1[C@@H](C)c1ccc(C#CC2CC2)cc1] |

-continued
| Compound No. | Structure |
|---|---|
| I-21 | 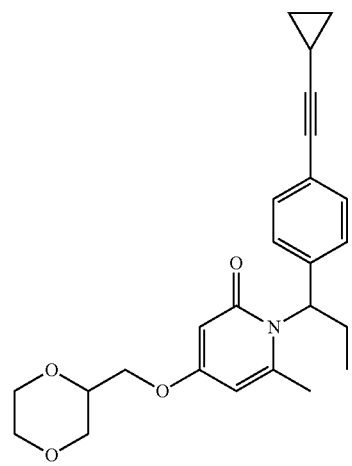 [SMILES: CCC(c1ccc(C#CC2CC2)cc1)n1c(C)cc(OCC2COCCO2)cc1=O] |
| I-22 | 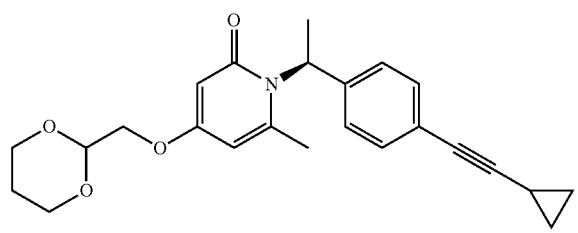 [SMILES: Cc1cc(OCC2OCCCO2)cc(=O)n1[C@@H](C)c1ccc(C#CC2CC2)cc1] |
| I-23 | 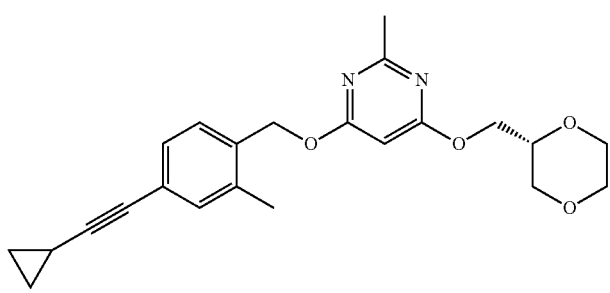 [SMILES: Cc1nc(OCc2ccc(C#CC3CC3)cc2C)cc(OC[C@H]2COCCO2)n1] |
| I-24 | 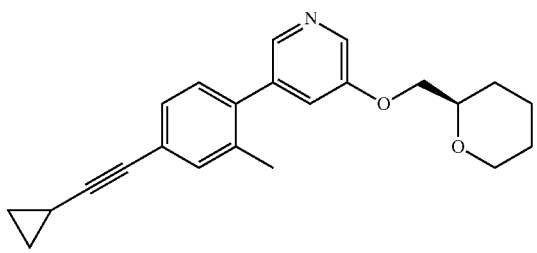 [SMILES: Cc1cc(C#CC2CC2)ccc1-c1cncc(OC[C@H]2CCCCO2)c1] |
| I-25 | 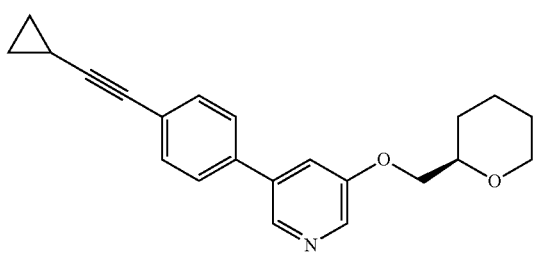 [SMILES: C(#CC1CC1)c1ccc(-c2cncc(OC[C@H]3CCCCO3)c2)cc1] |

-continued
| Compound No. | Structure |
|---|---|
| I-26 | 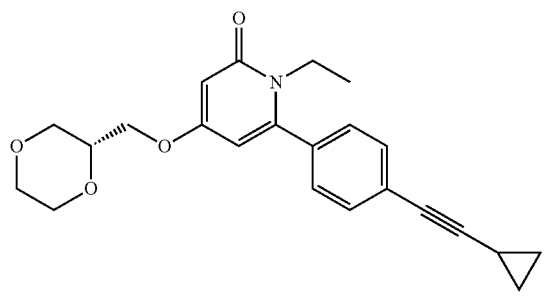 [SMILES: CCn1c(-c2ccc(C#CC3CC3)cc2)cc(OC[C@H]2COCCO2)cc1=O] |
| I-27 | 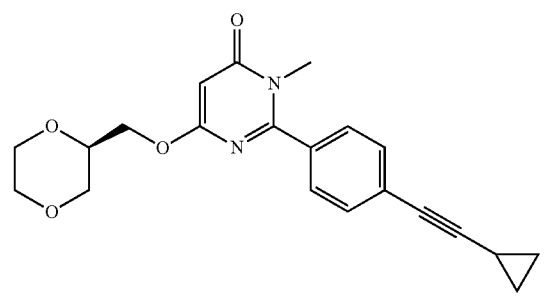 [SMILES: Cn1c(-c2ccc(C#CC3CC3)cc2)nc(OC[C@H]2COCCO2)cc1=O] |
| I-28 | 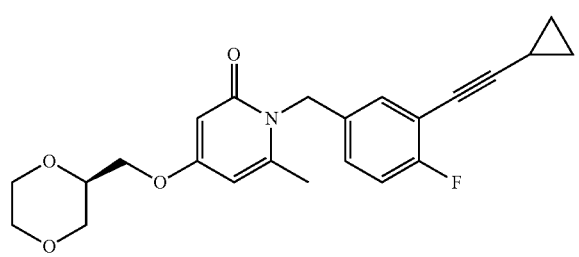 [SMILES: Cc1cc(OC[C@H]2COCCO2)cc(=O)n1Cc1ccc(F)c(C#CC2CC2)c1] |
| I-29 | 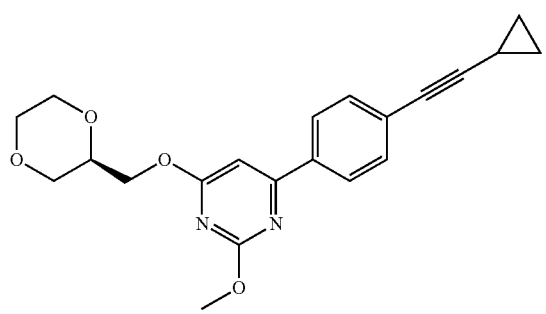 [SMILES: COc1nc(OC[C@H]2COCCO2)cc(-c2ccc(C#CC3CC3)cc2)n1] |
| I-30 | 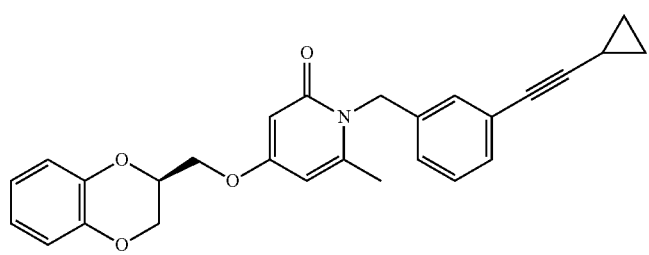 [SMILES: Cc1cc(OC[C@H]2COc3ccccc3O2)cc(=O)n1Cc1cccc(C#CC2CC2)c1] |

-continued
| Compound No. | Structure |
|---|---|
| I-31 | 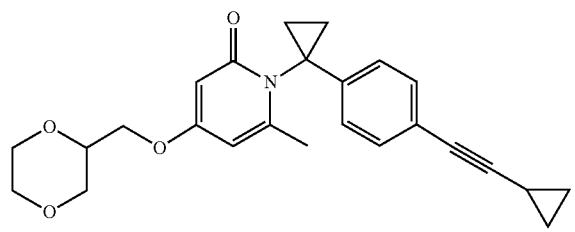 [SMILES: Cc1cc(OCC2COCCO2)cc(=O)n1C1(c2ccc(C#CC3CC3)cc2)CC1] |
| I-32 | 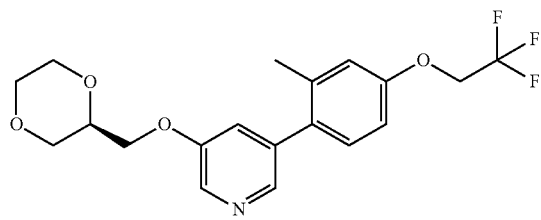 [SMILES: Cc1cc(OCC(F)(F)F)ccc1-c1cncc(OC[C@H]2COCCO2)c1] |
| I-33 | 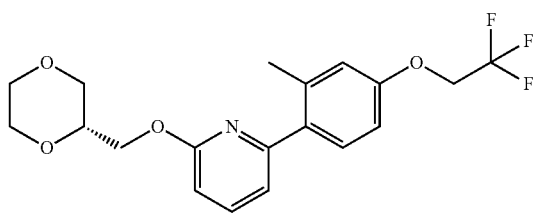 [SMILES: Cc1cc(OCC(F)(F)F)ccc1-c1cccc(OC[C@H]2COCCO2)n1] |
| I-34 | 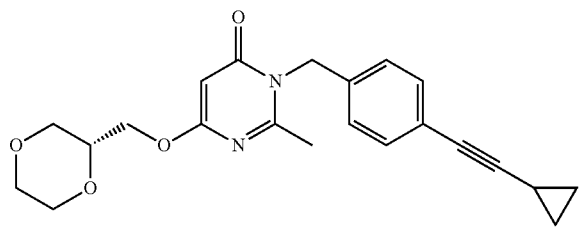 |
| I-35 | 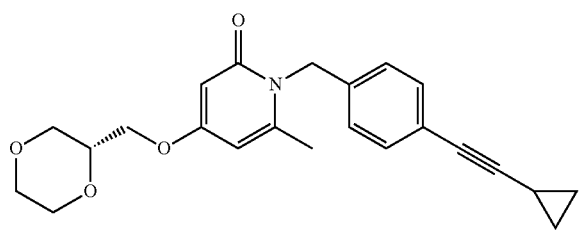 [SMILES: Cc1cc(OC[C@H]2COCCO2)cc(=O)n1Cc1ccc(C#CC2CC2)cc1] |
| I-36 | 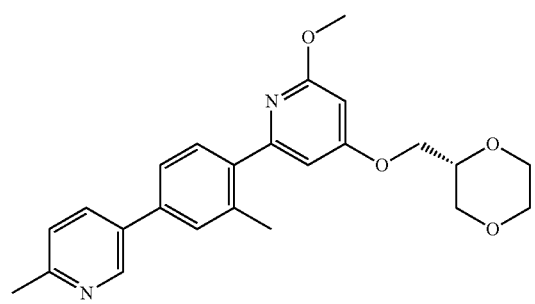 [SMILES: COc1cc(OC[C@H]2COCCO2)cc(-c2ccc(-c3ccc(C)nc3)cc2C)n1] |

| Compound No. | Structure |
|---|---|
| I-37 | 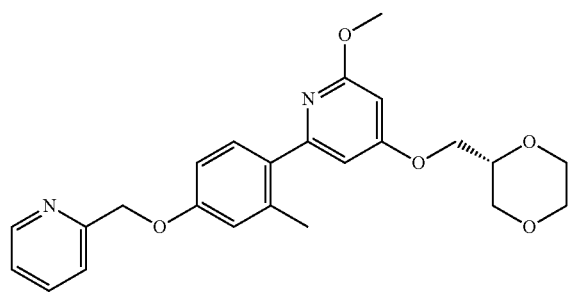 [SMILES: COc1cc(OC[C@H]2COCCO2)cc(-c2ccc(OCc3ccccn3)cc2C)n1] |
| I-38 | 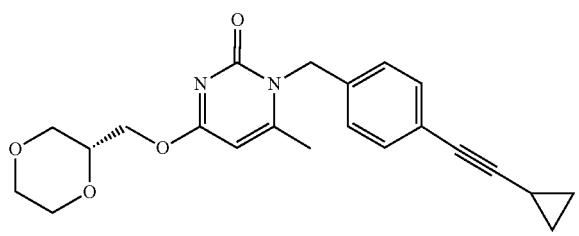 [SMILES: Cc1cc(OC[C@H]2COCCO2)nc(=O)n1Cc1ccc(C#CC2CC2)cc1] |
| I-39 | 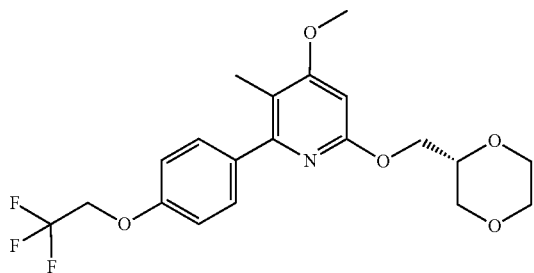 [SMILES: COc1cc(OC[C@H]2COCCO2)nc(-c2ccc(OCC(F)(F)F)cc2)c1C] |
| I-40 | 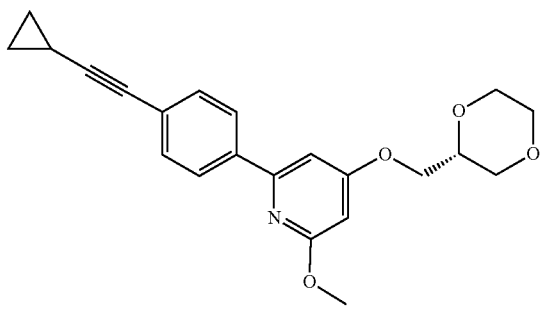 [SMILES: COc1cc(OC[C@H]2COCCO2)cc(-c2ccc(C#CC3CC3)cc2)n1] |
| I-41 | 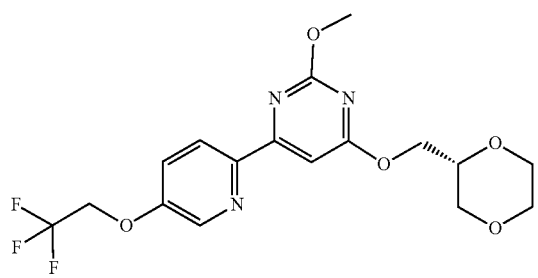 [SMILES: COc1nc(OC[C@H]2COCCO2)cc(-c2ccc(OCC(F)(F)F)cn2)n1] |

| Compound No. | Structure |
|---|---|
| I-42 | 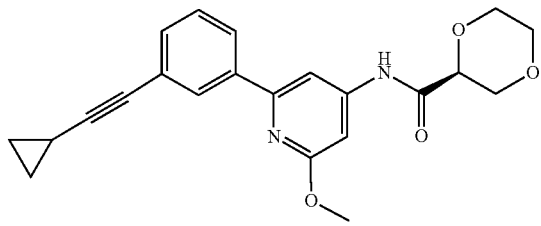 [SMILES: COc1cc(NC(=O)[C@@H]2COCCO2)cc(-c2cccc(C#CC3CC3)c2)n1] |
| I-43 | 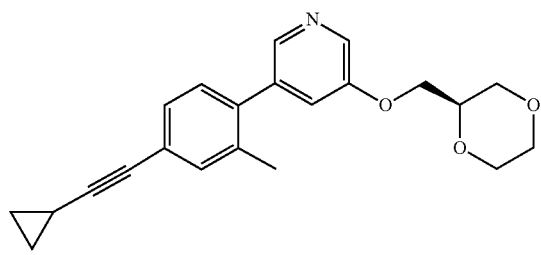 [SMILES: Cc1cc(C#CC2CC2)ccc1-c1cncc(OC[C@H]2COCCO2)c1] |
| I-44 | 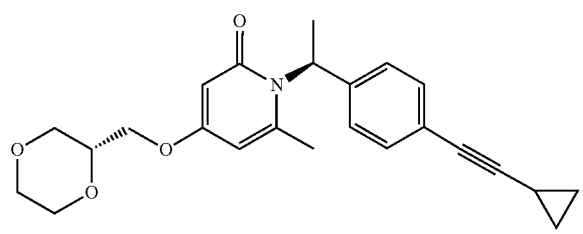 [SMILES: Cc1cc(OC[C@H]2COCCO2)cc(=O)n1[C@@H](C)c1ccc(C#CC2CC2)cc1] |
| I-45 | 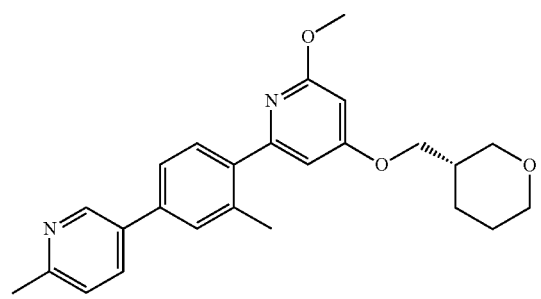 [SMILES: COc1cc(OC[C@H]2CCCOC2)cc(-c2ccc(-c3ccc(C)nc3)cc2C)n1] |
| I-46 | 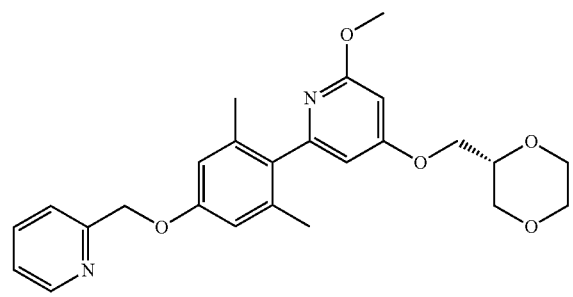 |

-continued
| Compound No. | Structure |
|---|---|
| I-47 | 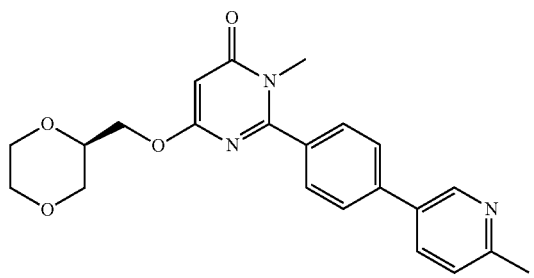 [SMILES: Cc1ccc(-c2ccc(-c3nc(OC[C@H]4COCCO4)cc(=O)n3C)cc2)cn1] |
| I-48 | 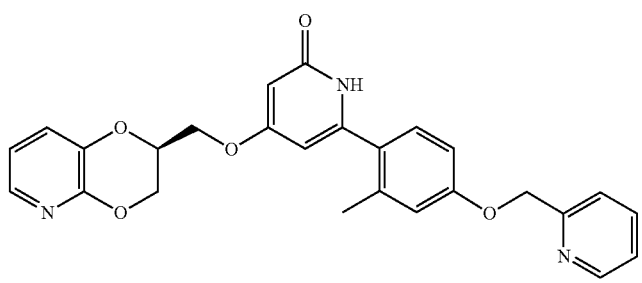 [SMILES: Cc1cc(OCc2ccccn2)ccc1-c1cc(OC[C@H]2COc3ncccc3O2)cc(=O)[nH]1] |
| I-49 | 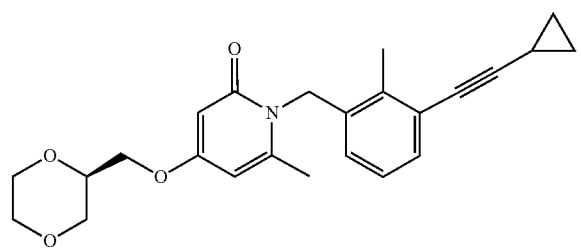 [SMILES: Cc1c(C#CC2CC2)cccc1Cn1c(C)cc(OC[C@H]2COCCO2)cc1=O] |
| I-50 | 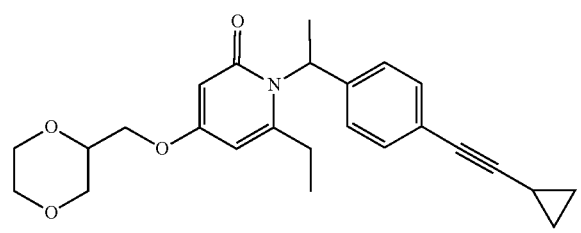 [SMILES: CCc1cc(OCC2COCCO2)cc(=O)n1C(C)c1ccc(C#CC2CC2)cc1] |
| I-51 | 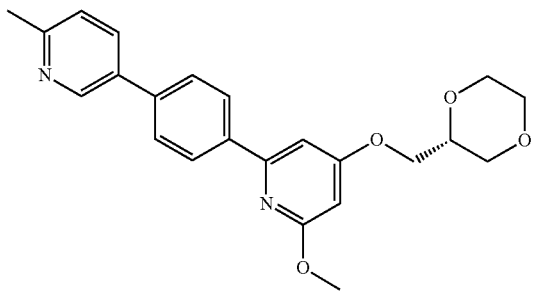 [SMILES: COc1cc(OC[C@H]2COCCO2)cc(-c2ccc(-c3ccc(C)nc3)cc2)n1] |

-continued

| Compound No. | Structure |
|---|---|
| I-52 | 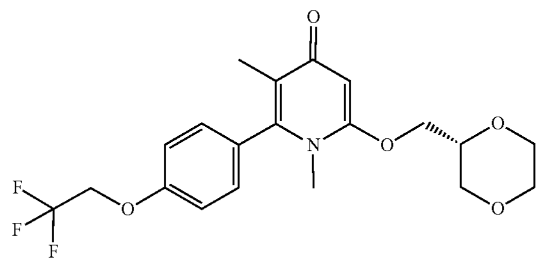 [SMILES: Cc1c(-c2ccc(OCC(F)(F)F)cc2)n(C)c(OC[C@H]2COCCO2)cc1=O] |
| I-53 | 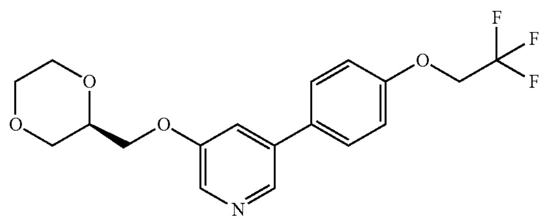 [SMILES: FC(F)(F)COc1ccc(-c2cncc(OC[C@H]3COCCO3)c2)cc1] |
| I-54 | 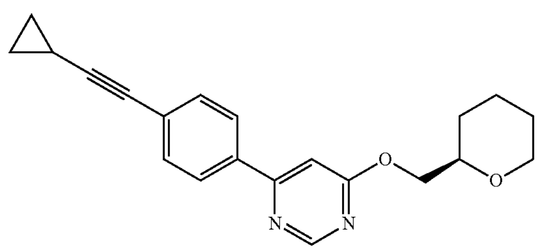 [SMILES: C(#CC1CC1)c1ccc(-c2cc(OC[C@H]3CCCCO3)ncn2)cc1] |
| I-55 | 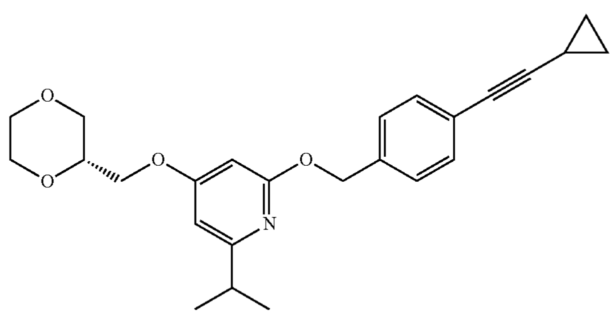 [SMILES: CC(C)c1cc(OC[C@H]2COCCO2)cc(OCc2ccc(C#CC3CC3)cc2)n1] |
| I-56 | 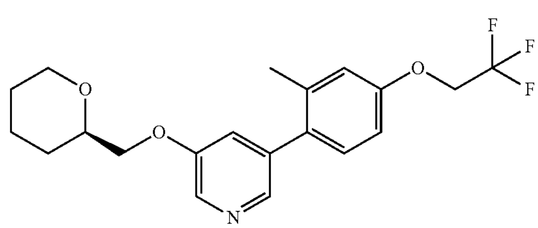 [SMILES: Cc1cc(OCC(F)(F)F)ccc1-c1cncc(OC[C@H]2CCCCO2)c1] |
| I-57 | 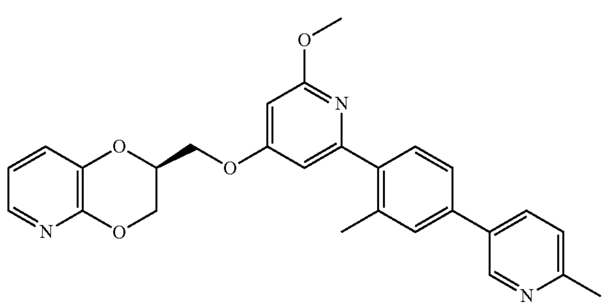 [SMILES: COc1cc(OC[C@H]2COc3ncccc3O2)cc(-c2ccc(-c3ccc(C)nc3)cc2C)n1] |

-continued
| Compound No. | Structure |
|---|---|
| I-58 | 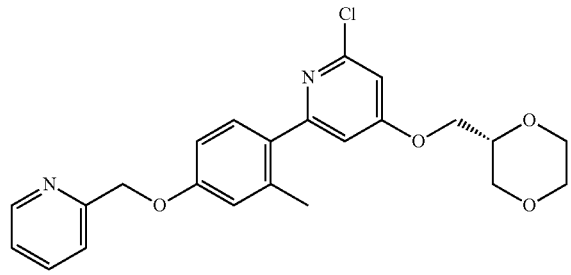 [SMILES: Cc1cc(OCc2ccccn2)ccc1-c1cc(OC[C@H]2COCCO2)cc(Cl)n1] |
| I-59 | 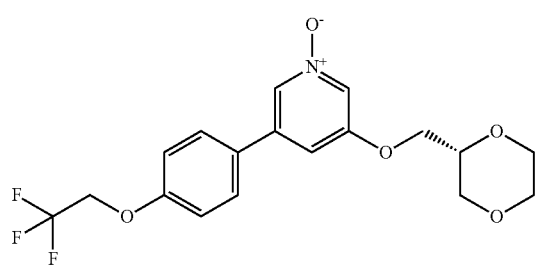 [SMILES: [O-][n+]1cc(OC[C@H]2COCCO2)cc(-c2ccc(OCC(F)(F)F)cc2)c1] |
| I-60 | 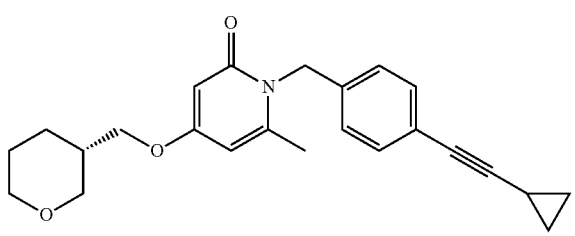 [SMILES: Cc1cc(OC[C@H]2CCCOC2)cc(=O)n1Cc1ccc(C#CC2CC2)cc1] |
| I-61 | 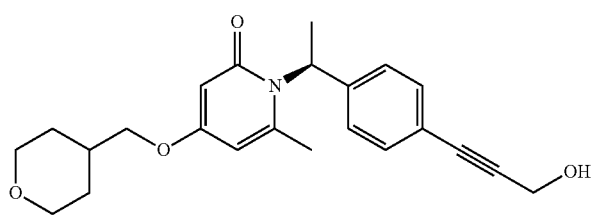 [SMILES: Cc1cc(OCC2CCOCC2)cc(=O)n1[C@@H](C)c1ccc(C#CCO)cc1] |
| I-62 | 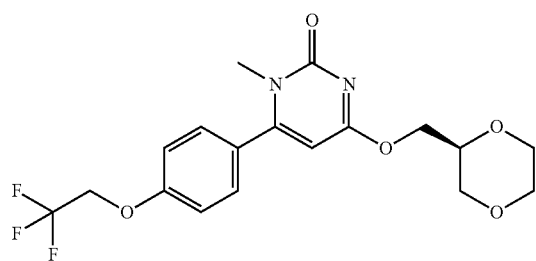 [SMILES: Cn1c(-c2ccc(OCC(F)(F)F)cc2)cc(OC[C@@H]2COCCO2)nc1=O] |
| I-63 | 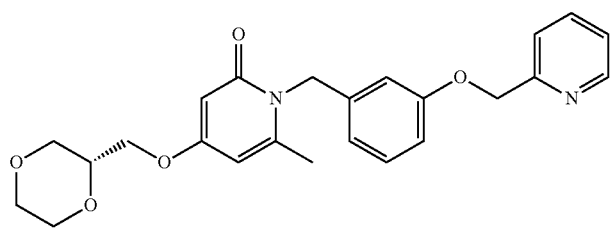 [SMILES: Cc1cc(OC[C@H]2COCCO2)cc(=O)n1Cc1cccc(OCc2ccccn2)c1] |

-continued
| Compound No. | Structure |
|---|---|
| I-64 | 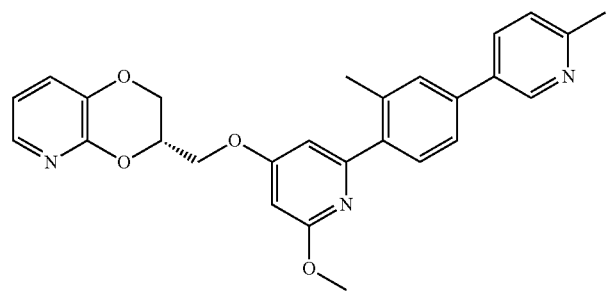 [SMILES: COc1cc(OC[C@H]2COc3cccnc3O2)cc(-c2ccc(-c3ccc(C)nc3)cc2C)n1] |
| I-65 | 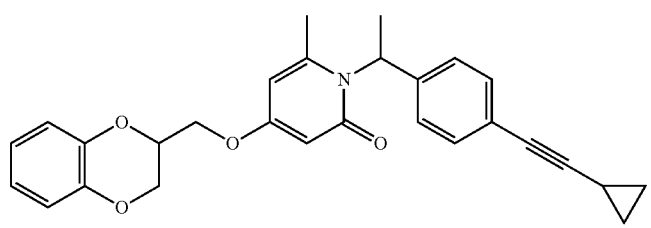 [SMILES: Cc1cc(OCC2COc3ccccc3O2)cc(=O)n1C(C)c1ccc(C#CC2CC2)cc1] |
| I-66 | 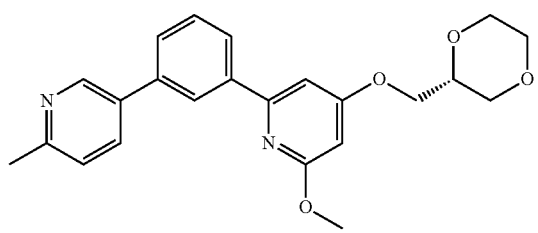 [SMILES: COc1cc(OC[C@H]2COCCO2)cc(-c2cccc(-c3ccc(C)nc3)c2)n1] |
| I-67 | 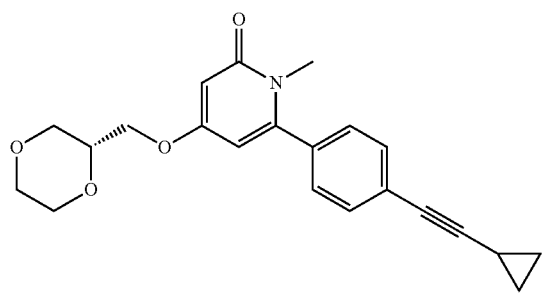 [SMILES: Cn1c(-c2ccc(C#CC3CC3)cc2)cc(OC[C@H]2COCCO2)cc1=O] |
| I-68 | 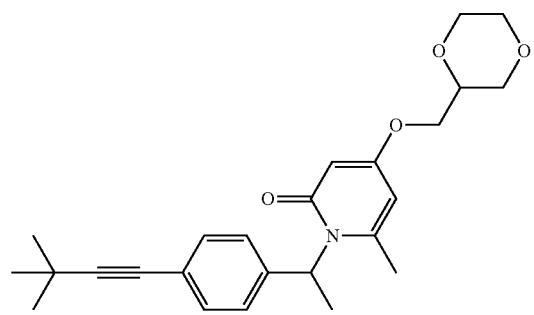 [SMILES: Cc1cc(OCC2COCCO2)cc(=O)n1C(C)c1ccc(C#CC(C)(C)C)cc1] |

-continued
| Compound No. | Structure |
|---|---|
| I-69 | 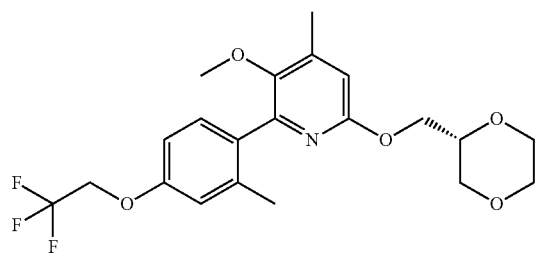 [SMILES: COc1c(C)cc(OC[C@H]2COCCO2)nc1-c1ccc(OCC(F)(F)F)cc1C] |
| I-70 | 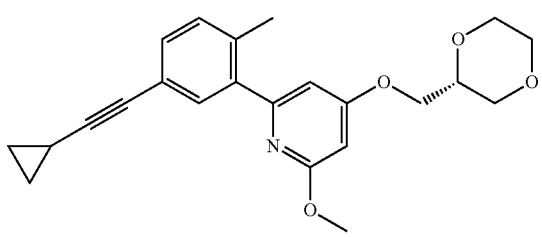 [SMILES: COc1cc(OC[C@H]2COCCO2)cc(-c2cc(C#CC3CC3)ccc2C)n1] |
| I-71 | 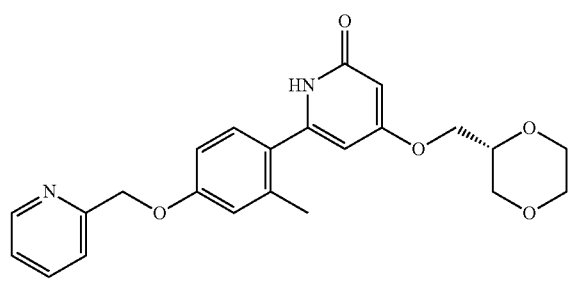 [SMILES: Cc1cc(OCc2ccccn2)ccc1-c1cc(OC[C@H]2COCCO2)cc(=O)[nH]1] |
| I-72 | 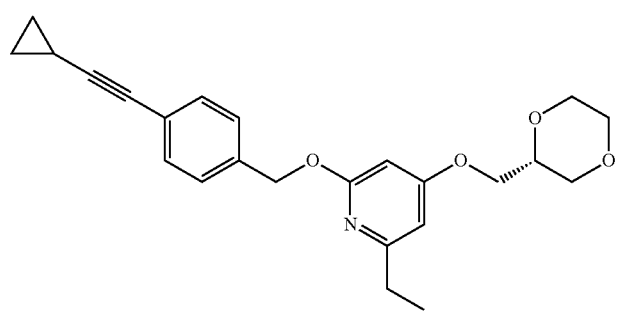 [SMILES: CCc1cc(OC[C@H]2COCCO2)cc(OCc2ccc(C#CC3CC3)cc2)n1] |
| I-73 | 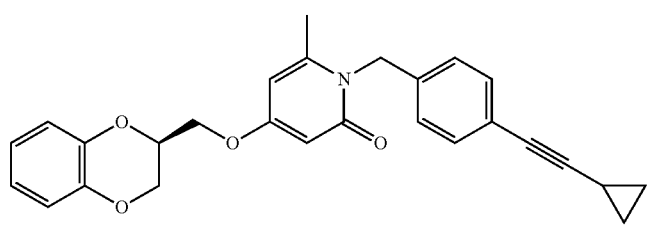 |

-continued
| Compound No. | Structure |
|---|---|
| I-74 | 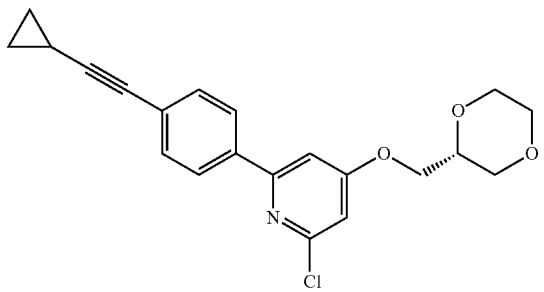 [SMILES: Clc1cc(OC[C@H]2COCCO2)cc(-c2ccc(C#CC3CC3)cc2)n1] |
| I-75 | 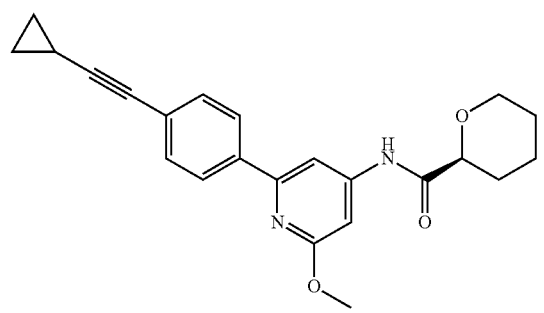 [SMILES: COc1cc(NC(=O)[C@@H]2CCCCO2)cc(-c2ccc(C#CC3CC3)cc2)n1] |
| I-76 | 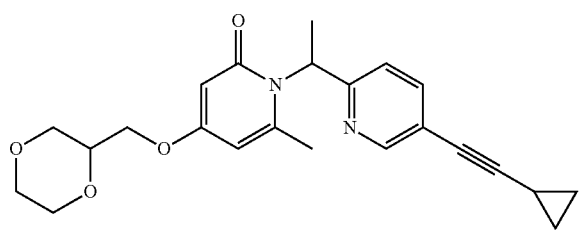 |
| I-77 | 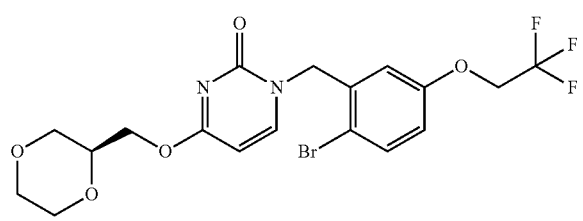 [SMILES: O=c1nc(OC[C@@H]2COCCO2)ccn1Cc1cc(OCC(F)(F)F)ccc1Br] |
| I-78 | 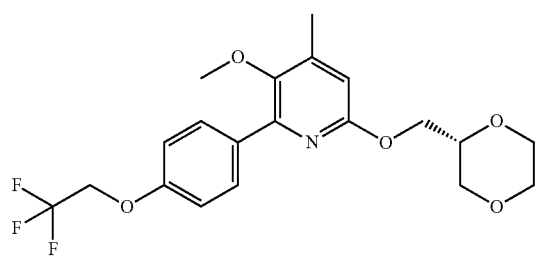 [SMILES: COc1c(C)cc(OC[C@H]2COCCO2)nc1-c1ccc(OCC(F)(F)F)cc1] |
| I-79 | 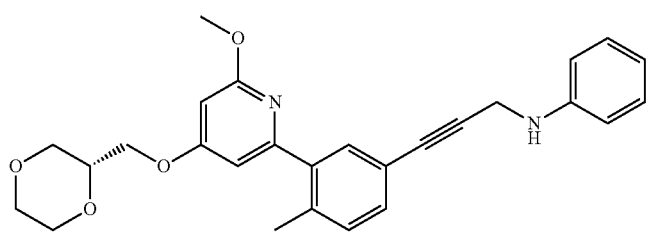 [SMILES: COc1cc(OC[C@H]2COCCO2)cc(-c2cc(C#CCNc3ccccc3)ccc2C)n1] |

| Compound No. | Structure |
|---|---|
| I-80 | 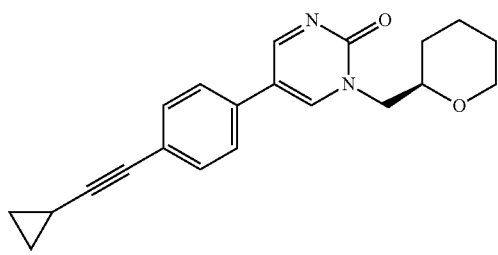 [SMILES: O=c1ncc(-c2ccc(C#CC3CC3)cc2)cn1C[C@H]1CCCCO1] |
| I-81 | 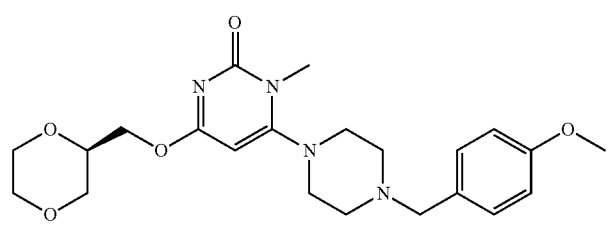 [SMILES: COc1ccc(CN2CCN(c3cc(OC[C@H]4COCCO4)nc(=O)n3C)CC2)cc1] |
| I-82 | 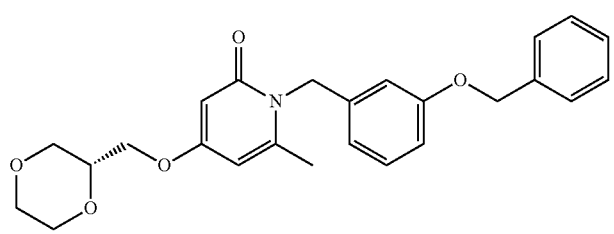 [SMILES: Cc1cc(OC[C@H]2COCCO2)cc(=O)n1Cc1cccc(OCc2ccccc2)c1] |
| I-83 | 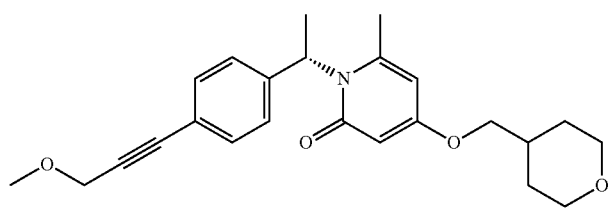 [SMILES: COCC#Cc1ccc([C@H](C)n2c(C)cc(OCC3CCOCC3)cc2=O)cc1] |
| I-84 | 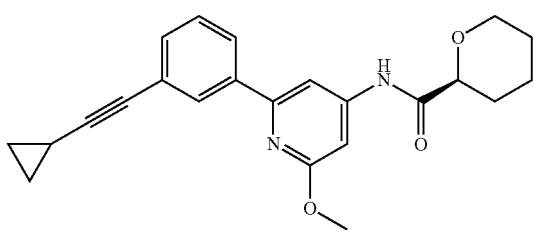 [SMILES: COc1cc(NC(=O)[C@@H]2CCCCO2)cc(-c2cccc(C#CC3CC3)c2)n1] |
| I-85 | 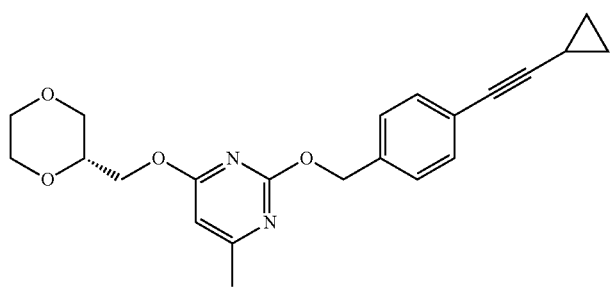 [SMILES: Cc1cc(OC[C@H]2COCCO2)nc(OCc2ccc(C#CC3CC3)cc2)n1] |

| Compound No. | Structure |
|---|---|
| I-86 | 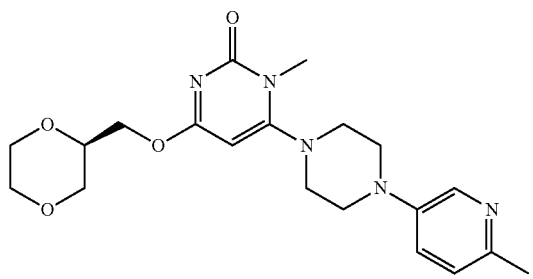 [SMILES: Cc1ccc(N2CCN(c3cc(OC[C@H]4COCCO4)nc(=O)n3C)CC2)cn1] |
| I-87 | 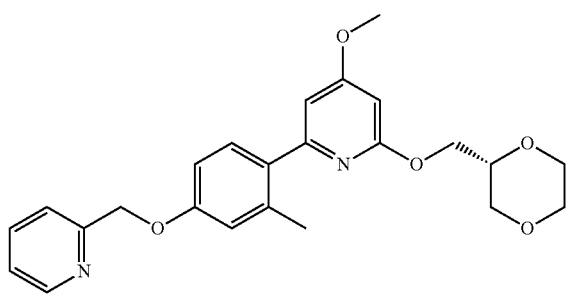 [SMILES: COc1cc(OC[C@H]2COCCO2)nc(-c2ccc(OCc3ccccn3)cc2C)c1] |
| I-88 | 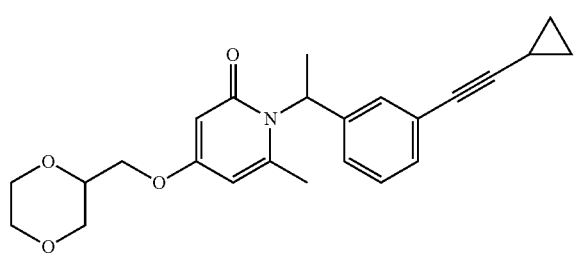 [SMILES: Cc1cc(OCC2COCCO2)cc(=O)n1C(C)c1cccc(C#CC2CC2)c1] |
| I-89 | 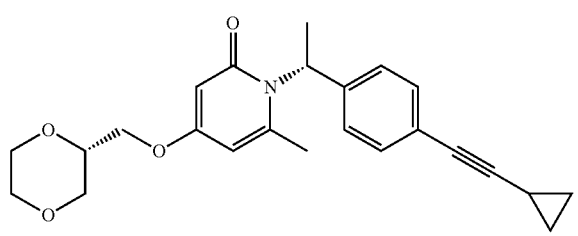 [SMILES: Cc1cc(OC[C@@H]2COCCO2)cc(=O)n1[C@H](C)c1ccc(C#CC2CC2)cc1] |
| I-90 | 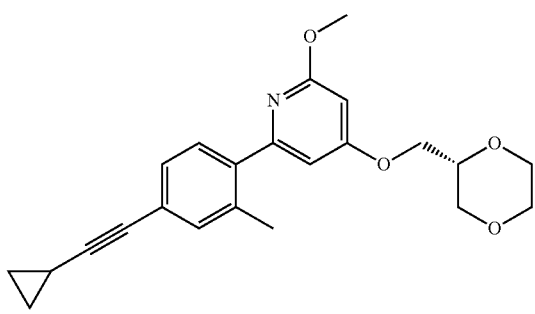 [SMILES: COc1cc(OC[C@H]2COCCO2)cc(-c2ccc(C#CC3CC3)cc2C)n1] |

-continued
| Compound No. | Structure |
|---|---|
| I-91 | 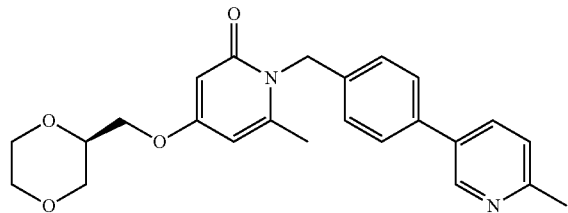 [SMILES: Cc1ccc(-c2ccc(Cn3c(C)cc(OC[C@H]4COCCO4)cc3=O)cc2)cn1] |
| I-92 | 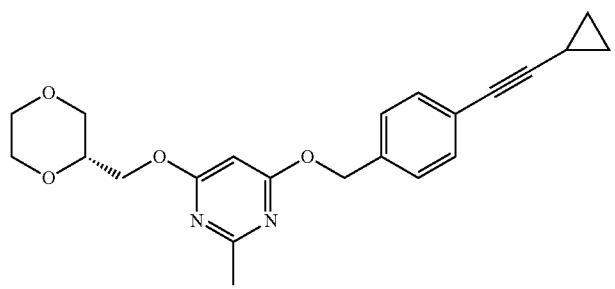 [SMILES: Cc1nc(OCc2ccc(C#CC3CC3)cc2)cc(OC[C@H]2COCCO2)n1] |
| I-93 | 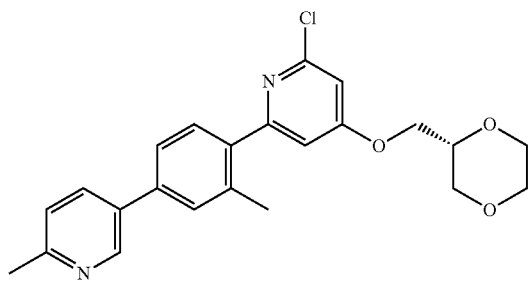 [SMILES: Cc1ccc(-c2ccc(-c3cc(OC[C@H]4COCCO4)cc(Cl)n3)c(C)c2)cn1] |
| I-94 | 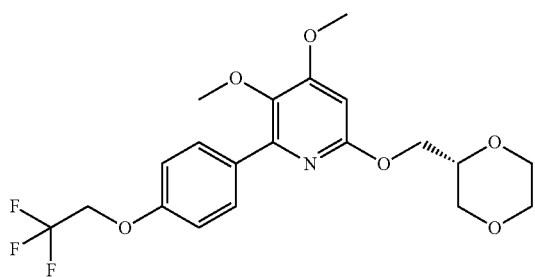 [SMILES: COc1cc(OC[C@H]2COCCO2)nc(-c2ccc(OCC(F)(F)F)cc2)c1OC] |
| I-95 | 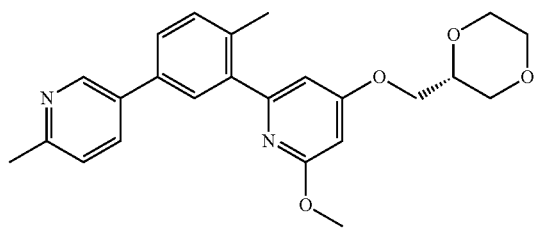 [SMILES: COc1cc(OC[C@H]2COCCO2)cc(-c2cc(-c3ccc(C)nc3)ccc2C)n1] |
| I-96 | 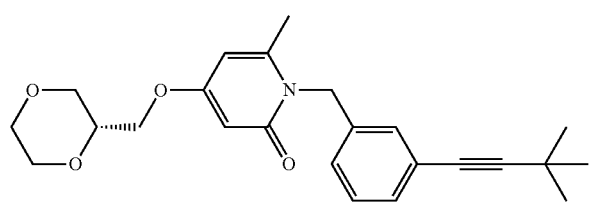 [SMILES: Cc1cc(OC[C@H]2COCCO2)cc(=O)n1Cc1cccc(C#CC(C)(C)C)c1] |

| Compound No. | Structure |
|---|---|
| I-97 | 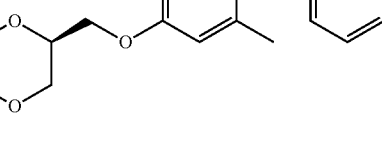 |
| I-98 | 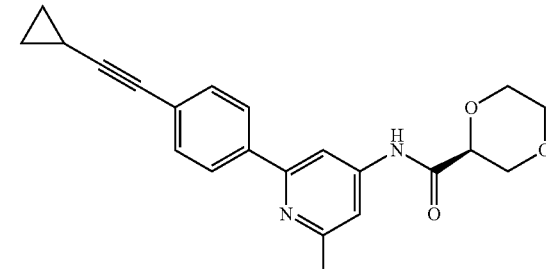 |
| I-99 | 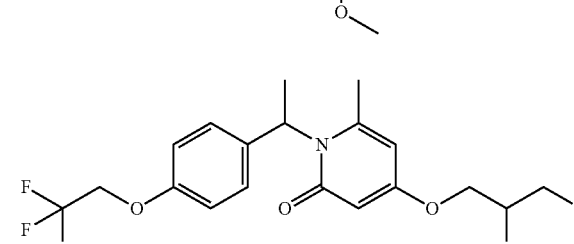 |
| I-100 | 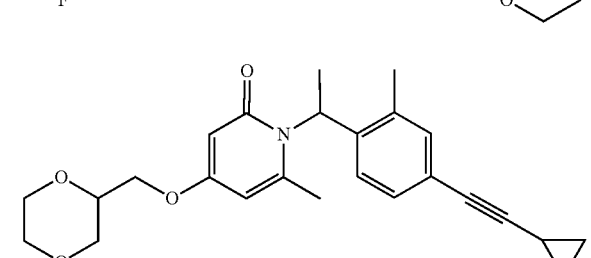 |
| I-101 | 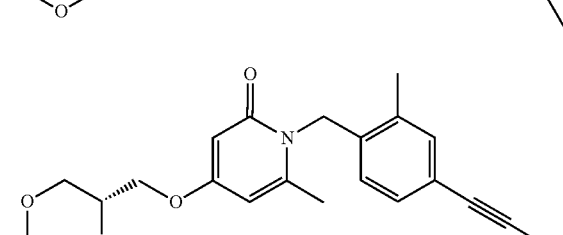 |
| I-102 | 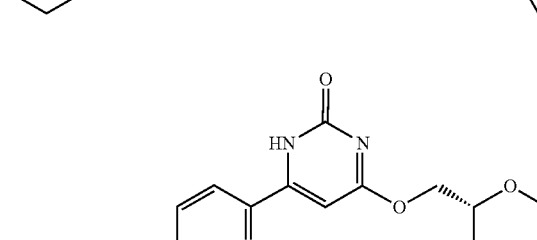 |

| Compound No. | Structure |
|---|---|
| I-103 | 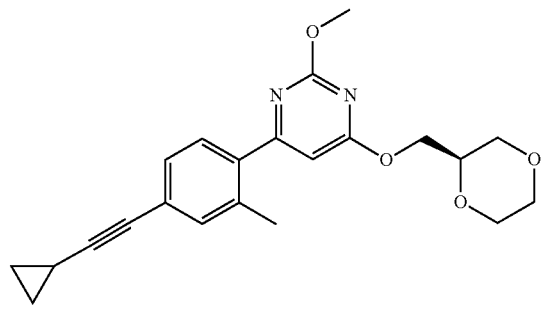 [SMILES: COc1nc(OC[C@H]2COCCO2)cc(-c2ccc(C#CC3CC3)cc2C)n1] |
| I-104 | 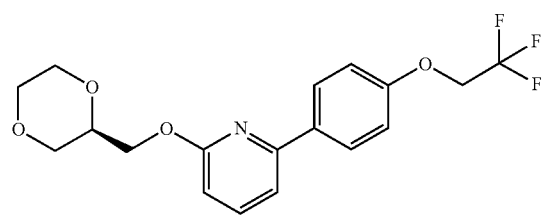 [SMILES: FC(F)(F)COc1ccc(-c2cccc(OC[C@H]3COCCO3)n2)cc1] |
| I-105 | 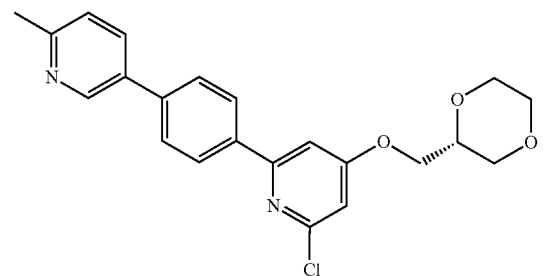 [SMILES: Cc1ccc(-c2ccc(-c3cc(OC[C@H]4COCCO4)cc(Cl)n3)cc2)cn1] |
| I-106 | 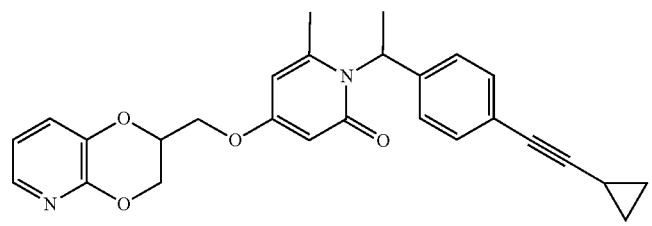 [SMILES: Cc1cc(OCC2COc3ncccc3O2)cc(=O)n1C(C)c1ccc(C#CC2CC2)cc1] |
| I-107 | 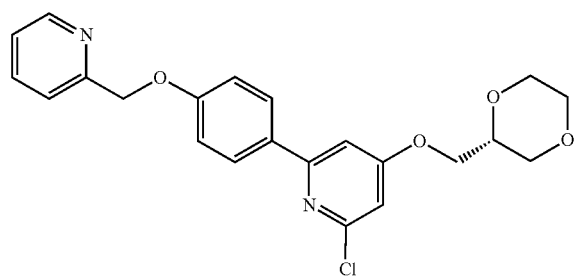 [SMILES: Clc1cc(OC[C@H]2COCCO2)cc(-c2ccc(OCc3ccccn3)cc2)n1] |

-continued
| Compound No. | Structure |
|---|---|
| I-108 | 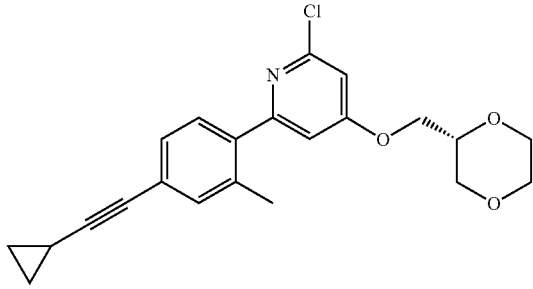 [SMILES: Cc1cc(C#CC2CC2)ccc1-c1cc(OC[C@H]2COCCO2)cc(Cl)n1] |
| I-109 | 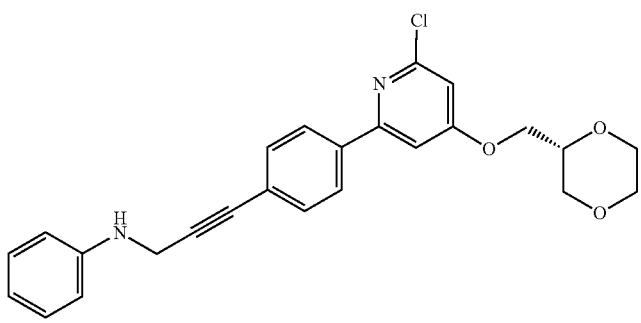 |
| I-110 | 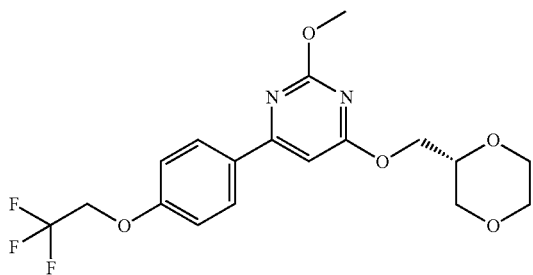 |
| I-111 | 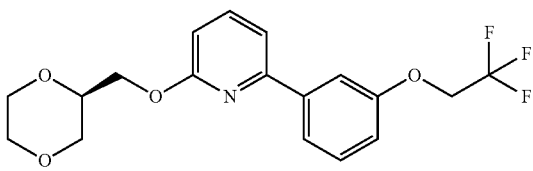 [SMILES: FC(F)(F)COc1cccc(-c2cccc(OC[C@H]3COCCO3)n2)c1] |
| I-112 | 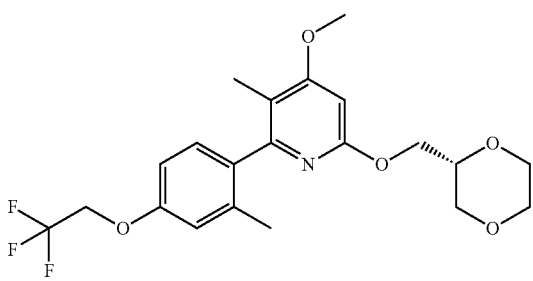 [SMILES: COc1cc(OC[C@H]2COCCO2)nc(-c2ccc(OCC(F)(F)F)cc2C)c1C] |
| I-113 | 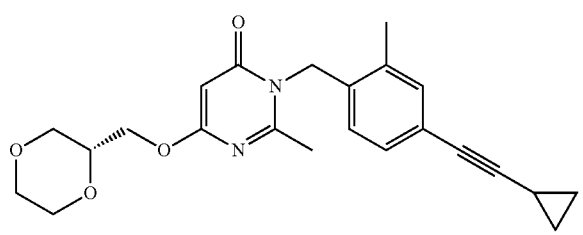 |

| Compound No. | Structure |
|---|---|
| I-114 | 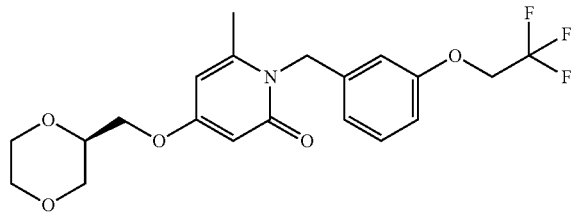 [SMILES: Cc1cc(OC[C@H]2COCCO2)cc(=O)n1Cc1cccc(OCC(F)(F)F)c1] |
| I-115 | 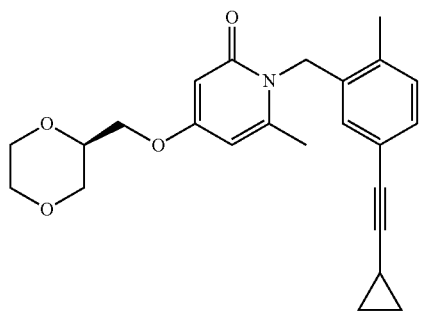 [SMILES: Cc1ccc(C#CC2CC2)cc1Cn1c(C)cc(OC[C@H]2COCCO2)cc1=O] |
| I-116 | 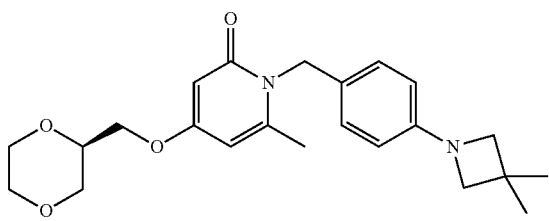 [SMILES: Cc1cc(OC[C@H]2COCCO2)cc(=O)n1Cc1ccc(N2CC(C)(C)C2)cc1] |
| I-117 | 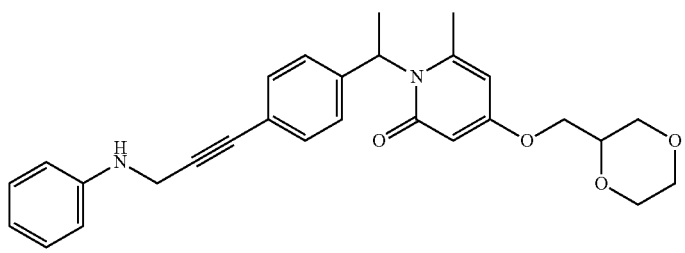 [SMILES: Cc1cc(OCC2COCCO2)cc(=O)n1C(C)c1ccc(C#CCNc2ccccc2)cc1] |
| I-118 | 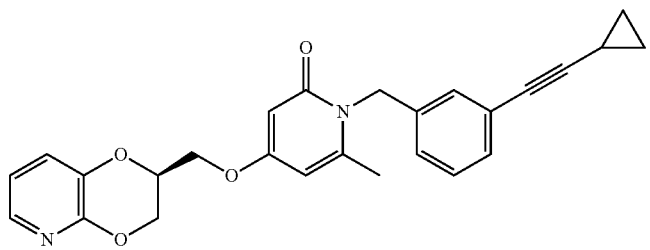 [SMILES: Cc1cc(OC[C@H]2COc3ncccc3O2)cc(=O)n1Cc1cccc(C#CC2CC2)c1] |
| I-119 | 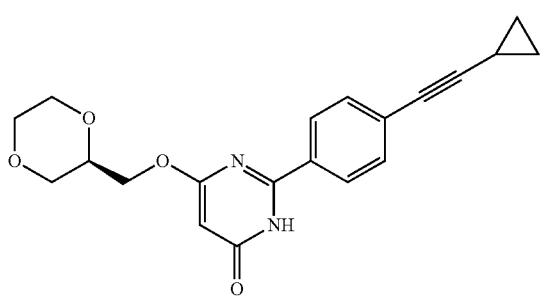 [SMILES: O=c1cc(OC[C@H]2COCCO2)nc(-c2ccc(C#CC3CC3)cc2)[nH]1] |

| Compound No. | Structure |
|---|---|
| I-120 | 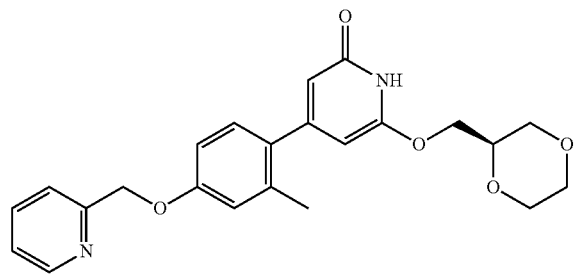 [SMILES: Cc1cc(OCc2ccccn2)ccc1-c1cc(OC[C@H]2COCCO2)[nH]c(=O)c1] |
| I-121 | 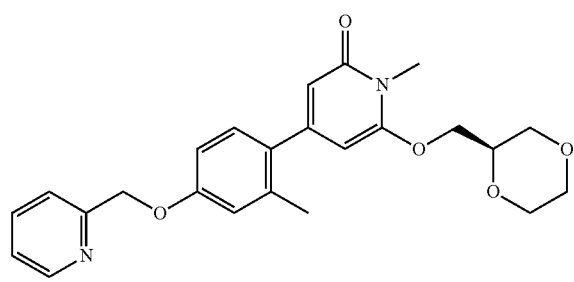 [SMILES: Cc1cc(OCc2ccccn2)ccc1-c1cc(OC[C@H]2COCCO2)n(C)c(=O)c1] |
| I-122 | 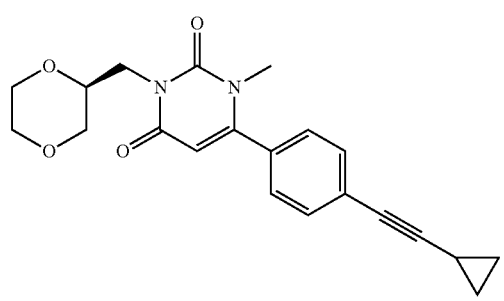 [SMILES: Cn1c(-c2ccc(C#CC3CC3)cc2)cc(=O)n(C[C@H]2COCCO2)c1=O] |
| I-123 | 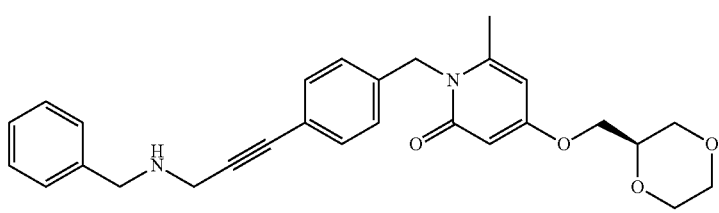 [SMILES: Cc1cc(OC[C@H]2COCCO2)cc(=O)n1Cc1ccc(C#CCNCc2ccccc2)cc1] |
| I-124 | 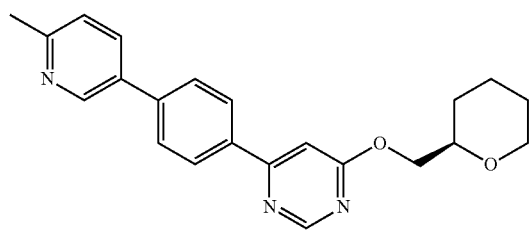 [SMILES: Cc1ccc(-c2ccc(-c3cc(OC[C@H]4CCCCO4)ncn3)cc2)cn1] |

-continued
| Compound No. | Structure |
|---|---|
| I-125 | 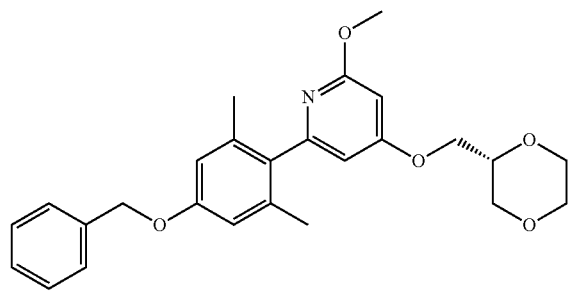 [SMILES: COc1cc(OC[C@H]2COCCO2)cc(-c2c(C)cc(OCc3ccccc3)cc2C)n1] |
| I-126 | 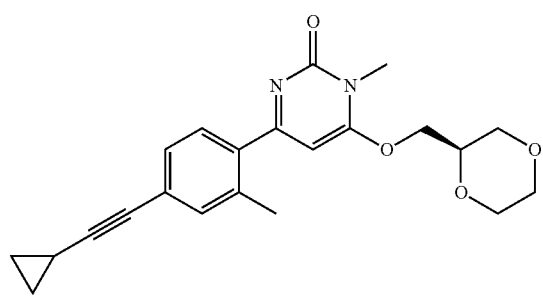 [SMILES: Cc1cc(C#CC2CC2)ccc1-c1cc(OC[C@H]2COCCO2)n(C)c(=O)n1] |
| I-127 | 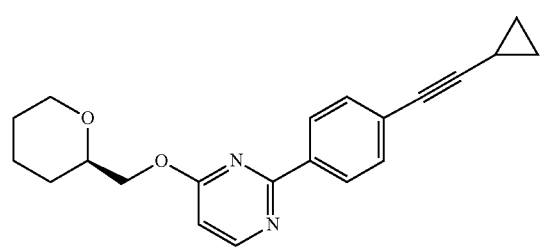 |
| I-128 | 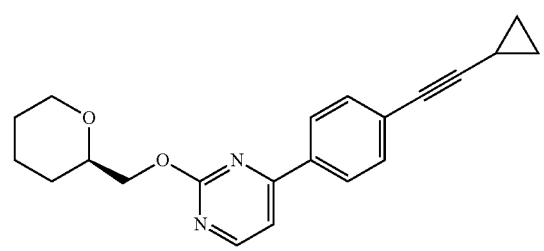 [SMILES: C(#CC1CC1)c1ccc(-c2ccnc(OC[C@H]3CCCCO3)n2)cc1] |
| I-129 | 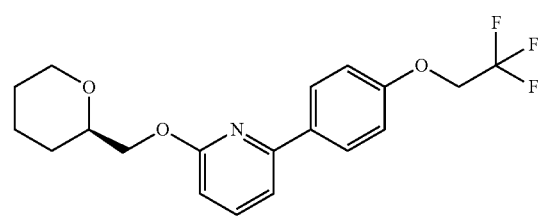 [SMILES: FC(F)(F)COc1ccc(-c2cccc(OC[C@H]3CCCCO3)n2)cc1] |

| Compound No. | Structure |
|---|---|
| I-130 | 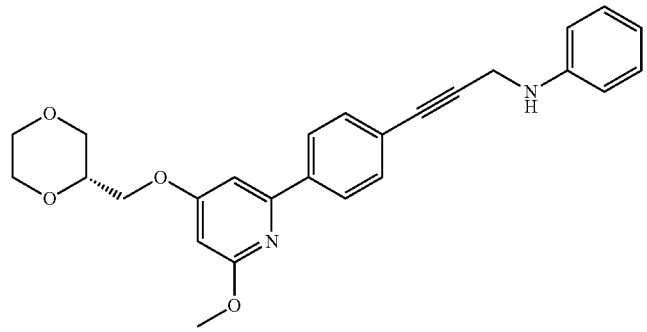 [SMILES: COc1cc(OC[C@H]2COCCO2)cc(-c2ccc(C#CCNc3ccccc3)cc2)n1] |
| I-131 | 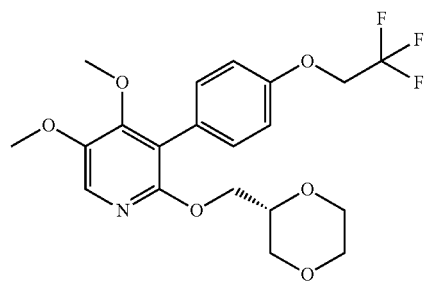 [SMILES: COc1cnc(OC[C@H]2COCCO2)c(-c2ccc(OCC(F)(F)F)cc2)c1OC] |
| I-132 | 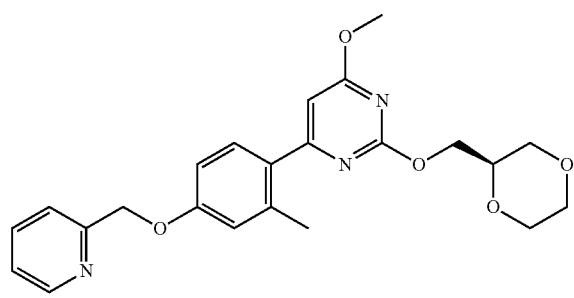 [SMILES: COc1cc(-c2ccc(OCc3ccccn3)cc2C)nc(OC[C@H]2COCCO2)n1] |
| I-133 | 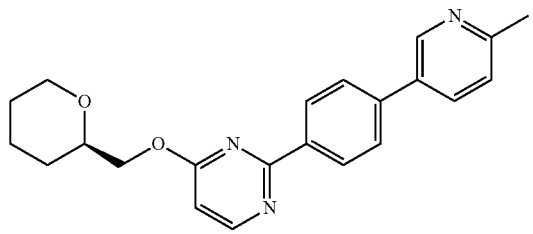 [SMILES: Cc1ccc(-c2ccc(-c3nccc(OC[C@H]4CCCCO4)n3)cc2)cn1] |
| I-134 | 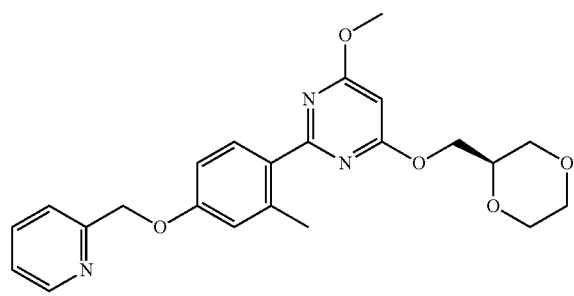 |

| Compound No. | Structure |
|---|---|
| I-135 | 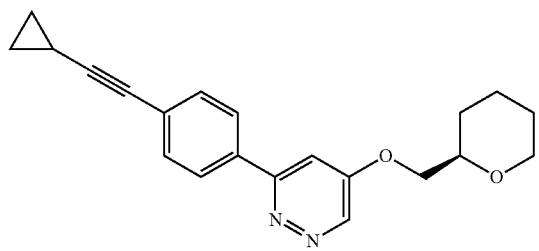 [SMILES: C(#CC1CC1)c1ccc(-c2cc(OC[C@H]3CCCCO3)cnn2)cc1] |
| I-136 | 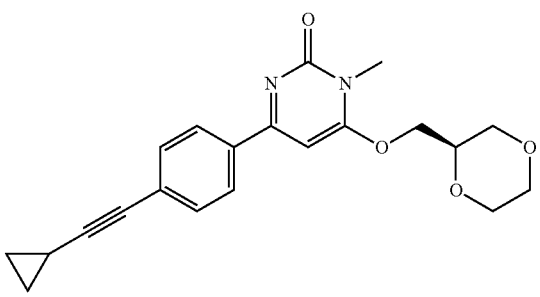 [SMILES: Cn1c(OC[C@H]2COCCO2)cc(-c2ccc(C#CC3CC3)cc2)nc1=O] |
| I-137 | 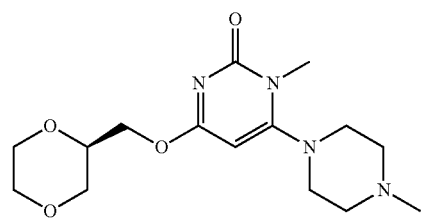 [SMILES: CN1CCN(c2cc(OC[C@H]3COCCO3)nc(=O)n2C)CC1] |
| I-138 | 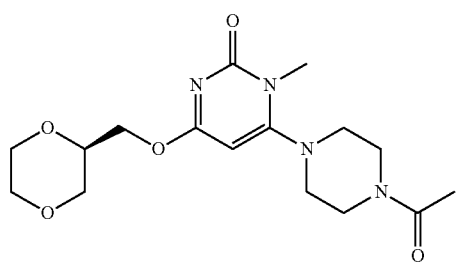 [SMILES: CC(=O)N1CCN(c2cc(OC[C@H]3COCCO3)nc(=O)n2C)CC1] |
| I-139 | 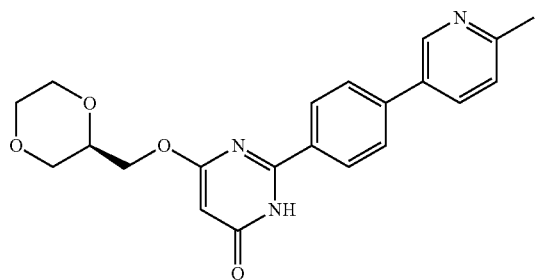 [SMILES: Cc1ccc(-c2ccc(-c3nc(OC[C@H]4COCCO4)cc(=O)[nH]3)cc2)cn1] |

-continued
| Compound No. | Structure |
|---|---|
| I-140 | 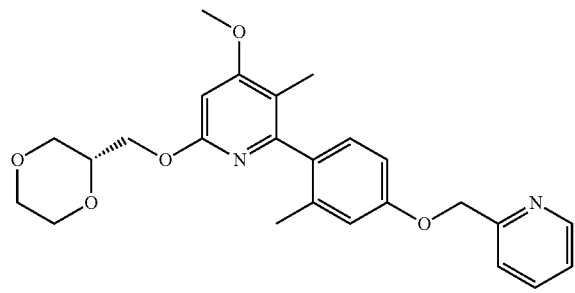 [SMILES: COc1cc(OC[C@H]2COCCO2)nc(-c2ccc(OCc3ccccn3)cc2C)c1C] |
| I-141 | 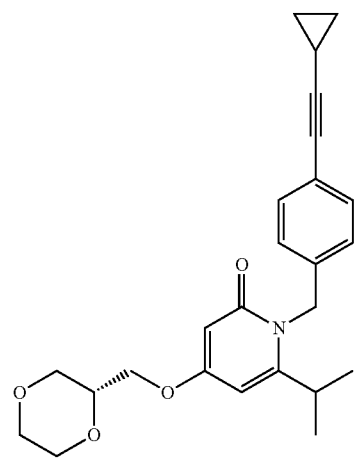 [SMILES: CC(C)c1cc(OC[C@H]2COCCO2)cc(=O)n1Cc1ccc(C#CC2CC2)cc1] |
| I-142 | 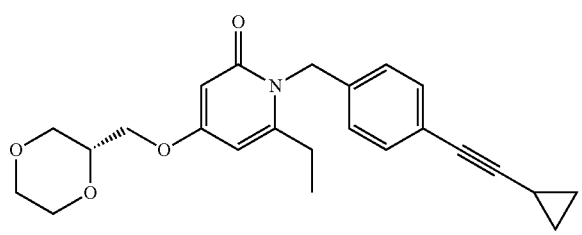 |
| I-143 | 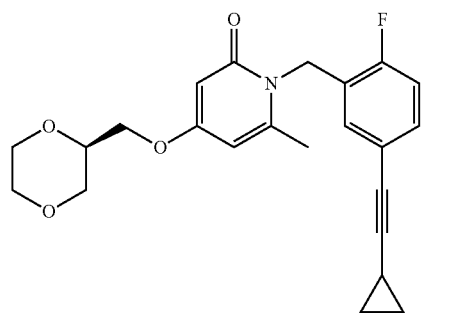 |
| I-144 | 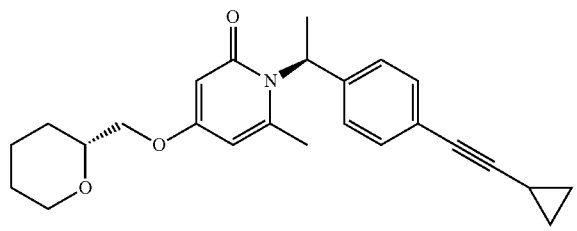 |

| Compound No. | Structure |
|---|---|
| I-145 | 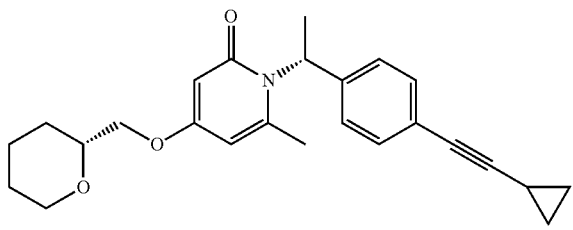 [SMILES: Cc1cc(OC[C@H]2CCCCO2)cc(=O)n1[C@H](C)c1ccc(C#CC2CC2)cc1] |
| I-146 | 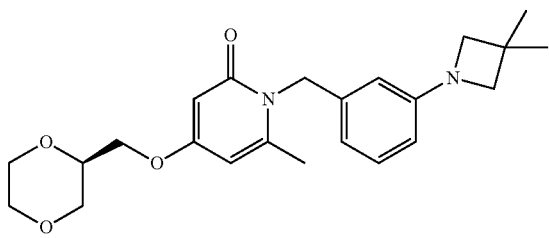 [SMILES: Cc1cc(OC[C@H]2COCCO2)cc(=O)n1Cc1cccc(N2CC(C)(C)C2)c1] |
| I-147 | 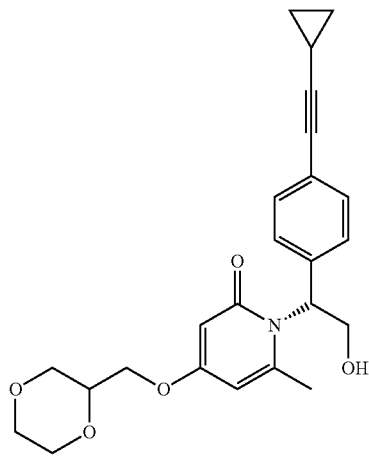 |
| I-148 | 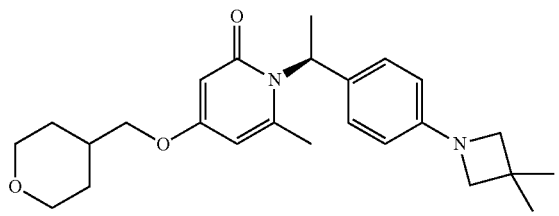 [SMILES: Cc1cc(OCC2CCOCC2)cc(=O)n1[C@@H](C)c1ccc(N2CC(C)(C)C2)cc1] |
| I-149 | 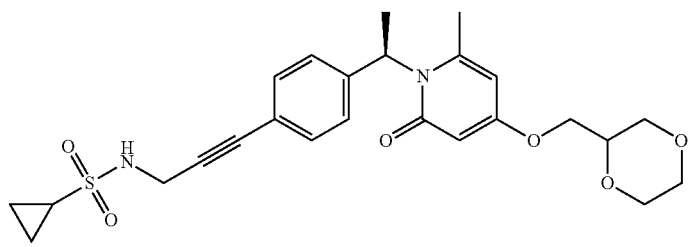 [SMILES: Cc1cc(OCC2COCCO2)cc(=O)n1[C@H](C)c1ccc(C#CCNS(=O)(=O)C2CC2)cc1] |

-continued
| Compound No. | Structure |
|---|---|
| I-150 | 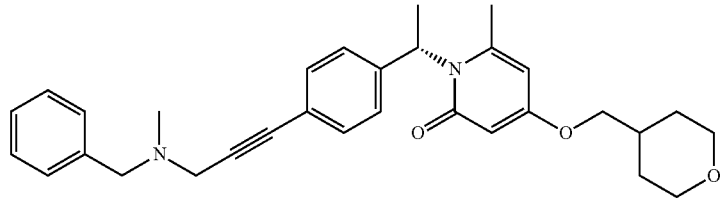 [SMILES: Cc1cc(OCC2CCOCC2)cc(=O)n1[C@@H](C)c1ccc(C#CCN(C)Cc2ccccc2)cc1] |
| I-151 | 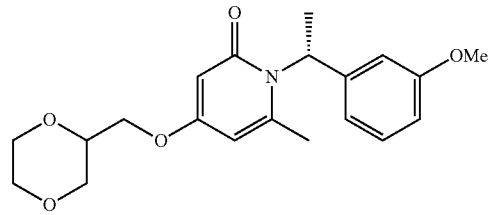 [SMILES: COc1cccc([C@@H](C)n2c(C)cc(OCC3COCCO3)cc2=O)c1] |
| I-152 | 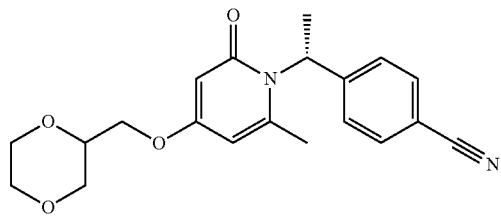 [SMILES: Cc1cc(OCC2COCCO2)cc(=O)n1[C@H](C)c1ccc(C#N)cc1] |
| I-153 | 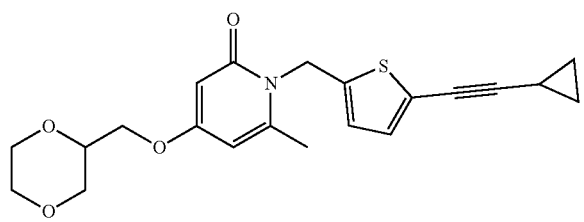 |
| I-154 | 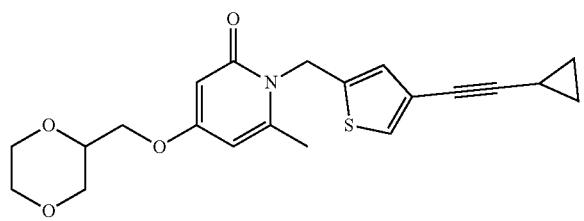 [SMILES: Cc1cc(OCC2COCCO2)cc(=O)n1Cc1cc(C#CC2CC2)cs1] |
| I-155 | 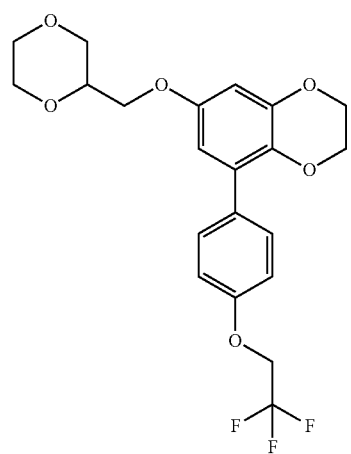 [SMILES: FC(F)(F)COc1ccc(-c2cc(OCC3COCCO3)cc3c2OCCO3)cc1] |

-continued
| Compound No. | Structure |
|---|---|
| I-156 | 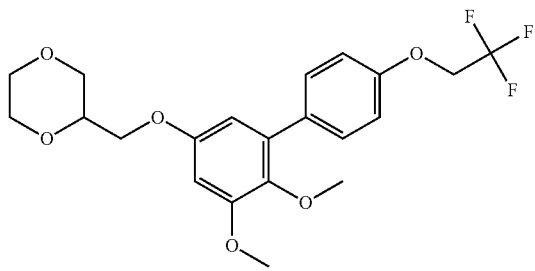 [SMILES: COc1cc(OCC2COCCO2)cc(-c2ccc(OCC(F)(F)F)cc2)c1OC] |
| I-157 | 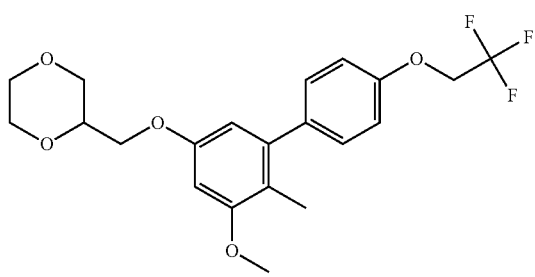 [SMILES: COc1cc(OCC2COCCO2)cc(-c2ccc(OCC(F)(F)F)cc2)c1C] |
| I-158 | 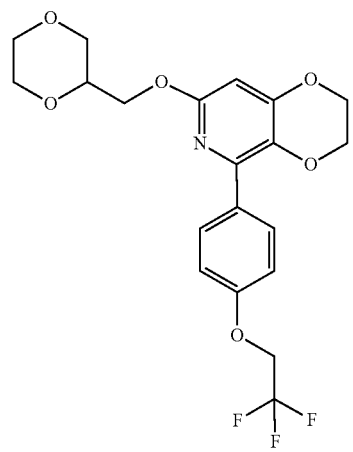 [SMILES: FC(F)(F)COc1ccc(-c2nc(OCC3COCCO3)cc3c2OCCO3)cc1] |
| I-159 | 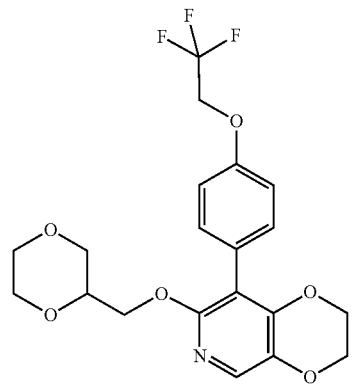 [SMILES: FC(F)(F)COc1ccc(-c2c(OCC3COCCO3)ncc3c2OCCO3)cc1] |

| Compound No. | Structure |
|---|---|
| I-160 | 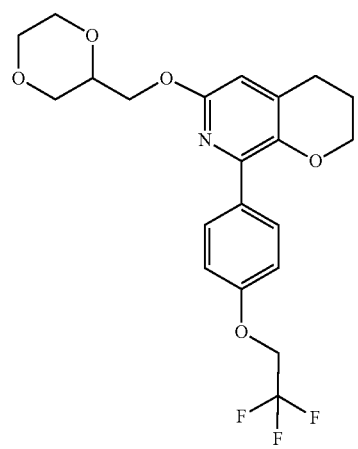 [SMILES: FC(F)(F)COc1ccc(-c2nc(OCC3COCCO3)cc3c2OCCC3)cc1] |
| I-161 | 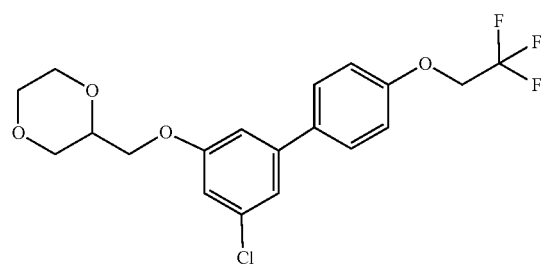 [SMILES: FC(F)(F)COc1ccc(-c2cc(Cl)cc(OCC3COCCO3)c2)cc1] |
| I-162 | 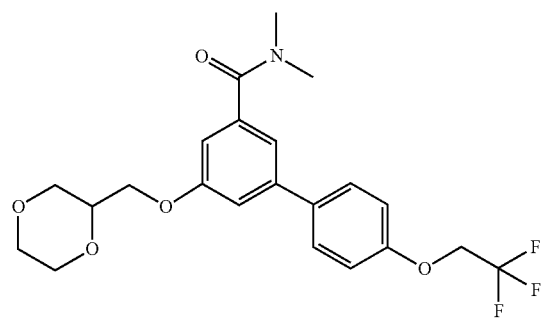 [SMILES: CN(C)C(=O)c1cc(OCC2COCCO2)cc(-c2ccc(OCC(F)(F)F)cc2)c1] |
| I-163 | 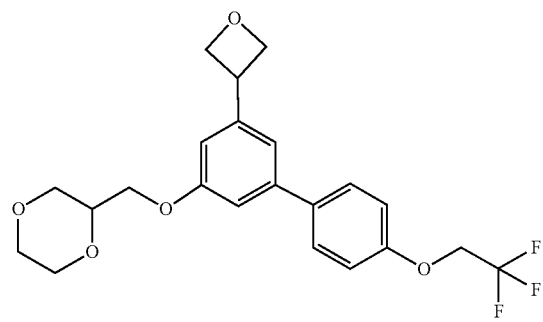 [SMILES: FC(F)(F)COc1ccc(-c2cc(OCC3COCCO3)cc(C3COC3)c2)cc1] |

-continued
| Compound No. | Structure |
|---|---|
| I-164 | 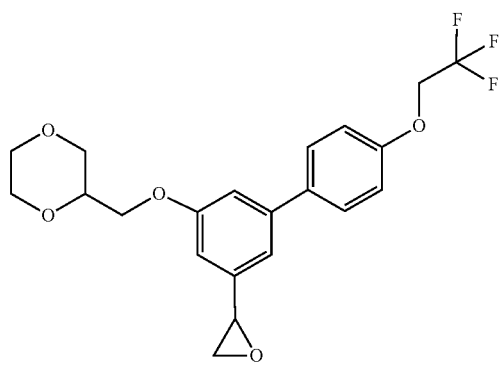 [SMILES: FC(F)(F)COc1ccc(-c2cc(OCC3COCCO3)cc(C3CO3)c2)cc1] |
| I-165 | 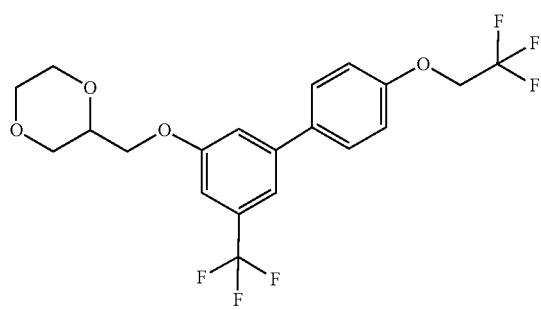 [SMILES: FC(F)(F)COc1ccc(-c2cc(OCC3COCCO3)cc(C(F)(F)F)c2)cc1] |
| I-166 | 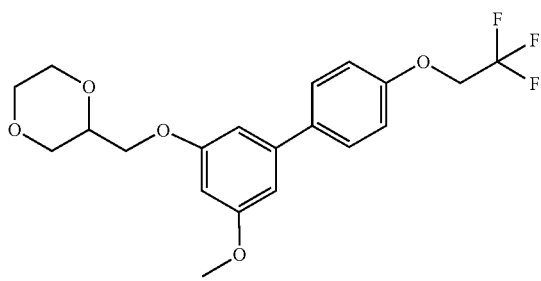 [SMILES: COc1cc(OCC2COCCO2)cc(-c2ccc(OCC(F)(F)F)cc2)c1] |
| I-167 | 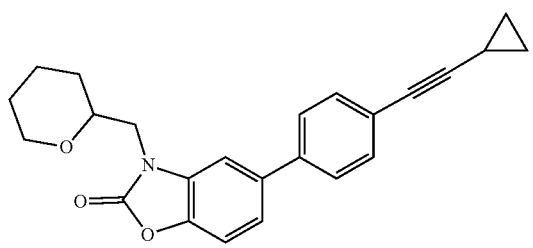 [SMILES: O=c1oc2ccc(-c3ccc(C#CC4CC4)cc3)cc2n1CC1CCCCO1] |
| I-168 | 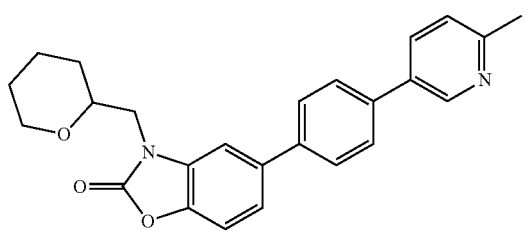 [SMILES: Cc1ccc(-c2ccc(-c3ccc4oc(=O)n(CC5CCCCO5)c4c3)cc2)cn1] |

| Compound No. | Structure |
|---|---|
| I-169 | 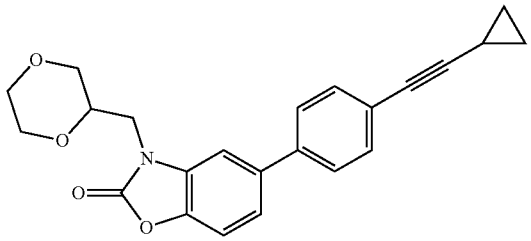 [SMILES: O=c1oc2ccc(-c3ccc(C#CC4CC4)cc3)cc2n1CC1COCCO1] |
| I-174 | 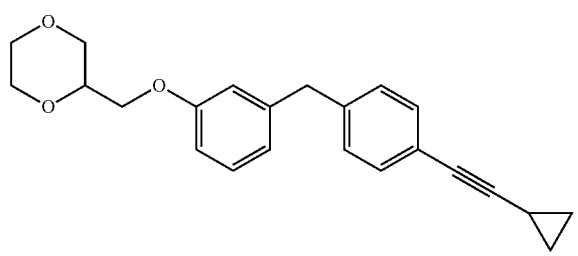 [SMILES: C(#CC1CC1)c1ccc(Cc2cccc(OCC3COCCO3)c2)cc1] |
| I-176 | 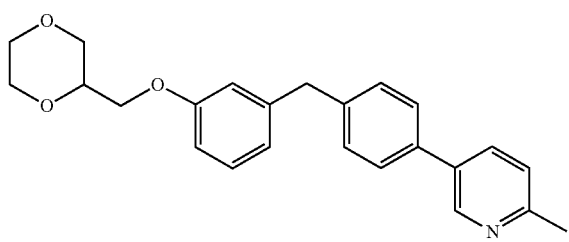 [SMILES: Cc1ccc(-c2ccc(Cc3cccc(OCC4COCCO4)c3)cc2)cn1] |
| I-177 | 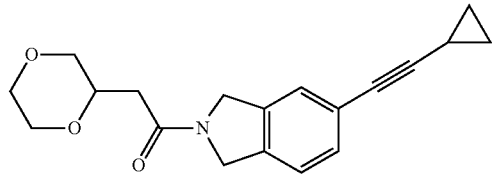 [SMILES: CCc1cc(C#CC2CC2)ccc1CNC(=O)CC1COCCO1] |
| I-180 | 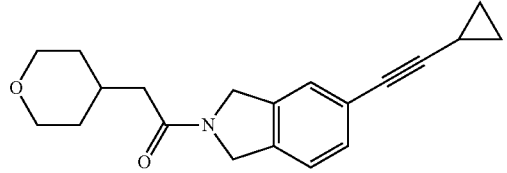 [SMILES: O=C(CC1CCOCC1)N1Cc2ccc(C#CC3CC3)cc2C1] |
| I-181 | 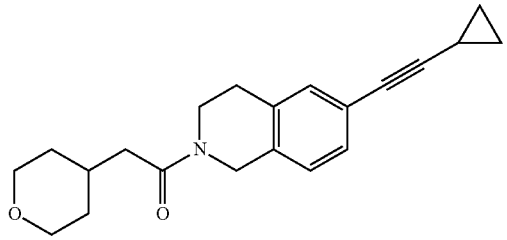 [SMILES: O=C(CC1CCOCC1)N1CCc2cc(C#CC3CC3)ccc2C1] |

-continued
| Compound No. | Structure |
|---|---|
| I-183 | 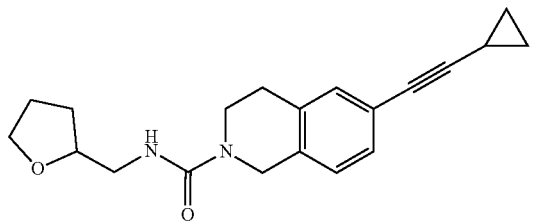 [SMILES: O=C(NCC1CCCO1)N1CCc2cc(C#CC3CC3)ccc2C1] |
| I-184 | 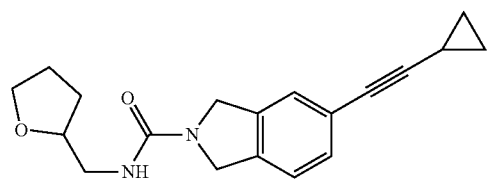 |
| I-186 | 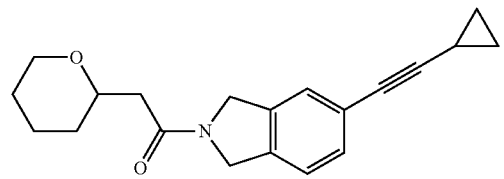 |
| I-187 | 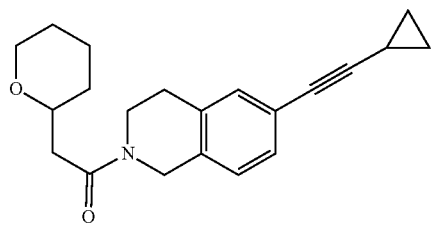 [SMILES: O=C(CC1CCCCO1)N1CCc2cc(C#CC3CC3)ccc2C1] |
| I-197 | 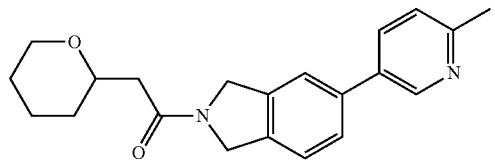 [SMILES: Cc1ccc(-c2ccc3c(c2)CN(C(=O)CC2CCCCO2)C3)cn1] |
| I-203 | 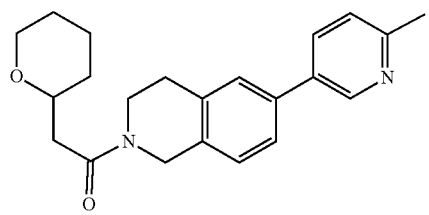 [SMILES: Cc1ccc(-c2ccc3c(c2)CCN(C(=O)CC2CCCCO2)C3)cn1] |
| I-206 | 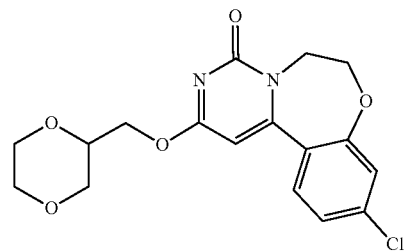 [SMILES: O=c1nc(OCC2COCCO2)cc2n1CCOc1cc(Cl)ccc1-2] |

| Compound No. | Structure |
|---|---|
| I-210 | 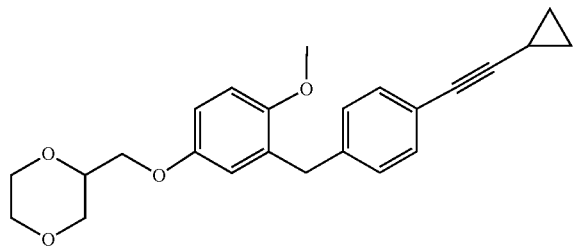 [SMILES: COc1ccc(OCC2COCCO2)cc1Cc1ccc(C#CC2CC2)cc1] |
| I-211 | 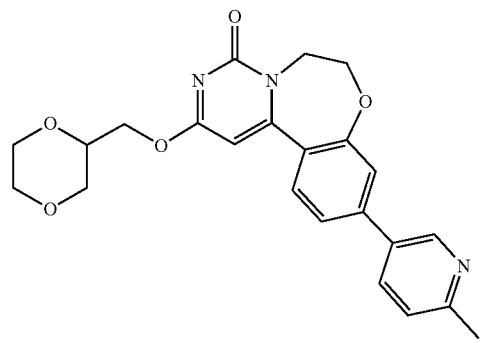 [SMILES: Cc1ccc(-c2ccc3c(c2)OCCn2c-3cc(OCC3COCCO3)nc2=O)cn1] |
| I-214 | 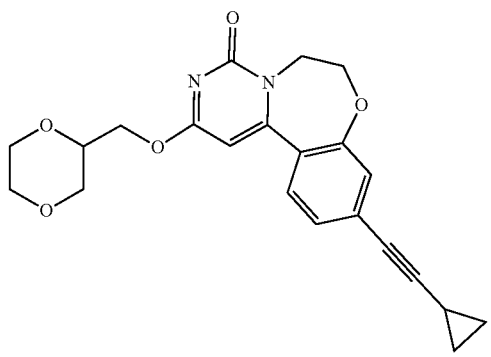 [SMILES: O=c1nc(OCC2COCCO2)cc2n1CCOc1cc(C#CC3CC3)ccc1-2] |
| I-215 | 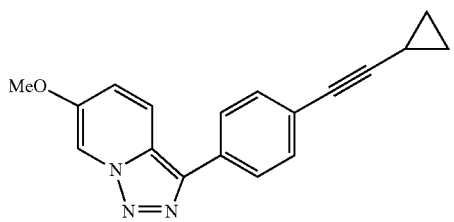 [SMILES: COc1ccc2c(-c3ccc(C#CC4CC4)cc3)nnn2c1] |
| I-216 | 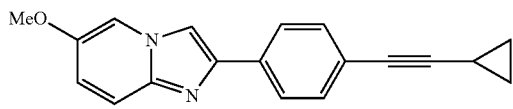 [SMILES: COc1ccc2nc(-c3ccc(C#CC4CC4)cc3)cn2c1] |
| I-217 | 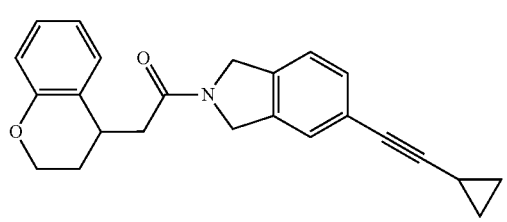 [SMILES: O=C(CC1CCOc2ccccc21)N1Cc2ccc(C#CC3CC3)cc2C1] |

-continued
| Compound No. | Structure |
|---|---|
| I-218 | 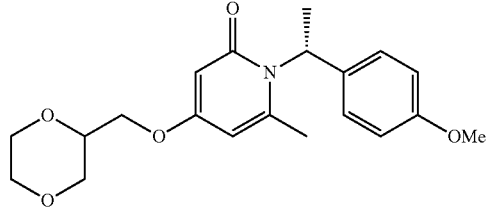 [SMILES: COc1ccc([C@@H](C)n2c(C)cc(OCC3COCCO3)cc2=O)cc1] |
| I-219 | 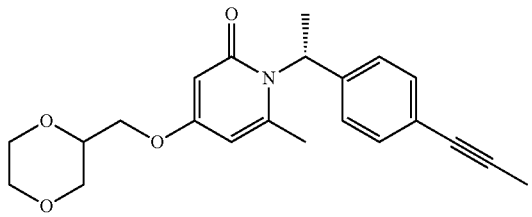 [SMILES: CC#Cc1ccc([C@@H](C)n2c(C)cc(OCC3COCCO3)cc2=O)cc1] |
| I-220 | 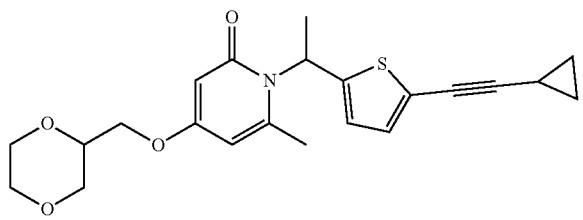 [SMILES: Cc1cc(OCC2COCCO2)cc(=O)n1C(C)c1ccc(C#CC2CC2)s1] |
| I-221 | 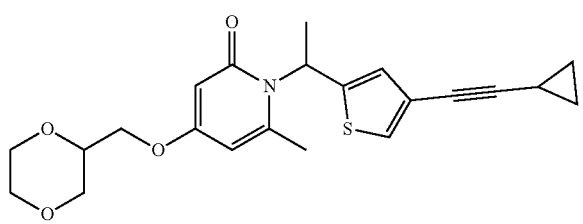 [SMILES: Cc1cc(OCC2COCCO2)cc(=O)n1C(C)c1cc(C#CC2CC2)cs1] |
| I-222 | 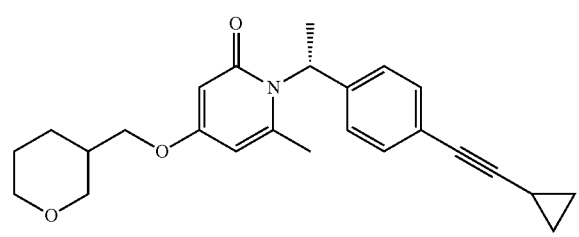 [SMILES: Cc1cc(OCC2CCCOC2)cc(=O)n1[C@H](C)c1ccc(C#CC2CC2)cc1] |
| I-223 | 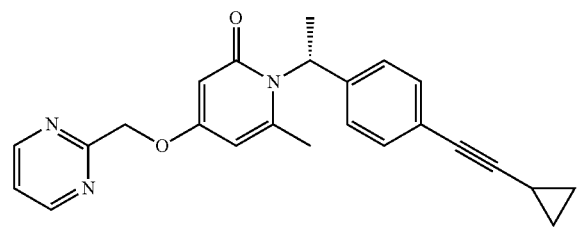 |
| I-224 | 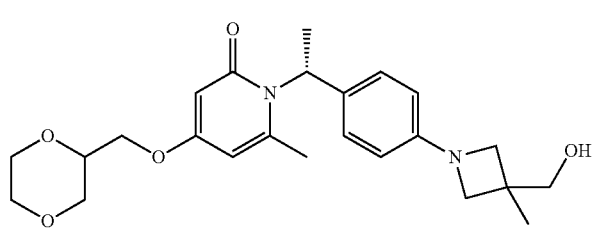 [SMILES: Cc1cc(OCC2COCCO2)cc(=O)n1[C@H](C)c1ccc(N2CC(C)(CO)C2)cc1] |

-continued
| Compound No. | Structure |
|---|---|
| I-225 | 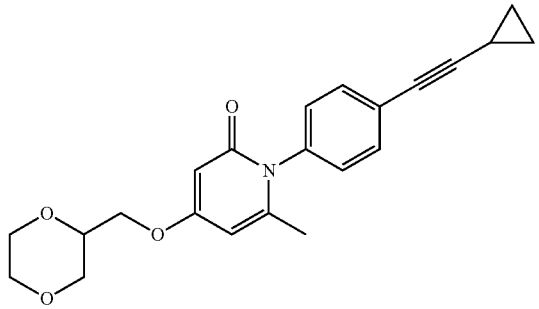 [SMILES: Cc1cc(OCC2COCCO2)cc(=O)n1-c1ccc(C#CC2CC2)cc1] |
| I-226 | 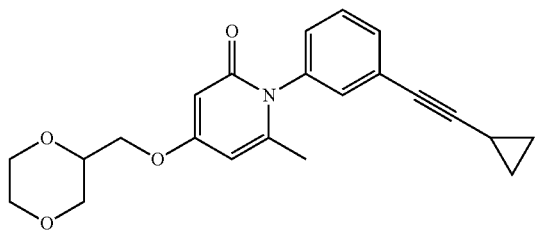 [SMILES: Cc1cc(OCC2COCCO2)cc(=O)n1-c1cccc(C#CC2CC2)c1] |
| I-227 | 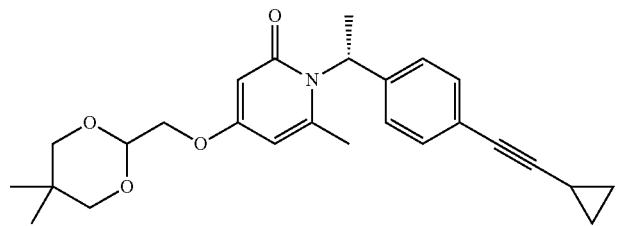 [SMILES: Cc1cc(OCC2OCC(C)(C)CO2)cc(=O)n1[C@H](C)c1ccc(C#CC2CC2)cc1] |
| I-228 | 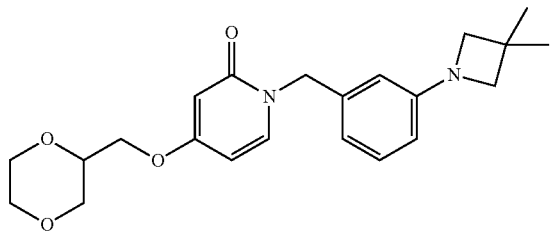 [SMILES: CC1(C)CN(c2cccc(Cn3ccc(OCC4COCCO4)cc3=O)c2)C1] |
| I-229 | 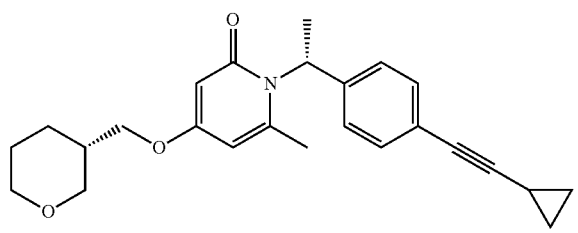 [SMILES: Cc1cc(OC[C@H]2CCCOC2)cc(=O)n1[C@H](C)c1ccc(C#CC2CC2)cc1] |
| I-230 | 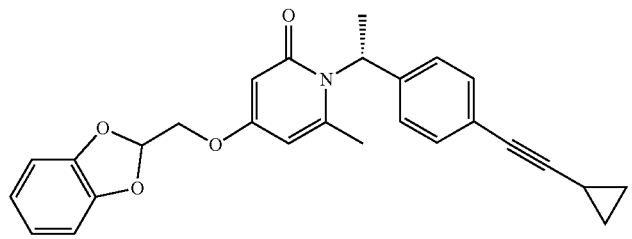 [SMILES: Cc1cc(OCC2Oc3ccccc3O2)cc(=O)n1[C@H](C)c1ccc(C#CC2CC2)cc1] |

-continued
| Compound No. | Structure |
|---|---|
| I-231 | 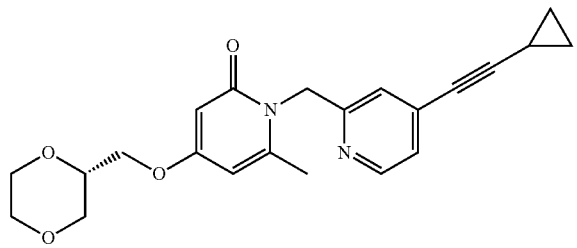 [SMILES: Cc1cc(OC[C@@H]2COCCO2)cc(=O)n1Cc1cc(C#CC2CC2)ccn1] |
| I-232 | 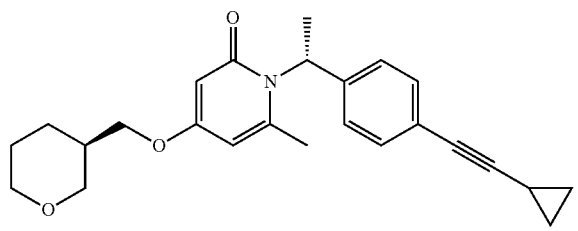 [SMILES: Cc1cc(OC[C@@H]2CCCOC2)cc(=O)n1[C@H](C)c1ccc(C#CC2CC2)cc1] |
| I-233 | 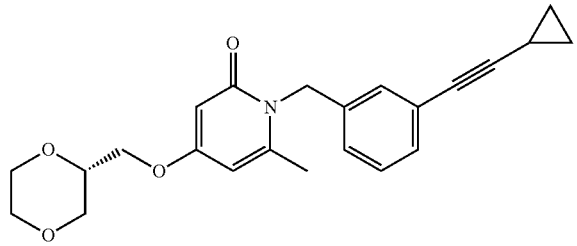 [SMILES: Cc1cc(OC[C@@H]2COCCO2)cc(=O)n1Cc1cccc(C#CC2CC2)c1] |
| I-234 | 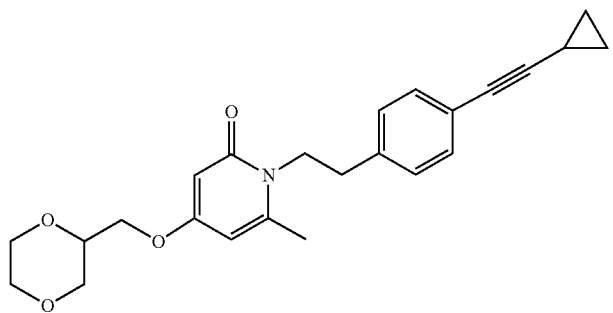 [SMILES: Cc1cc(OCC2COCCO2)cc(=O)n1CCc1ccc(C#CC2CC2)cc1] |
| I-235 | 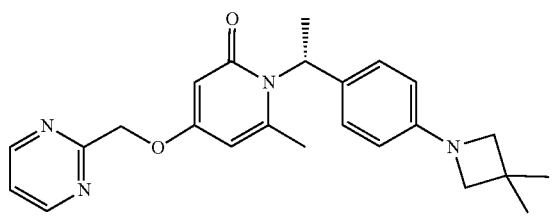 [SMILES: Cc1cc(OCc2ncccn2)cc(=O)n1[C@H](C)c1ccc(N2CC(C)(C)C2)cc1] |
| I-236 | 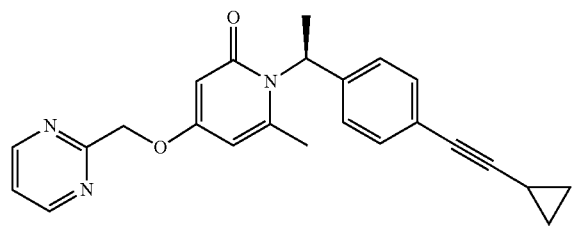 [SMILES: Cc1cc(OCc2ncccn2)cc(=O)n1[C@@H](C)c1ccc(C#CC2CC2)cc1] |

| Compound No. | Structure |
|---|---|
| I-237 | 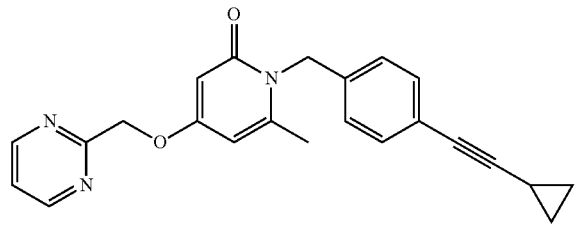 [SMILES: Cc1cc(OCc2ncccn2)cc(=O)n1Cc1ccc(C#CC2CC2)cc1] |
| I-238 | 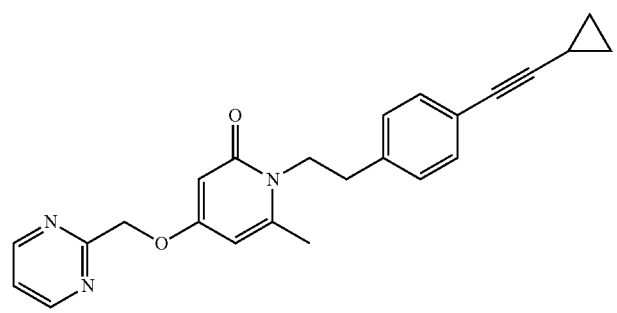 [SMILES: Cc1cc(OCc2ncccn2)cc(=O)n1CCc1ccc(C#CC2CC2)cc1] |
| I-239 | 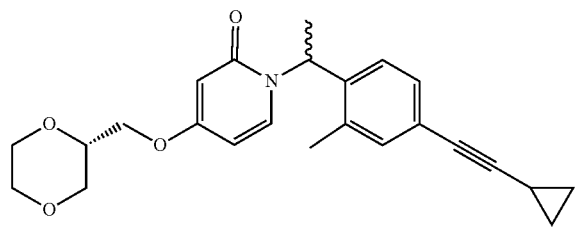 [SMILES: Cc1cc(C#CC2CC2)ccc1C(C)n1ccc(OC[C@@H]2COCCO2)cc1=O] |
| I-240 | 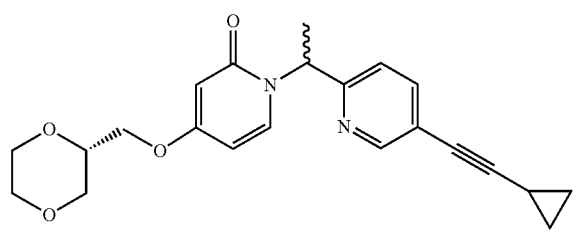 [SMILES: CC(c1ccc(C#CC2CC2)cn1)n1ccc(OC[C@@H]2COCCO2)cc1=O] |
| I-241 | 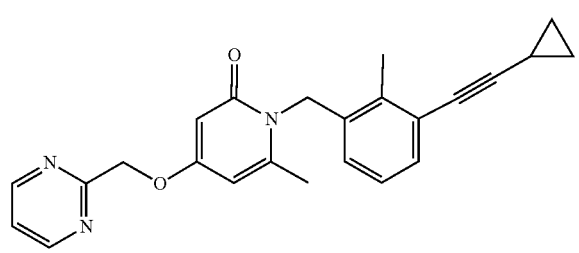 [SMILES: Cc1c(C#CC2CC2)cccc1Cn1c(C)cc(OCc2ncccn2)cc1=O] |
| I-242 | 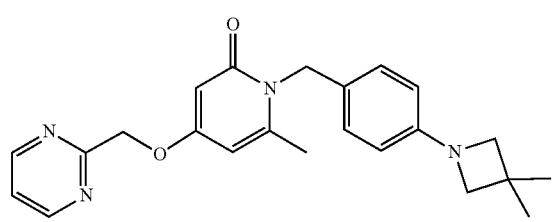 [SMILES: Cc1cc(OCc2ncccn2)cc(=O)n1Cc1ccc(N2CC(C)(C)C2)cc1] |

-continued

| Compound No. | Structure |
|---|---|
| I-243 | 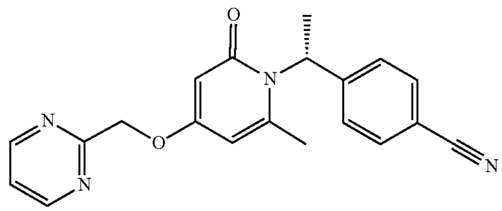 [SMILES: Cc1cc(OCc2ncccn2)cc(=O)n1[C@H](C)c1ccc(C#N)cc1] |
| I-244 | 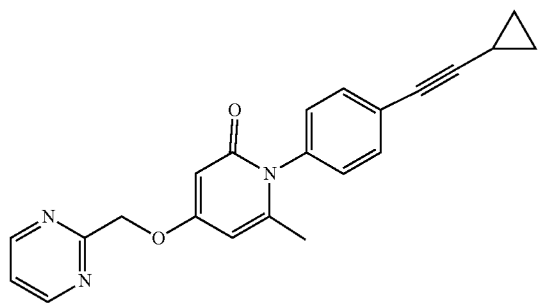 [SMILES: Cc1cc(OCc2ncccn2)cc(=O)n1-c1ccc(C#CC2CC2)cc1] |
| I-245 | 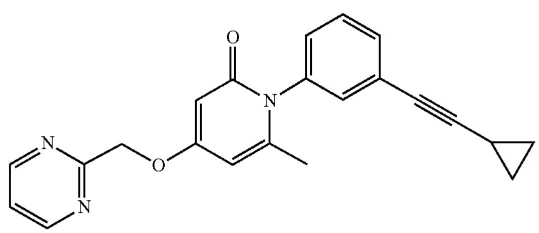 [SMILES: Cc1cc(OCc2ncccn2)cc(=O)n1-c1cccc(C#CC2CC2)c1] |
| I-246 | 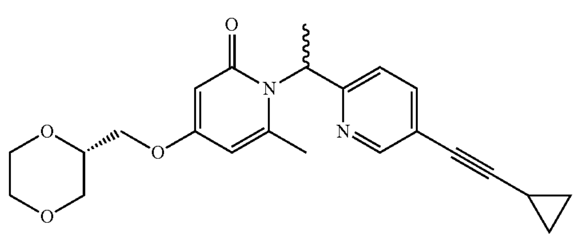 [SMILES: Cc1cc(OC[C@@H]2COCCO2)cc(=O)n1C(C)c1ccc(C#CC2CC2)cn1] |
| I-247 | 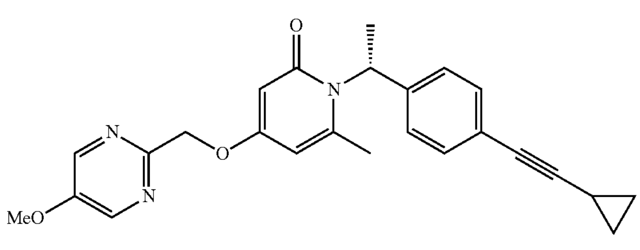 [SMILES: COc1cnc(COc2cc(C)n([C@H](C)c3ccc(C#CC4CC4)cc3)c(=O)c2)nc1] |
| I-248 | 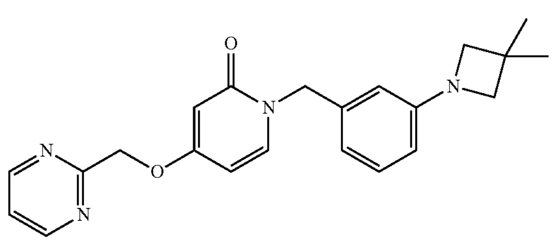 [SMILES: CC1(C)CN(c2cccc(Cn3ccc(OCc4ncccn4)cc3=O)c2)C1] |

-continued
| Compound No. | Structure |
|---|---|
| I-249 | 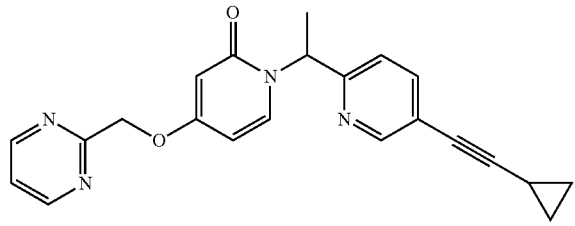 |
| I-250 | 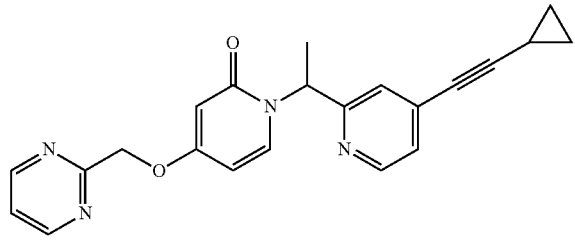 [SMILES: CC(c1cc(C#CC2CC2)ccn1)n1ccc(OCc2ncccn2)cc1=O] |
| I-251 | 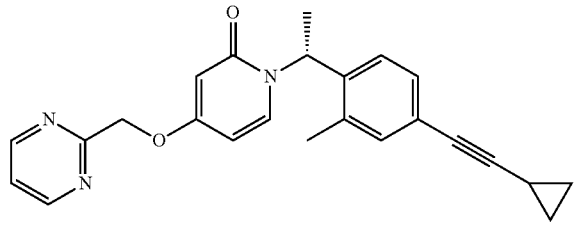 [SMILES: Cc1cc(C#CC2CC2)ccc1[C@@H](C)n1ccc(OCc2ncccn2)cc1=O] |
| I-252 | 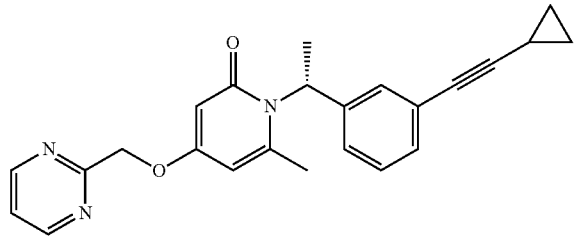 [SMILES: Cc1cc(OCc2ncccn2)cc(=O)n1[C@H](C)c1cccc(C#CC2CC2)c1] |
| I-253 | 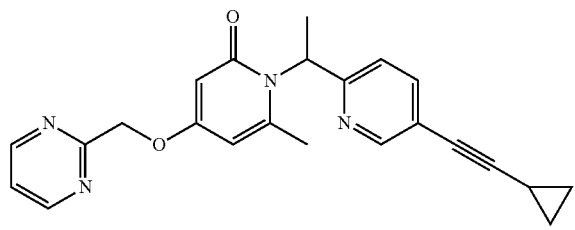 |
| I-254 | 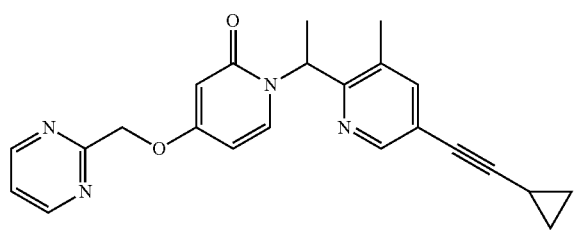 [SMILES: Cc1cc(C#CC2CC2)cnc1C(C)n1ccc(OCc2ncccn2)cc1=O] |

-continued

| Compound No. | Structure |
|---|---|
| I-255 | 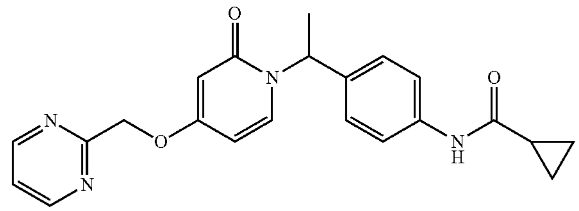 [SMILES: CC(c1ccc(NC(=O)C2CC2)cc1)n1ccc(OCc2ncccn2)cc1=O] |
| I-256 | 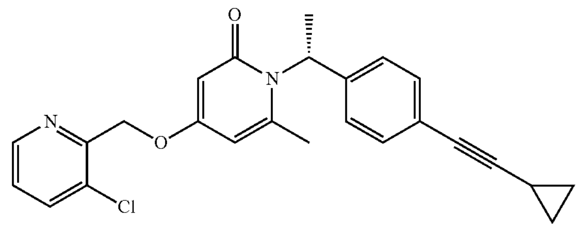 [SMILES: Cc1cc(OCc2ncccc2Cl)cc(=O)n1[C@H](C)c1ccc(C#CC2CC2)cc1] |
| I-257 | 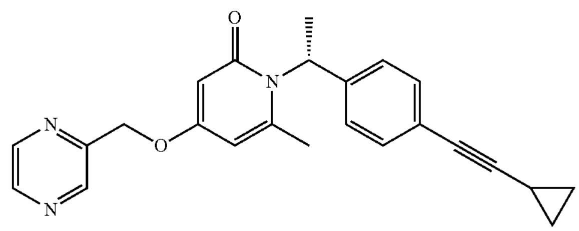 [SMILES: Cc1cc(OCc2cnccn2)cc(=O)n1[C@H](C)c1ccc(C#CC2CC2)cc1] |
| I-258 | 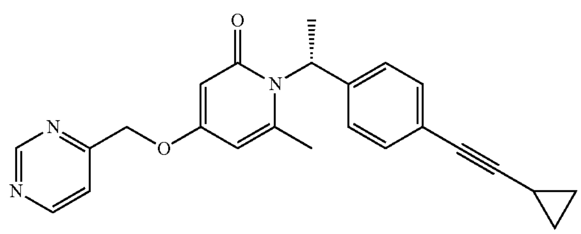 [SMILES: Cc1cc(OCc2ccncn2)cc(=O)n1[C@H](C)c1ccc(C#CC2CC2)cc1] |
| I-259 | 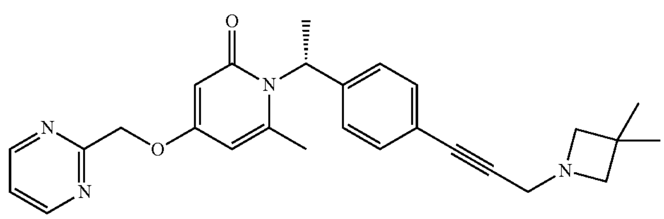 |
| I-260 | 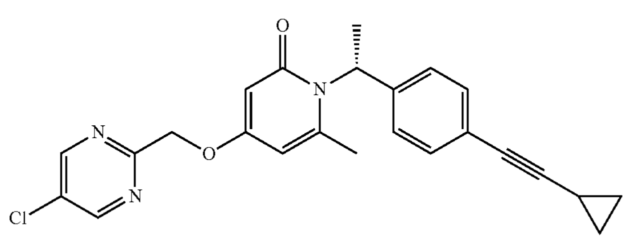 [SMILES: Cc1cc(OCc2ncc(Cl)cn2)cc(=O)n1[C@H](C)c1ccc(C#CC2CC2)cc1] |

-continued

| Compound No. | Structure |
|---|---|
| I-261 | 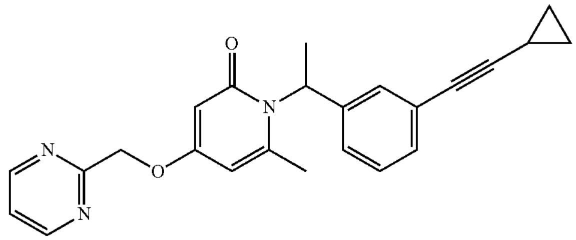 [SMILES: Cc1cc(OCc2ncccn2)cc(=O)n1C(C)c1cccc(C#CC2CC2)c1] |
| I-262 | 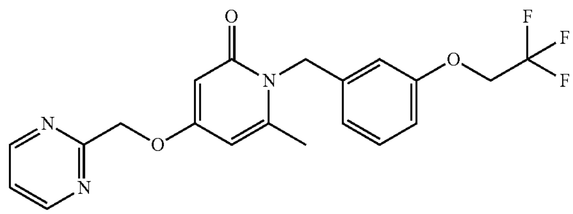 [SMILES: Cc1cc(OCc2ncccn2)cc(=O)n1Cc1cccc(OCC(F)(F)F)c1] |
| I-263 | 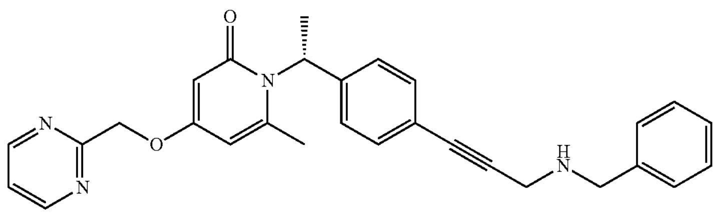 [SMILES: Cc1cc(OCc2ncccn2)cc(=O)n1[C@H](C)c1ccc(C#CCNCc2ccccc2)cc1] |
| I-264 | 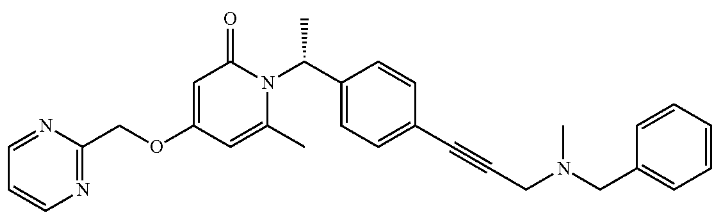 [SMILES: Cc1cc(OCc2ncccn2)cc(=O)n1[C@H](C)c1ccc(C#CCN(C)Cc2ccccc2)cc1] |
| I-265 | 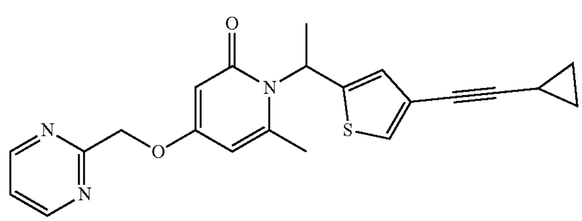 [SMILES: Cc1cc(OCc2ncccn2)cc(=O)n1C(C)c1cc(C#CC2CC2)cs1] |
| I-266 | 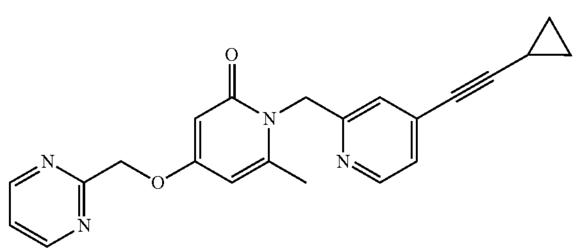 [SMILES: Cc1cc(OCc2ncccn2)cc(=O)n1Cc1cccc(C#CC2CC2)c1] |

-continued
| Compound No. | Structure |
|---|---|
| I-267 | 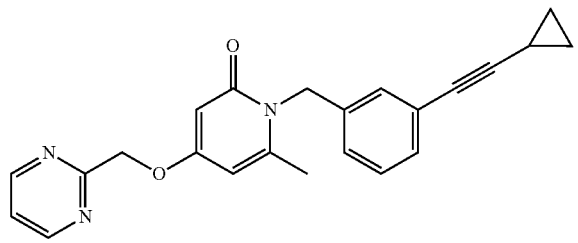 |
| I-268 | 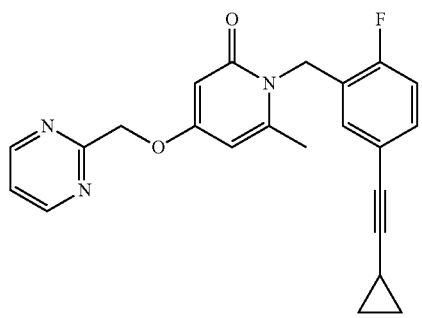 |
| I-269 | 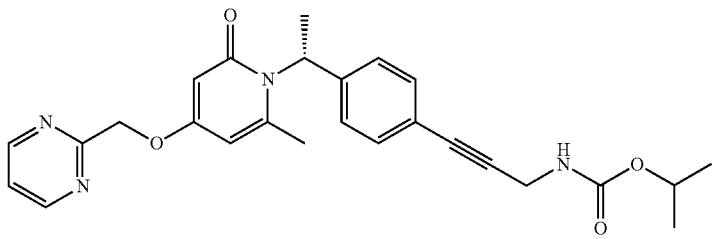 [SMILES: Cc1cc(OCc2ncccn2)cc(=O)n1[C@H](C)c1ccc(C#CCNC(=O)OC(C)C)cc1] |
| I-270 | 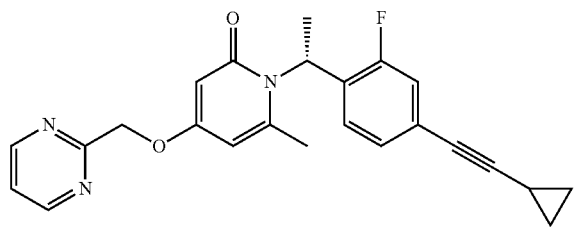 [SMILES: Cc1cc(OCc2ncccn2)cc(=O)n1[C@H](C)c1ccc(C#CC2CC2)cc1F] |
| I-271 | 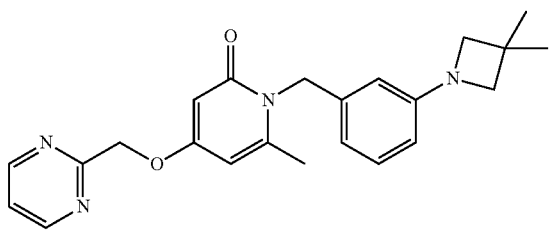 [SMILES: Cc1cc(OCc2ncccn2)cc(=O)n1Cc1cccc(N2CC(C)(C)C2)c1] |
| I-272 | 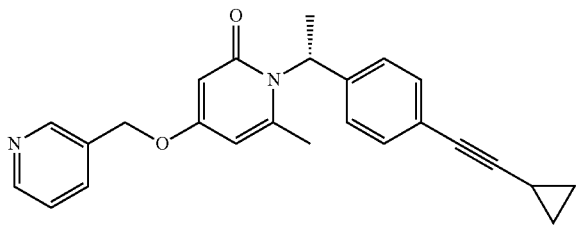 |

-continued
| Compound No. | Structure |
|---|---|
| I-273 | 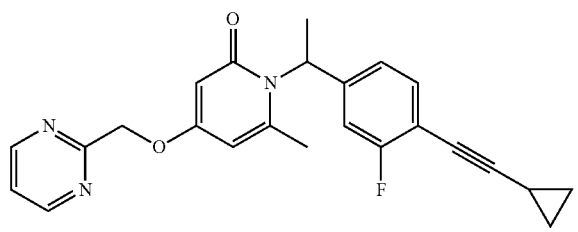 [SMILES: Cc1cc(OCc2ncccn2)cc(=O)n1C(C)c1ccc(C#CC2CC2)c(F)c1] |
| I-274 | 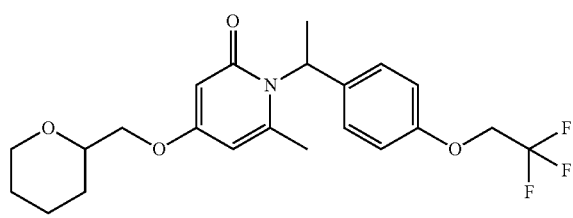 [SMILES: Cc1cc(OCC2CCCCO2)cc(=O)n1C(C)c1ccc(OCC(F)(F)F)cc1] |
| I-275 | 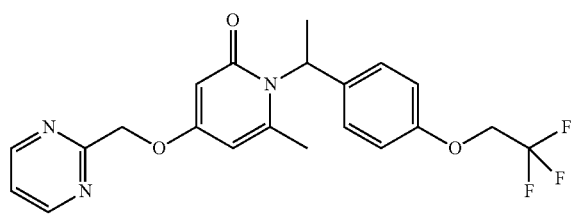 [SMILES: Cc1cc(OCc2ncccn2)cc(=O)n1C(C)c1ccc(OCC(F)(F)F)cc1] |
| I-276 | 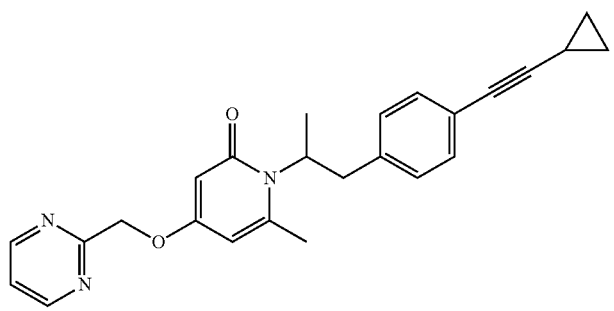<br>Enantiomer I |
| I-277 | 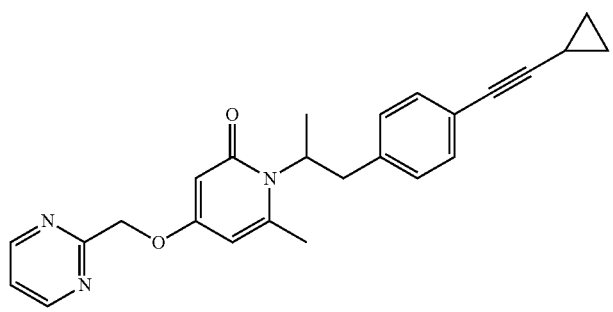<br>Enantiomer II |

-continued
| Compound No. | Structure |
|---|---|
| I-278 | 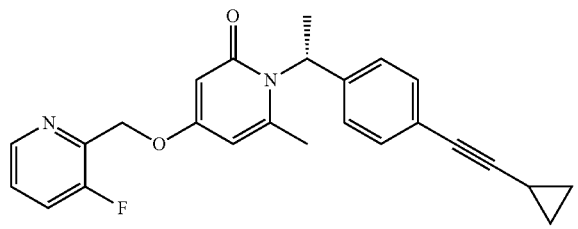 |
| I-279 | 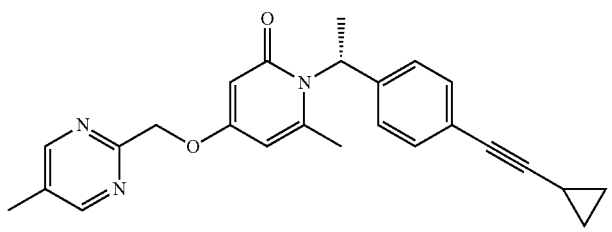 [SMILES: Cc1cnc(COc2cc(C)n([C@H](C)c3ccc(C#CC4CC4)cc3)c(=O)c2)nc1] |
| I-280 | 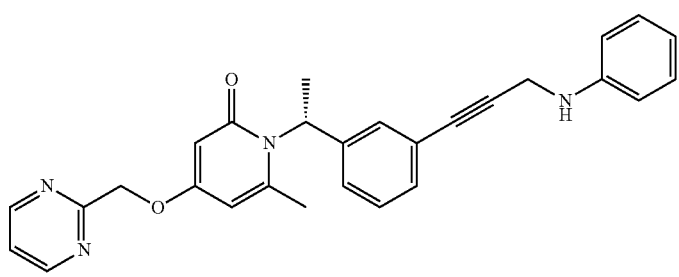 [SMILES: Cc1cc(OCc2ncccn2)cc(=O)n1[C@H](C)c1cccc(C#CCNc2ccccc2)c1] |
| I-281 | 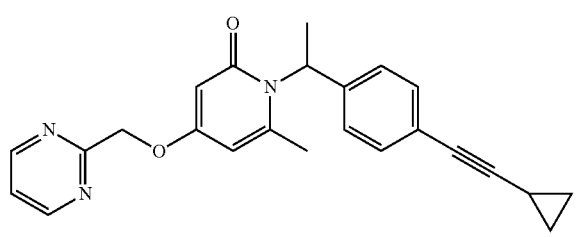  Enantiomer I |
| I-282 | 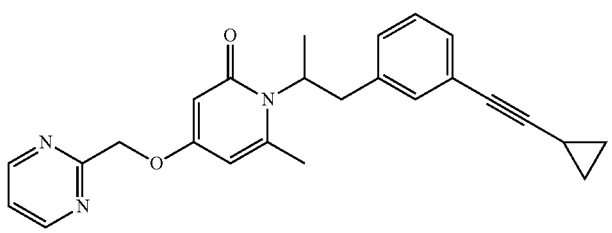  Enantiomer II |
| I-283 | 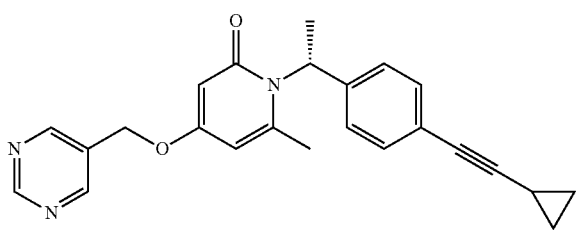 [SMILES: Cc1cc(OCc2cncnc2)cc(=O)n1[C@H](C)c1ccc(C#CC2CC2)cc1] |

-continued
| Compound No. | Structure |
|---|---|
| I-284 | 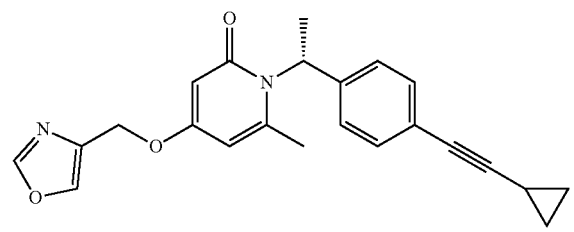 |
| I-285 | 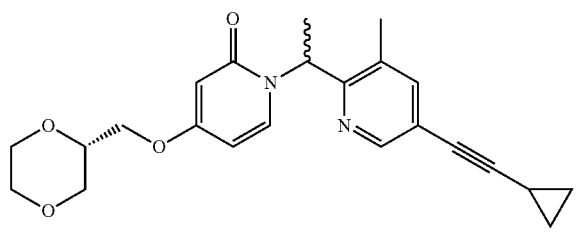 |
| I-286 | 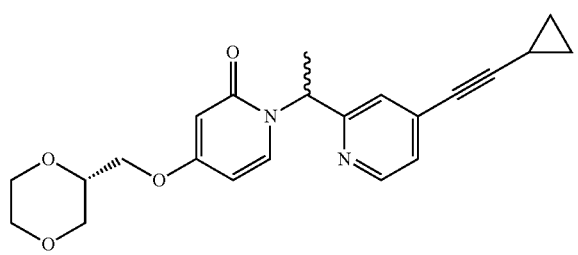 [SMILES: CC(c1cc(C#CC2CC2)ccn1)n1ccc(OC[C@@H]2COCCO2)cc1=O] |
| I-287 | 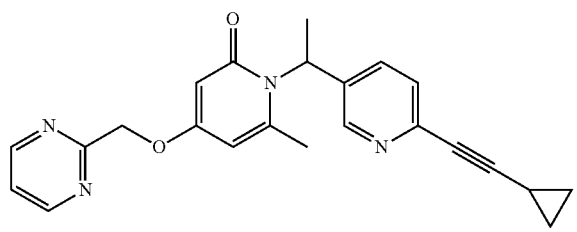 [SMILES: Cc1cc(OCc2ncccn2)cc(=O)n1C(C)c1ccc(C#CC2CC2)nc1] |
| I-288 | 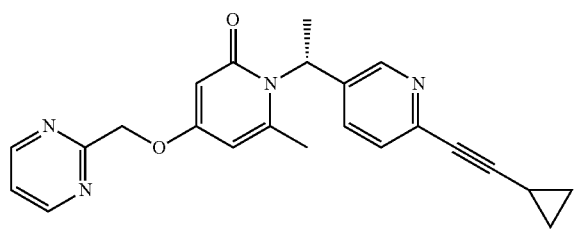 |
| I-289 | 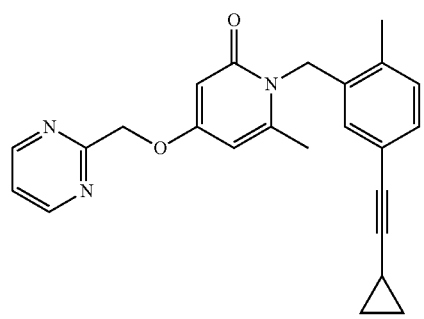 [SMILES: Cc1ccc(C#CC2CC2)cc1Cn1c(C)cc(OCc2ncccn2)cc1=O] |

| Compound No. | Structure |
|---|---|
| I-290 | 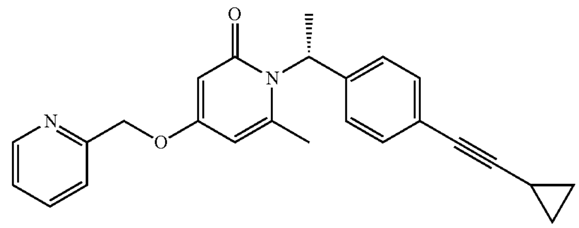 |
| I-291 | 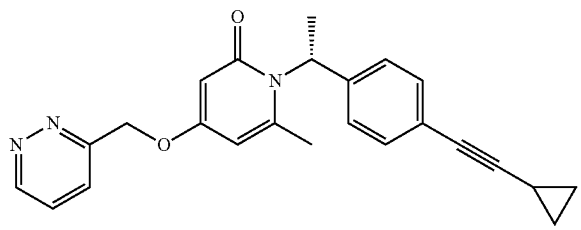 [SMILES: Cc1cc(OCc2cccnn2)cc(=O)n1[C@H](C)c1ccc(C#CC2CC2)cc1] |
| I-292 | 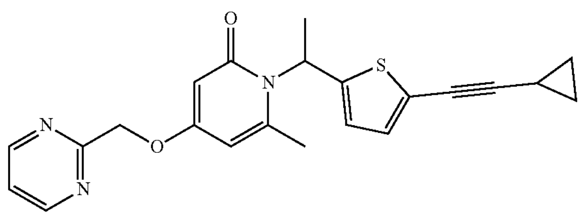 [SMILES: Cc1cc(OCc2ncccn2)cc(=O)n1C(C)c1ccc(C#CC2CC2)s1] |
| I-293 | 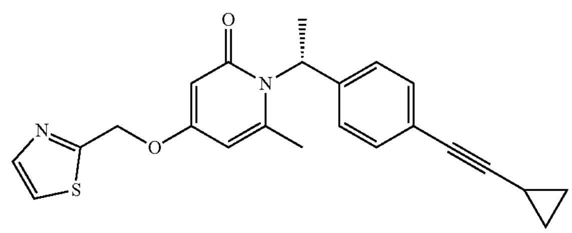 |
| I-294 | 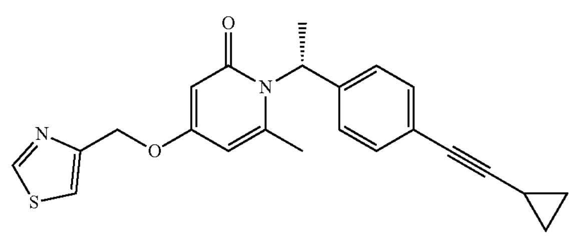 |
| I-295 | 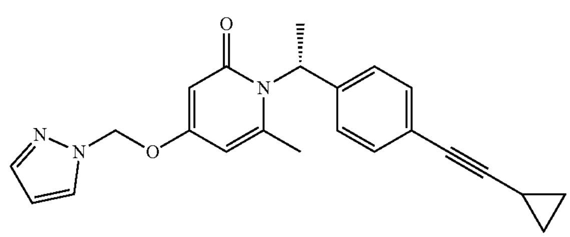 [SMILES: Cc1cc(OCn2cccn2)cc(=O)n1[C@H](C)c1ccc(C#CC2CC2)cc1] |

-continued

| Compound No. | Structure |
|---|---|
| I-296 | 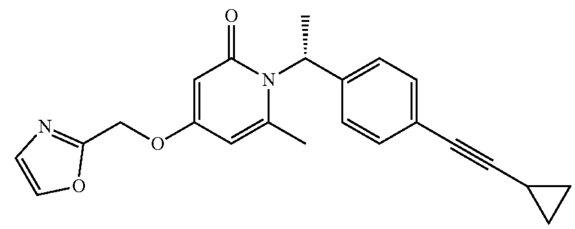 |
| I-297 | 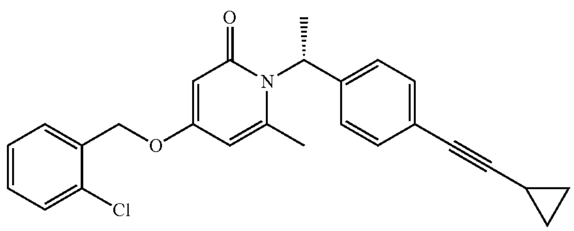 |
| I-298 | 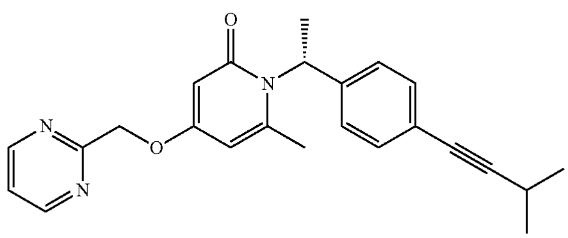 [SMILES: Cc1cc(OCc2ncccn2)cc(=O)n1[C@H](C)c1ccc(C#CC(C)C)cc1] |
| I-299 | 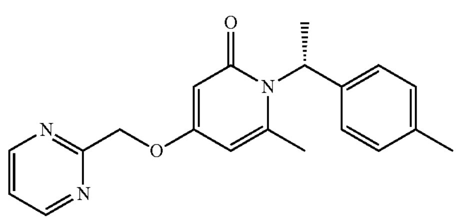 [SMILES: Cc1ccc([C@@H](C)n2c(C)cc(OCc3ncccn3)cc2=O)cc1] |
| I-300 | 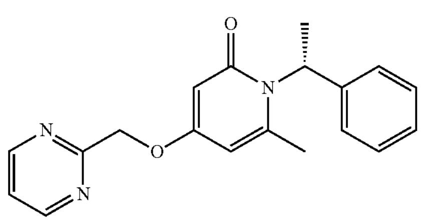 [SMILES: Cc1cc(OCc2ncccn2)cc(=O)n1[C@H](C)c1ccccc1] |
| I-301 | 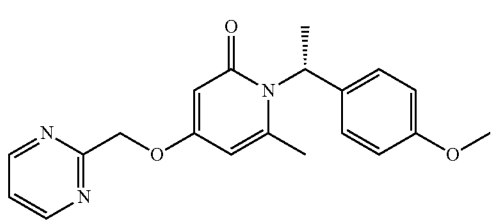 [SMILES: COc1ccc([C@@H](C)n2c(C)cc(OCc3ncccn3)cc2=O)cc1] |

-continued

| Compound No. | Structure |
|---|---|
| I-302 | 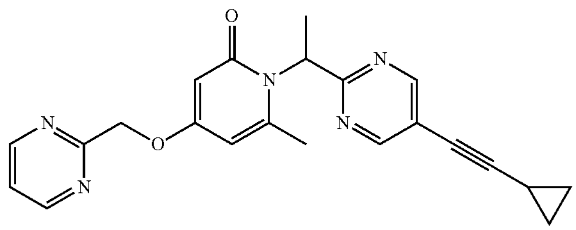 |
| I-303 | 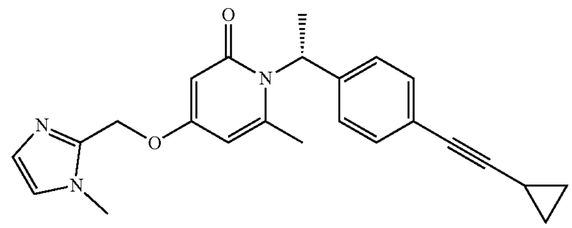 [SMILES: Cc1cc(OCc2nccn2C)cc(=O)n1[C@H](C)c1ccc(C#CC2CC2)cc1] |
| I-304 | 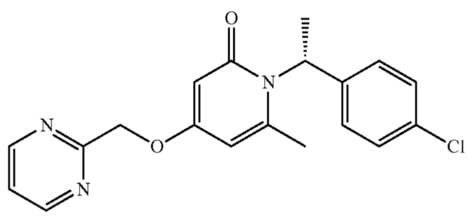 [SMILES: Cc1cc(OCc2ncccn2)cc(=O)n1[C@H](C)c1ccc(Cl)cc1] |
| I-305 | 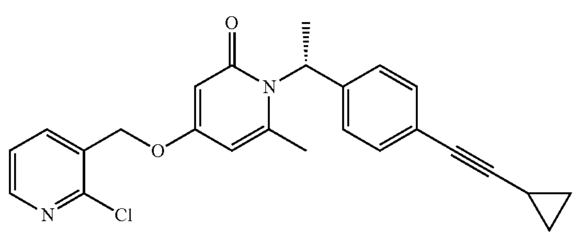 [SMILES: Cc1cc(OCc2cccnc2Cl)cc(=O)n1[C@H](C)c1ccc(C#CC2CC2)cc1] |
| I-306 | 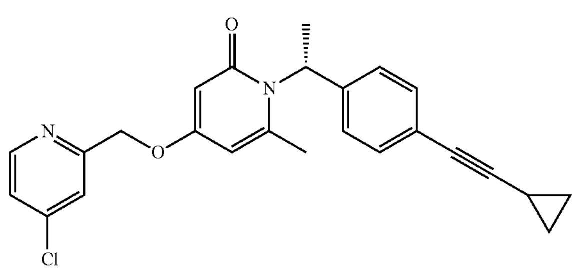 [SMILES: Cc1cc(OCc2cc(Cl)ccn2)cc(=O)n1[C@H](C)c1ccc(C#CC2CC2)cc1] |
| I-307 | 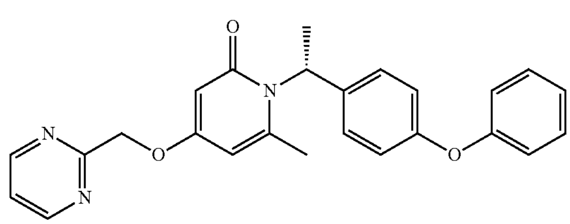 [SMILES: Cc1cc(OCc2ncccn2)cc(=O)n1[C@H](C)c1ccc(Oc2ccccc2)cc1] |

-continued
| Compound No. | Structure |
|---|---|
| I-308 | 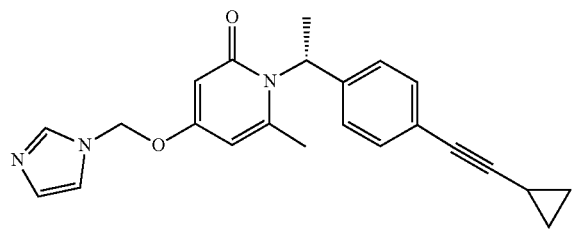 [SMILES: Cc1cc(OCn2ccnc2)cc(=O)n1[C@H](C)c1ccc(C#CC2CC2)cc1] |
| I-309 | 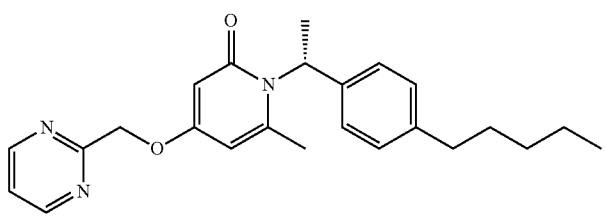 [SMILES: CCCCCc1ccc([C@@H](C)n2c(C)cc(OCc3ncccn3)cc2=O)cc1] |
| I-310 | 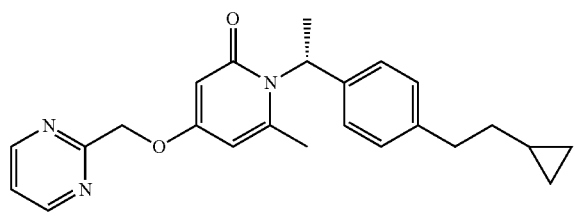 [SMILES: Cc1cc(OCc2ncccn2)cc(=O)n1[C@H](C)c1ccc(CCC2CC2)cc1] |
| I-311 | 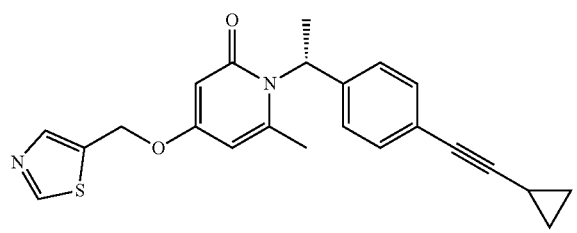 [SMILES: Cc1cc(OCc2cncs2)cc(=O)n1[C@H](C)c1ccc(C#CC2CC2)cc1] |
| I-312 | 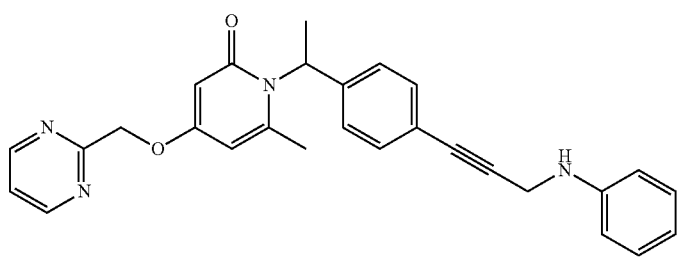 [SMILES: Cc1cc(OCc2ncccn2)cc(=O)n1C(C)c1ccc(C#CCNc2ccccc2)cc1] |
| I-313 | 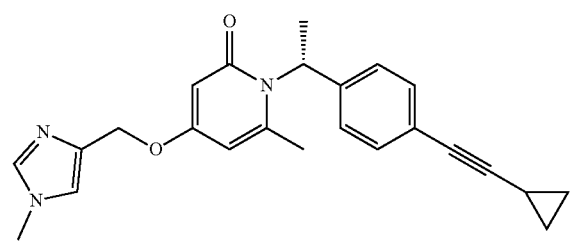 [SMILES: Cc1cc(OCc2cn(C)cn2)cc(=O)n1[C@H](C)c1ccc(C#CC2CC2)cc1] |

| Compound No. | Structure |
|---|---|
| I-314 | 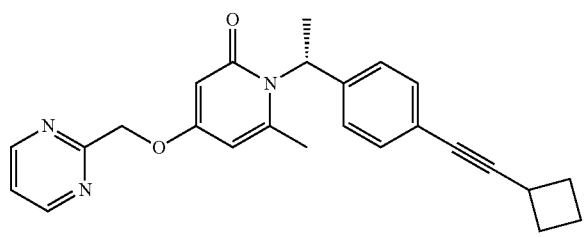 [SMILES: Cc1cc(OCc2ncccn2)cc(=O)n1[C@H](C)c1ccc(C#CC2CCC2)cc1] |
| I-315 | 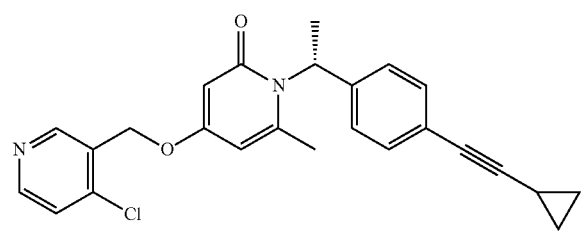 [SMILES: Cc1cc(OCc2cnccc2Cl)cc(=O)n1[C@H](C)c1ccc(C#CC2CC2)cc1] |
| I-316 | 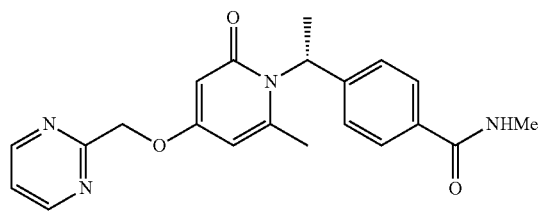 [SMILES: CNC(=O)c1ccc([C@@H](C)n2c(C)cc(OCc3ncccn3)cc2=O)cc1] |
| I-317 | 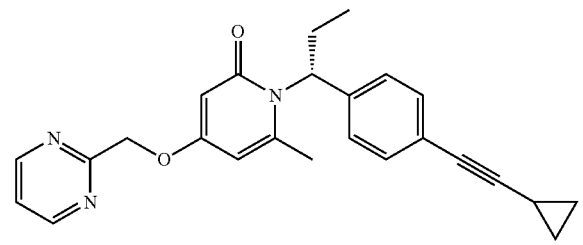 [SMILES: CC[C@H](c1ccc(C#CC2CC2)cc1)n1c(C)cc(OCc2ncccn2)cc1=O] |
| I-318 | 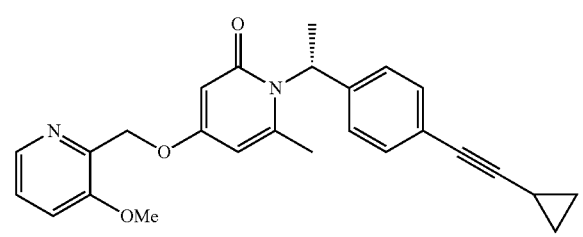 [SMILES: COc1cccnc1COc1cc(C)n([C@H](C)c2ccc(C#CC3CC3)cc2)c(=O)c1] |
| I-320 | 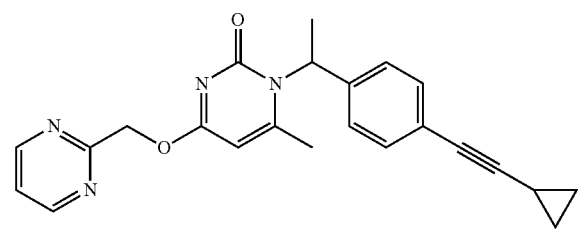 [SMILES: Cc1cc(OCc2ncccn2)nc(=O)n1C(C)c1ccc(C#CC2CC2)cc1] |

-continued

| Compound No. | Structure |
|---|---|
| I-321 | 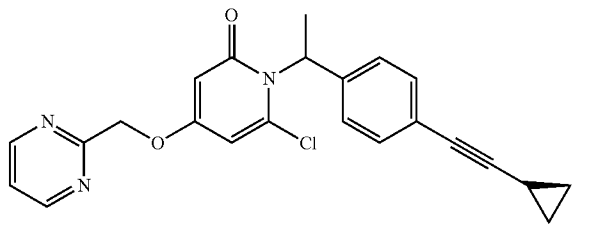 |
| I-322 | 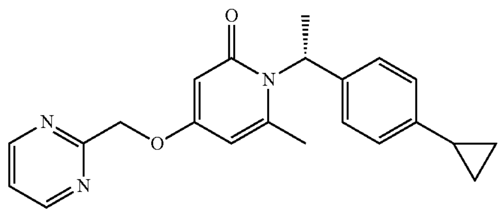 |
| I-323 | 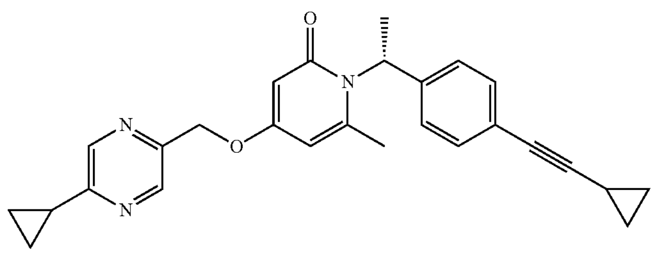 [SMILES: Cc1cc(OCc2cnc(C3CC3)cn2)cc(=O)n1[C@H](C)c1ccc(C#CC2CC2)cc1] |
| I-324 | 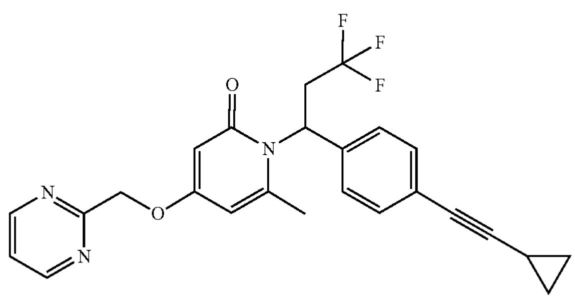 [SMILES: Cc1cc(OCc2ncccn2)cc(=O)n1C(CC(F)(F)F)c1ccc(C#CC2CC2)cc1] |
| I-325 | 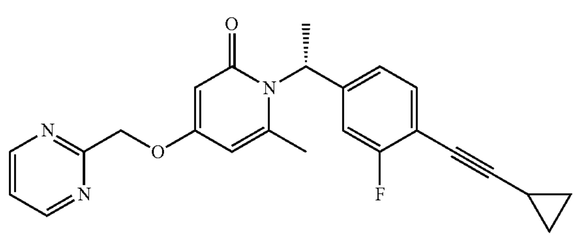 |
| I-326 | 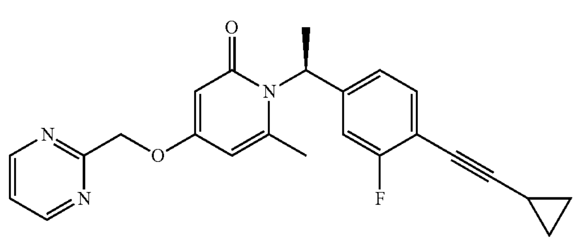 |

-continued
| Compound No. | Structure |
|---|---|
| I-327 | 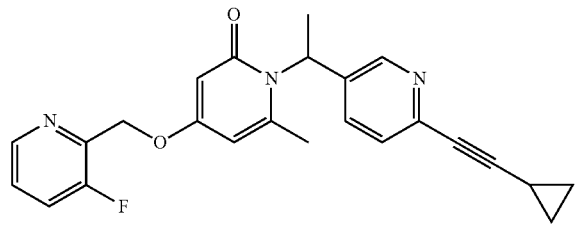 [SMILES: Cc1cc(OCc2ncccc2F)cc(=O)n1C(C)c1ccc(C#CC2CC2)nc1] |
| I-329 | 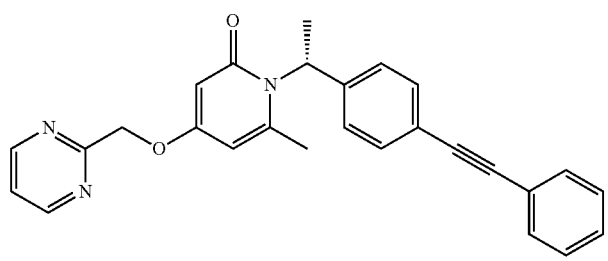 [SMILES: Cc1cc(OCc2ncccn2)cc(=O)n1[C@H](C)c1ccc(C#Cc2ccccc2)cc1] |
| I-340 | 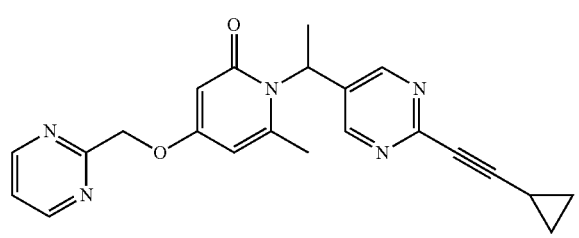 |
| I-341 | 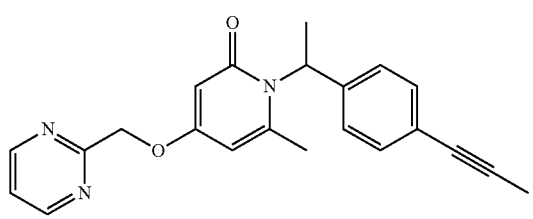 [SMILES: CC#Cc1ccc(C(C)n2c(C)cc(OCc3ncccn3)cc2=O)cc1] |
| I-342 | 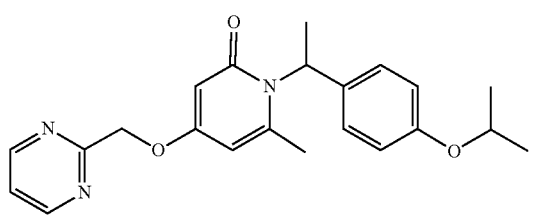 [SMILES: Cc1cc(OCc2ncccn2)cc(=O)n1C(C)c1ccc(OC(C)C)cc1] |
| I-343 | 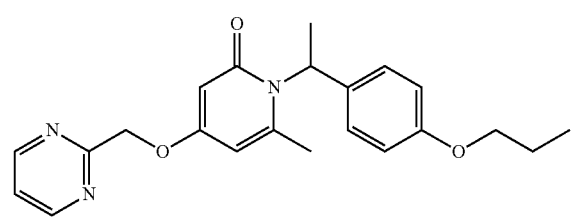 [SMILES: CCCOc1ccc(C(C)n2c(C)cc(OCc3ncccn3)cc2=O)cc1] |

-continued
| Compound No. | Structure |
|---|---|
| I-344 | 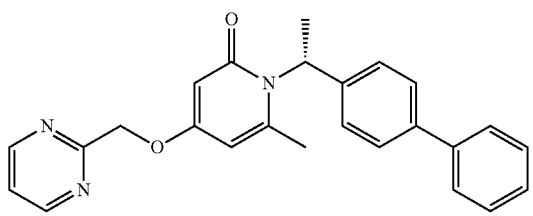 [SMILES: Cc1cc(OCc2ncccn2)cc(=O)n1[C@H](C)c1ccc(-c2ccccc2)cc1] |
| I-345 | 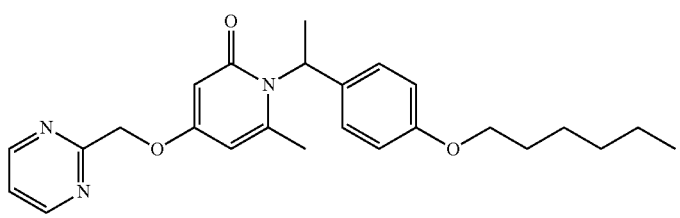 [SMILES: CCCCCCOc1ccc(C(C)n2c(C)cc(OCc3ncccn3)cc2=O)cc1] |
| I-346 | 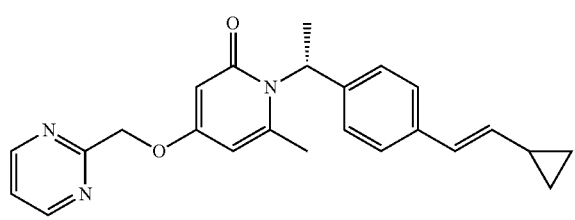 [SMILES: Cc1cc(OCc2ncccn2)cc(=O)n1[C@H](C)c1ccc(/C=C/C2CC2)cc1] |
| I-346 | 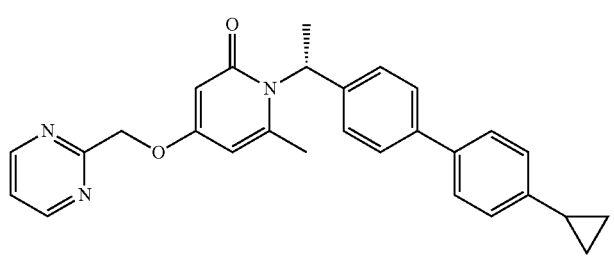 [SMILES: Cc1cc(OCc2ncccn2)cc(=O)n1[C@H](C)c1ccc(-c2ccc(C3CC3)cc2)cc1] |
| I-347 | 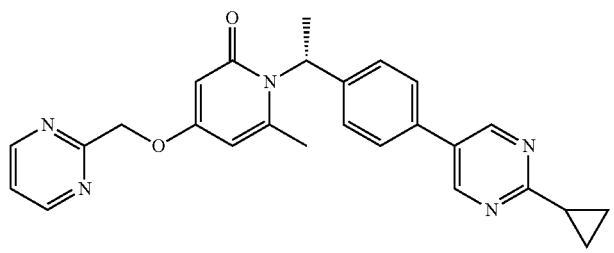 |
| I-348 | 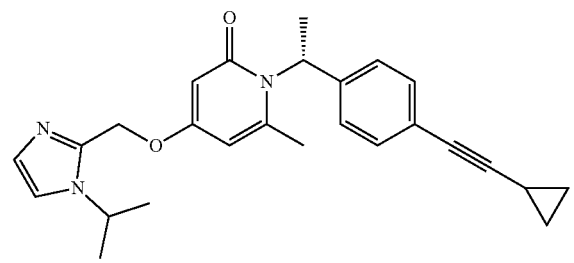 [SMILES: Cc1cc(OCc2nccn2C(C)C)cc(=O)n1[C@H](C)c1ccc(C#CC2CC2)cc1] |

-continued
| Compound No. | Structure |
|---|---|
| I-349 | 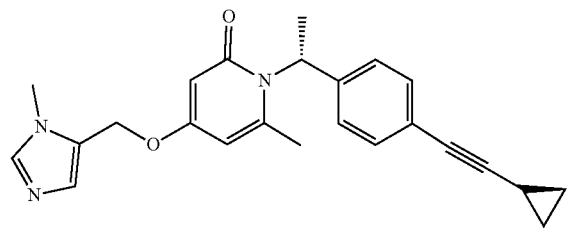 |
| I-350 | 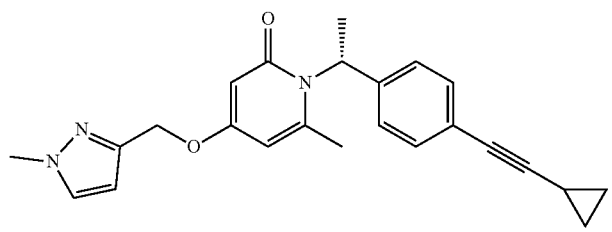 [SMILES: Cc1cc(OCc2ccn(C)n2)cc(=O)n1[C@H](C)c1ccc(C#CC2CC2)cc1] |
| I-351 | 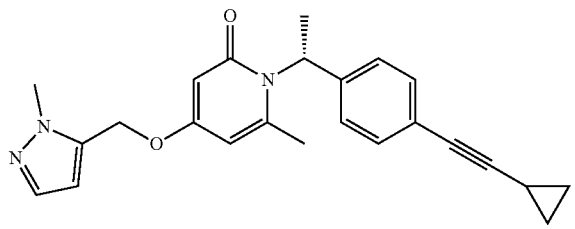 [SMILES: Cc1cc(OCc2ccnn2C)cc(=O)n1[C@H](C)c1ccc(C#CC2CC2)cc1] |
| I-352 | 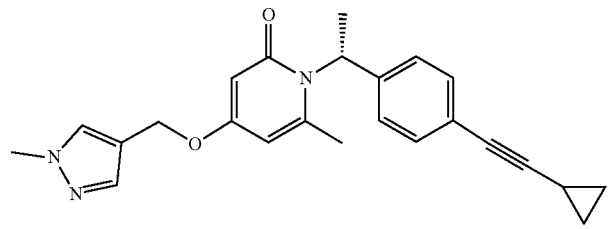 [SMILES: Cc1cc(OCc2cnn(C)c2)cc(=O)n1[C@H](C)c1ccc(C#CC2CC2)cc1] |
| I-353 | 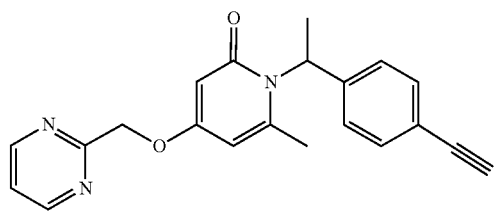 [SMILES: C#Cc1ccc(C(C)n2c(C)cc(OCc3ncccn3)cc2=O)cc1] |
| I-354 | 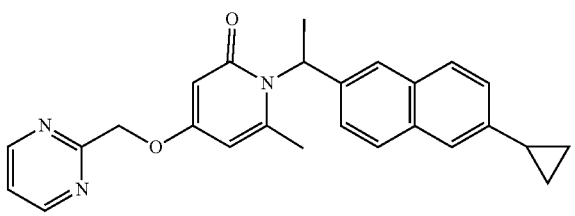 [SMILES: Cc1cc(OCc2ncccn2)cc(=O)n1C(C)c1ccc2cc(C3CC3)ccc2c1] |

| Compound No. | Structure |
|---|---|
| I-355 | 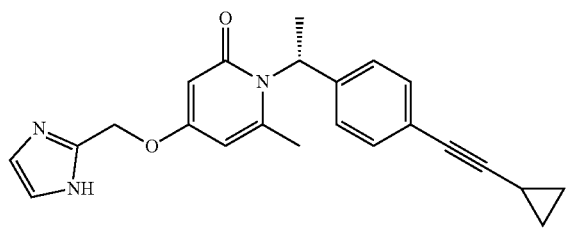 |
| I-356 | 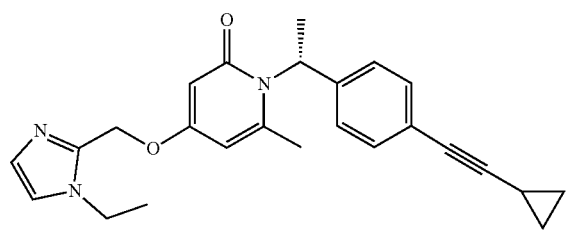 [SMILES: CCn1ccnc1COc1cc(C)n([C@H](C)c2ccc(C#CC3CC3)cc2)c(=O)c1] |
| I-357 | 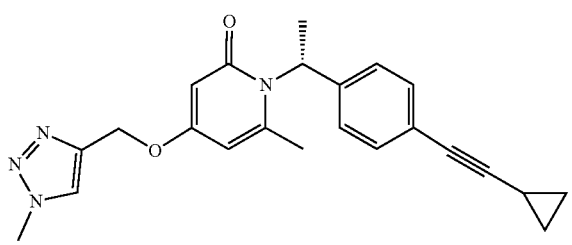 [SMILES: Cc1cc(OCc2cn(C)nn2)cc(=O)n1[C@H](C)c1ccc(C#CC2CC2)cc1] |
| I-358 | 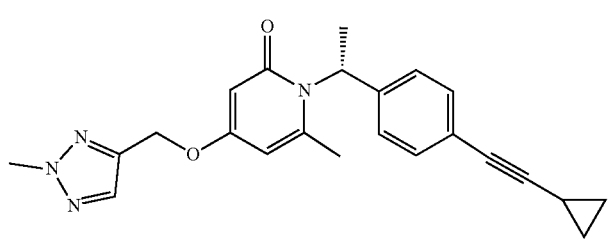 [SMILES: Cc1cc(OCc2cnn(C)n2)cc(=O)n1[C@H](C)c1ccc(C#CC2CC2)cc1] |
| I-359 | 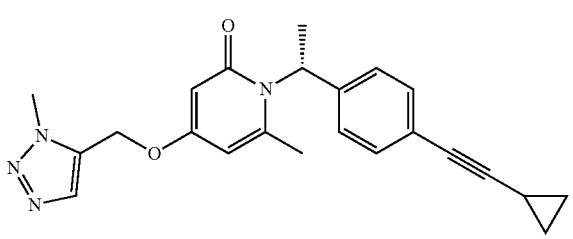 [SMILES: Cc1cc(OCc2cnnn2C)cc(=O)n1[C@H](C)c1ccc(C#CC2CC2)cc1] |
| I-360 | 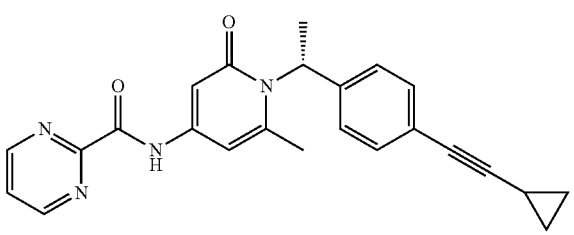 [SMILES: Cc1cc(NC(=O)c2ncccn2)cc(=O)n1[C@H](C)c1ccc(C#CC2CC2)cc1] |

-continued

| Compound No. | Structure |
|---|---|
| I-361 | 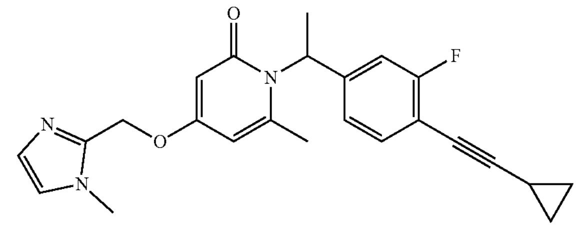 |
| I-362 | 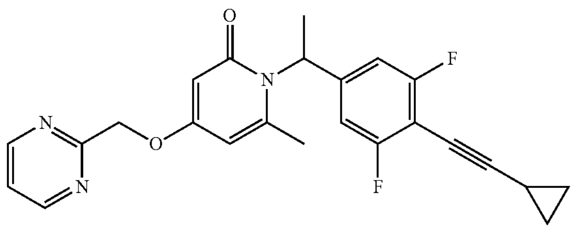 |
| I-363 | 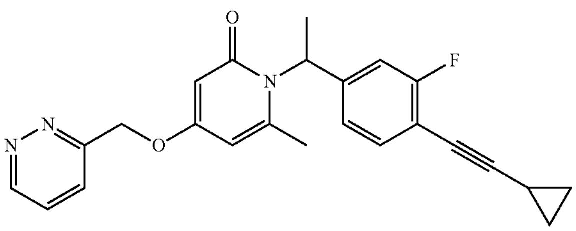 [SMILES: Cc1cc(OCc2cccnn2)cc(=O)n1C(C)c1ccc(C#CC2CC2)c(F)c1] |
| I-364 | 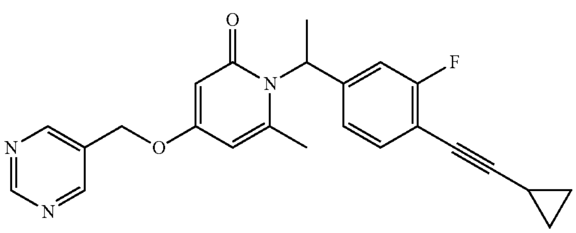 [SMILES: Cc1cc(OCc2cncnc2)cc(=O)n1C(C)c1ccc(C#CC2CC2)c(F)c1] |
| I-365 | 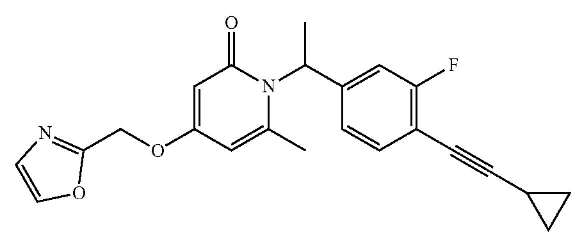 [SMILES: Cc1cc(OCc2ncco2)cc(=O)n1C(C)c1ccc(C#CC2CC2)c(F)c1] |
| I-366 | 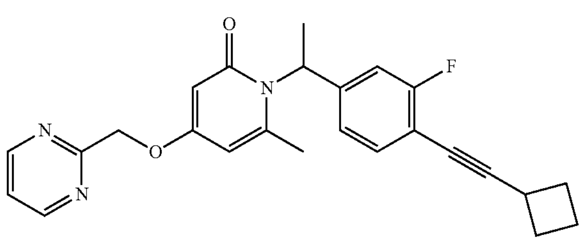 [SMILES: Cc1cc(OCc2ncccn2)cc(=O)n1C(C)c1ccc(C#CC2CCC2)c(F)c1] |

-continued
| Compound No. | Structure |
|---|---|
| I-368 | 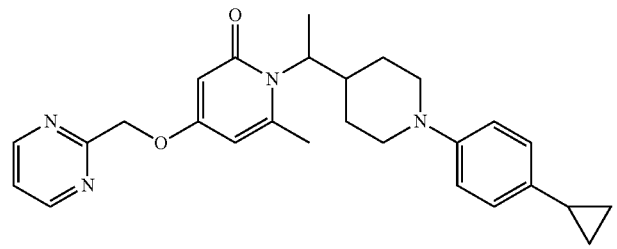 [SMILES: Cc1cc(OCc2ncccn2)cc(=O)n1C(C)C1CCN(c2ccc(C3CC3)cc2)CC1] |
| I-369 | 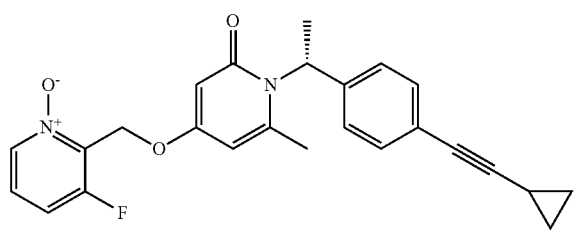 [SMILES: Cc1cc(OCc2c(F)ccc[n+]2[O-])cc(=O)n1[C@H](C)c1ccc(C#CC2CC2)cc1] |
| I-372 | 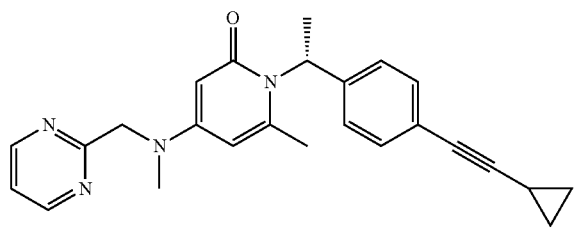 [SMILES: Cc1cc(N(C)Cc2ncccn2)cc(=O)n1[C@H](C)c1ccc(C#CC2CC2)cc1] |
| I-373 | 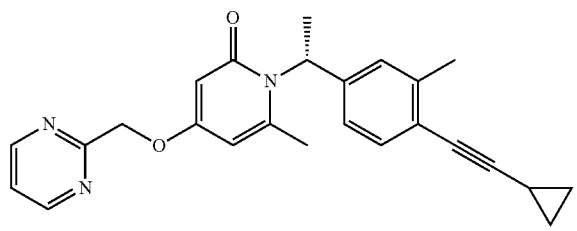 |
| I-374 | 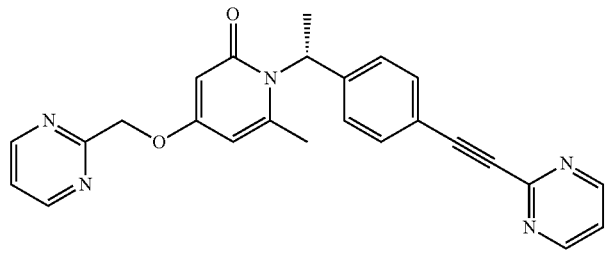 [SMILES: Cc1cc(OCc2ncccn2)cc(=O)n1[C@H](C)c1ccc(C#Cc2ncccn2)cc1] |
| I-375 | 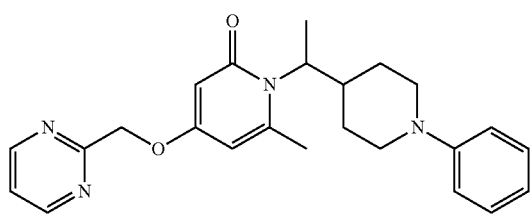 [SMILES: Cc1cc(OCc2ncccn2)cc(=O)n1C(C)C1CCN(c2ccccc2)CC1] |

-continued
| Compound No. | Structure |
|---|---|
| I-376 | 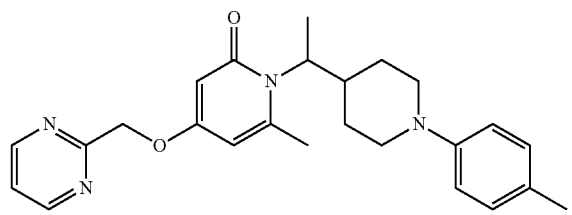 [SMILES: Cc1ccc(N2CCC(C(C)n3c(C)cc(OCc4ncccn4)cc3=O)CC2)cc1] |
| I-377 | 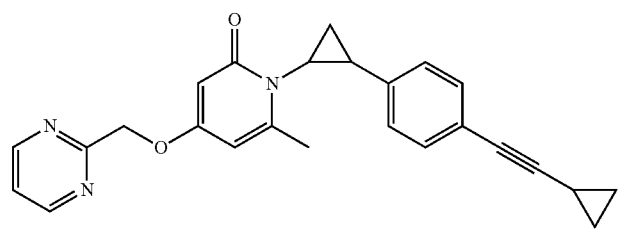 [SMILES: Cc1cc(OCc2ncccn2)cc(=O)n1C1CC1c1ccc(C#CC2CC2)cc1] |
| I-378 | 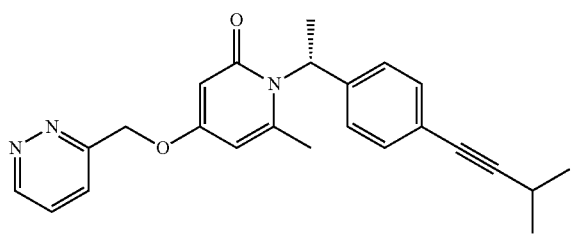 [SMILES: Cc1cc(OCc2cccnn2)cc(=O)n1[C@H](C)c1ccc(C#CC(C)C)cc1] |
| I-379 | 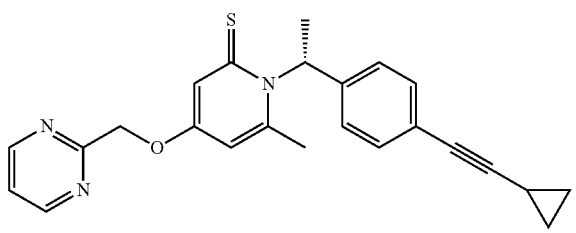 |
| I-380 | 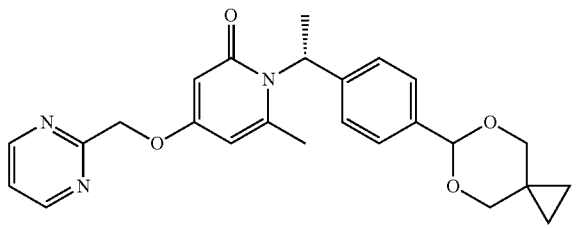 [SMILES: Cc1cc(OCc2ncccn2)cc(=O)n1[C@H](C)c1ccc(C2OCC3(CC3)CO2)cc1] |
| I-381 | 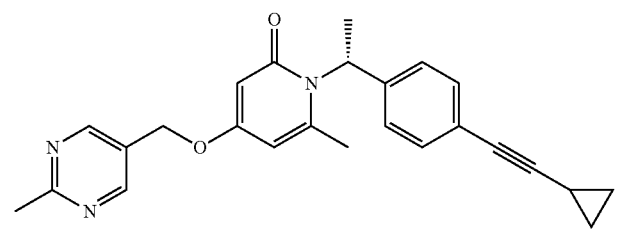 |

-continued
| Compound No. | Structure |
|---|---|
| I-382 | 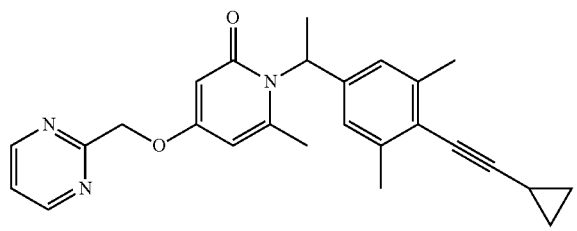 |
| I-383 | 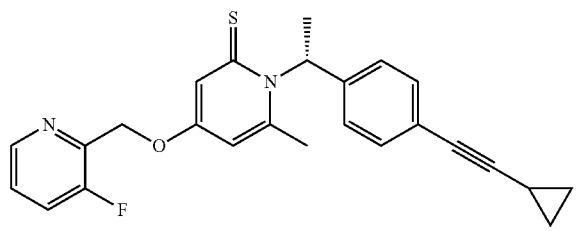 |
| I-384 | 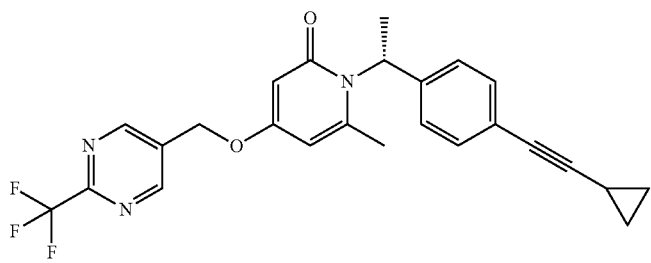 [SMILES: Cc1cc(OCc2cnc(C(F)(F)F)nc2)cc(=O)n1[C@H](C)c1ccc(C#CC2CC2)cc1] |
| I-385 | 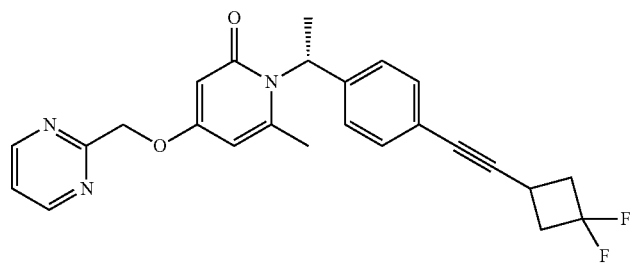 [SMILES: Cc1cc(OCc2ncccn2)cc(=O)n1[C@H](C)c1ccc(C#CC2CC(F)(F)C2)cc1] |
| I-386 | 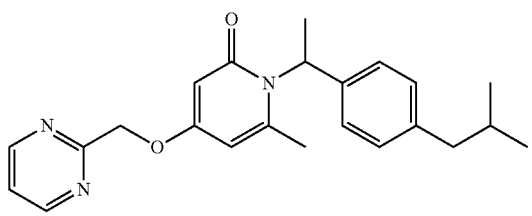 [SMILES: Cc1cc(OCc2ncccn2)cc(=O)n1C(C)c1ccc(CC(C)C)cc1] |
| I-387 | 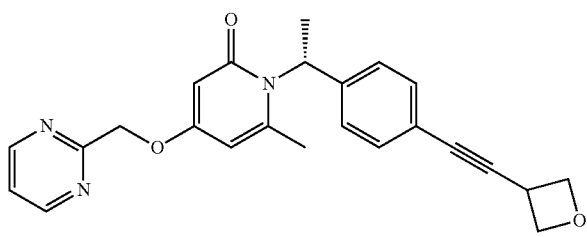 [SMILES: Cc1cc(OCc2ncccn2)cc(=O)n1[C@H](C)c1ccc(C#CC2COC2)cc1] |

| Compound No. | Structure |
|---|---|
| I-388 | 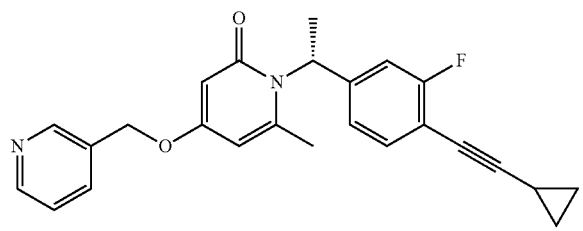 |
| I-389 | 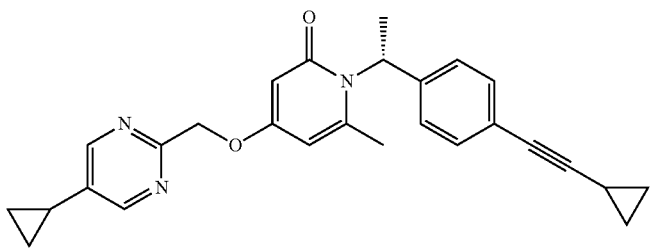 [SMILES: Cc1cc(OCc2ncc(C3CC3)cn2)cc(=O)n1[C@H](C)c1ccc(C#CC2CC2)cc1] |
| I-390 | 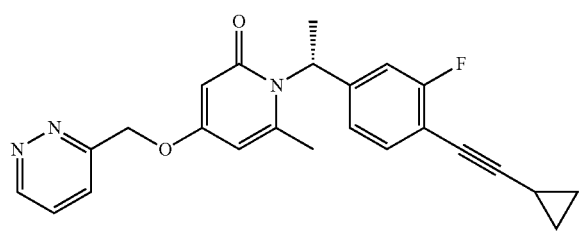 |
| I-391 | 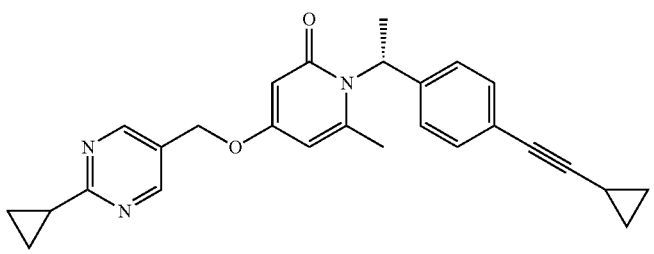 [SMILES: Cc1cc(OCc2cnc(C3CC3)nc2)cc(=O)n1[C@H](C)c1ccc(C#CC2CC2)cc1] |
| I-392 | 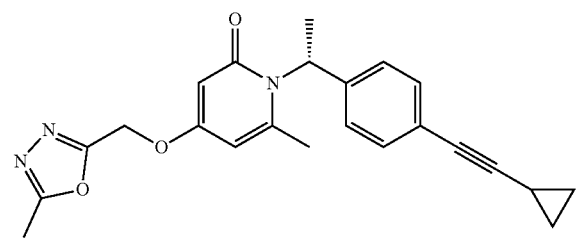 |
| I-393 | 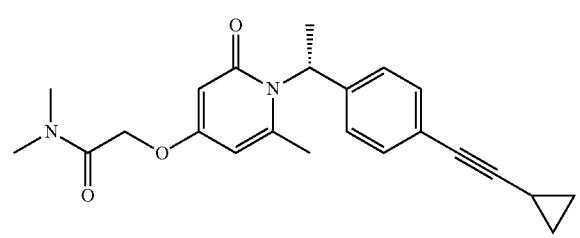 |

| Compound No. | Structure |
|---|---|
| I-394 | *(structure)* |
| I-395 | *(structure)* |
| I-396 | *(structure)* |

9. A pharmaceutical composition comprising a compound of claim 1, or a pharmaceutically acceptable salt thereof, and a pharmaceutically acceptable carrier, adjuvant, or vehicle.

10. A method of inhibiting GPR84 in a biological sample comprising contacting the sample with the compound of claim 1 or a pharmaceutically acceptable salt thereof.

11. A method of treating a GPR84-mediated disorder, disease, or condition in a patient comprising administering to said patient in need thereof the compound of claim 1 or a pharmaceutically acceptable salt thereof, wherein the GPR84-mediated disorder, disease, or condition is selected from idiopathic pulmonary fibrosis, Crohn's disease, ulcerative colitis, or inflammatory bowel disease.

12. The method of claim 11, wherein the disorder, disease, or condition is inflammatory bowel disease.

13. The method of claim 11, wherein the disorder, disease, or condition is idiopathic pulmonary fibrosis (IPF).

14. The compound of claim 5, wherein L¹ is a C$_{1-5}$ bivalent straight or branched saturated hydrocarbon chain wherein 1-2 methylene units of the chain are independently and optionally replaced with —O—.

15. The method of claim 13, wherein the compound is

*(structure)* or a pharmaceutically acceptable salt thereof.

16. The method of claim 13, wherein the compound is

*(structure)* or a pharmaceutically acceptable salt thereof.

17. The method of claim 13, wherein the compound is

*(structure)* or a pharmaceutically acceptable salt thereof.

18. The pharmaceutical composition of claim 9, wherein the pharmaceutical composition comprises (i)

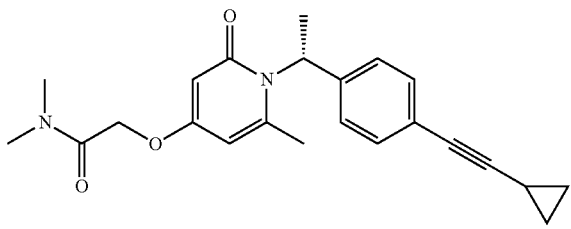 [SMILES: Cc1cc(OCC(=O)N(C)C)cc(=O)n1[C@H](C)c1ccc(C#CC2CC2)cc1]

or a pharmaceutically acceptable salt thereof and (ii) a pharmaceutically acceptable carrier, adjuvant, or vehicle.

19. The pharmaceutical composition of claim 9, wherein the pharmaceutical composition comprises (i)

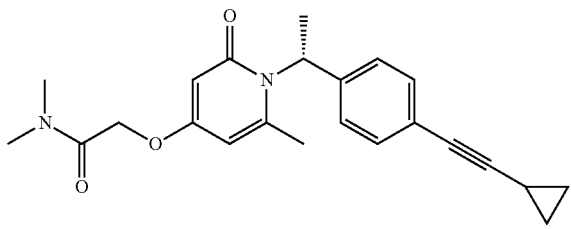 [SMILES: Cc1cc(OCC(=O)N(C)C)cc(=O)n1[C@H](C)c1ccc(C#CC2CC2)cc1]

and (ii) a pharmaceutically acceptable carrier, adjuvant, or vehicle.

20. The pharmaceutical composition of claim 9, wherein the pharmaceutical composition comprises (i)

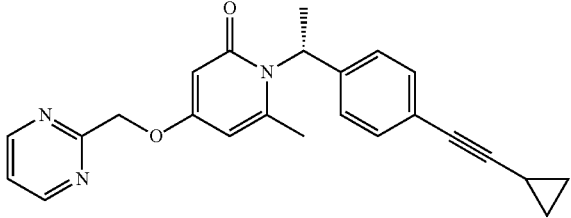

or a pharmaceutically acceptable salt thereof and (ii) a pharmaceutically acceptable carrier, adjuvant, or vehicle.

21. The pharmaceutical composition of claim 9, wherein the pharmaceutical composition comprises (i)

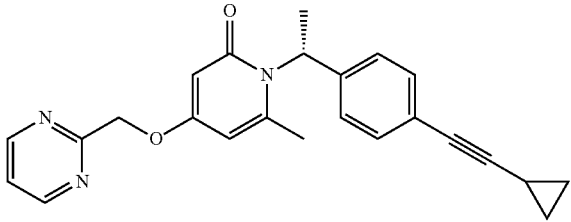

and (ii) a pharmaceutically acceptable carrier, adjuvant, or vehicle.

22. The pharmaceutical composition of claim 9, wherein the pharmaceutical composition comprises (i)

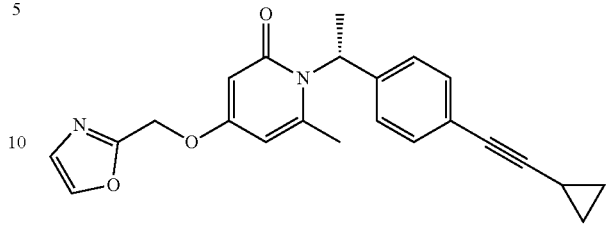

or a pharmaceutically acceptable salt thereof and (ii) a pharmaceutically acceptable carrier, adjuvant, or vehicle.

23. The pharmaceutical composition of claim 9, wherein the pharmaceutical composition comprises (i)

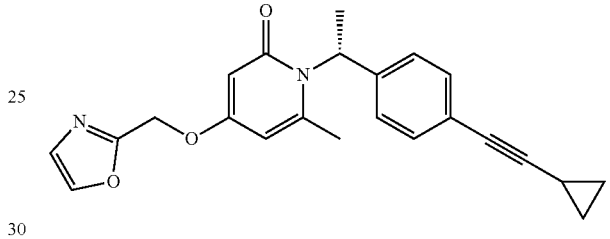

and (ii) a pharmaceutically acceptable carrier, adjuvant, or vehicle.

24. The compound of claim 8, wherein the compound is

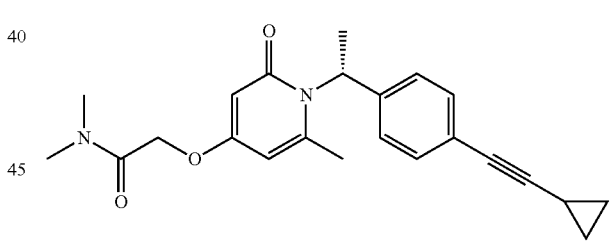

or a pharmaceutically acceptable salt thereof.

25. The compound of claim 8, wherein the compound is

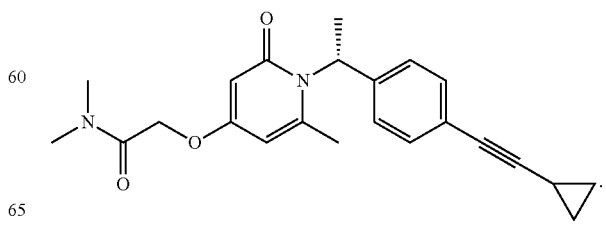

26. The compound of claim 8, wherein the compound is
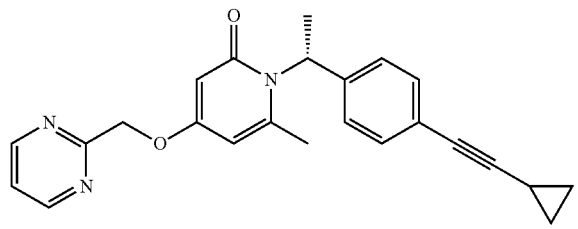
or a pharmaceutically acceptable salt thereof.
27. The compound of claim 8, wherein the compound is
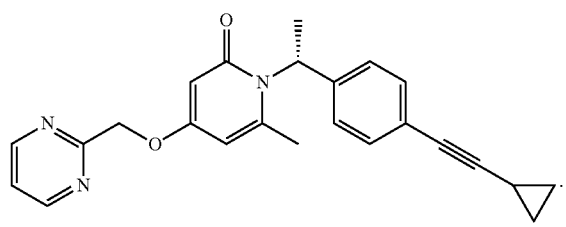 [SMILES: Cc1cc(OCc2ncccn2)cc(=O)n1[C@H](C)c1ccc(C#CC2CC2)cc1]
28. The compound of claim 8, wherein the compound is
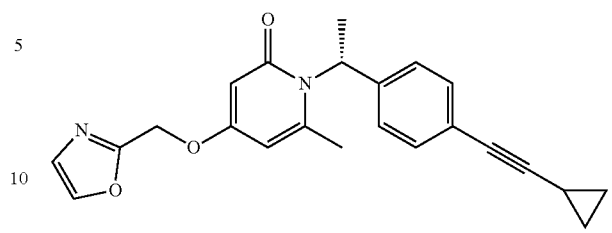
or a pharmaceutically acceptable salt thereof.
29. The compound of claim 8, wherein the compound is
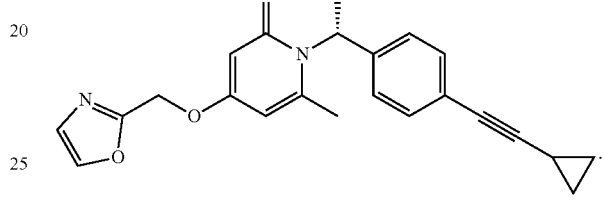
* * * * *